United States Patent
Bunin et al.

(10) Patent No.: US 12,162,892 B2
(45) Date of Patent: Dec. 10, 2024

(54) CD16a BINDING AGENTS AND USES THEREOF

(71) Applicant: KLEO PHARMACEUTICALS, INC., New Haven, CT (US)

(72) Inventors: Anna Bunin, Rego Park, NY (US); Lawrence G. Iben, Bethany, CT (US); Douglas Manion, Madison, CT (US); David Adam Spiegel, Hamden, CT (US); Matthew Ernest Welsch, New Haven, CT (US)

(73) Assignee: KLEO PHARMACEUTICALS, INC., New Haven, CT (US)

(*) Notice: Subject to any disclaimer, the term of this patent is extended or adjusted under 35 U.S.C. 154(b) by 57 days.

(21) Appl. No.: 17/990,427

(22) Filed: Nov. 18, 2022

(65) Prior Publication Data

US 2024/0051966 A1 Feb. 15, 2024

Related U.S. Application Data

(62) Division of application No. 16/960,534, filed as application No. PCT/US2019/012703 on Jan. 8, 2019, now Pat. No. 11,572,370.

(60) Provisional application No. 62/614,607, filed on Jan. 8, 2018.

(51) Int. Cl.
C07D 495/04 (2006.01)
A61K 47/68 (2017.01)

(52) U.S. Cl.
CPC ........ *C07D 495/04* (2013.01); *A61K 47/6849* (2017.08)

(58) Field of Classification Search
CPC .................................................. C07D 495/04
See application file for complete search history.

(56) References Cited

U.S. PATENT DOCUMENTS

| | | | |
|---|---|---|---|
| 5,538,852 A | 7/1996 | Carlson et al. | |
| 2003/0054424 A1 | 3/2003 | Allen et al. | |
| 2015/0368261 A1 | 12/2015 | Demin et al. | |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home » Thesis Resources » Find ETDs" Online: "https://ndltd.org/thesis-resources/find-etds/" Accessed Jan. 31, 2023.*
Irwin "ZINC—A Free Database of Commercially Available Compounds for Virtual Screening" J. Chem. Inf. Model. 2005, 45, 177-182.*
Kim "PubChem in 2021: new data content and improved web interfaces" Nucleic Acids Research, 2021, vol. 49, Database issue Published online Nov. 5, 2020.*
STN Registry/ZRegistry (Cas RegistrySM) Sep. 2016 2 pages.*
Pahl, Cancer Immunol Res; 6(5) May 2018, 517-527.*
Coënon. Frontiers in Immunology, Jun. 2022 | vol. 13 | Article 913215, 1-10.*
Bruggeman et al., "Enhanced Effector Functions Due to Antibody Defucosylation Depend on the Effector Cell Fcy Receptor Profile," The Journal of Immunology, (2017), vol. 199, 204-211.
International Search Report; International Application No. PCT/US2019/12703; International Filing Date—Jan. 8, 2019; Date of Mailing—May 14, 2019; 4 pages.
Lazar et al., "Engineered Antibody Fc Variants with Enhanced Effector Function," The Proceedings of the National Academy of Sciences, (2006), vol. 103, (No. 11), 4005-4010.
Patterson et al., "Improving Serum Stability of Site-Specific Antibody Conjugates with Sulfone Linkers," Bioconjugate Chemistry, (2014), vol. 25, 1402-1407.
Ramirez et al., "Defining Causative Factors Contributing in the Activation of Hedgehog Signaling in Diffuse Large B-Cell Lymphoma," Leuk. Res., (2012), vol. 36, (No. 10), 1267-1273.
Stopforth et al., "Regulation of Monoclonal Antibody Immunotherapy by FcyRIIB," Journal of Immunology, (2016), vol. 36, (Suppl 1), S88-S94.
Sun et al., "Carbohydrate and Protein Immobilization onto Solid Surfaces by Sequential Diels—Alder and Azide—Alkyne Cycloadditions," Bioconjugate Chem., (2006), vol. 17, (No. 1), 2006, 52-57.
Schumacher, et al., "Current Status: Site-Specific Antibody Drug Conjugates," J. Clinical Immunology, (2016), vol. 36, (Suppl. 1), S100-S107.
Rostovtsev et al., "A Stepwise Huisgen Cycloaddition Process: Copper(I)-Catalyzed Regioselective "Ligation" of Azides and Terminal Alkynes," Angew. Chem. Int. Ed., (2002), vol. 41, (No. 14), 2596-2599.
Russell, et al., "Antibody-Antigen Binding in Organic Solvents," Biochemical and Biophysical Research Communications, (1989), vol. 158, (No. 1), 80-85.

* cited by examiner

*Primary Examiner* — Nizal S Chandrakumar
(74) *Attorney, Agent, or Firm* — CANTOR COLBURN LLP

(57) ABSTRACT

Among other things, the present disclosure provides compounds, compositions thereof, and methods of using the same. In some embodiments, compounds of the present disclosure bind to Fc receptors, e.g., CD16a. In some embodiments, compounds of the present disclosure are useful for treating various conditions, disorders or diseases including cancer.

11 Claims, No Drawings

CD16a BINDING AGENTS AND USES THEREOF

CROSS REFERENCE TO RELATED APPLICATIONS

This application is a Divisional of U.S. application Ser. No. 16/960,534 filed on Jul. 7, 2020, which is a US National Stage Application of International Application No. PCT/US2019/012703, filed on Jan. 8, 2019, which claims priority of U.S. Provisional Application No. 62/614,607, filed on Jan. 8, 2018, the content of each of which is hereby incorporated by reference in its entirety.

TECHNICAL FIELD

The present disclosure encompasses technologies for modulating immune activities, e.g., for treatment of various conditions, disorders or diseases. In some embodiments, the present disclosure relates to compounds and methods useful as enhancing activities of antibodies, e.g., monoclonal antibodies. In some embodiments, the disclosure also provides pharmaceutically acceptable compositions comprising provided compounds and methods of using said compositions in the treatment of various conditions, disorders or diseases, e.g., various cancers.

BACKGROUND

The search for new therapeutic agents has been greatly aided in recent years by the discovery and development of monoclonal antibody therapeutic agents. Several of such agents elicit their therapeutic effect through the concomitant engagement of extracellular receptors of a targeted diseased cell with immune effector cells. Strategies for improving the therapeutic efficacy of monoclonal antibodies (mAbs) have involved engineering antibodies (i.e. mutated amino acids, altered glycosylation) to enhance the binding to Fc receptors.

SUMMARY OF THE INVENTION

Many immune activities involve recruitment of immune cells (e.g., NK cells) to damaged, diseased, and/or defective cells (e.g., cancer cells), tissues (e.g., tumors, certain wounds, etc.), foreign objects and/or entities (e.g., infectious agents), etc. Among other things, the present disclosure provides technologies, e.g., compounds, compositions, methods, etc., that are particularly useful for triggering, generating, encouraging, and/or enhancing recruitment of immune cells to their target sites, which, among other things, can provide improved biological effects (e.g., improved therapeutic effects, lower toxicity, fewer/less severe side effects, etc.

In some embodiments, the present disclosure provides technologies that can modulate activities of certain Fc receptors. In some embodiments, the present disclosure provides compounds that can bind certain Fc receptors and compositions and methods thereof. In some embodiments, provided technologies can trigger, generate, encourage and/or enhance one or more immune activities by enhanced recruitment of immune cells that express such Fc receptors. In some embodiments, provided technologies utilize binding moieties to enhance binding to Fc receptors. In some embodiments, this approach allows for enhanced binding of antibodies, e.g., monoclonal antibodies, to Fc receptors. Among other things, such enhanced binding can provide enhanced recruitment of immune cells expressing such Fc receptors and provide improved biological results, e.g., improved therapeutic effects, lower toxicity, fewer/less severe side effects, etc.

Particularly, in some embodiments, the present disclosure provides technologies that can modulate CD16a as demonstrated herein. Among other things, the present disclosure encompasses the recognition that certain forms of CD16a (low-affinity forms, e.g., CD16a-158F) may not interact with therapeutic agents (e.g., antibodies) as effectively as other forms (high-affinity forms, e.g., CD16a-158V). Without the intention to be limited by any theory, Applicant recognizes that such less effective interactions may lead to less effective recruitments of immune cells expressing CD16a (e.g., NK cells) and/or reduced therapeutic effects (e.g., in heterozygous or homozygous subjects expressing a low-affinity form). In some embodiments, the present disclosure provides technologies comprising agents that can bind to CD16a. In some embodiments, provided technologies increase interactions of CD16a with therapeutic agents, e.g., antibodies. In some embodiments, provided technologies increase recruitment of immune cells expressing CD16a, e.g., NK cells. In some embodiments, CD16a is a high-affinity form, e.g., 158V. In some embodiments, CD16a is a low-affinity form, e.g., 158F. As demonstrated herein, among other things, provided technologies can surprisingly and effectively enhance interactions with low-affinity CD16a (e.g., 158F) and recruitment of immune cells expressing such CD16a.

In some embodiments, a provided agent, e.g., a CD16a-binding agent, is a small molecule agent (e.g., having a MW smaller than 3000, 2500, 2000, 1500, or 1000). In some embodiments, a provided agent is a conjugate of a small molecule agent (e.g., a CD16a-binding small molecule agent) with another agent, e.g., antibodies, targeting moieties, etc., optionally through a linker. In some embodiments, a provided agent, e.g., a CD16a-binding agent, enhances interactions with various forms of CD16a, e.g., both high- and low-affinity forms. In some embodiments, a provided agent, e.g., a CD16a binding agent, selectively enhances binding of a high-affinity form of CD16a (e.g., as measured by fold increase compared to absence of such an agent and/or presence of a suitable control agent (e.g., an antibody not conjugated with a CD16a-binding small molecule agent as a control agent for a conjugate agent of the same antibody and a CD16a-binding small molecule agent)); in some embodiments, a provided agent, e.g., a CD16a binding agent, selectively enhances binding of a low-affinity form of CD16a. In some embodiments, a provided agent, e.g., a CD16a-binding agent, selectively binds to CD16a (a low affinity form and/or a high affinity form) compared to one or more other receptors, e.g., CD3ed, CD38, etc. In some embodiments, a provided agent, e.g., a CD16a-binding agent, binds to one or more other receptors, e.g., CD32a, CD32b, CD16b, CD38, etc., and/or enhances recruitment of immune cells expressing such receptor(s). In some embodiments, a provided agent, e.g., a CD16a-binding agent, binds to one or more Fc receptors other than CD16a, e.g., in some embodiments, CD32a, and/or enhances recruitment of immune cells expressing such receptor(s). In some embodiments, a CD32a is CD32a-H167. In some embodiments, a CD32a is CD32a-R167. In some embodiments, both alleles of a subject express CD32a-H167. In some embodiments, both alleles of a subject express CD32a-R167. In some embodiments, one allele of a subject expresses CD32a-H167 and the other CD32a-R167.

Among other things, the present disclosure provides MATEs™ (monoclonal antibody therapeutic enhancers) technologies that can enhance desired immune responses of a subject, e.g., a patient. In some embodiments, by covalently linking the CD16a small molecule ligands of the present disclosure to antibodies, e.g., mAbs, benefits such as, for example, enhanced antibody-dependent cell-mediated cytotoxicity (ADCC) activity can be achieved. Among other things, the MATEs (monoclonal antibody therapeutic enhancers) platform comprises the provision of compounds comprising two distinct segments: 1) an antibody, e.g., a monoclonal antibody, and 2) a binding moiety that enhances binding to receptors expressed on immune cells, e.g., CD16a. These enhanced antibodies can be prepared using a wide variety of antibodies, e.g., mAbs and binding moieties, thereby allowing tremendous versatility to address various diseases.

In some embodiments, a provided small molecule agent, e.g., a CD-16 binding agent, is conjugated with another agent optionally via a linker. In some embodiments, a provided small molecule agent is conjugated with an antibody optionally via a linker. In some embodiments, an antibody binds to an antigen of a damaged, diseased, and/or defective cells (e.g., cancer cells), tissues (e.g., tumors, certain wounds, etc.), foreign objects and/or entities (e.g., infectious agents), etc. In some embodiments, an antibody, e.g., a monoclonal antibody (mAb), attaches to disease cells targeted for destruction. In some embodiments, a binding moiety is a CD16a binding moiety (CBM) that binds to CD16a which is expressed by various types of cells and in some embodiments, is a principal receptor on NK cells. In some embodiments, CD16a binds to Fc portions of IgG antibodies which then activates immune cells, e.g., NK cells, for immune activities such as ADCC.

Provided technologies are useful for treating various conditions, disorders or diseases through modulation of immune activities, for example, many diseases that are amenable to treatment with ADCC-enhancing monoclonal antibodies. These diseases include many cancer and infectious diseases. In some embodiments, a cancer is one for which therapeutic responses and/or effects (e.g., survival) are not related to CD16a genotype. In some embodiments, a cancer is chronic lymphocytic leukemia. In some embodiments, a cancer is one for which therapeutic responses and/or effects (e.g., survival) are related to CD16a genotype. In some embodiments, a cancer is follicular lymphoma. In some embodiments, provided technologies are useful for treating a cancer in a subject independently of the subject's genotype.

In some embodiments, an agent, e.g., a CD16a binding agent, is a compound having the structure of formula A:

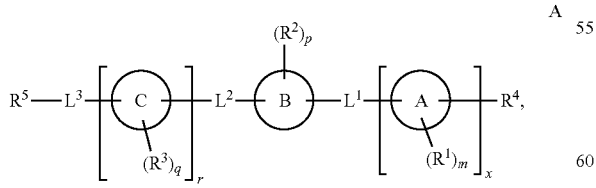

or a pharmaceutically acceptable salt thereof, wherein:
each of $R^1$, $R^2$, $R^3$, $R^4$, and $R^5$ is independently hydrogen, halogen, —CN, —$N_3$, —$NO_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)$_2$OR, —S(O)(NH)R, —S(O)$_2$N(R)$_2$, or R;

each of Ring A, Ring B and Ring C is independently an optionally substituted monocyclic, bicyclic, or polycyclic 3-40 membered ring having 0-20 heteroatoms;

each of $L^1$, $L^2$ and $L^3$ is independently a covalent bond, or a bivalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—, and one or more carbon and heteroatoms of the group are optionally and independently replaced with $Cy^L$;

each n is independently 1-50;

each -Cy- is independently an optionally substituted, bivalent, monocyclic, bicyclic, or polycyclic 3-40 membered ring having 0-20 heteroatoms;

each $Cy^L$ is independently an optionally substituted, polyvalent, monocyclic, bicyclic, or polycyclic 3-40 membered ring having 0-20 heteroatoms;

each of m, p and q is independently 0, 1, 2, 3, 4 or 5;

each of r and x is independently 0, 1, or 2;

each R' is independently —R, —OR, —C(O)R, —C(O)OR, or —S(O)$_2$R;

each R is independently —H, or an optionally substituted group selected from $C_{1-30}$ aliphatic, $C_{1-30}$ heteroaliphatic having 1-10 heteroatoms, $C_{6-30}$ aryl, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, monocyclic, bicyclic, or polycyclic 3-40 membered ring having, in addition to the atom, 0-20 heteroatoms; or:

two or more R groups on two or more atoms are optionally and independently taken together with their intervening atoms to form an optionally substituted, monocyclic, bicyclic, or polycyclic 3-40 membered ring having, in addition to the intervening atoms, 0-20 heteroatoms.

In some embodiments, Ring B is or comprises an optionally substituted spiro-bicyclic ring. In some embodiments, a compound of the present disclosure, e.g., a compound of formula A, has the structure of formula A-I:

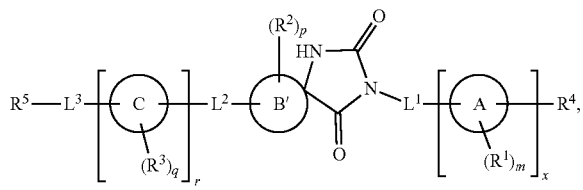

A-I or a pharmaceutically acceptable salt thereof, wherein Ring B' is an optionally substituted monocyclic, bicyclic, or polycyclic 3-35 membered ring having 0-18 heteroatoms, and each other variable is independently as defined and described herein.

In some embodiments, a compound of the present disclosure, e.g., a compound of formula A, has the structure of formula A-II:

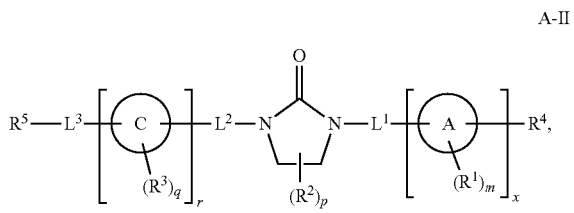

A-II or a pharmaceutically acceptable salt thereof, wherein each variable is independently as defined and described herein.

In some embodiments, a compound of the present disclosure, e.g., a compound of formula A, has the structure of formula A-III:

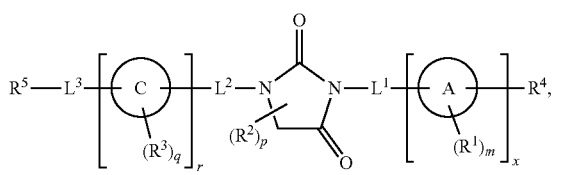

A-III or a pharmaceutically acceptable salt thereof, wherein each variable is independently as defined and described herein.

In some embodiments, a compound of the present disclosure, e.g., a compound of formula A, has the structure of formula A-IV:

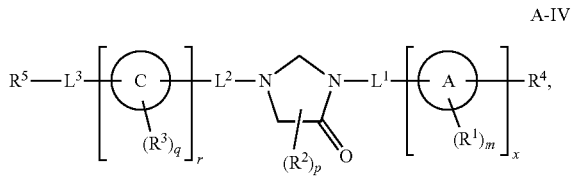

A-IV or a pharmaceutically acceptable salt thereof, wherein each variable is independently as defined and described herein.

In some embodiments, x is 0. In some embodiments, x is 1. In some embodiments, x is 2. In some embodiments, r is 0. In some embodiments, r is 1. In some embodiments, r is 2. In some embodiments, $R^4$ is —H. In some embodiments, $R^5$ is —H.

In some embodiments, an agent, e.g., a CD16a binding agent, is conjugated with another agent, e.g., a targeting moiety (e.g., antibodies (as described herein, including monoclonal antibodies, polyclonal antibodies, various modified forms and fragments thereof), peptides, proteins, small molecules, adjuvants, cytokines, viruses, vaccines, therapeutic agents, etc.). In some embodiments, a targeting moiety is an immunology targeting anti-cancer agents selected from antibodies, e.g., monoclonal antibodies, polyclonal antibodies, antibody fragments, peptides, proteins, small molecules, adjuvants, cytokines, oncolytic viruses, vaccines, bi-specific molecules and cellular therapeutic agents.

In some embodiments, a useful compound of the present disclosure, e.g., a conjugate of an agent, has the structure of formula C:

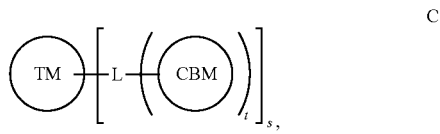

C or a pharmaceutically acceptable salt thereof, wherein,
TM is a targeting moiety;
each L is independently a linker moiety;
CBM is a CD16a binding moiety, or

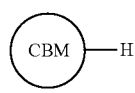

is a compound of formula A or a pharmaceutically acceptable salt thereof; and
each of t and s is independently 1-1000.

In some embodiments, TM is an antibody or a fragment thereof as described herein. In some embodiments, TM is a monoclonal antibody or a fragment thereof. In some embodiments, TM is a polyclonal antibody or a fragment thereof.

In some embodiments, each L is independently a covalent bond, or a bivalent or polyvalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—, and one or more carbon and heteroatoms of the group are optionally and independently replaced with $Cy^L$, wherein each variable is independently described herein.

In some embodiments, L is $L^1$ as defined and described herein. In some embodiments, L is $L^2$ as defined and described herein. In some embodiments, L is $L^3$ as defined and described herein.

In some embodiments, t is 1. In some embodiments, t is 1-900. In some embodiments, t is 1-800. In some embodiments, t is 1-700. In some embodiments, t is 1-600. In some embodiments, t is 1-500. In some embodiments, t is 1-400. In some embodiments, t is 1-300. In some embodiments, t is 1-200. In some embodiments, t is 1-100. In some embodiments, t is 1-90. In some embodiments, t is 1-80. In some embodiments, t is 1-70. In some embodiments, t is 1-60. In some embodiments, t is 1-50. In some embodiments, t is 1-40. In some embodiments, t is 1-30. In some embodiments, t is 1-20. In some embodiments, t is 1-10. In some embodiments, t is 1, 2, 3, 4, 5, 6, 7, 8, 9, or 10. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 15. In some embodiments, t is 20. In some embodiments, t is 25. In some embodiments, t is 30. In some embodiments, t is 40. In some embodiments, t is 50. In some embodiments, t is 60. In some embodiments, t is 70. In some embodiments, t is 80. In some embodiments, t is 90. In some embodiments, t is 100. In some embodiments, t is 150. In some embodiments, t is 200. In some embodiments, t is 250. In some embodiments, t is 300. In some embodiments, t is 400. In some embodiments, t is 500. In some embodiments, t is 600. In some embodiments, t is 700. In some embodiments, t is 800. In some embodiments, t is 900. In some embodiments, t is 1000.

In some embodiments, s is 1. In some embodiments, s is 1-900. In some embodiments, s is 1-800. In some embodiments, s is 1-700. In some embodiments, s is 1-600. In some embodiments, s is 1-500. In some embodiments, s is 1-400. In some embodiments, s is 1-300. In some embodiments, s is 1-200. In some embodiments, s is 1-100. In some embodiments, s is 1-90. In some embodiments, s is 1-80. In some embodiments, s is 1-70. In some embodiments, s is 1-60. In some embodiments, s is 1-50. In some embodiments, s is 1-40. In some embodiments, s is 1-30. In some embodiments, s is 1-20. In some embodiments, s is 1-10. In some embodiments, s is 1, 2, 3, 4, 5, 6, 7, 8, 9, or 10. In some embodiments, s is 1. In some embodiments, s is 2. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 15. In some embodiments, s is 20. In some embodiments, s is 25. In some embodiments, s is 30. In some embodiments, s is 40. In some embodiments, s is 50. In some embodiments, s is 60. In some embodiments, s is 70. In some embodiments, s is 80. In some embodiments, s is 90. In some embodiments, s is 100. In some embodiments, s is 150. In some embodiments, s is 200. In some embodiments, s is 250. In some embodiments, s is 300. In some embodiments, s is 400. In some embodiments, s is 500. In some embodiments, s is 600. In some embodiments, s is 700. In some embodiments, s is 800. In some embodiments, s is 900. In some embodiments, s is 1000.

In some embodiments, CBM is a CD16a binding moiety. In some embodiments, CBM is a derivative of a CD-16 binding agent, e.g., a compound of formula A or a pharmaceutically acceptable salt thereof.

In some embodiments, CBM is of such a structure that

is a compound of formula A, A-I, A-III, or A-IV. In some embodiments, CBM is

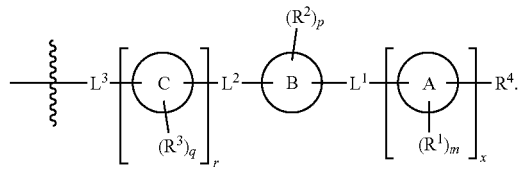

In some embodiments, CBM is

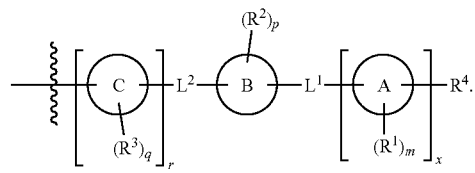

In some embodiments,

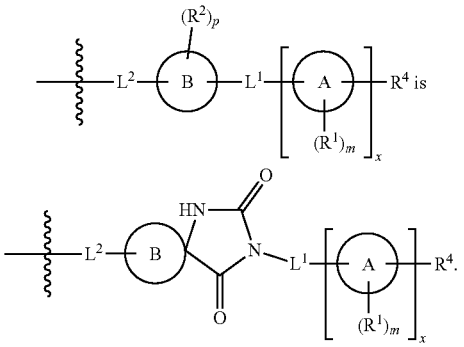

In some embodiments,

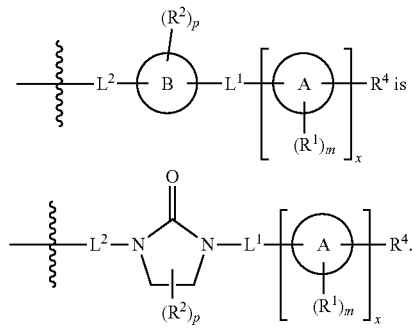

In some embodiments,

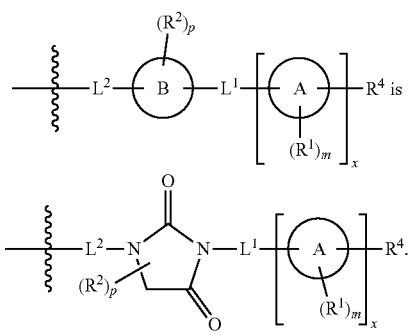

In some embodiments,

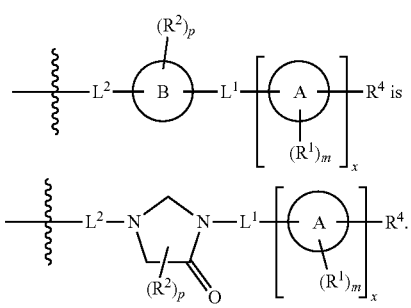

In some embodiments, a compound of the present disclosure, e.g., a compound of formula C, has the structure of formula C-I:

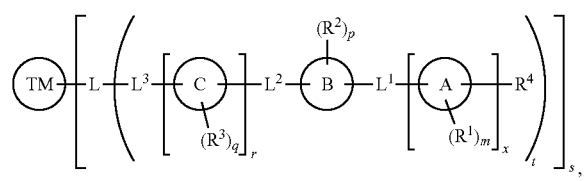

C-I or a pharmaceutically acceptable salt thereof, wherein each variable is independently as defined and described herein.

In some embodiments, the present disclosure relates to bifunctional compounds, e.g., having the following structure of formula C-II:

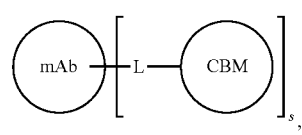

C-II wherein mAb is a monoclonal antibody or a fragment thereof, and each other variable is independently as defined and described herein. In some embodiments, a compound of formula C is a compound of formula C-II.

In some embodiments, in a compound described herein, e.g., a compound of formula C-II, mAb is a monoclonal antibody; L is a bivalent moiety that connects mAb to CBM; CBM is a CD16a binding moiety; and s is 1, 2, 3, 4, 5, or 6. In some embodiments, a compound of formula C is a compound of formula C-II.

In some embodiments, the present application relates to bifunctional compounds having the following structure of formula C-III:

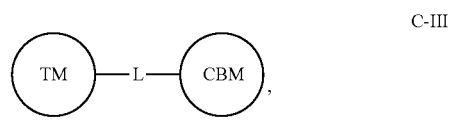

C-III wherein each variable is independently as defined and described herein. In some embodiments, a compound of formula C is a compound of formula C-III.

In some embodiments, in a compound described herein, e.g., a compound of formula C-III, TM is a targeting moiety; L is a bivalent moiety that connects TM to CBM; and CBM is a CD16a binding moiety.

In some embodiments, Ring B is or comprises an optionally substituted spiro-bicyclic ring. In some embodiments, a compound of the present disclosure, e.g., a compound of formula C, has the structure of formula C-IV:

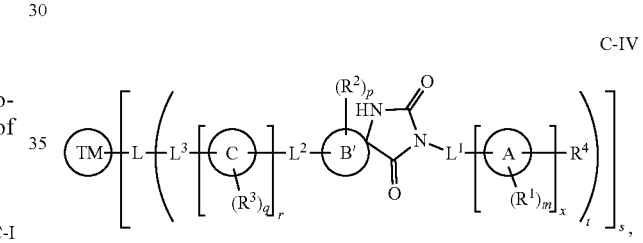

C-IV or a pharmaceutically acceptable salt thereof, wherein Ring B' is an optionally substituted monocyclic, bicyclic, or polycyclic 3-35 membered ring having 0-18 heteroatoms, and each other variable is independently as defined and described herein.

In some embodiments, a compound of the present disclosure, e.g., a compound of formula C, has the structure of formula C-V:

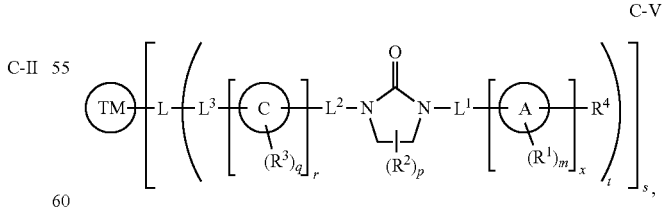

C-V or a pharmaceutically acceptable salt thereof, wherein each variable is independently as defined and described herein.

In some embodiments, a compound of the present disclosure, e.g., a compound of formula C, has the structure of formula C-VI:

C-VI

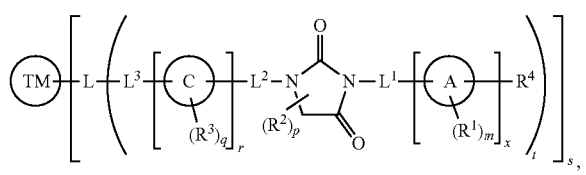

or a pharmaceutically acceptable salt thereof, wherein each variable is independently as defined and described herein.

In some embodiments, a compound of the present disclosure, e.g., a compound of formula C, has the structure of formula C-VII:

C-VII

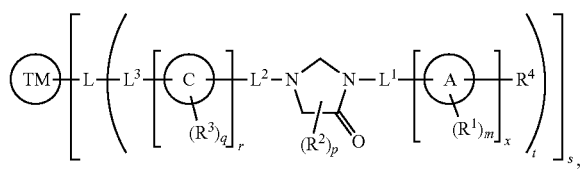

or a pharmaceutically acceptable salt thereof, wherein each variable is independently as defined and described herein.

In some embodiments, compounds of the present disclosure, e.g., compounds of formula C, C-I, C-II, C-III, C-IV, C-V, C-VI, C-VII, etc., have the structure of formula I.

I

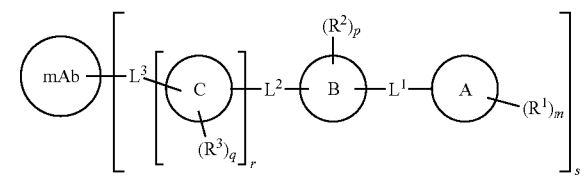

or a pharmaceutically acceptable salt thereof, wherein each variable is as defined and described herein.

Among other things, it is demonstrated herein that compounds of the present disclosure, e.g., those of formula C, C-I, C-II, C-III, C-IV, C-V, C-VI, C-VII, etc., and pharmaceutically acceptable compositions thereof, are effective as monoclonal antibody therapy enhancers.

In some embodiments, compounds of the present disclosure, and pharmaceutically acceptable compositions thereof, are useful for treating a variety of diseases, disorders or conditions. In some embodiments, such conditions, disorders or diseases are targeted by ADCC (antibody-dependent cell-mediated cytotoxicity)-enhancing monoclonal antibodies, and include those described herein. As appreciated by those skilled in the art, many immunological mechanisms, e.g., ADCC, ADCP (antibody-dependent cellular phagocytosis), etc., may be involved and utilized either individually or in combination for treatment of conditions, disorders or diseases.

In some embodiments, compounds provided by this invention are useful for, e.g., study of antibody-dependent cell-mediated cytotoxicity in biological and pathological phenomena; study of cell-mediated immune defense occurring in bodily tissues; and comparative evaluation of new compounds within the MATEs (monoclonal antibody therapeutic enhancers) platform in vitro or in vivo, etc.

DETAILED DESCRIPTION OF CERTAIN EMBODIMENTS

1. General Description of Certain Embodiments

Among other things, the present disclosure provides technologies that can trigger, generate, encourage and/or enhance recruitment of immune cells to target sites, e.g., diseased cells such as cancer cells, and trigger, generate, encourage and/or enhance suppression, inhibition and/or killing of such diseased cells. In some embodiments, one or more such beneficial effects comprises interaction of provided agents, e.g., compounds of formula A, C, etc. with receptors (e.g., CD16a) expressed by immune cells (e.g., NK cells). In some embodiments, agents of the present disclosure can bind (either covalently or non-covalently) to antibodies and immune cells expressing CD16a. In some embodiments, compounds of the present invention, and compositions thereof, are useful as monoclonal antibody therapy enhancers.

Without wishing to be bound by any particular theory, it is believed that linkage of a CD16a binding moiety to a targeting moiety, e.g., a monoclonal antibody, results in improved immune cell receptor binding of such a targeting moiety, e.g., a monoclonal antibody and improved immune activities, e.g., antibody-dependent cell-mediated cytotoxicity.

In some embodiments, an agent of the present disclosure is a compound having the structure of formula A or C or a pharmaceutically acceptable salt thereof.

In certain embodiments, the present invention provides a compound of formula I:

I

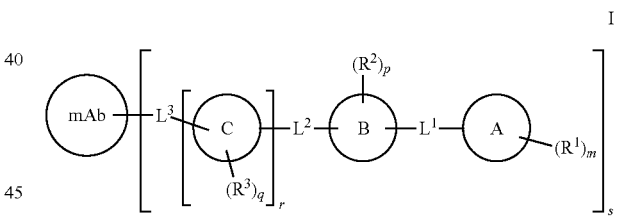

or a pharmaceutically acceptable salt thereof.

In some embodiments, in a compound, e.g., a compound of formula A, C, C-I, C-IV, C-V, C-VI, C-VII, I, etc., Ring A is selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, or 8-10 membered bicyclic heteroaryl having 1-5 heteroatoms independently selected from nitrogen, oxygen, or sulfur;

Ring B is a bivalent ring selected from phenylenyl, 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups;

Ring C is a bivalent ring selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur;

$L^1$ is a covalent bond, —$CH_2$—, —CH(R)—, or —C(R)$_2$—;

$L^2$ is a covalent bond, —NHC(O)—, —C(O)NH—, —$CH_2$—, —CH(R)—, —C(R)$_2$—, —C(O)—, or —S(O)$_2$—;

$L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

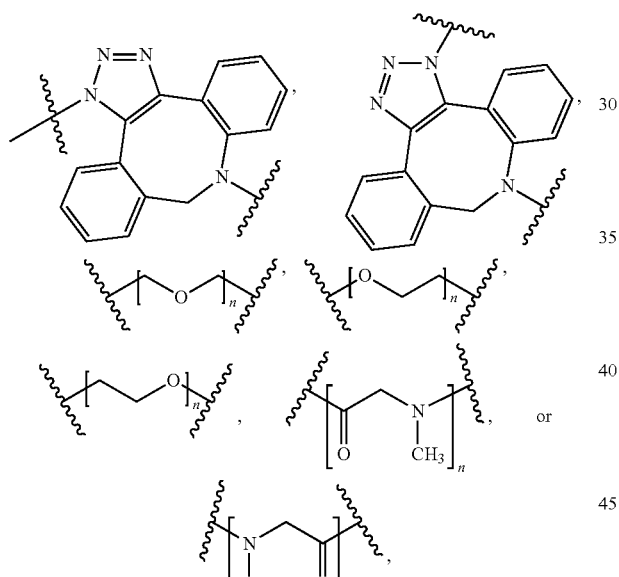

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups;

mAb is a monoclonal antibody;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each instance of $R^1$, and $R^3$ is independently hydrogen, halogen, —CN, —$NO_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R;

each instance of $R^2$ is independently hydrogen, halogen, —CN, —$NO_2$, or $C_{1-3}$ aliphatic;

m is 0, 1, 2, 3, 4 or 5;

each instance of n is independently selected from 1, 2, 3, 4, 5, 6, 7, 8, 9, or 10;

p is 0, 1, or 2;

q is 0, 1, 2, 3, or 4;

r is 0 or 1, wherein when r is 0,

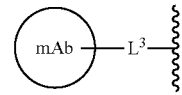

is directly attached to

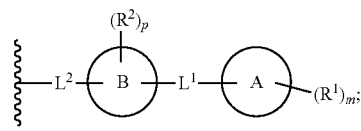

and s is 1, 2, 3, 4, 5, or 6.

2. Definitions

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.:

Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has, unless otherwise indicated, a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

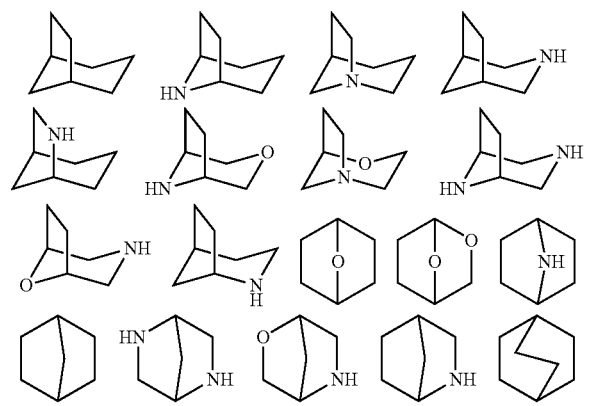
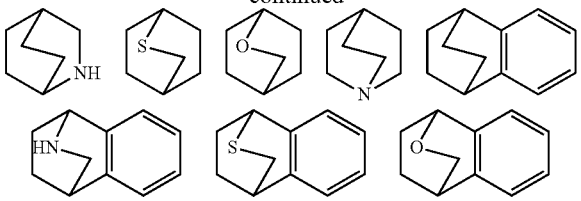

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means an atom that is not carbon or hydrogen. In some embodiments, a heteroatom is oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent (e.g., $C_{1-8}$, $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

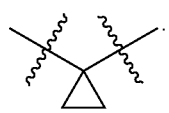 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic or polycyclic ring systems having a total of five to fourteen (or otherwise specified) ring members, wherein at least one ring in the system is aromatic and wherein each ring in the system contains 3 to 7 ring members (or otherwise specified). The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms (or otherwise specified), preferably 5, 6, or 9 ring atoms; having, e.g., 6, 10, or 14, π electrons shared in a cyclic array; and having, in addition to carbon atoms, from one to five (or otherwise specified) heteroatoms. The term "heteroatom" typically refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic, or otherwise specified, heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the present disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with $R°$; —$(CH_2)_{0-4}O(CH_2)_{0-4}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, —$SC(S)SR°$; —$(CH_2)_{0-4}SC(O)R°$; —$(CH_2)_{0-4}C(O)NR°_2$; —$C(S)NR°_2$; —$C(S)SR°$; —$(CH_2)_{0-4}C(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; —$SiR°_3$; —$(C_{1-4}$ straight or branched alkylene)O—$N(R°)_2$; or —$(C_{1-4}$ straight or branched alkylene)C(O)O—$N(R°)_2$, wherein each $R°$ may be substituted as defined below and is independently hydrogen, $C_{1-6}$ aliphatic, —$CH_2Ph$, —$O(CH_2)_{0-4}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-4}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^°$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R* is unsubstituted or where preceded by "halo" is substituted only with one or more halogens, and is independently C$_{1-4}$ aliphatic, —CH$_2$Ph, —O(CH$_2$)$_{0-4}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R; wherein each R$^†$ is independently hydrogen, C$_{1-4}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, R$^x$, of a provided compound comprises one or more deuterium atoms.

As used herein, the term "binder" is defined as a compound that binds to its target, e.g., CD16a, with measurable affinity. In certain embodiments, an binder has a binding constant of less than about 50 μM, less than about 1 μM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a target, e.g., CD16a, activity between a sample comprising a compound of the present disclosure, or composition thereof, and such a target, e.g., CD16a, and an equivalent sample comprising such a target, e.g., CD16a, in the absence of said compound, or composition thereof.

3. Description of Exemplary Embodiments

In some embodiments, the present disclosure provides useful agents, e.g., compounds having the structure of formula A or a pharmaceutically acceptable salt thereof. In some embodiments, such agents bind to one or more receptors, e.g., Fc receptors, expressed by immune cells. In some embodiments, such agents are useful for modulating activities of such receptors and/or cells expressing such receptors.

In some embodiments, a receptor is CD16a. In some embodiments, provided agents bind to a high-affinity (toward IgG, e.g., 158V) form of CD16a. In some embodiments, provided agents bind to a low-affinity (toward IgG, e.g., 158F) form of CD16a. In some embodiments, provided agents bind to both high-affinity and low-affinity forms of CD16a. In some embodiments, provided technologies are particularly useful as they can trigger, generate, encourage and/or enhance interactions with and recruitments of CD16a-expressing immune cells, and/or beneficial immune activities from such cells (e.g., killing of diseased cells such as cancer cells), even when such immune cells express a low-affinity form of CD16a. In some embodiments, one allele of a subject encodes a high-affinity CD16a (e.g., 158V), and the other allele encodes a low-affinity CD16a (e.g., 158F). In some embodiments, both alleles of a subject encode low affinity CD16a (e.g., In some embodiments, both alleles of a subject encode high affinity CD16a (e.g., 158V). As reported, a large percentage of subjects contain one or two alleles encoding a low-affinity, e.g., 158F, form of CD16a, and many therapeutic agents, e.g., antibodies, suffer from low response rates and/or reduced therapeutic effects when administered to such subjects for treating a variety of cancers. Among other things, the present disclosure provides technologies that can deliver improved response rates and/or therapeutic effects for treating such cancers in such subjects. Various other technologies were reported or are in development to enhance CD16a interactions with antibodies, e.g., through manipulation of IgG Fc glycosylation (e.g., at asparagine at position 297; see, e.g., Bruggeman, et al., J

*Immunol.* 2017 Jul. 1; 199(1):204-211), modulation of CD32b (see, e.g., Stopforth, et al., J Clin Immunol (2016) 36 (Suppl 1): S88-S94), engineered fc variants (see, e.g., Lazar, et al., *Proc Natl Acad Sci USA.* 2006 Mar. 14; 103(11):4005-10), etc. Technologies of the present disclosure can optionally be utilized in combination with one or more such other technologies. Among other things, technologies of the present disclosure can provide a number of advantages, including improved results, lower manufacturing cost, wide applicability with a variety of therapeutic agents, etc.

CD16a-expressing immune cells were widely reported and/or can be readily identified using available technologies. In some embodiments, CD16a-expressing immune cells are mast cells. In some embodiments, CD16a-expressing immune cells are NK cells. In some embodiments, CD16a-expressing immune cells are macrophages.

In some embodiments, a provided agent, e.g., a CD16a-binding agent, selectively binds to CD16a (a low affinity form and/or a high affinity form) compared to one or more other receptors, e.g., CD3ed, CD38, etc. In some embodiments, a provided agent selectively binds to CD16a over CD3ed. In some embodiments, a provided agent selectively binds to CD16a over CD38. In some embodiments, a provided agent selectively binds to CD16a over CD32b.

In some embodiments, a provided agent additionally or alternatively binds to one or more other receptors, e.g., CD32a, CD32b, CD16b, CD3ed, CD38, etc., and/or enhances recruitment of immune cells expressing such receptor(s). In some embodiments, a provided agent, e.g., a CD16a-binding agent, binds to one or more Fc receptors other than CD16a, e.g., in some embodiments, CD32a, and/or enhances recruitment of immune cells expressing such receptor(s). In some embodiments, a CD32a is CD32a-H167. In some embodiments, a CD32a is CD32a-R167. In some embodiments, both alleles of a subject express CD32a-H167. In some embodiments, both alleles of a subject express CD32a-R167. In some embodiments, one allele of a subject expresses CD32a-H167 and the other CD32a-R167. In some embodiments, a provided agent binds to CD32b and/or enhances recruitment of immune cells expressing CD32b. In some embodiments, a provided agent binds to CD3ed and/or enhances recruitment of immune cells expressing CD3ed. In some embodiments, a provided agent binds to CD38 and/or enhances recruitment of immune cells expressing CD38. In some embodiments, a provided agent binds to CD16b and/or enhances recruitment of immune cells expressing CD16b.

Various assays for assessing binding (e.g., affinity, selectivity, kinetics, etc.) are available in the art and can be utilized in accordance with the present disclosure, including those described in the Examples.

In some embodiments, an agent, e.g., a CD16a binding agent, is a compound having the structure of formula A:

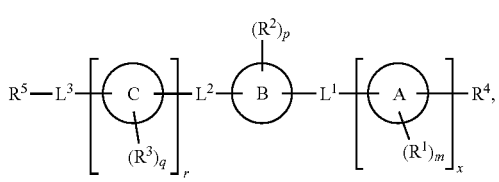

or a pharmaceutically acceptable salt thereof, wherein each variable is independently as defined and described herein.

In some embodiments, the present disclosure provides conjugates of an agent, e.g., a CD-16a binding compound, with another agent, e.g., a targeting moiety.

In some embodiments, a targeting moiety is an antibody. In some embodiments, an antibody is a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects $CH_2$ and $CH_3$ domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered such glycosylation. For purposes of the present disclosure, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]

In some embodiments, a targeting moiety is an immunology targeting anti-cancer agent.

In some embodiments, a targeting moiety is or comprises a peptide. In some embodiments, a targeting moiety is or comprises a protein. In some embodiments, a targeting moiety is or comprises an antibody or a fragment thereof. In some embodiments, a targeting moiety is or comprises a monoclonal antibody or a fragment thereof. In some embodiments, a targeting moiety is or comprises a polyclonal antibody or a fragment thereof.

In some embodiments, a targeting moiety is or comprises an adjuvant. In some embodiments, a targeting moiety is or comprises a cytokine. In some embodiments, a targeting moiety is or comprises a virus. In some embodiments, a targeting moiety is or comprises a oncolytic virus. In some embodiments, a targeting moiety is or comprises a vaccine. In some embodiments, a targeting moiety is or comprises a therapeutic agent, e.g., a therapeutic antibody or a fragment thereof. In some embodiments, a targeting moiety is or comprises a cellular therapeutic agent. In some embodiments, a therapeutic agent is a cancer therapeutic agent. In some embodiments, a targeting moiety is or comprises a bi-specific molecules.

In some embodiments, a useful compound of the present disclosure, e.g., a conjugate of an agent, has the structure of formula C:

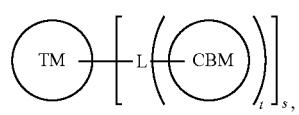

C or a pharmaceutically acceptable salt thereof, wherein each variable is independently as defined and described herein.

In some embodiments, a compound of the present disclosure, e.g., a compound of formula C, has the structure of formula C-I:

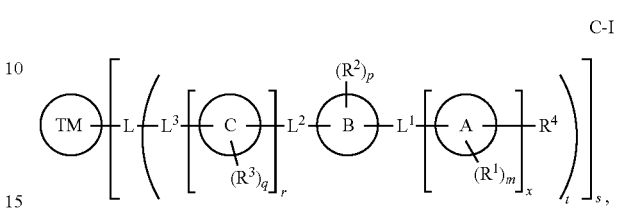

C-I or a pharmaceutically acceptable salt thereof, wherein each variable is independently as defined and described herein. In some embodiments, a compound of the present disclosure, e.g., a compound of formula C, C-I, etc., has the structure of formula C-IV or a pharmaceutically acceptable salt thereof. In some embodiments, a compound of the present disclosure, e.g., a compound of formula C, C-I, etc., has the structure of formula C-V or a pharmaceutically acceptable salt thereof. In some embodiments, a compound of the present disclosure, e.g., a compound of formula C, C-I, etc., has the structure of formula C-VI or a pharmaceutically acceptable salt thereof. In some embodiments, a compound of the present disclosure, e.g., a compound of formula C, C-I, etc., has the structure of formula C-VII or a pharmaceutically acceptable salt thereof.

In some embodiments, the present disclosure relates to bifunctional compounds, e.g., having the following structure of formula C-I:

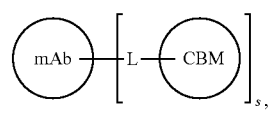

C-II wherein each variable is independently as defined and described herein.

In some embodiments, the present application relates to bifunctional compounds having the following structure of formula C-III.

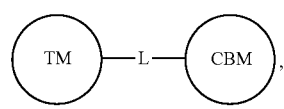

C-III wherein each variable is independently as defined and described herein.

As described above, in certain embodiments, the present invention provides a compound of formula I:

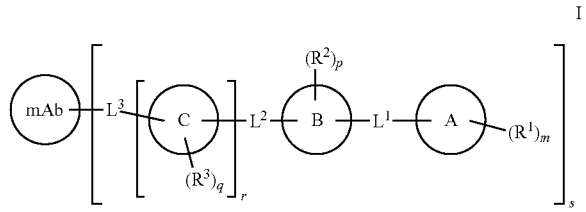

or a pharmaceutically acceptable salt thereof, wherein each variable is independently as defined and described herein.

In some embodiments, a ring, e.g., Ring A, Ring B, Ring C, -Cy-, $Cy^L$, one formed by two or more R groups taken together with their intervening atoms, can be either monovalent, bivalent or polyvalent, and is independently an optionally substituted monocyclic, bicyclic, or polycyclic 3-40 membered ring having 0-20 heteroatoms.

In some embodiments, a ring is an optionally substituted monocyclic 3-40 (e.g., 4, 5, 6, 7, 8, 9, 10, 11, 12, 13, 14, 15, 16, 17, 18, 19, 20, 21, 22, 23, 24, 25, 30, 35 or 40) membered saturated, partially saturated or aromatic ring having 0-20 (e.g., 1, 2, 3, 4, 5, 6, 7, 8, 9, 10, 15 or 20) heteroatoms. In some embodiments, a ring is 3-10 membered. In some embodiments, a ring is 3-membered. In some embodiments, a ring is 4-membered. In some embodiments, a ring is 5-membered. In some embodiments, a ring is 6-membered. In some embodiments, a ring is 7-membered. In some embodiments, a ring is 8-membered. In some embodiments, a ring is saturated. In some embodiments, a ring is partially unsaturated. In some embodiments, a ring is aromatic. In some embodiments, a ring is an optionally substituted monocyclic 3-10 membered monocyclic saturated carbocyclic ring. In some embodiments, a ring is an optionally substituted 3-10 membered monocyclic partially unsaturated carbocyclic ring. In some embodiments, a ring is an optionally substituted 3-10 monocyclic membered heterocyclyl ring having 1-5 heteroatoms. In some embodiments, a ring is optionally substituted phenyl ring. In some embodiments, a ring is an optionally substituted 5- or 6-membered heteroaryl ring having 1-5 heteroatoms.

In some embodiments, a ring is an optionally substituted bicyclic, or polycyclic 4-40 (e.g., 4, 5, 6, 7, 8, 9, 10, 11, 12, 13, 14, 15, 16, 17, 18, 19, 20, 21, 22, 23, 24, 25, 30, 35 or 40) membered ring having 0-20 (e.g., 1, 2, 3, 4, 5, 6, 7, 8, 9, 10, 15 or 20) heteroatoms, wherein each monocyclic unit is independently 3-40 (e.g., 4, 5, 6, 7, 8, 9, 10, 11, 12, 13, 14, 15, 16, 17, 18, 19, 20, 21, 22, 23, 24, 25, 30, 35 or 40) membered, saturated, partially saturated or aromatic, and has 0-20 (e.g., 1, 2, 3, 4, 5, 6, 7, 8, 9, 10, 15 or 20) heteroatoms. In some embodiments, a ring is bicyclic. In some embodiments, a ring is polycyclic. In some embodiments, each monocyclic ring unit of a bicyclic or polycyclic ring group is independently a monocyclic ring as described herein. In some embodiments, at least one or each monocyclic ring unit is independently 3-10 membered. In some embodiments, at least one or each monocyclic ring unit is independently 3-, 4-, 5-, 6-, 7- or 8-membered. In some embodiments, at least one or each monocyclic ring unit is independently saturated. In some embodiments, at least one or each monocyclic ring unit is independently partially saturated. In some embodiments, at least one or each monocyclic ring unit is independently aromatic.

In some embodiments, at least one or each monocyclic ring unit is independently an optionally substituted 3-10 membered monocyclic partially unsaturated carbocyclic ring. In some embodiments, at least one or each monocyclic ring unit is independently an optionally substituted 3-10 monocyclic membered heterocyclyl ring having 1-5 heteroatoms. In some embodiments, at least one or each monocyclic ring unit is independently optionally substituted phenyl ring. In some embodiments, at least one or each monocyclic ring unit is independently an optionally substituted 5- or 6-membered heteroaryl ring having 1-5 heteroatoms. In some embodiments, at least one or each monocyclic ring unit is independently an optionally substituted group selected from a 3-10 membered monocyclic partially unsaturated carbocyclic ring, a 3-10 monocyclic membered heterocyclyl ring having 1-5 heteroatoms, a phenyl ring, a 5- or 6-membered heteroaryl ring having 1-5 heteroatoms.

In some embodiments, a ring has 0-20 heteroatoms. In some embodiments, a ring has 1-20 heteroatoms. In some embodiments, a ring has 1-10 heteroatoms. In some embodiments, a ring has 1-5 heteroatoms. In some embodiments, a ring has 1, 2, 3, 4, 5, 6, 7, 8, 9, 10, 11, 12, 13, 14, 15, 16, 17, 18, 19, or 20 heteroatoms. In some embodiments, a ring has 0 heteroatom. In some embodiments, a ring has 1 heteroatom. In some embodiments, a ring has 2 heteroatoms. In some embodiments, a ring has 3 heteroatoms. In some embodiments, a ring has 4 heteroatoms. In some embodiments, a ring has 5 heteroatoms. In some embodiments, each heteroatom is independently selected from nitrogen, oxygen and sulfur. In some embodiments, at least one heteroatom is nitrogen. In some embodiments, at least one heteroatom is oxygen. In some embodiments, at least one heteroatom is sulfur. In some embodiments, each heteroatom is nitrogen. In some embodiments, each heteroatom is oxygen. In some embodiments, each heteroatom is sulfur.

In some embodiments, a ring is an optionally substituted group selected from 3-7 membered saturated or partially unsaturated carbocyclyl, 4-12 membered saturated or partially unsaturated carbocyclyl, phenyl, 8-10 membered bicyclic aryl, 3-7 membered saturated or partially unsaturated heterocyclyl having 1-5 heteroatoms independently selected from nitrogen, oxygen and sulfur, 4-12 membered saturated or partially unsaturated heterocyclyl having 1-5 heteroatoms independently selected from nitrogen, oxygen and sulfur, 5-6 membered heteroaryl with 1-4 heteroatoms independently selected from nitrogen, oxygen and sulfur, and 8-12 membered bicyclic heteroaryl having 1-5 heteroatoms independently selected from nitrogen, oxygen, and sulfur.

In some embodiments, a Ring is an optionally substituted group selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, or 8-10 membered bicyclic heteroaryl having 1-5 heteroatoms independently selected from nitrogen, oxygen, or sulfur.

Additional ring embodiments are described herein, e.g., those described for Ring A, Ring B, Ring C, R, Cy, $Cy^L$, etc.

In some embodiments, Ring A is independently an optionally substituted monocyclic, bicyclic, or polycyclic 3-40 membered ring having 0-20 heteroatoms as described herein. In some embodiments, Ring A is an optionally substituted group selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, or 8-10 membered bicyclic heteroaryl having 1-5 heteroatoms independently selected from nitrogen, oxygen, or sulfur.

In some embodiments, Ring A is selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, or 8-10 membered bicyclic heteroaryl having 1-5 heteroatoms independently selected from nitrogen, oxygen, or sulfur.

In some embodiments, Ring A is an optionally substituted 3-7 membered saturated or partially unsaturated carbocyclic ring. In some embodiments, Ring A is an optionally substituted 3-membered saturated or partially unsaturated carbocyclic ring. In some embodiments, Ring A is an optionally substituted 4-membered saturated or partially unsaturated carbocyclic ring. In some embodiments, Ring A is an optionally substituted 5-membered saturated or partially unsaturated carbocyclic ring. In some embodiments, Ring A is an optionally substituted 6-membered saturated or partially unsaturated carbocyclic ring. In some embodiments, Ring A is an optionally substituted 7-membered saturated or partially unsaturated carbocyclic ring. In some embodiments, Ring A is saturated. In some embodiments, Ring A is partially unsaturated. In some embodiments, Ring A is an optionally substituted cyclopropyl ring. In some embodiments, Ring A is an optionally substituted cyclobutyl ring. In some embodiments, Ring A is an optionally substituted cyclopentyl ring. In some embodiments, Ring A is an optionally substituted cyclohexyl ring. In some embodiments, Ring A is an optionally substituted cycloheptyl ring. In some embodiments, Ring A is a cyclopropyl ring. In some embodiments, Ring A is a cyclobutyl ring. In some embodiments, Ring A is a cyclopentyl ring. In some embodiments, Ring A is a cyclohexyl ring. In some embodiments, Ring A is a cycloheptyl ring.

In some embodiments, Ring A is an optionally substituted phenyl ring. In some embodiments, Ring A is phenyl.

In some embodiments, Ring A is an optionally substituted 3-7 membered saturated or partially unsaturated heterocyclyl having 1-2 heteroatoms independently selected from nitrogen, oxygen or sulfur. In some embodiments, Ring A is an optionally substituted 5-7 membered saturated or partially unsaturated heterocyclyl having 1-2 heteroatoms independently selected from nitrogen, oxygen or sulfur. In some embodiments, Ring A is 5-7 membered saturated or partially unsaturated heterocyclyl having 1-2 heteroatoms independently selected from nitrogen, oxygen or sulfur. In some embodiments, Ring A is an optionally substituted 3-membered saturated or partially unsaturated heterocyclyl having 1-2 heteroatoms independently selected from nitrogen, oxygen or sulfur. In some embodiments, Ring A is an optionally substituted 4-membered saturated or partially unsaturated heterocyclyl having 1-2 heteroatoms independently selected from nitrogen, oxygen or sulfur. In some embodiments, Ring A is an optionally substituted 5-membered saturated or partially unsaturated heterocyclyl having 1-2 heteroatoms independently selected from nitrogen, oxygen or sulfur. In some embodiments, Ring A is an optionally substituted 6-membered saturated or partially unsaturated heterocyclyl having 1-2 heteroatoms independently selected from nitrogen, oxygen or sulfur. In some embodiments, Ring A is an optionally substituted 7-membered saturated or partially unsaturated heterocyclyl having 1-2 heteroatoms independently selected from nitrogen, oxygen or sulfur. In some embodiments, Ring A is an optionally substituted heterocyclyl having one heteroatom. In some embodiments, a heteroatom is nitrogen. In some embodiments, Ring A is optionally substituted

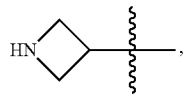

wherein

indicates a bond with $L^1$ or Ring B. In some embodiments, Ring A is

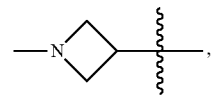 [SMILES: *C1CN(C)C1]

wherein

indicates a bond with $L^1$ or Ring B. In some embodiments, Ring A is optionally substituted

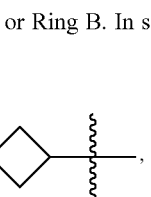

wherein

indicates a bond with $L^1$ or Ring B. In some embodiments, Ring A is

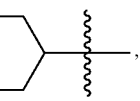

wherein

indicates a bond with $L^1$ or Ring B.

In some embodiments, Ring A is an optionally substituted 5-6 membered heteroaryl ring with 1-4 heteroatoms independently selected from nitrogen, oxygen or sulfur. In some embodiments, Ring A is 5-6 membered heteroaryl with 1-4 heteroatoms independently selected from nitrogen, oxygen or sulfur. In some embodiments, Ring A is an optionally substituted 5-membered heteroaryl ring with 1-4 heteroatoms independently selected from nitrogen, oxygen or sulfur. In some embodiments, Ring A is an optionally substituted 6-membered heteroaryl ring with 1-4 heteroatoms independently selected from nitrogen, oxygen or sulfur. In some embodiments, such Ring A has 1 heteroatom. In some embodiments, such Ring A has 2 heteroatoms. In some embodiments, such Ring A has 3 heteroatoms. In some embodiments, such Ring A has 4 heteroatoms. In some embodiments, at least one heteroatom is nitrogen. In some embodiments, each heteroatom is nitrogen. In some embodiments, Ring A is optionally substituted

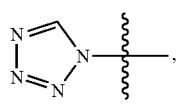

wherein

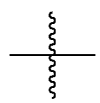

indicates a bond with $L^1$ or Ring B. In some embodiments, Ring A is

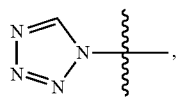

wherein

indicates a bond with $L^1$ or Ring B. In some embodiments, Ring A is optionally substituted

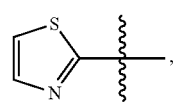

wherein

indicates a bond with $L^1$ or Ring B. In some embodiments, Ring A is

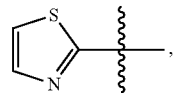

wherein

indicates a bond with $L^1$ or Ring B. In some embodiments, Ring A is optionally substituted

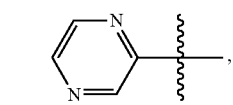

wherein

indicates a bond with $L^1$ or Ring B. In some embodiments, Ring A is

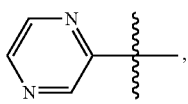

wherein

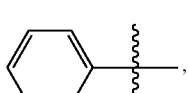

indicates a bond with $L^1$ or Ring B. In some embodiments, Ring A is optionally substituted

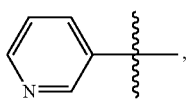 [SMILES: *c1cccnc1]

wherein

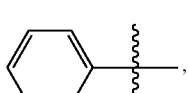

indicates a bond with L¹ or Ring B. In some embodiments, Ring A is

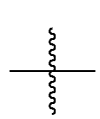

wherein

indicates a bond with L¹ or Ring B.

In some embodiments, Ring A is an optionally substituted 8-10 membered bicyclic heteroaryl ring having 1-5 heteroatoms independently selected from nitrogen, oxygen, or sulfur. In some embodiments, Ring A is an 8-10 membered bicyclic heteroaryl ring having 1-5 heteroatoms independently selected from nitrogen, oxygen, or sulfur. In some embodiments, Ring A is an 8-10 membered bicyclic heteroaryl ring having 2 heteroatoms independently selected from nitrogen, oxygen, or sulfur. In some embodiments, Ring A is an 8-10 membered bicyclic heteroaryl ring having 2 nitrogen ring atoms. In some embodiments, Ring A is 8-membered. In some embodiments, Ring A is 9-membered. In some embodiments, Ring A is 10-membered. In some embodiments, a monocyclic unit is 5-membered. In some embodiments, a monocyclic unit is 6-membered. In some embodiments, Ring A is an optionally substituted

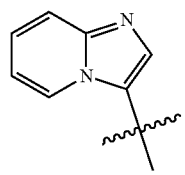 [SMILES: *c1cnc2ccccn12]

group wherein

indicates a bond with L¹ or Ring B. In some embodiments, Ring A is

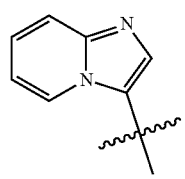 [SMILES: *c1cnc2ccccn12]

wherein

indicates a bond with L¹ or Ring B. In some embodiments, Ring A is an optionally substituted

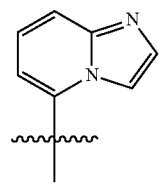 [SMILES: *c1cccc2nccn12]

group wherein

indicates a bond with L¹ or Ring B. In some embodiments, Ring A is

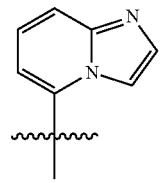 [SMILES: *c1cccc2nccn12]

wherein

indicates a bond with L¹ or Ring B.

In some embodiments, Ring A is selected from those depicted in Table 1, below.

In some embodiments, Ring B is independently an optionally substituted monocyclic, bicyclic, or polycyclic 3-40 membered ring having 0-20 heteroatoms as described herein.

In some embodiments, Ring B is a bivalent ring selected from phenylenyl, 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups.

In some embodiments, Ring B is phenylenyl. In some embodiments, Ring B is 5-6 membered heteroarylenyl having 1-4 heteroatoms independently selected from nitrogen, oxygen, or sulfur. In some embodiments, Ring B is 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group. In some embodiments, Ring B is 4-7 membered saturated or partially unsaturated heterocyclylenyl having 1-2 heteroatoms independently selected from nitrogen, oxygen or sulfur. In some embodiments, Ring B is optionally further substituted with 1-3 oxo groups.

In some embodiments, Ring B is an optionally substituted bivalent 4-, 5- or 6-membered monocyclic heterocyclyl ring having 1-3 heteroatoms. In some embodiments, Ring B is an optionally substituted bivalent 4-, 5- or 6-membered monocyclic heterocyclyl ring having 1-3 heteroatoms, wherein one heteroatom is nitrogen and is bonded to $L^1$. In some embodiments, Ring B is an optionally substituted bivalent 4-, 5- or 6-membered monocyclic heterocyclyl ring having 1 or 2 heteroatoms, wherein one heteroatom is nitrogen and is bonded to $L^1$. In some embodiments, Ring B is an optionally substituted bivalent 5-membered monocyclic heterocyclyl ring having 2 nitrogen ring atoms, wherein one nitrogen ring atom is bonded to $L^1$. In some embodiments, Ring B is an optionally substituted 5-membered monocyclic heterocyclyl ring having 2 nitrogen ring atoms, one of which is bonded to $L^1$ and the other $L^2$. In some embodiments, Ring B is optionally substituted

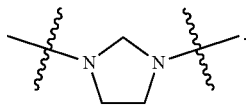

In some embodiments, Ring B is optionally substituted

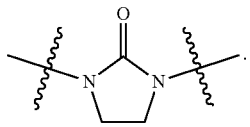 [SMILES: *N1CCN(*)C1=O]

In some embodiments, Ring B is optionally substituted

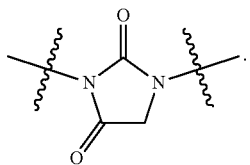 [SMILES: *N1CC(=O)N(*)C1=O]

In some embodiments, Ring B is

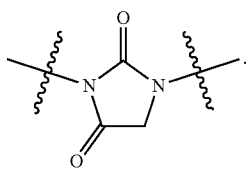 [SMILES: *N1CC(=O)N(*)C1=O]

In some embodiments, the nitrogen atom between the two carbonyl groups is bonded to $L^1$. In some embodiments, Ring B is

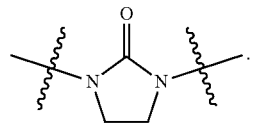 [SMILES: *N1CCN(*)C1=O]

In some embodiments, Ring B is an optionally substituted 5-membered monocyclic heterocyclyl ring having one nitrogen ring atom which is bonded to $L^1$. In some embodiments, Ring B is optionally substituted

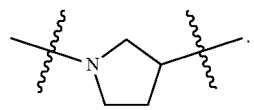 [SMILES: *C1CCN(*)C1]

In some embodiments, Ring B is optionally substituted

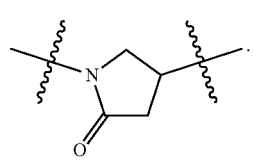 [SMILES: *C1CC(=O)N(*)C1]

In some embodiments, Ring B is

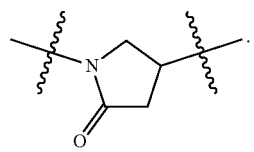 [SMILES: *C1CC(=O)N(*)C1]

In some embodiments, a nitrogen atom is bonded to $L^1$.

In some embodiments, Ring B is or comprises an optionally substituted bicyclic ring. In some embodiments, Ring B is or comprises an optionally substituted spiro-bicyclic ring, wherein each monocyclic ring is independently as described herein. In some embodiments, one monocyclic ring is Ring B'. In some embodiments, one monocyclic ring is optionally substituted

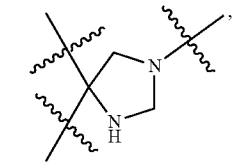 [SMILES: *N1CNC(*)(*)C1]

and the other is Ring B'. In some embodiments, each monocyclic ring is independently an optionally substituted 3-10 membered saturated or partially unsaturated ring having 0-5 heteroatoms. In some embodiments, each monocyclic ring is independently 3-, 4-, 5-, 6-, 7- or 8-membered. In some embodiments, at least one monocyclic ring is saturated. In some embodiments, both monocyclic rings are saturated. In some embodiments, at least one monocyclic ring is a carbocyclic ring. In some embodiments, at least one monocyclic ring is independently an optionally substituted monocyclic heterocyclyl ring have 1-5 heteroatoms. In some embodiments, each monocyclic ring is independently an optionally substituted monocyclic heterocyclyl ring have 1-5 heteroatoms. In some embodiments, each monocyclic ring is independently an optionally substituted 3-, 4-, 5-, 6-, 7- or 8-membered, saturated, monocyclic heterocyclyl ring have 1-5 heteroatoms. In some embodiments, each monocyclic ring independently comprises one or two nitrogen ring atoms. In some embodiments, each monocyclic ring independently comprises one or two nitrogen ring atoms, and no other ring heteroatoms. In some embodiments, a monocyclic ring is an optionally substituted 4-, 5- or 6-membered heterocyclyl ring having 1 or 2 heteroatoms, wherein one heteroatom is nitrogen and is bonded to $L^1$. In some embodiments, a monocyclic ring is an optionally substituted 5-membered heterocyclyl ring having 2 nitrogen ring atoms, wherein one nitrogen ring atom is bonded to $L^1$. In some embodiments, a monocyclic ring is optionally substituted

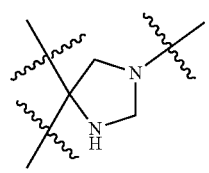

In some embodiments, a monocyclic ring is optionally substituted

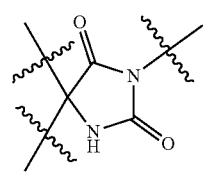

In some embodiments, a monocyclic ring is

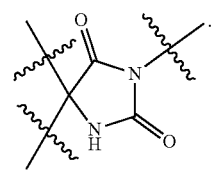 [SMILES: *N1C(=O)NC(*)(*)C1=O]

In some embodiments, a monocyclic ring is an optionally substituted 3-, 4-, 5-, 6-, or 7-membered heterocyclyl ring having one nitrogen ring atom. In some embodiments, a monocyclic ring is an optionally substituted 3-, 4-, 5-, 6-, or 7-membered heterocyclyl ring having one nitrogen ring atom which is bonded to $L^2$. In some embodiments, such a ring is 3-membered. In some embodiments, such a ring is 4-membered. In some embodiments, such a ring is 5-membered. In some embodiments, such a ring is 6-membered. In some embodiments, such a ring is 7-membered. In some embodiments, a monocyclic ring is optionally substituted

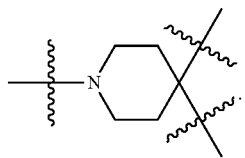 [SMILES: *N1CCC(*)(*)CC1]

In some embodiments, a monocyclic ring is

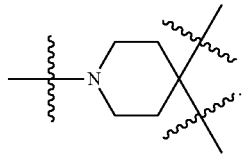 [SMILES: *N1CCC(*)(*)CC1]

In some embodiments, Ring B is optionally substituted

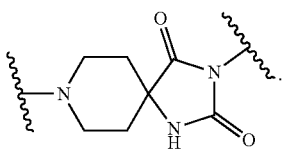 [SMILES: *N1CCC2(CC1)NC(=O)N(*)C2=O]

In some embodiments, Ring B is

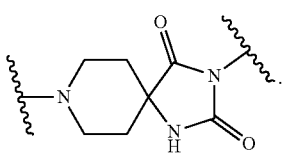 [SMILES: *N1CCC2(CC1)NC(=O)N(*)C2=O]

In some embodiments, a monocyclic ring is optionally substituted

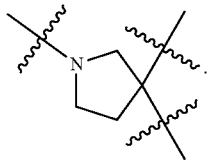 [SMILES: *N1CCC(*)(*)C1]

In some embodiments, a monocyclic ring is

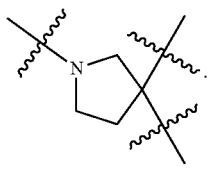 [SMILES: *N1CCC(*)(*)C1]

In some embodiments, Ring B is optionally substituted

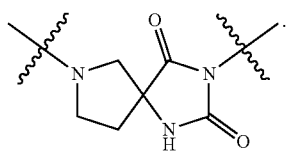 [SMILES: *N1CCC2(C1)NC(=O)N(*)C2=O]

In some embodiments, Ring B is

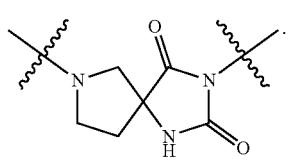 [SMILES: *N1CCC2(C1)NC(=O)N(*)C2=O]

In some embodiments, a monocyclic ring is an optionally substituted 3-10 membered saturated or partially unsaturated carbocyclic ring. In some embodiments, such a ring is saturated. In some embodiments, such a ring is partially unsaturated. In some embodiments, such a ring is 3-membered. In some embodiments, such a ring is 4-membered. In some embodiments, such a ring is 5-membered. In some embodiments, such a ring is 6-membered. In some embodiments, such a ring is 7-membered. In some embodiments, such a ring is optionally substituted

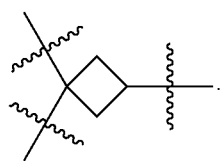 [SMILES: *C1CC(*)(*)C1]

In some embodiments, such a ring is

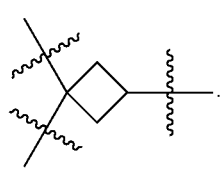 [SMILES: *C1CC(*)(*)C1]

In some embodiments, Ring B is optionally substituted

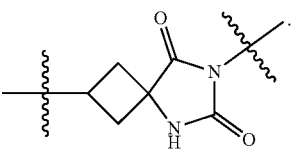 [SMILES: *C1CC2(C1)NC(=O)N(*)C2=O]

In some embodiments, Ring B is

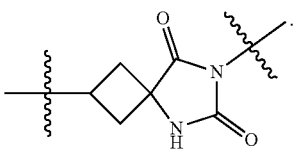 [SMILES: *C1CC2(C1)NC(=O)N(*)C2=O]

In some embodiments, Ring B is optionally substituted

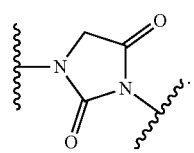 [SMILES: *N1CC(=O)N(*)C1=O]

In some embodiments, Ring B is optionally substituted

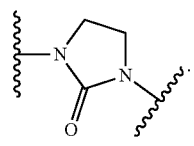 [SMILES: *N1CCN(*)C1=O]

In some embodiments, Ring B is optionally substituted

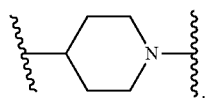

In some embodiments, Ring B is optionally substituted

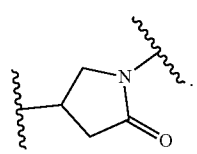 [SMILES: *C1CC(=O)N(*)C1]

In some embodiments, Ring B is optionally substituted

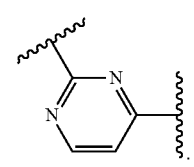 [SMILES: *c1ccnc(*)n1]

In some embodiments, Ring B is optionally substituted

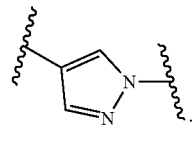 [SMILES: *c1cnn(*)c1]

In some embodiments, Ring B is

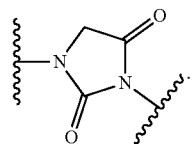 [SMILES: *N1CC(=O)N(*)C1=O]

In some embodiments, Ring B is

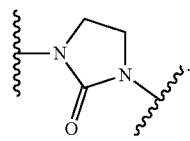 [SMILES: *N1CCN(*)C1=O]

In some embodiments, Ring B is


In some embodiments, Ring B is


In some embodiments, Ring B is

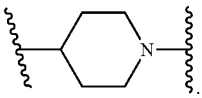

In some embodiments, Ring B is

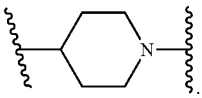

In some embodiments, Ring B is optionally substituted

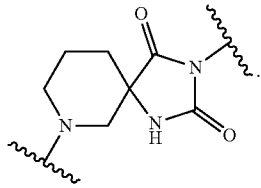 [SMILES: *N1CCCC2(C1)NC(=O)N(*)C2=O]

In some embodiments, Ring B is optionally substituted

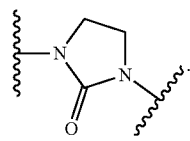

In some embodiments, Ring B is optionally substituted

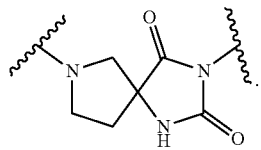 [SMILES: *N1CCC2(C1)NC(=O)N(*)C2=O]

In some embodiments, Ring B is optionally substituted

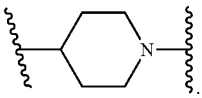

In some embodiments, Ring B is optionally substituted

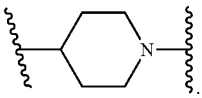

In some embodiments, Ring B is optionally substituted

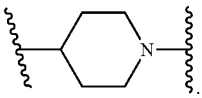

In some embodiments, Ring B is

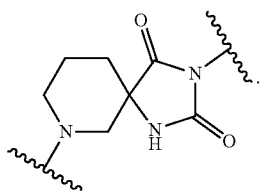 [SMILES: *N1CCCC2(C1)NC(=O)N(*)C2=O]

In some embodiments, Ring B is

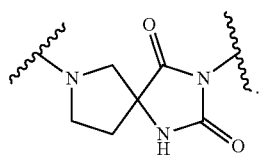 [SMILES: *N1CCC2(C1)NC(=O)N(*)C2=O]

In some embodiments, Ring B is

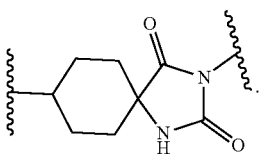 [SMILES: *C1CCC2(CC1)NC(=O)N(*)C2=O]

In some embodiments, Ring B is

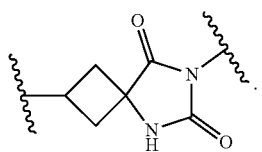 [SMILES: *C1CC2(C1)NC(=O)N(*)C2=O]

In some embodiments, Ring B is

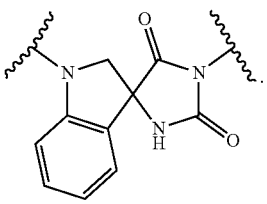 [SMILES: *N1C(=O)NC2(CN(*)c3ccccc32)C1=O]

In some embodiments, Ring B is

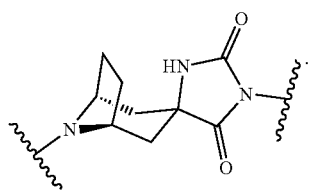 [SMILES: *N1C(=O)NC2(C[C@H]3CC[C@@H](C2)N3*)C1=O]

In some embodiments, Ring B is selected from those depicted in Table 1, below.

In some embodiments, Ring B' is an optionally substituted monocyclic ring. In some embodiments, Ring B' is an optionally substituted bicyclic ring. In some embodiments, Ring B' is an optionally substituted polycyclic ring. In some embodiments, Ring B' has one or more heteroatoms. In some embodiments, Ring B' is an optionally substituted hydrocarbon ring. In some embodiments, Ring B' is bonded to $L^2$. In some embodiments, a hydrocarbon Ring B' is bonded to an —N(R)— group of $L^2$.

In some embodiments, Ring B' is an optionally substituted monocyclic 3-10 membered saturated or partially unsaturated ring having 0-5 heteroatoms. In some embodiments, Ring B' is saturated. In some embodiments, Ring B' is unsaturated. In some embodiments, Ring B' is 3-membered. In some embodiments, Ring B' is 4-membered. In some embodiments, Ring B' is 5-membered. In some embodiments, Ring B' is 6-membered. In some embodiments, Ring B' is 7-membered. In some embodiments, Ring B' is 8-membered. In some embodiments, Ring B' has 1-5 heteroatoms. In some embodiments, Ring B's has one heteroatom. In some embodiments, at least one ring heteroatom is nitrogen. In some embodiments, such a nitrogen atom is bonded to $L^2$. In some embodiments, Ring B' is an optionally substituted cycloaliphatic ring. In some embodiments, Ring B' is an optionally substituted cycloalkyl ring. In some embodiments, a hydrocarbon Ring B' is bonded to an —N(R)— group of $L^2$.

In some embodiments, Ring B' is optionally substituted

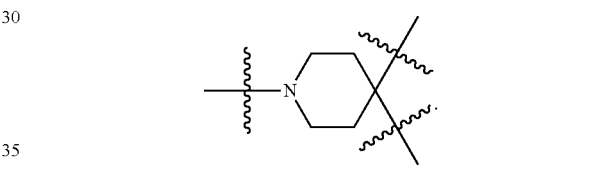

In some embodiments, Ring B' is

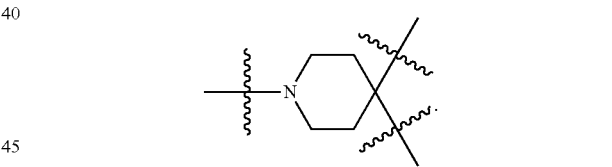

In some embodiments, Ring B is optionally substituted

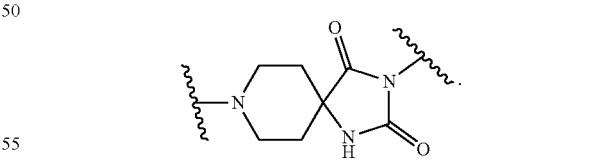

In some embodiments, Ring B is

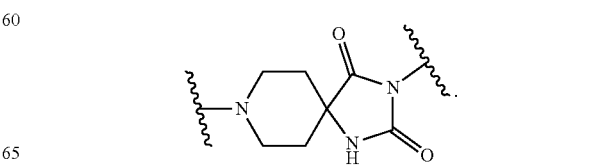

In some embodiments, Ring B' is optionally substituted

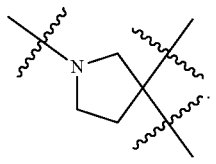 [SMILES: *N1CCC(*)(*)C1]

In some embodiments Ring B' is

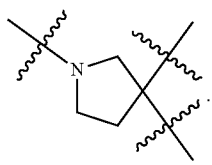 [SMILES: *N1CCC(*)(*)C1]

In some embodiments, Ring B is optionally substituted

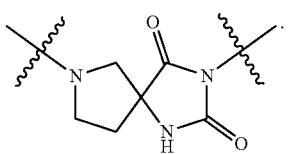 [SMILES: *N1CCC2(C1)NC(=O)N(*)C2=O]

In some embodiments, Ring B is

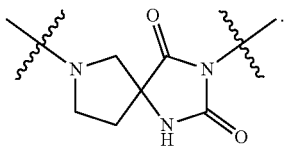 [SMILES: *N1CCC2(C1)NC(=O)N(*)C2=O]

In some embodiments, Ring B' is an optionally substituted 3-10 membered saturated or partially unsaturated carbocyclic ring. In some embodiments, Ring B' is saturated. In some embodiments, Ring B' is partially unsaturated. In some embodiments, Ring B' is 3-membered. In some embodiments, Ring B' is 4-membered. In some embodiments, Ring B' is 5-membered. In some embodiments, Ring B' is 6-membered. In some embodiments Ring B' is 7-membered. In some embodiments, Ring B' is optionally substituted

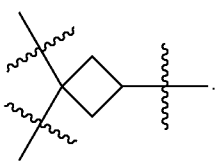 [SMILES: *C1CC(*)(*)C1]

In some embodiments, Ring B' is

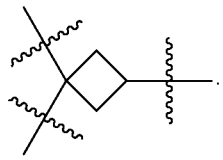 [SMILES: *C1CC(*)(*)C1]

In some embodiments, Ring B is optionally substituted

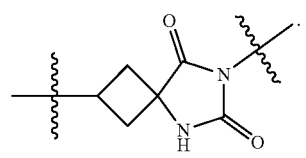 [SMILES: *C1CC2(C1)NC(=O)N(*)C2=O]

In some embodiments, Ring B is

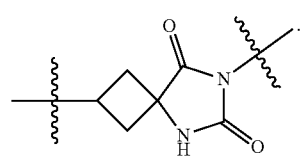 [SMILES: *C1CC2(C1)NC(=O)N(*)C2=O]

In some embodiments, Ring B' is selected from those depicted in Table 1, below.

In some embodiments, Ring C is independently an optionally substituted monocyclic, bicyclic, or polycyclic 3-40 membered ring having 0-20 heteroatoms as described herein.

In some embodiments, r is 0 and Ring C is absent. In some embodiments, r is 1. In some embodiments, r is 2, and one Ring C is bonded to $L^2$ and the other bonded to $L^3$.

In some embodiments, Ring C is an optionally substituted group selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur.

In some embodiments, Ring C is a bivalent ring selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur.

In some embodiments, Ring C is phenylenyl. In some embodiments, Ring C is 4-7 membered saturated or partially unsaturated carbocyclylenyl. In some embodiments, Ring C is 4-7 membered saturated or partially unsaturated heterocyclylenyl having 1-2 heteroatoms independently selected from nitrogen, oxygen, or sulfur. In some embodiments, Ring C is 5-6 membered heteroarylenyl having 1-4 heteroatoms independently selected from nitrogen, oxygen, or sulfur.

In some embodiments, Ring C is an optionally substituted phenyl ring. In some embodiments, Ring C is an optionally substituted phenyl ring which is bonded to $L^2$. In some embodiments, Ring C is optionally substituted In some embodiments, Ring C is

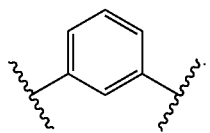

In some embodiments, Ring C is optionally substituted

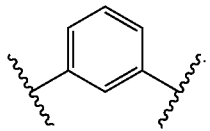

In some embodiments, Ring C is

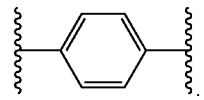

In some embodiments, such a Ring C is bonded to $L^2$. In some embodiments, such a Ring C is bonded to $L^3$. In some embodiments, such a Ring C is bonded to both $L^2$ and $L^3$.

In some embodiments, Ring C is an optionally substituted 3-10 membered saturated or partially unsaturated heterocyclyl having 1-4 heteroatoms independently selected from nitrogen, oxygen and sulfur. In some embodiments, Ring C is an optionally substituted 3-7 membered saturated or partially unsaturated heterocyclyl having 1-4 heteroatoms independently selected from nitrogen, oxygen and sulfur. In some embodiments, Ring C is an optionally substituted 5-6 membered heterocyclic ring having 1-4 heteroatoms. In some embodiments, Ring C is an optionally substituted 5-6 membered heterocyclic ring having 1 heteroatom. In some embodiments, Ring C is an optionally substituted 5-6 membered heterocyclic ring having 2 heteroatoms. In some embodiments, Ring C is an optionally substituted 3-membered saturated or partially unsaturated heterocyclyl having 1-2 heteroatoms independently selected from nitrogen, oxygen and sulfur. In some embodiments, Ring C is an optionally substituted 4-membered saturated or partially unsaturated heterocyclyl having 1-2 heteroatoms independently selected from nitrogen, oxygen and sulfur. In some embodiments, Ring C is an optionally substituted 5-membered saturated or partially unsaturated heterocyclyl having 1-2 heteroatoms independently selected from nitrogen, oxygen and sulfur. In some embodiments, Ring C is an optionally substituted 6-membered saturated or partially unsaturated heterocyclyl having 1-2 heteroatoms independently selected from nitrogen, oxygen and sulfur. In some embodiments, Ring C is an optionally substituted 7-membered saturated or partially unsaturated heterocyclyl having 1-2 heteroatoms independently selected from nitrogen, oxygen and sulfur. In some embodiments, a ring is 5-membered. In some embodiments, a ring is 6-membered. In some embodiments, Ring C is an optionally substituted heterocyclyl having one heteroatom. In some embodiments, each heteroatom is nitrogen. In some embodiments, a ring nitrogen atom is bonded to $L^3$ or L or another Ring C. In some embodiments, Ring C is optionally substituted

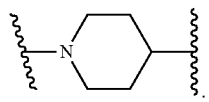

In some embodiments, Ring C is

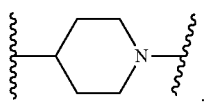

In some embodiments, Ring C is optionally substituted

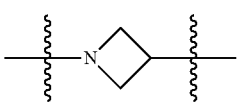

In some embodiments, Ring C is

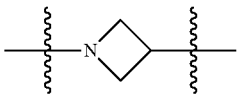

In some embodiments, Ring C is an optionally substituted 5-6 membered heteroaryl group having 1-4 heteroatoms. In some embodiments, Ring C is an optionally substituted 5-membered heteroaryl group having 1-4 heteroatoms. In some embodiments, Ring C is an optionally substituted 5-6 membered heteroaryl ring having 1 heteroatom. In some embodiments, Ring C is an optionally substituted 5-6 membered heteroaryl ring having 2 heteroatoms. In some embodiments, at least one heteroatom is nitrogen. In some embodiments, each heteroatom is nitrogen. In some embodiments, Ring C is an optionally substituted 5-membered heteroaryl group having 1-4 nitrogen ring atoms. In some embodiments, Ring C is optionally substituted

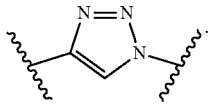 [SMILES: *c1cn(*)nn1]

In some embodiments, Ring C is

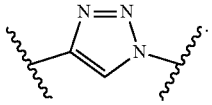 [SMILES: *c1cn(*)nn1]

In some embodiments, Ring C is optionally substituted

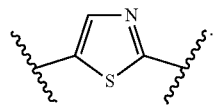

In some embodiments, Ring C is

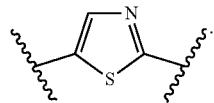 [SMILES: *c1cnc(*)s1]

In some embodiments, Ring C is an optionally substituted 6-membered heteroaryl group having 1-4 nitrogen ring atoms. In some embodiments, Ring C is optionally substituted

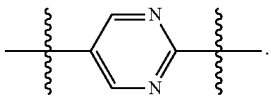 [SMILES: *c1cnc(*)nc1]

In some embodiments, Ring C is

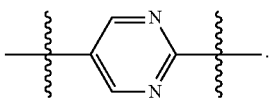 [SMILES: *c1cnc(*)nc1]

In some embodiments, a Ring C is bonded to $L^2$. In some embodiments, the carbon between the two nitrogen atoms is bonded to $L^2$. In some embodiments, the carbon between the two nitrogen atoms is bonded to another Ring C. In some embodiments, a Ring C is bonded to $L^3$. In some embodiments, a Ring C is bonded to another Ring C.

In some embodiments, Ring C is an optionally substituted 8-10 membered bicyclic heteroaryl ring having 1-5 heteroatoms independently selected from nitrogen, oxygen and sulfur. In some embodiments, Ring C is an 8-10 membered bicyclic heteroaryl ring having 1-5 heteroatoms independently selected from nitrogen, oxygen and sulfur. In some embodiments, Ring C is an 8-10 membered bicyclic heteroaryl ring having 2 heteroatoms independently selected from nitrogen, oxygen and sulfur. In some embodiments, Ring C is an 8-10 membered bicyclic heteroaryl ring having 2 nitrogen ring atoms. In some embodiments, Ring C is 8-membered. In some embodiments, Ring C is 9-membered. In some embodiments, Ring C is 10-membered. In some embodiments, a monocyclic unit is 5-membered. In some embodiments, a monocyclic unit is 6-membered. In some embodiments, a 5-membered ring is bonded to $L^2$. In some embodiments, a 6-membered ring is bonded to $L^2$. In some embodiments, Ring C is an optionally substituted

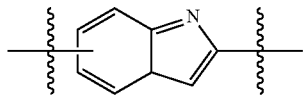

group. In some embodiments, Ring C is an optionally substituted

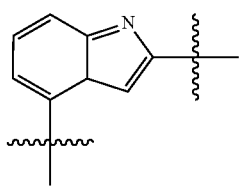 [SMILES: *C1=CC2C(*)=CC=CC2=N1]

group. In some embodiments, Ring C is

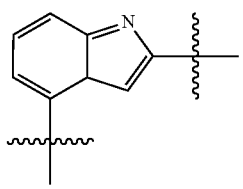 [SMILES: *C1=CC2C(*)=CC=CC2=N1]

group. In some embodiments, Ring C is an optionally substituted

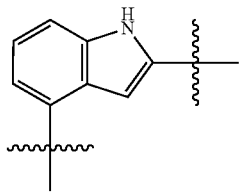 [SMILES: *c1cc2c(*)cccc2[nH]1]

group. In some embodiments, Ring C is

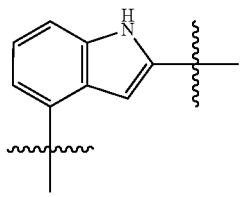 [SMILES: *c1cc2c(*)cccc2[nH]1]

group. In some embodiments, Ring C is an optionally substituted

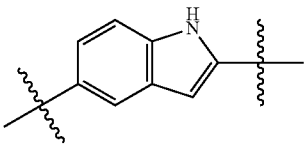 [SMILES: *c1ccc2[nH]c(*)cc2c1]

group. In some embodiments, Ring C is

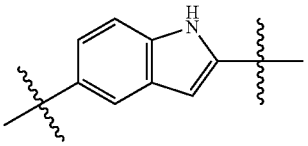 [SMILES: *c1ccc2[nH]c(*)cc2c1]

group. In some embodiments, Ring C is an optionally substituted

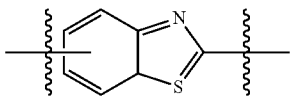

group. In some embodiments, Ring C is an optionally substituted

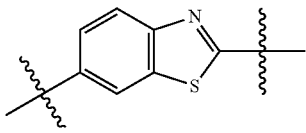 [SMILES: *c1ccc2nc(*)sc2c1]

group. In some embodiments, Ring C is

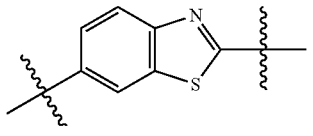 [SMILES: *c1ccc2nc(*)sc2c1]

group. In some embodiments, the phenyl ring is bonded to L². In some embodiments, the 5-membered ring is bonded to L². In some embodiments, a monocyclic unit is 6-membered and has one or more heteroatoms. In some embodiments, such a monocyclic unit is bonded to L². In some embodiments, Ring C is an optionally substituted

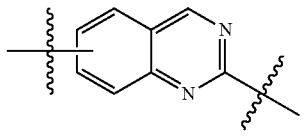

group.
In some embodiments, Ring C is an optionally substituted

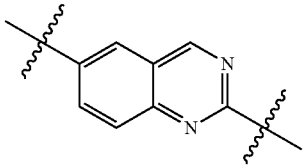 [SMILES: *c1ccc2nc(*)ncc2c1]

group. In some embodiments, Ring C is

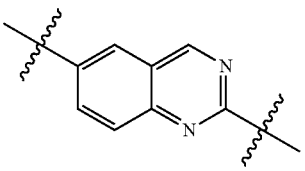 [SMILES: *c1ccc2nc(*)ncc2c1]

group. In some embodiments, the carbon between the two nitrogen atoms is bonded to L².

In some embodiments, Ring C is selected from those depicted in Table 1, below.

As described herein, each L is independently a linker moiety. In some embodiments, each L is independently a covalent bond, or a bivalent or polyvalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]— or —[(—C(O)—C(R')$_2$—N(R')—)$_n$]—, and one or more carbon and heteroatoms of the group are optionally and independently replaced with Cy$^L$. In some embodiments, L is bivalent. In some embodiments, L is trivalent (e.g., bonded to two amino acid residues through —S—, and

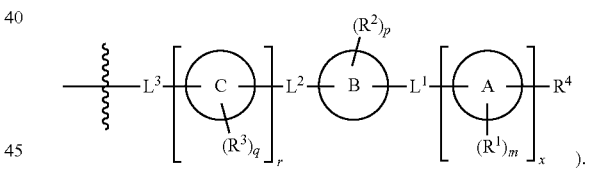

In some embodiments, L is L¹ as described herein. In some embodiments, L is L² as described herein. In some embodiments, L is L³ as described herein.

In some embodiments, L is selected from those depicted in Table 1, below.

In some embodiments, each of L¹, L² and L³ is independently a covalent bond, or a bivalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')₂—C(R')₂—)ₙ]— or —[(—C(O)—C(R')₂—N(R')—)ₙ]—, and one or more carbon and heteroatoms of the group are optionally and independently replaced with Cy$^L$. In some embodiments, each of L¹, L² and L³ is independently a covalent bond, or a bivalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')₂—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)₂—, —S(O)₂N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')₃]—, —[(—O—C(R')₂—C(R')₂—)ₙ]— or —[(—C(O)—C(R')₂—N(R')—)ₙ]—.

In some embodiments, one or more methylene units are independently replaced. In some embodiments, one or more methylene units are independently replaced with -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)₂—, —S(O)₂N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')₃]—, —[(—O—C(R')₂—C(R')₂—)ₙ]— or —[(—C(O)—C(R')₂—N(R')—)ₙ]—. In some embodiments, at least one methylene unit is replaced with -Cy-. In some embodiments, at least one methylene unit is replaced with —O—. In some embodiments, at least one methylene unit is replaced with —S—. In some embodiments, at least one methylene unit is replaced with —S—S—. In some embodiments, at least one methylene unit is replaced with —N(R')—. In some embodiments, at least one methylene unit is replaced with —C(O)—. In some embodiments, at least one methylene unit is replaced with —C(S)—. In some embodiments, at least one methylene unit is replaced with —C(NR')—. In some embodiments, at least one methylene unit is replaced with —C(O)N(R')—. In some embodiments, at least one methylene unit is replaced with —N(R')C(O)N(R')—. In some embodiments, at least one methylene unit is replaced with —N(R')C(O)O—. In some embodiments, at least one methylene unit is replaced with —S(O)—. In some embodiments, at least one methylene unit is replaced with —S(O)₂—. In some embodiments, at least one methylene unit is replaced with —S(O)₂N(R')—. In some embodiments, at least one methylene unit is replaced with —C(O)S—. In some embodiments, at least one methylene unit is replaced with —C(O)O—. In some embodiments, at least one methylene unit is replaced with —P(O)(OR')—. In some embodiments, at least one methylene unit is replaced with —P(O)(SR')—. In some embodiments, at least one methylene unit is replaced with —P(O)(R')—. In some embodiments, at least one methylene unit is replaced with —P(O)(NR')—. In some embodiments, at least one methylene unit is replaced with —P(S)(OR')—. In some embodiments, at least one methylene unit is replaced with —P(S)(SR')—. In some embodiments, at least one methylene unit is replaced with —P(S)(R')—. In some embodiments, at least one methylene unit is replaced with —P(S)(NR')—. In some embodiments, at least one methylene unit is replaced with —P(R')—. In some embodiments, at least one methylene unit is replaced with —P(OR')—. In some embodiments, at least one methylene unit is replaced with —P(SR')—. In some embodiments, at least one methylene unit is replaced with —P(NR')—. In some embodiments, at least one methylene unit is replaced with —P(OR')[B(R')₃]—. In some embodiments, at least one methylene unit is replaced with —[(—O—C(R')₂—C(R')₂—)ₙ]—. In some embodiments, at least one methylene unit is replaced with —[(—C(O)—C(R')₂—N(R')—)ₙ]—.

In some embodiments, one or more methylene units are independently replaced with -Cy-, wherein -Cy- is as defined and described herein. In some embodiments, -Cy- is bonded to R⁵. In some embodiments, -Cy- is bonded to Ring C.

In some embodiments, -Cy- is an optionally substituted ring as described herein. In some embodiments, -Cy- is Ring A as described herein. In some embodiments, -Cy- is bivalent Ring B as described herein. In some embodiments, -Cy- is bivalent Ring C as described herein.

In some embodiments, -Cy- is an optionally substituted bivalent 3-10 membered saturated or partially unsaturated monocyclic carbocyclic ring. In some embodiments, -Cy- is an optionally substituted bivalent cyclobutyl ring. In some embodiments, -Cy- is a bivalent cyclobutyl ring. In some embodiments, -Cy- is an optionally substituted bivalent cyclopropyl ring. In some embodiments, -Cy- is a bivalent cyclopropyl ring.

In some embodiments, -Cy- is an optionally substituted bivalent 4-30 membered bicyclic or polycyclic carbocyclic ring, wherein each monocyclic unit is independently saturated or partially unsaturated. In some embodiments, each monocyclic unit is independently 3-10 membered.

In some embodiments, -Cy- is optionally substituted bivalent 5-6 membered heteroaryl having 1-4 heteroatoms. In some embodiments, -Cy- is optionally substituted bivalent 5-membered heteroaryl having 1-4 heteroatoms. In some embodiments, -Cy- is optionally substituted bivalent 5-membered heteroaryl having 1-4 ring nitrogen atoms. In some embodiments, -Cy- is optionally substituted

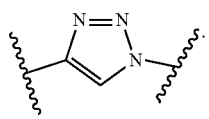 [SMILES: *c1cn(*)nn1]

In some embodiments, -Cy- is

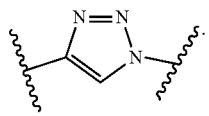 [SMILES: *c1cn(*)nn1]

In some embodiments, -Cy- is optionally substituted

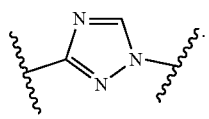 [SMILES: *c1ncn(*)n1]

In some embodiments, -Cy- is

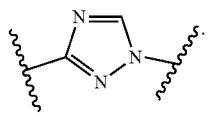 [SMILES: *c1ncn(*)n1]

In some embodiments, -Cy- is optionally substituted

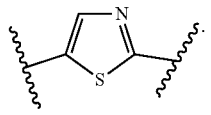 [SMILES: *c1cnc(*)s1]

In some embodiments, -Cy- is

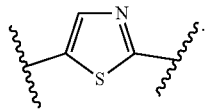 [SMILES: *c1cnc(*)s1]

In some embodiments, -Cy- is optionally substituted bivalent 6-membered heteroaryl having 1-4 ring nitrogen atoms. In some embodiments, -Cy- is optionally substituted

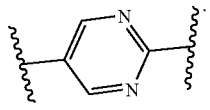

In some embodiments, -Cy- is

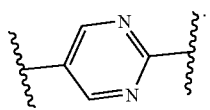

In some embodiments, -Cy- is an optionally substituted bivalent 3-10 membered monocyclic saturated or partially unsaturated heterocyclic ring having 1-5 heteroatoms. In some embodiments, at least one heteroatom is nitrogen. In some embodiments, each heteroatom is nitrogen. In some embodiments, -Cy- is optionally substituted

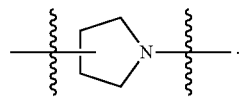

In some embodiments, -Cy- is optionally substituted

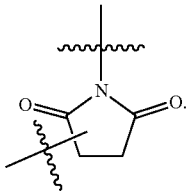

In some embodiments, -Cy- is

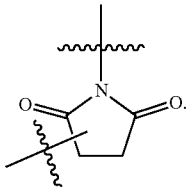

In some embodiments, -Cy- is optionally substituted

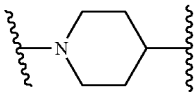

In some embodiments, -Cy- is

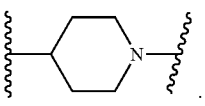

In some embodiments, -Cy- is optionally substituted

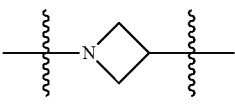

In some embodiments, -Cy- is

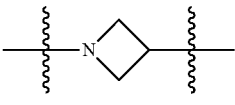

In some embodiments, -Cy- is an optionally substituted bivalent 4-30 membered bicyclic or polycyclic heterocyclic ring having 1-10 heteroatoms, wherein each monocyclic unit is independently saturated or partially unsaturated. In some embodiments, each monocyclic unit is independently 3-10 membered and has 1-5 heteroatoms.

In some embodiments, -Cy- is an optionally substituted 4-30 membered bicyclic or polycyclic ring having 0-10 heteroatoms. In some embodiments, one or more monocyclic units have 1-5 heteroatoms. In some embodiments, one or more monocyclic units have no heteroatoms. In some embodiments, at least one heteroatom is nitrogen. In some embodiments, each heteroatom is nitrogen. In some embodiments, each monocyclic unit of the bicyclic or polycyclic ring is independently saturated, partially unsaturated or aromatic. In some embodiments, at least one monocyclic unit is saturated. In some embodiments, at least one monocyclic unit is partially unsaturated. In some embodiments, -Cy- comprises a —C≡C— group. In some embodiments, at least one monocyclic unit is aromatic. In some embodiments, -Cy- is optionally substituted

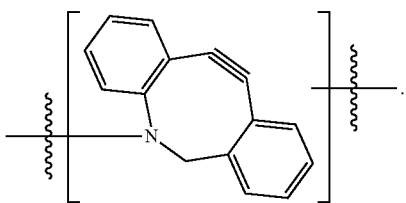

In some embodiments, -Cy- is

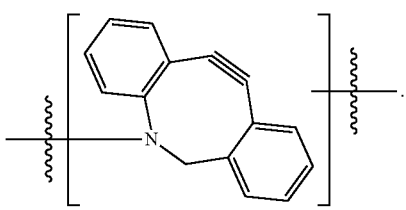

In some embodiments, -Cy- comprises

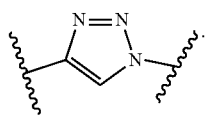 [SMILES: *c1cn(*)nn1]

In some embodiments, -Cy- is optionally substituted

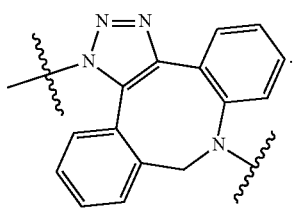 [SMILES: *N1Cc2ccccc2-c2c(nnn2*)-c2ccccc21]

In some embodiments, -Cy- is optionally substituted

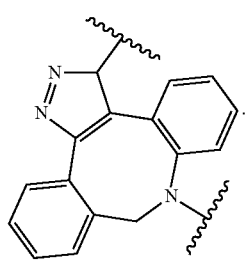 [SMILES: *C1N=NC2=C1c1ccccc1N(*)Cc1ccccc12]

In some embodiments, -Cy- is

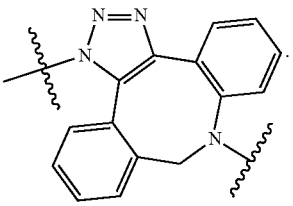 [SMILES: *N1Cc2ccccc2-c2c(nnn2*)-c2ccccc21]

In some embodiments, -Cy- is

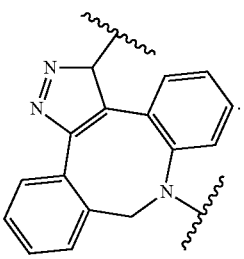 [SMILES: *C1N=NC2=C1c1ccccc1N(*)Cc1ccccc12]

In some embodiments, -Cy- is an optionally substituted bivalent phenyl ring. In some embodiments, -Cy- is a bivalent phenyl ring. In some embodiments, -Cy- is

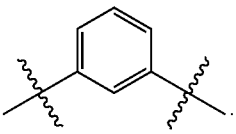 [SMILES: *c1cccc(*)c1]

In some embodiments, -Cy- is

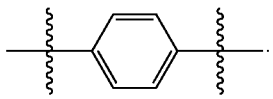 [SMILES: *c1ccc(*)cc1]

In some embodiments, -Cy- is

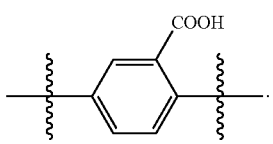 [SMILES: *c1ccc(*)c(C(=O)O)c1]

In some embodiments, -Cy- is an optionally substituted 8-20 membered bicyclic or polycyclic heteroaryl ring having 1-10 heteroatoms independently selected from nitrogen, oxygen, or sulfur. In some embodiments, -Cy- is an optionally substituted 8-10 membered bicyclic heteroaryl ring having 1-5 heteroatoms independently selected from nitrogen, oxygen, or sulfur. In some embodiments, -Cy- is an 8-10 membered bicyclic heteroaryl ring having 1-5 heteroatoms independently selected from nitrogen, oxygen, or sulfur. In some embodiments, -Cy- an 8-10 membered bicyclic heteroaryl ring having 2 heteroatoms independently selected from nitrogen, oxygen, or sulfur. In some embodiments, -Cy- is an 8-10 membered bicyclic heteroaryl ring having 2 nitrogen ring atoms. In some embodiments, -Cy- is 8-membered. In some embodiments, -Cy- is 9-membered. In some embodiments, -Cy- is 10-membered. In some embodiments, a monocyclic unit is 5-membered. In some embodiments, a monocyclic unit is 6-membered. In some embodiments, -Cy- is optionally substituted

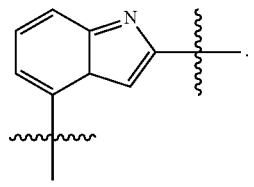 [SMILES: *C1=CC2C(*)=CC=CC2=N1]

In some embodiments, -Cy- is

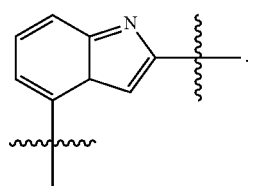 [SMILES: *C1=CC2C(*)=CC=CC2=N1]

In some embodiments, -Cy- is optionally substituted

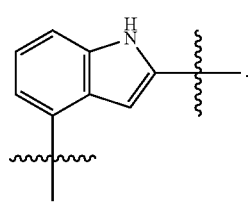 [SMILES: *c1cc2c(*)cccc2[nH]1]

In some embodiments, -Cy- is

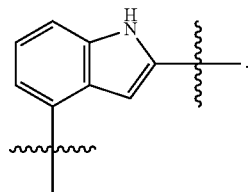 [SMILES: *c1cc2c(*)cccc2[nH]1]

In some embodiments, -Cy- is optionally substituted

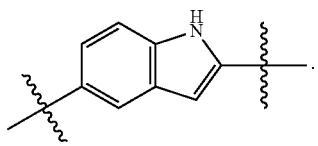 [SMILES: *c1ccc2[nH]c(*)cc2c1]

In some embodiments, -Cy- is

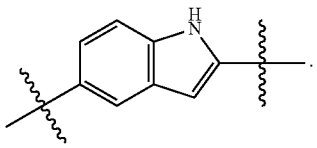 [SMILES: *c1ccc2[nH]c(*)cc2c1]

In some embodiments, -Cy- is optionally substituted

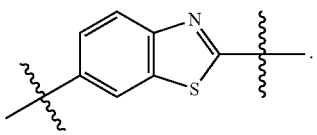 [SMILES: *c1ccc2nc(*)sc2c1]

In some embodiments, -Cy- is

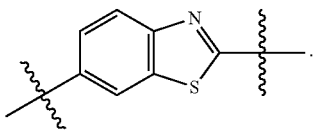 [SMILES: *c1ccc2nc(*)sc2c1]

In some embodiments, -Cy- is optionally substituted

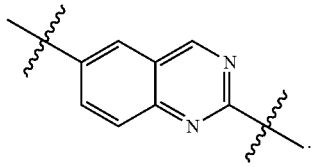 [SMILES: *c1ccc2nc(*)ncc2c1]

In some embodiments, -Cy- is

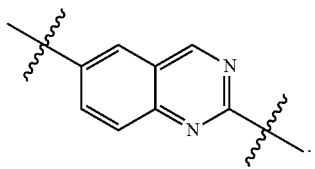 [SMILES: *c1ccc2nc(*)ncc2c1]

In some embodiments, -Cy- is selected from those depicted in Table 1, below.

In some embodiments, one or more carbon or heteroatoms are replaced with $Cy^L$. In some embodiments, $Cy^L$ is an optionally substituted ring as described herein. In some embodiments, $Cy^L$ is an optionally substituted tetravalent phenyl ring.

In some embodiments, $Cy^L$ is selected from those depicted in Table 1, below.

In some embodiments, each of L, $L^1$, $L^2$, and $L^3$ is independently an optionally substituted $C_{1-50}$ aliphatic or heteroaliphatic group wherein 0-30 methylene units of the group are independently replaced as described herein. In some embodiments, each of L, $L^1$, $L^2$, and $L^3$ is independently an optionally substituted $C_{1-10}$, $C_{1-15}$, $C_{1-20}$, $C_{1-25}$, $C_{1-30}$, $C_{1-35}$, $C_{1-40}$, $C_{1-45}$, $C_{1-50}$, $C_1$, $C_2$, $C_3$, $C_4$, $C_5$, $C_6$, $C_7$, $C_8$, $C_9$, $C_{10}$, $C_{15}$, $C_{20}$, $C_{25}$, $C_{30}$, $C_{35}$, $C_{40}$, $C_{45}$, or $C_{50}$ aliphatic or heteroaliphatic group wherein 0-30 methylene units of the group are independently replaced as described herein. In some embodiments, a heteroaliphatic group has 1-5, 1-10, 1-15, 1-20, 1-25, 1-30, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 heteroatoms. In some embodiments, 0-5, 0-10, 0-15, 0-20, 0-25, 0-30, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 methylene units of the group are independently replaced as described herein.

In some embodiments, $L^1$ is a covalent bond, or a bivalent, saturated or unsaturated, straight or branched group selected from $C_{1-10}$ aliphatic and $C_{1-10}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]— or —[(—C(O)—C(R')$_2$—N(R')—)$_n$]—.

In some embodiments, $L^1$ is a covalent bond, or a bivalent, saturated or unsaturated, straight or branched $C_{1-6}$ aliphatic, wherein 0-4 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]— or —[(—C(O)—C(R')$_2$—N(R')—)$_n$]—. In some embodiments, $L^1$ is a covalent bond, or a bivalent, saturated or unsaturated, straight or branched $C_{1-6}$ aliphatic, wherein 0-4 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L is a covalent bond, or a bivalent, saturated or unsaturated, straight or branched $C_{1-4}$ aliphatic, wherein 0-4 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, $L^1$ is a covalent bond, or a bivalent, saturated or unsaturated, straight or branched $C_{1-3}$ aliphatic, wherein 0-2 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, $L^1$ is a covalent bond, or a bivalent, saturated or unsaturated, straight or branched $C_{1-2}$ aliphatic, wherein 0-1 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, $L^2$ is a covalent bond, or an optionally substituted methylene group which is optionally and independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, $L^2$ is a covalent bond, or an optionally substituted —CH$_2$CH$_2$— wherein 0-2 methylene units are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, $L^2$ is a covalent bond, or an optionally substituted —CH$_2$CH$_2$— wherein 0-2 methylene units are independently replaced with -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, $L^2$ is a covalent bond, or an optionally substituted —CH$_2$CH$_2$— wherein 0-2 methylene units are independently replaced with -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

In some embodiments, L is a covalent bond, —CH$_2$—, —CH(R)—, or —C(R)$_2$—. In some embodiments, $L^1$ is a covalent bond, —CH$_2$—, —CH(R)—, —C(R)$_2$—, or -Cy-.

In some embodiments, L is a covalent bond. In some embodiments, $L^1$ is optionally substituted —CH$_2$—. In some embodiments, $L^1$ is —CH$_2$—. In some embodiments, $L^1$ is —CH(R)—. In some embodiments, $L^1$ is —C(R)$_2$—.

In some embodiments, $L^1$ is optionally substituted —CH$_2$CH$_2$—. In some embodiments, $L^1$ is —CH$_2$CH$_2$—.

In some embodiments, one or more methylene unites of $L^1$ are replaced with —N(R')—. In some embodiments, one or more methylene unites of $L^1$ are replaced with —NH—. In some embodiments, one or more methylene unites of L are replaced with —S(O)$_2$—. In some embodiments, one or more methylene unites of $L^1$ are replaced with —S(O)$_2$N (R')—. In some embodiments, one or more methylene unites of $L^1$ are replaced with —S(O)$_2$NH—.

In some embodiments, L is optionally substituted —CH$_2$CH$_2$NH—. In some embodiments, $L^1$ is —CH$_2$CH$_2$NH—. In some embodiments, $L^1$ is optionally substituted —CH$_2$CH$_2$NHS(O)$_2$—. In some embodiments, $L^1$ is —CH$_2$CH$_2$NHS(O)$_2$—. In some embodiments, the —CH$_2$— is bonded to Ring B.

In some embodiments, one or more methylene unites of $L^1$ are replaced with -Cy-, wherein each -Cy- is independently as described herein.

In some embodiments, $L^1$ is -Cy- wherein -Cy- is as described herein. In some embodiments, L is an optionally substituted bivalent phenyl ring. In some embodiments, $L^1$ is a bivalent phenyl ring. In some embodiments, $L^1$ is

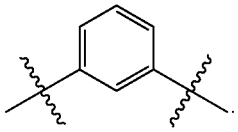 [SMILES: *c1cccc(*)c1]

In some embodiments, $L^1$ is optionally substituted bivalent 5-membered heteroaryl having 1-4 ring nitrogen atoms. In some embodiments, $L^1$ is optionally substituted

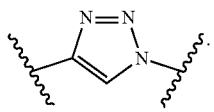

In some embodiments, $L^1$ is

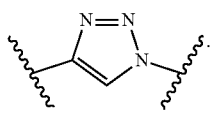

In some embodiments, $L^1$ is optionally substituted

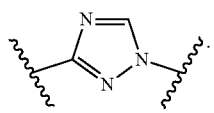

In some embodiments, $L^1$ is

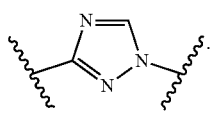

In some embodiments, $L^1$ is optionally substituted

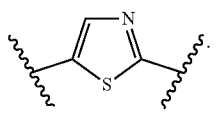

In some embodiments, $L^1$ is

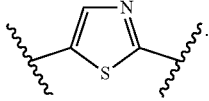

In some embodiments, $L^1$ is optionally substituted bivalent 6-membered heteroaryl having 1-4 ring nitrogen atoms. In some embodiments, $L^1$ is optionally substituted

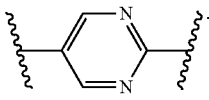

In some embodiments, $L^1$ is

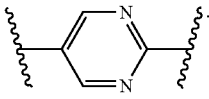 [SMILES: *c1cnc(*)nc1]

In some embodiments, $L^1$ is optionally substituted -Cy-CH$_2$—. In some embodiments, $L^1$ is optionally substituted

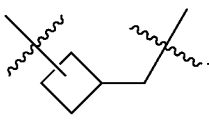

In some embodiments, $L^1$ is

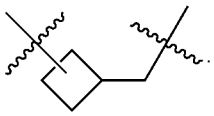

In some embodiments, L is selected from those depicted in Table 1, below.

In some embodiments, $L^2$ is a covalent bond, or a bivalent, saturated or unsaturated, straight or branched group selected from $C_{1-10}$ aliphatic and $C_{1-10}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N (R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]— or —[(—C(O)—C(R')$_2$—N(R')—)$_n$]—.

In some embodiments, $L^2$ is a covalent bond, or a bivalent, saturated or unsaturated, straight or branched $C_{1-6}$ aliphatic, wherein 0-4 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]— or —[(—C(O)—C(R')$_2$—N(R')—)$_n$]—. In some embodiments, L$^2$ is a covalent bond, or a bivalent, saturated or unsaturated, straight or branched C$_{1-6}$ aliphatic, wherein 0-4 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L$^2$ is a covalent bond, or a bivalent, saturated or unsaturated, straight or branched C$_{1-4}$ aliphatic, wherein 0-4 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L$^2$ is a covalent bond, or a bivalent, saturated or unsaturated, straight or branched C$_{1-3}$ aliphatic, wherein 0-2 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L$^2$ is a covalent bond, or a bivalent, saturated or unsaturated, straight or branched C$_{1-2}$ aliphatic, wherein 0-1 methylene units of the group are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L$^2$ is a covalent bond, or an optionally substituted methylene group which is optionally and independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L$^2$ is a covalent bond, or an optionally substituted —CH$_2$CH$_2$— wherein 0-2 methylene units are independently replaced with —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L$^2$ is a covalent bond, or an optionally substituted —CH$_2$CH$_2$— wherein 0-2 methylene units are independently replaced with -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—. In some embodiments, L$^2$ is a covalent bond, or an optionally substituted —CH$_2$CH$_2$— wherein 0-2 methylene units are independently replaced with -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

In some embodiments, L$^2$ is a covalent bond, —NHC(O)—, —C(O)NH—, —CH$_2$—, —CH(R)—, —C(R)$_2$—, —C(O)—, or —S(O)$_2$—. In some embodiments, L$^2$ is a covalent bond, —NHC(O)—, —C(O)NH—, —CH$_2$—, —CH(R)—, —C(R)$_2$—, —C(O)—, —S(O)$_2$—, -Cy-C(O)—, -Cy-, —N(R')C(O)N(R')— or —S(O)$_2$N(R')—.

In some embodiments, L$^2$ is a covalent bond.

In some embodiments, L$^2$ is —C(O)N(R')—. In some embodiments, L$^2$ is —C(O)NH—. In some embodiments, —C(O)— is bonded to Ring B. In some embodiments, —C(O)— is bonded to Ring C.

In some embodiments. L$^2$ is —CH$_2$—. In some embodiments. L$^2$ is —CH(R)—. In some embodiments. L$^2$ is —C(R)$_2$—. In some embodiments. L$^2$ is —C(O)—. In some embodiments. L$^2$ is —S(O)$_2$—.

In some embodiments, L$^2$ is -Cy-C(O)— wherein -Cy- is as described herein. In some embodiments, L$^2$ is optionally substituted

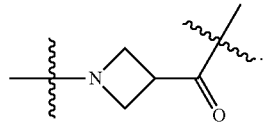 [SMILES: *C(=O)C1CN(*)C1]

In some embodiments, L$^2$ is

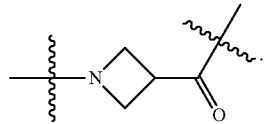 [SMILES: *C(=O)C1CN(*)C1]

In some embodiments, —C(O)— is bonded to Ring B.

In some embodiments, L$^2$ is -Cy- wherein -Cy- is as described herein.

In some embodiments, L$^2$ is —N(R')C(O)N(R')—. In some embodiments, L$^2$ is —NHC(O)NH—.

In some embodiments, one or more methylene unites of L$^2$ are replaced with —N(R')—. In some embodiments, one or more methylene unites of L$^2$ are replaced with —NH—.

In some embodiments, one or more methylene unites of $L^2$ are replaced with —S(O)$_2$—. In some embodiments, one or more methylene unites of $L^2$ are replaced with —S(O)$_2$N(R')—. In some embodiments, one or more methylene unites of $L^2$ are replaced with —S(O)$_2$NH—.

In some embodiments, $L^2$ is —S(O)$_2$N(R')—. In some embodiments, $L^2$ is —S(O)$_2$NH—. In some embodiments, —S(O)$_2$— is bonded to Ring C.

In some embodiments, $L^2$ is selected from those depicted in Table 1, below.

In some embodiments, $L^3$ is a covalent bond, or a bivalent, saturated or unsaturated, straight or branched group selected from $C_{1-50}$ aliphatic and $C_{1-50}$ heteroaliphatic having 1-30 hetereoatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]— or —[(—C(O)—C(R')$_2$—N(R')—)$_n$]—, and one or more carbon and heteroatoms of the group are optionally and independently replaced with Cy$^L$. In some embodiments, $L^3$ is a covalent bond, or a bivalent, saturated or unsaturated, straight or branched group selected from $C_{1-50}$ aliphatic and $C_{1-50}$ heteroaliphatic having 1-30 hetereoatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]— or —[(—C(O)—C(R')$_2$—N(R')—)$_n$]—.

In some embodiments, $L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

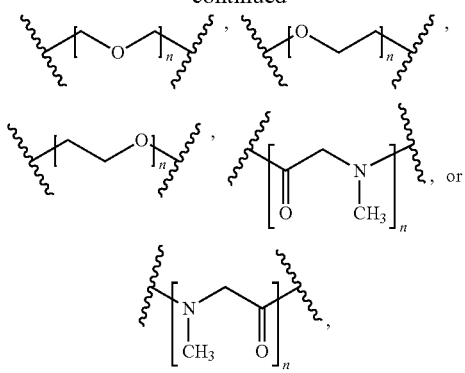

wherein: each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups.

In some embodiments, $L^3$ is a covalent bond. In some embodiments, $L^3$ is a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

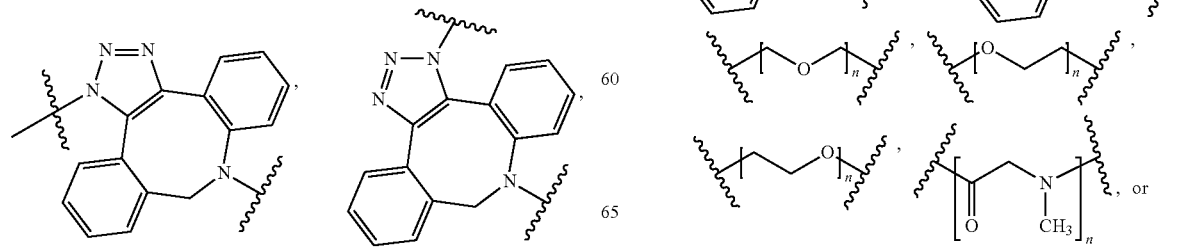

-continued

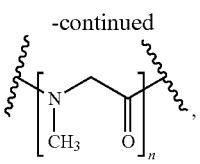, wherein, each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups.

In some embodiments, $L^3$ is

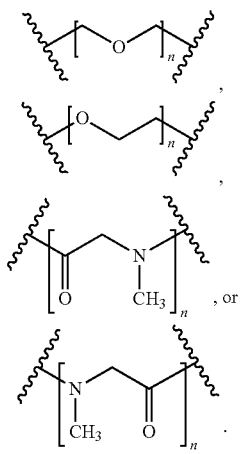

In some embodiments, $L^3$ is

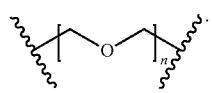

In some embodiments, $L^3$ is

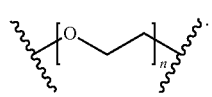

In some embodiments, $L^3$ is

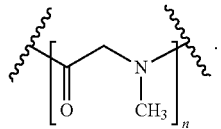

In some embodiments, $L^3$ is

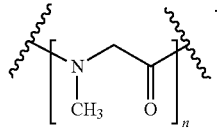

In some embodiments, $L^3$ is $-(CH_2CH_2O)_n-CH_2CH_2-$. In some embodiments, n is 1. In some embodiments, n is 2. In some embodiments, n is 3 In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15.

In some embodiments, one or more methylene units are independently replaced with —O—. In some embodiments, one or more methylene units are independently replaced with —C(O)O—. In some embodiments, one or more methylene units are independently replaced with —C(O)N(R')—. In some embodiments, one or more methylene units are independently replaced with —C(O)NH—. In some embodiments, one or more methylene units are independently replaced with —C(S)—. In some embodiments, one or more methylene units are independently replaced with —N(R')—. In some embodiments, one or more methylene units are independently replaced with —NH—.

In some embodiments, one or more methylene units are independently replaced with —[(—O—C(R')$_2$—C(R')$_2$—)$_n$]—. In some embodiments, one or more methylene units are independently replaced with —[(—O—CH$_2$—CH$_2$—)$_n$]—. In some embodiments, one or more methylene units are independently replaced with —O—CH$_2$—CH$_2$—.

In some embodiments, one or more methylene units are independently replaced with —[(—C(R')$_2$—O—C(R')$_2$—)$_n$]—. In some embodiments, one or more methylene units are independently replaced with —[(—CH$_2$—O—CH$_2$—)$_n$]—. In some embodiments, one or more methylene units are independently replaced with —CH$_2$—O—CH$_2$—.

In some embodiments, $L^3$ is a covalent bond.

In some embodiments, $L^3$ is -Cy- wherein -Cy- is as described herein. In some embodiments, -Cy- is or comprises

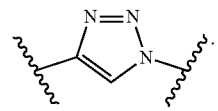.

In some embodiments, -Cy- is

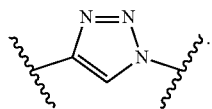

In some embodiments, -Cy- comprises a —C≡C— group. In some embodiments, -Cy- is or comprises optionally substituted

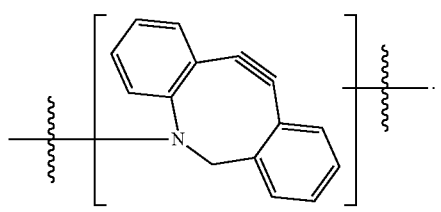

In some embodiments, -Cy- is or comprises

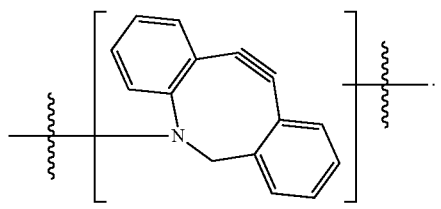

In some embodiments, -Cy- is or comprises optionally substituted

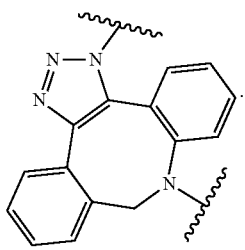 [SMILES: *N1Cc2ccccc2-c2nnn(*)c2-c2ccccc21]

In some embodiments, -Cy- is or comprises

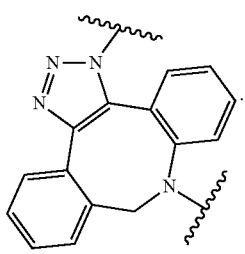 [SMILES: *N1Cc2ccccc2-c2nnn(*)c2-c2ccccc21]

In some embodiments, -Cy- is optionally substituted

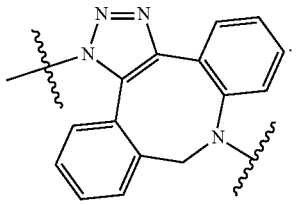 [SMILES: *N1Cc2ccccc2-c2c(nnn2*)-c2ccccc21]

In some embodiments, -Cy- is

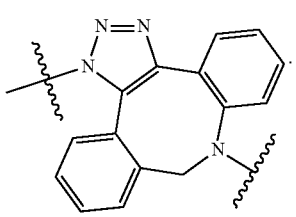 [SMILES: *N1Cc2ccccc2-c2c(nnn2*)-c2ccccc21]

In some embodiments, $L^3$ is optionally substituted -Cy-CH$_2$— wherein -Cy- is as described herein. In some embodiments, $L^3$ is optionally substituted

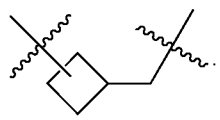

In some embodiments, $L^3$ is

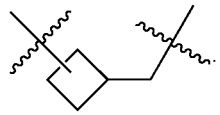

In some embodiments, $L^3$ is —C(O)—. In some embodiments, $L^3$ is —C(O)N(R')—. In some embodiments, $L^3$ is —C(O)NH—. In some embodiments, $L^3$ is -Cy-. In some embodiments, $L^3$ is —S(O)$_2$—. In some embodiments, $L^3$ is optionally substituted —CH$_2$—. In some embodiments, $L^3$ is —CH$_2$—.

In some embodiments, $L^3$ is bonded to Ring C via a —C(O)— group at one end of $L^3$. In some embodiments, $L^3$ is bonded to Ring C via an optionally substituted cyclic group at one end of $L^3$. In some embodiments, $L^3$ is bonded to Ring C via an optionally substituted heteroaryl group at one end of $L^3$. In some embodiments, a heteroaryl group is

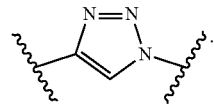 [SMILES: *c1cn(*)nn1]

In some embodiments, L³ is
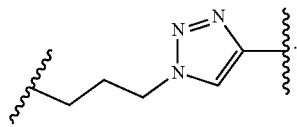 [SMILES: *CCCn1cc(*)nn1]
In some embodiments, L³ is
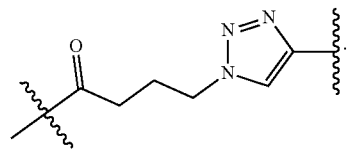 [SMILES: *C(=O)CCCn1cc(*)nn1]
In some embodiments, L³ is
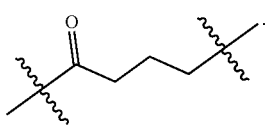 [SMILES: *CCCC(*)=O]
In some embodiments, L³ is
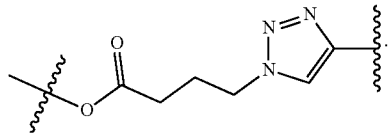 [SMILES: *OC(=O)CCCn1cc(*)nn1]
In some embodiments, L³ is
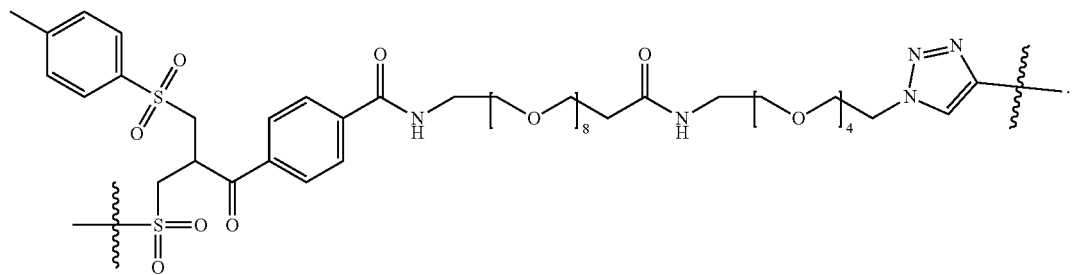
In some embodiments, L³ is
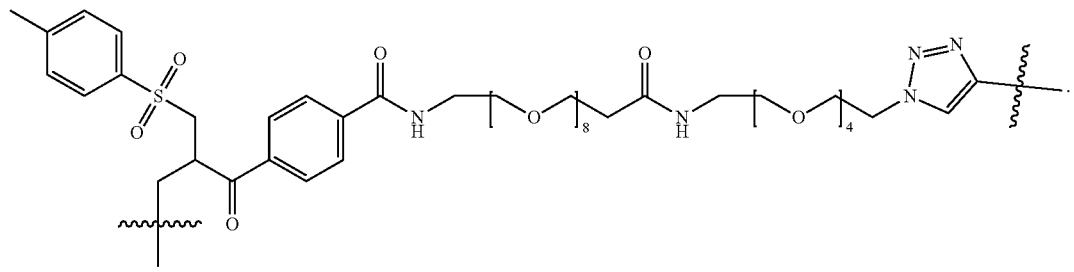
In some embodiments, L³ is
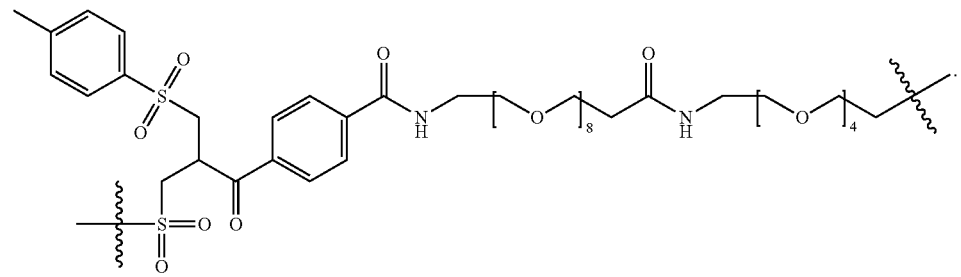

In some embodiments, L³ is
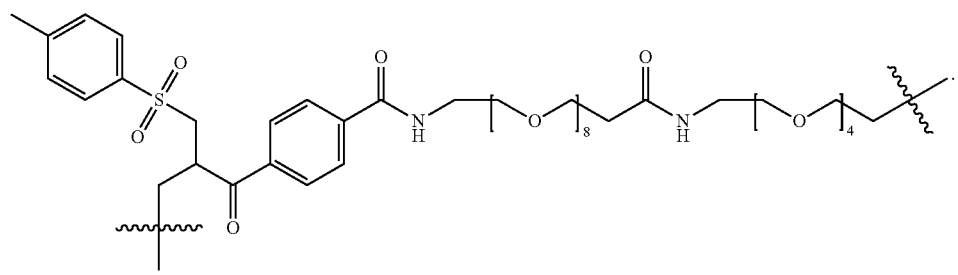
In some embodiments, L³ is
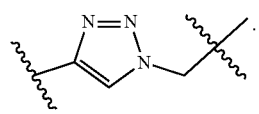 [SMILES: *Cn1cc(*)nn1]
In some embodiments, L³ is
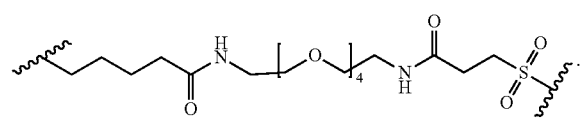
In some embodiments, L³ is
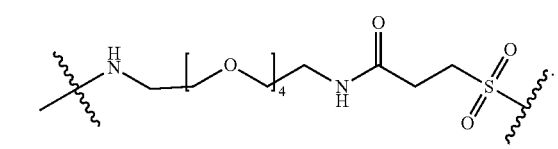
In some embodiments, L³ is
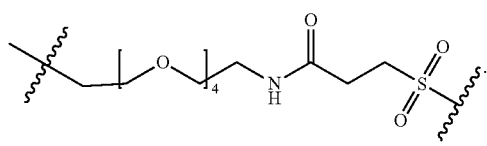
In some embodiments, L³ is
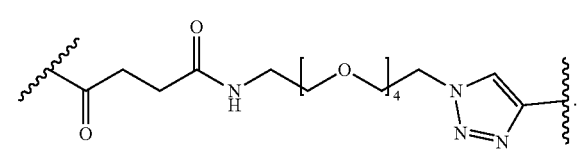
In some embodiments, L³ is
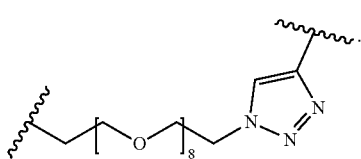
In some embodiments, L³ is
In some embodiments, L³ is
In some embodiments, L³ is
In some embodiments, L³ is
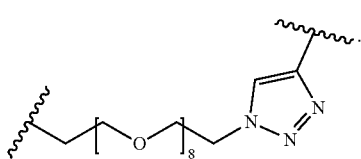

In some embodiments, L³ is
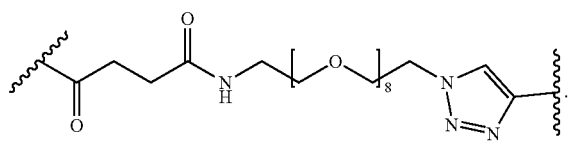
In some embodiments, L³ is
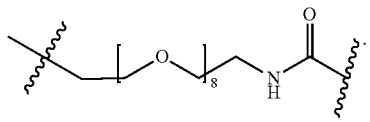
In some embodiments, L³ is
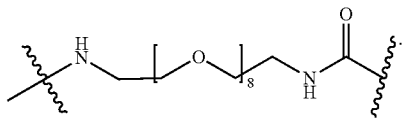
In some embodiments, L³ is
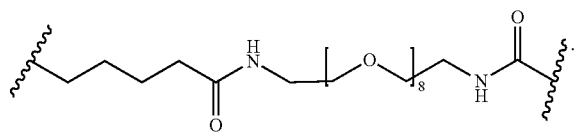
In some embodiments, L³ is
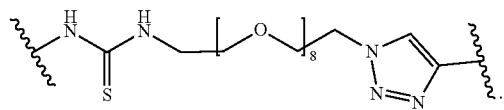
In some embodiments, L³ is
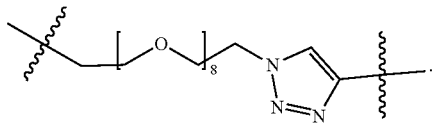
In some embodiments, L³ is
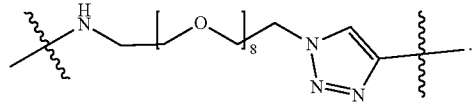
In some embodiments, L³ is
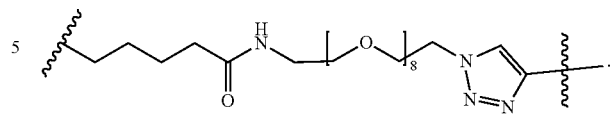
In some embodiments, L³ is
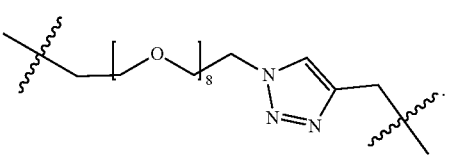
In some embodiments, L³ is
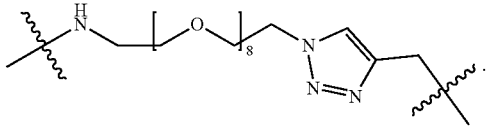
In some embodiments, L³ is
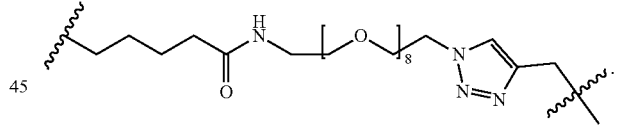
In some embodiments, L³ is
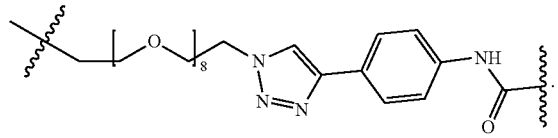
In some embodiments, L³ is
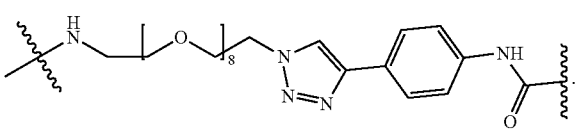

In some embodiments, L³ is
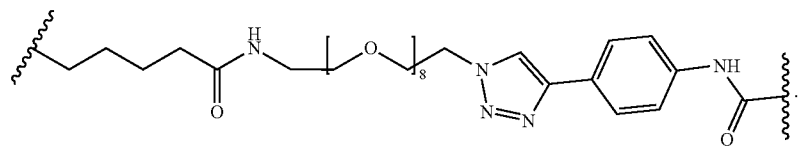
In some embodiments, L³ is
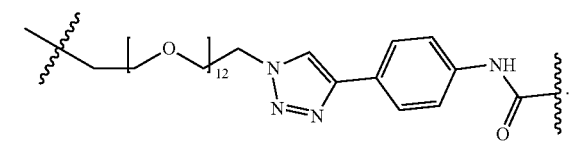
In some embodiments, L³ is
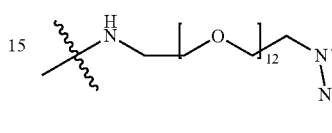
In some embodiments, L³ is
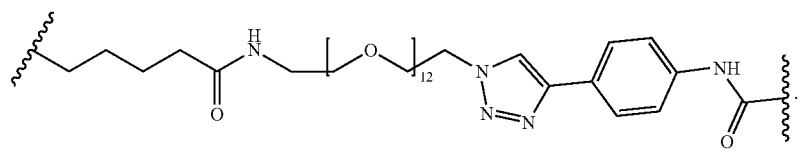
In some embodiments, L³ is
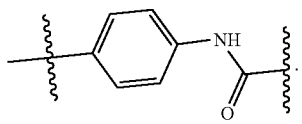 [SMILES: *C(=O)Nc1ccc(*)cc1]
In some embodiments, L³ is
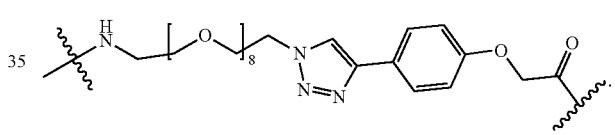
In some embodiments, L³ is
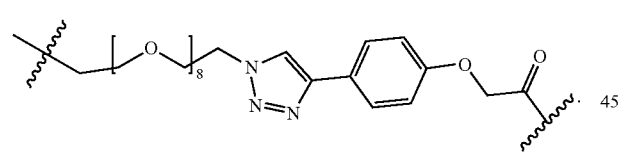
In some embodiments, L³ is
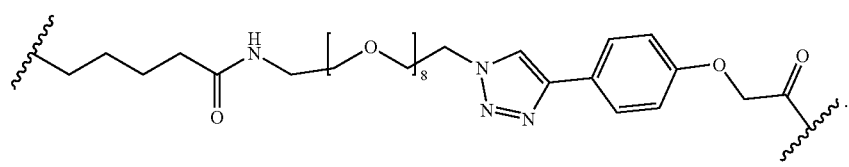

In some embodiments, L³ is
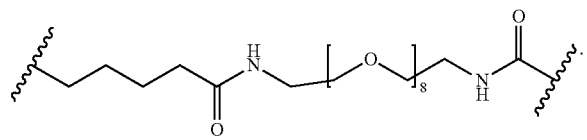
In some embodiments, L³ is
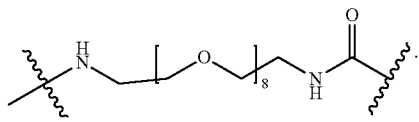
In some embodiments, L³ is
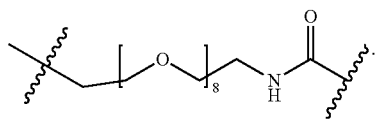
In some embodiments, L³ is
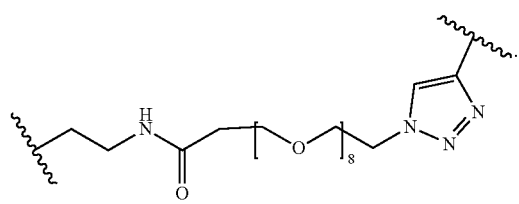
In some embodiments L³ is
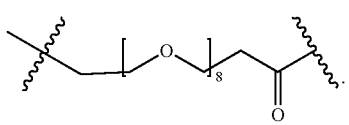
In some embodiments, L³ is
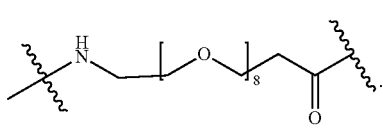
In some embodiments, L³ is
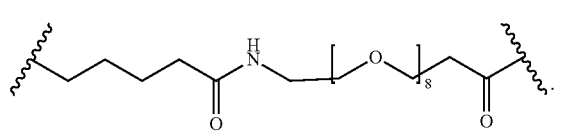
In some embodiments, L³ is
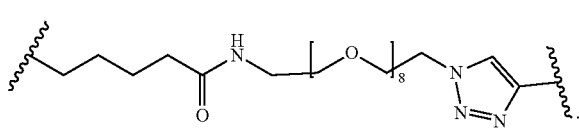
In some embodiments, L³ is
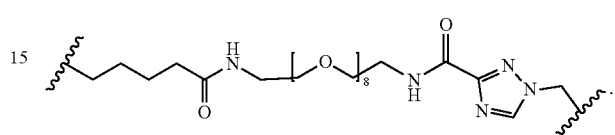
In some embodiments, L³ is
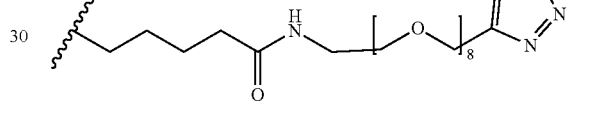
In some embodiments, L³ is
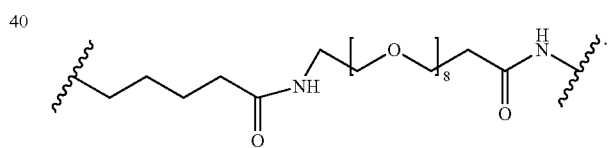
In some embodiments, L³ is
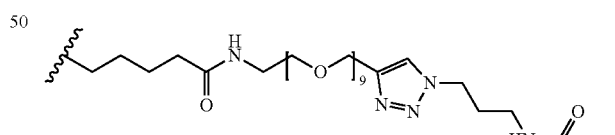
In some embodiments, L³ is
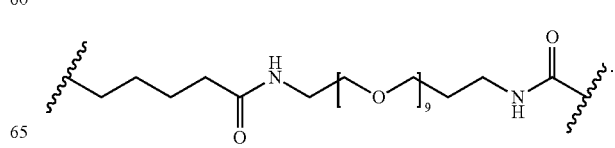

In some embodiments, L³ is
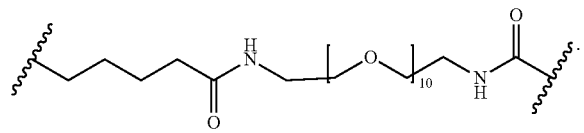
In some embodiments L³ is
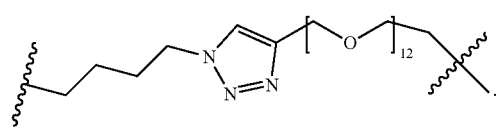
In some embodiments, L³ is
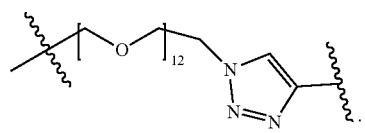
In some embodiments, L³ is
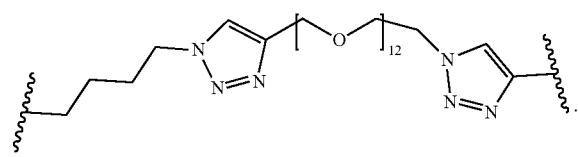
In some embodiments, L³ is
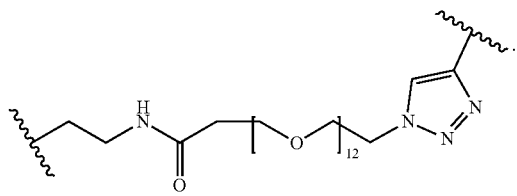
In some embodiments, L³ is
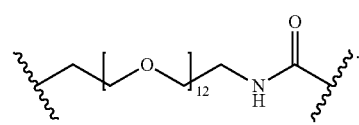
In some embodiments, L³ is
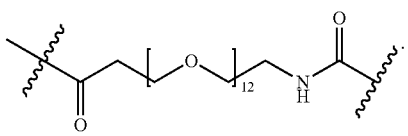
In some embodiments, L³ is
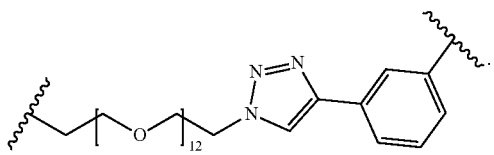
In some embodiments, L³ is
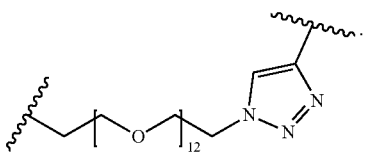
In some embodiments, L³ is
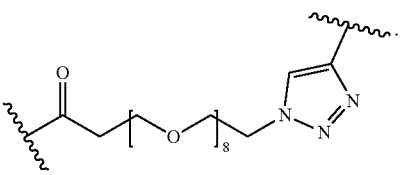
In some embodiments, L³ is
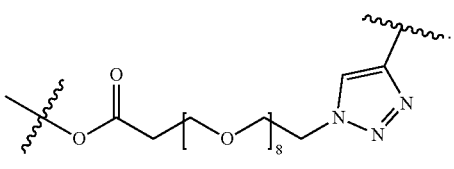
In some embodiments, L³ is
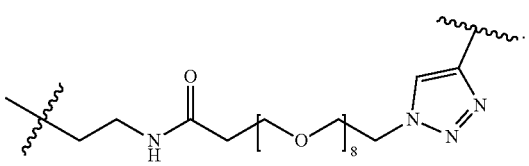

In some embodiments, L³ is
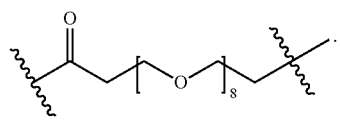
In some embodiments, L³ is
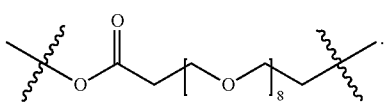
In some embodiments, L³ is
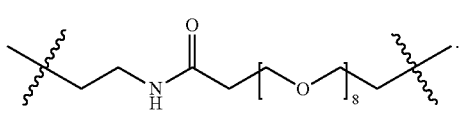
In some embodiments, L³ is
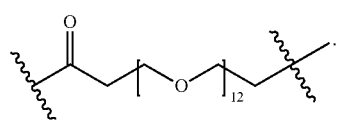
In some embodiments, L³ is
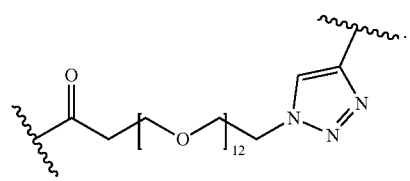
In some embodiments, L³ is
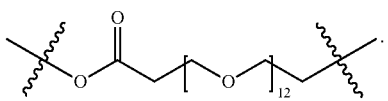
In some embodiments, L³ is
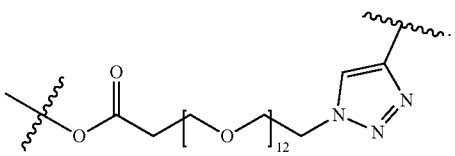
In some embodiments, L³ is
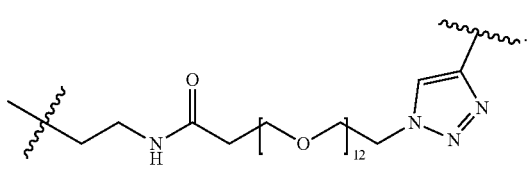
In some embodiments, L³ is
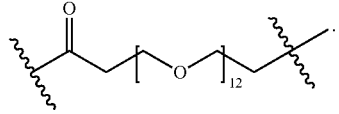
In some embodiments L³ is
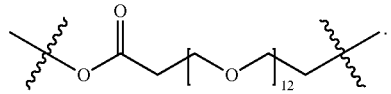
In some embodiments, L³ is
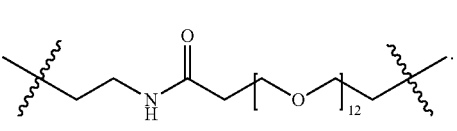
In some embodiments, L³ is
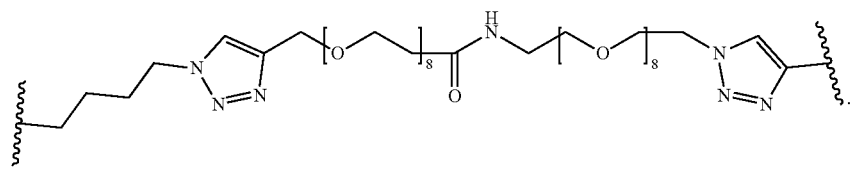
In some embodiments, L³ is
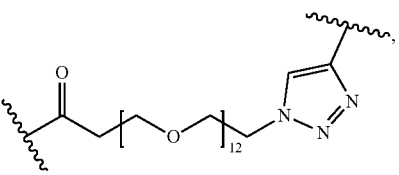

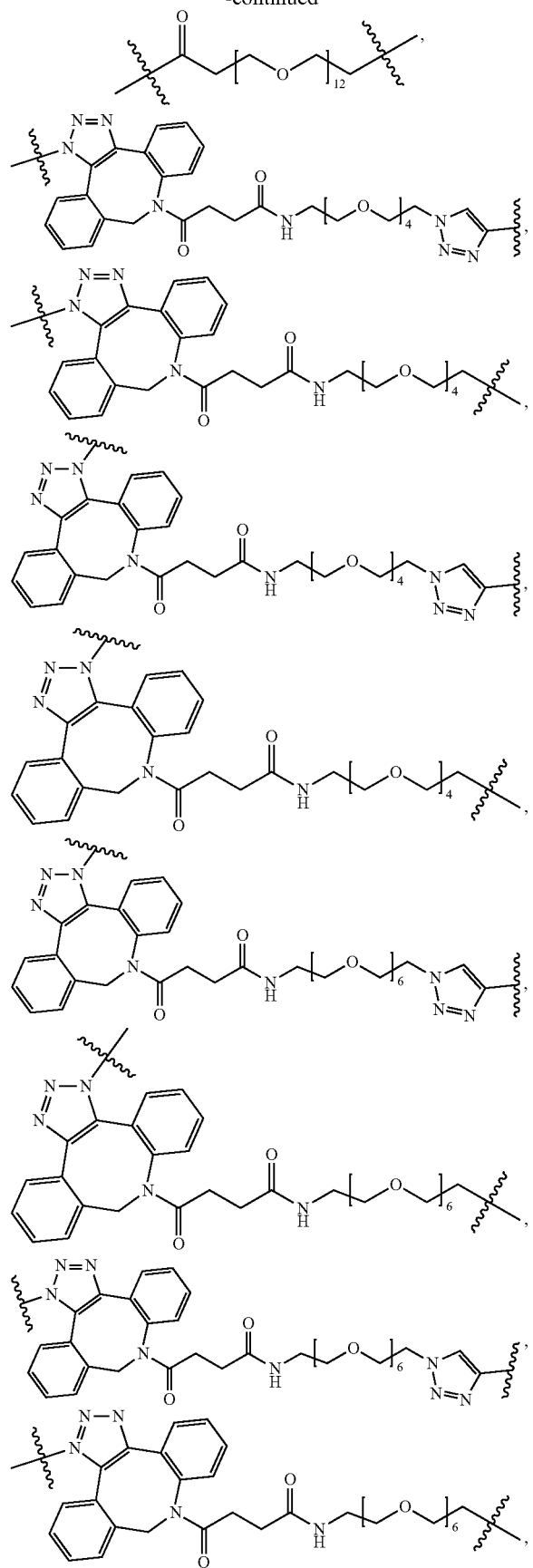
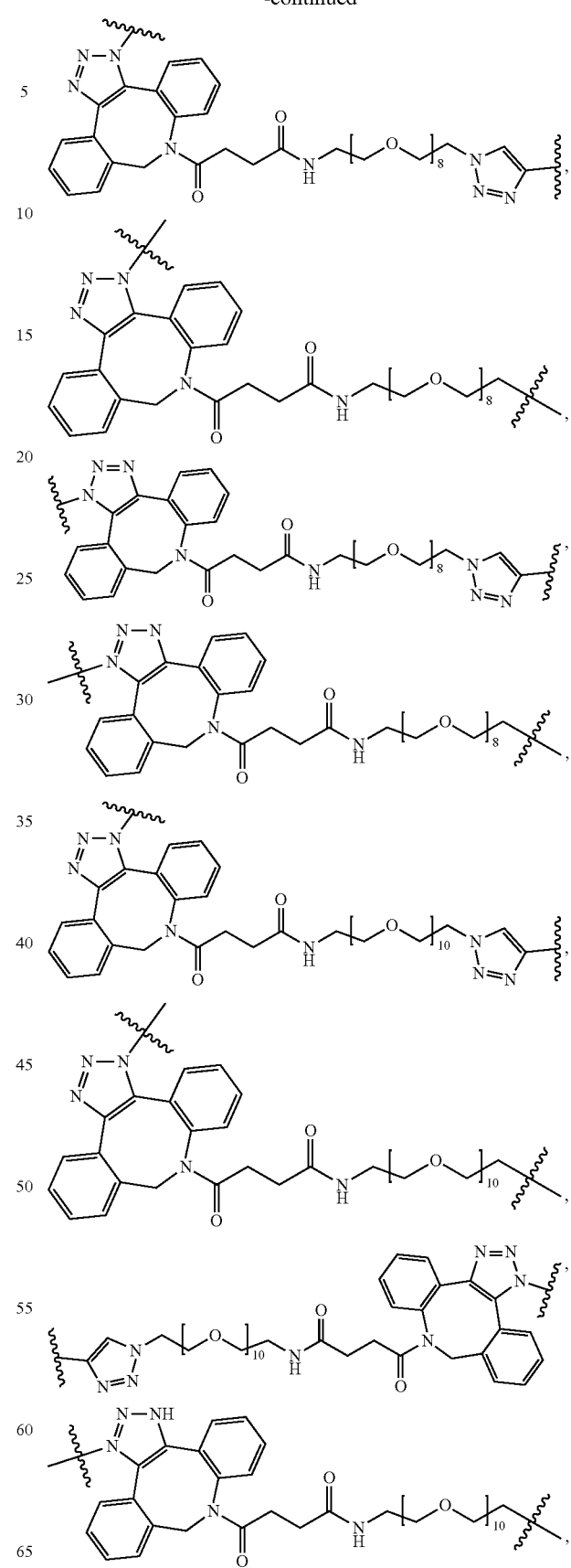

-continued

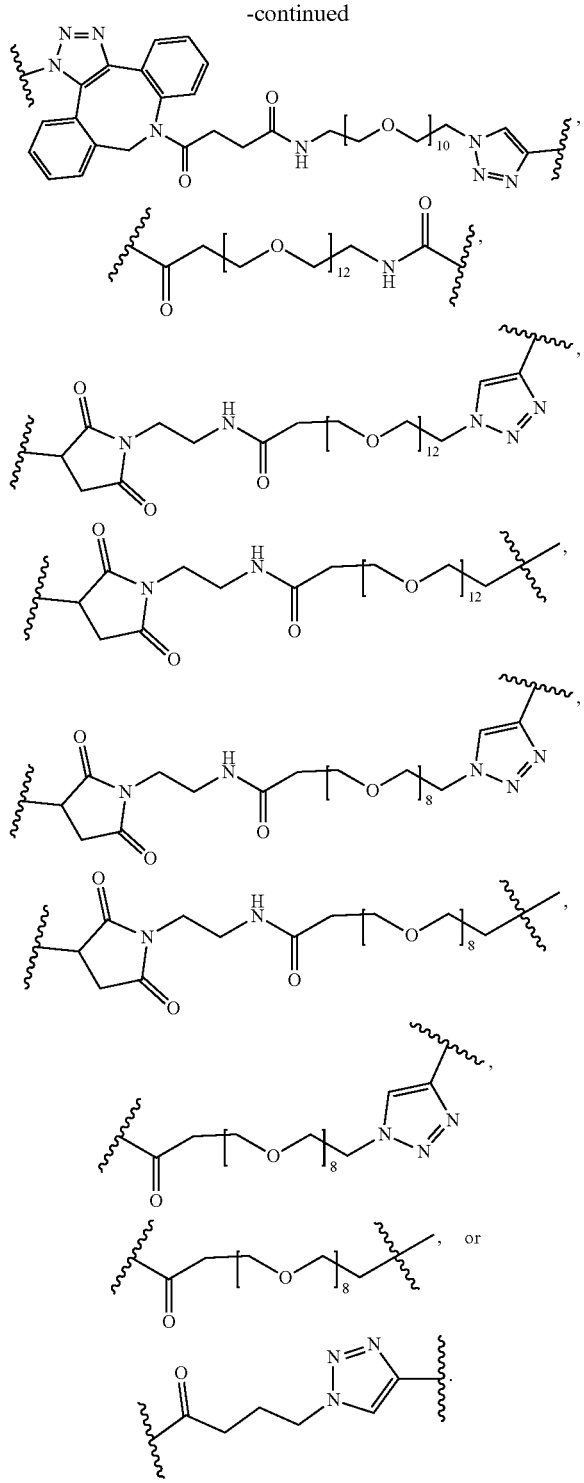

In some embodiments, each of $L^3$ and L is independently and optionally of sufficient size, e.g., to facilitate a compound for conjugation with another moiety (e.g., a targeting moiety), to help with interaction with another moiety, etc. In some embodiments, $L^3$ comprises 10-500, 10-400, 10-300, 10-250, 10-200, 10-150, 10-100, 15-500, 15-400, 15-300, 15-250, 15-200, 15-150, 15-100, 20-500, 20-400, 20-300, 20-250, 20-200, 20-150, 20-100, 25-500, 25-400, 25-300, 25-250, 25-200, 25-150, 25-100, or 10, 15, 20, 25, 30, 35, 40, 45, 50, 60, 70, 80, 90, 100, 110, 120, 130, 140, 150, 160, 170, 180, 190, 200 or more carbon and heteroatoms. In some embodiments, L comprises 10-500, 10-400, 10-300, 10-250, 10-200, 10-150, 10-100, 15-500, 15-400, 15-300, 15-250, 15-200, 15-150, 15-100, 20-500, 20-400, 20-300, 20-250, 20-200, 20-150, 20-100, 25-500, 25-400, 25-300, 25-250, 25-200, 25-150, 25-100, or 10, 15, 20, 25, 30, 35, 40, 45, 50, 60, 70, 80, 90, 100, 110, 120, 130, 140, 150, 160, 170, 180, 190, 200 or more carbon and heteroatoms. In some embodiments, $L^3$ comprises 10, 15, 20, 25, 30, 35, 40, 45, 50, 60, 70, 80, 90, 100, 110, 120, 130, 140, 150, 160, 170, 180, 190, 200 or more carbon heteroatoms. In some embodiments, L comprises 10, 15, 20, 25, 30, 35, 40, 45, 50, 60, 70, 80, 90, 100, 110, 120, 130, 140, 150, 160, 170, 180, 190, 200 or more carbon heteroatoms. In some embodiments, a number is at least 10. In some embodiments, a number is at least 15. In some embodiments, a number is at least 20. In some embodiments, a number is at least 25. In some embodiments, a number is at least 30. In some embodiments, a number is at least 40. In some embodiments, a number is at least 50. In some embodiments, a number is at least 60. In some embodiments, a number is at least 70. In some embodiments, a number is at least 80. In some embodiments, a number is at least 90. In some embodiments, a number is at least 100.

In some embodiments, $L^3$ is selected from those depicted in Table 1, below.

Compounds or chemical groups of the present disclosure may contain one or more heteroatoms. In some embodiments, a heteroatom is selected from nitrogen, oxygen and sulfur. In some embodiments, a heteroatom is nitrogen. In some embodiments, a heteroatom is oxygen. In some embodiments, a heteroatom is oxygen.

As described herein, each R' is independently —R, —OR, —C(O)R, —C(O)OR, or —S(O)$_2$R. In some embodiments, R' is —R. In some embodiments, R' is —OR. In some embodiments, R' is —C(O)R. In some embodiments, R' is —C(O)OR. In some embodiments, R' is —S(O)$_2$R.

In some embodiments, R is independently —H, or an optionally substituted group selected from $C_{1-30}$ aliphatic, $C_{1-30}$ heteroaliphatic having 1-10 heteroatoms, $C_{6-30}$ aryl, 5-30 membered heteroaryl having 1-10 heteroatoms, and 3-30 membered heterocyclyl having 1-10 heteroatoms. In some embodiments, two R groups are optionally and independently taken together to form a covalent bond. In some embodiments, two or more R groups on the same atom are optionally and independently taken together with the atom to form an optionally substituted, monocyclic, bicyclic, or polycyclic 3-40 membered ring having, in addition to the atom, 0-20 heteroatoms. In some embodiments, two or more R groups on two or more atoms are optionally and independently taken together with their intervening atoms to form an optionally substituted, monocyclic, bicyclic, or polycyclic 3-40 membered ring having, in addition to the intervening atoms, 0-20 heteroatoms.

In some embodiments, each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, R is hydrogen.

In some embodiments, R is optionally substituted C$_{1-30}$ aliphatic. In some embodiments, R is optionally substituted C$_{1-20}$ aliphatic. In some embodiments, R is optionally substituted C$_{1-15}$ aliphatic. In some embodiments, R is optionally substituted C$_{1-10}$ aliphatic. In some embodiments, R is optionally substituted C$_{1-6}$ aliphatic. In some embodiments, R is optionally substituted C$_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl.

In some embodiments, R is optionally substituted C$_{3-30}$ cycloaliphatic. In some embodiments, R is optionally substituted C$_{3-20}$ cycloaliphatic. In some embodiments, R is optionally substituted C$_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted C$_{1-30}$ heteroaliphatic having 1-10 heteroatoms independently selected from oxygen, nitrogen, sulfur, phosphorus and silicon. In some embodiments, R is optionally substituted C$_{1-20}$ heteroaliphatic having 1-10 heteroatoms. In some embodiments, R is optionally substituted C$_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted C$_{1-30}$ heteroaliphatic comprising 1-10 groups independently selected from

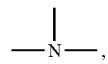

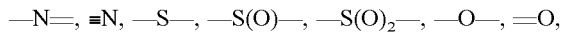

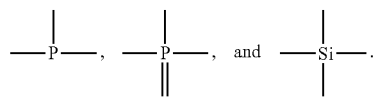

In some embodiments, R is optionally substituted C$_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is an optionally substituted 5,6-fused heteroaryl ring having three heteroatoms independently selected from nitrogen, oxygen, and sulfur. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. In some embodiments, R is an optionally substituted 6,6-fused heteroaryl ring having 2 heteroatoms independently selected from nitrogen, oxygen, and sulfur. In some embodiments, R is optionally substituted quinazoline or a quinoxaline.

In some embodiments, R is an optionally substituted 3-30 membered heterocyclic ring having 1-10 heteroatoms independently selected from oxygen, nitrogen, sulfur, phosphorus and silicon. In some embodiments, R is an optionally substituted 3-30 membered heterocyclic ring having 1-10 heteroatoms independently selected from oxygen, nitrogen, and sulfur. In some embodiments, R is an optionally substituted 3-30 membered heterocyclic ring having 1-5 heteroatoms independently selected from oxygen, nitrogen, sulfur, phosphorus and silicon. In some embodiments, R is an optionally substituted 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms.

In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 5-membered partially unsaturated heterocyclic ring having 2 heteroatoms independently selected from nitrogen, oxygen, and sulfur. In some embodiments, R is an optionally substituted 5-membered partially unsaturated heterocyclic ring having no more than 1 heteroatom. In some embodiments, R is an optionally substituted 5-membered partially unsaturated heterocyclic ring having no more than 1 heteroatom, wherein the heteroatom is nitrogen. In some embodiments, R is an optionally substituted 5-membered partially unsaturated heterocyclic ring having no more than 1 heteroatom, wherein the heteroatom is oxygen. In some embodiments, R is an optionally substituted 5-membered partially unsaturated heterocyclic ring having no more than 1 heteroatom, wherein the heteroatom is sulfur. In some embodiments, R is an optionally substituted 5-membered partially unsaturated heterocyclic ring having 2 oxygen atoms. In some embodiments, R is an optionally substituted 5-membered partially unsaturated heterocyclic ring having 2 nitrogen atoms.

In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 6-membered partially unsaturated heterocyclic ring having 2 heteroatoms independently selected from nitrogen, oxygen, and sulfur. In some embodiments, R is an optionally substituted 6-membered partially unsaturated heterocyclic ring having no more than 1 heteroatom. In some embodiments, R is an optionally substituted 6-membered partially unsaturated heterocyclic ring having no more than 1 heteroatom, wherein the heteroatom is nitrogen. In some embodiments, R is an optionally substituted 6-membered partially unsaturated heterocyclic ring having no more than 1 heteroatom, wherein the heteroatom is oxygen. In some embodiments, R is an optionally substituted 6-membered partially unsaturated heterocyclic ring having no more than 1 heteroatom, wherein the heteroatom is sulfur. In some embodiments, R is an optionally substituted 6-membered partially unsaturated heterocyclic ring having 2 oxygen atoms. In some embodiments, R is an optionally substituted 6-membered partially unsaturated heterocyclic ring having 2 nitrogen atoms.

In certain embodiments, R is a 3-7 membered saturated or partially unsaturated heterocyclic ring having 1-2 heteroatoms independently selected from nitrogen, oxygen, and sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl.

In certain embodiments, R is an optionally substituted 5-6 membered partially unsaturated monocyclic ring having 1-2 heteroatoms independently selected from oxygen, nitrogen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, two R groups are optionally and independently taken together to form a covalent bond. In some embodiments, —C=O is formed. In some embodiments, —C=C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

In some embodiments, mAb is a monoclonal antibody. In some embodiments, mAb is a fragment of a monoclonal antibody.

In some embodiments, TM or mAb is a therapeutic antibody or a fragment thereof, e.g., a FDA-approved antibody for therapeutic uses. In some embodiments, such an antibody is useful for treating cancer. FDA-approved therapeutic antibodies can be readily obtained at www.fda.gov.

In some embodiments, an antibody, e.g., mAb, is selected from adalimumab, alemtuzumab, atezolizumab, avelumab, ipilimumab, dcetuximab, daratumumab, dinutuximab, elotuzumab, ibritumomab tiuxetan, imgatuzumab, infliximab, ipilimumab, necitumumab, obinutuzumab, ofatumumab, pertuzumab, reslizumab, rituximab, trastuzumab, mogamulizumab, AMP-224, FS-102, GSK-2857916, ARGX-111, ARGX-110, AFM-13, APN-301, BI-836826, BI-836858, enoblituzumab, otlertuzumab, veltuzumab, KHK-4083, BIW-8962, ALT-803, carotuximab, epratuzumab, inebilizumab, isatuximab, margetuximab, MOR-208, ocaratuzumab, talacotuzumab, tremelimumab, benralizumab, lumiliximab, MOR-208, Ifibatuzumab, GSK2831781, SEA-CD40, KHK-2823, or BI836858.

In some embodiments, an antibody, e.g., mAb, is selected from anti-CD16/-CD33 antibody (cancer), University of Minnesota; anti-CD16/anti-CD33 antibody (cancer), Oxis International/Altor BioScience; anti-EGFR recombinant Fc engineered IgA2m antibody (cancer), Shire; anti-WT1/HLA-A2 mAb (cancer), Eureka/Memorial Sloan-Kettering Cancer Center/Novartis; Fc engineered aglycosylated therapeutic IgG antibodies, Clayton/University of Texas at Austin; or ocaratuzumab (subcutaneous, B-cell lymphoma/rheumatoid arthritis), MENTRIK.

In some embodiments, mAb is selected from those depicted in Table 1, below.

Technologies for preparing conjugates, e.g., antibody conjugates, are widely available and can be utilized in accordance with the present disclosure. Among other things, many compounds in Table 1 contain reactive groups that can be utilized for conjugating useful agents, e.g., CD16a-binding agents, with targeting moieties, e.g., antibodies and fragments thereof. For example, in some embodiments,

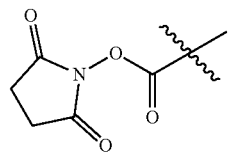 [SMILES: *C(=O)ON1C(=O)CCC1=O]

can react with an reactive group, e.g., an amino group, to form an amide bond and provide a conjugate. In some embodiments,

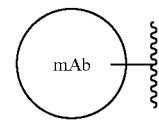

is used to indicate attachment of a moiety, e.g.,

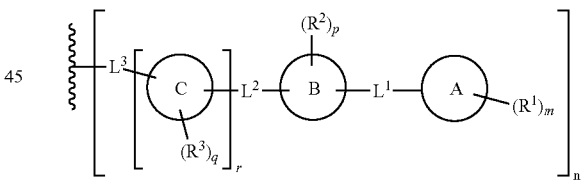

to any modifiable C, N, O or S atom of a monoclonal antibody.

In some embodiments, each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, R is hydrogen. In some embodiments, R is an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, R is selected from those depicted in Table 1, below.

In some embodiments, each instance of $R^1$ and $R^3$ is independently hydrogen, halogen, —CN, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R.

In some embodiments, $R^1$ is hydrogen, halogen, —CN, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R.

In some embodiments, R is —H. In some embodiments, each R is —H. In some embodiments, all occurrences of $R^1$ are the same. In some embodiments, at least one $R^1$ is different from another.

In some embodiments, $R^1$ is halogen. In some embodiments, $R^1$ is fluoro. In some embodiments, $R^1$ is —Cl. In some embodiments, $R^1$ is —Br. In some embodiments, $R^1$ is —I. In some embodiments, $R^1$ is —CN. In some embodiments, $R^1$ is —OR wherein R is as defined and described herein. In some embodiments, $R^1$ is —OCH$_3$. In some embodiments, $R^1$ is —OEt.

In some embodiments, $R^1$ is R as described herein. In some embodiments, $R^1$ is optionally substituted C$_{1-6}$ aliphatic. In some embodiments, $R^1$ is methyl. In some embodiments, $R^1$ is —CF$_3$.

In some embodiments, $R^1$ is an optionally substituted 5-6 membered heteroaryl with 1-4 heteroatoms independently selected from nitrogen, oxygen or sulfur. In some embodiments, R is 5-membered heteroaryl with 1-4 heteroatoms independently selected from nitrogen, oxygen or sulfur. In some embodiments, $R^1$ is 6-membered heteroaryl with 1-4 heteroatoms independently selected from nitrogen, oxygen or sulfur. In some embodiments, such $R^1$ has 1 heteroatom. In some embodiments, such $R^1$ has 2 heteroatoms. In some embodiments, such $R^1$ has 3 heteroatoms. In some embodiments, such $R^1$ has 4 heteroatoms. In some embodiments, at least one heteroatom is nitrogen. In some embodiments, each heteroatom is nitrogen. In some embodiments, $R^1$ is optionally substituted

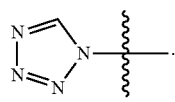 [SMILES: *n1cnnn1]

In some embodiments, $R^1$ is

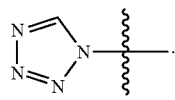

In some embodiments, an occurrence of $R^1$ is at the 2'-position (e.g., o-position if Ring A is an optionally substituted phenyl ring). In some embodiments, an occurrence of $R^1$ is at the 3'-position. In some embodiments, an occurrence of $R^1$ is at the 4'-position.

In some embodiments, $R^1$ is —S(O)$_2$OR. In some embodiments, $R^1$ is —S(O)$_2$OH.

In some embodiments, $R^1$ is selected from those depicted in Table 1, below.

In some embodiments, each instance of $R^2$ is independently hydrogen, halogen, —CN, —NO$_2$, or C$_{1-3}$ aliphatic.

In some embodiments, $R^2$ is hydrogen, halogen, —CN, —NO$_2$, or C$_{1-3}$ aliphatic. In some embodiments, $R^2$ is —H. In some embodiments, each $R^2$ is —H.

In some embodiments, $R^2$ is $R^1$ as described herein. In some embodiments, $R^2$ is $R^4$ as described herein. In some embodiments, $R^2$ is R as described herein.

In some embodiments, $R^2$ is —CH$_3$.

In some embodiments, $R^2$ is selected from those depicted in Table 1, below.

In some embodiments, $R^3$ is hydrogen, halogen, —CN, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R. In some embodiments, $R^3$ is —H. In some embodiments, each $R^3$ is —H.

In some embodiments, $R^3$ is $R^1$ as described herein. In some embodiments, $R^3$ is $R^4$ as described herein. In some embodiments, $R^3$ is R as described herein.

In some embodiments, an occurrence of $R^3$ is a reactive group that can be utilized for conjugation with another agent, e.g., a targeting moiety. In some embodiments, $R^3$ is —COOH or an activated form thereof. In some embodiments, $R^3$ is —CN. In some embodiments, $R^3$ is —NH$_2$. In some embodiments, $R^3$ is —N$_3$. In some embodiments, $R^3$ is —C≡CH.

In some embodiments, $R^3$ is selected from those depicted in Table 1, below.

In some embodiments, $R^4$ is $R^1$ wherein $R^1$ is as defined and described herein. In some embodiments, $R^4$ is —H. In some embodiments, $R^4$ is halogen. In some embodiments, $R^4$ is —F. In some embodiments, $R^4$ is —Cl. In some embodiments, $R^4$ is —Br. In some embodiments, $R^4$ is —I. In some embodiments, $R^4$ is —CN. In some embodiments, $R^4$ is —OR wherein R is as defined and described herein. In some embodiments, $R^4$ is —OCH$_3$. In some embodiments, $R^4$ is fluoro. In some embodiments, $R^4$ is —OEt. In some embodiments, each of $R^1$ and $R^4$ is —H.

In some embodiments, $R^4$ is R as described herein. In some embodiments, $R^4$ is optionally substituted C$_{1-6}$ aliphatic. In some embodiments, $R^4$ is methyl. In some embodiments, $R^4$ is —CF$_3$.

In some embodiments, $R^4$ is R wherein R is an optionally substituted cyclic group, e.g., cycloaliphatic, heterocyclyl, phenyl aryl, heteroaryl, etc.

In some embodiments, $R^4$ is optionally substituted 3-10 membered saturated or partially unsaturated carbocyclyl. In some embodiments, $R^4$ is optionally substituted 3-7 membered saturated or partially unsaturated carbocyclyl. In some embodiments, $R^4$ is optionally substituted 3-membered saturated or partially unsaturated carbocyclyl. In some embodiments, $R^4$ is optionally substituted 4-membered saturated or partially unsaturated carbocyclyl. In some embodiments, $R^4$ is optionally substituted 5-membered saturated or partially unsaturated carbocyclyl. In some embodiments, $R^4$ is optionally substituted 6-membered saturated or partially unsaturated carbocyclyl. In some embodiments, $R^4$ is optionally substituted 7-membered saturated or partially unsaturated carbocyclyl. In some embodiments, $R^4$ is saturated. In some embodiments, $R^4$ is partially unsaturated. In some embodiments, $R^4$ is optionally substituted cyclopropyl. In some embodiments, $R^4$ is optionally substituted cyclobutyl. In some embodiments, $R^4$ is optionally substituted cyclopentyl. In some embodiments, $R^4$ is optionally substituted cyclohexyl. In some embodiments, $R^4$ is optionally substituted cycloheptyl. In some embodiments, $R^4$ is cyclopropyl. In some embodiments, $R^4$ is cyclobutyl. In some embodiments, $R^4$ is cyclopentyl. In some embodiments, $R^4$ is cyclohexyl. In some embodiments, $R^4$ cycloheptyl.

In some embodiments, $R^4$ is optionally substituted 4-20 membered bicyclic or polycyclic saturated or partially unsaturated carbocyclyl. In some embodiments, $R^4$ is optionally substituted 4-12 membered bicyclic saturated or partially unsaturated carbocyclyl. In some embodiments, $R^4$ is 4-, 5-, 6-, 7-, 8-, 9-, 10-, 11- or 12-membered. In some embodiments, $R^4$ is saturated. In some embodiments, $R^4$ is partially unsaturated.

In some embodiments, $R^4$ is optionally substituted 3-10 membered saturated or partially unsaturated heterocyclyl having 1-5 heteroatoms independently selected from nitrogen, oxygen or sulfur. In some embodiments, $R^4$ is optionally substituted 3-7 membered saturated or partially unsaturated heterocyclyl having 1-2 heteroatoms independently selected from nitrogen, oxygen or sulfur. In some embodiments, $R^4$ is optionally substituted 5-7 membered saturated or partially unsaturated heterocyclyl having 1-2 heteroatoms independently selected from nitrogen, oxygen or sulfur. In some embodiments, $R^4$ is 5-7 membered saturated or partially unsaturated heterocyclyl having 1-2 heteroatoms independently selected from nitrogen, oxygen or sulfur. In some embodiments, $R^4$ is optionally substituted 3-membered saturated or partially unsaturated heterocyclyl having 1-2 heteroatoms independently selected from nitrogen, oxygen or sulfur. In some embodiments, $R^4$ is optionally substituted 4-membered saturated or partially unsaturated heterocyclyl having 1-2 heteroatoms independently selected from nitrogen, oxygen or sulfur. In some embodiments, $R^4$ is optionally substituted 5-membered saturated or partially unsaturated heterocyclyl having 1-2 heteroatoms independently selected from nitrogen, oxygen or sulfur. In some embodiments, $R^4$ is optionally substituted 6-membered saturated or partially unsaturated heterocyclyl having 1-2 heteroatoms independently selected from nitrogen, oxygen or sulfur. In some embodiments, $R^4$ is optionally substituted 7-membered saturated or partially unsaturated heterocyclyl having 1-2 heteroatoms independently selected from nitrogen, oxygen or sulfur. In some embodiments, $R^4$ is optionally substituted heterocyclyl having one heteroatom. In some embodiments, at least one heteroatom is nitrogen. In some embodiments, each heteroatom is nitrogen. In some embodiments, at least one heteroatom is sulfur. In some embodiments, at least one heteroatom is oxygen. In some embodiments, $R^4$ is optionally substituted

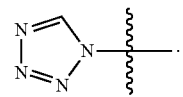

In some embodiments, $R^4$ is

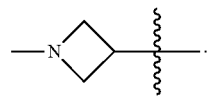

In some embodiments, $R^4$ is optionally substituted

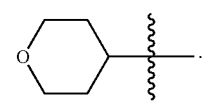

In some embodiments, $R^4$ is

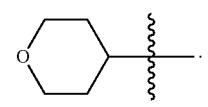

In some embodiments, $R^4$ is optionally substituted 4-20 membered bicyclic or polycyclic saturated or partially unsaturated heterocyclyl having 1-10 heteroatoms independently selected from nitrogen, oxygen or sulfur. In some embodiments, $R^4$ is optionally substituted 4-12 membered bicyclic saturated or partially unsaturated heterocyclyl having 1-5 heteroatoms independently selected from nitrogen, oxygen or sulfur. In some embodiments, $R^4$ is 4-, 5-, 6-, 7-, 8-, 9-, 10-, 11- or 12-membered. In some embodiments, $R^4$ is saturated. In some embodiments, $R^4$ is partially unsaturated. In some embodiments, at least one heteroatom is nitrogen. In some embodiments, each heteroatom is nitrogen. In some embodiments, at least one heteroatom is sulfur. In some embodiments, at least one heteroatom is oxygen.

In some embodiments, $R^4$ is an optionally substituted 5-6 membered heteroaryl with 1-4 heteroatoms independently selected from nitrogen, oxygen or sulfur. In some embodiments, $R^4$ is 5-membered heteroaryl with 1-4 heteroatoms independently selected from nitrogen, oxygen or sulfur. In some embodiments, $R^4$ is 6-membered heteroaryl with 1-4 heteroatoms independently selected from nitrogen, oxygen or sulfur. In some embodiments, such $R^4$ has 1 heteroatom. In some embodiments, such $R^4$ has 2 heteroatoms. In some embodiments, such $R^4$ has 3 heteroatoms. In some embodiments, such $R^4$ has 4 heteroatoms. In some embodiments, at least one heteroatom is nitrogen. In some embodiments, each heteroatom is nitrogen. In some embodiments, at least one heteroatom is sulfur. In some embodiments, at least one heteroatom is oxygen. In some embodiments, each heteroatom is nitrogen. In some embodiments, $R^4$ is optionally substituted

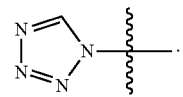

In some embodiments, $R^4$ is

In some embodiments, each heteroatom is nitrogen. In some embodiments, $R^4$ is optionally substituted

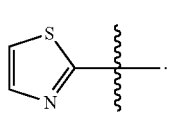 [SMILES: *c1nccs1]

In some embodiments, $R^4$ is

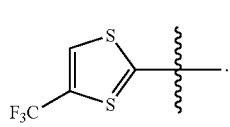

In some embodiments, $R^4$ is optionally substituted

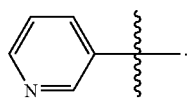

In some embodiments, $R^4$ is

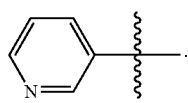

In some embodiments, $R^4$ is optionally substituted

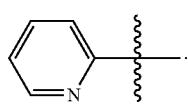

In some embodiments, $R^4$ is In some embodiments, $R^4$ is optionally substituted

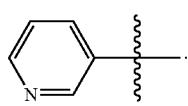

In some embodiments, $R^4$ is

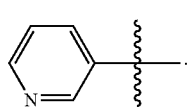 [SMILES: *c1cccnc1]

In some embodiments, $R^4$ is optionally substituted

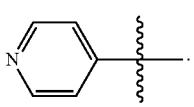

In some embodiments, $R^4$ is

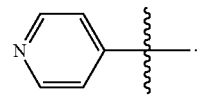

In some embodiments, $R^4$ is optionally substituted

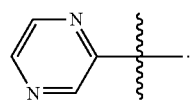

In some embodiments, $R^4$ is

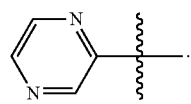

In some embodiments, $R^4$ is optionally substituted

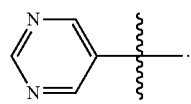

In some embodiments, $R^4$ is

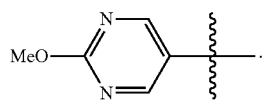

In some embodiments, $R^4$ is optionally substituted phenyl. In some embodiments, $R^4$ is phenyl. In some embodiments, $R^4$ is 2-cyanophenyl. In some embodiments, $R^4$ is 3-cyanophenyl. In some embodiments, $R^4$ is 4-cyanophenyl. In some embodiments, $R^4$ is 2-chlorophenyl. In some embodiments, $R^4$ is 3-chlorophenyl. In some embodiments, $R^4$ is 4-chlorophenyl. In some embodiments, $R^4$ is 2,4-dimethoxyphenyl. In some embodiments, $R^4$ is 2,4-difluorophenyl. In some embodiments, $R^4$ is 2-methoxyphenyl. In some embodiments, $R^4$ is 3-methoxyphenyl. In some embodiments, $R^4$ is 4-methoxyphenyl. In some embodiments, $R^4$ is 4-ethoxyphenyl. In some embodiments, $R^4$ is

In some embodiments, $R^4$ is 4-cyclopropylphenyl. In some embodiments, $R^4$ is 3-trifluoromethoxyphenyl.

In some embodiments, $R^4$ is optionally substituted 10-14 membered bicyclic or polycyclic aryl.

In some embodiments, $R^4$ is optionally substituted 8-20 membered bicyclic or polycyclic heteroaryl having 1-10 heteroatoms independently selected from nitrogen, oxygen, or sulfur. In some embodiments, $R^4$ is optionally substituted 8-10 membered bicyclic heteroaryl having 1-5 heteroatoms independently selected from nitrogen, oxygen, or sulfur. In some embodiments, R$^4$ is 8-10 membered bicyclic heteroaryl having 1-5 heteroatoms independently selected from nitrogen, oxygen, or sulfur. In some embodiments, R$^4$ is optionally substituted 8-10 membered bicyclic heteroaryl having 1 heteroatom independently selected from nitrogen, oxygen, or sulfur. In some embodiments, R$^4$ is optionally substituted 8-10 membered bicyclic heteroaryl having 2 heteroatoms independently selected from nitrogen, oxygen, or sulfur. In some embodiments, R$^4$ is optionally substituted 8-10 membered bicyclic heteroaryl having 3 heteroatoms independently selected from nitrogen, oxygen, or sulfur. In some embodiments, R$^4$ is optionally substituted 8-10 membered bicyclic heteroaryl having 4 heteroatoms independently selected from nitrogen, oxygen, or sulfur. In some embodiments, R$^4$ is optionally substituted 8-10 membered bicyclic heteroaryl having 5 heteroatoms independently selected from nitrogen, oxygen, or sulfur. In some embodiments, at least one heteroatom is nitrogen. In some embodiments, each heteroatom is nitrogen. In some embodiments, at least one heteroatom is sulfur. In some embodiments, at least one heteroatom is oxygen. In some embodiments, R$^4$ is 8-10 membered bicyclic heteroaryl having 2 nitrogen atoms. In some embodiments, R$^4$ is 8-membered. In some embodiments, R$^4$ is 9-membered. In some embodiments, R$^4$ is 10-membered. In some embodiments, a monocyclic unit is 5-membered. In some embodiments, a monocyclic unit is 6-membered. In some embodiments, R$^4$ is optionally substituted

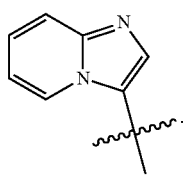 [SMILES: *c1cnc2ccccn12]

In some embodiments, R$^4$ is

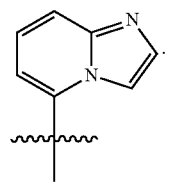

In some embodiments, R$^4$ is optionally substituted

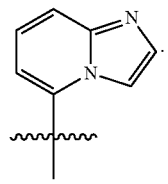 [SMILES: *c1cccc2nccn12]

In some embodiments, R$^4$ is

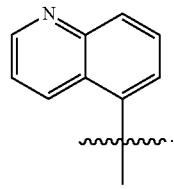 [SMILES: *c1cccc2ncccc12]

In some embodiments, R$^4$ is optionally substituted

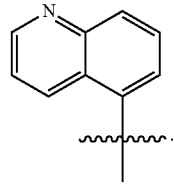 [SMILES: *c1cccc2ncccc12]

In some embodiments, R$^4$ is

In some embodiments, R$^4$ is —S(O)$_2$OR. In some embodiments, R$^4$ is —S(O)$_2$OH.

In some embodiments, R$^4$ is —NRS(O)$_2$R, wherein each R is independently as described herein. In some embodiments, R$^4$ is —NHS(O)$_2$R. In some embodiments, R$^4$ is —NHS(O)$_2$CH$_3$.

In some embodiments, R$^4$ is —S(O)$_2$R, wherein R is as described herein. In some embodiments, R$^4$ is —S(O)$_2$CH$_3$.

In some embodiments, R$^4$ is selected from those depicted in Table 1, below.

In some embodiments, R$^5$ is R as defined and described herein. In some embodiments, R is an optionally substituted monocyclic, bicyclic or polycyclic group. In some embodiments, R is an optionally substituted bicyclic or polycyclic group, wherein each monocyclic unit is independently an optionally substituted 3-10 membered saturated, partially unsaturated, or aromatic monocyclic ring having 0-5 heteroatoms. In some embodiments, R is an optionally substituted bicyclic or polycyclic group, wherein each monocyclic unit is independently an optionally substituted group selected from a 3-10 membered cycloaliphatic ring, a phenyl ring, a 3-10 membered heterocyclic ring having 1-5 heteroatoms, and a 5-6 membered heteroaryl ring having 1-5 heteroatoms. In some embodiments, R$^5$ is optionally substituted In some embodiments, R⁵ is

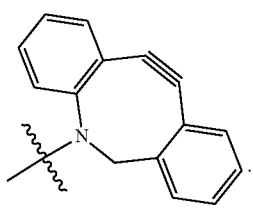 [SMILES: *N1Cc2ccccc2C#Cc2ccccc21]

In some embodiments, R⁵ is

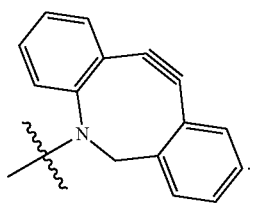 [SMILES: *N1Cc2ccccc2C#Cc2ccccc21]

In some embodiments, R⁵ is

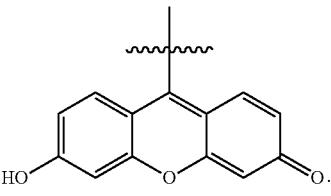 [SMILES: *c1c2ccc(=O)cc-2oc2cc(O)ccc12]

In some embodiments, R⁵ is optionally substituted phenyl. In some embodiments, R⁵ is phenyl. In some embodiments, R⁵ is 4-methylphenyl.

In some embodiments, R⁵ is —H. In some embodiments, R⁵ is an optionally substituted ring group. In some embodiments, R⁵ is optionally substituted 3-10 membered heterocyclyl having 1-5 heteroatoms. In some embodiments, R⁵ is optionally substituted

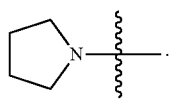 [SMILES: *N1CCCC1]

In some embodiments, R⁵ is optionally substituted

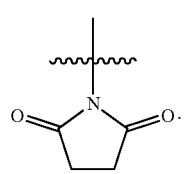 [SMILES: *N1C(=O)CCC1=O]

In some embodiments, R⁵ is

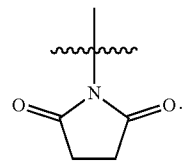

In some embodiments, R⁵ is or comprises optionally substituted CH₂=CH—C(O)—. In some embodiments, R⁵ is optionally substituted

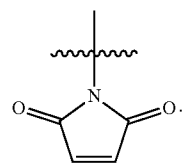

In some embodiments, R⁵ is

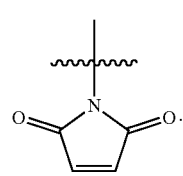

In some embodiments, R⁵ is —OR wherein R is as defined and described herein. In some embodiments, R⁵ is —C(O)OR wherein R is as defined and described herein. In some embodiments, R is optionally substituted

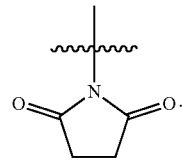

In some embodiments, R is

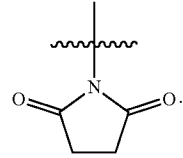

In some embodiments, R⁵ is optionally substituted

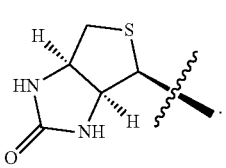

In some embodiments, $R^5$ is

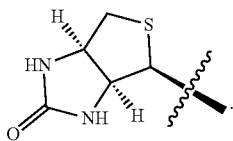

In some embodiments, $R^5$ is

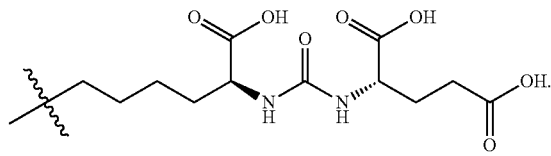 [SMILES: *CCCC[C@H](NC(=O)N[C@@H](CCC(=O)O)C(=O)O)C(=O)O]

In some embodiments, $R^5$ is

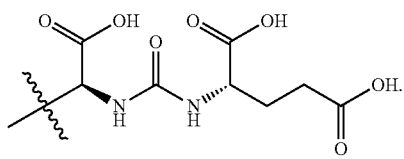 [SMILES: *[C@H](NC(=O)N[C@@H](CCC(=O)O)C(=O)O)C(=O)O]

In some embodiments, $R^5$ is —NRS(O)$_2$R, wherein each R is independently as described herein. In some embodiments, $R^5$ is —NHS(O)$_2$R. In some embodiments, $R^5$ is —NHS(O)$_2$CH$_3$.

In some embodiments, $R^5$ is —S(O)$_2$R, wherein R is as described herein. In some embodiments, $R^5$ is —S(O)$_2$CH$_3$. In some embodiments, $R^5$ is —S(O)$_2$R, wherein R is optionally substituted phenyl. In some embodiments, R is 4-methylphenyl.

In some embodiments, $R^5$ is a reactive group that can be utilized for conjugation with another agent, e.g., a targeting moiety. In some embodiments, $R^5$ is —COOH or an activated form thereof. In some embodiments, $R^5$ is

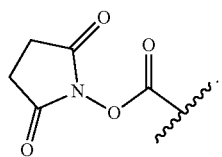 [SMILES: *C(=O)ON1C(=O)CCC1=O]

In some embodiments, $R^5$ is —CN. In some embodiments, $R^5$ is or comprises —N(R)$_2$. In some embodiments, $R^5$ is —N(R)$_2$. In some embodiments, $R^5$ is —NHR. In some embodiments, $R^5$ is —NH$_2$. In some embodiments, $R^5$ is —N$_3$. In some embodiments, $R^5$ is or comprises —C≡C—. In some embodiments, $R^5$ is —C≡CH. In some embodiments, $R^5$ is

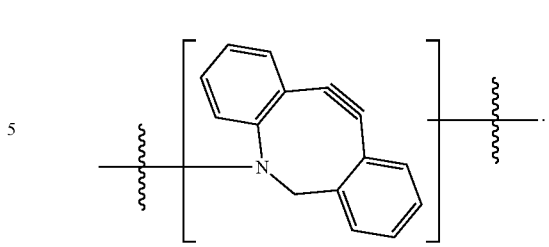

In some embodiments, $R^5$ is

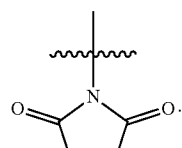

In some embodiments, $R^5$ is —SH.

In some embodiments, $R^5$ is selected from those depicted in Table 1, below.

In some embodiments, each of $R^1$, $R^2$ and $R^3$ is —H. In some embodiments, each of $R^1$, $R^2$, $R^3$ and $R^4$ is —H. In some embodiments, each of $R^1$, $R^2$, $R^3$, $R^4$ and $R^5$ is —H.

In some embodiments, m is 0, 1, 2, 3, 4 or 5. In some embodiments, m is 0. In some embodiments, m is 1. In some embodiments, m is 2. In some embodiments, m is 3. In some embodiments, m is 4. In some embodiments, m is 5.

In some embodiments, m is selected from those depicted in Table 1, below.

In some embodiments, each instance of n is independently selected from 1, 2, 3, 4, 5, 6, 7, 8, 9, or 10.

In some embodiments, each n is independently 1-50. In some embodiments, n is 1-50. In some embodiments, n is 1-40. In some embodiments, n is 1-30. In some embodiments, n is 1-25. In some embodiments, n is 1-20. In some embodiments, n is 1-15. In some embodiments, n is 1-12. In some embodiments, n is 1-10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20.

In some embodiments, n is selected from those depicted in Table 1, below.

In some embodiments, p is 0, 1, 2, 3, 4, or 5. In some embodiments, p is 0, 1, or 2.

In some embodiments, p is 0. In some embodiments, p is 1. In some embodiments, p is 2. In some embodiments, p is 3. In some embodiments, p is 4. In some embodiments, p is 5.

In some embodiments, p is selected from those depicted in Table 1, below.

In some embodiments, q is 0, 1, 2, 3, 4, or 5. In some embodiments, q is 0, 1, 2, 3, or 4.

In some embodiments, q is 0. In some embodiments, q is 1. In some embodiments, q is 2. In some embodiments, q is 3. In some embodiments, q is 4. In some embodiments, q is 5.

In some embodiments, q is selected from those depicted in Table 1, below.

In some embodiments, r is 0 or 1, wherein when r is 0,

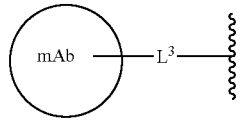

is directly attached to

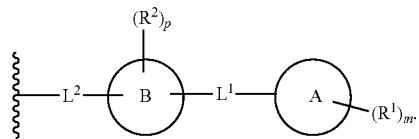

In some embodiments, r is 0 and

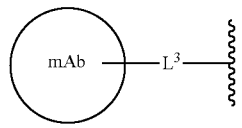

is directly attached to

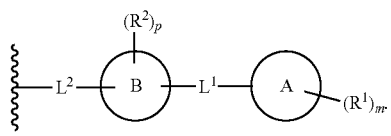

In some embodiments, r is 1.

In some embodiments, r is selected from those depicted in Table 1, below.

In some embodiments, s is 1, 2, 3, 4, 5, or 6.

In some embodiments, s is 1. In some embodiments, s is 2. In some embodiments, s is 3. In some embodiments, s is 4. In some embodiments, s is 5. In some embodiments, s is 6.

In some embodiments, s is selected from those depicted in Table 1, below.

In some embodiments, Ring B is

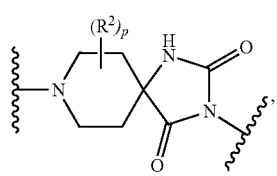

and the 5-membered ring is bonded to $L^1$.

In certain embodiments, the present invention provides a compound of formula I, wherein Ring B is

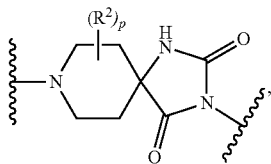

thereby forming a compound of formula I-a:

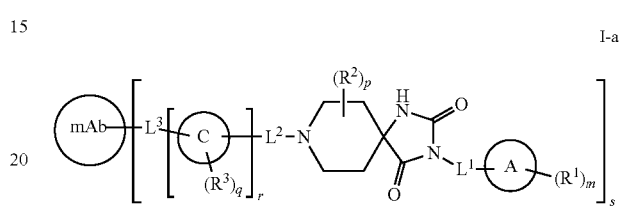

or a pharmaceutically acceptable salt thereof, wherein each of Ring A, Ring C, $R^1$, $R^2$, $R^3$, $L^1$, $L^2$, $L^3$, mAb, m, p, q, r, and s is as defined above and described in embodiments herein, both singly and in combination.

In some embodiments, Ring B is

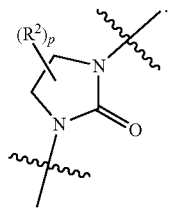

In some embodiments, $L^1$ is optionally substituted —$CH_2$—. In some embodiments, $L^2$ is a covalent bond. In some embodiments, $L^1$ is optionally substituted —$CH_2$—, and $L^2$ is a covalent bond.

In some embodiments, Ring B is

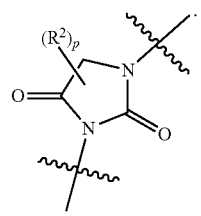

In some embodiments, both $L^1$ and $L^2$ are covalent bond.

In some embodiments, Ring B is and the nitrogen atom is bonded to $L^1$. In some embodiments, $L^2$ is —NHC(O)—, wherein —C(O)— is bonded to Ring B.

In certain embodiments, the present invention provides a compound of formula I, wherein Ring B is

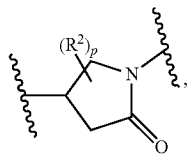

$L^1$ is a covalent bond, and $L^2$ is —NHC(O)—, thereby forming a compound of formula I-b:

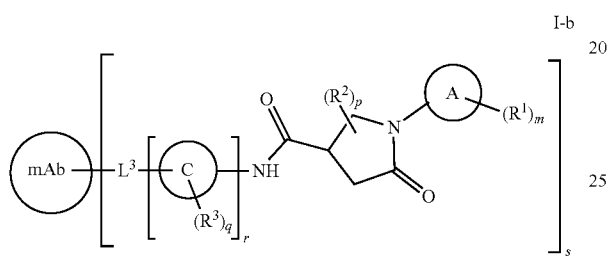

I-b or a pharmaceutically acceptable salt thereof, wherein each of Ring A, Ring C, $R^1$, $R^2$, $R^3$, $L^3$, mAb, m, p, q, r, and s is as defined above and described in embodiments herein, both singly and in combination.

In certain embodiments, the present invention provides a compound of formula II:

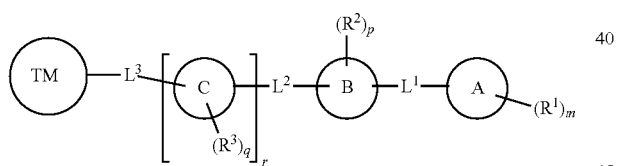

II or a pharmaceutically acceptable salt thereof, wherein each variable is independently as defined and described herein. In some embodiments, a compound of formula C is a compound of formula II.

In some embodiments, in a compound of the present disclosure (e.g., a compound of formula II):

Ring A is selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, 8-10 membered bicyclic heteroaryl having 1-5 heteroatoms independently selected from nitrogen, oxygen, or sulfur;

Ring B is a bivalent ring selected from phenylenyl, 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups;

Ring C is a bivalent ring selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur;

$L^1$ is a covalent bond, —CH$_2$—, —CH(R)—, or —C(R)$_2$—;

$L^2$ is a covalent bond, —NHC(O)—, —C(O)NH—, —CH$_2$—, —CH(R)—, —C(R)$_2$—, —C(O)—, or —S(O)$_2$—;

$L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

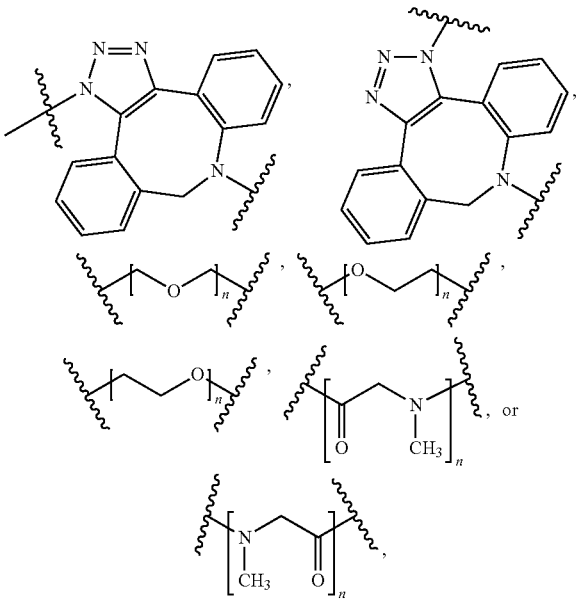

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups;

TM is a targeting moiety;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each instance of $R^1$, and $R^3$ is independently hydrogen, halogen, —CN, —$NO_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R;

each instance of $R^2$ is independently hydrogen, halogen, —CN, —$NO_2$, or $C_{1-3}$ aliphatic;

m is 0, 1, 2, 3, 4 or 5;

each instance of n is independently selected from 1, 2, 3, 4, 5, 6, 7, 8, 9, or 10;

p is 0, 1, or 2;

q is 0, 1, 2, 3, or 4; and r is 0 or 1, wherein when r is 0,

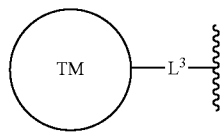

is directly attached to

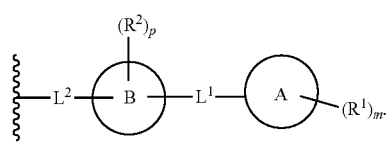

In some embodiments, TM is a targeting moiety. In some embodiments, TM is or comprises an adjuvant. In some embodiments, TM is or comprises a cytokine. In some embodiments, TM is or comprises a virus. In some embodiments, TM is or comprises a oncolytic virus. In some embodiments, TM is or comprises a vaccine. In some embodiments, TM is or comprises a therapeutic agent, e.g., a therapeutic antibody or a fragment thereof. In some embodiments, TM is or comprises a cellular therapeutic agent. In some embodiments, a therapeutic agent is a cancer therapeutic agent. In some embodiments, TM is or comprises a bi-specific molecules.

A targeting moiety (TM) is a moiety that can bind a target, is a detectable moiety, or is capable of forming a covalent bond or triazole ring. In some embodiments, TM is a reactive moiety that can react with one or more reactive groups of a target, e.g., an amino group, thiol group, and/or an acid group of a peptide or protein (e.g., an antibody or a fragment thereof). one that can react with —SH.

In some embodiments, a TM is

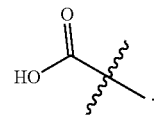

In some embodiments, TM is or comprises an activated carboxylic acid group. In some embodiments, a TM is

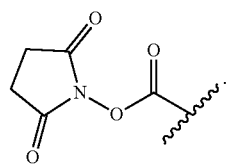 [SMILES: *C(=O)ON1C(=O)CCC1=O]

In some embodiments, such a group reacts with an amino group under suitable conditions. In some embodiments, TM is or comprises an electrophilic group, e.g., in some embodiments, a TM is

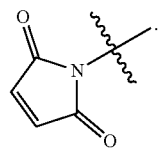 [SMILES: *N1C(=O)C=CC1=O]

In some embodiments, such a group reacts with a —SH group under suitable conditions. In some embodiments, TM is or comprises a dienophile or dipolarophile group. In some embodiments, TM comprises —C≡C—. In some embodiments, TM comprises —C≡C—. In some embodiments, TM is or comprises —C≡CH. In some embodiments, TM is —C≡CH. In some embodiments, TM is or comprises

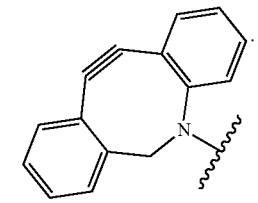 [SMILES: *N1Cc2ccccc2C#Cc2ccccc21]

In some embodiments, a TM is

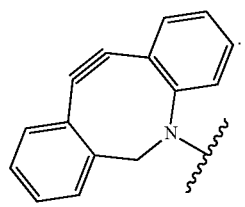

In some embodiments, such a group can undergo a cycloaddition reaction, e.g., a click chemistry reaction, under suitable conditions. In some embodiments, TM is or comprises a diene or a 1,3-dipole, each of which may independently contain one or more heteroatoms. In some embodiments, TM is or comprises —N₃. In some embodiments, such a group can undergo a cycloaddition reaction, e.g., a click chemistry reaction, under suitable conditions.

In some embodiments, TM is a or comprises a detectable moiety.

In some embodiments, a TM comprises

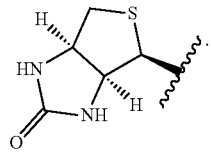

In some embodiments, a TM comprises

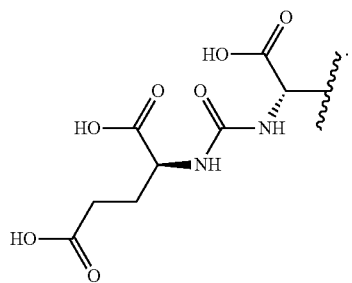 [SMILES: *[C@H](NC(=O)N[C@@H](CCC(=O)O)C(=O)O)C(=O)O]

In some embodiments, a TM comprises

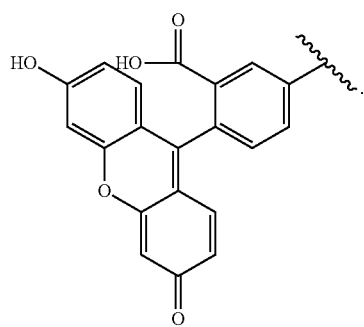 [SMILES: *c1ccc(-c2c3ccc(=O)cc-3oc3cc(O)ccc23)c(C(=O)O)c1]

In some embodiments, a TM is

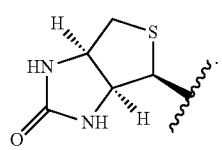

In some embodiments, a TM is

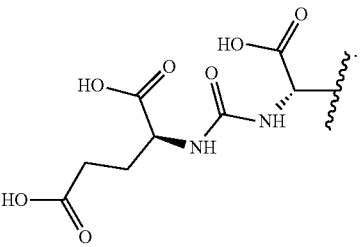 [SMILES: *[C@H](NC(=O)N[C@@H](CCC(=O)O)C(=O)O)C(=O)O]

In some embodiments, a TM is

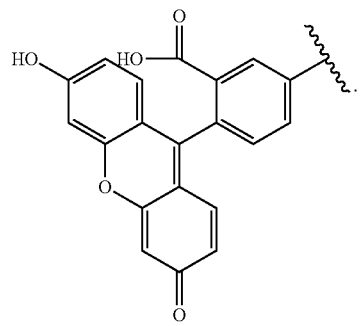 [SMILES: *c1ccc(-c2c3ccc(=O)cc-3oc3cc(O)ccc23)c(C(=O)O)c1]

In some embodiments, TM is selected from those depicted in Table 1, below.

In some embodiments,

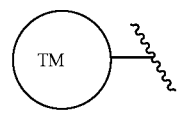

indicates attachment of a moiety (e.g.,

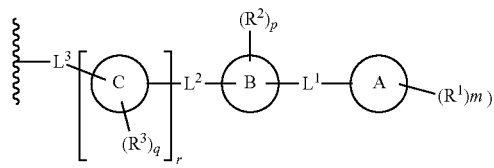

to any modifiable C, N, O or S atom of the targeting moiety (TM).

As defined generally above, and described in embodiments herein, Ring A, Ring B, Ring C, $L^1$, $L^2$, $L^3$, R, $R^1$, $R^2$, $R^3$, m, n, p, q, or r of a compound of formula II are as those described for a compound of formula I.

In some embodiments, Ring A, Ring B, Ring C, $L^1$, $L^2$, $L^3$, R, $R^1$, $R^2$, $R^3$, m, n, p, q, or r of a compound of formula II is selected from those depicted in Table 1, below.

In certain embodiments, the present invention provides a compound of formula II, wherein Ring B is

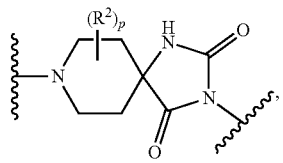

thereby forming a compound of formula II-a:

II-a

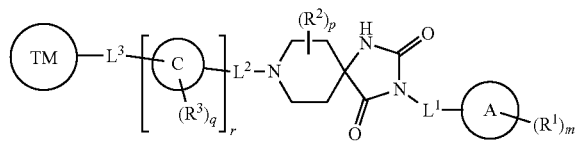

or a pharmaceutically acceptable salt thereof, wherein each of Ring A, Ring C, R¹, R², R³, L¹, L², L³, TM, m, p, q, and r is as defined above and described in embodiments herein, both singly and in combination.

In certain embodiments, the present invention provides a compound of formula II, wherein Ring B is

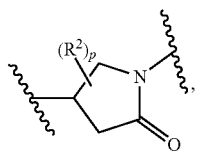

L¹ is a covalent bond, and L² is —NHC(O)—, thereby forming a compound of formula II-b:

II-b

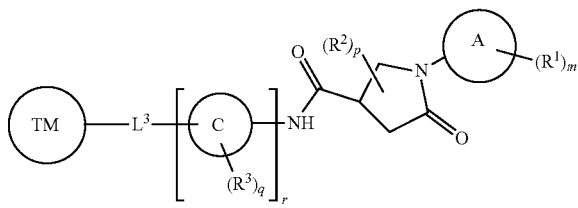

or a pharmaceutically acceptable salt thereof, wherein each of Ring A, Ring C, R¹, R², R³, L³, TM, m, p, q, and r is as defined above and described in embodiments herein, both singly and in combination.

In some embodiments, a compound of formula C, C-I, C-II, C-IV, etc., has the structure of formula II-a. In some embodiments, a compound of formula C, C-I, C-II, C-VII, etc., has the structure of formula II-b.

Exemplary compounds of the invention are set forth in Table 1, below.

In certain embodiments, the present disclosure provides a compound of formula III:

III

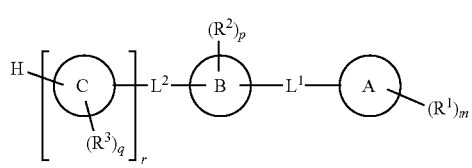

or a pharmaceutically acceptable salt thereof, wherein each variable is independently as defined and described herein.

In some embodiments, in a provided compound of the present disclosure (e.g., a compound of formula A, a compound of formula III, etc.), H is hydrogen;

Ring A is selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, 8-10 membered bicyclic heteroaryl having 1-5 heteroatoms independently selected from nitrogen, oxygen, or sulfur;

Ring B is a bivalent ring selected from phenylenyl, 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups;

Ring C is a bivalent ring selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur;

L¹ is a covalent bond, —CH₂—, —CH(R)—, or —C(R)₂—;

L² is a covalent bond, —NHC(O)—, —C(O)NH—, —CH₂—, —CH(R)—, —C(R)₂—, —C(O)—, or —S(O)₂—;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each instance of R¹, and R³ is independently hydrogen, halogen, —CN, —NO₂, —C(O)R, —C(O)OR, —C(O)N(R)₂, —N(R)₂, —NRC(O)R, —NRC(O)N(R)₂, —NRC(O)OR, —NRS(O)₂R, —NRS(O)₂N(R)₂, —OR, —P(O)(R)$_2$, —SR, —S(O)R, —S(O)$_2$R, —S(O)(NH)R, —S(O)$_2$N(R)$_2$, or R;

each instance of R$^2$ is independently hydrogen, halogen, —CN, —NO$_2$, or C$_{1-3}$ aliphatic;

m is 0, 1, 2, 3, 4 or 5;

each instance of n is independently selected from 1, 2, 3, 4, 5, 6, 7, 8, 9, or 10;

p is 0, 1, or 2;

q is 0, 1, 2, 3, or 4; and r is 0 or 1, wherein when r is 0,

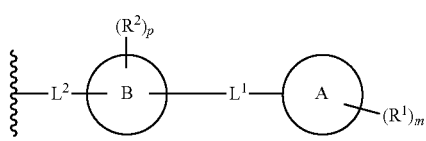

is bound to hydrogen,

In some embodiments, in a provided compound of the present disclosure (e.g., a compound of formula A, a compound of formula III, etc.), H is hydrogen;

L$^1$ is a covalent bond, —CH$_2$—, —CH(R)—, or —C(R)$_2$—;

L$^2$ is a covalent bond, —NHC(O)—, —C(O)NH—, —CH$_2$—, —CH(R)—, —C(R)$_2$—, —C(O)—, or —S(O)$_2$—; and each R is independently hydrogen or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, in a provided compound of the present disclosure (e.g., a compound of formula A, a compound of formula III, etc.), H is hydrogen;

L$^1$ is a covalent bond, —CH$_2$—, —CH(R)—, or —C(R)$_2$—;

L$^2$ is a covalent bond, —NHC(O)—, —C(O)NH—, —CH$_2$—, —CH(R)—, —C(R)$_2$—, —C(O)—, or —S(O)$_2$—;

L$^3$ is a covalent bond or a bivalent, saturated or unsaturated, straight or branched C$_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

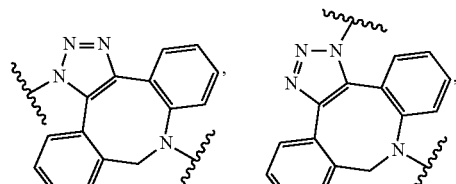

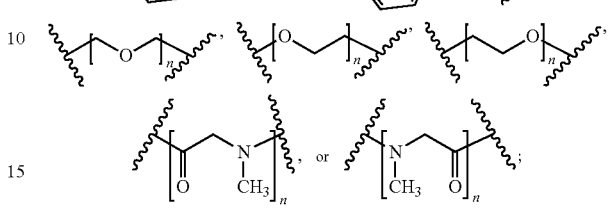

each instance of n is independently selected from 1, 2, 3, 4, 5, 6, 7, 8, 9, or 10;

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups; and each R is independently hydrogen or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In certain embodiments, the present disclosure provides a compound of formula IV:

IV

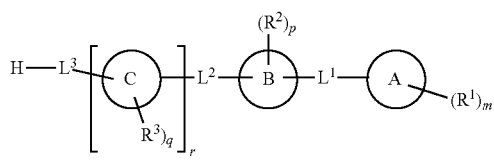

or a pharmaceutically acceptable salt thereof, wherein each variable is independently as defined and described herein.

In some embodiments, in a compound of the present disclosure (e.g., a compound of formula A, III, IV, etc.), H is hydrogen;

Ring A is selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, 8-10 membered bicyclic heteroaryl having 1-5 heteroatoms independently selected from nitrogen, oxygen, or sulfur;

Ring B is a bivalent ring selected from phenylenyl, 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups;

Ring C is a bivalent ring selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur;

$L^1$ is a covalent bond, —CH$_2$—, —CH(R)—, or —C(R)$_2$—;

$L^2$ is a covalent bond, —NHC(O)—, —C(O)NH—, —CH$_2$—, —CH(R)—, —C(R)$_2$—, —C(O)—, or —S(O)$_2$—;

$L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

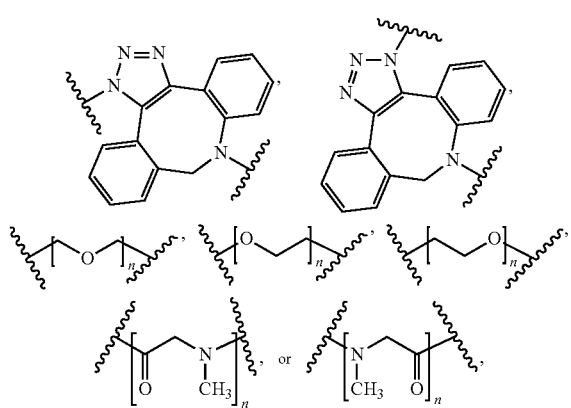

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each instance of $R^1$, and $R^3$ is independently hydrogen, halogen, —CN, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R;

each instance of $R^2$ is independently hydrogen, halogen, —CN, —NO$_2$, or $C_{1-3}$ aliphatic;

m is 0, 1, 2, 3, 4 or 5;

each instance of n is independently selected from 1, 2, 3, 4, 5, 6, 7, 8, 9, or 10;

p is 0, 1, or 2;

q is 0, 1, 2, 3, or 4; and r is 0 or 1, wherein when r is 0,

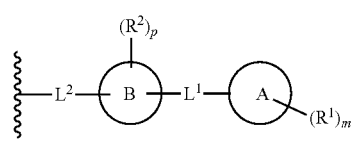

is bound to

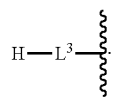

In some embodiments, a compound of formula A is a compound of formula III. In some embodiments, a compound of formula A is a compound of formula IV.

In some embodiments, in a compound, e.g., a compound of formula I, C-I, etc.:

- Ring A is selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, or 8-10 membered bicyclic heteroaryl having 1-5 heteroatoms independently selected from nitrogen, oxygen, or sulfur;
- Ring B is a bivalent ring selected from phenylenyl, 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups;
- Ring C is a bivalent ring selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur;
- $L^1$ is a covalent bond, —$CH_2$—, —CH(R)—, or —C(R)$_2$—;
- $L^2$ is a covalent bond, —NHC(O)—, —C(O)NH—, —$CH_2$—, —CH(R)—, —C(R)$_2$—, —C(O)—, or —S(O)$_2$—;
- $L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

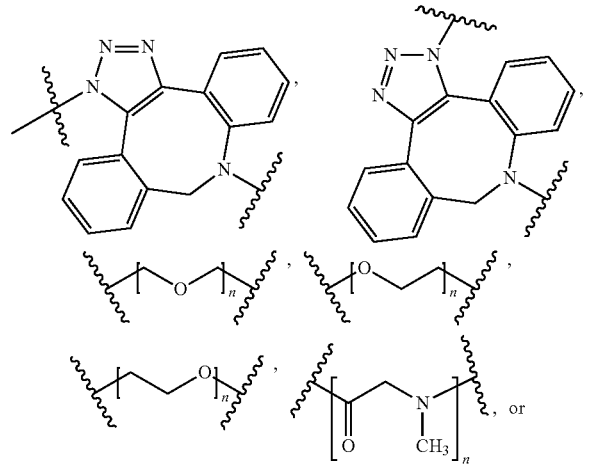

-continued

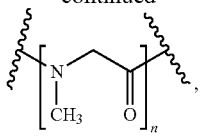

wherein:
- each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups;
- mAb is a monoclonal antibody;
- each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;
- each instance of $R^1$, and $R^3$ is independently hydrogen, halogen, —CN, —$NO_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R;
- each instance of $R^2$ is independently hydrogen, halogen, —CN, —$NO_2$, or $C_{1-3}$ aliphatic;
- m is 0, 1, 2, 3, 4 or 5;
- each instance of n is independently selected from 1, 2, 3, 4, 5, 6, 7, 8, 9, or 10;
- p is 0, 1, or 2;
- q is 0, 1, 2, 3, or 4;
- r is 0 or 1, wherein when r is 0,

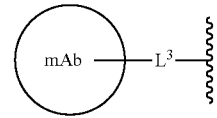

is directly attached to

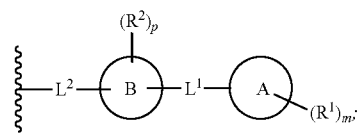

and
s is 1, 2, 3, 4, 5, or 6.

In some embodiments, in a provided compound of the present disclosure (e.g., a compound of formula A, a compound of formula III, etc.), H is hydrogen;

$L^1$ is a covalent bond, —$CH_2$—, —CH(R)—, or —C(R)$_2$—;

$L^2$ is a covalent bond, —NHC(O)—, —C(O)NH—, —$CH_2$—, —CH(R)—, —C(R)$_2$—, —C(O)—, or —S(O)$_2$—; and each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, in a provided compound of the present disclosure (e.g., a compound of formula A, a compound of formula III, etc.), H is hydrogen;

$L^1$ is a covalent bond, —$CH_2$—, —CH(R)—, or —C(R)$_2$—;

$L^2$ is a covalent bond, —NHC(O)—, —C(O)NH—, —$CH_2$—, —CH(R)—, —C(R)$_2$—, —C(O)—, or —S(O)$_2$—;

$L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

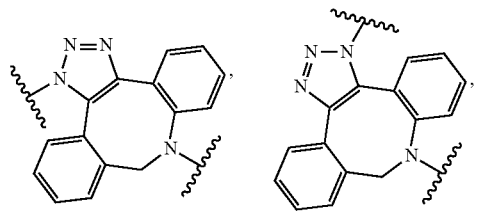

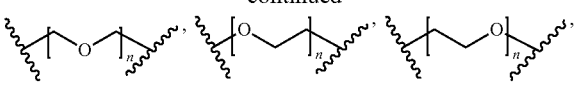

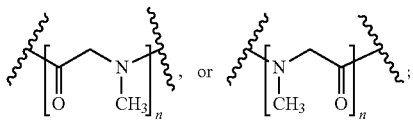

each instance of n is independently selected from 1, 2, 3, 4, 5, 6, 7, 8, 9, or 10;

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups; and each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

Certain compounds are listed as examples in Table 1:

TABLE 1
Exemplary compounds
| Compound No. | Structure |
|---|---|
| I-1 | 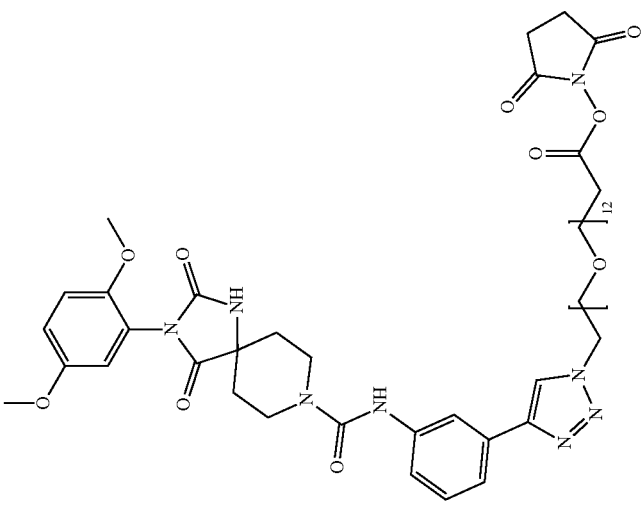 |

TABLE 1-continued
Exemplary compounds
| Compound No. | Structure |
|---|---|
| I-2 | 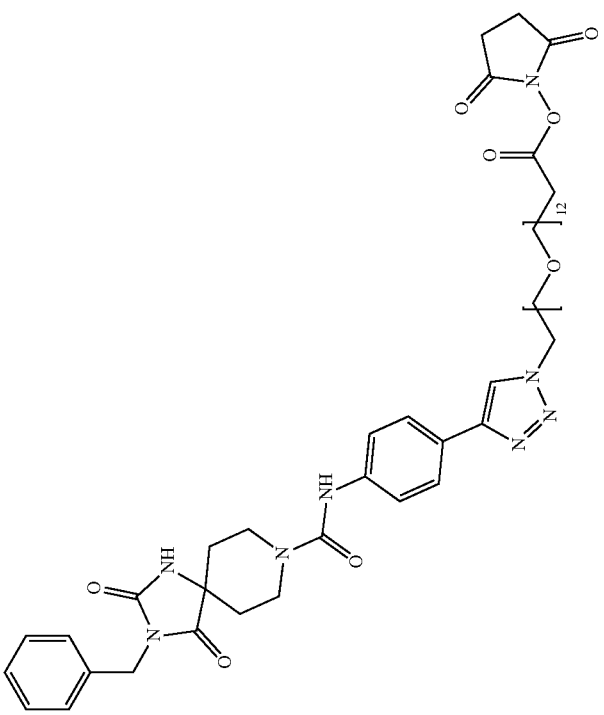 |
| I-3 | 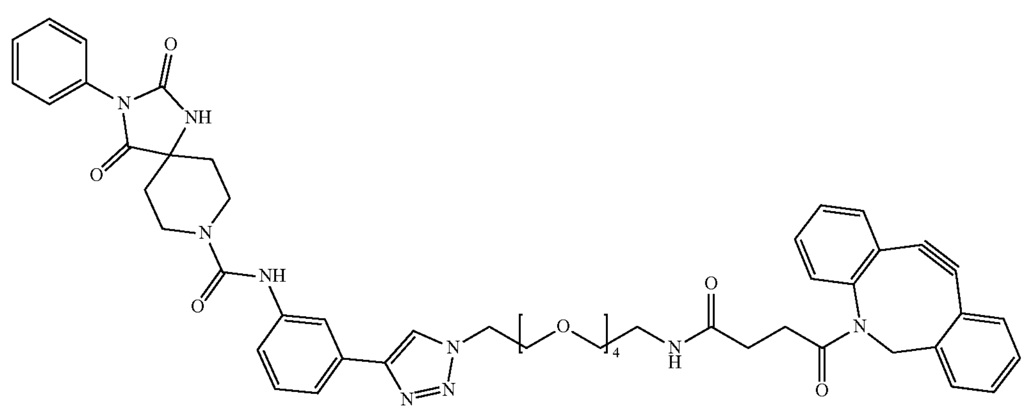 |

TABLE 1-continued
Exemplary compounds
| Compound No. | Structure |
|---|---|
| I-4 | 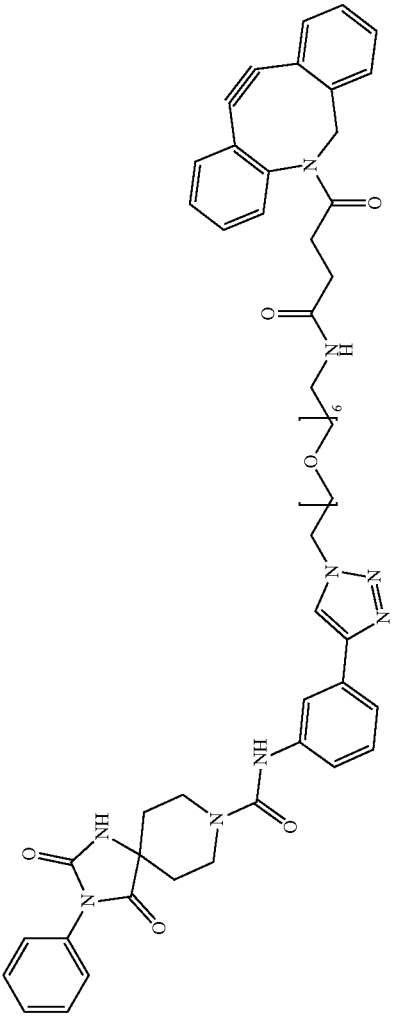 |
| I-5 | 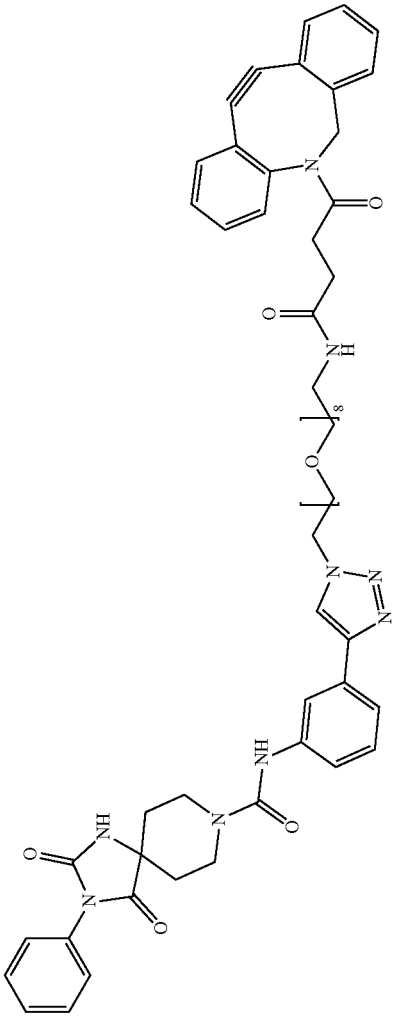 |

TABLE 1-continued

Exemplary compounds

| Compound No. | Structure |
|---|---|
| I-6 | 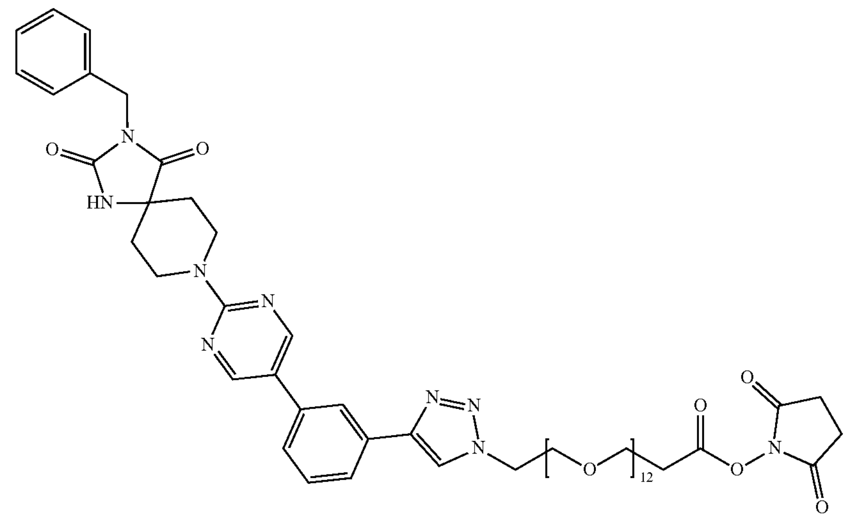 |
| I-7 | 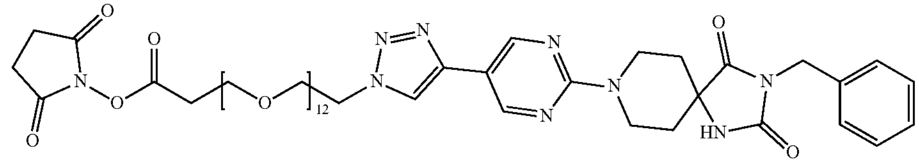 |
| I-8 | 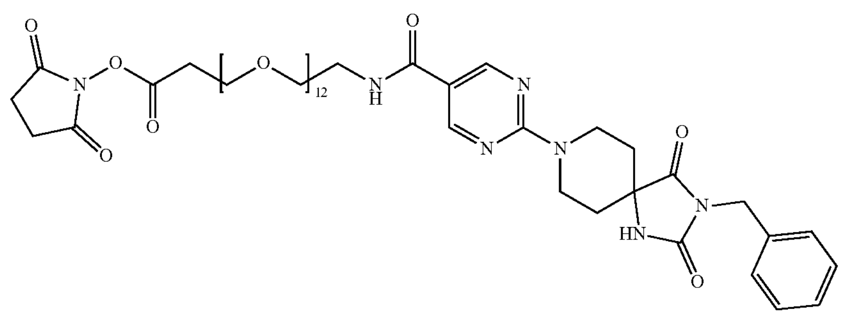 |

TABLE 1-continued
Exemplary compounds
| Compound No. | Structure |
|---|---|
| I-9 | 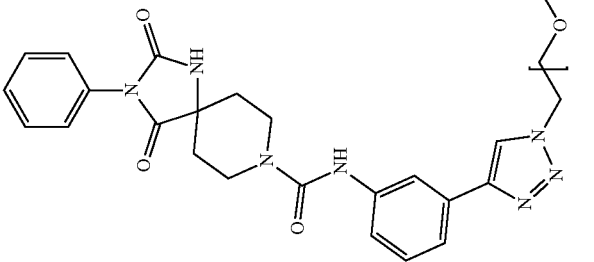 |
| I-10 | 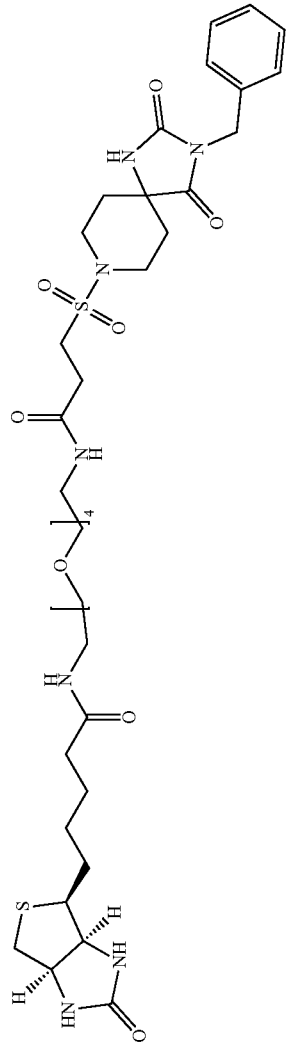 |

TABLE 1-continued
Exemplary compounds
| Compound No. | Structure |
|---|---|
| I-11 | 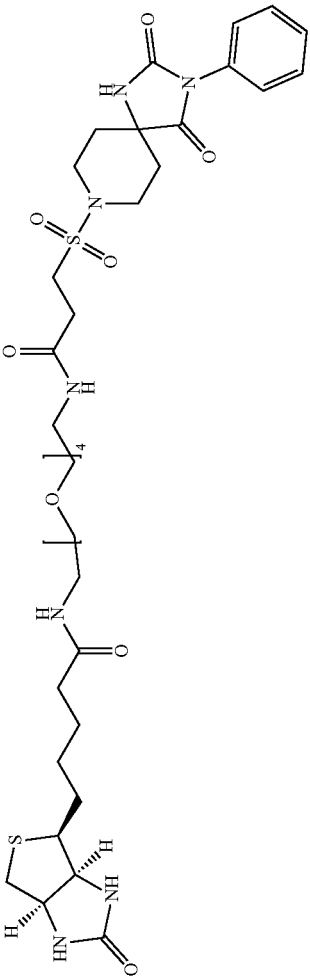 |
| I-12 | 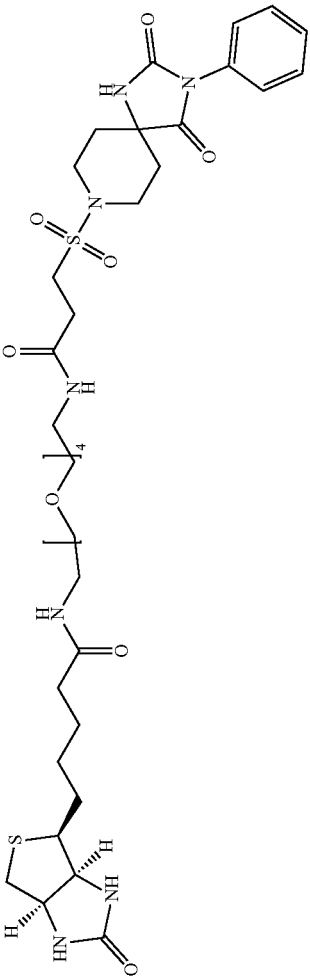 |

TABLE 1-continued
Exemplary compounds
| Compound No. | Structure |
|---|---|
| I-13 | 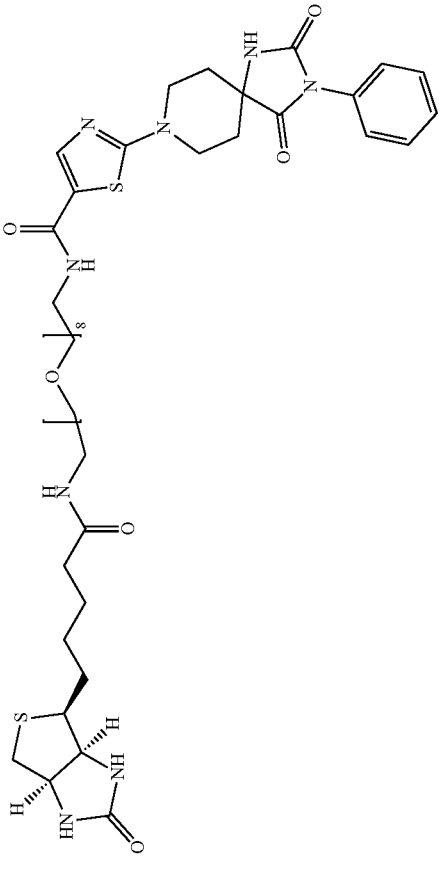 |
| I-14 | 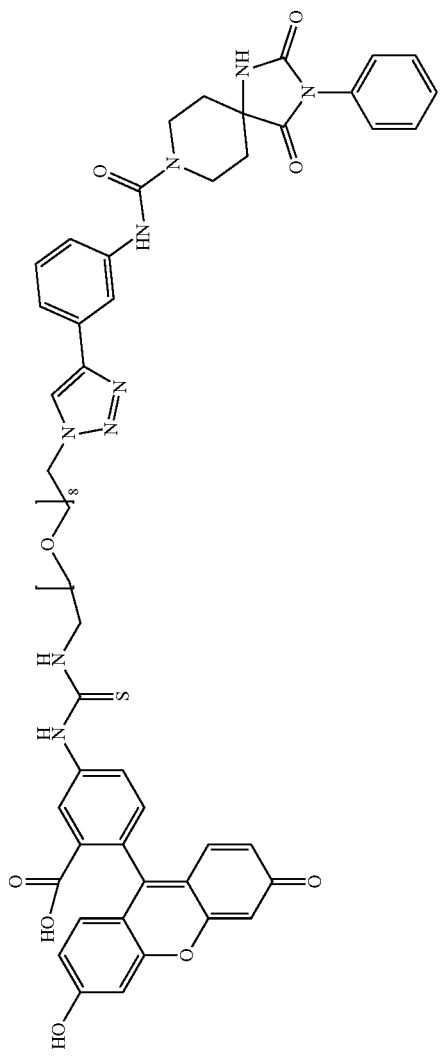 |

TABLE 1-continued

Exemplary compounds

| Compound No. | Structure |
|---|---|
| I-15 | 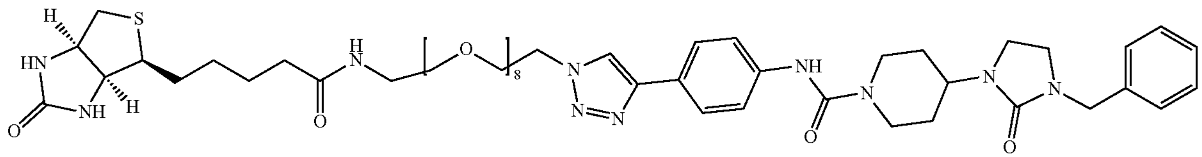 |
| I-16 | 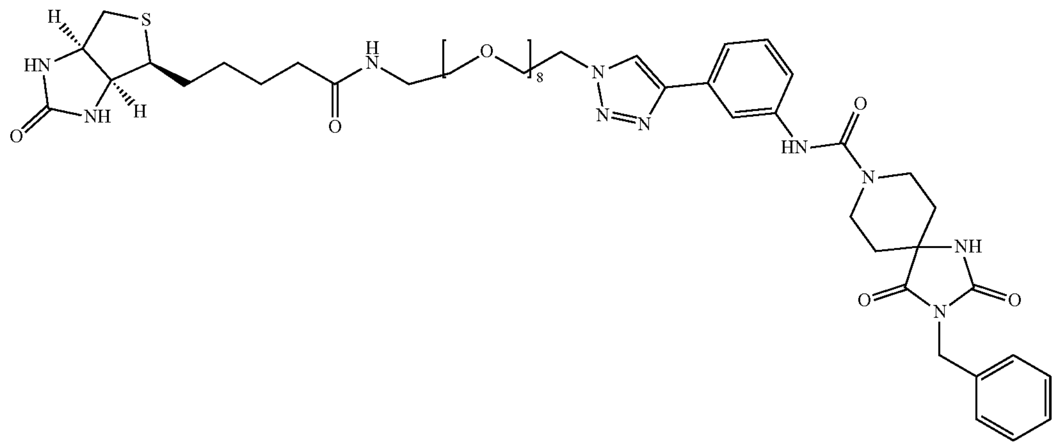 |
| I-17 | 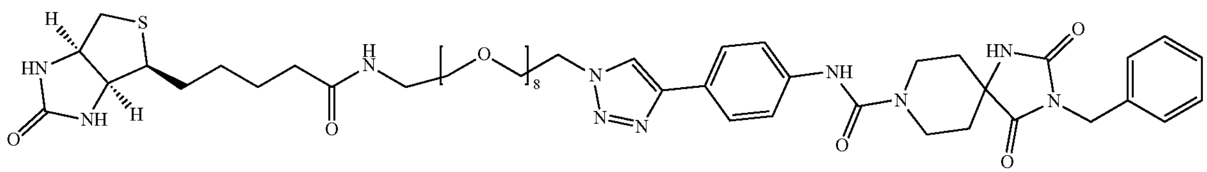 |
| I-18 | 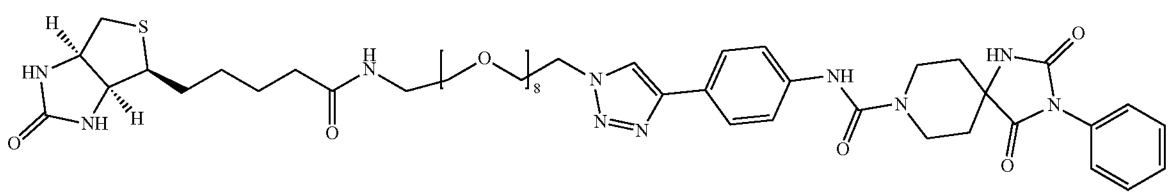 |

TABLE 1-continued

Exemplary compounds

| Compound No. | Structure |
|---|---|
| I-19 | 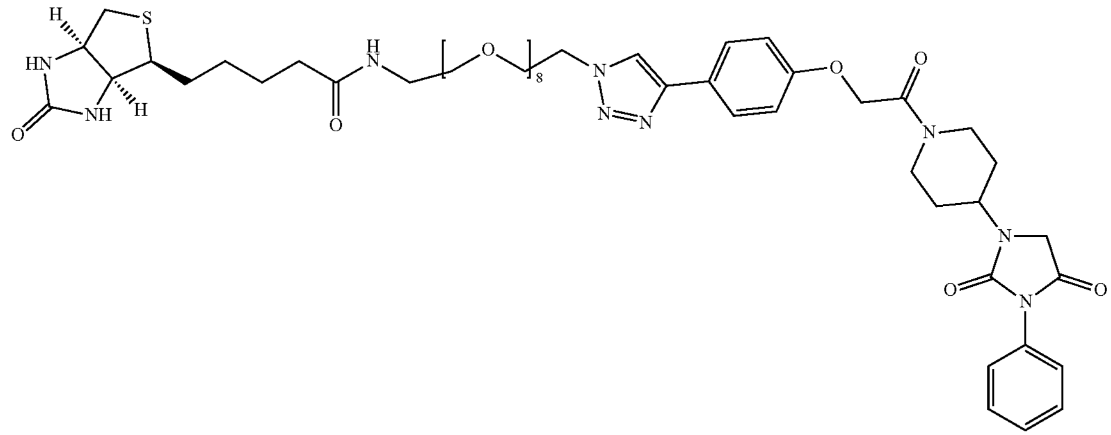 |
| I-20 | 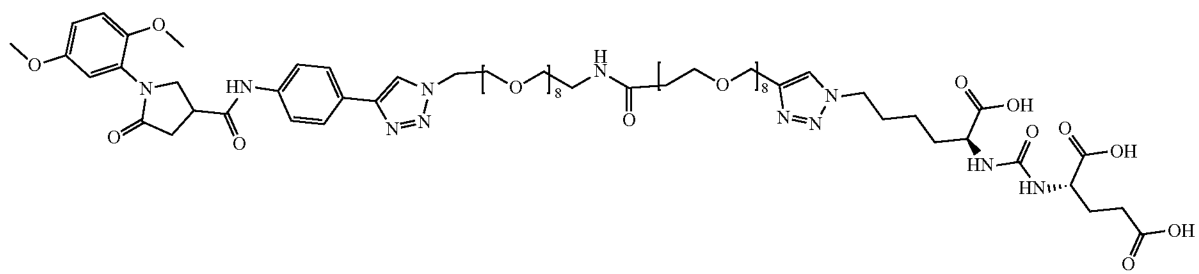 |

TABLE 1-continued

Exemplary compounds

| Compound No. | Structure |
|---|---|
| I-21 | 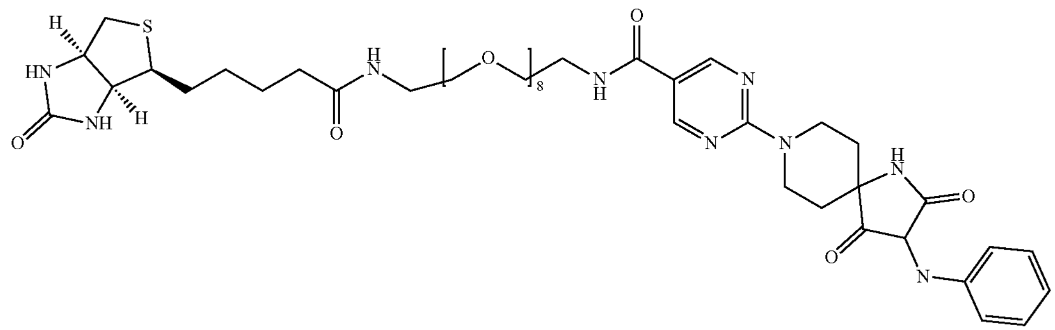 |
| I-22 | 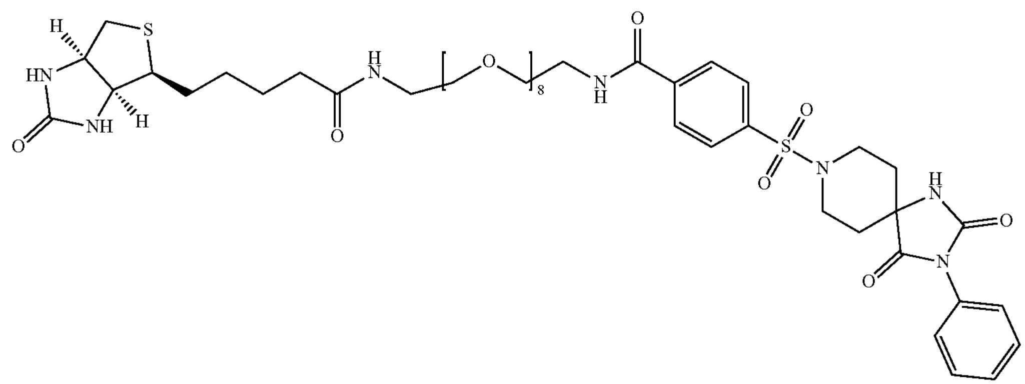 |

TABLE 1-continued
Exemplary compounds
| Compound No. | Structure |
|---|---|
| I-23 | 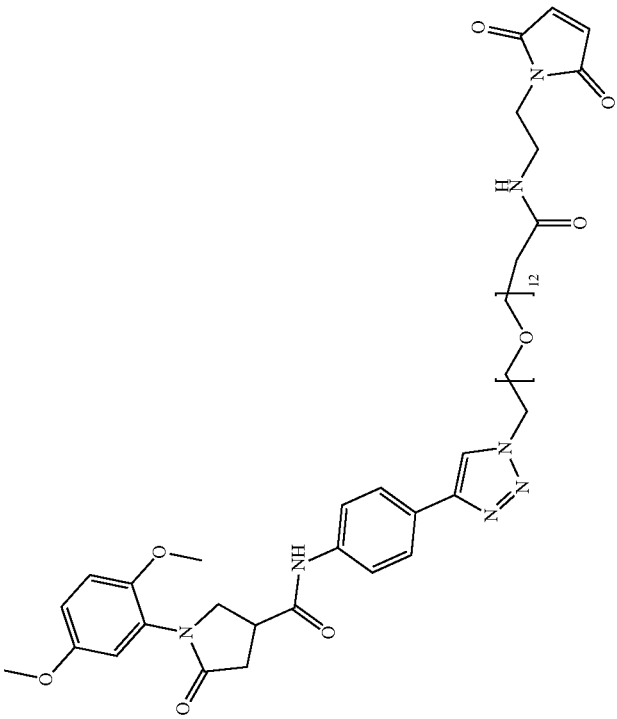 |

TABLE 1-continued
Exemplary compounds
| Compound No. | Structure |
|---|---|
| I-24 | 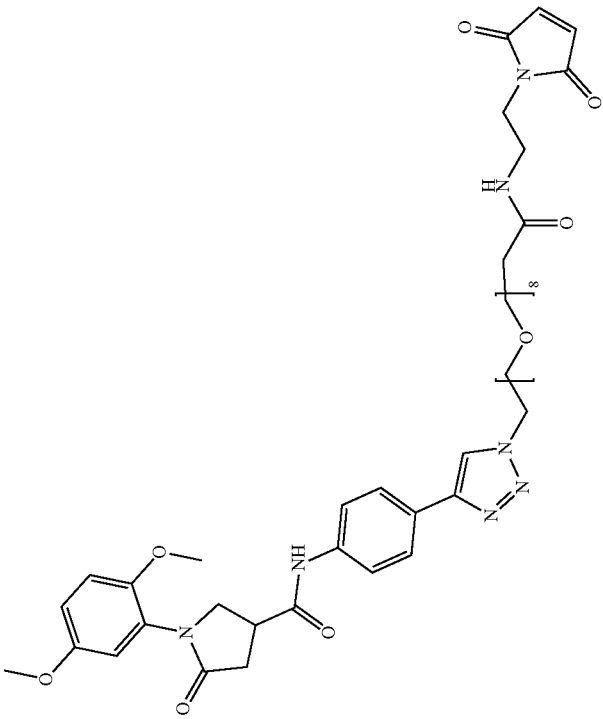 |

TABLE 1-continued
Exemplary compounds
| Compound No. | Structure |
|---|---|
| I-25 | 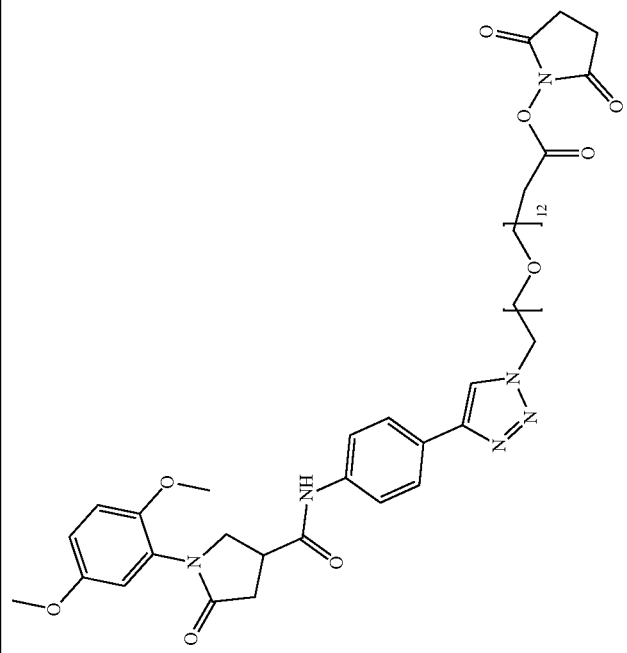 |

TABLE 1-continued
Exemplary compounds
| Compound No. | Structure |
|---|---|
| I-26 | 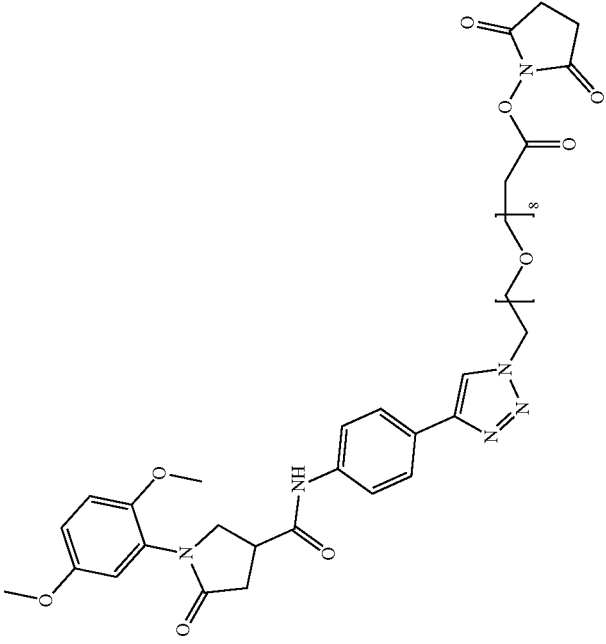 |

TABLE 1-continued
Exemplary compounds
| Compound No. | Structure |
|---|---|
| I-27 | 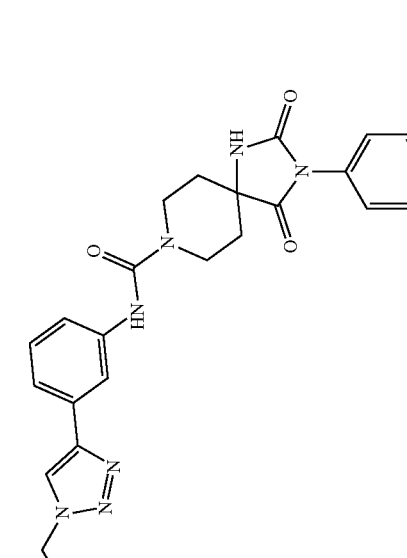 |
| I-28 | 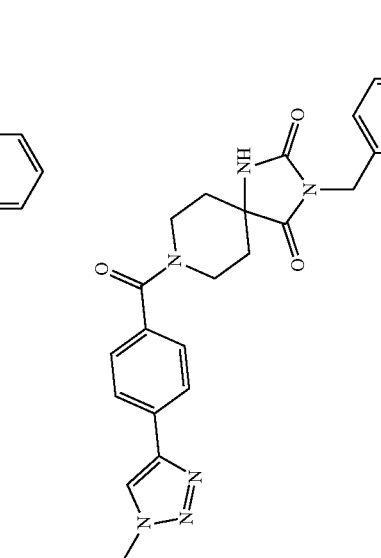 |
| I-29 | 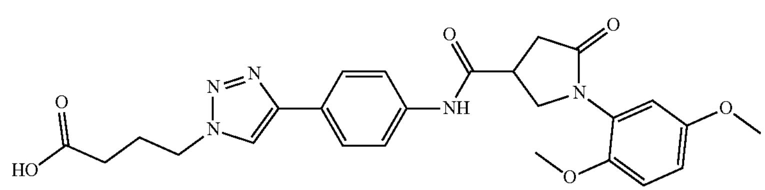 [SMILES: COc1ccc(OC)c(N2CC(C(=O)Nc3ccc(-c4cn(CCCC(=O)O)nn4)cc3)CC2=O)c1] |

TABLE 1-continued

Exemplary compounds

| Compound No. | Structure |
|---|---|
| I-30 | 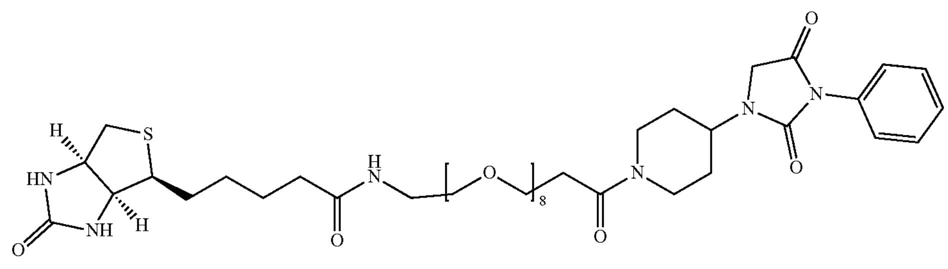 |
| I-31 | 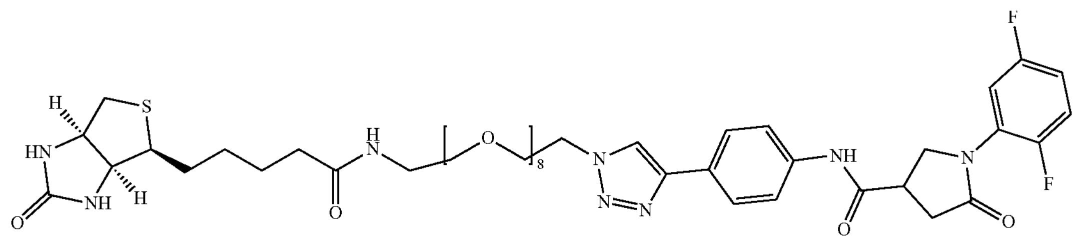 |
| I-32 | 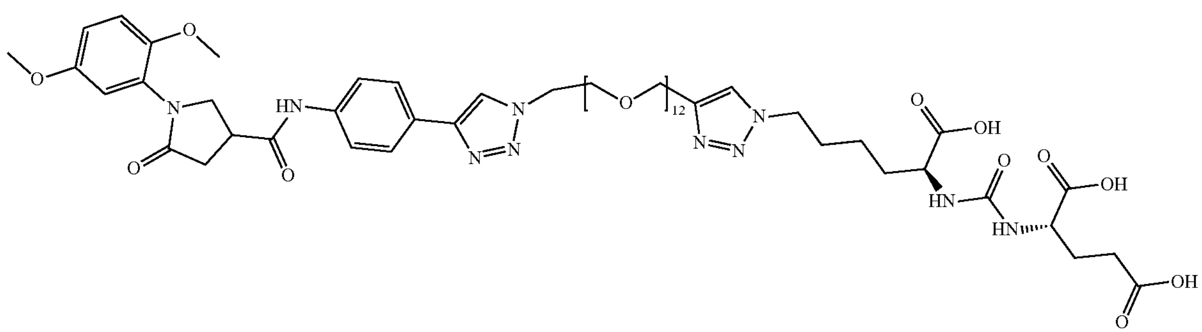 |

TABLE 1-continued

Exemplary compounds

| Compound No. | Structure |
|---|---|
| I-33 | 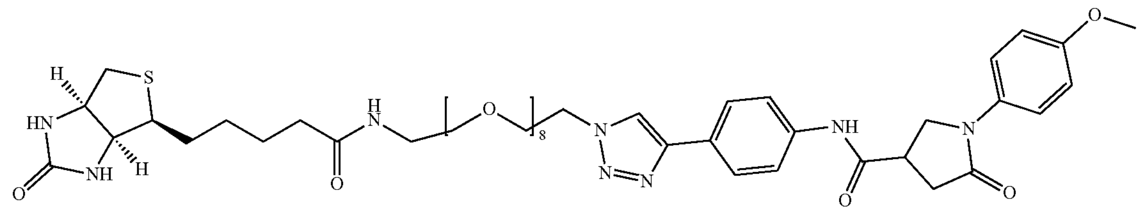 |
| I-34 | 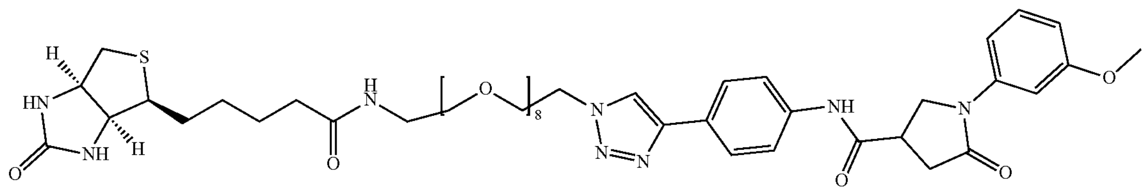 |
| I-35 | 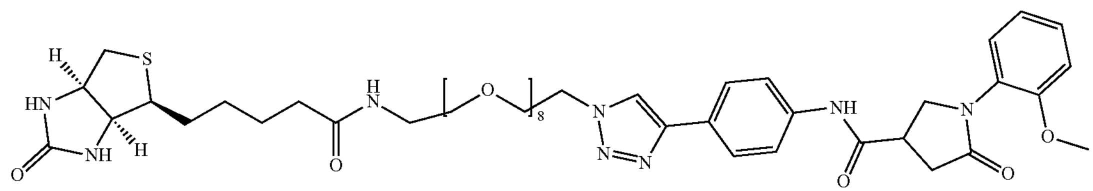 |
| I-36 | 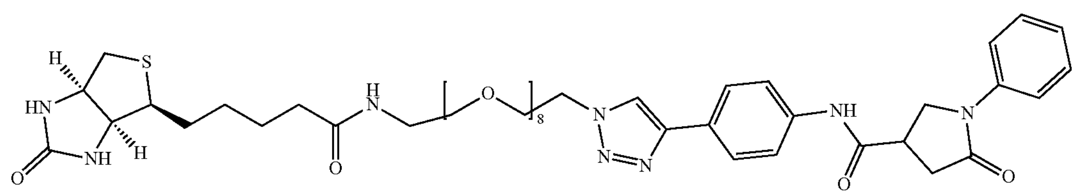 |

TABLE 1-continued
Exemplary compounds
| Compound No. | Structure |
|---|---|
| I-37 | 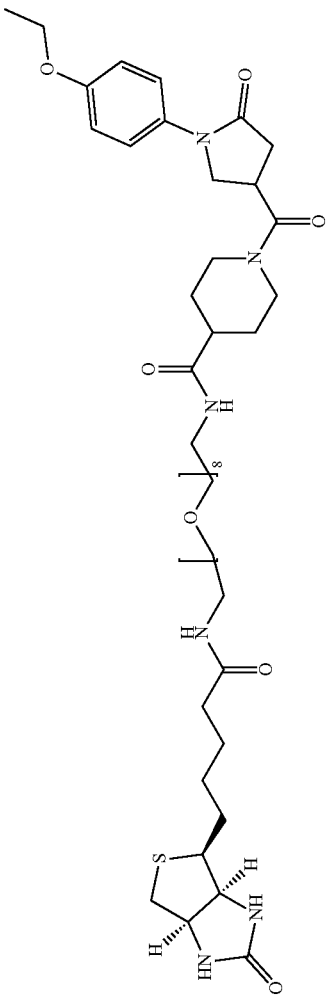 |
| I-38 | 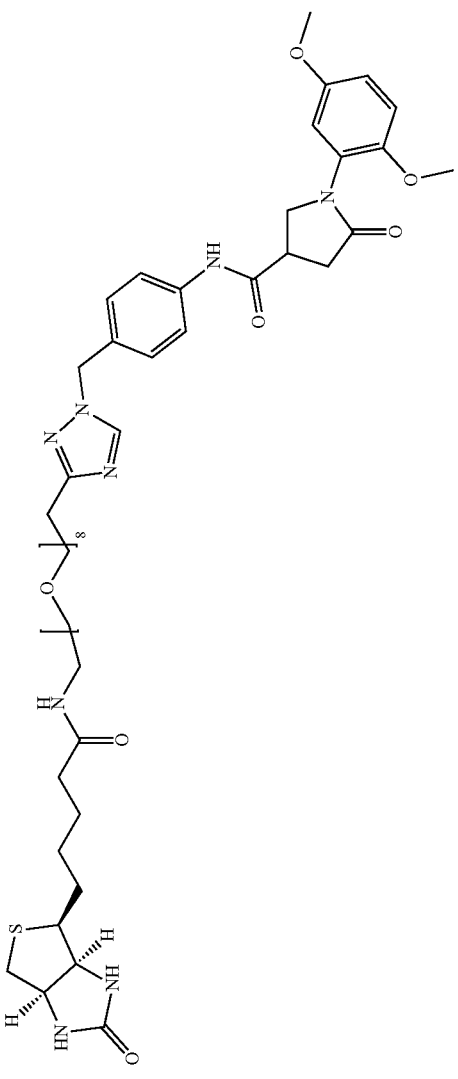 |

TABLE 1-continued

Exemplary compounds

| Compound No. | Structure |
|---|---|
| I-39 | 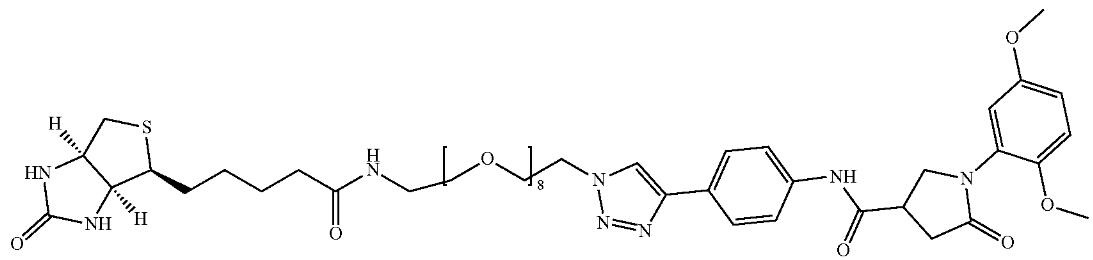 |
| I-40 | 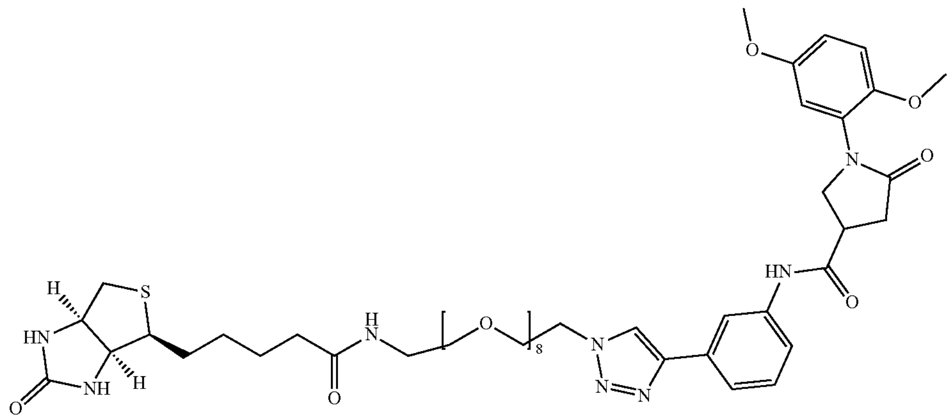 |

TABLE 1-continued
Exemplary compounds
| Compound No. | Structure |
|---|---|
| I-41 | 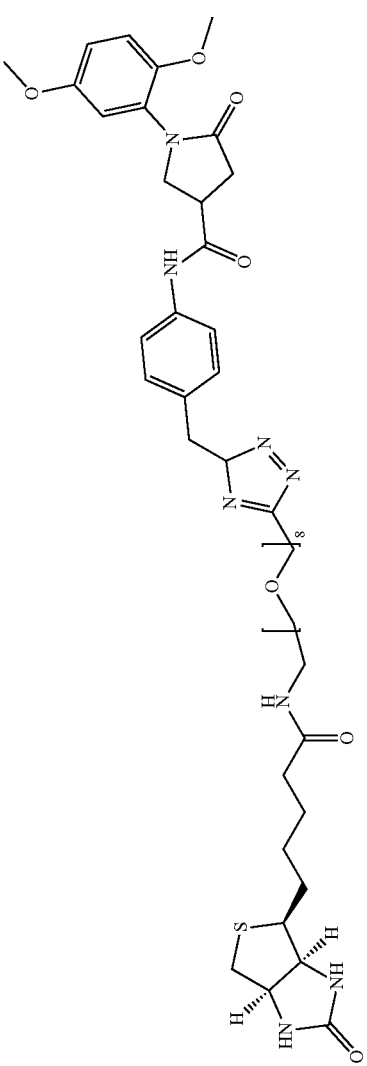 |
| I-42 | 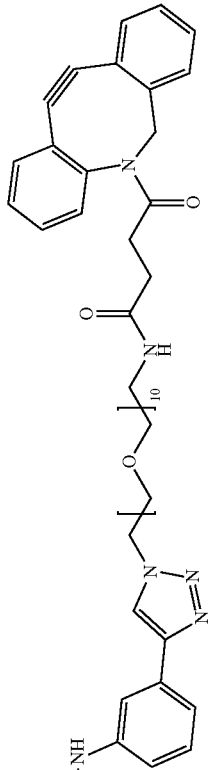 |

TABLE 1-continued
Exemplary compounds
| Compound No. | Structure |
|---|---|
| I-43 | 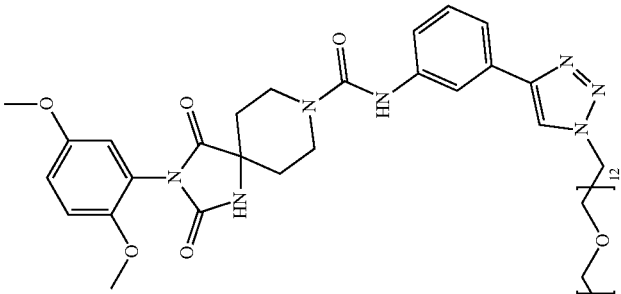 |

TABLE 1-continued
Exemplary compounds
| Compound No. | Structure |
|---|---|
| I-44 | 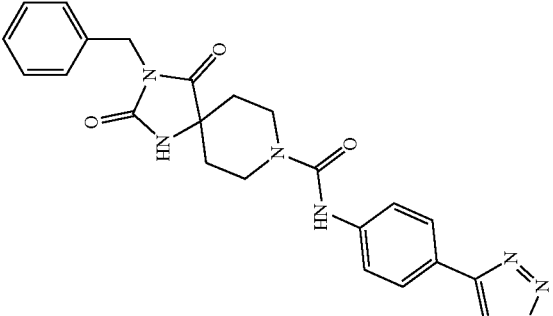 |

TABLE 1-continued
Exemplary compounds
| Compound No. | Structure |
|---|---|
| I-45 | 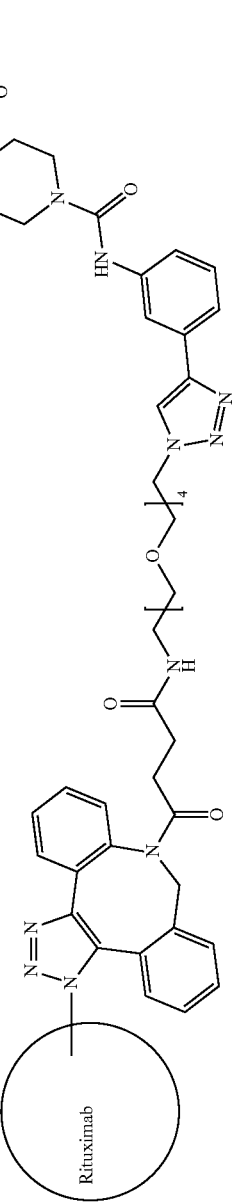 |
| I-46 | 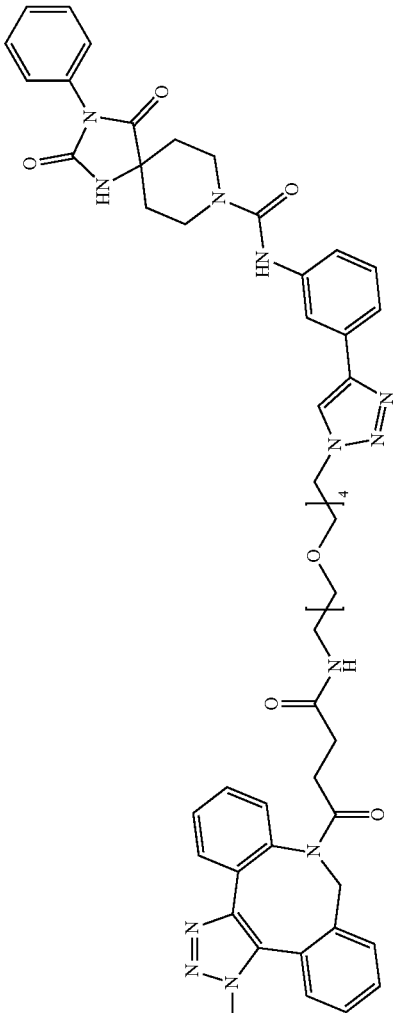 |

TABLE 1-continued

Exemplary compounds

| Compound No. | Structure |
|---|---|
| I-47 | 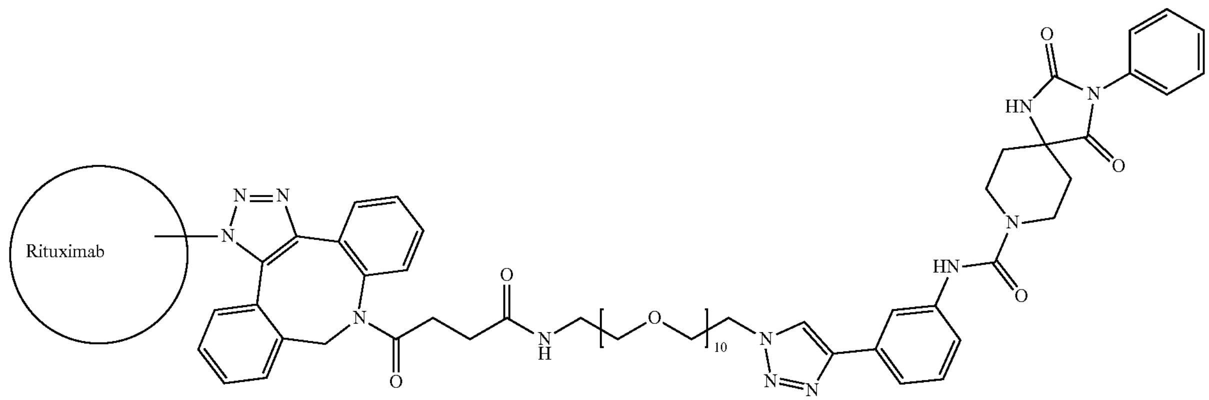 |
| I-48 | 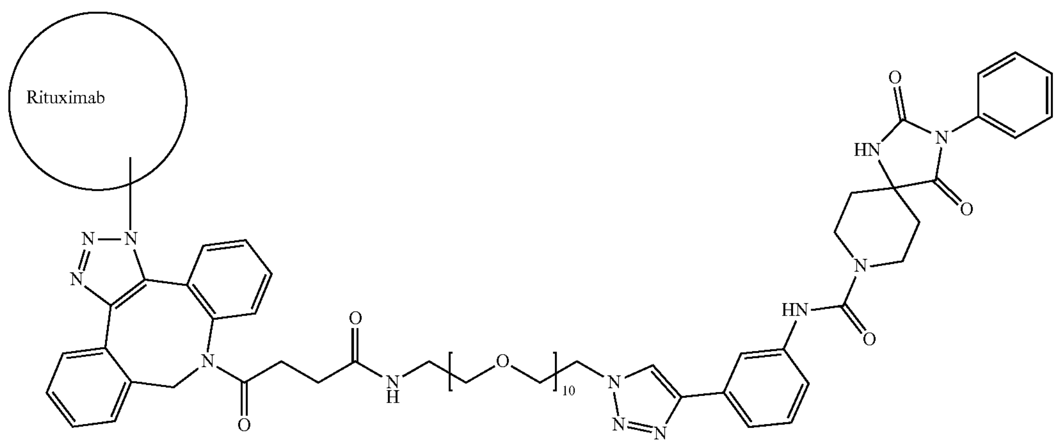 |

TABLE 1-continued
Exemplary compounds
| Compound No. | Structure |
|---|---|
| I-49 | 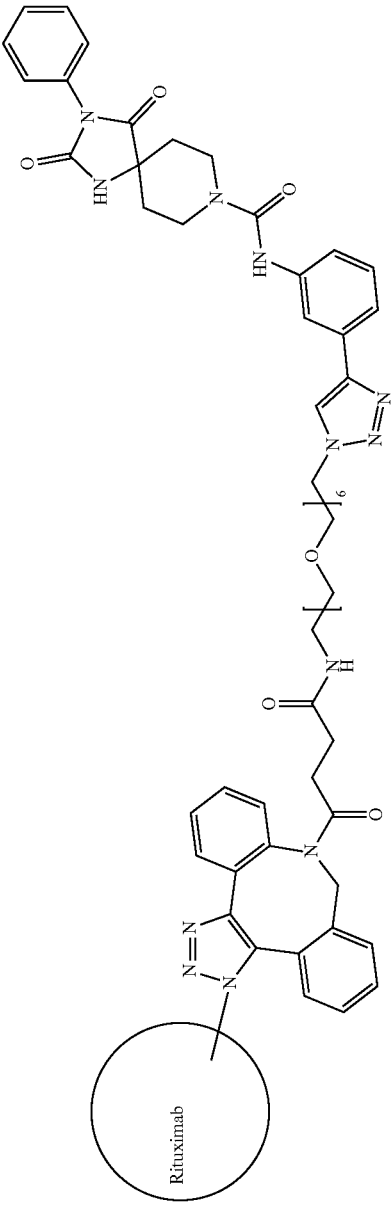 |
| I-50 | 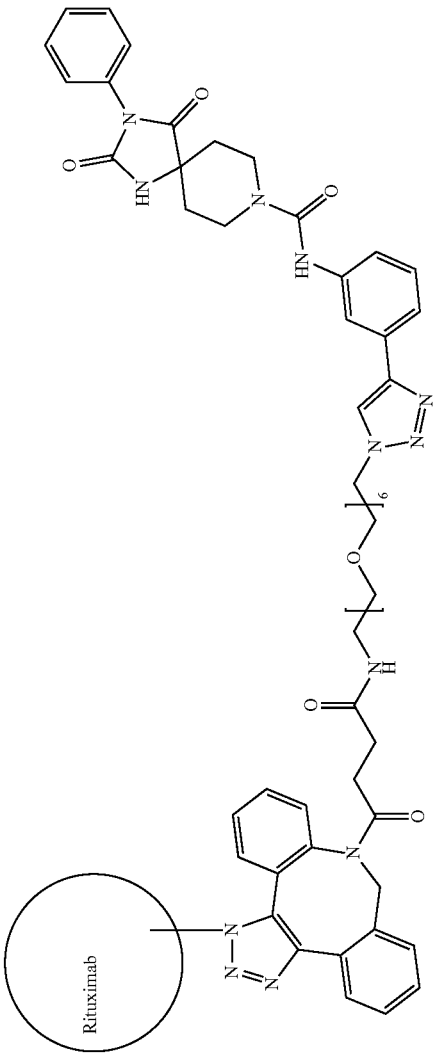 |

TABLE 1-continued
Exemplary compounds
| Compound No. | Structure |
|---|---|
| I-51 | 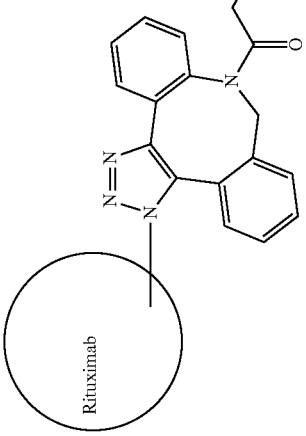 |
| I-52 | 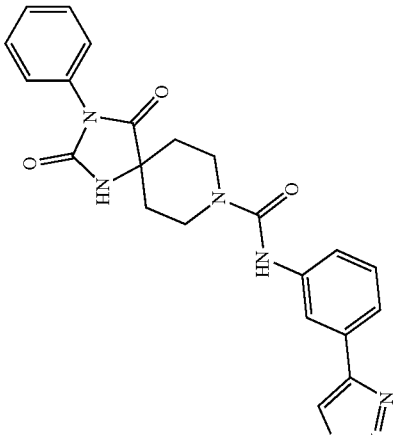 |

TABLE 1-continued
Exemplary compounds
| Compound No. | Structure |
|---|---|
| I-53 | 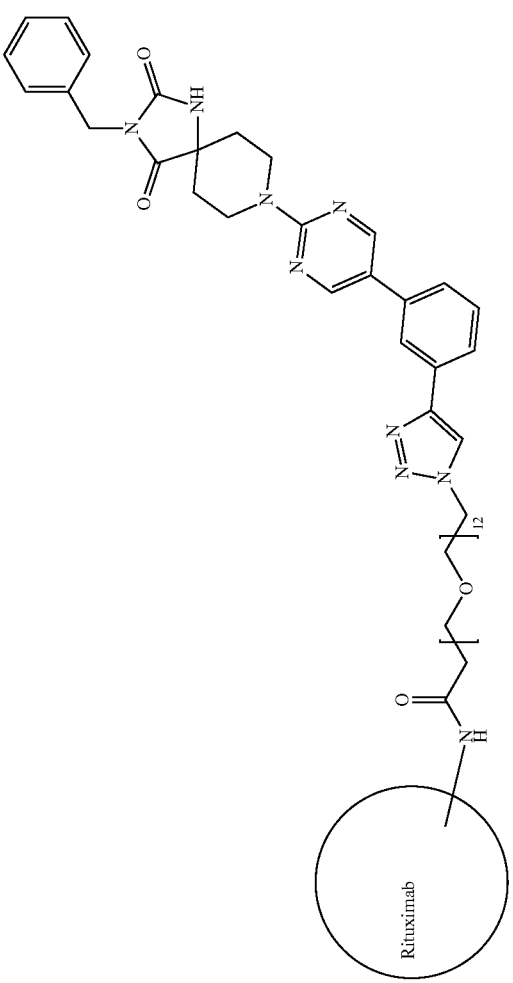 |
| I-54 | 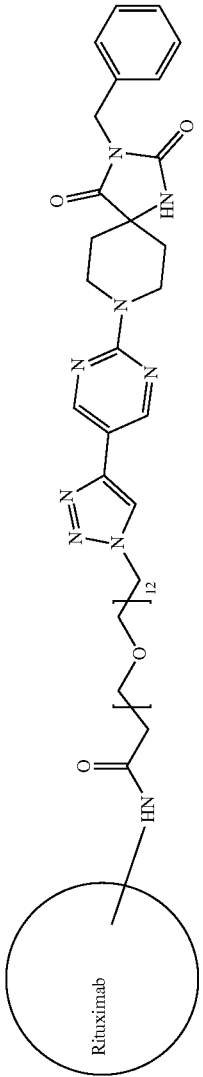 |

TABLE 1-continued
Exemplary compounds
| Compound No. | Structure |
|---|---|
| I-55 | 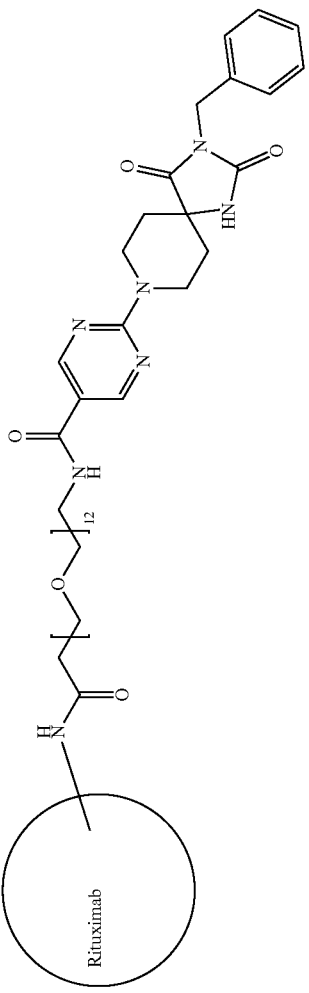 |
| I-56 | 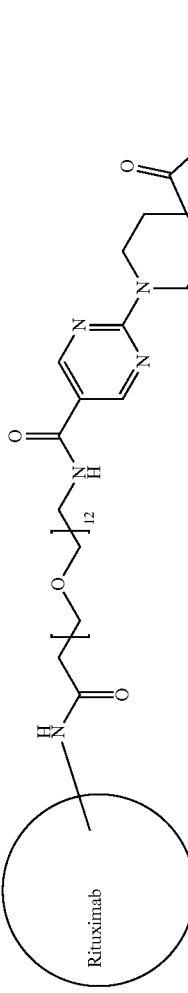 |

TABLE 1-continued
Exemplary compounds
| Compound No. | Structure |
|---|---|
| I-57 | 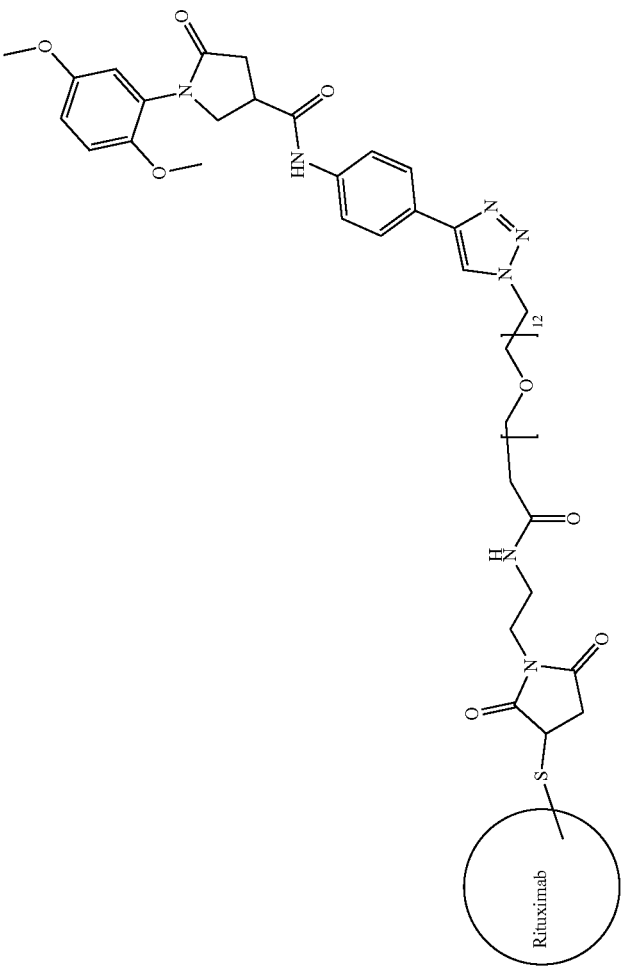 |

TABLE 1-continued
Exemplary compounds
| Compound No. | Structure |
|---|---|
| I-58 | 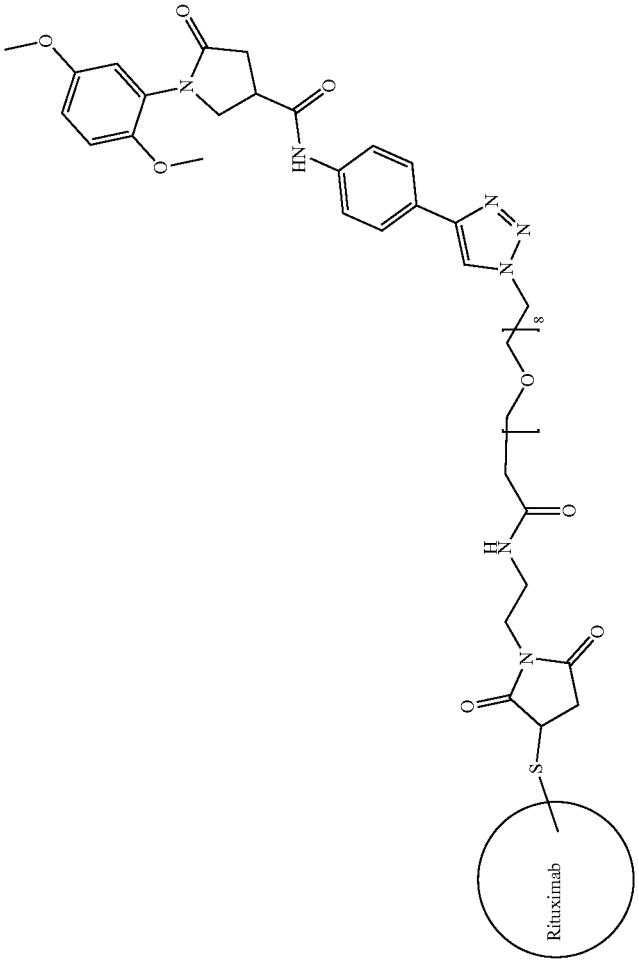 |

TABLE 1-continued
Exemplary compounds
| Compound No. | Structure |
|---|---|
| I-59 | 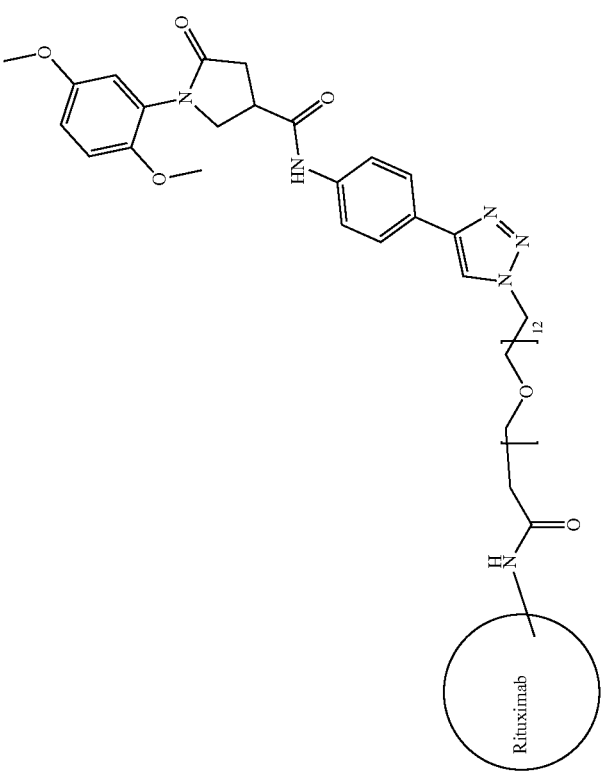 |

TABLE 1-continued
Exemplary compounds
| Compound No. | Structure |
|---|---|
| I-60 | 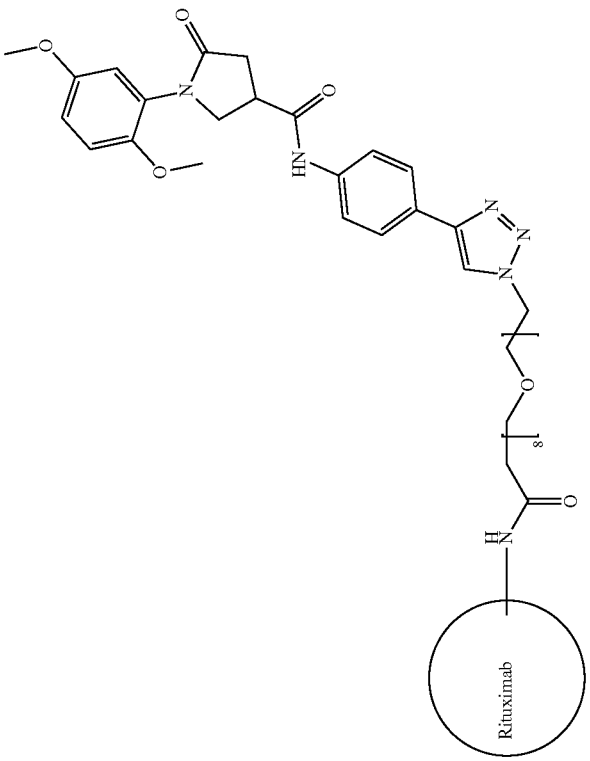 |
| I-61 | 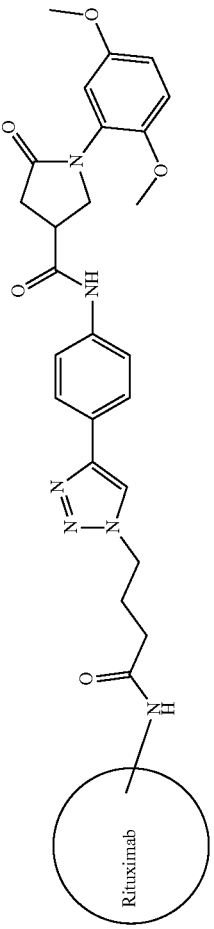 |

TABLE 1-continued

Exemplary compounds

| Compound No. | Structure |
|---|---|
| I-62 | 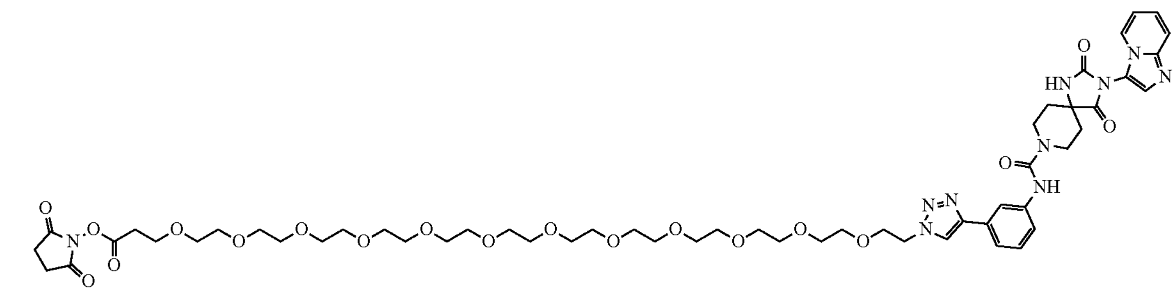 [SMILES: O=C(CCOCCOCCOCCOCCOCCOCCOCCOCCOCCOCCOCCOCCn1cc(-c2cccc(NC(=O)N3CCC4(CC3)NC(=O)N(c3cnc5ccccn35)C4=O)c2)nn1)ON1C(=O)CCC1=O] |
| I-63 | 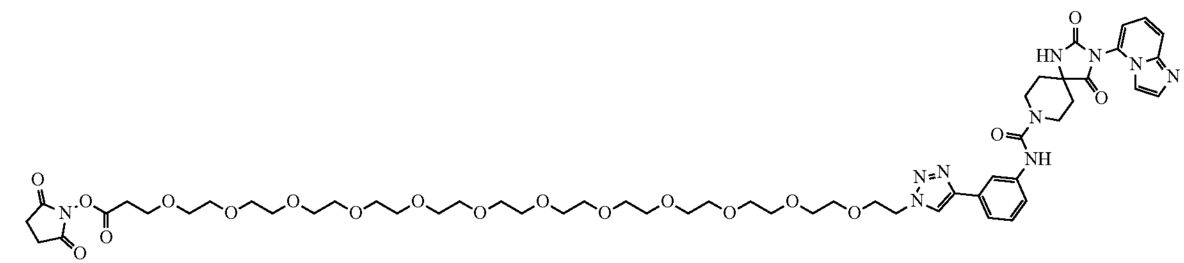 [SMILES: O=C(CCOCCOCCOCCOCCOCCOCCOCCOCCOCCOCCOCCOCCn1cc(-c2cccc(NC(=O)N3CCC4(CC3)NC(=O)N(c3cccc5nccn35)C4=O)c2)nn1)ON1C(=O)CCC1=O] |
| I-64 | 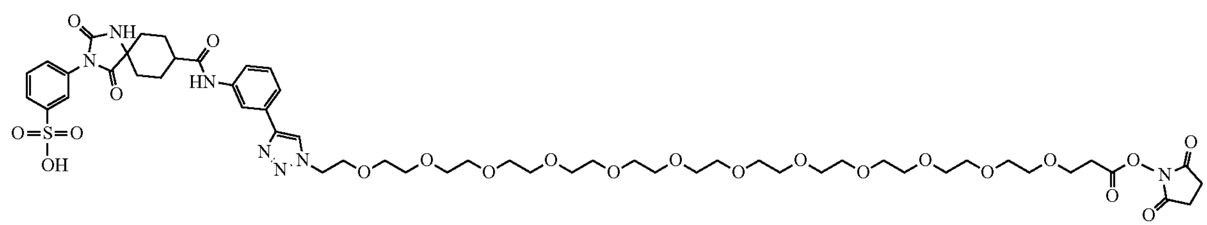 [SMILES: O=C(CCOCCOCCOCCOCCOCCOCCOCCOCCOCCOCCOCCOCCn1cc(-c2cccc(NC(=O)C3CCC4(CC3)NC(=O)N(c3cccc(S(=O)(=O)O)c3)C4=O)c2)nn1)ON1C(=O)CCC1=O] |

TABLE 1-continued

Exemplary compounds

| Compound No. | Structure |
|---|---|
| I-65 | 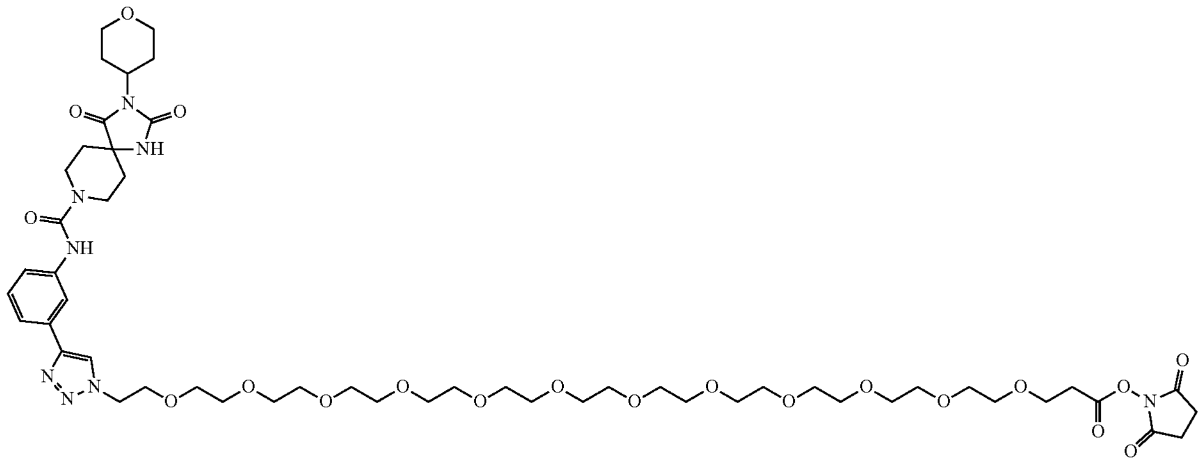 [SMILES: O=C(CCOCCOCCOCCOCCOCCOCCOCCOCCOCCOCCOCCOCCn1cc(-c2cccc(NC(=O)N3CCC4(CC3)NC(=O)N(C3CCOCC3)C4=O)c2)nn1)ON1C(=O)CCC1=O] |
| I-66 | 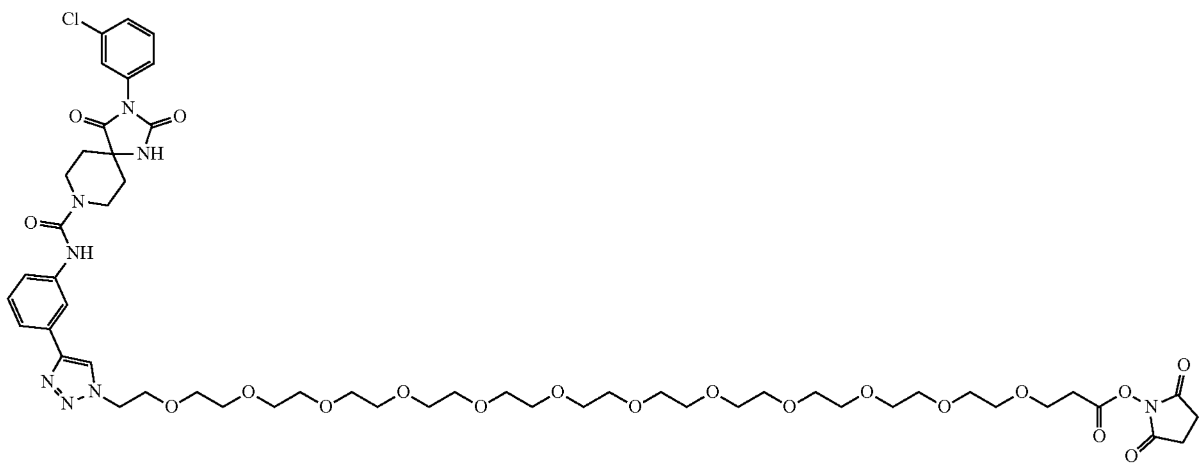 [SMILES: O=C(CCOCCOCCOCCOCCOCCOCCOCCOCCOCCOCCOCCOCCn1cc(-c2cccc(NC(=O)N3CCC4(CC3)NC(=O)N(c3cccc(Cl)c3)C4=O)c2)nn1)ON1C(=O)CCC1=O] |

TABLE 1-continued

Exemplary compounds

| Compound No. | Structure |
|---|---|
| I-67 | 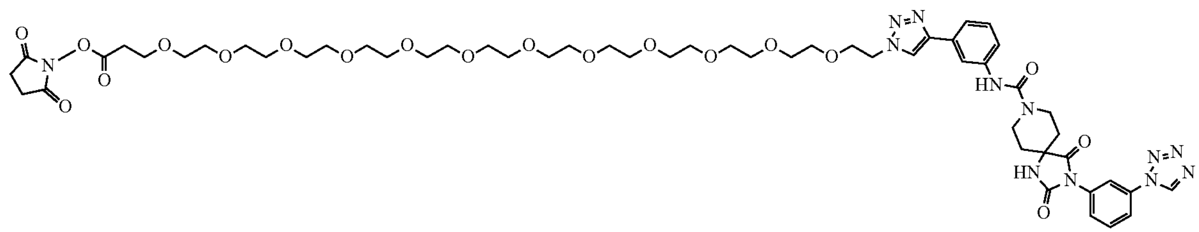 [SMILES: O=C(CCOCCOCCOCCOCCOCCOCCOCCOCCOCCOCCOCCOCCn1cc(-c2cccc(NC(=O)N3CCC4(CC3)NC(=O)N(c3cccc(-n5cnnn5)c3)C4=O)c2)nn1)ON1C(=O)CCC1=O] |
| I-68 | 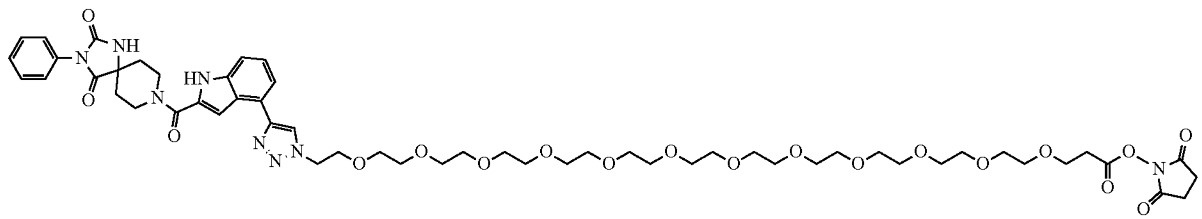 [SMILES: O=C(CCOCCOCCOCCOCCOCCOCCOCCOCCOCCOCCOCCOCCn1cc(-c2cccc3[nH]c(C(=O)N4CCC5(CC4)NC(=O)N(c4ccccc4)C5=O)cc23)nn1)ON1C(=O)CCC1=O] |
| I-69 | 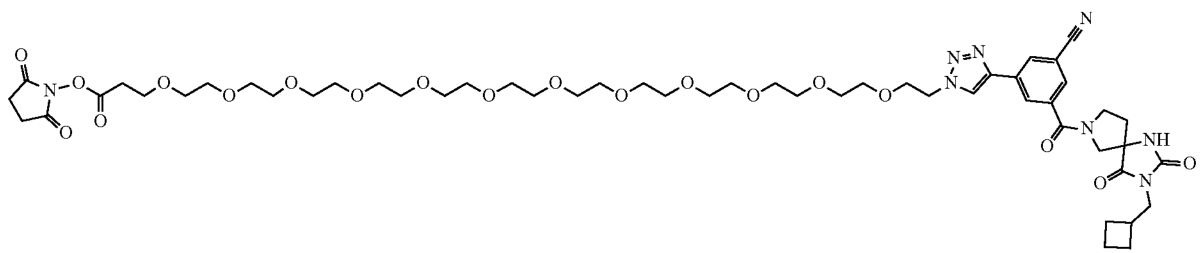 [SMILES: N#Cc1cc(C(=O)N2CCC3(C2)NC(=O)N(CC2CCC2)C3=O)cc(-c2cn(CCOCCOCCOCCOCCOCCOCCOCCOCCOCCOCCOCCOCCC(=O)ON3C(=O)CCC3=O)nn2)c1] |

TABLE 1-continued
Exemplary compounds
| Compound No. | Structure |
|---|---|
| I-70 | 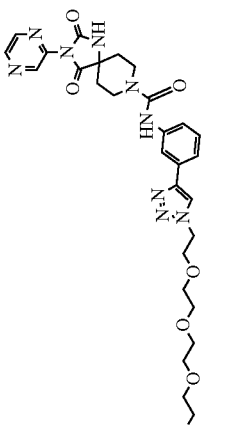 |
| I-71 | 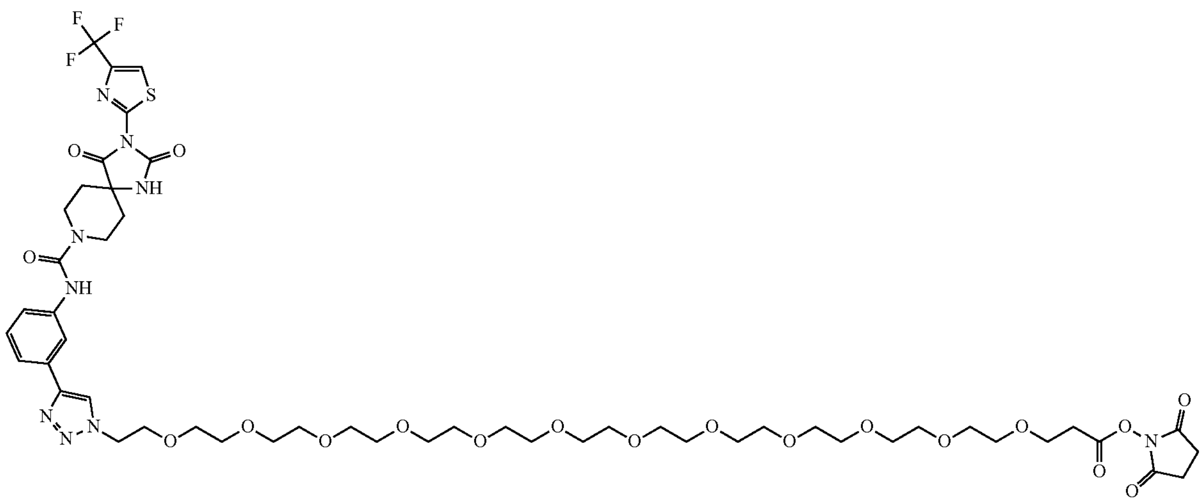 [SMILES: O=C(CCOCCOCCOCCOCCOCCOCCOCCOCCOCCOCCOCCOCCn1cc(-c2cccc(NC(=O)N3CCC4(CC3)NC(=O)N(c3nc(C(F)(F)F)cs3)C4=O)c2)nn1)ON1C(=O)CCC1=O] |

TABLE 1-continued

Exemplary compounds

| Compound No. | Structure |
| --- | --- |
| I-72 | 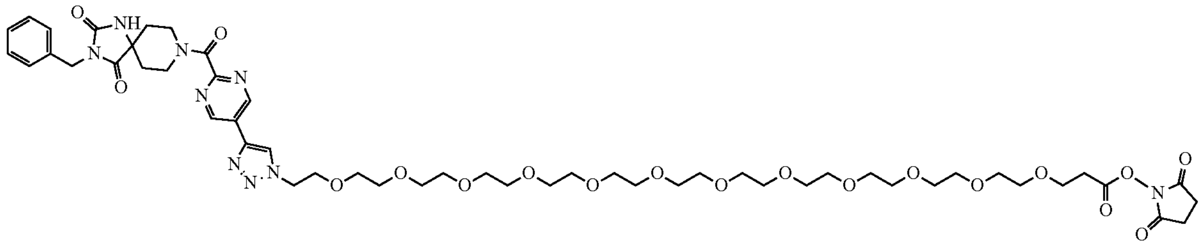 [SMILES: O=C(CCOCCOCCOCCOCCOCCOCCOCCOCCOCCOCCOCCOCCn1cc(-c2cnc(C(=O)N3CCC4(CC3)NC(=O)N(Cc3ccccc3)C4=O)nc2)nn1)ON1C(=O)CCC1=O] |
| I-73 | 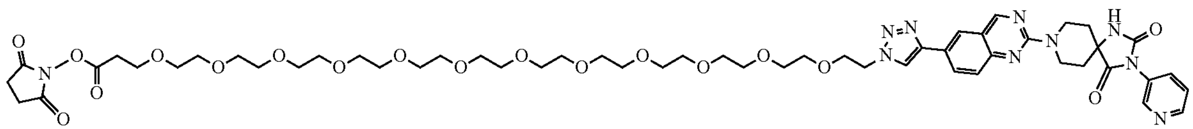 [SMILES: O=C(CCOCCOCCOCCOCCOCCOCCOCCOCCOCCOCCOCCOCCn1cc(-c2ccc3nc(N4CCC5(CC4)NC(=O)N(c4cccnc4)C5=O)ncc3c2)nn1)ON1C(=O)CCC1=O] |
| I-74 | 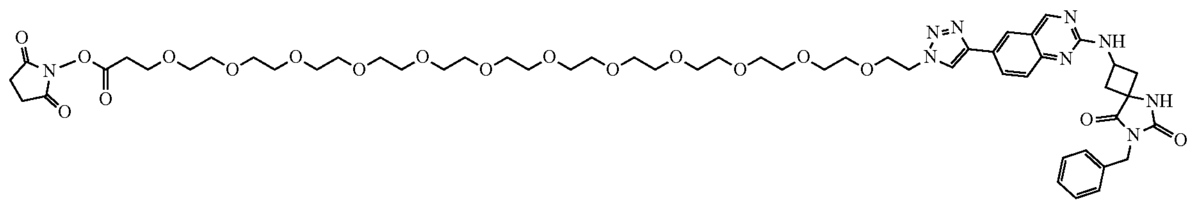 [SMILES: O=C(CCOCCOCCOCCOCCOCCOCCOCCOCCOCCOCCOCCOCCn1cc(-c2ccc3nc(NC4CC5(C4)NC(=O)N(Cc4ccccc4)C5=O)ncc3c2)nn1)ON1C(=O)CCC1=O] |
| I-75 | 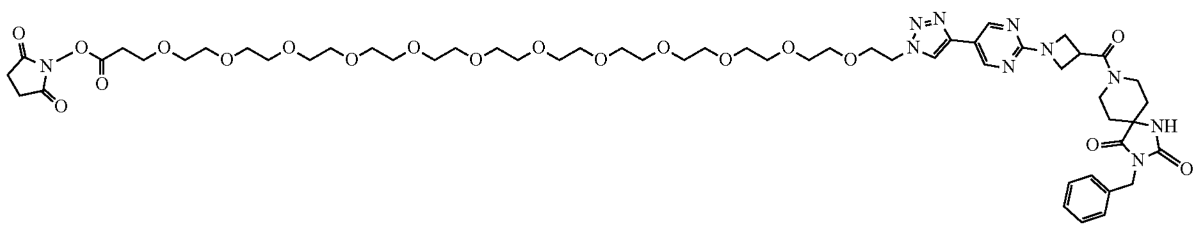 [SMILES: O=C(CCOCCOCCOCCOCCOCCOCCOCCOCCOCCOCCOCCOCCn1cc(-c2cnc(N3CC(C(=O)N4CCC5(CC4)NC(=O)N(Cc4ccccc4)C5=O)C3)nc2)nn1)ON1C(=O)CCC1=O] |

TABLE 1-continued

Exemplary compounds

| Compound No. | Structure |
|---|---|
| I-76 | 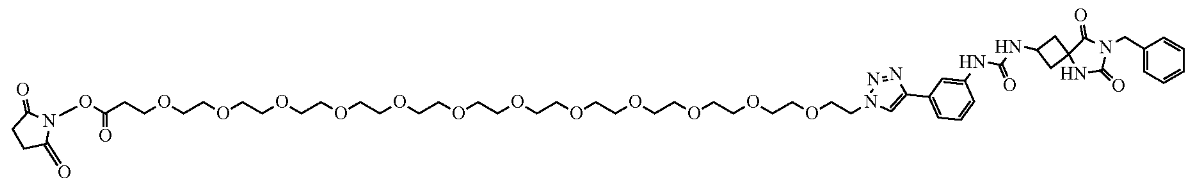 [SMILES: O=C(Nc1cccc(-c2cn(CCOCCOCCOCCOCCOCCOCCOCCOCCOCCOCCOCCOCCC(=O)ON3C(=O)CCC3=O)nn2)c1)NC1CC2(C1)NC(=O)N(Cc1ccccc1)C2=O] |
| I-77 | 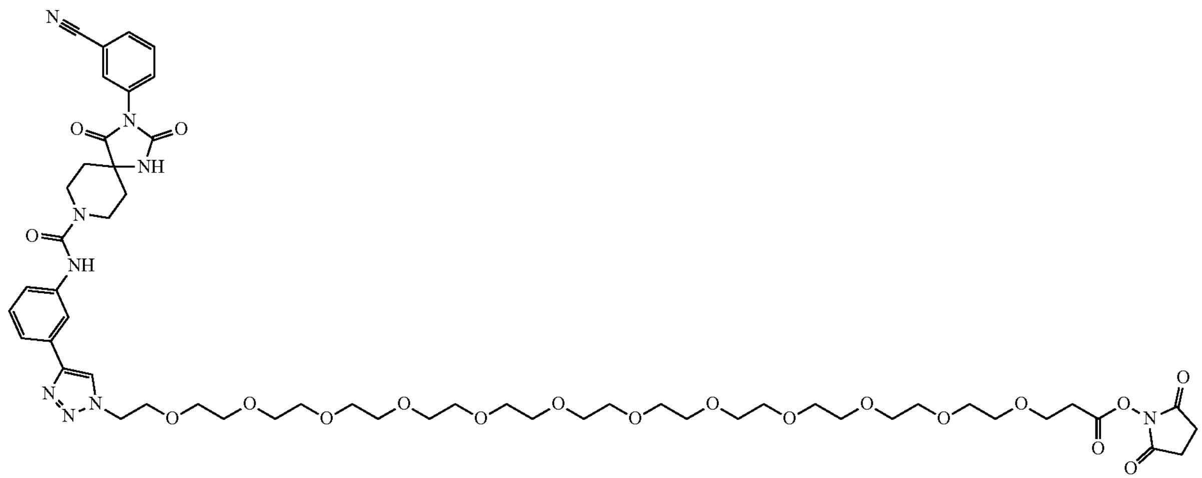 [SMILES: N#Cc1cccc(N2C(=O)NC3(CCN(C(=O)Nc4cccc(-c5cn(CCOCCOCCOCCOCCOCCOCCOCCOCCOCCOCCOCCOCCC(=O)ON6C(=O)CCC6=O)nn5)c4)CC3)C2=O)c1] |
| I-78 | 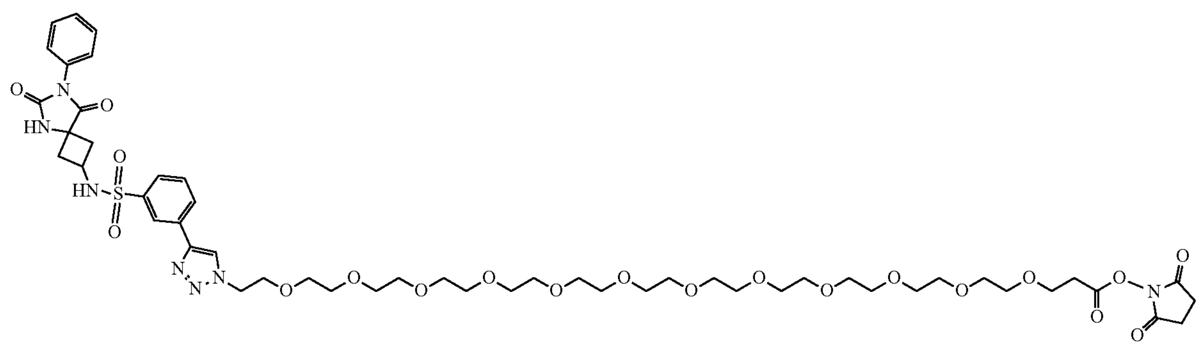 [SMILES: O=C(CCOCCOCCOCCOCCOCCOCCOCCOCCOCCOCCOCCOCCn1cc(-c2cccc(S(=O)(=O)NC3CC4(C3)NC(=O)N(c3ccccc3)C4=O)c2)nn1)ON1C(=O)CCC1=O] |

TABLE 1-continued

Exemplary compounds

| Compound No. | Structure |
|---|---|
| I-79 | 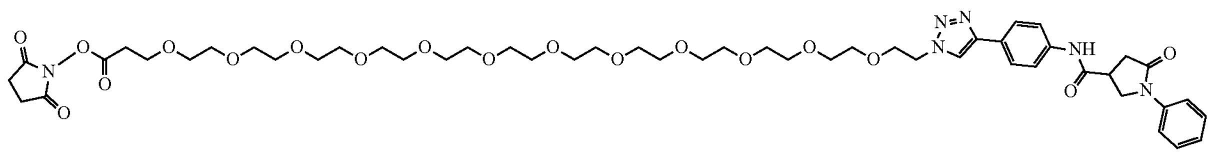 [SMILES: O=C(CCOCCOCCOCCOCCOCCOCCOCCOCCOCCOCCOCCOCCn1cc(-c2ccc(NC(=O)C3CC(=O)N(c4ccccc4)C3)cc2)nn1)ON1C(=O)CCC1=O] |
| I-80 | 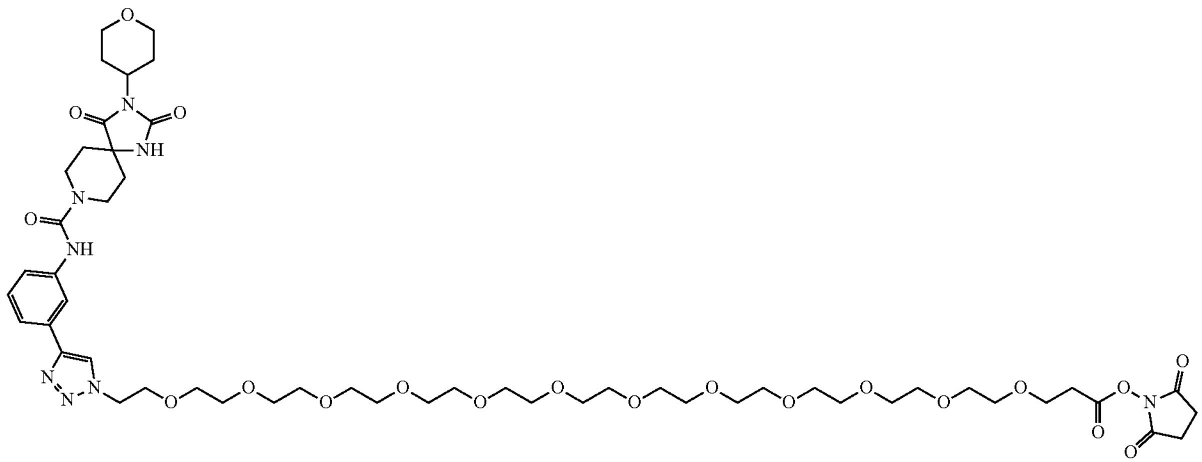 [SMILES: O=C(CCOCCOCCOCCOCCOCCOCCOCCOCCOCCOCCOCCOCCn1cc(-c2cccc(NC(=O)N3CCC4(CC3)NC(=O)N(C3CCOCC3)C4=O)c2)nn1)ON1C(=O)CCC1=O] |

TABLE 1-continued

Exemplary compounds

| Compound No. | Structure |
|---|---|
| I-81 | 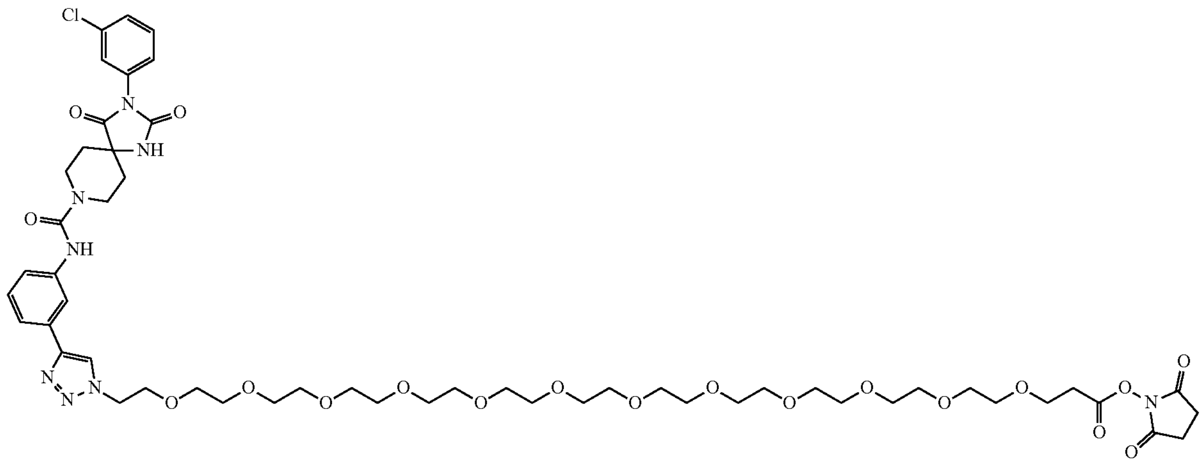 [SMILES: O=C(CCOCCOCCOCCOCCOCCOCCOCCOCCOCCOCCOCCOCCn1cc(-c2cccc(NC(=O)N3CCC4(CC3)NC(=O)N(c3cccc(Cl)c3)C4=O)c2)nn1)ON1C(=O)CCC1=O] |
| I-82 | 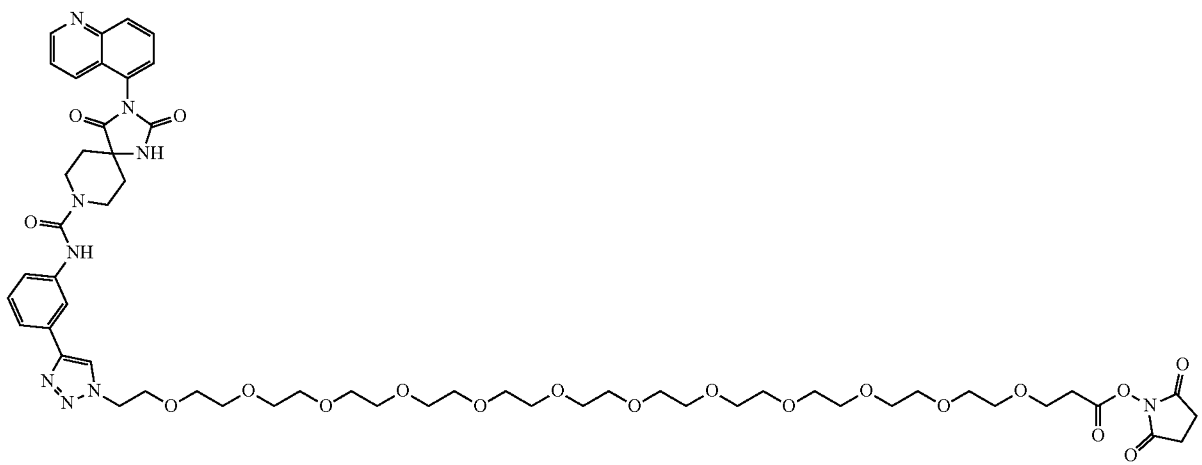 [SMILES: O=C(CCOCCOCCOCCOCCOCCOCCOCCOCCOCCOCCOCCOCCn1cc(-c2cccc(NC(=O)N3CCC4(CC3)NC(=O)N(c3cccc5ncccc35)C4=O)c2)nn1)ON1C(=O)CCC1=O] |

TABLE 1-continued

Exemplary compounds

| Compound No. | Structure |
|---|---|
| I-83 | 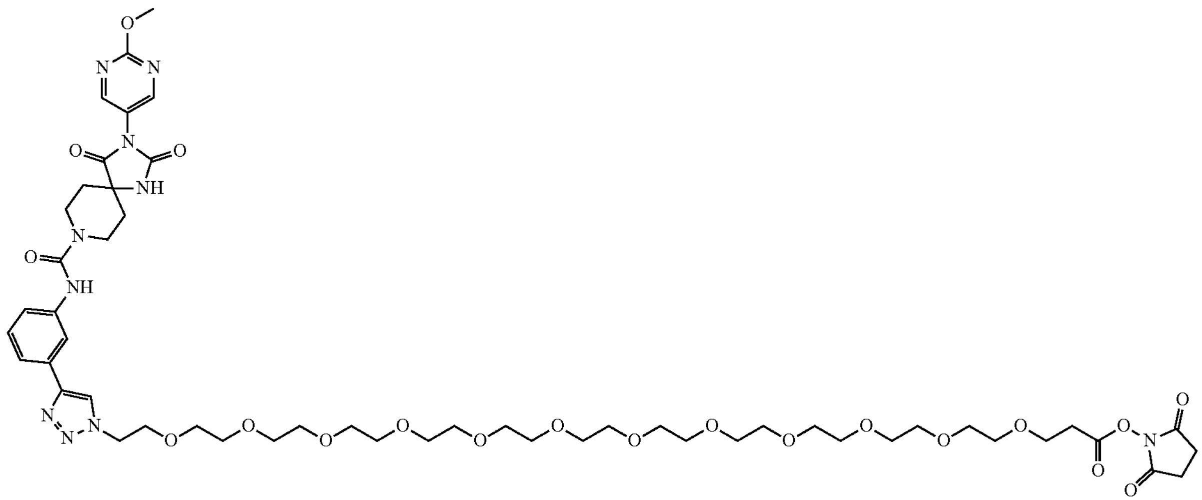 [SMILES: COc1ncc(N2C(=O)NC3(CCN(C(=O)Nc4cccc(-c5cn(CCOCCOCCOCCOCCOCCOCCOCCOCCOCCOCCOCCOCCC(=O)ON6C(=O)CCC6=O)nn5)c4)CC3)C2=O)cn1] |
| I-84 | 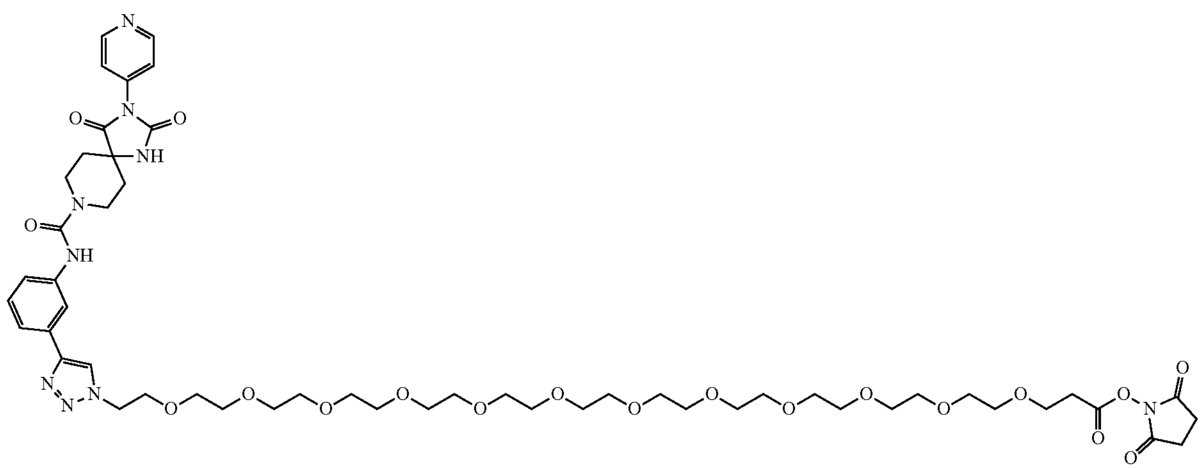 [SMILES: O=C(CCOCCOCCOCCOCCOCCOCCOCCOCCOCCOCCOCCOCCn1cc(-c2cccc(NC(=O)N3CCC4(CC3)NC(=O)N(c3ccncc3)C4=O)c2)nn1)ON1C(=O)CCC1=O] |

TABLE 1-continued
Exemplary compounds
| Compound No. | Structure |
|---|---|
| I-85 | 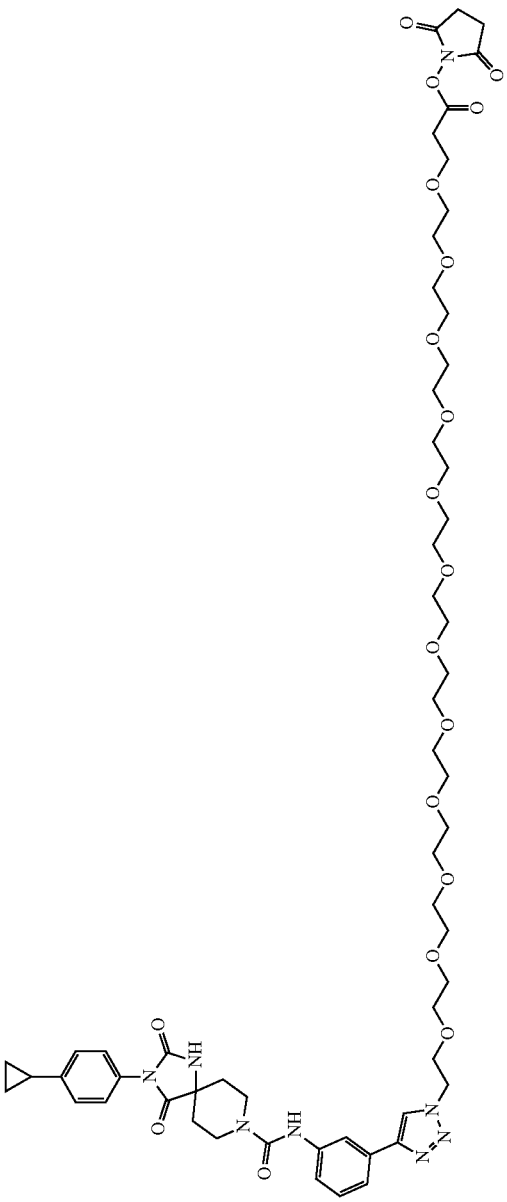 |
| I-86 | 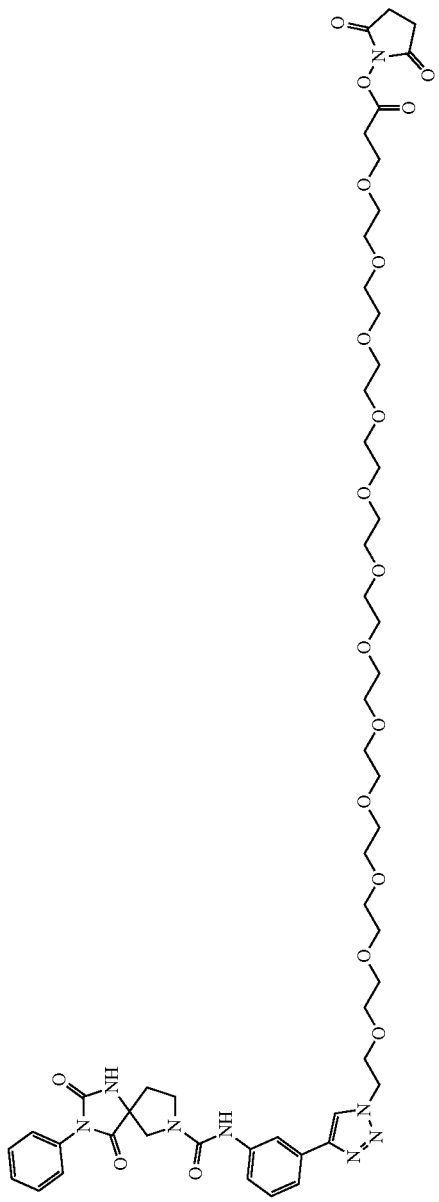 |

TABLE 1-continued
Exemplary compounds
| Compound No. | Structure |
|---|---|
| I-87 | 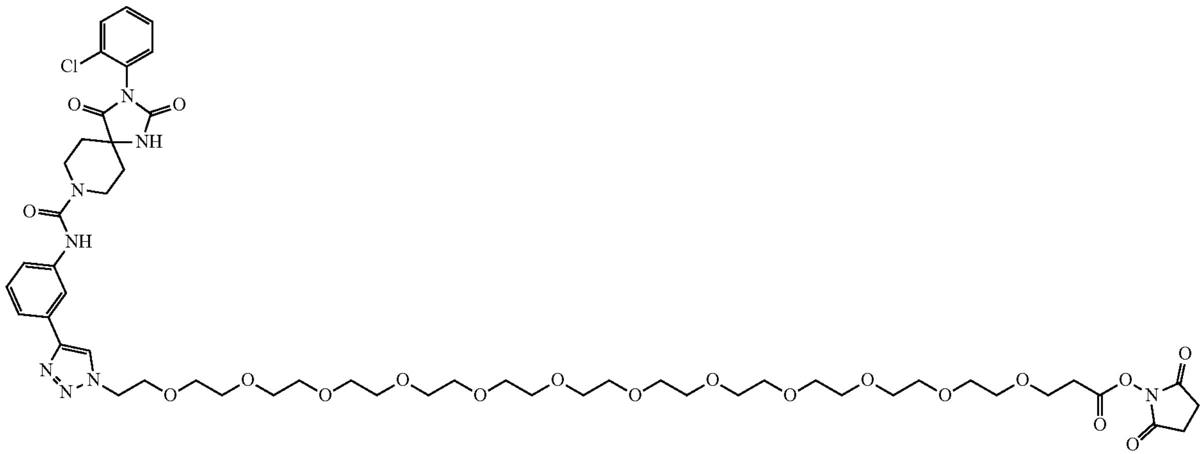 [SMILES: O=C(CCOCCOCCOCCOCCOCCOCCOCCOCCOCCOCCOCCOCCn1cc(-c2cccc(NC(=O)N3CCC4(CC3)NC(=O)N(c3ccccc3Cl)C4=O)c2)nn1)ON1C(=O)CCC1=O] |
| I-88 | 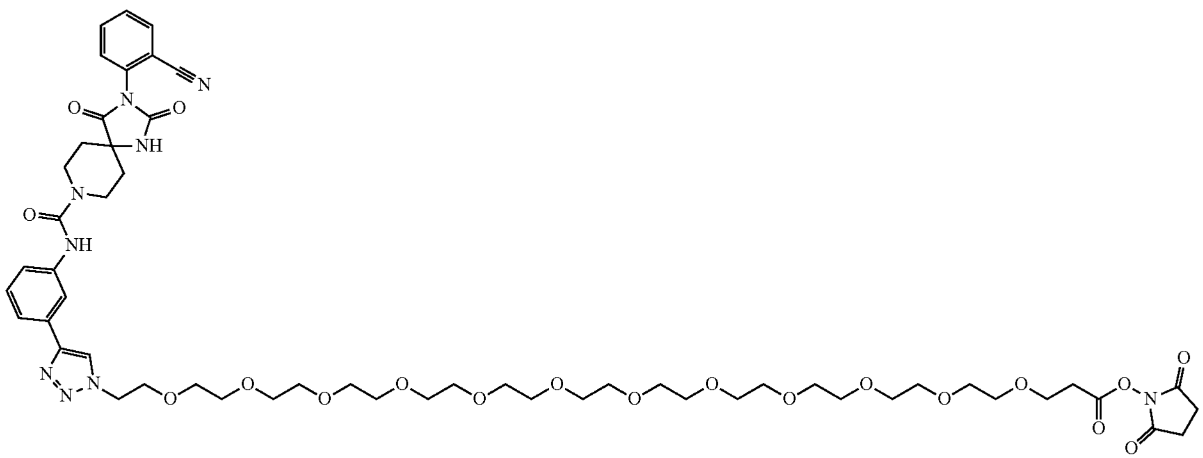 [SMILES: N#Cc1ccccc1N1C(=O)NC2(CCN(C(=O)Nc3cccc(-c4cn(CCOCCOCCOCCOCCOCCOCCOCCOCCOCCOCCOCCOCCC(=O)ON5C(=O)CCC5=O)nn4)c3)CC2)C1=O] |

TABLE 1-continued
Exemplary compounds
| Compound No. | Structure |
|---|---|
| I-89 | 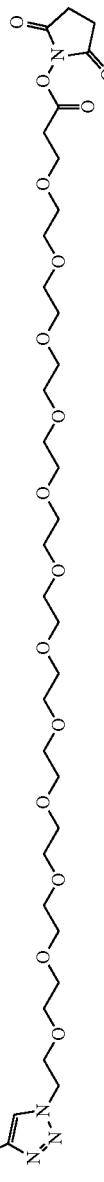 |

TABLE 1-continued
Exemplary compounds
| Compound No. | Structure |
|---|---|
| I-90 | 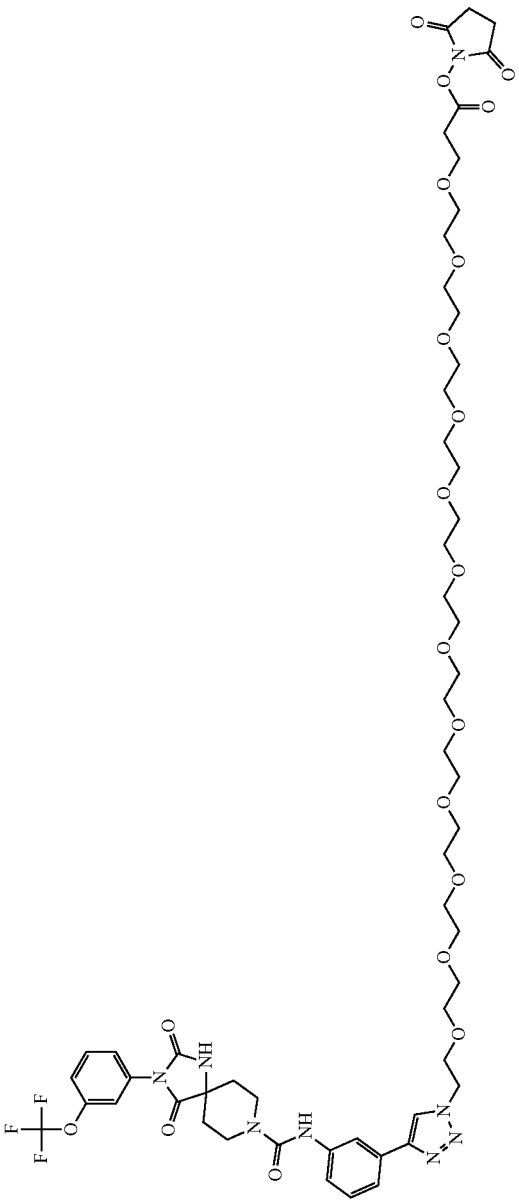 |
| I-91 | 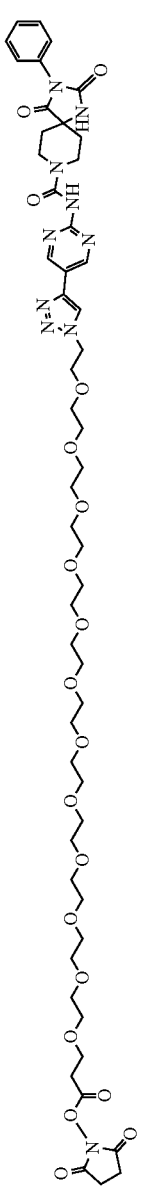 |

TABLE 1-continued
Exemplary compounds
| Compound No. | Structure |
|---|---|
| I-92 | 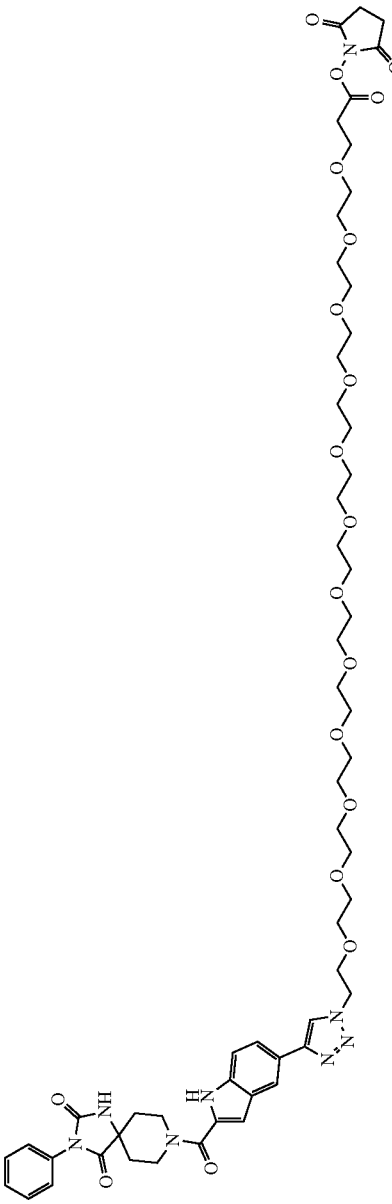 |
| I-93 | 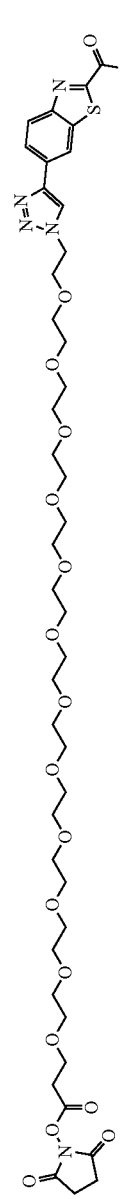 |

TABLE 1-continued

Exemplary compounds

| Compound No. | Structure |
|---|---|
| I-94 | 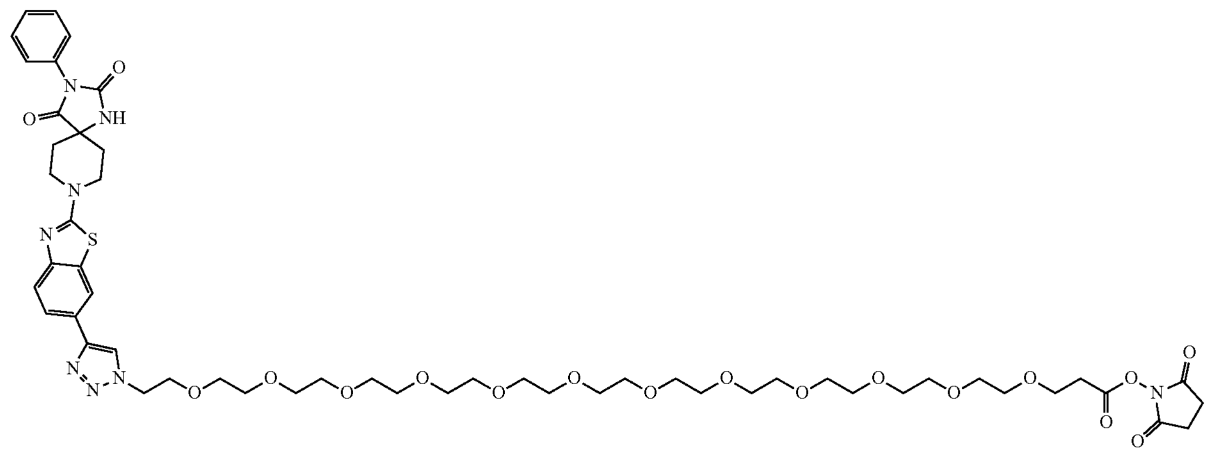 [SMILES: O=C(CCOCCOCCOCCOCCOCCOCCOCCOCCOCCOCCOCCOCCn1cc(-c2ccc3nc(N4CCC5(CC4)NC(=O)N(c4ccccc4)C5=O)sc3c2)nn1)ON1C(=O)CCC1=O] |
| I-95 | 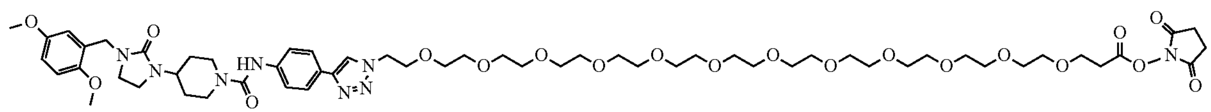 [SMILES: COc1ccc(OC)c(CN2CCN(C3CCN(C(=O)Nc4ccc(-c5cn(CCOCCOCCOCCOCCOCCOCCOCCOCCOCCOCCOCCOCCC(=O)ON6C(=O)CCC6=O)nn5)cc4)CC3)C2=O)c1] |
| I-96 | 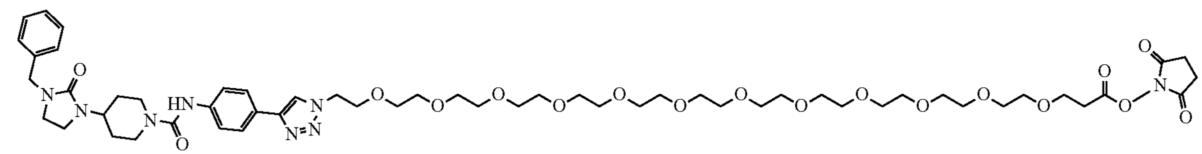 [SMILES: O=C(CCOCCOCCOCCOCCOCCOCCOCCOCCOCCOCCOCCOCCn1cc(-c2ccc(NC(=O)N3CCC(N4CCN(Cc5ccccc5)C4=O)CC3)cc2)nn1)ON1C(=O)CCC1=O] |
| I-97 | 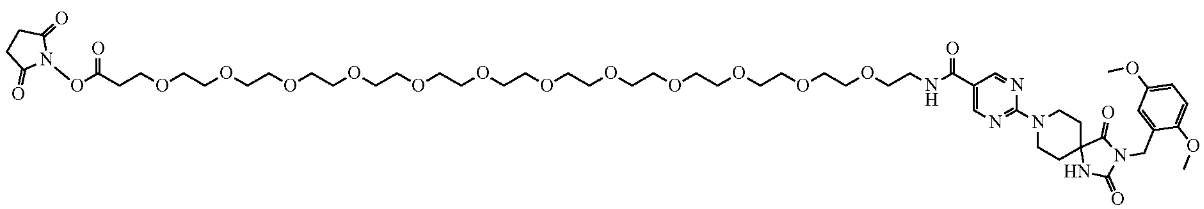 [SMILES: COc1ccc(OC)c(CN2C(=O)NC3(CCN(c4ncc(C(=O)NCCOCCOCCOCCOCCOCCOCCOCCOCCOCCOCCOCCOCCC(=O)ON5C(=O)CCC5=O)cn4)CC3)C2=O)c1] |

TABLE 1-continued
Exemplary compounds
| Compound No. | Structure |
|---|---|
| I-98 | 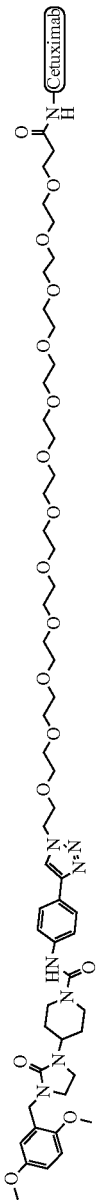 |
| I-99 | 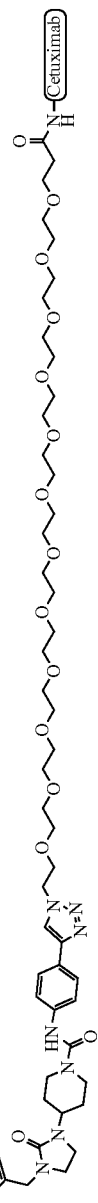 |
| I-100 | 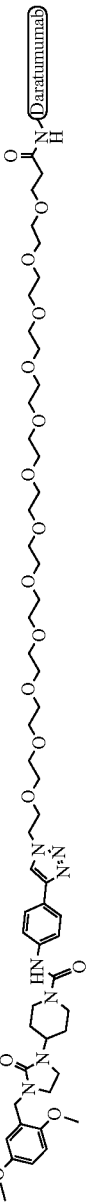 |
| I-101 | 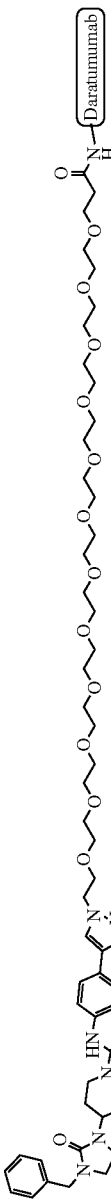 |

In some embodiments, the present invention provides a compound set forth in Table 1, above, or a pharmaceutically acceptable salt thereof.

4. General Methods of Providing the Present Compounds

Compounds of the present disclosure may be prepared or isolated in general by synthetic and/or semi-synthetic methods known to those skilled in the art for analogous compounds and by methods described in detail in the Examples, herein.

Certain compounds, e.g., of formula C (e.g., wherein TM is an antibody or a fragment thereof), I, etc. may be prepared by treating targeting moieties, e.g., antibodies or fragments thereof (e.g., monoclonal antibodies), with certain compounds comprising reactive groups, e.g., those of formula C, II, etc. wherein TM is or comprise a reactive group. In some embodiments, compounds of formula II, wherein the targeting moiety is a reactive moiety capable of forming covalent bond(s) with a monoclonal antibody may be used to prepare compounds of formula I.

Exemplary reactive groups are described below. In some embodiments, TM is or comprises such a reactive group, which can be optionally reacted with a targeting moiety, e.g., an antibody or a fragment thereof, to form an antibody conjugate (e.g., of formula C, I, etc.).

Nhs Esters:

In some embodiments, compounds of formula C or II, wherein TM is an NHS ester,

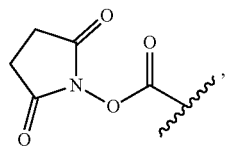 [SMILES: *C(=O)ON1C(=O)CCC1=O]

are capable of forming a conjugate (e.g., a compound of formula I or C which has a different TM) wherein $L^3$ comprises

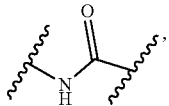 [SMILES: *NC(*)=O]

by forming an amide bond with a lysine residue, e.g., of a monoclonal antibody or a fragment thereof as shown in Scheme I below. In scheme I, the portion of $L^3$ comprising the amide bond formed by the NHS ester moiety is shown for clarity.

Scheme I—covalent modification of a lysine residue of mAb to form a compound of formula I, wherein $L^3$ comprises

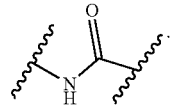 [SMILES: *NC(*)=O]

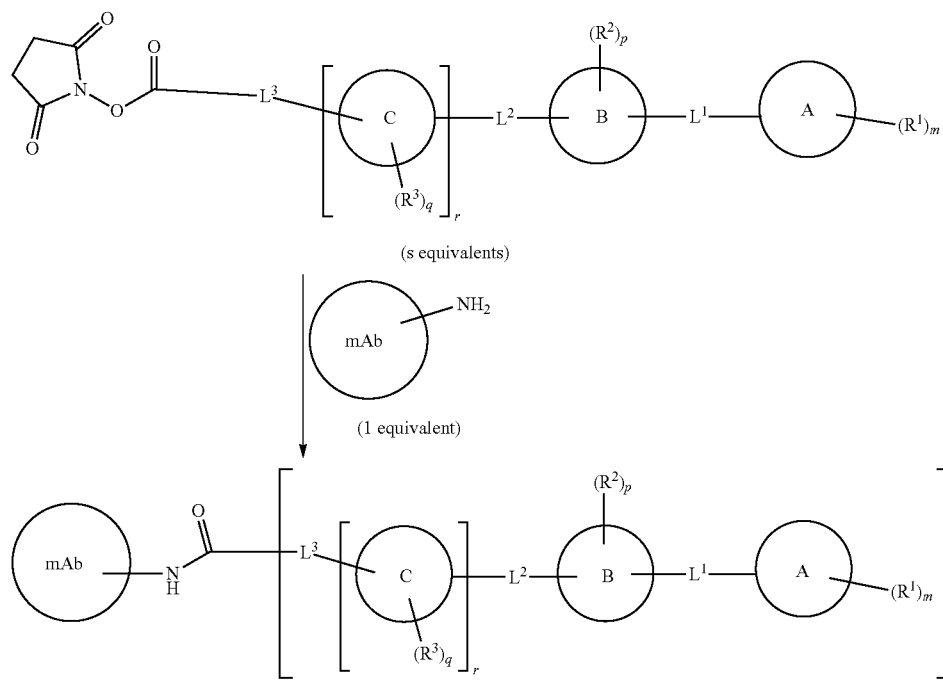

DIBO Moiety:

In some embodiments, a means of conjugation is via triazole groups, e.g., formed by click reactions. In some embodiments, a means of achieving click reactions (triazole formation), e.g., while maintaining cell viability, is the introduction of cyclooctynes, where the strain in the eight-membered ring allows the reaction with azides to occur in the absence of catalysts. One such class of reagents is comprised of the so-called DIBO moiety:

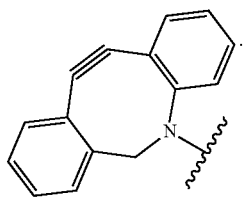 [SMILES: *N1Cc2ccccc2C#Cc2ccccc21]

Enzymatically, chemically, or metabolically azide-modified macromolecules can be labeled without the metal catalysts, which prevents damage of proteins.

In some embodiments, compounds of formula II or C, wherein TM is a DIBO moiety,

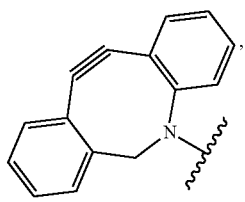 [SMILES: *N1Cc2ccccc2C#Cc2ccccc21]

are capable of forming a compound of formula I or another compound of formula C, wherein $L^3$ comprises

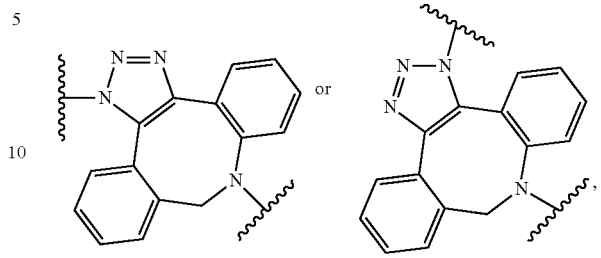

by forming a triazole ring with an azide residue of a targeting moiety, e.g., of a monoclonal antibody as shown in Scheme II below. Depending in the reaction geometry, two regioisomeric products can be formed. The portion of $L^3$ comprising

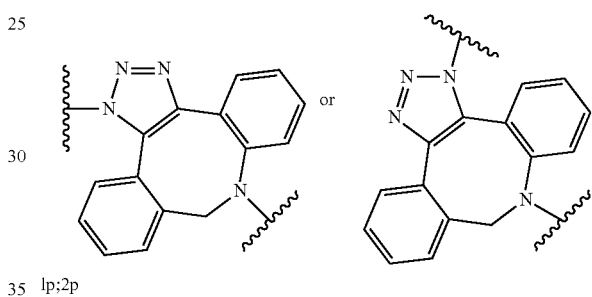

1p;2p formed by the reaction with the DIBO moiety is indicated in Scheme II for clarity.

Scheme II—triazole formation with an engineered azide moiety of mAb to form a compound of formula I, wherein $L^3$ comprises

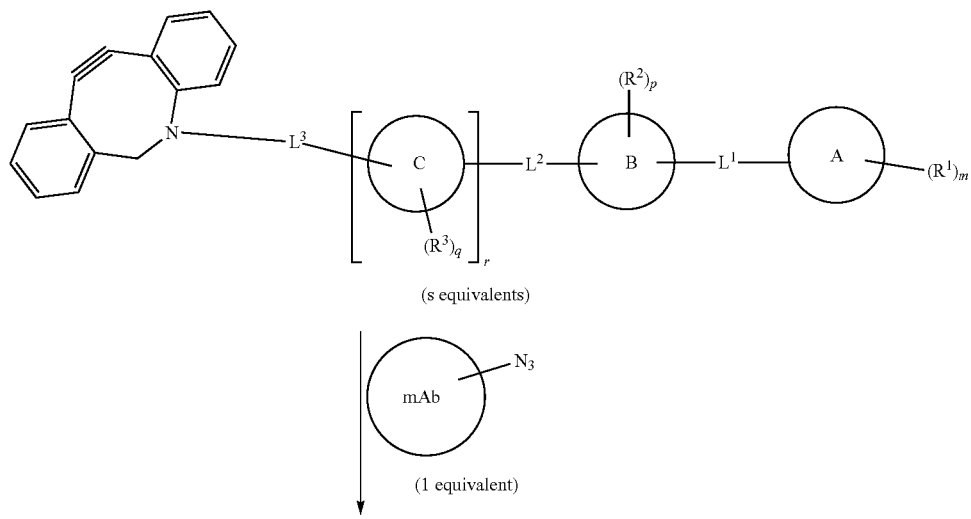

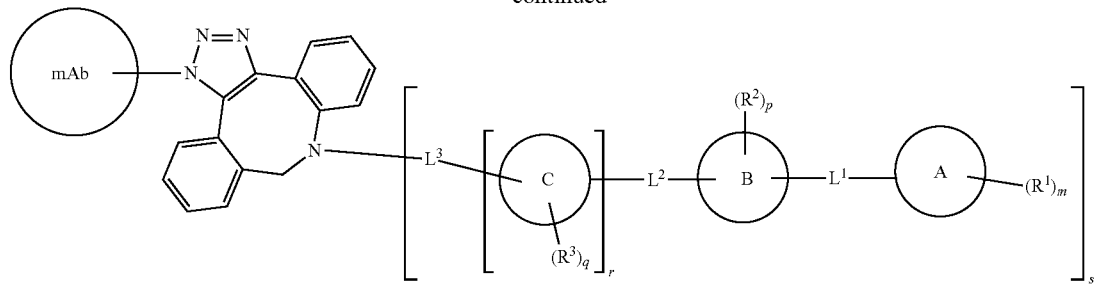

and/or

Maleimide Moiety:

In some embodiments, compounds of formula II or C, wherein TM is a maleimide moiety,

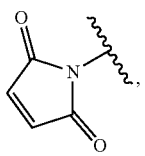 [SMILES: *N1C(=O)C=CC1=O]

are capable of forming an thioether bond with a cysteine residue, e.g., of the monoclonal antibody as shown in Scheme III below. This can form a compound of formula I or another compound of formula C, wherein $L^3$ comprises

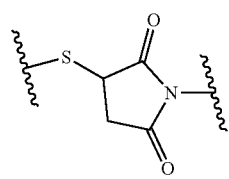 [SMILES: *SC1CC(=O)N(*)C1=O]

as indicated below. The portion of $L^3$ comprising

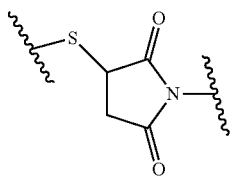 [SMILES: *SC1CC(=O)N(*)C1=O]

in shown in Scheme III below for clarity.

Scheme III—covalent modification of a cysteine residue of mAb to form a compound of formula I, wherein $L^3$ comprises

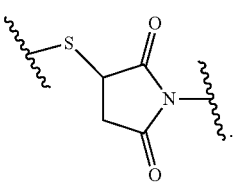 [SMILES: *SC1CC(=O)N(*)C1=O]

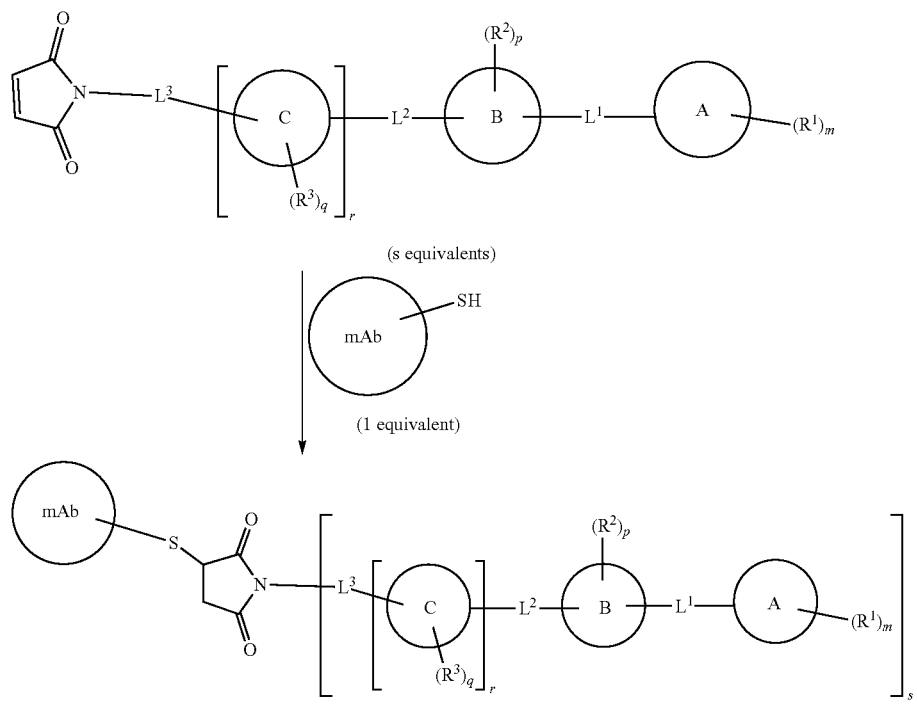

One of skill in the art will appreciate that compounds of the present disclosure, e.g., of formula I, may contain one or more stereocenters, and may be present as an racemic or diastereomeric mixture. One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

In some embodiments, the present disclosure provides a method for preparing a compound having the structure of formula C, I, etc., or a salt thereof, comprising steps of:
  providing a first compound of formula A or a salt thereof, wherein $R^5$ is a reactive group,
  providing a second compound of formula TM-$R^6$ or a salt thereof, wherein TM is as described in the present disclosure, and $R^6$ is a reactive group, and
  reacting $R^5$ with $R^6$ to form a compound of formula C, I, etc., or a salt thereof.

In some embodiments, the present disclosure provides a method, comprising steps of:
  providing a first compound of formula A or a salt thereof,
  providing a second compound of formula $R^6$-$L^3$-H or a salt thereof, wherein each of $R^6$ and $L^3$ is as defined and described herein,
  reacting $R^5$ of the first compound with $R^6$ of the second compound to form a third compound which is a compound of formula A or a salt thereof.

In some embodiments, $R^6$ is hydrogen, halogen, —CN, —$N_3$, —$NO_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)$_2$OR, —S(O)(NH)R, —S(O)$_2$N(R)$_2$, or R.

In some embodiments, $L^3$ of the first compound becomes part of $L^3$ of the third compound. In some embodiments, $L^3$ of the first compound is a covalent bond. In some embodiments, $L^3$ of the first compound is an optionally substituted bivalent $C_{1-3}$ hydrocarbon chain wherein 0-3 methylene unit are independently replaced as described herein. In some embodiments, $L^3$ of the third compound is an optionally substituted bivalent $C_{3-10}$ hydrocarbon chain wherein 0-3 methylene unit are independently replaced as described herein.

In some embodiments, a reaction between two reactive groups, e.g., $R^5$ and $R^6$, is performed at the presence of an activating agent, catalyst, etc. Suitable conditions, e.g., temperatures, concentrations, solvents, etc. for various chemical reactions are readily available in the art and can be utilized in accordance with the present disclosure. In some embodiments, each of $R^5$ and $R^6$ is independently a reactive group, e.g., one as described for $R^5$, and $R^5$ and $R^6$ can react with each other. In some embodiments, one of two reactive groups, e.g., $R^5$ and $R^6$, is or comprises —COOH or an activated derivative thereof

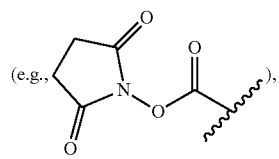 [SMILES: *C(=O)ON1C(=O)CCC1=O]

and the other is or comprises —OH. Such a pair of reactive groups, e.g., $R^5$ and $R^6$, may react each other to form an ester under an esterification condition. In some embodiments, one of two reactive groups, e.g., $R^5$ and $R^6$, is or comprises —COOH or an activated derivative thereof (e.g., 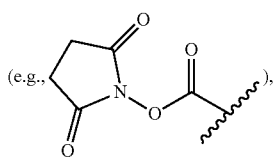 [SMILES: *C(=O)ON1C(=O)CCC1=O]), and the other is or comprises an amino group (e.g., —NH$_2$, N(R)$_2$, or —NHR, etc.). Such a pair of reactive groups, e.g., R$^5$ and R$^6$, may react each other to form an amide under an amidation condition. In some embodiments, two reactive groups, e.g., R$^5$ and R$^6$, can react with each via a cycloaddition reaction, e.g., a [4+2] or [3+2] cycloaddition reaction. In some embodiments, one of two reactive groups, e.g., R$^5$ and R$^6$, is or comprises a dienophile or dipolarophile group (e.g., comprising —C═C—, —C≡C—, etc.), and the other is or comprises a diene or dipole group (e.g., a hydrocarbon diene, a diene comprising one or more heteroatoms, a 1,3-dipole, etc.). In some embodiments, one of two reactive groups, e.g., R$^5$ and R$^6$, is or comprises —N$_3$, and the other is —C≡C—H or comprises —C≡C— (e.g., in a ring system). In some embodiments, one of two reactive groups, e.g., R$^5$ and R$^6$, is or comprises an electrophilic group

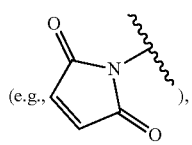 [SMILES: *N1C(=O)C=CC1=O]

and the other is or comprises a nucleophilic group (e.g., —SH).

In some embodiments, a reactive group is or comprises

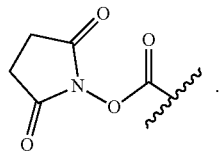 [SMILES: *C(=O)ON1C(=O)CCC1=O]

In some embodiments, a reactive group is or comprises an activated carboxylic acid group. In some embodiments, a reactive group is optionally substituted

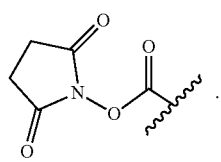

In some embodiments, a reactive group is

In some embodiments, such a group reacts with an amino group under suitable conditions. In some embodiments, a reactive group is —NR$_2$. In some embodiments, a reactive group is —NHR. In some embodiments, a reactive group is —NH$_2$. In some embodiments, a reactive group is or comprises an electrophilic group. In some embodiments, a reactive group is or comprises optionally substituted CH$_2$═CH—C(O)—, e.g., in some embodiments, a reactive group is

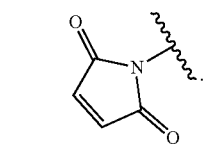 [SMILES: *N1C(=O)C=CC1=O]

In some embodiments, such a group reacts with a —SH group under suitable conditions. In some embodiments, a reactive group is a nucleophilic group. In some embodiments, a reactive group is —SH. In some embodiments, a reactive group is or comprises a dienophile or dipolarophile group. In some embodiments, a reactive group comprises —C≡C—. In some embodiments, a reactive group comprises —C═C—. In some embodiments, a reactive group is or comprises —C≡CH. In some embodiments, a reactive group is —C≡CH. In some embodiments, a reactive group is or comprises

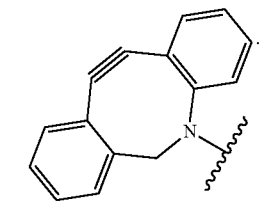 [SMILES: *N1Cc2ccccc2C#Cc2ccccc21]

In some embodiments, a reactive group is

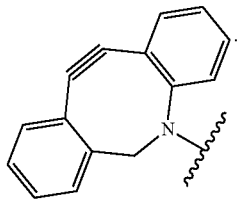 [SMILES: *N1Cc2ccccc2C#Cc2ccccc21]

In some embodiments, such a group can undergo a cycloaddition reaction, e.g., a click chemistry reaction, under suitable conditions. In some embodiments, a reactive group is or comprises a diene or a 1,3-dipole, each of which may independently contain one or more heteroatoms. In some embodiments, a reactive group is or comprises —N$_3$. In some embodiments, such a group can undergo a cycloaddition reaction, e.g., a click chemistry reaction, under suitable conditions. In some embodiments, a reactive group is or comprises a bis-sulfone group, e.g., (RO$_2$SCH$_2$)$_2$CHC(O)— wherein each R is independently as defined and described herein (e.g., see compound I-70). In some embodiments, a bis-sulfone group can react with two —SH (e.g., of targeting moieties such as antibodies and/or fragments thereof) to form a bridged disulfide (e.g., (—SCH$_2$)$_2$CHC(O)—).

In some embodiments, R⁵ is or comprises

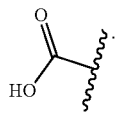

In some embodiments, R⁵ is or comprises an activated carboxylic acid group. In some embodiments, R⁵ is optionally substituted

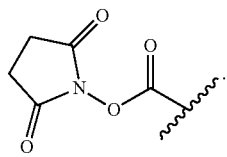 [SMILES: *C(=O)ON1C(=O)CCC1=O]

In some embodiments, R⁵ is

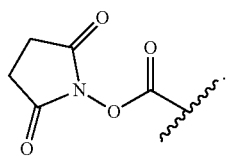 [SMILES: *C(=O)ON1C(=O)CCC1=O]

In some embodiments, such a group reacts with an amino group under suitable conditions. In some embodiments, R⁵ is —NR₂. In some embodiments, R⁵ is —NHR. In some embodiments, R⁵ is —NH₂. In some embodiments, R⁵ is or comprises an electrophilic group. In some embodiments, R⁵ is or comprises optionally substituted CH₂=CH—C(O)—. In some embodiments, R⁵ is

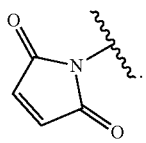

In some embodiments, such a group reacts with a —SH group under suitable conditions. In some embodiments, R⁵ is a nucleophilic group. In some embodiments, R⁵ is —SH. In some embodiments, R⁵ is or comprises a dienophile or dipolarophile group. In some embodiments, R⁵ comprises —C≡C—. In some embodiments, R⁵ comprises —C≡C—. In some embodiments, R⁵ is or comprises —C≡CH. In some embodiments, R⁵ is —C≡CH. In some embodiments, R⁵ is or comprises

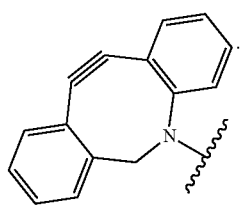 [SMILES: *N1Cc2ccccc2C#Cc2ccccc21]

In some embodiments, R⁵ is

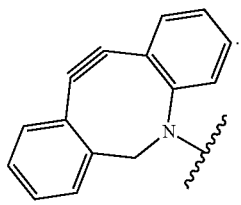

In some embodiments, such R⁵ can undergo a cycloaddition reaction, e.g., a click chemistry reaction, under suitable conditions. In some embodiments, R⁵ is or comprises a diene or a 1,3-dipole, each of which may independently contain one or more heteroatoms. In some embodiments, R⁵ is or comprises —N₃. In some embodiments, such a group can undergo a cycloaddition reaction, e.g., a click chemistry reaction, under suitable conditions. In some embodiments, R⁵ is or comprises a bis-sulfone group, e.g., (RO₂SCH₂)₂CH C(O)— wherein each R is independently as defined and described herein (e.g., see compound I-70). In some embodiments, a bis-sulfone group can react with two —SH (e.g., of targeting moieties such as antibodies and/or fragments thereof) to form a bridged disulfide (e.g., (—SCH₂)₂CHC (O)—).

In some embodiments, R⁶ is or comprises

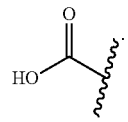

In some embodiments, R⁶ is or comprises an activated carboxylic acid group. In some embodiments, R⁶ is optionally substituted

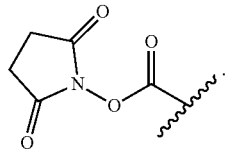 [SMILES: *C(=O)ON1C(=O)CCC1=O]

In some embodiments, R⁶ is

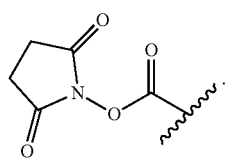 [SMILES: *C(=O)ON1C(=O)CCC1=O]

In some embodiments, such a group reacts with an amino group under suitable conditions. In some embodiments, R⁶ is —NR₂. In some embodiments, R⁶ is —NHR. In some embodiments, R⁶ is —NH₂. In some embodiments, R⁶ is or comprises an electrophilic group. In some embodiments, R⁶ is or comprises optionally substituted CH₂=CH—C(O)—. In some embodiments, R⁶ is

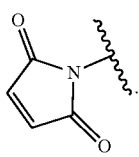 [SMILES: *N1C(=O)C=CC1=O]

In some embodiments, such a group reacts with a —SH group under suitable conditions. In some embodiments, $R^6$ is a nucleophilic group. In some embodiments, $R^6$ is —SH. In some embodiments, $R^6$ is or comprises a dienophile or dipolarophile group. In some embodiments, $R^6$ comprises —C≡C—. In some embodiments, $R^6$ comprises —C≡C—. In some embodiments, $R^6$ is or comprises —C≡CH. In some embodiments, $R^6$ is —C≡CH. In some embodiments, $R^6$ is or comprises

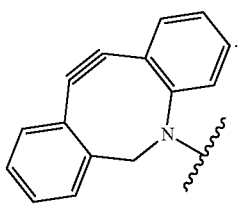 [SMILES: *N1Cc2ccccc2C#Cc2ccccc21]

In some embodiments, $R^6$ is

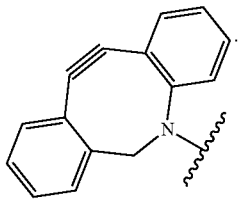 [SMILES: *N1Cc2ccccc2C#Cc2ccccc21]

In some embodiments, such $R^6$ can undergo a cycloaddition reaction, e.g., a click chemistry reaction, under suitable conditions. In some embodiments, $R^6$ is or comprises a diene or a 1,3-dipole, each of which may independently contain one or more heteroatoms. In some embodiments, $R^6$ is or comprises —$N_3$. In some embodiments, such a group can undergo a cycloaddition reaction, e.g., a click chemistry reaction, under suitable conditions. In some embodiments, $R^6$ is or comprises a bis-sulfone group, e.g., $(RO_2SCH_2)_2CH$ C(O)— wherein each R is independently as defined and described herein (e.g., see compound I-70). In some embodiments, a bis-sulfone group can react with two —SH (e.g., of targeting moieties such as antibodies and/or fragments thereof) to forma a bridged disulfide (e.g., (—$SCH_2)_2CHC$(O)—).

As readily appreciated by those skilled in the art, compounds of the present disclosure that contain reactive groups, e.g., compounds of formula A or salts thereof, can readily react with targeting moieties, e.g., antibodies and/or fragments thereof, to form new compounds, e.g., conjugates of formula C. For example, compounds containing NHS ester groups may react with amino groups of targeting moieties, compounds containing maleimide moieties may react with —SH of targeting moieties, compounds comprising alkene and/or alkyne groups (e.g., —C≡C—) may react with targeting moieties comprising dienophiles or dipolarophiles (e.g., —$N_3$), and vice versa. Certain examples are described in the Examples herein.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the present disclosure provides a composition comprising a compound of this present disclosure or a pharmaceutically acceptable derivative thereof and a pharmaceutically acceptable carrier, adjuvant, or vehicle. In some embodiments, the amount of compound in compositions of this present disclosure is such that is effective to measurably bind a receptor described herein, e.g., a Fc receptor like CD16a, in a biological sample or in a patient. In certain embodiments, the amount of compound in compositions of this invention is such that is effective to measurably bind CD16a in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

As used herein, the term "active metabolite or residue thereof" means that a metabolite or residue thereof is also a binder of a receptor described herein, e.g., a Fc receptor like CD16a.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Typically, the compositions containing mAbs are administered intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this present disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

When formulated for oral administration, pharmaceutically acceptable compositions of this invention are formulated for administration with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In some embodiments, compounds and compositions thereof described herein are generally useful for modulating functions of receptors that such compounds bind to. In some embodiments, compounds and compositions thereof described herein can improve binding to certain receptors, increase incruitment of immune effector cells expressing such receptors, and/or provide improved therapeutic effects. In some embodiments, compounds and compositions described herein are generally useful for the binding and recruitment of CD16a to cells expressing cell surface accessible epitopes that would be of therapeutic benefit to remove by immune-mediated cytotoxicity.

Examples of cell surface accessible epitopes on cells that would be of therapeutic benefit to remove by immune-mediated cytotoxicity include, but are not limited to, the following: oncology epitopes such as CD19, CD20, CD21, CD22, CD30, CD33, CD37, CD38, CD40, CD52, CD56, CD66, CD70, CD72, CD79a/b, CD123, CD180, CD174, CD276, CD326 endothelian B receptor, CRIPTO, FAP, mesothelin, GD2, 5T4, Alpha v Beta 6, GPNMB, Nectin-4, LIV1A, MUC16 (CA125), TIM-1, ED-B, PMEL 17, Endothelin B receptor, PSMA, STEAP-1, TENB2, CAIX, UPAR, CXCR4, EGFR family, PDL1, BCMA, PDGFR, VEGFR family, EphA3, Lag3, CTLA4, Endoglin, IL2, CCR4, OX40, WT1, or HLA-A2; autoimmune epitopes such as Anti-TNF (transmembrane) or IL5; and infectious disease epitopes such as GP120.

Indications where ADCC-enhancement is perceived to have benefit include, but are not limited to: cancer indications such as Lymphoma, Leukemia, Lung, CRC, Pancreatic, Breast, Brain, Ovarian, Melanoma, Prostate, Renal, Mesothelioma, Bone, and Head/Neck cancer; autoimmune indications such as Rheumatological disorders, Neurological disorders, Hematological diseases, and Inflammatory diseases; and infectious disease such as HIV.

As described generally above, ADCC enhancement is applicable to cancer and infectious diseases. However, a binding moiety that is an antagonist of an Fc receptor could be applied to other disorders such as autoimmune or neurodegenerative disorders. Fc receptors are appealing targets in the treatment of inflammatory autoimmune diseases. Targeting approaches include blocking activating Fc receptors, activating inhibitory FcγRIIb, and utilizing activating receptors for antigen targeting and ADCC-mediated cell depletion.

In some embodiments, the disorder, disease or condition is selected from the group consisting of a cancer, a neurodegenerative disorder, a viral disease, an autoimmune disease, an inflammatory disorder, immunodeficiency disorders, a proliferative disorder, and an infectious disease.

In some embodiments, the cancer or proliferative disorder is selected the group consisting of a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, and intravascular large B-cell lymphoma.

In some embodiments, the neurodegenerative disease is selected from the group consisting of Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

In some embodiments, the inflammatory disorder is selected from the group consisting of conditions of the eye such as ocular allergy, conjunctivitis, keratoconjunctivitis sicca, and vernal conjunctivitis; diseases affecting the nose including allergic rhinitis; and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, vulvitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acute and chronic gout, chronic gouty arthritis, psoriasis, psoriatic arthritis, rheumatoid arthritis, Juvenile rheumatoid arthritis, Cryopyrin Associated Periodic Syndrome (CAPS), and osteoarthritis.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the present invention provides a method for treating one or more disorders, diseases, and/or conditions wherein the disorder, disease, or condition is a cancer, a viral disease, an autoimmune disease, immunodeficiency disorders, a proliferative disorder, or an infectious disease.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an autoimmune disease, an inflammatory disease, an infectious disease, or a viral disease.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present disclosure provides a composition comprising a compound described herein (e.g., of formula A, C, or I) and one or more additional therapeutic agents. The therapeutic agent may be administered together with a compound described herein (e.g., of formula A, C, or I), or may be administered prior to or following administration of a compound described herein (e.g., of formula A, C, or I). Suitable therapeutic agents are described in further detail below. In certain embodiments, a compound described herein (e.g., of formula A, C, or I) may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound described herein (e.g., of formula A, C, or I) may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound described herein (e.g., of formula A, C, or I) and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a compound described herein (e.g., of formula A, C, or I) and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a compound described herein (e.g., of formula A, C, or I) and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-i" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound described herein (e.g., of formula A, C, or I) and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a compound described herein (e.g., of formula A, C, or I) and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a compound described herein (e.g., of formula A, C, or I) and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound described herein (e.g., of formula A, C, or I) and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound described herein (e.g., of formula A, C, or I) and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a compound described herein (e.g., of formula A, C, or I) and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a compound described herein (e.g., of formula A, C, or I) and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound described herein (e.g., of formula A, C, or I) and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound described herein (e.g., of formula A, C, or I) and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound described herein (e.g., of formula A, C, or I) and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound described herein (e.g., of formula A, C, or I) and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenstrom's macroglobulinemia comprising administering to a patient in need thereof a compound described herein (e.g., of formula A, C, or I) and one or more additional therapeutic agents selected from chlorambucil (Leukeran®), cvclophosphamide (Cvtoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, the present invention provides a method of treating Alzheiner's disease comprising administering to a patient in need thereof a compound described herein (e.g., of formula A, C, or I) and one or more additional therapeutic agents selected from donepezil (Aricept®), rivastigmine (Excelon®), galantamine (Razadyne®), tacrine (Cognex®), and memantine (Namenda®).

In another embodiment, the present invention provides a method of treating organ transplant rejection or graft vs. host disease comprising administering to a patient in need thereof a compound described herein (e.g., of formula A, C, or I) and one or more additional therapeutic agents selected from a steroid, cyclosporin, FK506, raparnycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound described herein (e.g., of formula A, C, or I) and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound described herein (e.g., of formula A, C, or I) and a PI3K inhibitor, wherein the disease is selected from a cancer, a neurodegenerative disorder, an angiogenic disorder, a viral disease, an autoimrmune disease, an inflammatory disorder, a horrmone-related disease, conditions associated with organ transplantation, inmmunodeficiency disorders, a destructive bone disorder, a proliferative disorder, an infectious disease, a condition associated with cell death, thrombin-induced platelet aggregation, chronic myelogenous leukemia (CML), chronic lynphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound described herein (e.g., of formula A, C, or I) and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minmal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Among other things, the present disclosure provides the following Embodiments:

1. A compound of formula A:

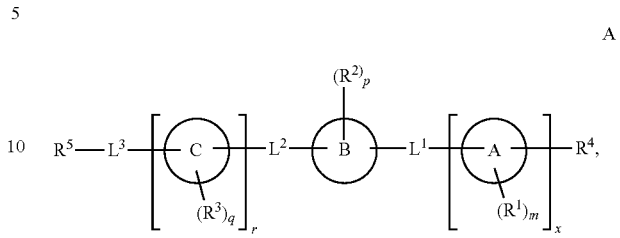

A or a pharmaceutically acceptable salt thereof, wherein:
each of $R^1$, $R^2$, $R^3$, $R^4$, and $R^5$ is independently hydrogen, halogen, —CN, —$N_3$, —$NO_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)$_2$OR, —S(O)(NH)R, —S(O)$_2$N(R)$_2$, or R;
each of Ring A, Ring B and Ring C is independently an optionally substituted monocyclic, bicyclic, or polycyclic 3-40 membered ring having 0-20 heteroatoms;
each of $L^1$, $L^2$ and $L^3$ is independently a covalent bond, or a bivalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—, and one or more carbon and heteroatoms of the group are optionally and independently replaced with $Cy^L$;
each n is independently 1-50;
each -Cy- is independently an optionally substituted, bivalent, monocyclic, bicyclic, or polycyclic 3-40 membered ring having 0-20 heteroatoms;
each $Cy^L$ is independently an optionally substituted, polyvalent, monocyclic, bicyclic, or polycyclic 3-40 membered ring having 0-20 heteroatoms;
each of m, p and q is independently 0, 1, 2, 3, 4 or 5;
each of r and x is independently 0, 1, or 2;
each R' is independently —R, —OR, —C(O)R, —C(O)OR, or —S(O)$_2$R; and
each R is independently —H, or an optionally substituted group selected from $C_{1-30}$ aliphatic, $C_{1-30}$ heteroaliphatic having 1-10 heteroatoms, $C_{6-30}$ aryl, 5-30 membered heteroaryl having 1-10 heteroatoms, and 3-30 membered heterocyclyl having 1-10 heteroatoms, or two R groups are optionally and independently taken together to form a covalent bond, or:
two or more R groups on the same atom are optionally and independently taken together with the atom to form an optionally substituted, monocyclic, bicyclic, or polycyclic 3-40 membered ring having, in addition to the atom, 0-20 heteroatoms; or:

two or more R groups on two or more atoms are optionally and independently taken together with their intervening atoms to form an optionally substituted, monocyclic, bicyclic, or polycyclic 3-40 membered ring having, in addition to the intervening atoms, 0-20 heteroatoms.

2. The compound of any one of the preceding embodiments, wherein $R^5$ is —H.
3. The compound of embodiment 1, wherein $R^5$ is an optionally substituted monocyclic, bicyclic or polycyclic group.
4. The compound of embodiment 3, wherein $R^5$ is optionally substituted phenyl.
5. The compound of embodiment 3, wherein $R^5$ is an optionally substituted bicyclic or polycyclic group, wherein each monocyclic unit is independently an optionally substituted 3-10 membered saturated, partially unsaturated, or aromatic monocyclic ring having 0-5 heteroatoms.
6. The compound of embodiment 3, wherein $R^5$ is optionally substituted 3-10 membered heterocyclyl having 1-5 heteroatoms.
7. The compound of embodiment 6, wherein $R^5$ is optionally substituted

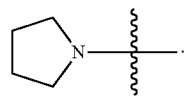 [SMILES: *N1CCCC1]

8. The compound of embodiment 6, wherein $R^5$ is optionally substituted

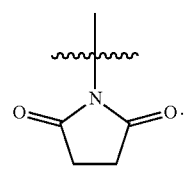 [SMILES: *N1C(=O)CCC1=O]

9. The compound of embodiment 6, wherein $R^5$ is

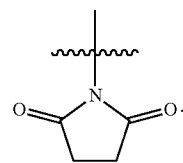 [SMILES: *N1C(=O)CCC1=O]

10. The compound of embodiment 1, wherein $R^5$ is —NRS(O)$_2$R.
11. The compound of embodiment 1, wherein $R^5$ is —CN.
12. The compound of embodiment 1, wherein $R^5$ is a reactive group.
13. The compound of embodiment 1 or 12, wherein $R^5$ is —COOH.

14. The compound of embodiment 1 or 12, wherein $R^5$ is

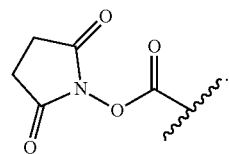 [SMILES: *C(=O)ON1C(=O)CCC1=O]

15. The compound of embodiment 1 or 12, wherein $R^5$ is —N(R)$_2$.
16. The compound of embodiment 1 or 12, wherein $R^5$ is —NH$_2$.
17. The compound of embodiment 1 or 12, wherein $R^5$ is

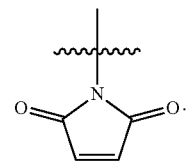 [SMILES: *N1C(=O)C=CC1=O]

18. The compound of embodiment 1 or 12, wherein $R^5$ is or comprises —N$_3$.
19. The compound of embodiment 1 or 12, wherein $R^5$ is —N$_3$.
20. The compound of embodiment 1 or 12, wherein $R^5$ comprises —C≡C—.
21. The compound of embodiment 1 or 12, wherein $R^5$ is —C≡C—H.
22. The compound of embodiment 1 or 12, wherein $R^5$ is

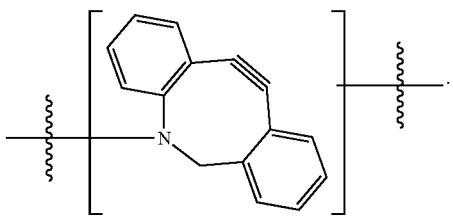

23. A compound of formula C-I:

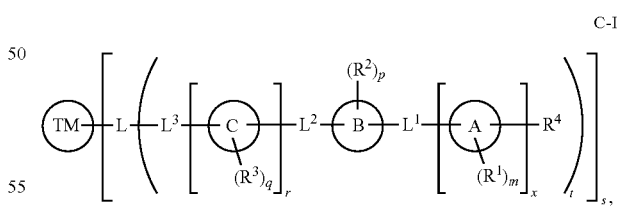

or a pharmaceutically acceptable salt thereof, wherein:
TM is a targeting moiety;
each L is independently a linker moiety;
each of t and s is independently 1-1000;
each of $R^1$, $R^2$, $R^3$, $R^4$, and $R^5$ is independently hydrogen, halogen, —CN, —N$_3$, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)$_2$OR, —S(O)(NH)R, —S(O)$_2$N(R)$_2$, or R;

each of Ring A, Ring B and Ring C is independently an optionally substituted monocyclic, bicyclic, or polycyclic 3-40 membered ring having 0-20 heteroatoms;

each of $L^1$, $L^2$ and $L^3$ is independently a covalent bond, or a bivalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—, and one or more carbon and heteroatoms of the group are optionally and independently replaced with Cy$^L$;

each n is independently 1-50;

each -Cy- is independently an optionally substituted, bivalent, monocyclic, bicyclic, or polycyclic 3-40 membered ring having 0-20 heteroatoms;

each Cy$^L$ is independently an optionally substituted, polyvalent, monocyclic, bicyclic, or polycyclic 3-40 membered ring having 0-20 heteroatoms;

each of m, p and q is independently 0, 1, 2, 3, 4 or 5;

each of r and x is independently 0, 1, or 2;

each R' is independently —R, —OR, —C(O)R, —C(O)OR, or —S(O)$_2$R; and each R is independently —H, or an optionally substituted group selected from $C_{1-30}$ aliphatic, $C_{1-30}$ heteroaliphatic having 1-10 heteroatoms, $C_{6-30}$ aryl, 5-30 membered heteroaryl having 1-10 heteroatoms, and 3-30 membered heterocyclyl having 1-10 heteroatoms, or two R groups are optionally and independently taken together to form a covalent bond, or:

two or more R groups on the same atom are optionally and independently taken together with the atom to form an optionally substituted, monocyclic, bicyclic, or polycyclic 3-40 membered ring having, in addition to the atom, 0-20 heteroatoms; or:

two or more R groups on two or more atoms are optionally and independently taken together with their intervening atoms to form an optionally substituted, monocyclic, bicyclic, or polycyclic 3-40 membered ring having, in addition to the intervening atoms, 0-20 heteroatoms.

24. The compound of embodiment 23, wherein TM is an antibody or a fragment thereof.

25. The compound of any one of embodiments 23-24, wherein TM is a monoclonal antibody or a fragment thereof.

26. The compound of any one of embodiments 23-25, wherein TM is cetuximab.

27. The compound of any one of embodiments 23-25, wherein TM is rituximab.

28. The compound of any one of embodiments 23-25, wherein TM is daratumumab.

29. The compound of any one of embodiments 23-25, wherein TM is adalimumab, alemtuzumab, atezolizumab, avelumab, ipilimumab, dcetuximab, daratumumab, dinutuximab, elotuzumab, ibritumomab tiuxetan, imgatuzumab, infliximab, ipilimumab, necitumumab, obinutuzumab, ofatumumab, pertuzumab, reslizumab, rituximab, trastuzumab, mogamulizumab, AMP-224, FS-102, GSK-2857916, ARGX-111, ARGX-110, AFM-13, APN-301, BI-836826, BI-836858, enoblituzumab, otlertuzumab, veltuzumab, KHK-4083, BIW-8962, ALT-803, carotuximab, epratuzumab, inebilizumab, isatuximab, margetuximab, MOR-208, ocaratuzumab, talacotuzumab, tremelimumab, benralizumab, lumiliximab, MOR-208, Ifibatuzumab, GSK2831781, SEA-CD40, KHK-2823, or BI836858, or a fragment thereof.

30. The compound of any one of embodiments 23-29, wherein each L is independently a covalent bond, or a bivalent or polyvalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—, and one or more carbon and heteroatoms of the group are optionally and independently replaced with Cy$^L$ 31. The compound of any one of embodiments 23-30, wherein one instance of t is 1.

32. The compound of any one of embodiments 23-30, wherein each t is 1.

33. The compound of embodiment 31 or 32, wherein each L independently a covalent bond, or a bivalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—.

34. The compound of any one of embodiments 23-33, wherein one or more methylene units are independently replaced with —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—.

35. The compound of any one of embodiments 23-33, wherein one or more methylene units are independently replaced with —[(—O—C(R')$_2$—C(R')$_2$—)$_n$]— or —[(—C(R')$_2$—O—C(R')$_2$—)$_n$]—.

36. The compound of any one of embodiments 23-35, wherein n is 1-20.

37. The compound of any one of embodiments 23-35, wherein each instance of n is independently selected from 1, 2, 3, 4, 5, 6, 7, 8, 9, or 10.

38. The compound of any one of embodiments 23-35, wherein n is 4, 6, 8, 10 or 12.

39. The compound of any one of embodiments 23-38, wherein one or more methylene units are independently replaced with -Cy-.

40. The compound of embodiment 39, wherein -Cy- is or comprises

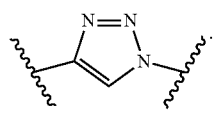 [SMILES: *c1cn(*)nn1]

41. The compound of embodiment 40, wherein -Cy- is

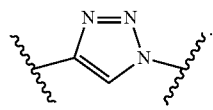 [SMILES: *c1cn(*)nn1]

42. The compound of embodiment 40, wherein -Cy- is

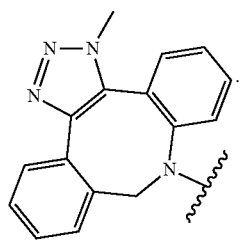 [SMILES: *N1Cc2ccccc2-c2nnn(C)c2-c2ccccc21]

43. The compound of embodiment 40, wherein -Cy- is

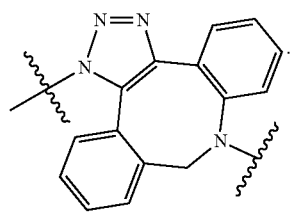 [SMILES: *N1Cc2ccccc2-c2c(nnn2*)-c2ccccc21]

44. The compound of embodiment 39, wherein -Cy- is or comprises —C≡C—.

45. The compound of embodiment 44, wherein -Cy- is or comprises

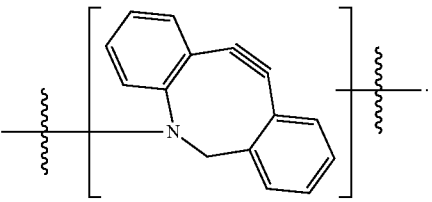

46. The compound of embodiment 31 or 32, wherein L is a covalent bond.

47. The compound of any one of the preceding embodiments, wherein $R^4$ is —S(O)$_2$OR.

48. The compound of any one of embodiments 1-46, wherein $R^4$ is —NRS(O)$_2$R.

49. The compound of any one of embodiments 1-46, wherein $R^4$ is —S(O)$_2$R.

50. The compound of any one of embodiments 1-46, wherein $R^4$ is —S(O)$_2$R.

51. The compound of any one of embodiments 1-46, wherein $R^4$ is —H.

52. The compound of any one of embodiments 1-46, wherein $R^4$ is R, wherein R is an optionally substituted cyclic group.

53. The compound of any one of embodiments 1-46, wherein $R^4$ is optionally substituted 3-10 membered saturated or partially unsaturated carbocyclyl.

54. The compound of embodiment 53, wherein $R^4$ is optionally substituted cyclopropyl.

55. The compound of any one of embodiments 1-46, wherein $R^4$ is optionally substituted 3-10 membered saturated or partially unsaturated heterocyclyl having 1-5 heteroatoms.

56. The compound of embodiment 55, wherein $R^4$ is optionally substituted

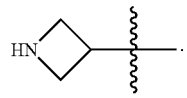 [SMILES: *C1CNC1]

57. The compound of embodiment 55, wherein $R^4$ is optionally substituted

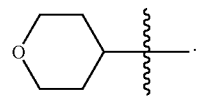

58. The compound of any one of embodiments 1-46, wherein $R^4$ is an optionally substituted 5-6 membered heteroaryl with 1-4 heteroatoms.

59. The compound of embodiment 58, wherein $R^4$ is optionally substituted

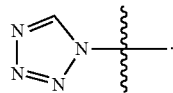

60. The compound of embodiment 58, wherein $R^4$ is optionally substituted

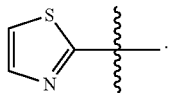

61. The compound of embodiment 58, wherein $R^4$ is optionally substituted

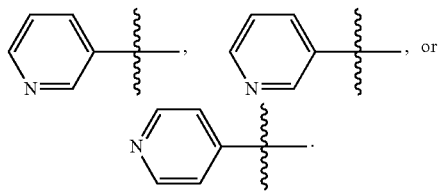

62. The compound of embodiment 58, wherein $R^4$ is optionally substituted

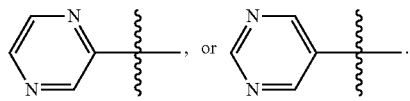

63. The compound of any one of embodiments 1-46, wherein $R^4$ is optionally substituted phenyl.
64. The compound of embodiment 63, wherein $R^4$ is phenyl.
65. The compound of any one of embodiments 1-46, wherein $R^4$ is optionally substituted 8-20 membered bicyclic or polycyclic heteroaryl having 1-10 heteroatoms.
66. The compound of embodiment 65, wherein $R^4$ is optionally substituted

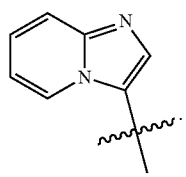 [SMILES: *c1cnc2ccccn12]

67. The compound of embodiment 65, wherein $R^4$ is optionally substituted

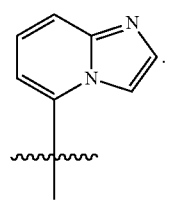 [SMILES: *c1cccc2nccn12]

68. The compound of any one of the preceding embodiments, wherein x is 1.
69. The compound of any one of embodiments 1-67, wherein x is 0.

70. A compound of formula IV or a pharmaceutically acceptable salt thereof.
71. The compound of any one of the preceding embodiments, wherein Ring B is an optionally substituted bivalent 4-, 5- or 6-membered monocyclic heterocyclyl ring having 1-3 heteroatoms.
72. The compound of embodiment 71, wherein one ring heteroatom of Ring B is nitrogen and is bonded to $L^1$.
73. The compound of embodiment 71, wherein Ring B is optionally substituted

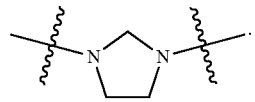 [SMILES: *N1CCN(*)C1]

74. The compound of embodiment 73, wherein Ring B is

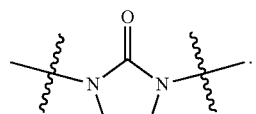

75. The compound of embodiment 73, wherein Ring B is

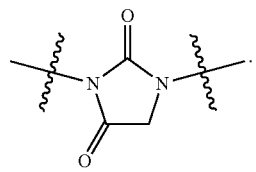 [SMILES: *N1CC(=O)N(*)C1=O]

76. The compound of embodiment 73, wherein Ring B is

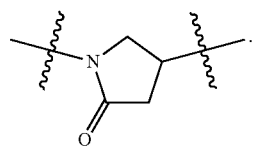 [SMILES: *C1CC(=O)N(*)C1]

77. The compound of embodiment 73, wherein Ring B is

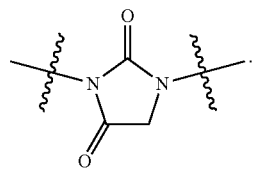 [SMILES: *N1CC(=O)N(*)C1=O]

78. The compound of any one of embodiments 1-70, wherein Ring B is or comprises an optionally substituted spiro-bicyclic ring.
79. The compound of any one of embodiments 1-70, wherein Ring B is an optionally substituted spiro-bicyclic ring.
80. The compound of any one of embodiments 78-79, wherein one ring is Ring B'.

81. The compound of any one of embodiments 78-80, wherein each monocyclic ring is independently an optionally substituted 3-10 membered saturated or partially unsaturated ring having 0-5 heteroatoms.
82. The compound of embodiment 81, wherein a first monocyclic ring is optionally substituted

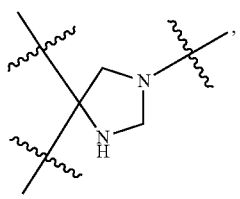 [SMILES: *N1CNC(*)(*)C1]

and a second is Ring B'.

83. The compound of embodiment 82, wherein the first monocyclic ring is optionally substituted

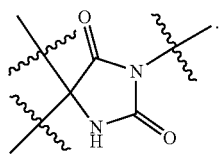 [SMILES: *N1C(=O)NC(*)(*)C1=O]

84. The compound of embodiment 82, wherein the first monocyclic ring is

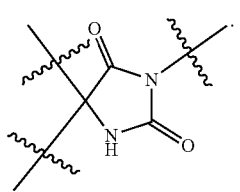 [SMILES: *N1C(=O)NC(*)(*)C1=O]

85. The compound of any one of embodiments 80-84, wherein Ring B' is an optionally substituted monocyclic 3-10 membered saturated or partially unsaturated ring having 0-5 heteroatoms.
86. The compound of embodiment 85, wherein Ring B' is saturated.
87. The compound of embodiment 85, wherein Ring B' is partially unsaturated.
88. The compound of any one of embodiments 85-87, wherein Ring B' is 3-membered.
89. The compound of any one of embodiments 85-87, wherein Ring B' is 4-membered.
90. The compound of any one of embodiments 85-87, wherein Ring B' is 5-membered.
91. The compound of any one of embodiments 85-87, wherein Ring B' is 6-membered.
92. The compound of any one of embodiments 85-87, wherein Ring B' is 7-membered.
93. The compound of any one of embodiments 85-87, wherein Ring B' is 8-membered.
94. The compound of any one of embodiments 85-93, wherein Ring B' is an optionally substituted cycloaliphatic ring.
95. The compound of embodiment 94, wherein Ring B' is bonded to an —N(R)— group of $L^2$.
96. The compound of any one of embodiments 85-93, wherein Ring B' has 1-5 heteroatoms.

97. The compound of embodiment 96, wherein at least heteroatom is nitrogen.
98. The compound of embodiment 97, wherein the nitrogen atom is bonded to $L^2$.
99. The compound of any one of embodiments 96-98, wherein Ring B' is optionally substituted

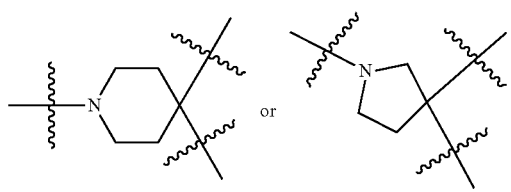

100. The compound of embodiment 99, wherein Ring B' is

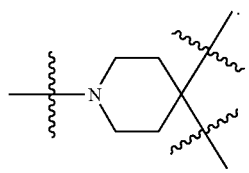 [SMILES: *N1CCC(*)(*)CC1]

101. The compound of embodiment 99, wherein Ring B' is

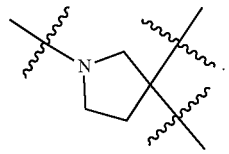 [SMILES: *N1CCC(*)(*)C1]

102. The compound of embodiment 99, wherein Ring B is

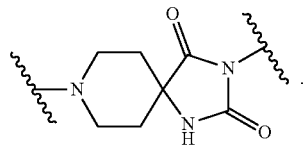 [SMILES: *N1CCC2(CC1)NC(=O)N(*)C2=O]

103. The compound of embodiment 99, wherein Ring B' is

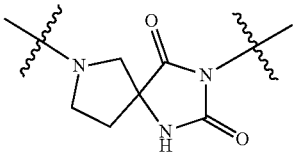

104. The compound of any one of embodiments 1-70, wherein Ring B is a bivalent ring selected from phenylenyl, 5-6 membered heteroarylenyl having 1-4 heteroatoms, 8-11 membered saturated or partially unsaturated spiro heterocyclylenyl having 1-4 heteroatoms, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms, wherein Ring B is optionally further substituted with 1-3 oxo groups.

105. The compound of any one of embodiments 1-22, and 47-69, wherein the compound is a compound of formula A or a pharmaceutically acceptable salt thereof, wherein the compound has the structure of formula A-I or a pharmaceutically acceptable salt thereof.

106. The compound of any one of embodiments 1-22, and 47-69, wherein the compound is a compound of formula A or a pharmaceutically acceptable salt thereof, wherein the compound has the structure of formula A-II or a pharmaceutically acceptable salt thereof.

107. The compound of any one of embodiments 1-22, and 47-69, wherein the compound is a compound of formula A or a pharmaceutically acceptable salt thereof, wherein the compound has the structure of formula A-III or a pharmaceutically acceptable salt thereof.

108. The compound of any one of embodiments 1-22, and 47-69, wherein the compound is a compound of formula A or a pharmaceutically acceptable salt thereof, wherein the compound has the structure of formula A-IV or a pharmaceutically acceptable salt thereof.

109. The compound of any one of embodiments 23-69, wherein the compound is a compound of formula C-I or a pharmaceutically acceptable salt thereof, wherein the compound has the structure of formula C-IV or a pharmaceutically acceptable salt thereof.

110. The compound of any one of embodiments 23-69, wherein the compound is a compound of formula C-I or a pharmaceutically acceptable salt thereof, wherein the compound has the structure of formula C-V or a pharmaceutically acceptable salt thereof.

111. The compound of any one of embodiments 23-69, wherein the compound is a compound of formula C-I or a pharmaceutically acceptable salt thereof, wherein the compound has the structure of formula C-VI or a pharmaceutically acceptable salt thereof.

112. The compound of any one of embodiments 23-69, wherein the compound is a compound of formula C-I or a pharmaceutically acceptable salt thereof, wherein the compound has the structure of formula C-VII or a pharmaceutically acceptable salt thereof.

113. The compound of any one of the preceding embodiments, wherein Ring A is an optionally substituted 3-10 membered saturated or partially unsaturated carbocyclyl ring.

114. The compound of embodiment 113, wherein Ring A is an optionally substituted cyclopropyl ring.

115. The compound of any one of embodiments 1-112, wherein Ring A is an optionally substituted 3-10 membered saturated or partially unsaturated heterocyclyl ring having 1-5 heteroatoms.

116. The compound of any one of embodiments 1-112, wherein Ring A is an optionally substituted 5-6 membered heteroaryl ring with 1-4 heteroatoms.

117. The compound of any one of embodiments 1-112, wherein Ring A is an optionally substituted phenyl ring.

118. The compound of embodiment 117, wherein Ring A is a phenyl ring.

119. The compound of any one of embodiments 1-112, wherein Ring A is an optionally substituted 8-20 membered bicyclic or polycyclic heteroaryl ring having 1-10 heteroatoms.

120. The compound of any one of embodiments 1-112, wherein Ring A is selected from phenyl, 5-7 membered saturated or partially unsaturated heterocyclyl having 1-2 heteroatoms, 5-6 membered heteroaryl with 1-4 heteroatoms, and 8-10 membered bicyclic heteroaryl having 1-5 heteroatoms.

121. The compound of any one of the preceding embodiments, wherein m is 1-5.

122. The compound of any one of embodiments 1-120, wherein m is 0.

123. The compound of any one of the preceding embodiments, wherein each instance of $R^1$ is independently hydrogen, halogen, —CN, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R.

124. The compound of any one of the preceding embodiments, wherein one or more $R^1$ is —H.

125. The compound of any one of the preceding embodiments, wherein one or more $R^1$ is —OR.

126. The compound of any one of the preceding embodiments, wherein one or more $R^1$ is halogen.

127. The compound of any one of the preceding embodiments, wherein one or more $R^1$ is —CN.

128. The compound of any one of the preceding embodiments, wherein $L^1$ is independently a covalent bond, or a bivalent, saturated or unsaturated, straight or branched group selected from $C_{1-6}$ aliphatic and $C_{1-6}$ heteroaliphatic having 1-3 heteroatoms, wherein 0-6 methylene units of the group are independently replaced with -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—.

129. The compound of any one of the preceding embodiments, wherein one or more methylene units in $L^1$ are replaced with -Cy-, —N(R'), or —S(O)$_2$—.

130. The compound of any one of the preceding embodiments, wherein one or more methylene units in $L^1$ are independently replaced with -Cy-.

131. The compound of any one of the preceding embodiments, wherein $L^1$ is -Cy- or -Cy-CH$_2$—.

132. The compound of embodiment 130 or 131, wherein one occurrence of -Cy- is an optionally substituted bivalent $C_{3-10}$ carbocyclic ring.

133. The compound of embodiment 130 or 131, wherein one occurrence of -Cy- is an optionally substituted bivalent phenyl ring.

134. The compound of embodiment 130 or 131, wherein -Cy- is an optionally substituted 5-6 membered heteroaryl ring having 1-4 ring nitrogen atoms.

135. The compound of embodiment 130 or 131, wherein -Cy- is an optionally substituted 5-6 membered

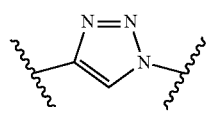 [SMILES: *c1cn(*)nn1]

ring.

136. The compound of embodiment 130 or 131, wherein -Cy- is an optionally substituted 5-6 membered

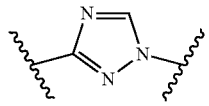 [SMILES: *c1ncn(*)n1]

ring.
137. The compound of embodiment 130 or 131, wherein -Cy- is an optionally substituted 5-6 membered

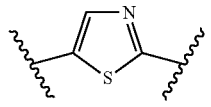 [SMILES: *c1cnc(*)s1]

ring.
138. The compound of embodiment 130 or 131, wherein -Cy- is an optionally substituted 5-6 membered

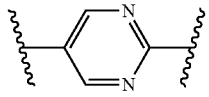 [SMILES: *c1cnc(*)nc1]

ring.
139. The compound of embodiment 130 or 131, wherein -Cy- is an optionally substituted 5-6 membered

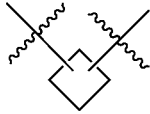

ring.
140. The compound of embodiment 128, wherein $L^1$ is a covalent bond, —CH$_2$—, —CH(R)—, or —C(R)$_2$—.
141. The compound of embodiment 128, wherein $L^1$ is a covalent bond.
142. The compound of any one of the preceding embodiments, wherein p is 0, 1 or 2.
143. The compound of any one of the preceding embodiments, wherein p is 0.
144. The compound of any one of embodiments 1-142, wherein p is 1, 2, 3, 4, or 5.
145. The compound of any one of the preceding embodiments, wherein each instance of $R^2$ is independently hydrogen, halogen, —CN, —NO$_2$, or $C_{1-3}$ aliphatic.
146. The compound of embodiment 145, wherein one or more instances of $R^2$ is —H.
147. The compound of embodiment 145, wherein each $R^2$ is —H.
148. The compound of any one of the preceding embodiments, wherein $L^2$ is independently a covalent bond, or a bivalent, saturated or unsaturated, straight or branched group selected from $C_{1-6}$ aliphatic and $C_{1-6}$ heteroaliphatic having 1-3 heteroatoms, wherein 0-6 methylene units of the group are independently replaced with -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, or —P(OR')[B(R')$_3$]—.
149. The compound of any one of the preceding embodiments, wherein one or more methylene units of $L^2$ are independently replaced with —NHC(O)—, —C(O)NH—, —CH$_2$—, —CH(R)—, —C(R)$_2$—, —C(O)—, —S(O)$_2$—, -Cy-C(O)—, -Cy-, —N(R')C(O)N(R')— or —S(O)$_2$N(R')—.
150. The compound of any one of embodiments 1-148, wherein $L^2$ is a covalent bond, —NHC(O)—, —C(O)NH—, —CH$_2$—, —CH(R)—, —C(R)$_2$—, —C(O)—, —S(O)$_2$—, -Cy-C(O)—, -Cy-, —N(R')C(O)N(R')— or —S(O)$_2$N(R')—.
151. The compound of embodiment 150, wherein $L^2$ is a covalent bond, —NHC(O)—, —C(O)NH—, —CH$_2$—, —CH(R)—, —C(R)$_2$—, —C(O)—, or —S(O)$_2$—.
152. The compound of embodiment 150, wherein $L^2$ is a covalent bond.
153. The compound of embodiment 150, wherein $L^2$ is —C(O)N(R')—.
154. The compound of embodiment 153, wherein the —C(O)— is bonded to Ring B.
155. The compound of embodiment 150, wherein $L^2$ is —C(R)$_2$—.
156. The compound of embodiment 150, wherein $L^2$ is —C(O)—.
157. The compound of embodiment 150, wherein $L^2$ is —S(O)$_2$—.
158. The compound of embodiment 150, wherein $L^2$ is -Cy-C(O)—.
159. The compound of embodiment 150, wherein $L^2$ is

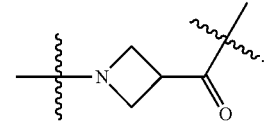

160. The compound of embodiment 158 or 159, wherein the —C(O)— is bonded to Ring B.
161. The compound of embodiment 150, wherein $L^2$ is —N(R')C(O)N(R')—.
162. The compound of embodiment 150, wherein $L^2$ is —S(O)$_2$N(R')—.
163. The compound of embodiment 162, wherein, —S(O)$_2$— is bonded to Ring C.
164. The compound of any one of the preceding embodiments, wherein Ring C is an optionally substituted phenyl ring.
165. The compound of any one of the preceding embodiments, wherein Ring C is an optionally substituted 3-10 membered saturated or partially unsaturated heterocyclyl having 1-4 heteroatoms.
166. The compound of embodiment 165, wherein Ring C is an optionally substituted 4-, 5- or 6-membered saturated having 1-4 heteroatoms.

167. The compound of embodiment 165, wherein Ring C is an optionally substituted

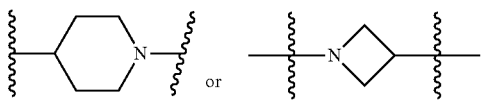 [SMILES: *C1CCN(*)CC1 ; *C1CN(*)C1]

ring.
168. The compound of any one of embodiments 1-163, wherein Ring C is an optionally substituted 5-6 membered heteroaryl group having 1-4 heteroatoms.
169. The compound of embodiment 168, wherein Ring C is an optionally substituted

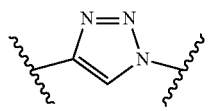 [SMILES: *c1cn(*)nn1]

ring.
170. The compound of embodiment 168, wherein Ring C is an optionally substituted

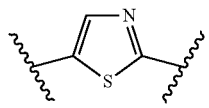 [SMILES: *c1cnc(*)s1]

ring.
171. The compound of embodiment 168, wherein Ring C is an optionally substituted

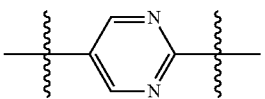 [SMILES: *c1cnc(*)nc1]

ring.
172. The compound of any one of embodiments 1-163, wherein Ring C is an optionally substituted 8-10 membered bicyclic heteroaryl ring having 1-5 heteroatoms.
173. The compound of embodiment 172, wherein Ring C is an optionally substituted

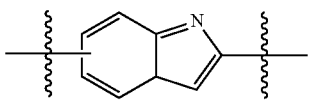

ring.
174. The compound of embodiment 172, wherein Ring C is an optionally substituted

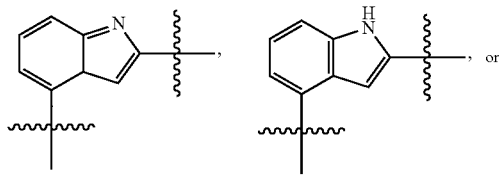

ring.

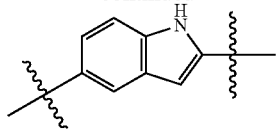

ring.
175. The compound of embodiment 172, wherein Ring C is an optionally substituted

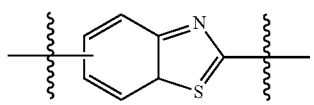

ring.
176. The compound of embodiment 172, wherein Ring C is an optionally substituted

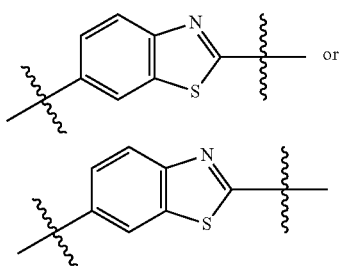

ring.
177. The compound of embodiment 172, wherein Ring C is an optionally substituted

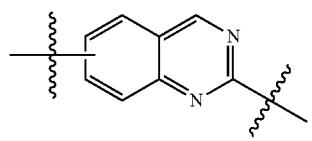

group.
178. The compound of embodiment 172, wherein Ring C is an optionally substituted

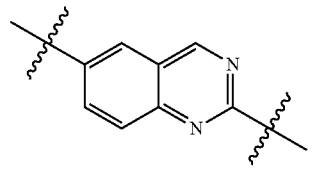 [SMILES: *c1ccc2nc(*)ncc2c1]

group.
179. The compound of any one of embodiments 175-178, wherein the carbon atom between two heteroatoms is bonded to $L^2$.
180. The compound of any one of embodiments 1-163, wherein Ring C is a bivalent ring selected from phenylenyl, 4-7 membered saturated or partially unsaturated carbocyclylenyl, 4-7 membered saturated or partially unsaturated heterocyclylenyl having 1-2 heteroatoms, and 5-6 membered heteroarylenyl having 1-4 heteroatoms.

181. The compound of any one of the preceding embodiments, wherein q is 0, 1, 2, 3 or 4.
182. The compound of any one of the preceding embodiments, wherein q is 0.
183. The compound of any one of embodiments 1-179, wherein q is 1, 2, 3, 4, or 5.
184. The compound of any one of the preceding embodiments, wherein each instance of $R^3$ is independently hydrogen, halogen, —CN, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R.
185. The compound of any one of the preceding embodiments, wherein one or more instances of $R^3$ is —H.
186. The compound of any one of the preceding embodiments, wherein each $R^3$ is —H.
187. The compound of any one of the preceding embodiments, wherein r is 0.
188. The compound of any one of embodiments 1-184, wherein r is 1.
189. The compound of any one of embodiments 1-184, wherein r is 2.
190. The compound of any one of the preceding embodiments, wherein $L^3$ independently a covalent bond, or a bivalent, saturated or unsaturated, straight or branched group selected from $C_{1-50}$ aliphatic and $C_{1-50}$ heteroaliphatic having 1-30 heteroatoms, wherein 0-30 methylene units of the group are independently replaced with an optionally substituted $C_{1-6}$ bivalent alkylene group, an optionally substituted $C_{1-6}$ alkenylene group, an optionally substituted bivalent $C_{1-6}$ heteroaliphatic group having 1-5 heteroatoms, —C≡C—, -Cy-, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—.
191. The compound any one of the preceding embodiments, wherein one or more methylene units are independently replaced with —[(—O—C(R')$_2$—C(R')$_2$—)$_n$]—, —[(—C(R')$_2$—O—C(R')$_2$—)$_n$]— or —[(—C(O)—C(R')$_2$—N(R')—)$_n$]—.
192. The compound any one of the preceding embodiments, wherein one or more methylene units are independently replaced with —[(—O—C(R')$_2$—C(R')$_2$—)$_n$]— or —[(—C(R')$_2$—O—C(R')$_2$—)$_n$]—.
193. The compound of any one of embodiments 190-192, wherein n is 1-20.
194. The compound of any one of embodiments 190-192, wherein each instance of n is independently selected from 1, 2, 3, 4, 5, 6, 7, 8, 9, or 10.
195. The compound of any one of embodiments 190-192, wherein n is 4, 6, 8, 10 or 12.
196. The compound of any one of embodiments 190-195, wherein one or more methylene units are independently replaced with -Cy-.

197. The compound of embodiment 196, wherein -Cy- is or comprises

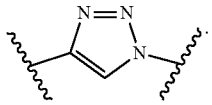 [SMILES: *c1cn(*)nn1]

198. The compound of embodiment 196, wherein -Cy- is

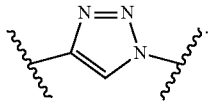

199. The compound of embodiment 196, wherein -Cy- is

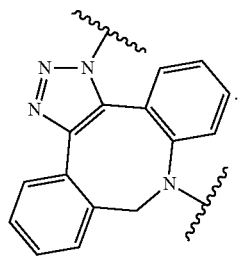 [SMILES: *N1Cc2ccccc2-c2nnn(*)c2-c2ccccc21]

200. The compound of embodiment 196, wherein -Cy- is

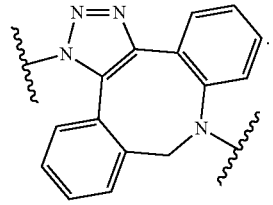 [SMILES: *N1Cc2ccccc2-c2c(nnn2*)-c2ccccc21]

201. The compound of embodiment 196, wherein -Cy- is or comprises —C≡C—.
202. The compound of embodiment 201, wherein -Cy- is or comprises

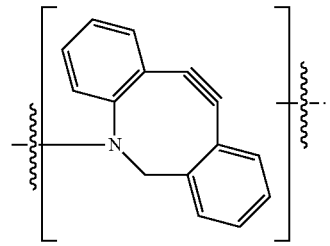

203. The compound of embodiment 190, wherein $L^3$ is a covalent bond.
204. The compound of embodiment 190, wherein $L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)

—O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

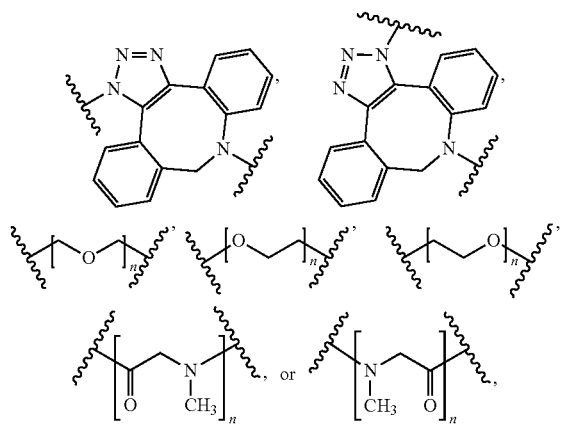

205. The compound of embodiment 204, wherein each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms, a 4-7 membered saturated or partially unsaturated spiro heterocyclylenyl having 1-2 heteroatoms, an 8-10 membered bicyclic saturated or partially unsaturated heterocyclylenyl having 1-2 heteroatoms, a 5-6 membered heteroarylenyl having 1-4 heteroatoms, or an 8-10 membered bicyclic heteroarylenyl having 1-5 heteroatoms, wherein -Cy- is additionally optionally substituted with 1-3 oxo groups.

206. The compound of any one of the preceding embodiments, wherein each R is independently —H, or an optionally substituted group selected from $C_{1-30}$ aliphatic, $C_{1-30}$ heteroaliphatic having 1-10 heteroatoms, $C_{6-30}$ aryl, 5-30 membered heteroaryl having 1-10 heteroatoms, and 3-30 membered heterocyclyl having 1-10 heteroatoms.

207. The compound of any one of the preceding embodiments, wherein each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms, a 5-6 membered monocyclic heteroaromatic ring having 1-4 heteroatoms, or an 8-10 membered bicyclic heteroaromatic ring having 1-5 heteroatoms.

208. The compound of any one of the preceding embodiments, wherein each heteroatom is independently selected from nitrogen, oxygen and sulfur.

209. A compound, wherein the compound is a conjugate of a compound of any one of embodiments 1-22 and 47-208, wherein the compound is a compound of formula A or a pharmaceutically acceptable salt thereof, and a targeting moiety.

210. A compound of formula C:

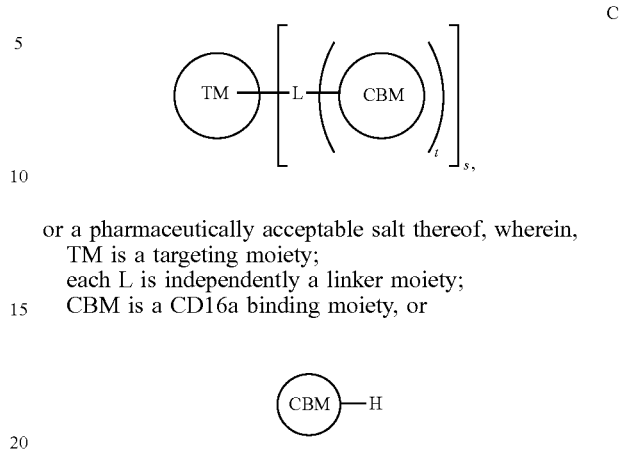

or a pharmaceutically acceptable salt thereof, wherein,
TM is a targeting moiety;
each L is independently a linker moiety;
CBM is a CD16a binding moiety, or

is a compound of formula A or a pharmaceutically acceptable salt thereof; and
each of t and s is independently 1-1000.

211. The compound of embodiment 210, wherein

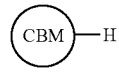

is a compound of formula A or a pharmaceutically acceptable salt thereof.

212. The compound of embodiment 210, wherein

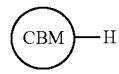

is a compound of any one of embodiments 1-22 and 47-208, wherein the compound is a compound of formula A or a pharmaceutically acceptable salt thereof.

213. The compound of any one of embodiments 209-212, wherein a targeting moiety is an antibody or a fragment thereof.

214. The compound of any one of embodiments 209-213, wherein a targeting moiety is a monoclonal antibody or a fragment thereof.

215. The compound of any one of embodiments 209-214, wherein TM is cetuximab.

216. The compound of any one of embodiments 209-214, wherein TM is rituximab.

217. The compound of any one of embodiments 209-214, wherein TM is daratumumab.

218. The compound of any one of embodiments 209-214, wherein a targeting moiety is adalimumab, alemtuzumab, atezolizumab, avelumab, ipilimumab, dcetuximab, daratumumab, dinutuximab, elotuzumab, ibritumomab tiuxetan, imgatuzumab, infliximab, ipilimumab, necitumumab, obinutuzumab, ofatumumab, pertuzumab, reslizumab, rituximab, trastuzumab, mogamulizumab, AMP-224, FS-102, GSK-2857916, ARGX-111, ARGX-110, AFM-13, APN-301, BI-836826, BI-836858, enoblituzumab, otlertuzumab, veltuzumab, KHK-4083, BIW-8962, ALT-803, carotuximab, epratuzumab, inebilizumab, isatuximab, margetuximab, MOR-208, ocaratuzumab, talacotuzumab, tremelimumab, benralizumab, lumiliximab, MOR-208, Ifibatuzumab, GSK2831781, SEA-CD40, KHK-2823, or BI836858, or a fragment thereof.

219. The compound of embodiment 209 or 210, wherein the compound is a compound of any one of embodiments 23-69 and 71-208, wherein the compound is a compound of formula C-I or a pharmaceutically acceptable salt thereof.

220. A compound of formula I:

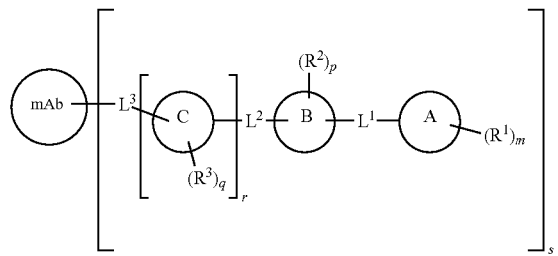

I or a pharmaceutically acceptable salt thereof, wherein:

Ring A is selected from phenyl, 5-7 membered saturated or partially unsaturated heterocyclyl having 1-2 heteroatoms independently selected from nitrogen, oxygen or sulfur, 5-6 membered heteroaryl with 1-4 heteroatoms independently selected from nitrogen, oxygen or sulfur, or 8-10 membered bicyclic heteroaryl having 1-5 heteroatoms independently selected from nitrogen, oxygen, or sulfur;

Ring B is a bivalent ring selected from phenylenyl, 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a $C_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups;

Ring C is a bivalent ring selected from phenylenyl, 4-7 membered saturated or partially unsaturated carbocyclylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur;

$L^1$ is a covalent bond, —CH$_2$—, —CH(R)—, or —C(R)$_2$—;

$L^2$ is a covalent bond, —NHC(O)—, —C(O)NH—, —CH$_2$—, —CH(R)—, —C(R)$_2$—, —C(O)—, or —S(O)$_2$—;

$L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

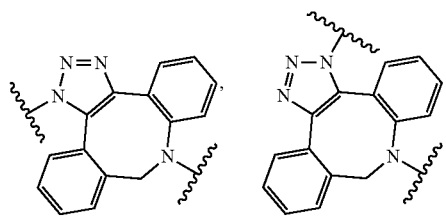

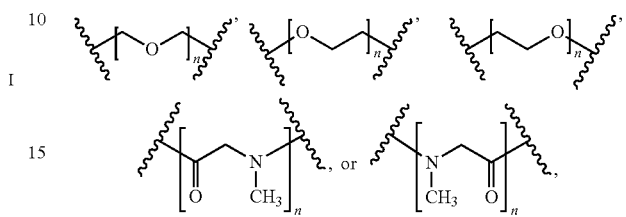

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, or sulfur, a 4-7 membered saturated or partially unsaturated spiro heterocyclylenyl having 1-2 heteroatoms independently selected from nitrogen, oxygen, or sulfur, an 8-10 membered bicyclic saturated or partially unsaturated heterocyclylenyl having 1-2 heteroatoms independently selected from nitrogen, oxygen, or sulfur, a 5-6 membered heteroarylenyl having 1-4 heteroatoms independently selected from nitrogen, oxygen, or sulfur, or an 8-10 membered bicyclic heteroarylenyl having 1-5 heteroatoms independently selected from nitrogen, oxygen, or sulfur, wherein -Cy- is additionally optionally substituted with 1-3 oxo groups;

mAb is a monoclonal antibody;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each instance of $R^1$, and $R^3$ is independently hydrogen, halogen, —CN, —NO$_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R;

each instance of $R^2$ is independently hydrogen, halogen, —CN, —NO$_2$, or $C_{1-3}$ aliphatic;

m is 0, 1, 2, 3, 4 or 5;

each instance of n is independently selected from 1, 2, 3, 4, 5, 6, 7, 8, 9, or 10;

p is 0, 1, or 2;

q is 0, 1, 2, 3, or 4;
r is 0 or 1, wherein when r is 0,

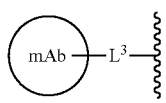

is directly attached to

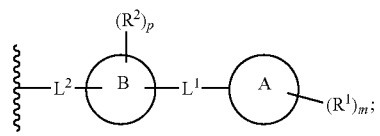

and
s is 1, 2, 3, 4, 5, or 6.
221. The compound of embodiment 220 of formula I-a or I-b:

226. The compound of any one of embodiments 220-225, wherein Ring C is phenylenyl, 4-7 membered saturated or partially unsaturated heterocyclylenyl having 1-2 heteroatoms independently selected from nitrogen, oxygen, or sulfur, or 5-6 membered heteroarylenyl having 1-4 heteroatoms independently selected from nitrogen, oxygen, or sulfur.
227. The compound of any one of embodiments 220-226, wherein L is a covalent bond, —CH$_2$—, or —CH(R)—.
228. The compound of any one of embodiments 220-227, wherein L$^2$ is a covalent bond, —NHC(O)—, —C(O)NH—, —CH$_2$—, —CH(R)—, —C(O)—, or —S(O)$_2$—.
229. The compound of any one of embodiments 220-228, wherein L$^3$ is a bivalent, saturated or unsaturated, straight or branched C$_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

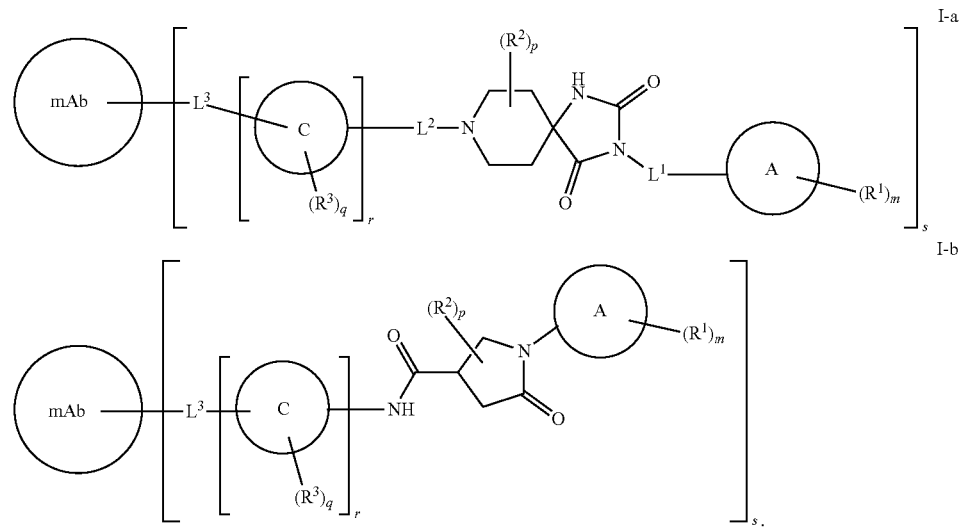

222. The compound of embodiment 220 of formula I-a.
223. The compound of embodiment 220 of formula I-b.
224. The compound of any one of embodiments 220-223, wherein Ring A is selected from phenyl, 5-6 membered heteroaryl with 1-4 heteroatoms independently selected from nitrogen, oxygen or sulfur, or 8-10 membered bicyclic heteroaryl having 1-5 heteroatoms independently selected from nitrogen, oxygen, or sulfur.
225. The compound of any one of embodiments 220-224, wherein Ring B is 5-6 membered heteroarylenyl having 1-4 heteroatoms independently selected from nitrogen, oxygen, or sulfur, 8-11 membered saturated or partially unsaturated spiro heterocyclylenyl having 1-4 heteroatoms independently selected from nitrogen, oxygen or sulfur, wherein one of the spirocyclic rings is optionally further substituted with a fused phenyl ring or a C$_{2-4}$ bridging group, or 4-7 membered saturated or partially unsaturated heterocyclylenyl having 1-2 heteroatoms independently selected from nitrogen, oxygen or sulfur, wherein Ring B is optionally further substituted with 1-3 oxo groups.

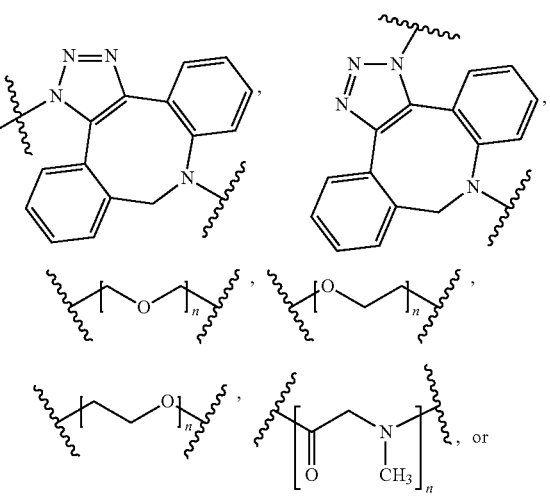

-continued

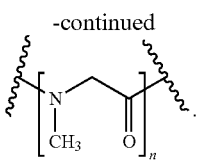

230. The compound of any one of embodiments 220-229, wherein TM is cetuximab.
231. The compound of any one of embodiments 220-229, wherein TM is rituximab.
232. The compound of any one of embodiments 220-229, wherein TM is daratumumab.
233. The compound of any one of embodiments 220-229, wherein mAb is adalimumab, alemtuzumab, atezolizumab, avelumab, ipilimumab, dcetuximab, daratumumab, dinutuximab, elotuzumab, ibritumomab tiuxetan, imgatuzumab, infliximab, ipilimumab, necitumumab, obinutuzumab, ofatumumab, pertuzumab, reslizumab, rituximab, trastuzumab, mogamulizumab, AMP-224, FS-102, GSK-2857916, ARGX-111, ARGX-110, AFM-13, APN-301, BI-836826, BI-836858, enoblituzumab, otlertuzumab, veltuzumab, KHK-4083, BIW-8962, ALT-803, carotuximab, epratuzumab, inebilizumab, isatuximab, margetuximab, MOR-208, ocaratuzumab, talacotuzumab, tremelimumab, benralizumab, lumiliximab, MOR-208, Ifibatuzumab, GSK2831781, SEA-CD40, KHK-2823, or BI836858.
234. The compound of any one of embodiments 220-233, wherein m is 0, 1, 2, 3, or 4.
235. The compound of any one of embodiments 220-234, wherein p is 0 or 1.
236. The compound of any one of embodiments 220-235, wherein q is 0, 1, 2, or 3.
237. The compound of any one of embodiments 220-236, wherein s is 1, 2, 3, 4, or 5.
238. The compound of any one of embodiments 220-237, wherein $L^1$ is a covalent bond, —$CH_2$—, or —CH(R)—.
239. The compound of any one of embodiments 220-238, wherein $L^2$ is a covalent bond, —NHC(O)—, —C(O)NH—, —$CH_2$—, —CH(R)—, —C(O)—, or —S(O)$_2$—.
240. A compound selected from those depicted in Table 1.
241. The compound of any one of the preceding embodiments, wherein the compound binds to CD16a with a $K_d$ of no more than 1, 10, 20, 30, 40, 50, 60, 70, 80, 90, 100, 200. 250, 300, 400, 500, 600, 700, 800, 900, 1000, 2000, 3000, 4000, 5000 nM.
242. The compound of any one of the preceding embodiments, wherein a CD16a is CD16a158V.
243. The compound of any one of the preceding embodiments, wherein a CD16a is CD16a158F.
244. The compound of any one of the preceding embodiments, wherein the compound binds to one or more other Fc receptors.
245. The compound of any one of the preceding embodiments, wherein the compound binds to one or more other Fc receptors selected from CD32a, CD32b, CD16b, CD38 and CD3ed.
246. The compound of any one of the preceding embodiments, wherein the compound binds to CD16a selectively over one or more other receptors.
247. The compound of any one of the preceding embodiments, wherein the compound binds to CD16a selectively over CD3ed.
248. The compound of any one of the preceding embodiments, wherein the compound binds to CD16a selectively over CD38.
249. The compound of any one of the preceding embodiments, wherein the compound recruits one or more effector cells expressing CD16a.
250. The compound of any one of the preceding embodiments, wherein the compound recruits one or more effector cells expressing one or more Fc receptors selected from CD32a, CD32b, CD16b, CD38 and CD3ed.
251. The compound of any one of the preceding embodiments, wherein the compound enhances recruitment one or more effector cells expressing CD16a.
252. The compound of any one of the preceding embodiments, wherein the compound enhances recruitment one or more effector cells expressing one or more Fc receptors selected from CD32a, CD32b, CD16b, CD38 and CD3ed.
253. The compound of any one of the preceding embodiments, wherein the compound enhances recruitment compared to that observed absence of the compound.
254. The compound of any one of the preceding embodiments, wherein the compound is a compound of any one of embodiments 23-69 and 71-253, wherein the compound is a compound of formula C or a pharmaceutically acceptable salt thereof, wherein the compound enhances recruitment compared to a corresponding reference compound having the structure of TM-H or a pharmaceutically acceptable salt thereof.
255. The compound of any one of the preceding embodiments, wherein the recruitment of the compound is at least 2, 3, 4, 5, 6, 7, 8, 9, 10, 11, 12, 13, 14, 15, 16, 17, 18, 19, 20, 21, 22, 23, 24, 25, 30, 40, 50, 60, 70, 80, 90, 100, 150, 200, 300, 400, 500, or 1000 fold of that of the reference compound or absence of the compound.
256. The compound of any one of embodiments 249-255, wherein a CD16a is CD16a158V.
257. The compound of any one of embodiments 249-256, wherein a CD16a is CD16a158F.
258. The compound of any one of the preceding embodiments, wherein the compound recruits effector cells expressing CD16a selectively over effector cells expressing one or more other receptors.
259. The compound of any one of the preceding embodiments, wherein the compound enhance recruitments of effector cells expressing CD16a selectively over effector cells expressing CD3ed but no or lower levels of CD16a.
260. The compound of any one of the preceding embodiments, wherein the compound enhance recruitments of effector cells expressing CD16a selectively over effector cells expressing CD38 but no or lower levels of CD16a.
261. A pharmaceutical composition comprising a compound according to any one of the preceding embodiments, and a pharmaceutically acceptable carrier, adjuvant, or vehicle.
262. A method for modulating a CD16a activity, comprising contacting a CD16a with a compound or composition of any one of the preceding embodiments.
263. A method of recruiting, or enhancing the existing recruiting ability, of CD16a expressing immune effector cells in a patient or biological sample comprising administering to said patient, or contacting said biological sample with a compound according to any one of embodiments 1-260 or a pharmaceutical composition thereof.
264. A method of treating a disorder, disease, or condition in which the engagement of CD16a expressing immune effector cells would be therapeutically beneficial in a patient comprising administering to said patient a compound according to any one of embodiments 1-260, or a pharmaceutical composition thereof.
265. The method of embodiment 264, wherein the disorder, disease or condition is selected from the group consisting of a cancer, a neurodegenerative disorder, a viral disease, an autoimmune disease, an inflammatory disorder, immunodeficiency disorders, a proliferative disorder, and an infectious disease.
266. A method for treating cancer, comprising administering to a subject suffering therefrom a therapeutically effective amount of a compound of any one of embodiments 1-260 or a pharmaceutically acceptable salt thereof.
267. The method of embodiment 265 or 266, wherein the cancer or proliferative disorder is selected the group consisting of a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenstrom's macroglobulinemia (WM), splenic marginal zone lymphoma, multiple myeloma, plasmacytoma, and intravascular large B-cell lymphoma.
268. The method of embodiment 265, wherein the neurodegenerative disease is selected from the group consisting of Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.
269. The method of embodiment 265, wherein the inflammatory disorder is selected from the group consisting of conditions of the eye such as ocular allergy, conjunctivitis, keratoconjunctivitis sicca, and vernal conjunctivitis; diseases affecting the nose including allergic rhinitis; and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, vulvitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, acute and chronic gout, chronic gouty arthritis, psoriasis, psoriatic arthritis, rheumatoid arthritis, Juvenile rheumatoid arthritis, Cryopyrin Associated Periodic Syndrome (CAPS), and osteoarthritis.

270. A method for preparing a compound having the structure of formula C or a salt thereof, comprising steps of:
providing a first compound of formula A or a salt thereof;
providing a second compound of formula TM-$R^6$ or a salt thereof, wherein TM is a targeting moiety, and $R^6$ is hydrogen, halogen, —CN, —$N_3$, —$NO_2$, —C(O)R, —C(O)OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)$_2$OR, —S(O)(NH)R, —S(O)$_2$N(R)$_2$, or R; and
reacting $R^5$ of the first compound with $R^6$ of the second to form a compound of formula C or a salt thereof.
271. The method of embodiment 270, wherein a compound having the structure of formula C is a compound having the structure of formula C-I.
272. The method of embodiment 270 or 271, wherein one of $R^5$ and $R^6$ is —COOH or an activated derivative thereof, and the other is —N(R)$_2$.
273. The method of embodiment 270 or 271, wherein one of $R^5$ and $R^6$ is

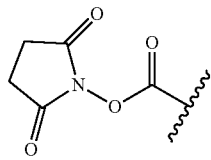 [SMILES: *C(=O)ON1C(=O)CCC1=O]

or an activated derivative thereof, and the other is —N(R)$_2$.
274. The method of embodiment 270 or 271, wherein one of $R^5$ and $R^6$ is or comprises an electrophilic group and the other is or comprises a nucleophilic group.
275. The method of embodiment 270 or 271, wherein one of $R^5$ and $R^6$ is or comprises

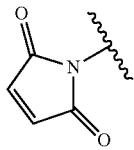

and the other is or comprises —SH.

276. The method of embodiment 270 or 271, wherein one of $R^5$ and $R^6$ is or comprises a diene or dipole group and the other is or comprises a —C≡C— or —C=C— group.
277. The method of embodiment 270 or 271, wherein one of $R^5$ and $R^6$ is a diene or 1,3-dipole
group and the other is an alkenyl or alkynyl group. 278. The method of embodiment 270 or 271, wherein one of $R^5$ and $R^6$ is or comprises —$N_3$ and the other comprises —C≡C—.
279. The method of embodiment 270 or 271, wherein one of $R^5$ and $R^6$ is or comprises —$N_3$ and the other is comprises —C≡C—H.
280. The method of embodiment 270 or 271, wherein one of $R^5$ and $R^6$ is or comprises —$N_3$ and the other is comprises

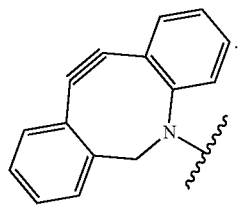 [SMILES: *N1Cc2ccccc2C#Cc2ccccc21]

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. Synthesis of 5-[(3aS,4S,6aR)-2-oxo-hexahydro-1H-thieno[3,4-d]imidazol-4-yl]-N-{14-[3-({3-benzyl-2,4-dioxo-1,3,8-triazaspiro[4.5]decan-8-yl}sulfonyl)propanamido]-3,6,9,12-tetraoxatetradecan-1-yl}pentanamide (I-10

Scheme 1

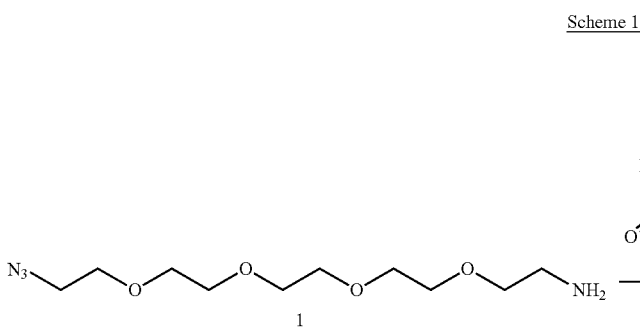

-continued
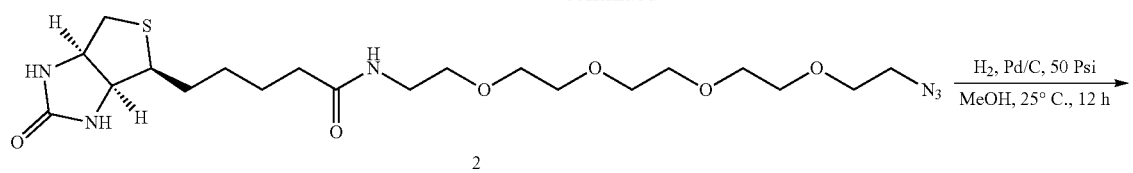
2
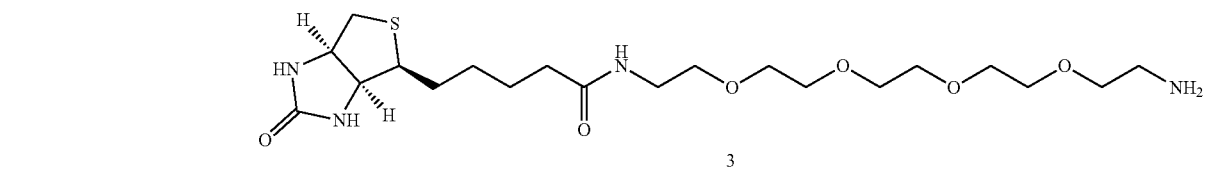
3
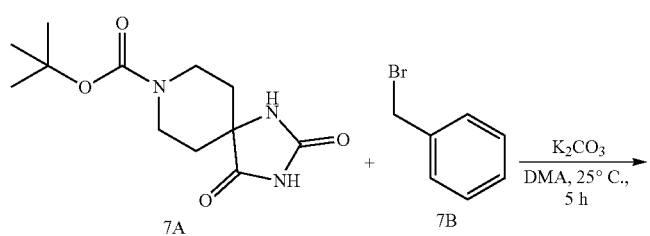
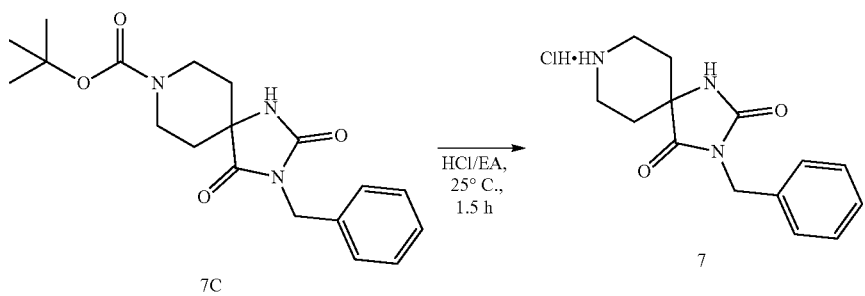
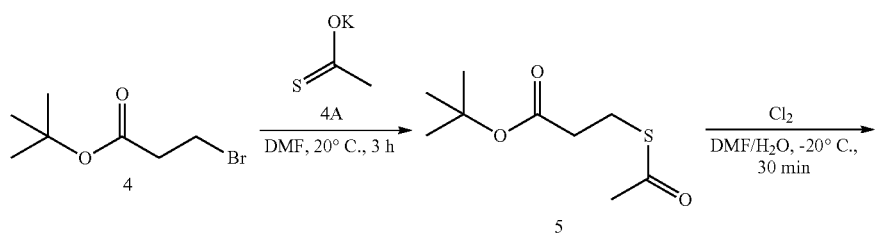
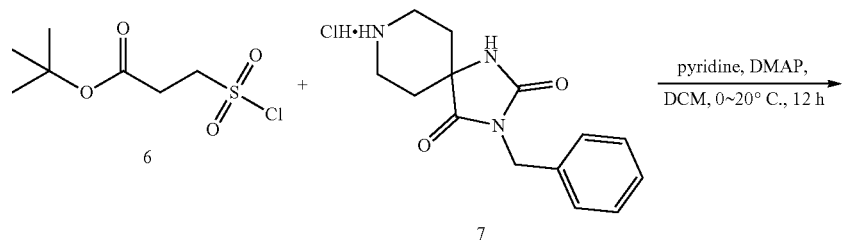
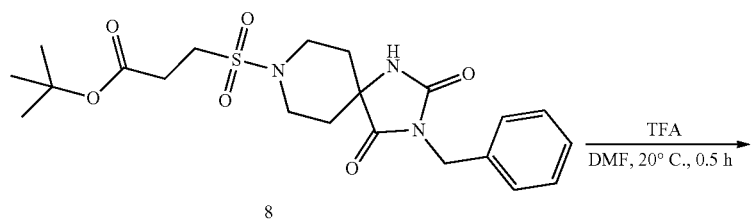

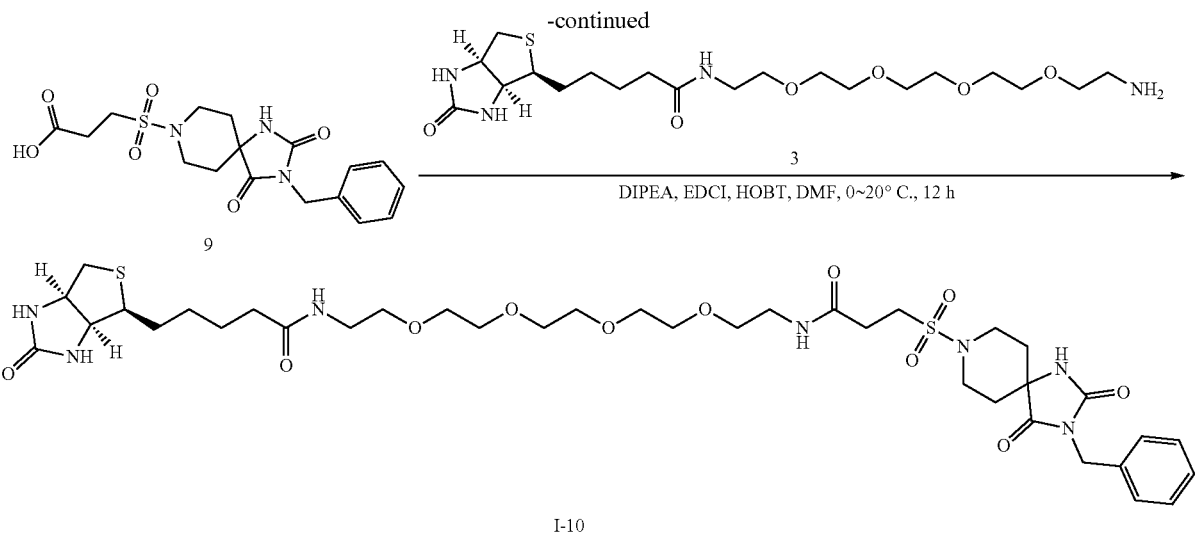

I-10

Step 1: Synthesis of Compound 2

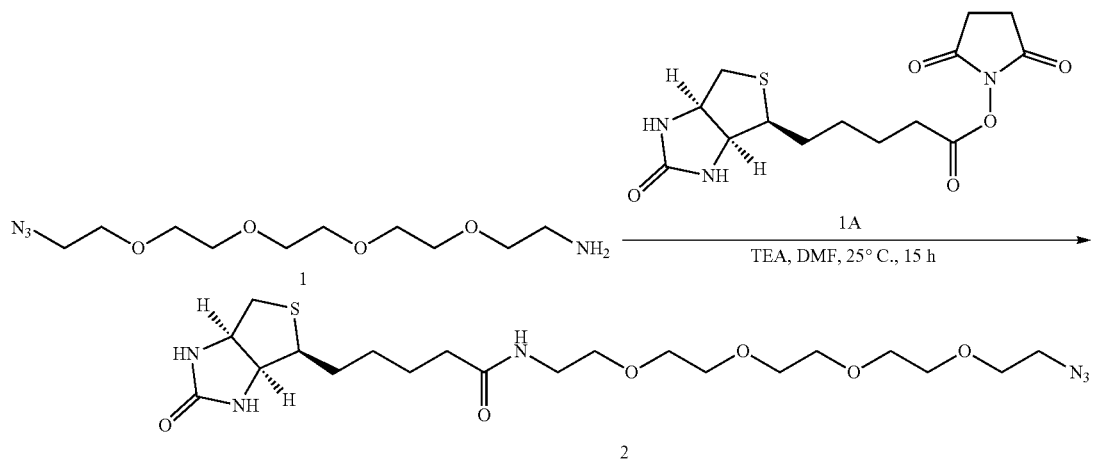

To a mixture of compound 1 (500 mg, 1.91 mmol, 1 eq) in DMF (5 mL) was added TEA (578.66 mg, 5.72 mmol, 795.95 μL, 3 eq) and compound 1A (780.88 mg, 2.29 mmol, 1.2 eq) at 25° C. under $N_2$. The mixture was stirred at 25° C. for 16 h. 1/50 of the reaction mixture was concentrated to remove the solvent. LCMS indicated the presence of the desired product. The mixture was concentrated under reduced pressure to yield a residue. The mixture was purified by prep-HPLC (TFA condition) according to HPLC. Compound 2 (937.6 mg, 1.28 mmol, 67.16% yield, 66.71% purity) was obtained as colorless liquid which was verified by LCMS and $^1$HNMR. LCMS: Rt=0.848 min, MS cal.: 488.24, [M+H]$^+$=489.3. HPLC: Rt=1.871 min. LCMS: Rt=0.851 min, MS cal.: 488.24, [M+H]$^+$=489.3. H NMR (400 MHz, METHANOL-$d_4$) δ=4.52 (dd, J=4.4, 7.8 Hz, 1H), 4.33 (dd, J=4.5, 7.9 Hz, 1H), 3.73-3.62 (m, 11H), 3.59-3.54 (m, 2H), 3.43-3.37 (m, 4H), 3.27-3.20 (m, 1H), 2.95 (dd, J=5.0, 12.7 Hz, 1H), 2.73 (d, J=12.7 Hz, 1H), 2.24 (t, J=7.4 Hz, 2H), 1.84-1.56 (m, 4H), 1.52-1.42 (m, 2H).

Step 2: Synthesis of Compound 3

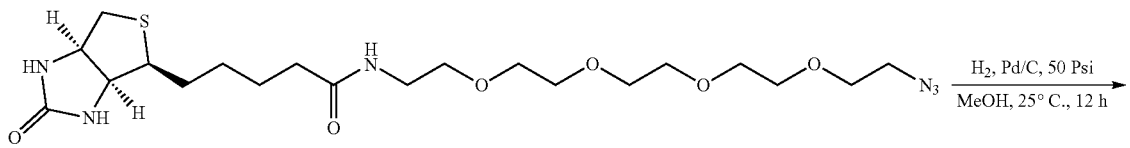

-continued

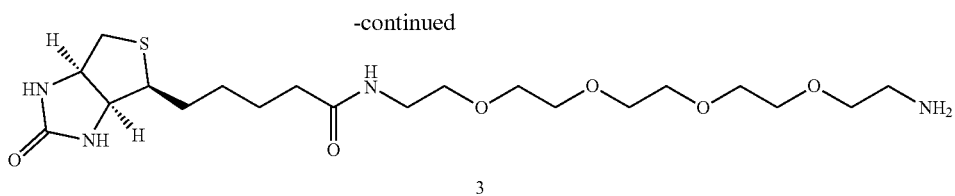

3

To a mixture of compound 2 (937.6 mg, 1.92 mmol, 1 eq) in MeOH (20 mL) was added Pd—C (233.06 mg, 1.92 mmol, 1 eq) at 25° C. The mixture was stirred at 25° C. for 12 h under H₂ (50 Psi). LCMS indicated the presence of the desired product and that the reaction was complete. The mixture was washed with MeOH (20 mL). The combined MeOH was concentrated to yield compound 3 (818.2 mg, 888.77 μmol, 46.32% yield, 50.25% purity) as a yellow oil and which was used for next step directly without further purification. LCMS: Rt=0.864 min, MS cal.: 462.25, [M+H]⁺=463.3, [1/2M+H]⁺=232.2.

Step 3: Synthesis of Compound 5

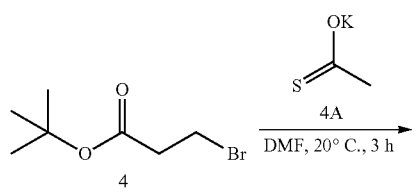

A solution of compound 4 (20 g, 95.66 mmol, 16.00 mL, 1 eq) and compound 4A (12.27 g, 95.66 mmol, 1 eq) in DMF (30 mL) was stirred at 20° C. for 3 h. ¹H NMR indicated that the starting material was consumed. The mixture was then extracted with ethyl acetate (20 mL×3). The combined ethyl acetate layers were washed with H₂O (25 mL×2), brine (30 mL), dried over Na₂SO₄, filtered and concentrated. Compound 5 (20 g, crude) was obtained as yellow oil and used for next step directly without further purification. H NMR (400 MHz, DMSO) δ ppm 1.40 (s, 9H) 2.32 (s, 3H) 2.98 (t, J=6.85 Hz, 2H).

Step 4: Synthesis of Compound 6

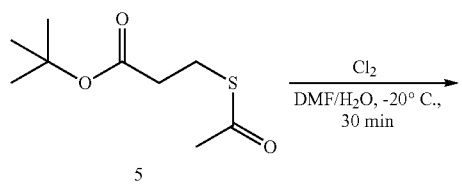

-continued

Cl₂ (24.48 mmol) was bubbled into a solution of compound 5 (2 g, 9.79 mmol, 1 eq) in DCM (100 mL) and H₂O (20 mL) at −20° C. for 30 minutes. TLC (Petroleum ether: Ethyl acetate=10:1; product Rf=0.30) showed the starting material was consumed and showed one new main spot. LCMS did not detect the desired product. The mixture was adjusted to pH=7 with saturated NaHCO₃ (50 mL) then extracted with DCM (50 mL×3). The combined DCM layers were washed with brine (15 mL), dried over Na₂SO₄, filtered and concentrated. Compound 6 (2 g, 8.75 mmol, 89.33% yield) was obtained as colorless oil which was checked by ¹H NMR and used in the next step directly without further purification. H NMR (400 MHz, DMSO) δ ppm 1.36 (s, 7H) 2.41-2.48 (m, 2H) 2.73 (t, J=7.70 Hz, 2H).

Step 5: Synthesis of Compound 7C

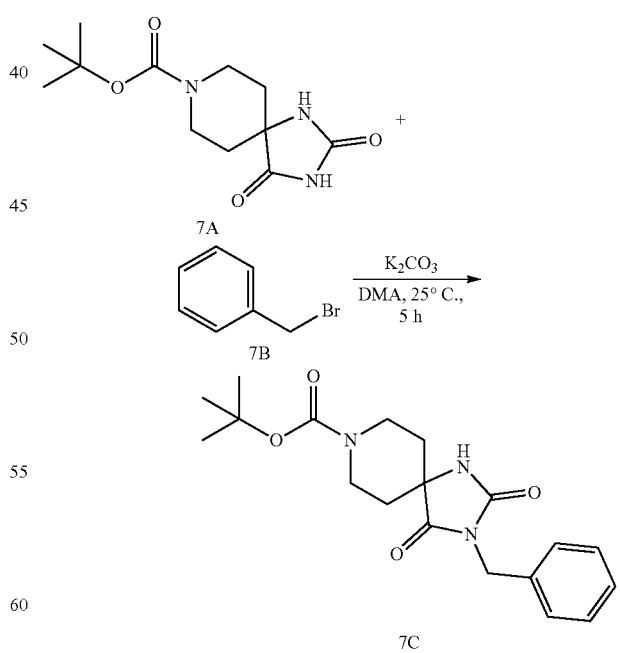

To a solution of compound 7A (3 g, 11.14 mmol, 1 eq) and compound 7B (2.48 g, 14.48 mmol, 1.72 mL, 1.3 eq) in DMF (25 mL) was added K₂CO₃ (4.62 g, 33.42 mmol, 3 eq) then the mixture was stirred at 25° C. for 5 hr. LCMS and TLC indicated the starting material was consumed completely. The reaction mixture was extracted with ethyl acetate (50 mL×3) and water (50 mL). The organic layers were washed with brine, dried over with $Na_2SO_4$, and concentrated under reduced pressure to yield a residue which was further purified by silica gel column (Petroleum ether:Ethyl acetate=20:1 to 2:1). Compound 7C (2.7 g, 7.51 mmol, 67.43% yield) was obtained as a white solid, and confirmed by $^1H$ NMR. LCMS: Rt=1.224 min, MS cal.: 359.4, $[M-55]^+$=304.2. $^1H$ NMR (400 MHz, MeOD) δ ppm 1.47 (s, 9H) 1.60 (dt, J=13.54, 3.81 Hz, 2H) 1.89 (ddd, J=13.82, 9.96, 4.34 Hz, 2H) 3.88-3.96 (m, 2H) 4.62 (s, 2H) 7.24-7.33 (m, 3H).

Step 6: Synthesis of Compound 7

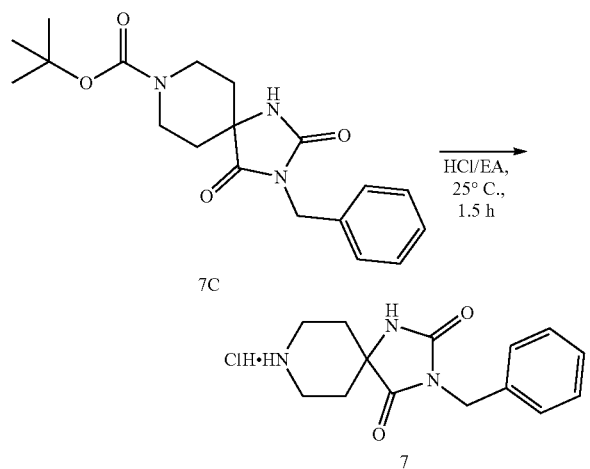

To a solution of compound 7C (1.58 g, 4.57 mmol, 1 eq) in EtOAc (20 mL) was added HCl/EtOAc (4 M, 20 mL, 17.49 eq), then the mixture was stirred at 25° C. for 1.5 hr. LCMS indicated that the starting material was consumed completely. The crude product was concentrated under reduced pressure to yield compound 7 (1.23 g, 4.37 mmol, 95.44% yield, HCl) as a yellow solid which was used in the next step directly, without further purification. LCMS: Rt=0.819 min, MS cal.: 281.74, $[M-35]^+$=246.1.

Step 7: Synthesis of Compound 8

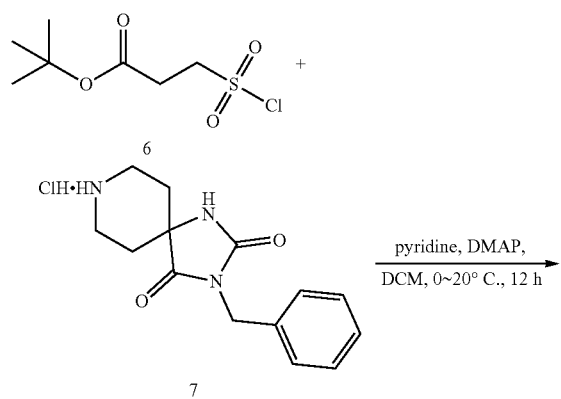

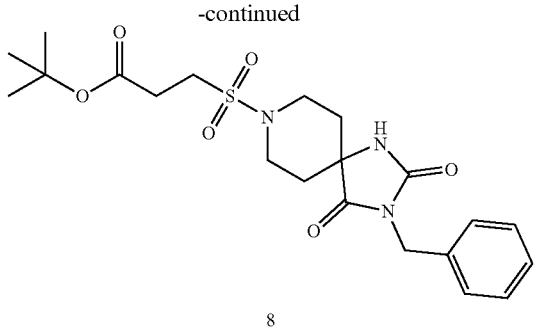

To a solution of compound 7 (200 mg, 771.30 μmol, 1 eq) in DCM (4 mL) was added DMAP (376.91 mg, 3.09 mmol, 4 eq) and DIPEA (199.37 mg, 1.54 mmol, 268.69 μL, 2 eq) at 0° C. Then compound 6 (264.58 mg, 1.16 mmol, 1.5 eq) was added to the mixture at 0° C. and the reaction was stirred at 20° C. for 12 h. The desired product was detected by LCMS, which also indicated reaction completion. The mixture was adjusted to pH=3 with HCl (1 M, 10 mL) then mixture was extracted with DCM (10 mL×3). The combined DCM layers were washed with brine (15 mL), dried over $Na_2SO_4$, filtered and concentrated. Compound 8 (200 mg, 221.47 μmol, 28.71% yield, 50% purity) was obtained as yellow solid checked by LCMS and $^1H$ NMR, and used in the next step without further purification. LCMS: ET15284-278-P1A1, Rt=1.212 min, MS cal.: 451.5, $[M-55]^+$=396.2. $^1H$ NMR (400 MHz, CDCl3) δ ppm 1.47 (s, 9H) 1.52-1.62 (m, 1H) 1.52-1.62 (m, 2H) 1.74-1.83 (m, 2H) 2.03-2.13 (m, 2H) 2.74 (t, J=7.46 Hz, 2H) 2.80 (br t, J=7.52 Hz, 1H) 3.21-3.29 (m, 2H) 3.30-3.40 (m, 2H) 3.66-3.76 (m, 2H) 4.66 (s, 2H) 7.28-7.37 (m, 6H).

Step 8: Synthesis of Compound 9

To a solution of compound 8 (50 mg, 110.73 μmol, 1 eq) in DCM (5 mL) was added TFA (1.89 g, 16.61 mmol, 1.23 mL, 150 eq) at 20° C. Then the mixture was stirred at 20° C. for 0.5 h. LCMS indicated the presence of the desired product and that the reaction was complete. Solvent was removed under reduced pressure to yield compound 9 (70 mg, 88.51 mol, 79.93% yield, 50% purity) as a brown oil which was verified by $^1H$ NMR. LCMS: Rt=1.044 min, MS cal.: 395.4, [M+H]⁺=396.2. $^1$H NMR (400 MHz, DMSO) δ 1.69 (br d, J=13.33 Hz, 2H) 1.87 (br d, J=10.88 Hz, 2H) 2.64 (br t, J=7.52 Hz, 2H) 3.15 (br s, 2H) 3.30 (br t, J=7.46 Hz, 2H) 4.54 (s, 2H) 7.20-7.29 (m, 3H) 7.30-7.37 (m, 2H) 8.96 (s, 1H).

Step 9: Synthesis of I-10

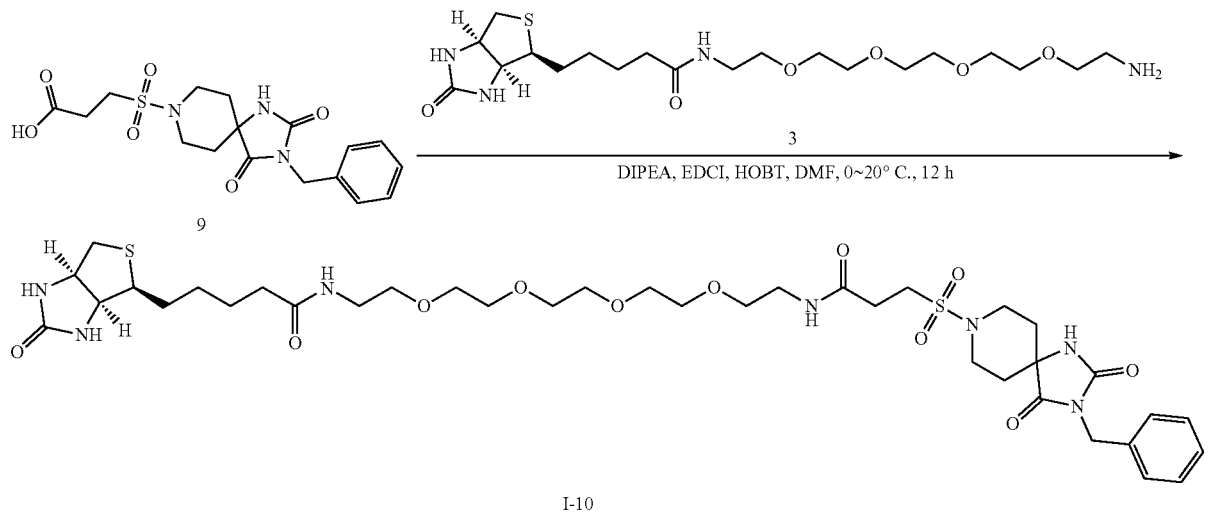

I-10

To a solution of compound 9 (30 mg, 60.69 μmol, 1 eq) in DMF (2 mL) was added DIPEA (23.53 mg, 182.07 μmol, 31.71 μL, 3 eq) and EDCI (12.80 mg, 66.76 μmol, 1.1 eq) at 20° C. Then the mixture was stirred at 20° C. for 0.5 h. Then compound 3 (42.12 mg, 91.04 μmol, 1.5 eq) was added to the mixture at 20° C. Then the reaction was stirred at 20° C. for 2 h. The desired product was not detected by LCMS and a significant amount of starting material remained. Additional compound 3 (56.15 mg, 121.38 μmol, 2 eq) was added to the mixture at 20° C. and the reaction was stirred at 20° C. for 12 h. LCMS indicated the presence of the desired product and that the reaction was complete. The residue was purified by prep-HPLC (TFA condition) according to HPLC. I-10 (7.02 mg, 8.29 μmol, 13.66% yield, 99.2% purity) was obtained as yellow oil which was verified by LCMS and $^1$H NMR. LCMS Rt=1.080 min, MS cal.: 840.2, [M+H]⁺=840.5. LCMS: Rt=2.709 min, MS cal.: 840.2, [M+H]⁺=840.5. HPLC: Rt=2.164 min. H NMR (400 MHz, DMSO) δ ppm 1.22-1.37 (m, 2H) 1.40-1.55 (m, 3H) 1.55-1.72 (m, 3H) 1.83-1.93 (m, 2H) 2.06 (t, J=7.40 Hz, 2H) 2.52-2.60 (m, 4H) 2.81 (dd, J=12.41, 5.07 Hz, 1H) 3.05-3.30 (m, 9H) 3.40 (dt, J=12.07, 6.01 Hz, 7H) 4.12 (dd, J=7.64, 4.34 Hz, 1H) 4.27-4.33 (m, 1H) 4.54 (s, 2H) 5.75 (s, 1H) 6.41 (br s, 1H) 7.20-7.29 (m, 3H) 7.30-7.36 (m, 2H) 7.82 (br t, J=5.50 Hz, 1H) 8.14 (br t, J=5.50 Hz, 1H) 8.95 (s, 1H).

Example 2: Synthesis of 5-[(3aS,4S,6aR)-2-oxo-hexahydro-1H-thieno[3,4-d]imidazol-4-yl]-N-{14-[3-({2,4-dioxo-3-phenyl-1,3,8-triazaspiro[4.5]decan-8-yl}sulfonyl)propanamido]-3,6,9,12-tetraoxatetradecan-1-yl}pentanamide (I-11

Scheme 2

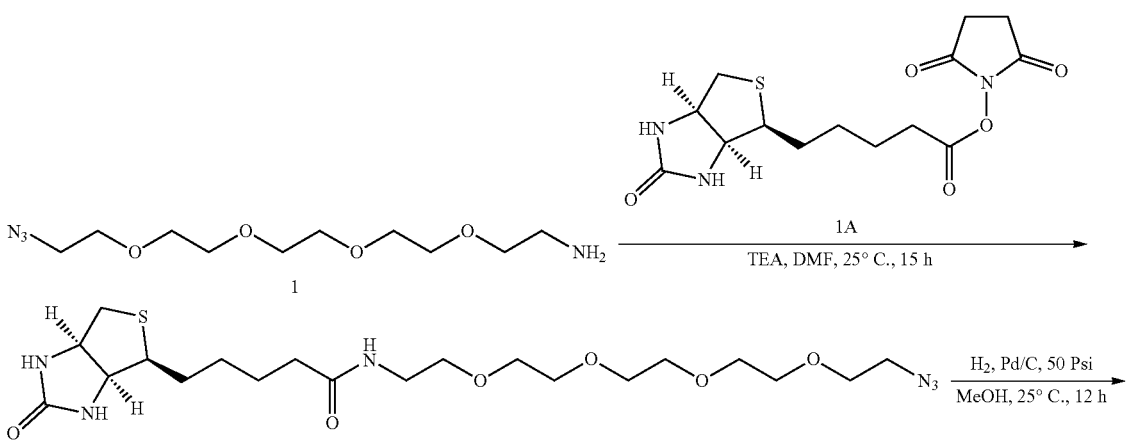

-continued
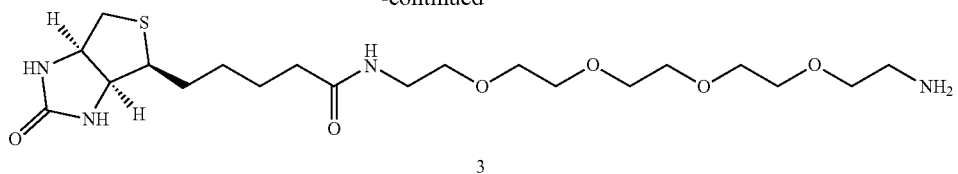
3
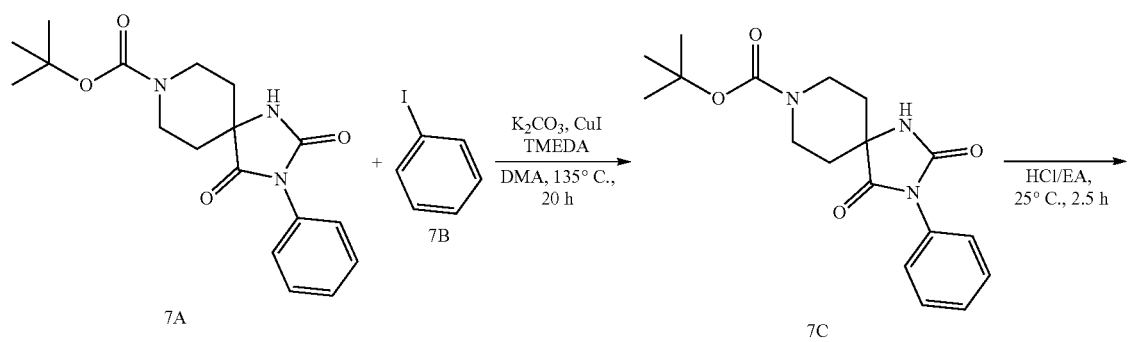
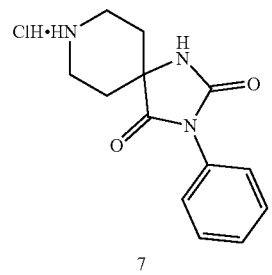
7
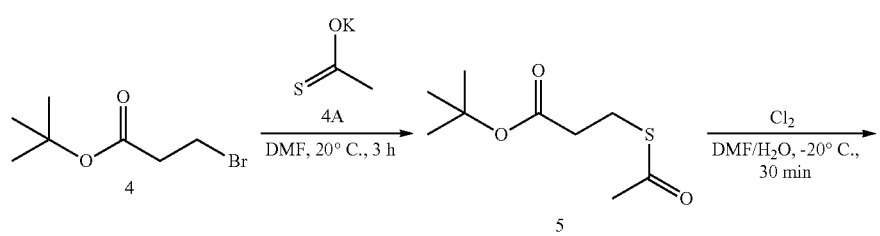
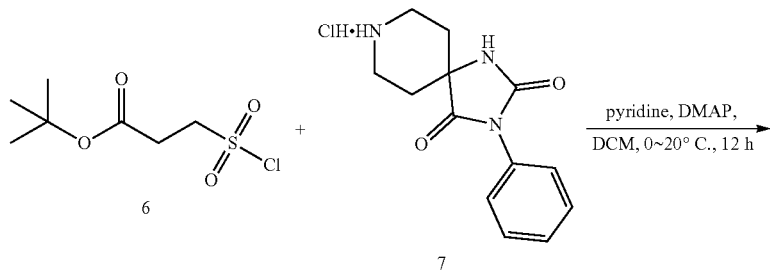
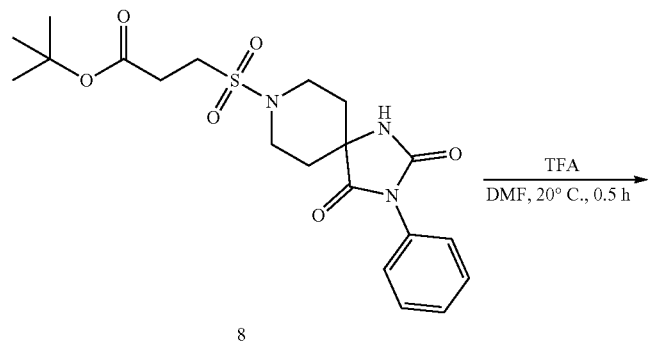

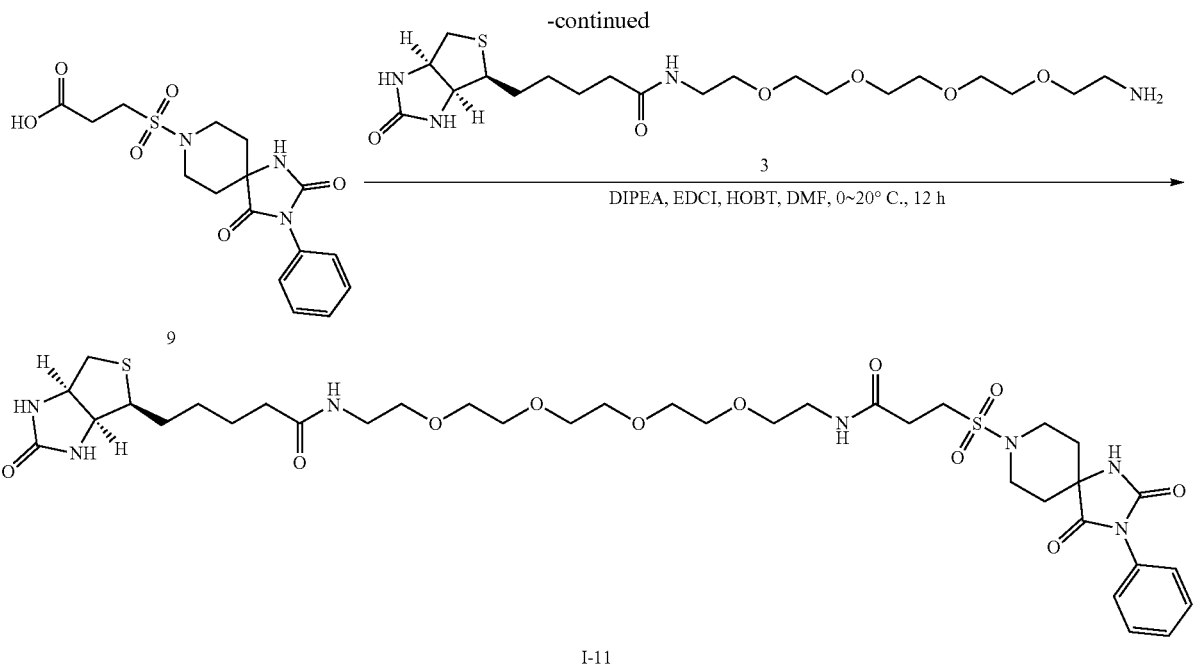

Step 1: Synthesis of Compound 2

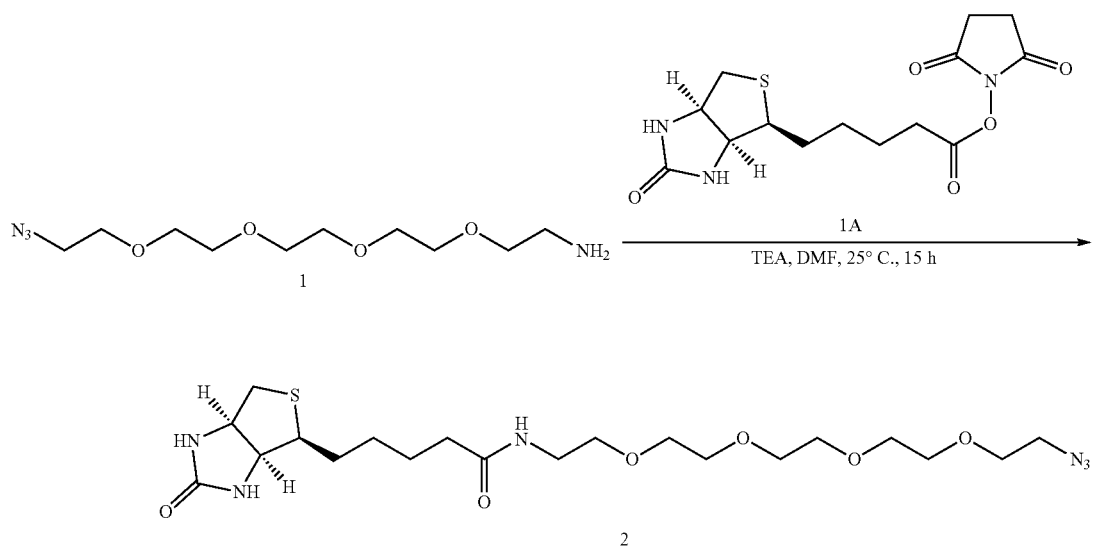

To a mixture of compound 1 (500 mg, 1.91 mmol, 1 eq) in DMF (5 mL) was added TEA (578.66 mg, 5.72 mmol, 795.95 µL, 3 eq) and compound 1A (780.88 mg, 2.29 mmol, 1.2 eq) at 25° C. under $N_2$. The mixture was stirred at 25° C. for 16 h. 1/50 of the reaction mixture was concentrated to remove the solvent. LCMS indicated the presence of the desired product. The mixture was concentrated under reduced pressure to yield a residue. The mixture was purified by prep-HPLC (TFA condition) according to HPLC. Compound 2 (937.6 mg, 1.28 mmol, 67.16% yield, 66.71% purity) was obtained as colorless liquid which was verified by LCMS and $^1$HNMR. LCMS: Rt=0.848 min, MS cal.: 488.24, [M+H]$^+$=489.3. HPLC: Rt=1.871 min. LCMS: Rt=0.851 min, MS cal.: 488.24, [M+H]$^+$=489.3. H NMR (400 MHz, METHANOL-$d_4$) δ=4.52 (dd, J=4.4, 7.8 Hz, 1H), 4.33 (dd, J=4.5, 7.9 Hz, 1H), 3.73-3.62 (m, 11H), 3.59-3.54 (m, 2H), 3.43-3.37 (m, 4H), 3.27-3.20 (m, 1H), 2.95 (dd, J=5.0, 12.7 Hz, 1H), 2.73 (d, J=12.7 Hz, 1H), 2.24 (t, J=7.4 Hz, 2H), 1.84-1.56 (m, 4H), 1.52-1.42 (m, 2H).

Step 2: Synthesis of Compound 3

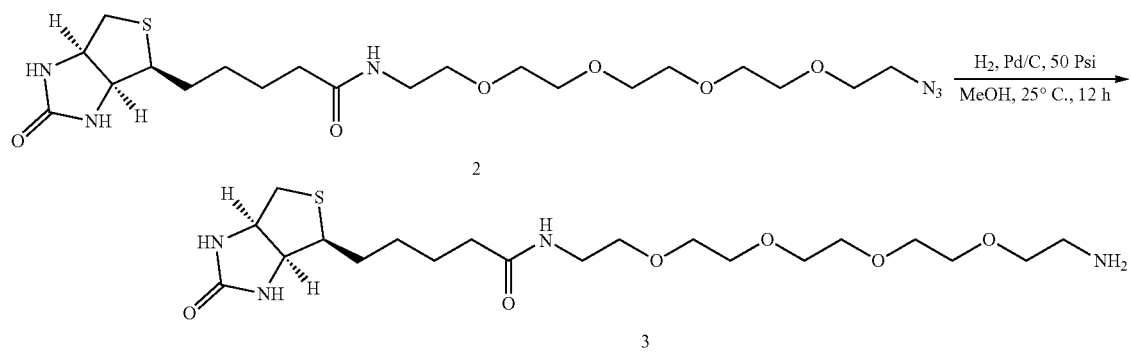

To a mixture of compound 2 (937.6 mg, 1.92 mmol, 1 eq) in MeOH (20 mL) was added Pd—C (233.06 mg, 1.92 mmol, 1 eq) at 25° C. The mixture was stirred at 25° C. for 12 h under $H_2$ (50 Psi). LCMS indicated the presence of the desired product and that the reaction was complete. The mixture was washed with MeOH (20 mL). The combined MeOH was concentrated to yield compound 3 (818.2 mg, 888.77 μmol, 46.32% yield, 50.25% purity) as a yellow oil and which was used for next step directly without further purification. LCMS: Rt=0.864 min, MS cal.: 462.25, $[M+H]^+$=463.3, $[1/2M+H]^+$=232.2.

Step 3: Synthesis of Compound 5

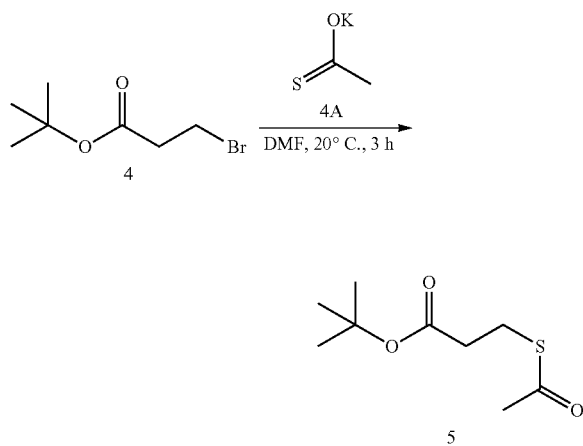

A solution of compound 4 (20 g, 95.66 mmol, 16.00 mL, 1 eq) and compound 4A (12.27 g, 95.66 mmol, 1 eq) in DMF (30 mL) was stirred at 20° C. for 3 h. $^1$H NMR showed the starting material was consumed. The mixture was then extracted with ethyl acetate (20 mL×3). The combined ethyl acetate layers were washed with $H_2O$ (25 mL×2), brine (30 mL), dried over $Na_2SO_4$, filtered and concentrated. Compound 5 (20 g, crude) was obtained as yellow oil and used for next step directly without further purification. $^1$H NMR (400 MHz, DMSO) δ ppm 1.40 (s, 9H) 2.32 (s, 3H) 2.98 (t, J=6.85 Hz, 2H).

Step 4: Synthesis of Compound 6

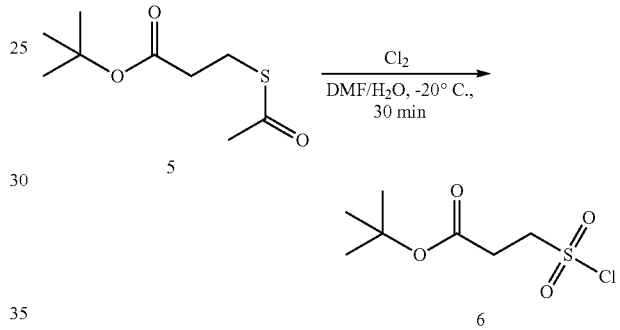

$Cl_2$ (24.48 mmol) was bubbled into a solution of compound 5 (2 g, 9.79 mmol, 1 eq) in DCM (100 mL) and $H_2O$ (20 mL) at −20° C. for 30 minutes. TLC (Petroleum ether: Ethyl acetate=10:1; product Rf=0.30) showed the starting material was consumed and showed one new main spot. LCMS did not detect the desired MS. The mixture was adjusted to pH=7 with saturated $NaHCO_3$ (50 mL) then extracted with DCM (50 mL×3). The combined DCM layers were washed with brine (15 mL), dried over $Na_2SO_4$, filtered and concentrated. Compound 6 (2 g, 8.75 mmol, 89.33% yield) was obtained as colorless oil which was checked by $^1$H NMR and used in the next step directly without further purification. $^1$H NMR (400 MHz, DMSO) δ ppm 1.36 (s, 7H) 2.41-2.48 (m, 2H) 2.73 (t, J=7.70 Hz, 2H).

Step 5: Synthesis of Compound 7C

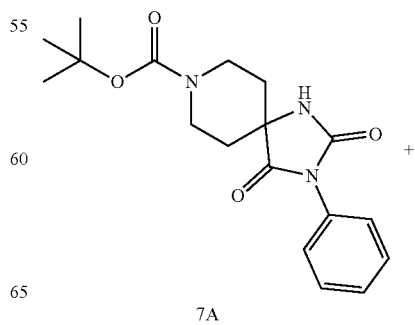

7A

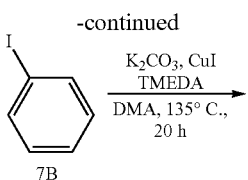

7B

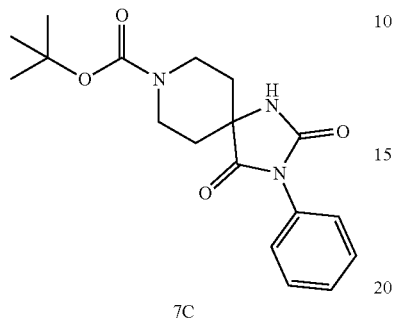

7C

To solution of compound 7A (3 g, 11.14 mmol, 1 eq) and compound 7B (3.41 g, 16.71 mmol, 1.86 mL, 1.5 eq) in DMA (30 mL) was added K₂CO₃ (4.62 g, 33.42 mmol, 3 eq), CuI (2.12 g, 11.14 mmol, 1 eq), and TMEDA (1.29 g, 11.14 mmol, 1.68 mL, 1 eq), sequentially. After the mixture was degassed with N₂ for three times, it was heated to 135° C. for 20 hr. LCMS and TLC indicated that the starting material was consumed completely. The reaction mixture was extracted with ethyl acetate (50 mL×3) and water (50 mL). The organic layers were washed with brine, dried over Na₂SO₄, and concentrated under reduced pressure to yield a residue which was further purified by silica gel column (Petroleum ether:Ethyl acetate=15:1 to 1:1). Compound 7C (1.58 g, 4.57 mmol, 41.06% yield) was obtained as a yellow solid, and was confirmed by ¹H NMR. LCMS: Rt=1.191 min, MS cal.: 345.3, [M-55]⁺=290.2. ¹H NMR (400 MHz, MeOD) δ ppm 1.48 (s, 7H) 1.78 (br d, J=14.11 Hz, 2H) 1.96-2.08 (m, 3H) 3.98 (br d, J=14.11 Hz, 2H) 7.36-7.42 (m, 3H) 7.44-7.51 (m, 2H).

Step 6: Synthesis of Compound 7

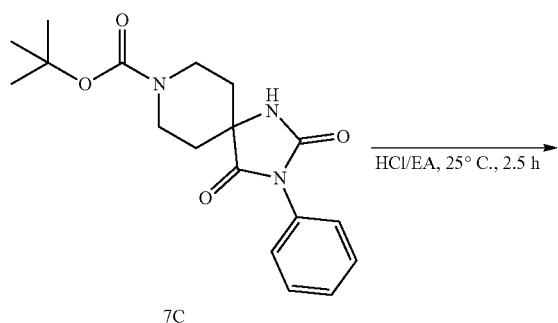

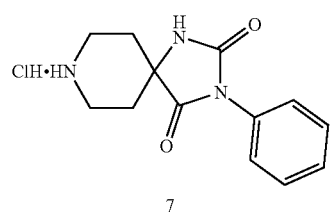

7

To a solution of compound 7C (1.58 g, 4.57 mmol, 1 eq) in EtOAc (20 mL) was added HCl/EtOAc (4 M, 20 mL, 17.49 eq), then the mixture was stirred at 25° C. for 1.5 hr. LCMS indicated the starting material was consumed completely and the crude product was concentrated under reduced pressure to yield a residue. Compound 7 (1.23 g, 4.37 mmol, 95.44% yield, HCl) was obtained as a yellow solid, and was used in next step directly, without further purification. LCMS: Rt=0.819 min, MS cal.: 281.7, [M-35]⁺=246.1.

Step 7: Synthesis of Compound 8

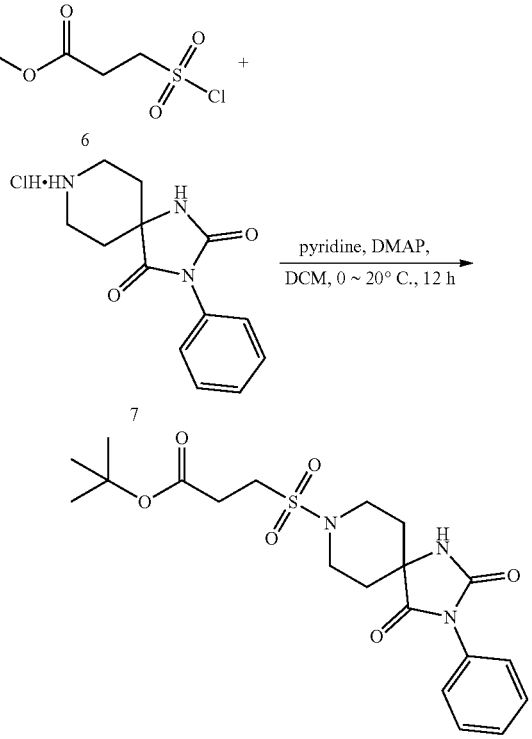

To a solution of compound 7 (250 mg, 887.35 μmol, 1 eq, HCl) in DCM (20 mL) was added DMAP (433.63 mg, 3.55 mmol, 4 eq) and DIPEA (229.36 mg, 1.77 mmol, 309.11 L, 2 eq) at 0° C. Then compound 6 (304.40 mg, 1.33 mmol, 1.5 eq) was added to the mixture at 0° C. and the reaction was stirred at 20° C. for 12 h. LCMS indicated the presence of the desired product and that the reaction was completed. TLC (DCM:MeOH=10:1, product Rf=0.80) indicated that the starting material was consumed and detected a new main spot. The mixture was adjusted to pH=3 with HCl (1 M, 10 mL) and the mixture was extracted with DCM (10 mL×3). The combined DCM layers were washed with brine (15 mL), dried over Na₂SO₄, filtered and concentrated. Compound 8 (375 mg, 548.56 μmol, 61.82% yield, 64% purity) was obtained as yellow solid which was verified by LCMS and ¹H NMR. LCMS: Rt=1.190 min, MS cal.: 451.5, [M-55]⁺=382.1. LCMS: Rt=1.187 min, MS cal.: 451.5, [M-55]⁺=382.1. ¹H NMR (400 MHz, CDCl3) δ ppm 1.46-1.50 (m, 8H) 1.89-1.99 (m, 2H) 2.17-2.26 (m, 2H) 2.72 (t, J=7.40 Hz, 2H) 3.22-3.29 (m, 2H) 3.38-3.46 (m, 2H) 3.71-3.80 (m, 2H) 7.36-7.43 (m, 3H) 7.45-7.52 (m, 2H).

Step 8: Synthesis of Compound 9

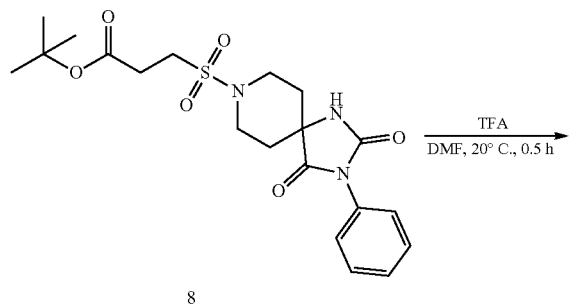

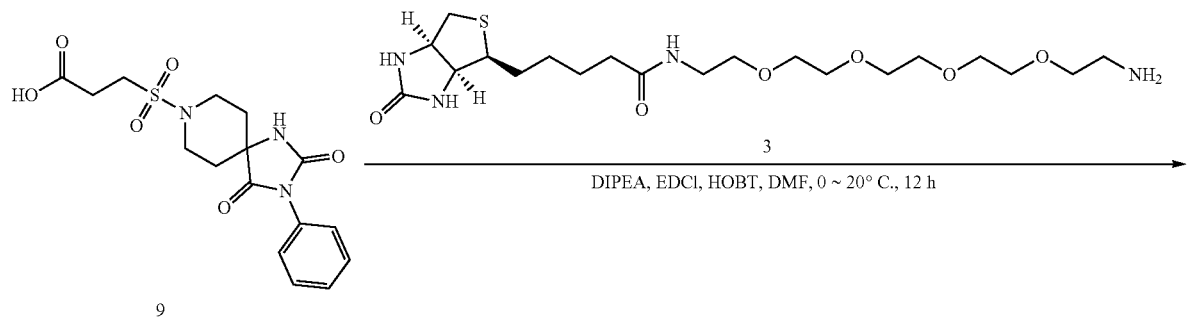

To a solution of compound 8 (300 mg, 685.70 μmol, 1 eq) in DCM (4 mL) was added TFA (7.82 g, 68.57 mmol, 5.08 mL, 100 eq) at 20° C. The reaction was stirred at 20° C. for 1 h. LCMS indicated the presence of the desired product and that the reaction was complete. Solvent was removed under reduced pressure to yield compound 9 (250 mg, 655.47 μmol, 95.59% yield) as brown solid which was verified by $^1$H NMR. LCMS: Rt=0.963 min, MS cal.: 381.4, [M+H]$^+$ =382.2. $^1$H NMR (400 MHz, CDCl3) δ ppm 1.10 (s, 1H) 1.42 (br d, J=13.33 Hz, 2H) 1.65-1.77 (m, 2H) 2.29-2.37 (m, 2H) 2.82-2.93 (m, 4H) 3.24-3.35 (m, 3H) 6.89-6.97 (m, 3H) 6.99-7.05 (m, 2H) 8.69 (s, 1H).

Step 9: Synthesis of I-11

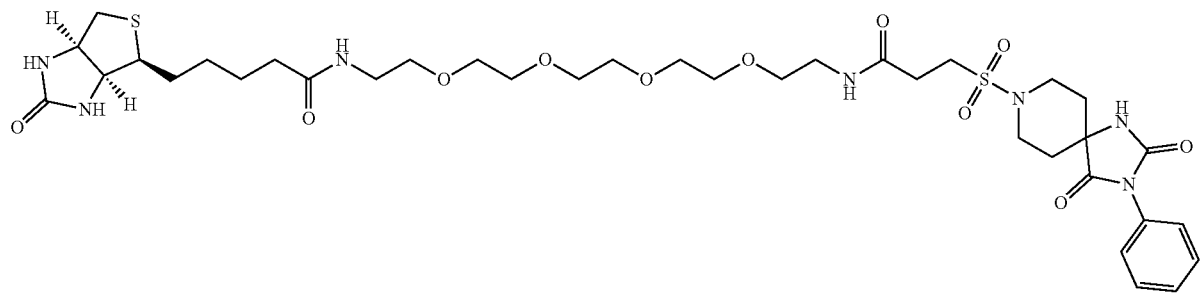

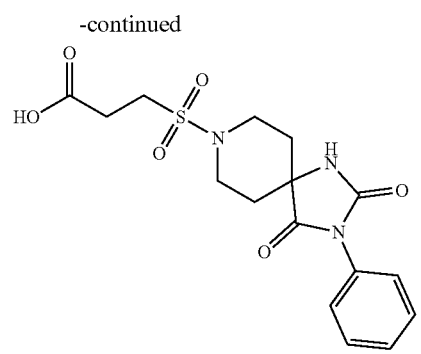

To a solution of compound 9 (25 mg, 65.55 μmol, 1 eq) in DCM (1 mL) was added EDCI (15.08 mg, 78.66 μmol, 1.2 eq), HOBt (10.63 mg, 78.66 μmol, 1.2 eq), and DIPEA (25.41 mg, 196.65 μmol, 34.25 μL, 3 eq) at 0° C. Then the mixture was stirred at 20° C. for 0.5 h then compound 3 (45.48 mg, 98.32 μmol, 1.5 eq) was added to the mixture at 20° C. and the reaction was stirred at 20° C. for 2 h. The desired product was detected by LCMS. However, LCMS indicated a significant amount of compound 9 remained. Additional compound 3 (60.65 mg, 131.10 μmol, 2 eq) was added to the mixture and the reaction was stirred at 20° C. for 10 h. Again LCMS indicated a significant amount of starting material so additional compound 3 (30.32 mg, 65.55 μmol, 1 eq), EDCI (6.28 mg, 32.78 μmol, 0.5 eq), and HOBt (4.43 mg, 32.78 mol, 0.5 eq) was added to the mixture at 0° C. and the reaction was stirred at 20° C. for 4 h. LCMS again indicated the reaction was not complete and additional EDCI (6.28 mg, 32.78 μmol, 0.5 eq) and HOBt (4.43 mg, 32.78 μmol, 0.5 eq) was added to the mixture and the reaction was stirred at 20° C. for 10 h. LCMS still indicated the reaction was not complete. Still, the mixture was extracted with DCM (5 mL×3) and the combined DCM layers were washed with brine (15 mL), dried over Na$_2$SO$_4$, filtered and concentrated. The resulting residue was purified by prep-HPLC (TFA condition) according to HPLC. I-11 (12.33 mg, 24.21 μmol, 36.94% yield) was obtained as yellow oil which was verified by LCMS and H NMR. LCMS: Rt=0.989 min, MS cal.: 825.9, [M+H]$^+$=826.4. LCMS: Rt=1.033 min, MS cal.: 825.9, [M+H]$^+$=826.4. LCMS: Rt=1.040 min, MS cal.: 825.9, [M+H]$^+$=826.4. LCMS: Rt=1.050 min, MS cal.: 825.9, [M+H]$^+$=826.4. LCMS: Rt=2.193 min, MS cal.: 825.9, [M+H]$^+$=826.3. HPLC: Rt=1.362 min. $^1$H NMR (400 MHz, DMSO) δ ppm 1.39-1.49 (m, 2H) 1.53-1.79 (m, 4H) 1.88-1.96 (m, 2H) 2.11-2.25 (m, 4H) 2.67-2.74 (m, 3H) 2.92 (dd, J=12.78, 4.95 Hz, 1H) 3.17-3.24 (m, 1H) 3.32-3.43 (m, 6H) 3.56 (dt, J=12.65, 5.53 Hz, 4H) 3.60-3.67 (m, 11H) 3.75 (dt, J=12.96, 4.71 Hz, 2H) 4.30 (dd, J=7.83, 4.40 Hz, 1H) 4.48 (dd, J=7.70, 4.89 Hz, 1H) 7.37-7.43 (m, 3H) 7.45-7.52 (m, 2H).

Example 3: Synthesis of 5-[(3aS,4S,6aR)-2-oxo-hexahydro-1H-thieno[3,4-d]imidazol-4-yl]-N-[14-(3-{[4-(2,4-dioxo-3-phenylimidazolidin-1-yl)piperidin-1-yl]sulfonyl}propanamido)-3,6,9,12-tetraoxatetradecan-1-yl]pentanamide (I-12

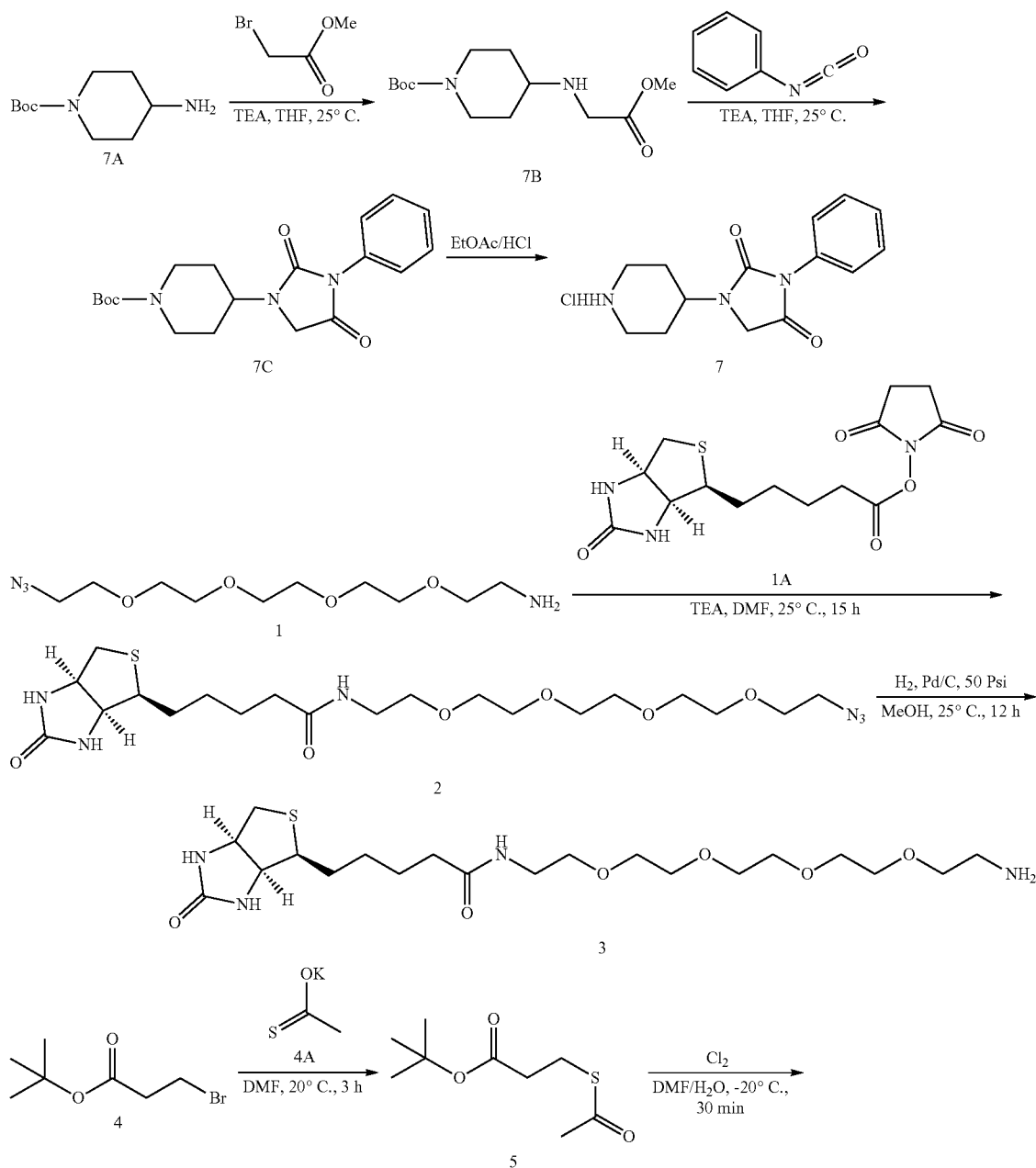

Scheme 3

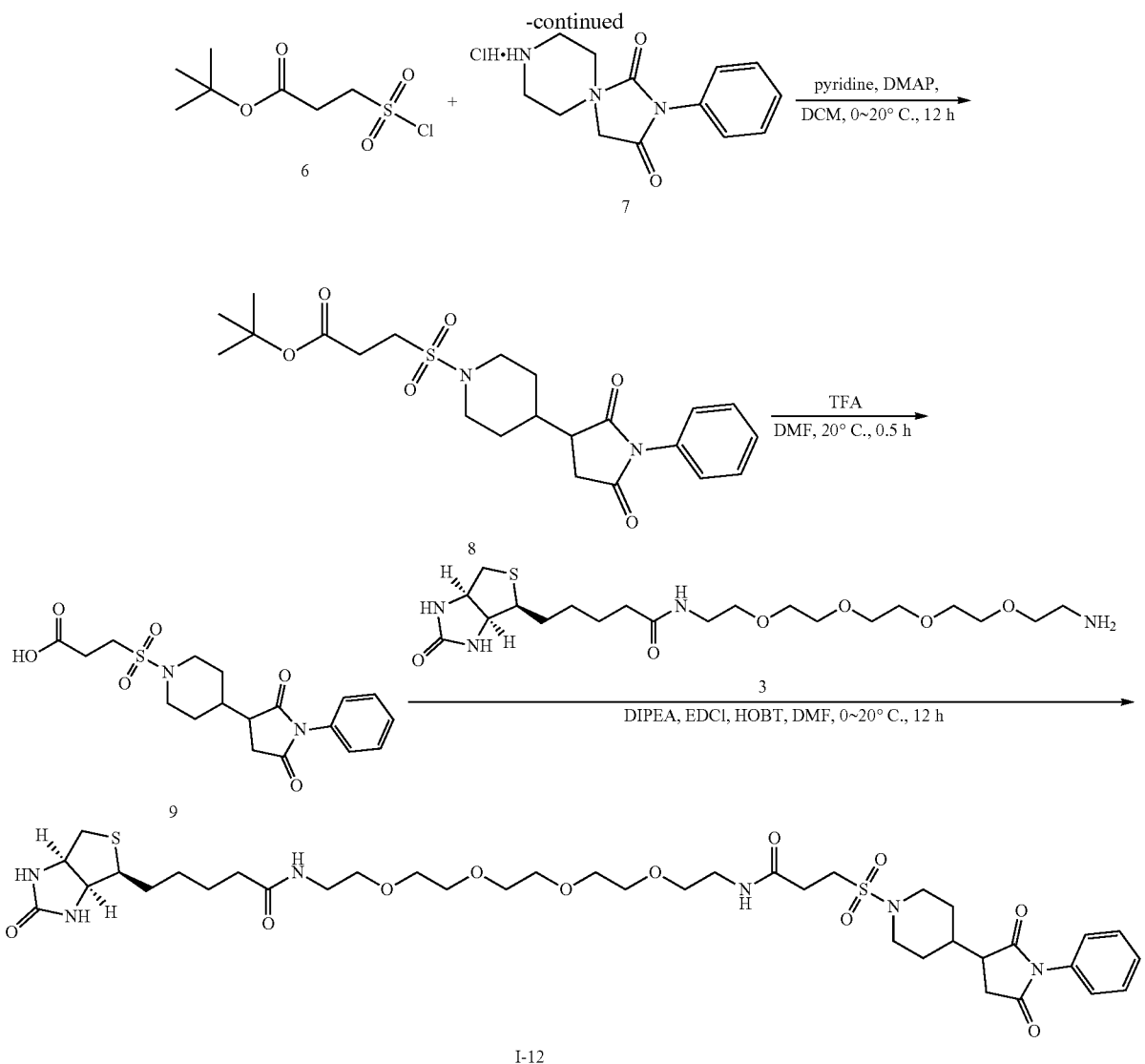

I-12

Step 1: Synthesis of Compound 7B

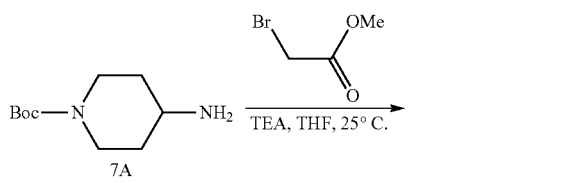

To a mixture of compound 7A (10 g, 49.93 mmol, 1 eq) in THF (150 mL) was added methyl-2-bromoacetate (7.64 g, 49.93 mmol, 4.71 mL, 1 eq) TEA (7.58 g, 74.90 mmol, 10.42 mL, 1.5 eq) at 25° C. under $N_2$. The mixture was stirred at 25° C. for 16 hours then concentrated under reduced pressure to remove solvent. The residue was diluted with $H_2O$ (50 mL) and extracted with EtOAc (150 mL; 50 mL×3). The combined organic layers were washed with saturated NaCl 20 mL (20 mL×1), dried over anhydrous $Na_2SO_4$, filtered and concentrated under reduced pressure to give a residue. Compound 7B (14 g, crude) was obtained as a yellow solid. LCMS: Rt=0.907 min, MS cal.: 272.2, [M+H]$^+$=273.2.

Step 2: Synthesis of Compound 7C

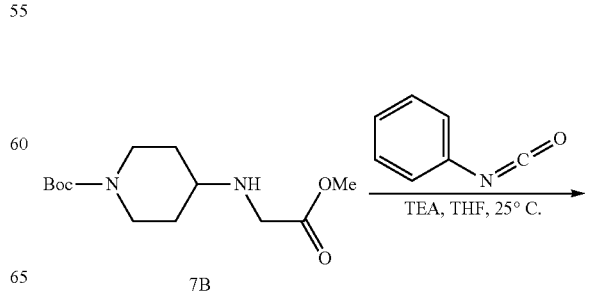

Step 3: Synthesis of Compound 7

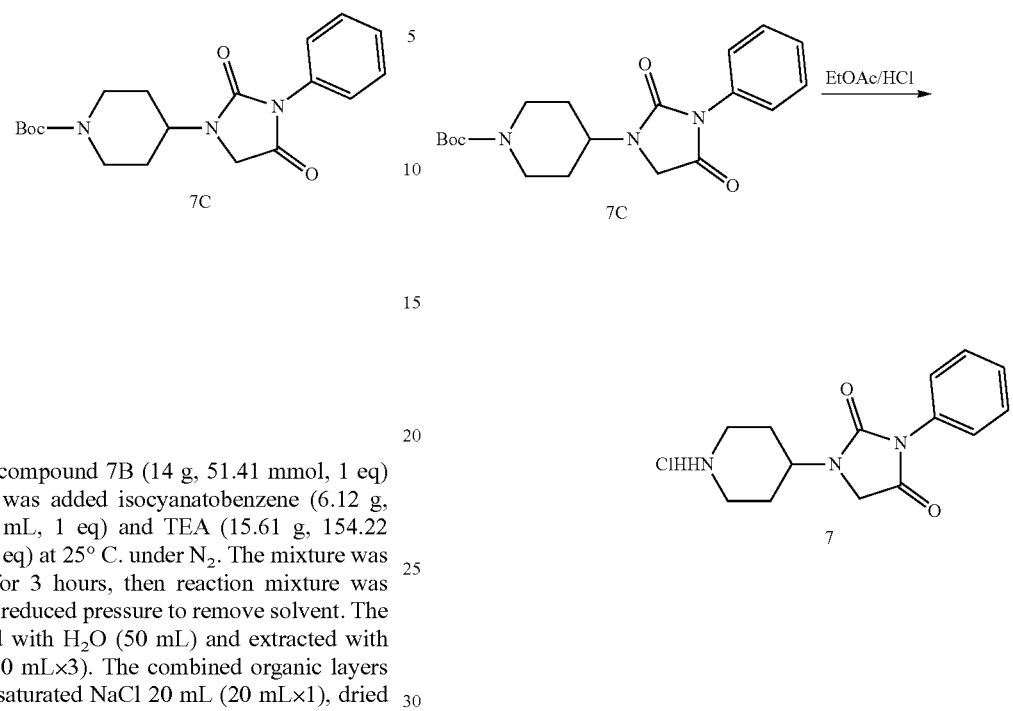

To a mixture of compound 7B (14 g, 51.41 mmol, 1 eq) in THF (150 mL) was added isocyanatobenzene (6.12 g, 51.41 mmol, 5.57 mL, 1 eq) and TEA (15.61 g, 154.22 mmol, 21.47 mL, 3 eq) at 25° C. under $N_2$. The mixture was stirred at 25° C. for 3 hours, then reaction mixture was concentrated under reduced pressure to remove solvent. The residue was diluted with $H_2O$ (50 mL) and extracted with EtOAc (150 mL; 50 mL×3). The combined organic layers were washed with saturated NaCl 20 mL (20 mL×1), dried over anhydrous $Na_2SO_4$, filtered and concentrated under reduced pressure to give a residue. Compound 7C (20 g, crude) was obtained as a yellow solid. LCMS: Rt=1.222 min, MS cal.: 359.2, [M-55]$^+$=304.2. $^1$H NMR (400 MHz, METHANOL-$d_4$) δ ppm 1.32 (t, J=7.34 Hz, 1H) 1.47 (s, 1H) 1.61-1.95 (m, 1H) 3.22 (q, J=7.25 Hz, 1H) 3.28-3.40 (m, 1H) 3.73 (br t, J=6.66 Hz, 1H) 4.16-4.27 (m, 1H) 7.33-7.52 (m, 1H).

A mixture of compound 7C (20 g, 55.65 mmol, 1 eq) in HCl/EtOAc (200 mL) was stirred at 25° C. for 16 hours. The reaction mixture was concentrated under reduced pressure to remove solvent to give a residue. Compound 7 (14 g, crude) was obtained as a yellow solid. LCMS: Rt=0.838 min, MS cal.: 259.3, [M+H]$^+$=260.2.

Step 4: Synthesis of Compound 2

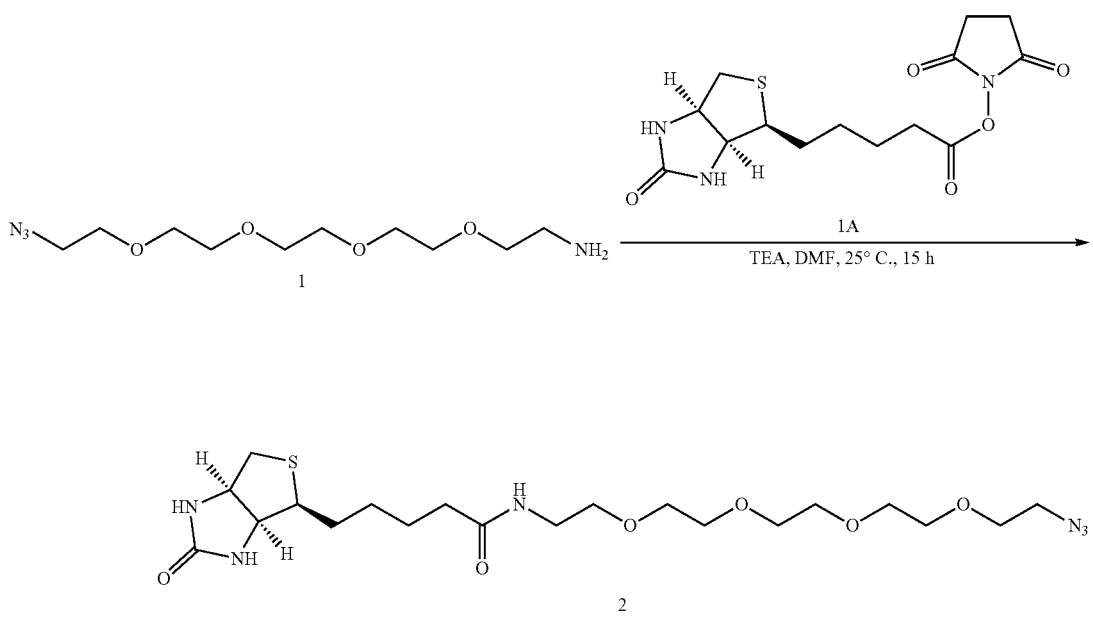

To a mixture of compound 1 (500 mg, 1.91 mmol, 1 eq) in DMF (5 mL) was added TEA (578.66 mg, 5.72 mmol, 795.95 μL, 3 eq) and compound 1A (780.88 mg, 2.29 mmol, 1.2 eq) at 25° C. under N$_2$. The mixture was stirred at 25° C. for 16 h. 1/50 of the reaction mixture was concentrated to remove the solvent. LCMS indicated the presence of the desired product. The mixture was concentrated under reduced pressure to yield a residue. The mixture was purified by prep-HPLC (TFA condition) according to HPLC. Compound 2 (937.6 mg, 1.28 mmol, 67.16% yield, 66.71% purity) was obtained as colorless liquid which was verified by LCMS and $^1$HNMR. LCMS: Rt=0.848 min, MS cal.: 488.24, [M+H]$^+$=489.3. HPLC: Rt=1.871 min. LCMS: Rt=0.851 min, MS cal.: 488.24, [M+H]$^+$=489.3. $^1$H NMR (400 MHz, METHANOL-d$_4$) δ=4.52 (dd, J=4.4, 7.8 Hz, 1H), 4.33 (dd, J=4.5, 7.9 Hz, 1H), 3.73-3.62 (m, 11H), 3.59-3.54 (m, 2H), 3.43-3.37 (m, 4H), 3.27-3.20 (m, 1H), 2.95 (dd, J=5.0, 12.7 Hz, 1H), 2.73 (d, J=12.7 Hz, 1H), 2.24 (t, J=7.4 Hz, 2H), 1.84-1.56 (m, 4H), 1.52-1.42 (m, 2H).

Step 5: Synthesis of Compound 3

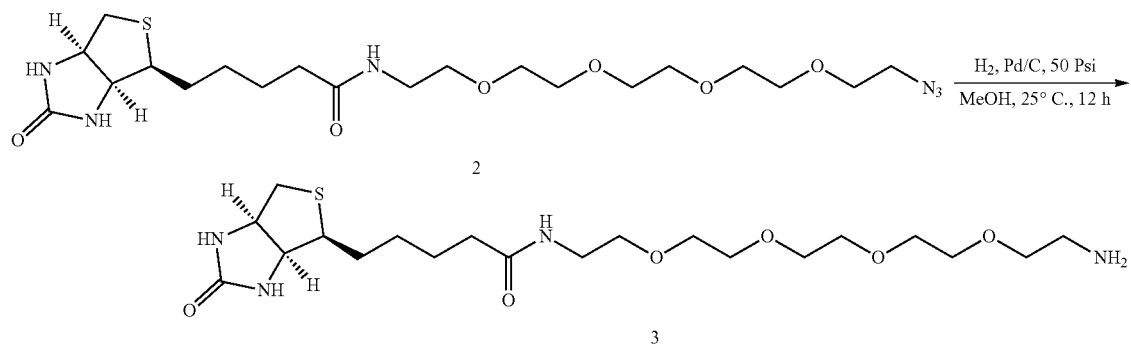

To a mixture of compound 2 (937.6 mg, 1.92 mmol, 1 eq) in MeOH (20 mL) was added Pd—C (233.06 mg, 1.92 mmol, 1 eq) at 25° C. The mixture was stirred at 25° C. for 12 h under H$_2$ (50 Psi). LCMS (Rt=0.864 min, m/z 463.3 (M+H) and m/z 232.2 (1/2M+H)) indicated the presence of the desired product and that the reaction was completed. The mixture was washed with MeOH (20 mL). The combined MeOH was concentrated to yield compound 3 (818.2 mg, 888.77 μmol, 46.32% yield, 50.25% purity) as a yellow oil and which was used for next step directly without further purification. LCMS: Rt=0.864 min, MS cal.: 462.25, [M+H]$^+$=463.3, [1/2M+H]$^+$=232.2.

Step 6: Synthesis of Compound 5

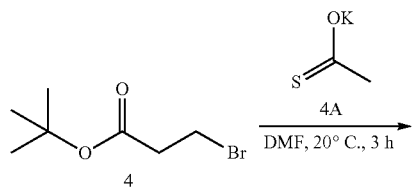

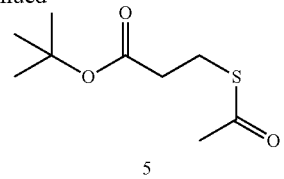

A solution of compound 4 (20 g, 95.66 mmol, 16.00 mL, 1 eq) and compound 4A (12.27 g, 95.66 mmol, 1 eq) in DMF (30 mL) was stirred at 20° C. for 3 h. $^1$H NMR indicated that the starting material was consumed. The mixture was then extracted with ethyl acetate (20 mL×3). The combined ethyl acetate layers were washed with H$_2$O (25 mL×2), brine (30 mL), dried over Na$_2$SO$_4$, filtered and concentrated. Compound 5 (20 g, crude) was obtained as yellow oil and used for next step directly without further purification. $^1$H NMR (400 MHz, DMSO) δ ppm 1.40 (s, 9H) 2.32 (s, 3H) 2.98 (t, J=6.85 Hz, 2H).

Step 7: Synthesis of Compound 6

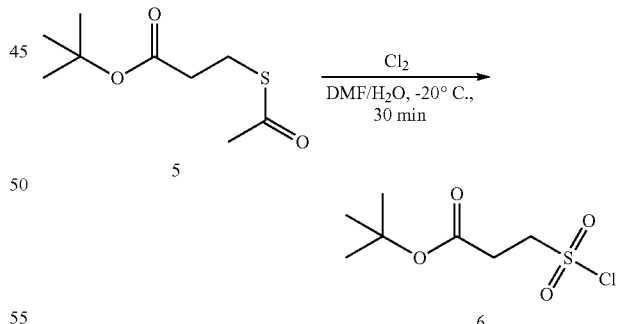

Cl$_2$ (24.48 mmol) was bubbled into a solution of compound 5 (2 g, 9.79 mmol, 1 eq) in DCM (100 mL) and H$_2$O (20 mL) at −20° C. for 30 minutes. TLC (Petroleum ether: Ethyl acetate=10:1; product Rf=0.30) showed the starting material was consumed and showed one new main spot. LCMS did not detect the desired product. The mixture was adjusted to pH=7 with saturated NaHCO$_3$ (50 mL) then extracted with DCM (50 mL×3). The combined DCM layers were washed with brine (15 mL), dried over Na$_2$SO$_4$, filtered and concentrated. Compound 6 (2 g, 8.75 mmol, 89.33% yield) was obtained as colorless oil which was checked by $^1$H NMR and used in the next step directly without further purification. H NMR (400 MHz, DMSO) δ ppm 1.36 (s, 7H) 2.41-2.48 (m, 2H) 2.73 (t, J=7.70 Hz, 2H).

Step 8: Synthesis of Compound 8

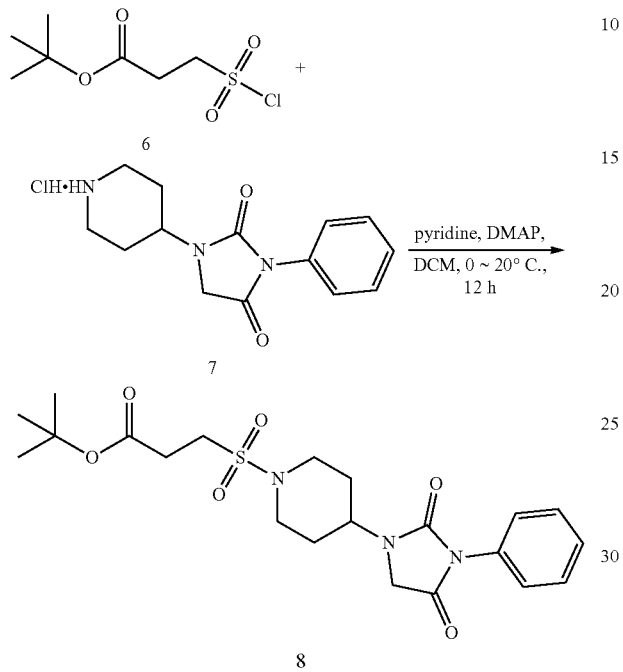

To a solution of compound 7 (250 mg, 845.27 μmol, 1 eq, HCl) in DCM (4 mL) was added DMAP (413.07 mg, 3.38 mmol, 4 eq) and pyridine (133.72 mg, 1.69 mmol, 136.45 μL, 2 eq) at 20° C. Then compound 6 (270.63 mg, 1.18 mmol, 1.4 eq) was added to the mixture at 0° C. and the reaction was stirred at 20° C. for 12 h. LCMS indicated the presence of the desired product and that the reaction was complete. The mixture was adjusted to pH=3 with HCl (1 M, 10 mL) and the mixture was extracted with DCM (10 mL×3). The combined DCM layers were washed with brine (15 mL), dried over $Na_2SO_4$, filtered and concentrated. Compound 8 (197 mg, crude) was obtained as yellow solid verified by LCMS and $^1$H NMR. LCMS: Rt=1.219 min, MS cal.: 451.5, [M-55]$^+$=396.1. LCMS: Rt=1.173 min, MS cal.: 451.5, [M-55]$^+$=396.1. $^1$H NMR (400 MHz, CDCl3) δ ppm 1.48 (s, 8H) 1.74-1.86 (m, 2H) 1.96 (br dd, J=11.91, 2.21 Hz, 2H) 2.74 (t, J=7.50 Hz, 2H) 2.94 (td, J=12.51, 2.32 Hz, 2H) 3.22-3.28 (m, 2H) 3.93-4.00 (m, 4H) 4.22 (tt, J=12.18, 4.02 Hz, 1H) 7.36-7.42 (m, 3H) 7.45-7.50 (m, 2H).

Step 9: Synthesis of Compound 9

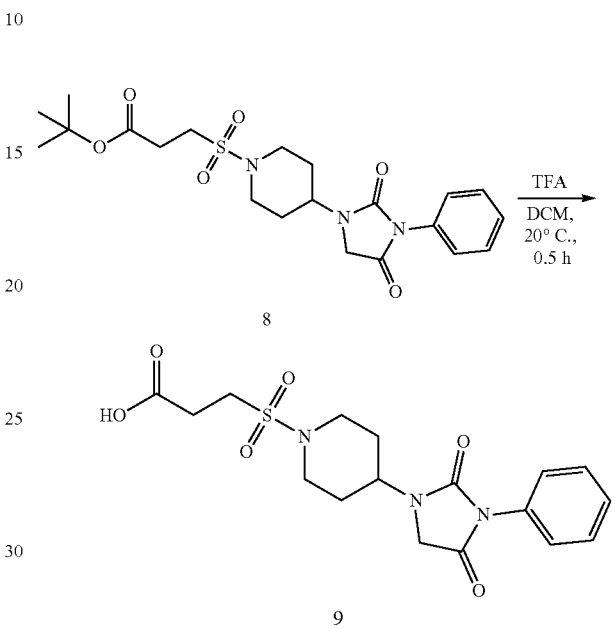

To a solution of compound 8 (197 mg, 436.29 μmol, 1 eq) in DCM (4 mL) was added TFA (5.97 g, 52.35 mmol, 3.88 mL, 120 eq) at 20° C. Then the reaction was stirred at 20° C. for 2 h. LCMS indicated the presence of the desired product and that the reaction was complete. The mixture was extracted with DCM (20 mL×3). The combined DCM layers were washed with brine (15 mL), dried over $Na_2SO_4$, filtered and concentrated. Compound 9 (150 mg, 379.33 μmol, 86.95% yield) was obtained as white solid and used for next step directly, without further purification. LCMS: Rt=0.994 min, MS cal.: 395.4, [M+H]$^+$=396.2.

Step 10: Synthesis of I-12

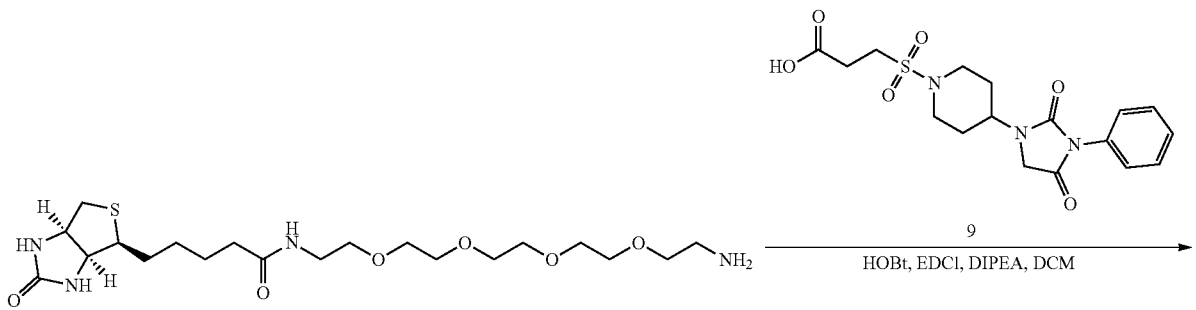

-continued

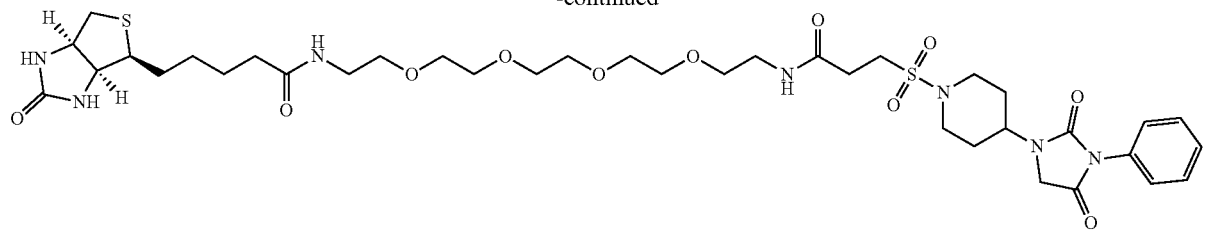

I-12

To a solution of compound 3 (175.48 mg, 379.33 μmol, 2 eq) and compound 9 (75 mg, 189.67 μmol, 1 eq) in DCM (5 mL) was added HOBt (38.44 mg, 284.50 μmol, 1.5 eq), EDCI (54.54 mg, 284.50 μmol, 1.5 eq), and DIPEA (73.54 mg, 569.00 μmol, 99.11 μL, 3 eq) at 0° C. The mixture was stirred at 20° C. for 12 hr. LCMS indicated that the reaction was complete. The mixture was washed with 10 mL sat. NH$_4$Cl, the organic layer was separated, concentrated, purified by prep-HPLC column (Waters Xbridge 150 mm*25 mm*5 um; mobile phase: A: water (0.04% NH$_3$·H$_2$O+10 mM NH$_4$HCO$_3$), B: ACN; gradient: 5%-35% B in 10 min) to give 1-12 (10.41 mg, 12.05 μmol, 6.35% yield, 97.2% purity) as a white solid, which was verified by LCMS and $^1$H NMR. LCMS: Rt=0.944 min, MS cal.: 839.35, [M+H]$^+$=840.0. LCMS: Rt=2.528 min, MS cal.: 839.35, [M+H]$^+$=840.5. $^1$H NMR (400 MHz, METHANOL-d4) δ ppm 7.44-7.51 (m, 2H) 7.36-7.43 (m, 3H) 4.48 (dd, J=7.67, 4.60 Hz, 1H) 4.30 (dd, J=7.89, 4.39 Hz, 1H) 4.05-4.17 (m, 3H) 3.86 (br d, J=12.72 Hz, 2H) 3.60-3.69 (m, 13H) 3.52-3.59 (m, 4H) 3.33-3.43 (m, 7H) 3.16-3.24 (m, 1H) 2.88-3.03 (m, 3H) 2.64-2.74 (m, 3H) 2.22 (t, J=7.24 Hz, 2H) 1.90-2.00 (m, 2H) 1.53-1.89 (m, 7H) 1.38-1.49 (m, 2H).

Example 4: 5-[(3aS,4S,6aR)-2-oxo-hexahydro-1H-thieno[3,4-d]imidazol-4-yl]-N-{26-[(2-{2,4-dioxo-3-phenyl-1,3,8-triazaspiro[4.5]decan-8-yl}-1,3-thiazol-5-yl)formamido]-3,6,9,12,15,18,21,24-octaoxahexacosan-1-yl}pentanamide, I-13

Scheme 4

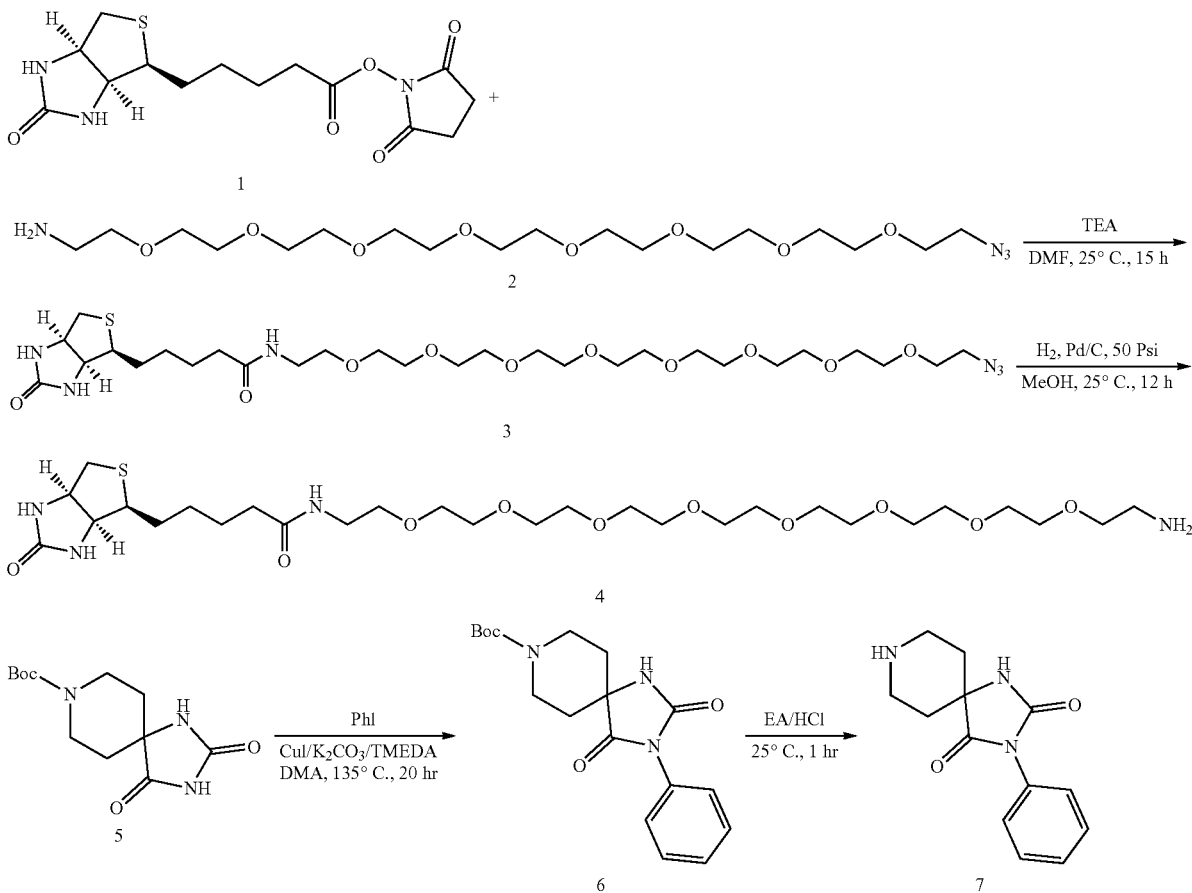

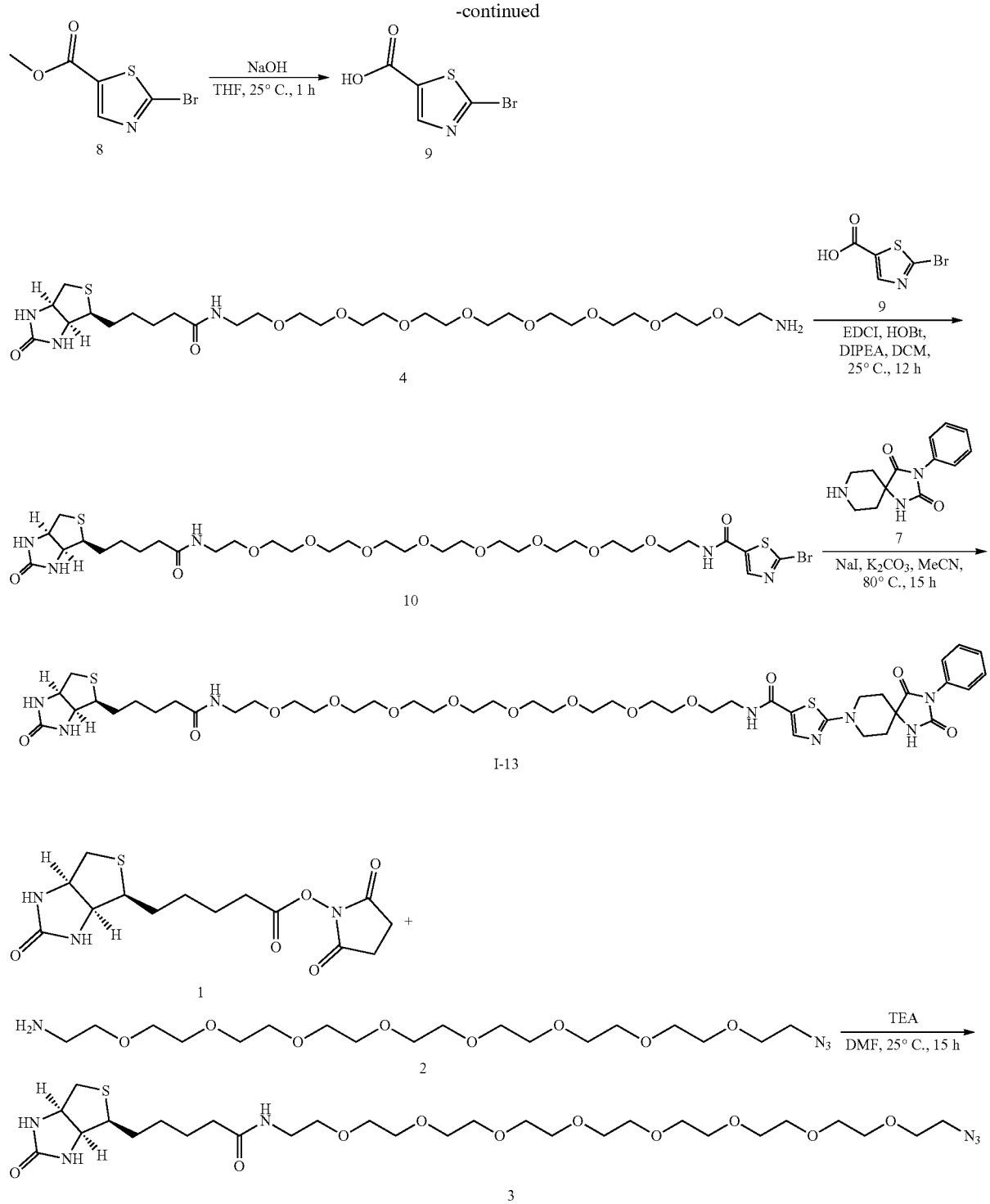

To a mixture of compound 2 (500 mg, 1.14 mmol, 1 eq) in DMF (5 mL) was added TEA (346.13 mg, 3.42 mmol, 476.11 μL, 3 eq) and compound 1 (467.10 mg, 1.37 mmol, 1.2 eq) at 25° C. under N2. The mixture was stirred at 25° C. for 16 h. Then 100 μL of the reaction mixture were concentrated to remove the solvent and the desired product was detected by LCMS. The mixture was concentrated and purified by prep-HPLC (TFA condition) according to HPLC. Compound 3 (633.1 mg, 415.97 μmol, 36.48% yield, 43.68% purity) was obtained as colorless liquid which was verified by LCMS and $^1$H NMR. LCMS: Rt=0.891 min, MS cal.: 664.35, [M+H]$^+$=665.4. HPLC: Rt=2.011 min. LCMS: Rt=0.888 min, MS cal.: 664.35, [M+H]$^+$=665.4. $^1$H NMR (400 MHz, METHANOL-d$_4$) δ=4.56-4.49 (m, 1H), 4.33 (dd, J=4.5, 7.9 Hz, 1H), 3.76-3.62 (m, 31H), 3.56 (t, J=5.4 Hz, 2H), 3.42-3.37 (m, 3H), 3.37 (s, 1H), 3.26-3.20 (m, 1H), 2.95 (dd, J=5.0, 12.7 Hz, 1H), 2.73 (d, J=12.7 Hz, 1H), 2.25 (t, J=7.4 Hz, 2H), 1.84-1.57 (m, 4H), 1.53-1.41 (m, 2H).

Step 2: Synthesis of Compound 4

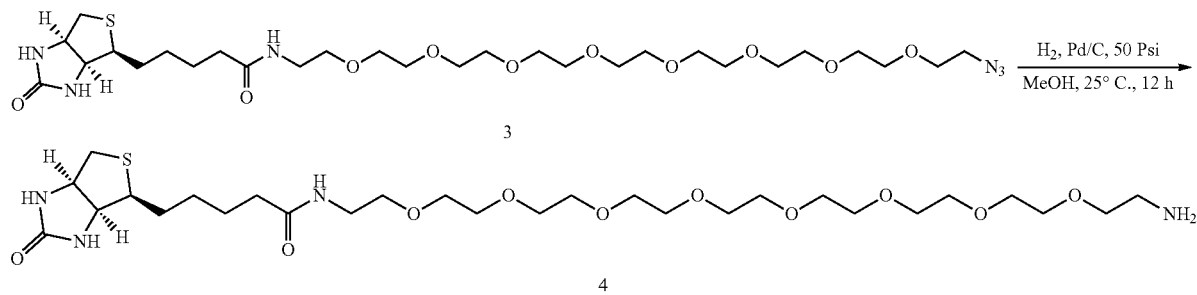

To a mixture of compound 3 (633.1 mg, 952.30 μmol, 1 eq) in MeOH (20 mL) was added Pd—C (115.66 mg, 952.30 μmol, 1 eq) at 25° C. The mixture was stirred at 25° C. for 12 h under $H_2$ (50 Psi). LCMS indicated the presence of the desired product and that the reaction was complete. The mixture was washed with MeOH (20 mL). The combined MeOH layers were concentrated to yield compound 4 (477.9 mg, 291.99 μmol, 30.66% yield, 39.03% purity) as a yellow oil and which used for next step directly, without further purification. LCMS: Rt=0.917 min, MS cal.: 638.36, $[M+H]^+$=639.4 and $[1/2M+H]^+$=320.3.

Step 3: Synthesis of Compound 6

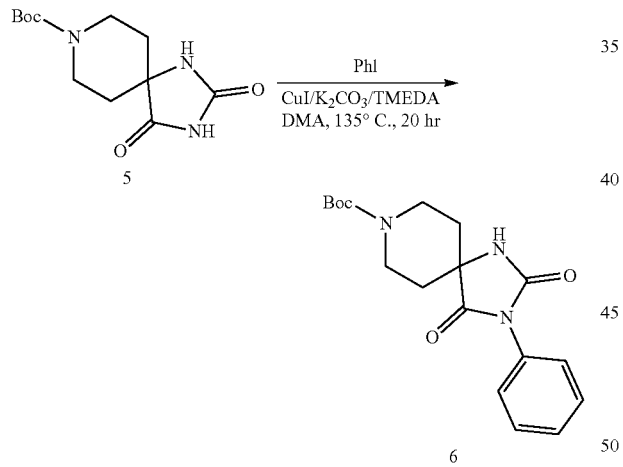

To solution of 5 (3 g, 11.14 mmol, 1 eq) and iodobenzene (3.41 g, 16.71 mmol, 1.86 mL, 1.5 eq) in DMA (30 mL) was added $K_2CO_3$ (4.62 g, 33.42 mmol, 3 eq), CuI (2.12 g, 11.14 mmol, 1 eq), and TMEDA (1.29 g, 11.14 mmol, 1.68 mL, 1 eq), sequentially. After the mixture was degassed with $N_2$ for three times, it was heated to 135° C. for 20 hr. TLC indicated that the starting material was consumed completely, which was confirmed by LCMS. The reaction mixture was extracted with Ethyl acetate (50 mL×3) and water (50 mL). The organic layers were washed with brine, dried over $Na_2SO_4$, and concentrated under reduced pressure to yield a residue which was further purified by silica gel column (Petroleum ether:Ethyl acetate=15:1 to 1:1). Compound 6 (1.58 g, 4.57 mmol, 41.06% yield) was obtained as a yellow solid, and was confirmed by $^1H$ NMR. LCMS: Rt=1.191 min, MS cal.: 345.3, $[M-55]^+$=290.2. $^1H$ NMR (400 MHz, MeOD) δ ppm 1.48 (s, 7H) 1.78 (br d, J=14.11 Hz, 2H) 1.96-2.08 (m, 3H) 3.98 (br d, J=14.11 Hz, 2H) 7.36-7.42 (m, 3H) 7.44-7.51 (m, 2H).

Step 4: Synthesis of Compound 7

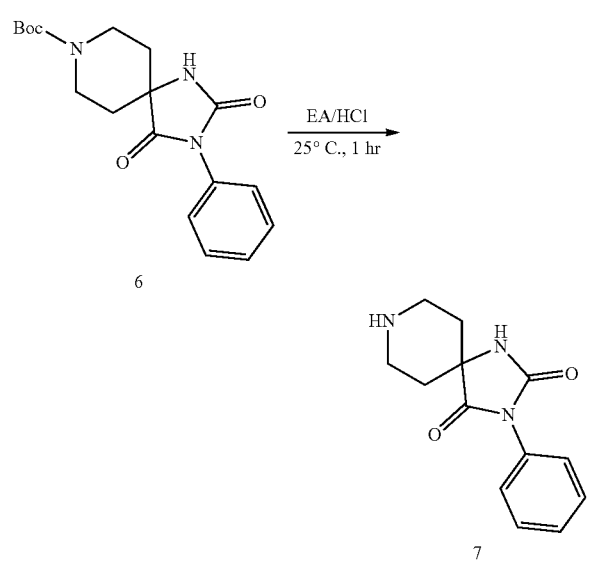

To a solution of compound 6 (1.58 g, 4.57 mmol, 1 eq) in EtOAc (20 mL) was added HCl/EtOAc (4 M, 20 mL, 17.49 eq), then the mixture was stirred at 25° C. for 1.5 hr. LCMS indicated the starting material was consumed completely and the crude product was concentrated under reduced pressure to yield a residue. Compound 7 (1.23 g, 4.37 mmol, 95.44% yield, HCl) was obtained as a yellow solid, and was used in next step directly, without further purification. LCMS: Rt=0.819 min, MS cal.: 281.7, $[M-35]^+$=246.1.

Step 5: Synthesis of Compound 9

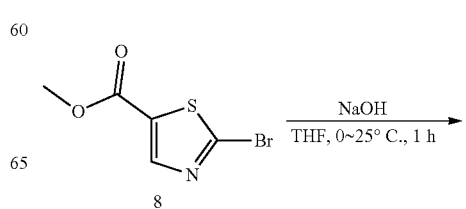

321
-continued

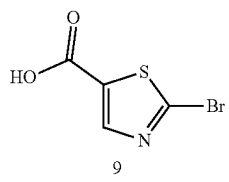
9

To a solution of compound 8 (1 g, 4.50 mmol, 1 eq) in THF (15 mL) was added NaOH (1 M, 5.40 mL, 1.2 eq) at 0° C. for 30 min. Then the mixture was stirred at 25° C. for 1 hr. TLC (PE:EA=5:1, Rf=0.03) showed the starting material was consumed completely. HCl (6M) was added to adjusted pH to 1, causing the mixture to become cloudy. The mixture was extracted with EA (10 mL×3) and the combined organic layers were dried over Na$_2$SO$_4$, filtered, and concentrated under reduced pressure to yield compound 9 (920.4 mg, crude) as a light yellow solid, which was confirmed by LCMS. LCMS: Rt=0.797 min, MS cal.: 208.03, [M+H]$^+$=207.9 and 209.9.

Step 6: Synthesis of Compound 10

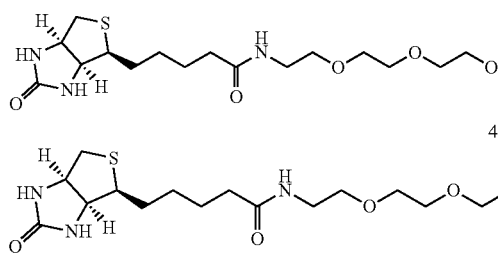

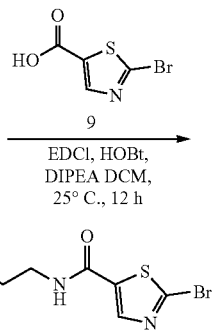

To a solution of compound 9 (26.05 mg, 125.23 μmol, 1 eq) in DCM (5 mL) was added compound 4 (96 mg, 150.28 μmol, 1.2 eq), EDCI (31.21 mg, 162.80 μmol, 1.3 eq), and HOBt (22.00 mg, 162.80 μmol, 1.3 eq), followed by DIPEA (48.56 mg, 375.70 μmol, 65.44 μL, 3 eq) at 0° C. The mixture was stirred at 25° C. for 12 hr. and the desired product was detected by LCMS. DCM (10 mL) was added to the mixture which was then washed with saturated solution of NH$_4$Cl (15 mL×2). The organic layer was dried over Na$_2$SO$_4$, filtered and concentrated under reduced pressure to give a residue which was further purified by prep-TLC (DCM:MeOH=10:1, Product Rf=0.55) to yield the compound 10 (45.6 mg, 38.17 μmol, 30.48% yield, 69.37% purity) as a yellow oil. LCMS: Rt=1.062 min, m/z 828.1 (M+H). $^1$H NMR (400 MHz, CHLOROFORM-d) δ=8.15 (br s, 1H), 8.07 (s, 1H), 7.20 (s, 1H), 6.89 (br d, J=5.3 Hz, 1H), 5.88 (s, 1H), 5.12 (s, 1H), 4.47-4.41 (m, 1H), 4.28-4.23 (m, 1H), 3.63-3.52 (m, 31H), 3.48 (br d, J=4.9 Hz, 2H), 3.41-3.34 (m, 2H), 3.13-3.05 (m, 1H), 2.84 (dd, J=4.9, 12.8 Hz, 1H), 2.66 (br d, J=12.8 Hz, 1H), 2.21-2.13 (m, 1H), 2.17 (br t, J=6.9 Hz, 1H), 2.02 (br s, 10H), 1.73-1.55 (m, 5H), 1.45-1.33 (m, 3H), 1.16-1.16 (m, 1H), 1.19 (br s, 2H), 0.83-0.74 (m, 1H).

Step 7: Synthesis of I-13

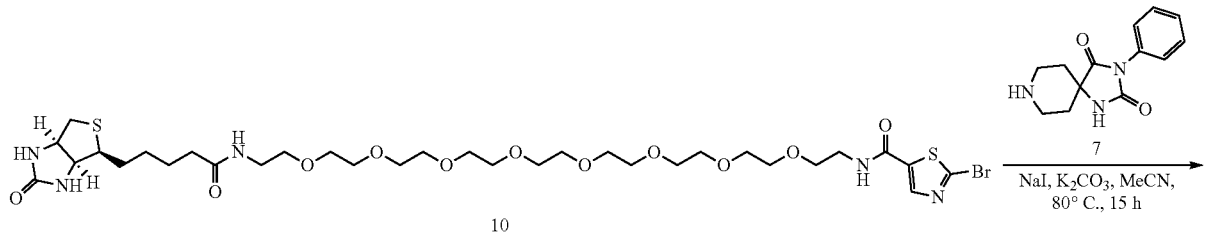

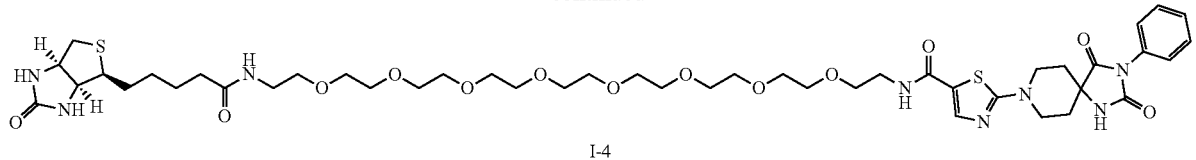

I-4

To a solution of compound 10 (35 mg, 42.23 μmol, 1 eq) and compound 7 (17.85 mg, 63.34 μmol, 1.5 eq, HCl) in CH₃CN (3 mL) was added NaI (6.33 mg, 42.23 μmol, 1 eq) and K₂CO₃ (17.51 mg, 126.68 μmol, 3 eq), then the mixture was stirred at 80° C. for 15 hr. The desired product was detected by LCMS and the mixture was filtered and concentrated. The residue was purified by prep-HPLC (TFA condition) according to HPLC to yield 1-13 (16.79 mg, 16.84 μmol, 39.88% yield, 99.62% purity) as white solid, which was verified by QC-LCMS and ¹H NMR. LCMS: Rt=1.657 min, MS cal.: 993.20, [1/2M+H]⁺=497.5. HPLC: Rt=2.273 min. QC-LCMS: Rt=1.711 min, MS cal.: 993.20, [1/2M+H]⁺=497.3. ¹H NMR (400 MHz, CHLOROFORM-d) δ=8.86 (br s, 1H), 8.05 (br s, 1H), 7.91 (s, 1H), 7.42-7.36 (m, 1H), 7.42-7.36 (m, 1H), 7.42-7.29 (m, 1H), 7.34-7.24 (m, 1H), 7.35-7.24 (m, 1H), 7.34-7.24 (m, 1H), 7.37-7.24 (m, 1H), 7.34-7.24 (m, 1H), 7.21-7.19 (m, 1H), 7.23-7.17 (m, 1H), 7.20 (s, 1H), 6.42 (br s, 1H), 5.08 (br s, 8H), 4.50-4.40 (m, 1H), 4.31-4.21 (m, 1H), 3.98 (br d, J=11.9 Hz, 2H), 3.76-3.65 (m, 1H), 3.61-3.49 (m, 34H), 3.46 (br d, J=4.6 Hz, 2H), 3.34 (br d, J=4.2 Hz, 2H), 3.12-3.02 (m, 1H), 2.81 (br dd, J=4.6, 12.8 Hz, 1H), 2.66 (br d, J=12.8 Hz, 1H), 2.28-2.08 (m, 4H), 1.92 (br d, J=13.4 Hz, 2H), 1.69-1.46 (m, 4H), 1.41-1.29 (m, 2H).

Example 5: Synthesis of 5-{[(26-{4-[3-({2,4-dioxo-3-phenyl-1,3,8-triazaspiro[4.5]decane-8-carbonyl}amino)phenyl]-1H-1,2,3-triazol-1-yl}-3,6,9,12,15,18,21,24-octaoxahexacosan-1-yl)carbamothioyl]amino}-2-(6-hydroxy-3-oxo-3H-xanthen-9-yl)benzoic acid (I-14

Scheme 5

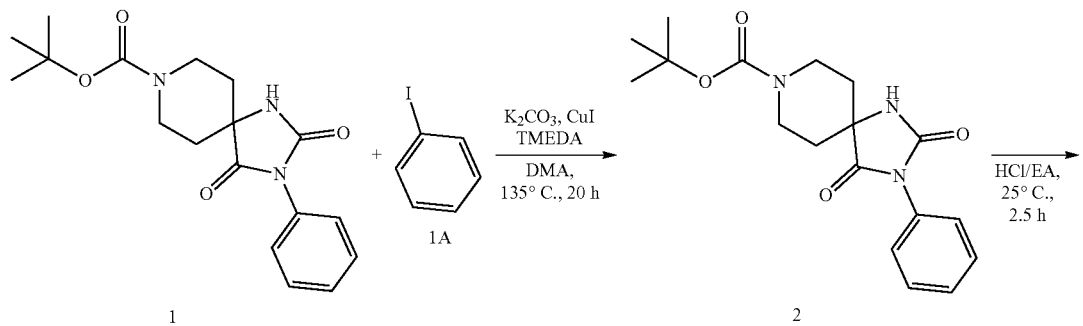

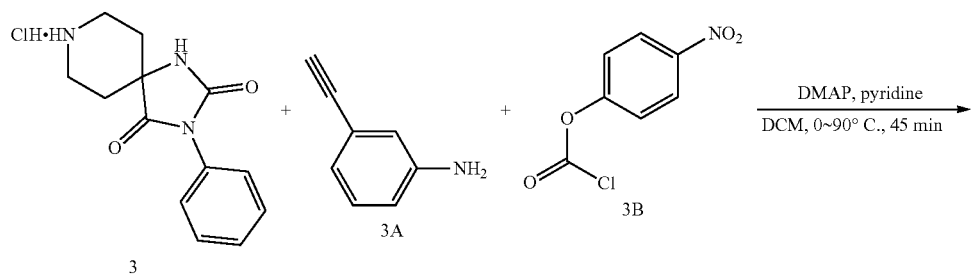

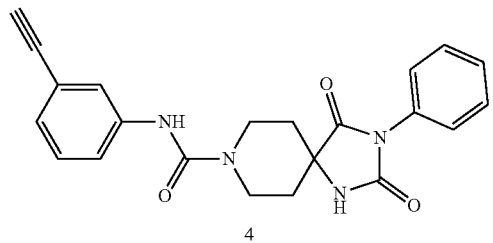

-continued

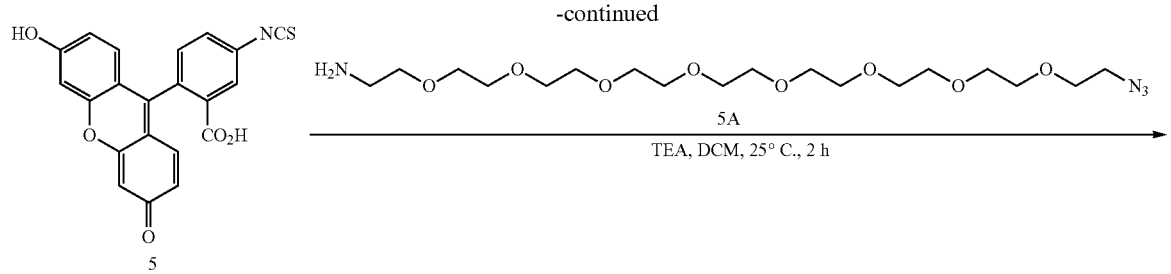

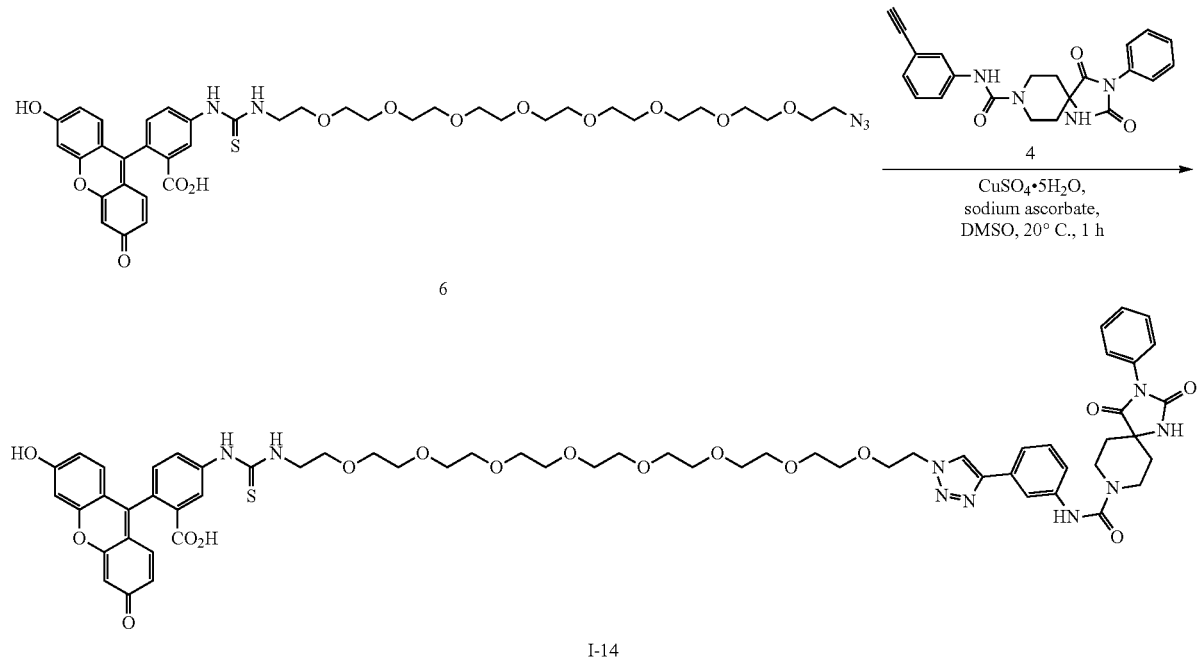

Step 1: Synthesis of Compound 2

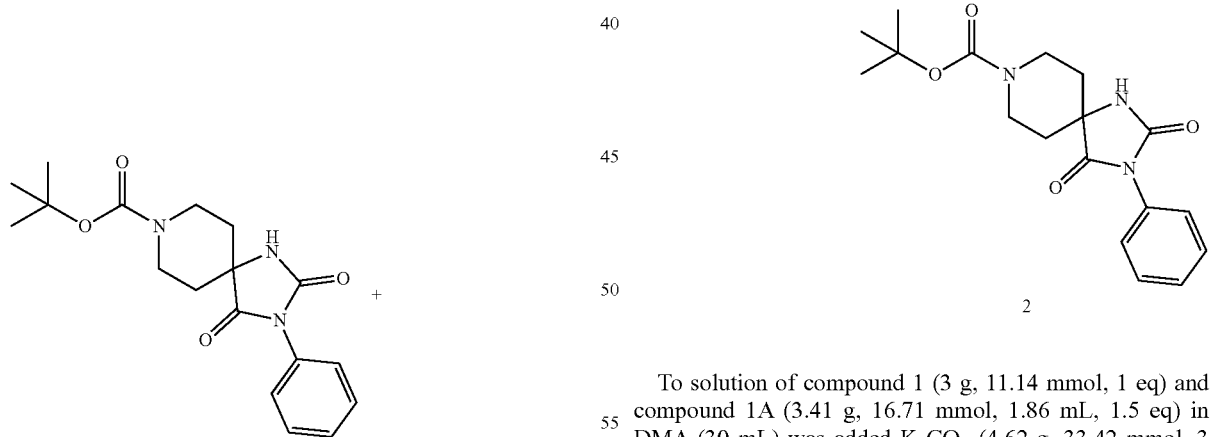

To solution of compound 1 (3 g, 11.14 mmol, 1 eq) and compound 1A (3.41 g, 16.71 mmol, 1.86 mL, 1.5 eq) in DMA (30 mL) was added $K_2CO_3$ (4.62 g, 33.42 mmol, 3 eq), CuI (2.12 g, 11.14 mmol, 1 eq), and TMEDA (1.29 g, 11.14 mmol, 1.68 mL, 1 eq), dropwise with stirring. After the mixture was degassed with $N_2$ for three times, it was heated to 135° C. for 20 hr. LCMS and TLC (Petroleum: EtOAc=1:1, Rf=0.6) indicated the presence of desired product and some unreacted starting material. The reaction mixture was diluted with EtOAc (100 mL) and water (100 mL). The organic layer was separated and washed with water (50 mL), and dried over $Na_2SO_4$. The organic phase was concentrated to give the crude product which was further purified by silica gel column (Petroleum:EtOAc=5:1 to 1:1) to yield compound 2 (700 mg, 2.03 mmol, 18.19% yield) as yellow solid. LCMS: Rt=1.187 min, MS cal.: 345.3, [M-55]+=290.1.

Step 2: Synthesis of Compound 3

Step 3: Synthesis of Compound 4

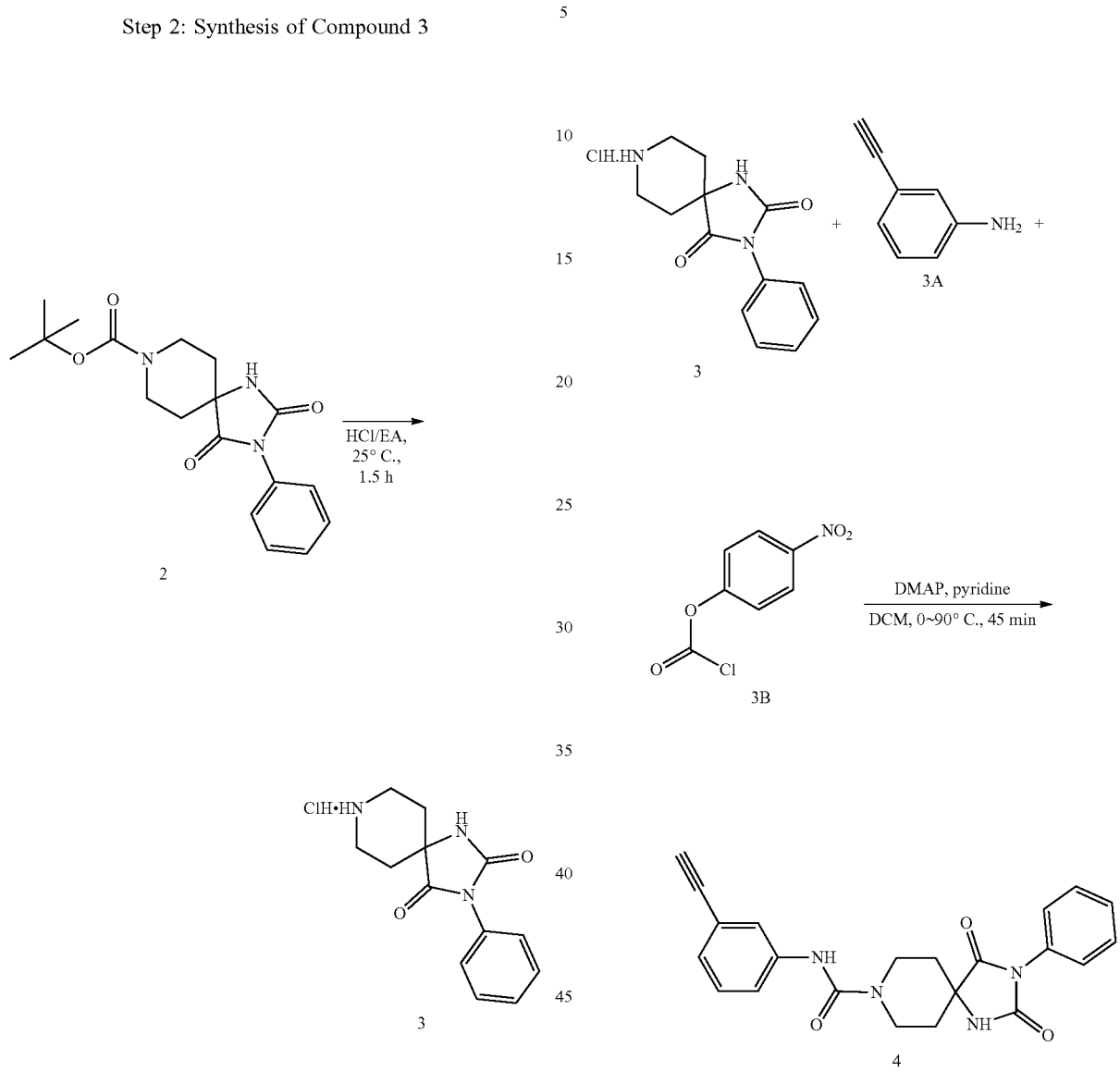

To a solution of compound 2 (700 mg, 2.03 mmol, 1 eq) in EtOAc (10 mL) was added HCl/EtOAc (4 M, 15 mL, 29.61 eq) at 25° C. LCMS indicated the presence of desired product and that the starting material was consumed completely. The mixture was concentrated under reduced pressure to give a crude compound 3 (500 mg, crude) as yellow solid. LCMS: Rt=0.849 min, MS cal.: 245.2, [M+H]$^+$=245.9.

To a mixture of compound 3B (143.09 mg, 709.88 μmol, 1 eq) in DCM (5 mL) was added Pyridine (112.30 mg, 1.42 mmol, 114.60 μL, 2 eq) and compound 3A (83.16 mg, 709.88 mol, 1 eq) in DCM (1 mL) at 0° C. After stirring at 0° C. for 15 min, compound 3 (0.2 g, 709.88 μmol, 1 eq, HCl) and DMAP (260.18 mg, 2.13 mmol, 3 eq) were added and the mixture was stirred at 90° C. for 0.5 h. LCMS indicated that the reaction was completed and the mixture was added to aq. HCl (1M, 20 mL) and extracted with DCM (20 mL×2). The combined organic layers were washed with brine (20 mL), dried over anhydrous Na$_2$SO$_4$, filtered and concentrated in vacuum. The residue was purified further by prep-TLC (Petroleum ether:Ethyl acetate=1:1, Rf=0.11) to yield product compound 4 (0.1 g, 231.71 μmol, 32.64% yield, 90% purity) as white solid, which was verified by LCMS. LCMS: Rt=1.206 min, MS cal.: 388.4, [M+H]+=389.0. LCMS: Rt=1.204 min, MS cal.: 388.4, [M+H]$^+$=389.0.

Step 4: Synthesis of Compound 6

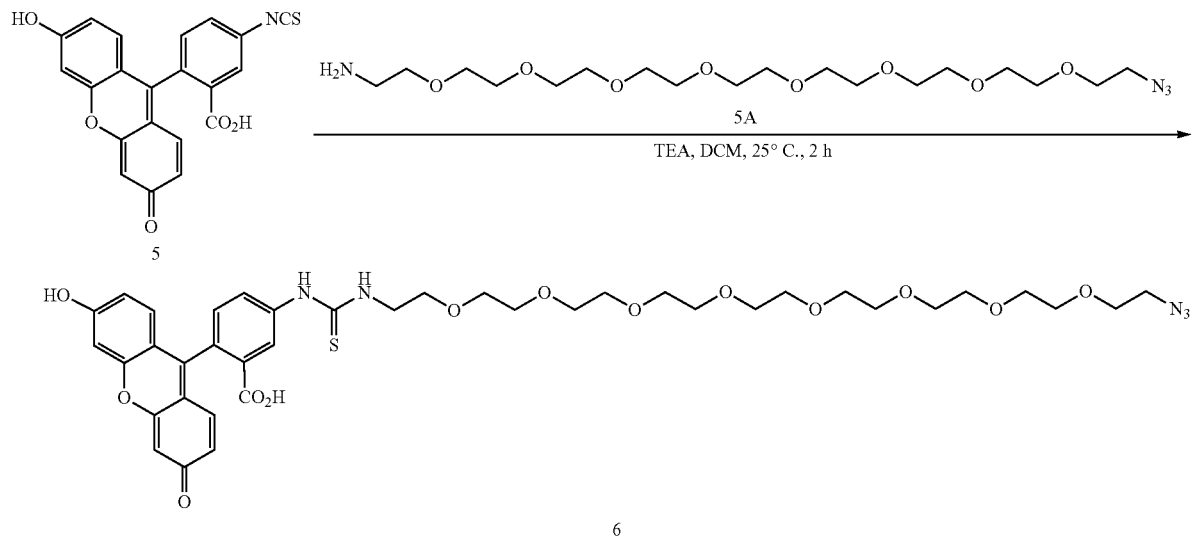

To a mixture of compound 5A (33.79 mg, 77.05 μmol, 1 eq) in DMF (1 mL) was added compound 5 (0.03 g, 77.05 μmol, 1 eq) and TEA (23.39 mg, 231.14 μmol, 32.17 μL, 3 eq) at 25° C. under $N_2$. The mixture was stirred at 25° C. for 2 h and LCMS indicated that the reaction was complete. The mixture was purified directly by prep-HPLC (column: Luna C18 100 mm*30 mm*5 um; mobile phase: A: water (0.1% TFA), B: ACN; gradient: 20%-60% over 11 min) to yield compound 6 (50 mg, 60.39 μmol, 78.39% yield) as a yellow oil. LCMS: Rt=1.220 min, MS cal.: 827.9, $[1/2M+H]^+$=828.2.

Step 7: Synthesis of I-14

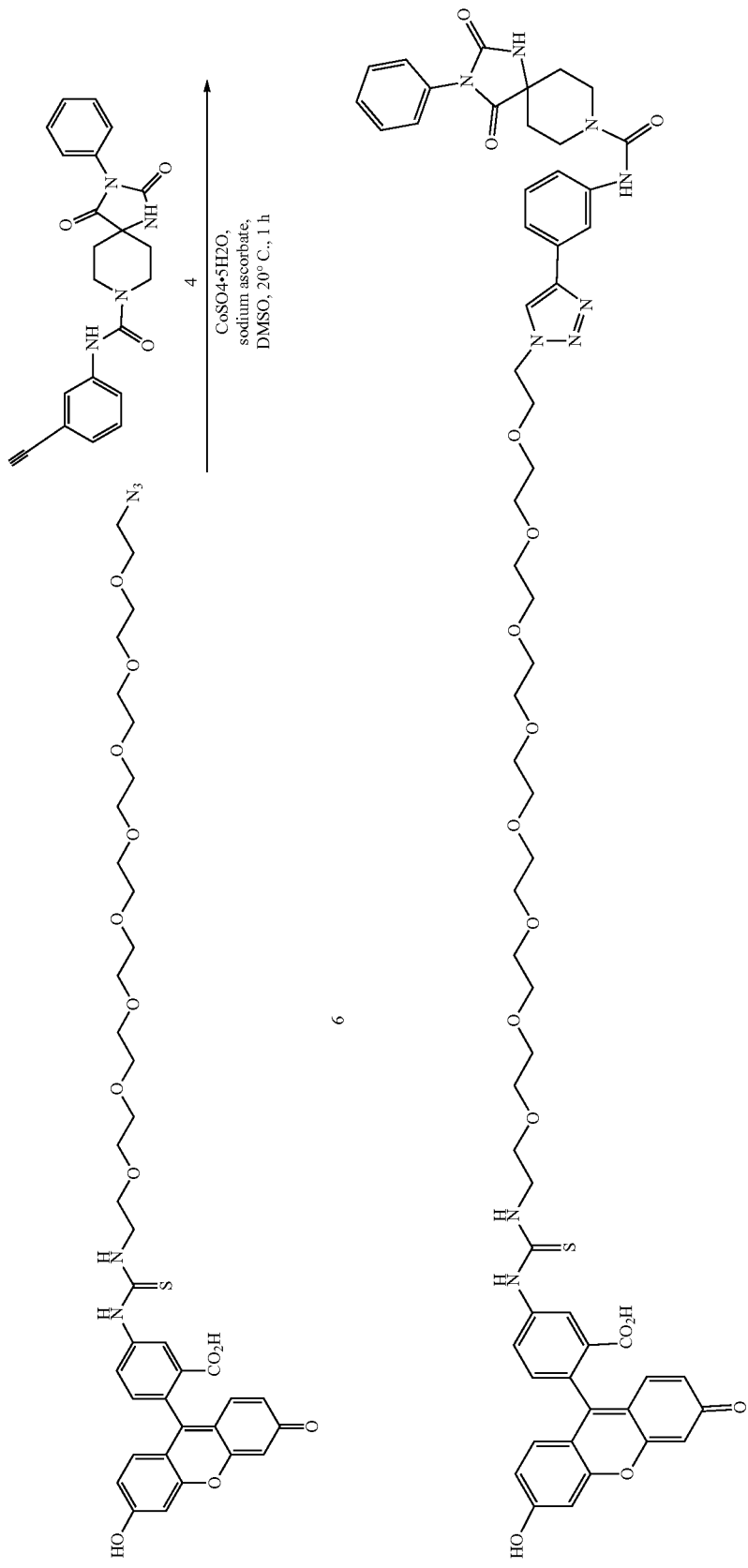

To a mixture of compound 6 (50 mg, 60.39 µmol, 1 eq) and compound 4 (23.46 mg, 60.39 µmol, 1 eq) in DMSO (1 mL) was added $CuSO_4 \cdot 5H_2O$ (4.52 mg, 18.12 µmol, 0.3 eq), and sodium ascorbate (23.93 mg, 120.79 µmol, 2 eq) at 25° C. The mixture was stirred at 25° C. for 1 h and LCMS indicated the presence of the desired product and that the starting material was consumed. The mixture was filtered then purified by prep-HPLC ($NH_4HCO_3$ and HCl conditions) to yield I-14 (10.57 mg, 7.25 µmol, 12.01% yield, 83.44% purity) as a yellow solid, which was verified by QC-LCMS and $^1H$ NMR. LCMS: Rt=0.894 min, MS cal.: 1215.46, $[1/2M-H]^+$=606.7 and $[M-H]^+$=1214.8. HPLC: Rt=1.903 min. QC-LCMS: Rt=2.940 min, MS cal.: 1215.46, $[1/2M+H]^+$=608.7. $^1H$ NMR (400 MHz, DMSO-d6) δ ppm 10.36 (br s, 1H), 9.15 (s, 1H), 8.78 (s, 1H), 8.45 (s, 1H), 8.34 (s, 1H), 8.26 (br s, 1H), 8.03 (s, 1H), 7.79 (br d, J=7.9 Hz, 1H), 7.72 (br d, J=9.8 Hz, 1H), 7.53-7.45 (m, 3H), 7.43-7.36 (m, 5H), 7.34-7.27 (m, 1H), 7.24 (s, 1H), 7.18 (d, J=8.3 Hz, 1H), 7.11 (s, 1H), 6.74-6.68 (m, 2H), 6.65-6.55 (m, 4H), 4.57 (br t, J=5.0 Hz, 2H), 4.11-4.00 (m, 2H), 3.87 (br t, J=5.0 Hz, 2H), 3.61 (br s, 1H), 3.57-3.53 (m, 1H), 3.52-3.44 (m, 1H), 3.61-3.43 (m, 30H), 3.42-3.26 (m, 4H), 2.08 (s, 1H), 2.05 (s, 1H), 1.99-1.88 (m, 2H), 1.85-1.75 (m, 2H), 1.27-1.23 (m, 1H).

Example 6: Synthesis of N-{4-[1-(26-{5-[(3aS,4S,6aR)-2-oxo-hexahydro-1H-thieno[3,4-d]imidazol-4-yl]pentanamido}-3,6,9,12,15,18,21,24-octaoxahexacosan-1-yl)-1H-1,2,3-triazol-4-yl]phenyl}-4-(3-benzyl-2-oxoimidazolidin-1-yl)piperidine-1-carboxamide (I-15

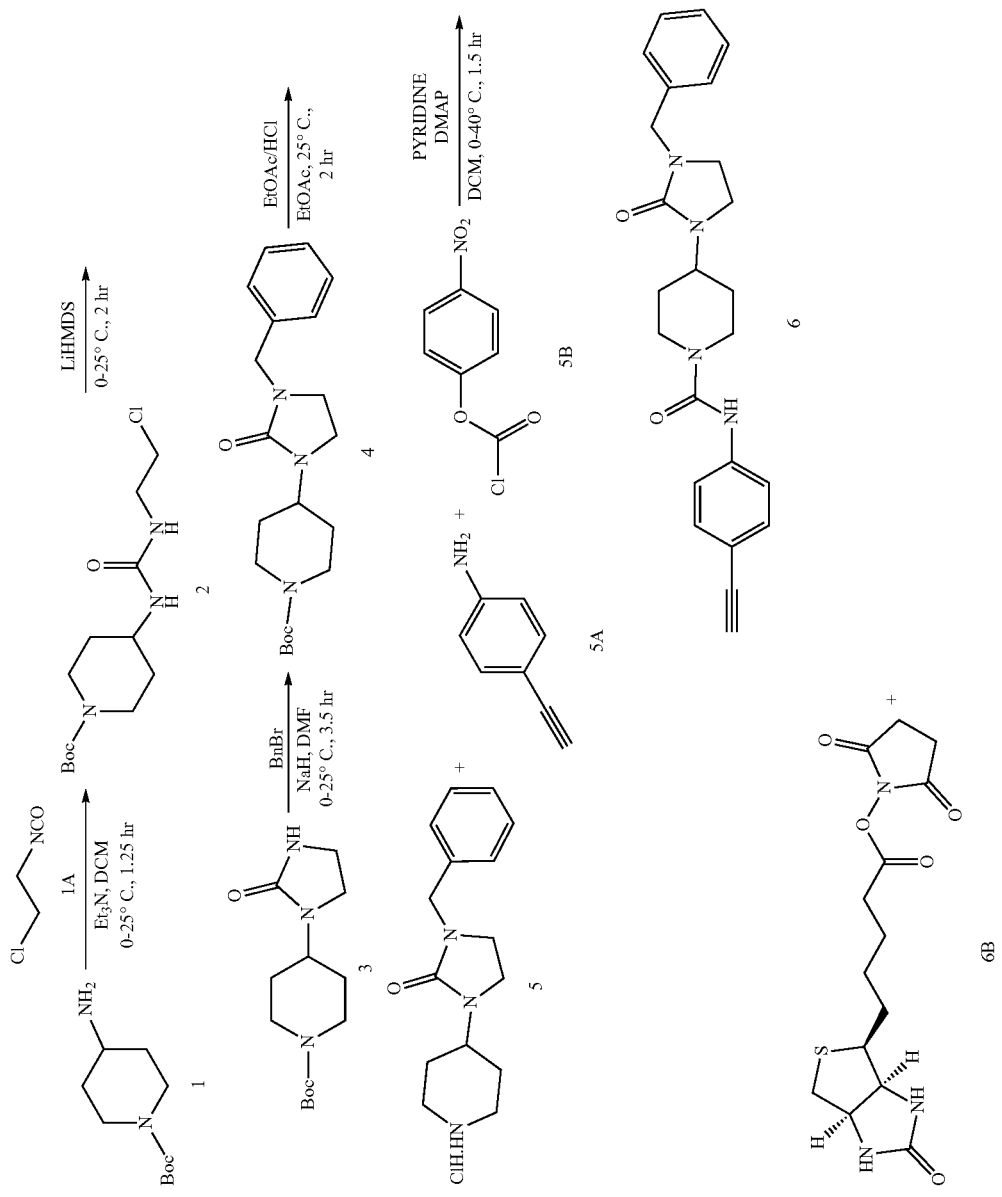

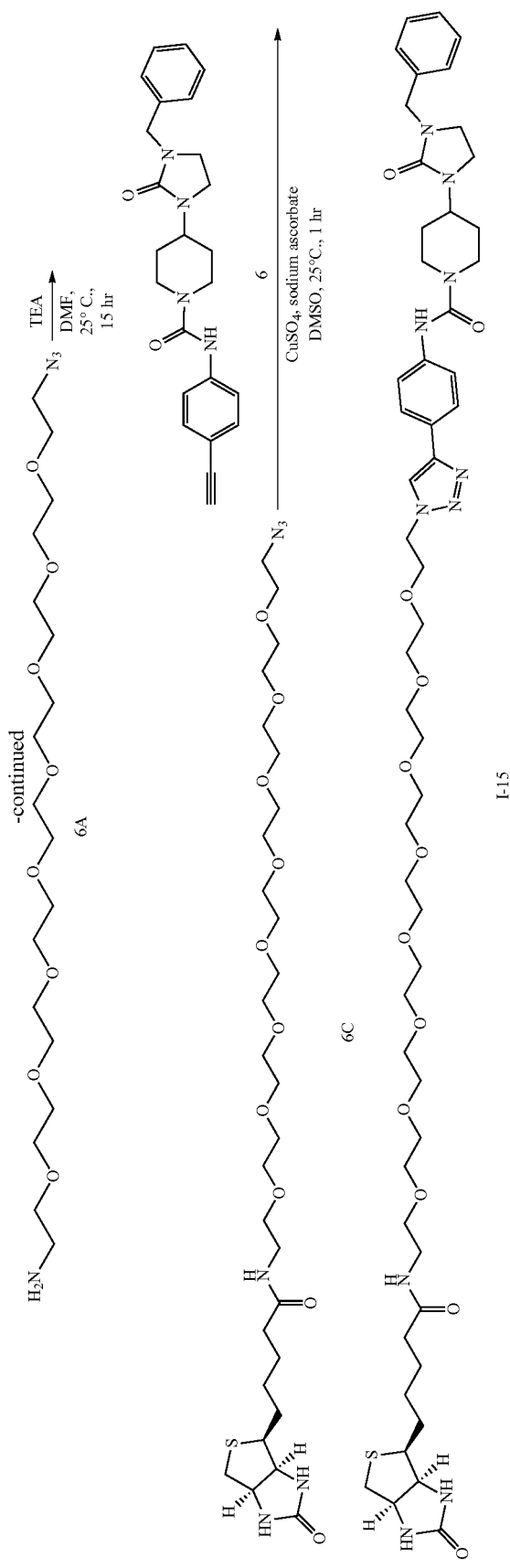

Step 1: Synthesis of Compound 2

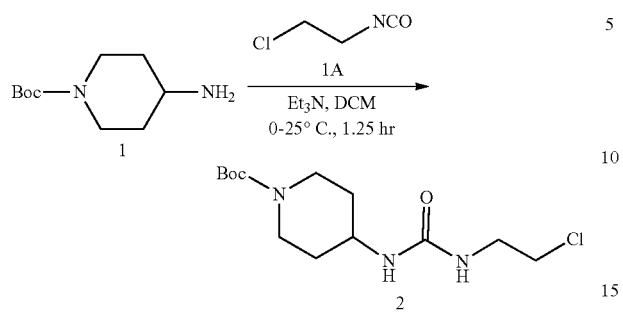

To a solution of compound 1 (2 g, 9.99 mmol, 1 eq) in DCM (20 mL) was added TEA (2.53 g, 24.97 mmol, 3.47 mL, 2.5 eq) and compound 1A (1.16 g, 10.98 mmol, 1.1 eq) at 0° C. with stirring for 15 min. Then the reaction mixture was stirred at 25° C. for 1 hr. TLC (DCM:MeOH=10:1, product Rf=0.64) indicated that the starting material was consumed completely and a new spot was detected. The reaction mixture was poured into 0.5 N HCl to adjust the pH to 5, then the organic layer was washed with brine and dried over with anhydrous $Na_2SO_4$. The water phase was extracted by EtOAc (10 mL×2), and the organic layers were combined, washed with brine, and dried over with anhydrous $Na_2SO_4$. Finally the organic layers were concentrated under reduced pressure to give a crude product which was purified further by silica gel column (Petroleum ether:EtOAc=5:1 to 1:1), to yield compound 2 (1.1 g, 3.60 mmol, 36.02% yield) as white solid, which was verified by TLC (DCM:MeOH=10:1, product $R_f$=0.64) as well as by H NMR. H NMR (400 MHz, DMSO-$d_6$) δ ppm 0.97-1.23 (m, 2H) 1.39 (s, 9H) 1.71 (br dd, J=12.72, 3.18 Hz, 2H) 2.84 (br s, 2H) 3.18-3.37 (m, 7H) 3.49-3.64 (m, 3H) 3.77 (br d, J=13.33 Hz, 2H) 5.56-6.42 (m, 2H).

Step 2: Synthesis of Compound 3

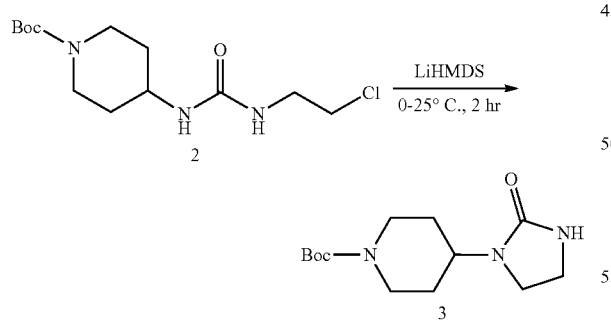

To a solution of compound 2 (200 mg, 654.02 μmol, 1 eq) in THF (3 mL) was added LiHMDS (1 M, 784.83 μL, 1.2 eq) with stirring dropwise at 0° C. Then the mixture was gradually warmed to 25° C. with stirring for 2 hr. LCMS indicated the presence of the desired product and that the starting material was consumed completely. The reaction was quenched by saturated $NH_4Cl$ (pH=7) followed by extraction with EtOAc (5 mL×2). The organic layers were washed with brine, dried over anhydrous $Na_2SO_4$, and concentrated under reduced pressure to give a residue yielding compound 3 (150 mg, 556.92 μmol, 85.15% yield) as yellow solid, which was used directly in the next step without further purification. LCMS: Rt=1.173 min, MS cal.: 269.3, [M+H]$^+$=214.1. $^1$H NMR (400 MHz, DMSO-$d_6$) δ ppm 1.35-1.44 (m, 9H) 1.46-1.57 (m, 2H) 1.59-1.75 (m, 1H) 2.66-2.89 (m, 2H) 3.16-3.30 (m, 2H) 3.58-3.70 (m, 1H) 3.76-3.90 (m, 1H) 4.01 (br d, J=8.16 Hz, 1H) 6.27 (s, 1H) 7.54 (br d, J=7.94 Hz, 1H).

Step 3: Synthesis of Compound 4

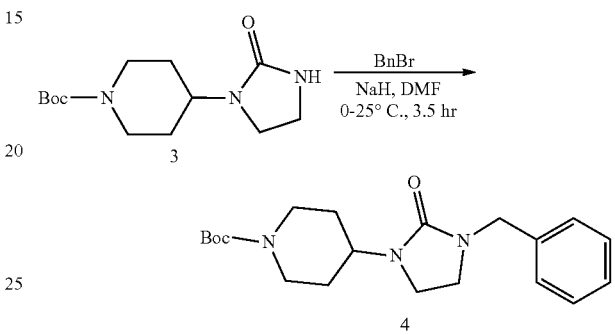

To a solution of compound 3 (300 mg, 1.11 mmol, 1 eq) in DMF (10 mL) was added NaH (66.83 mg, 1.67 mmol, 60% purity, 1.5 eq) at 0° C. dropwise with stirring for 30 min. Then bromomethylbenzene (285.76 mg, 1.67 mmol, 198.44 μL, 1.5 eq) was added dropwise at 0° C. Finally the reaction mixture was stirred at 25° C. for 3 hr. LCMS and TLC (Petroleum ether:EtOAc=1:1, $R_f$=0.6) indicated the presence of the desired product and that the starting material was consumed completely. The reaction was quenched by the addition of saturated $NH_4Cl$ to adjust the pH to 7, followed by extraction with EtOAc (15 mL×2). The organic layers were combined and washed with brine, dried over anhydrous $Na_2SO_4$, and concentrated under reduced pressure to give a residue which was purified further by silica gel column (Petroleum ether:EtOAc=5:1 to 1:1) to yield compound 4 (220 mg, 612.03 μmol, 54.95% yield) as a white oil. LCMS: Rt=1.216 min, MS cal.: 359.5, [M+H]$^+$=304.1.

Step 4: Synthesis of Compound 5

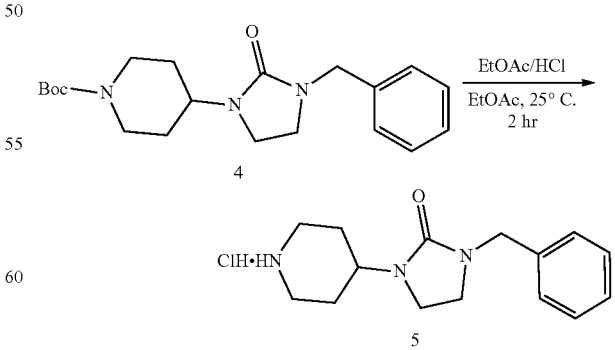

To a solution of compound 4 (200 mg, 556.39 μmol, 1 eq) in EtOAc (5 mL) was added HCl/EtOAc (4 M, 15 mL, 107.84 eq) at 25° C. with stirring. Then the mixture was stirred for 2 hr at 25° C. LCMS indicated the presence of the desired product and that the starting material was consumed completely. The reaction mixture was concentrated under reduced pressure to give a residue yielding compound 5 (180 mg, crude) as white solid, which was used directly in the next step. LCMS: Rt=0.901 min, MS cal.: 259.3, [M+H]$^+$ =260.1.

Step 5: Synthesis of Compound 6

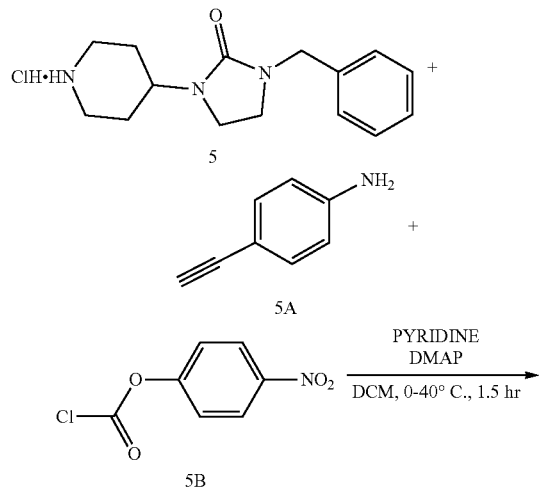

-continued

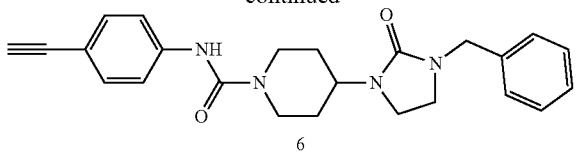

6

To a solution of compound 5B (81.77 mg, 405.67 μmol, 1.2 eq) in DCM (10 mL) was added Compound 5A (51.48 mg, 439.48 μmol, 1.3 eq) dropwise at 0° C. for 30 min. Then compound 5 (100 mg, 338.06 μmol, 1 eq, HCl), pyridine (80.22 mg, 1.01 mmol, 81.86 μL, 3 eq) and DMAP (123.90 mg, 1.01 mmol, 3 eq) were added. The mixture was stirred at 40° C. for 1 hr. LCMS and TLC (Petroleum ether: EtOAc=1:1, Product R$_f$=0.23) indicated the presence of the desired product and that the starting material was consumed completely. The reaction mixture was acidified to pH=7 with 0.5 N HCl, then the mixture was washed with water (15 mL×2). The organic layer was dried over anhydrous Na$_2$SO$_4$, concentrated under reduced pressure to give a residue which was purified further by prep-TLC (Petroleum ether:EtOAc=1:1) to yield compound 6 (35 mg, 86.96 μmol, 25.72% yield) as a yellow solid which was confirmed by TLC (Petroleum ether:EtOAc=1:1, Product R$_f$=0.23). LCMS: Rt=1.258 min, MS cal.: 402.5, [M+H]$^+$=403.1.

Step 6: Synthesis of Compound 6C

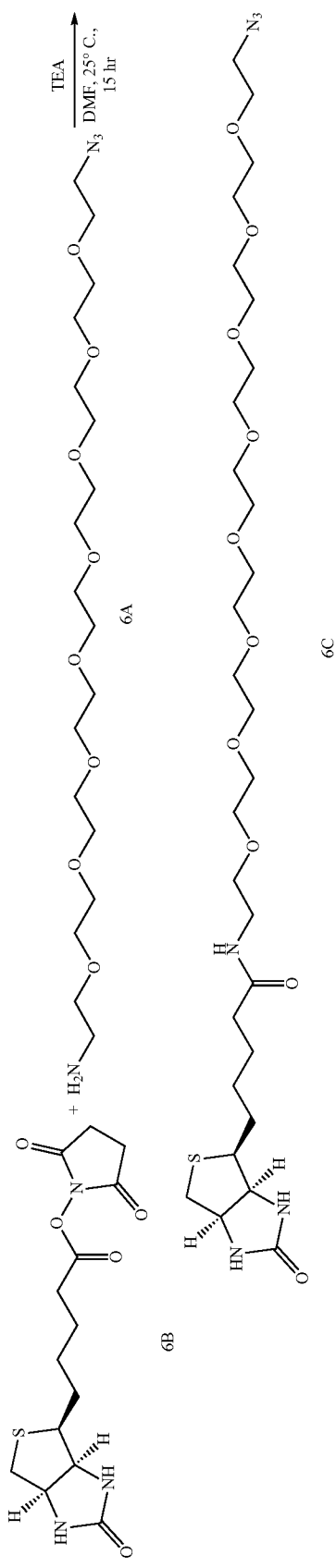

To a mixture of compound 6A (500 mg, 1.14 mmol, 1 eq) in DMF (5 mL) was added TEA (346.13 mg, 3.42 mmol, 476.11 µL, 3 eq) and compound 6B (467.10 mg, 1.37 mmol, 1.2 eq) at 25° C. under $N_2$. The mixture was stirred at 25° C. for 16 hr. Then 100 L of the reaction mixture were concentrated to remove the solvent and LCMS indicated the presence of desired product. The solvent was then removed under reduced pressure to give a residue that was purified further by prep-HPLC (TFA condition) according to HPLC yielding compound 6C (633.1 mg, 415.97 µmol, 36.48% yield, 43.68% purity) as a colorless liquid, which was verified by LCMS and $^1$H NMR. LCMS: Rt=0.891 min, MS cal.: 664.35, $[M+H]^+$=665.4. HPLC: Rt=2.011 min. LCMS: Rt=0.888 min, MS cal.: 664.35, $[M+H]^+$=665.4. $^1$H NMR (400 MHz, METHANOL-$d_4$) δ=4.56-4.49 (m, 1H), 4.33 (dd, J=4.5, 7.9 Hz, 1H), 3.76-3.62 (m, 31H), 3.56 (t, J=5.4 Hz, 2H), 3.42-3.37 (m, 3H), 3.37 (s, 1H), 3.26-3.20 (m, 1H), 2.95 (dd, J=5.0, 12.7 Hz, 1H), 2.73 (d, J=12.7 Hz, 1H), 2.25 (t, J=7.4 Hz, 2H), 1.84-1.57 (m, 4H), 1.53-1.41 (m, 2H).

Step 7: Synthesis of I-15

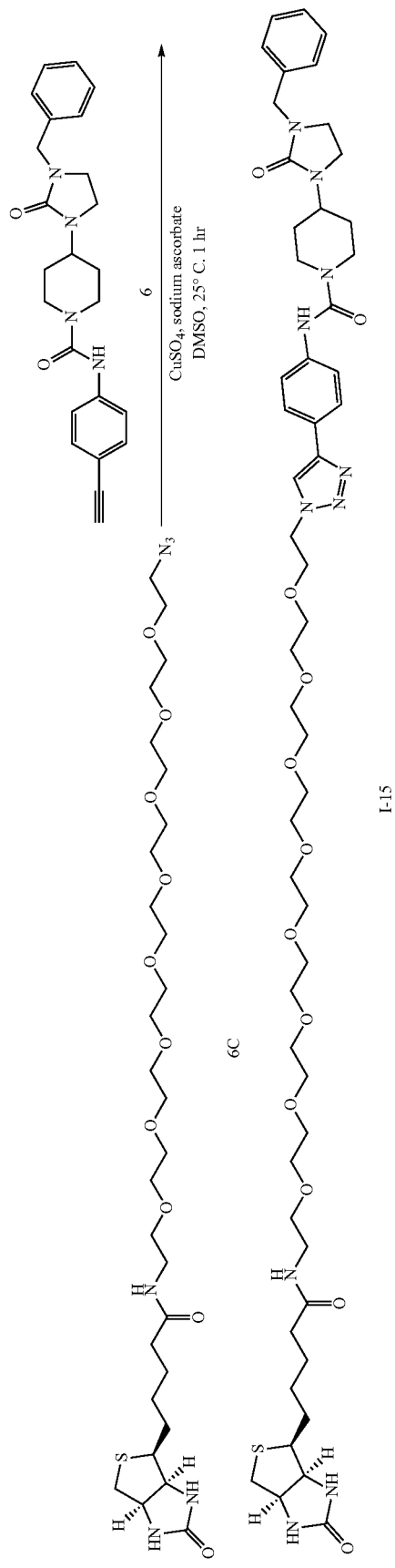

To a solution of compound 6 (24 mg, 59.63 μmol, 1 eq) and compound 6C (43.61 mg, 65.59 μmol, 1.1 eq) in DMSO (2 mL) was added sodium ascorbate (23.63 mg, 119.26 μmol, 2 eq) with stirring, followed by the addition of $CuSO_4 \cdot 5H_2O$ (4.47 mg, 17.89 μmol, 0.3 eq) with stirring. Finally the reaction mixture was stirred for 1 hr at 25° C. LCMS indicated the presence of the desired product and that the starting material was consumed completely. The reaction mixture was diluted with DMSO (1 mL) and was purified by prep-HPLC (TFA condition), according to HPLC to yield I-15 (12.8 mg, 11.99 μmol, 20.11% yield) as a white oil, which was confirmed by $^1$H NMR. LCMS: Rt=1.060 min, MS cal.: 1067.3, [1/2M+H]$^+$=534.6. HPLC: Rt=2.394 min. H NMR (400 MHz, METHANOL-$d_4$) δ ppm 8.33 (s, 1H) 7.74 (d, J=8.60 Hz, 2H) 7.48 (d, J=8.38 Hz, 2H) 7.23-7.37 (m, 5H) 4.62 (t, J=4.96 Hz, 2H) 4.47 (dd, J=7.72, 4.85 Hz, 1H) 4.25-4.37 (m, 5H) 3.87-3.98 (m, 3H) 3.48-3.68 (m, 32H) 3.32-3.40 (m, 4H) 3.13-3.27 (m, 4H) 2.86-3.02 (m, 3H) 2.69 (d, J=12.79 Hz, 1H) 2.20 (t, J=7.39 Hz, 2H) 1.50-1.83 (m, 9H) 1.42 (quin, J=7.50 Hz, 2H).

Example 7: Synthesis of N-{3-[1-(26-{5-[(3aS,4S,6aR)-2-oxo-hexahydro-1H-thieno[3,4-d]imidazol-4-yl]pentanamido}-3,6,9,12,15,18,21,24-octaoxahexacosan-1-yl)-1H-1,2,3-triazol-4-yl]phenyl}-3-benzyl-2,4-dioxo-1,3,8-triazaspiro[4.5]decane-8-carboxamide, I-16

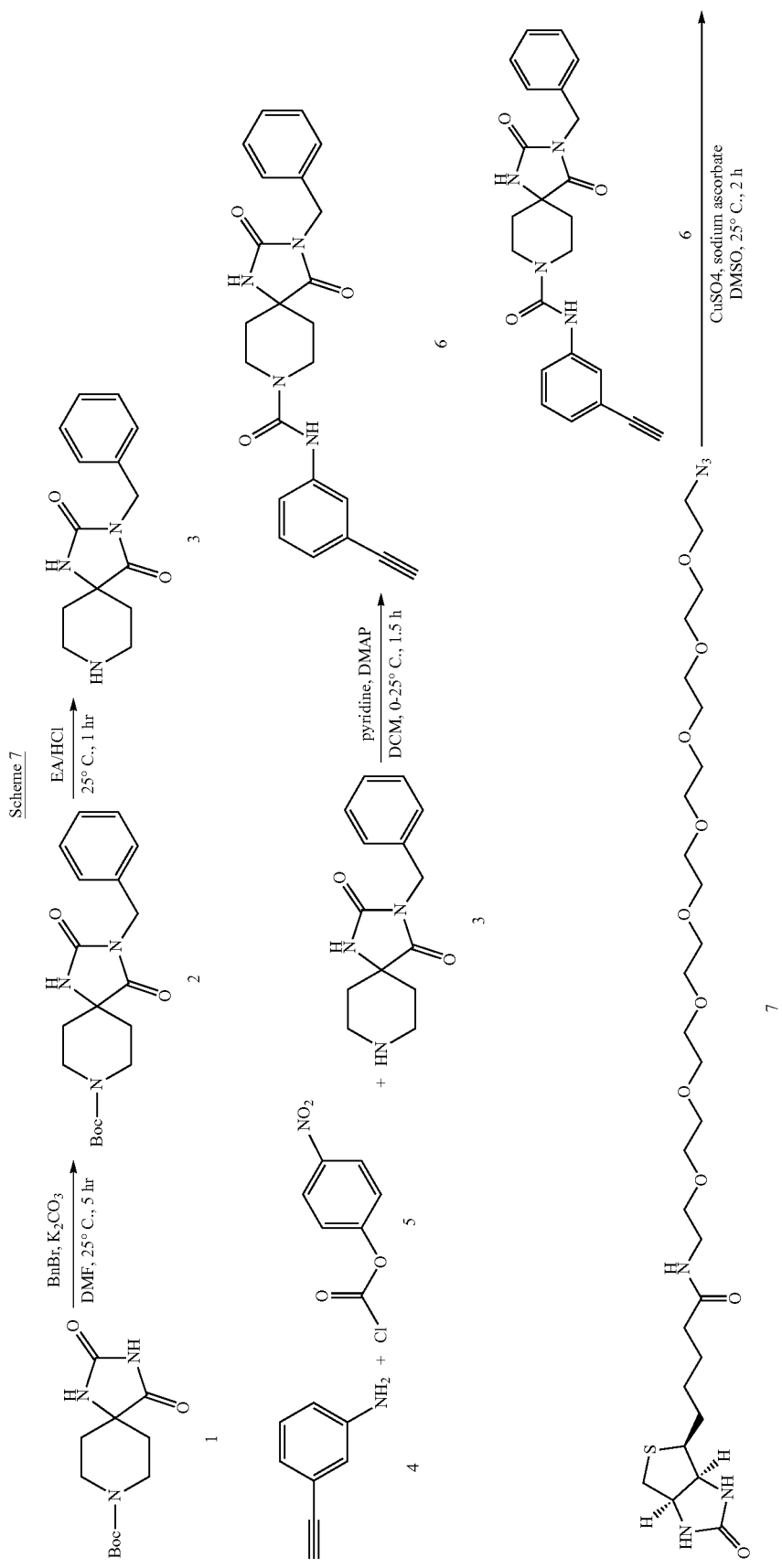

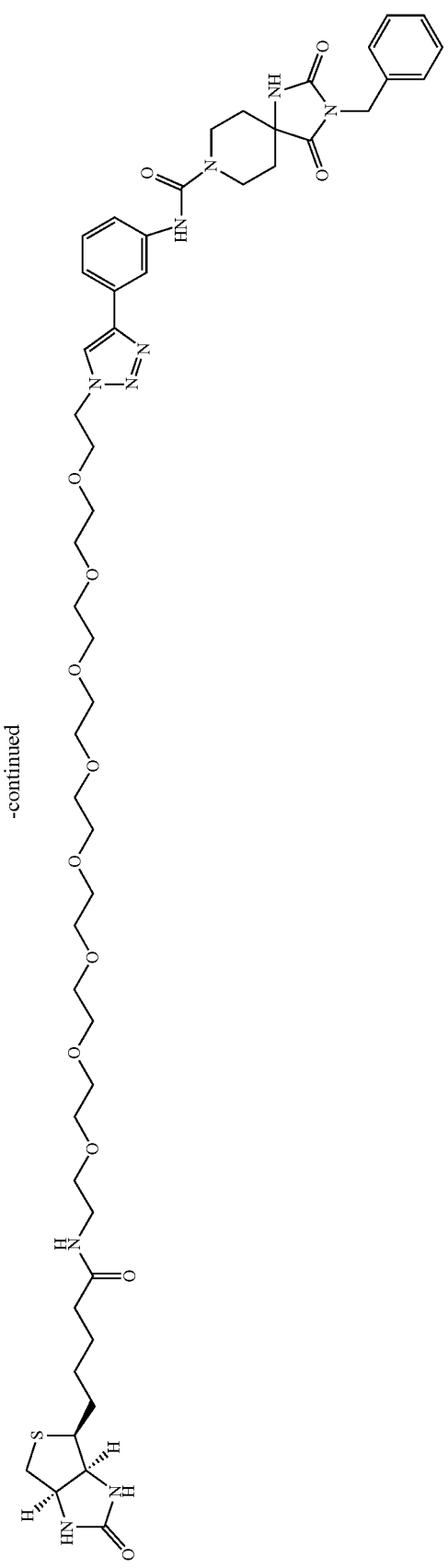
I-16

Step 1: Synthesis of Compound 2

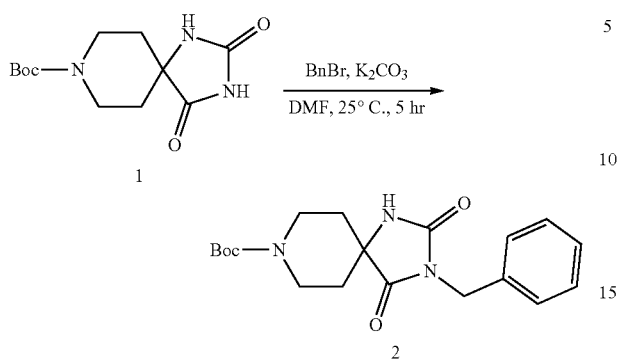

To a solution of compound 1 (3 g, 11.14 mmol, 1 eq) and bromomethylbenzene (2.48 g, 14.48 mmol, 1.72 mL, 1.3 eq) in DMF (25 mL) was added $K_2CO_3$ (4.62 g, 33.42 mmol, 3 eq), then the mixture was stirred at 25° C. for 5 hr. LCMS and TLC (Petroleum ether:Ethyl acetate=1:1, product Rf=0.51) indicated that the starting material was consumed completely. The reaction mixture was extracted with ethyl acetate (50 mL×3) and water (50 mL). The combined organic layers were washed with brine, dried over with $Na_2SO_4$, and concentrated under reduced pressure to give a residue which was purified further by silica gel column (Petroleum ether:Ethyl acetate=20:1 to 2:1) to yield compound 2 (2.7 g, 7.51 mmol, 67.43% yield) as a white solid, which it was confirmed by $^1H$ NMR. LCMS: Rt=1.224 min, MS cal.: 304.2, $[M+H]^+$=304.2. $^1H$ NMR (400 MHz, METHANOL-$d_4$) δ ppm 1.49 (s, 9H) 1.62 (dt, J=13.54, 3.81 Hz, 2H) 1.91 (ddd, J=13.82, 9.96, 4.34 Hz, 2H) 3.94 (dt, J=13.94, 4.83 Hz, 2H) 4.51-4.72 (m, 2H) 6.91-7.82 (m, 4H).

Step 2: Synthesis of Compound 3

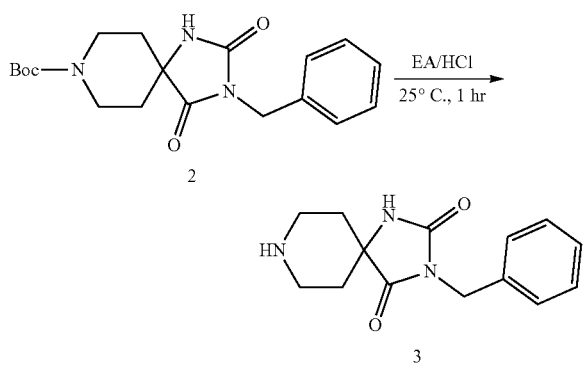

To a solution of compound 2 (2.7 g, 7.51 mmol, 1 eq) in EtOAc (20 mL) was added HCl/EtOAc (4M, 20 mL, 10.65 eq), followed by stirring at 25° C. for 1.5 hr. LCMS indicated that the starting material was consumed completely. The reaction mixture was concentrated under reduced pressure to give a residue yielding compound 3 (2.15 g, 7.27 mmol, 96.77% yield, HCl) as a white solid, which was used in next step directly, without further purification. LCMS: Rt=0.912 min, MS cal.: 295.8, $[M+H]^+$=260.2.

Step 3: Synthesis of Compound 6

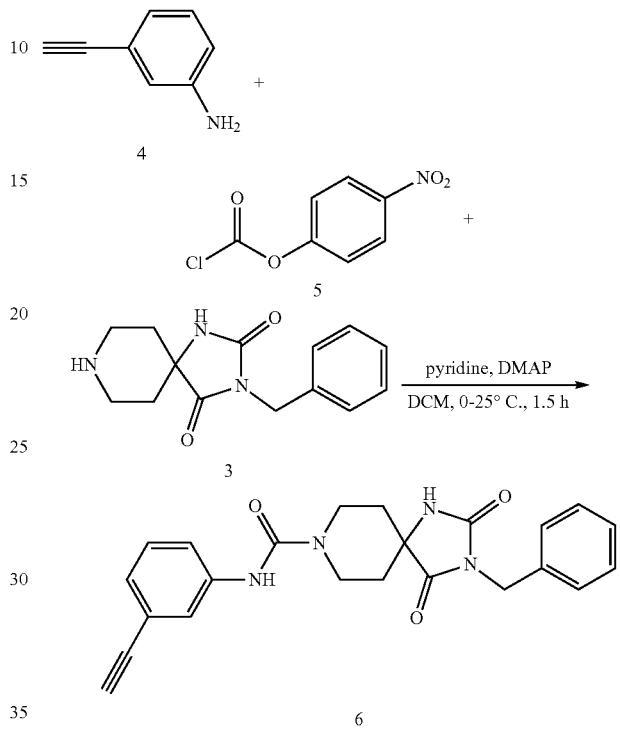

To a solution of compound 5 (81.78 mg, 405.73 μmol, 1.2 eq) in DCM (2 mL) was added compound 4 (51.49 mg, 439.54 μmol, 1.3 eq) dropwise at 0° C. for 30 min. Then compound 3 (100 mg, 338.11 μmol, 1 eq, HCl), pyridine (133.72 mg, 1.69 mmol, 136.45 μL, 5 eq), and DMAP (123.92 mg, 1.01 mmol, 3 eq) were added to the reaction mixture followed by stirring at 25° C. for 60 min. LCMS indicated the presence of the desired product. Water (5 mL) was added to the reaction mixture, which was then washed with HCl (0.5 M) and water (5 mL×2). The organic layer was dried over $Na_2SO_4$, concentrated under reduced pressure, and the resulting residue was purified by prep-TLC (PE:EA=1:1, Product Rf=0.21) to yield compound 6 (129.9 mg, 307.93 umol, 91.07% yield, 95.40% purity) as colorless solid, which was verified by LCMS and $^1H$ NMR. LCMS: Rt=1.159 min, MS cal.: 402.17, $[M+H]^+$=403.2. LCMS: Rt=1.195 min, MS cal.: 402.17, $[M+H]^+$=403.2. $^1H$ NMR (400 MHz, DMSO-$d_6$) δ=8.98 (s, 1H), 8.71 (s, 1H), 7.63 (s, 1H), 7.49 (br d, J=8.2 Hz, 1H), 7.41-7.22 (m, 6H), 7.05 (d, J=7.6 Hz, 1H), 4.56 (s, 2H), 4.12 (s, 1H), 4.05-3.95 (m, 2H), 3.94-3.94 (m, 1H), 3.29-3.17 (m, 2H), 1.99 (s, 1H), 1.90-1.79 (m, 2H), 1.63 (br d, J=13.4 Hz, 2H), 1.18 (t, J=7.1 Hz, 1H).

Step 4: Synthesis of I-16

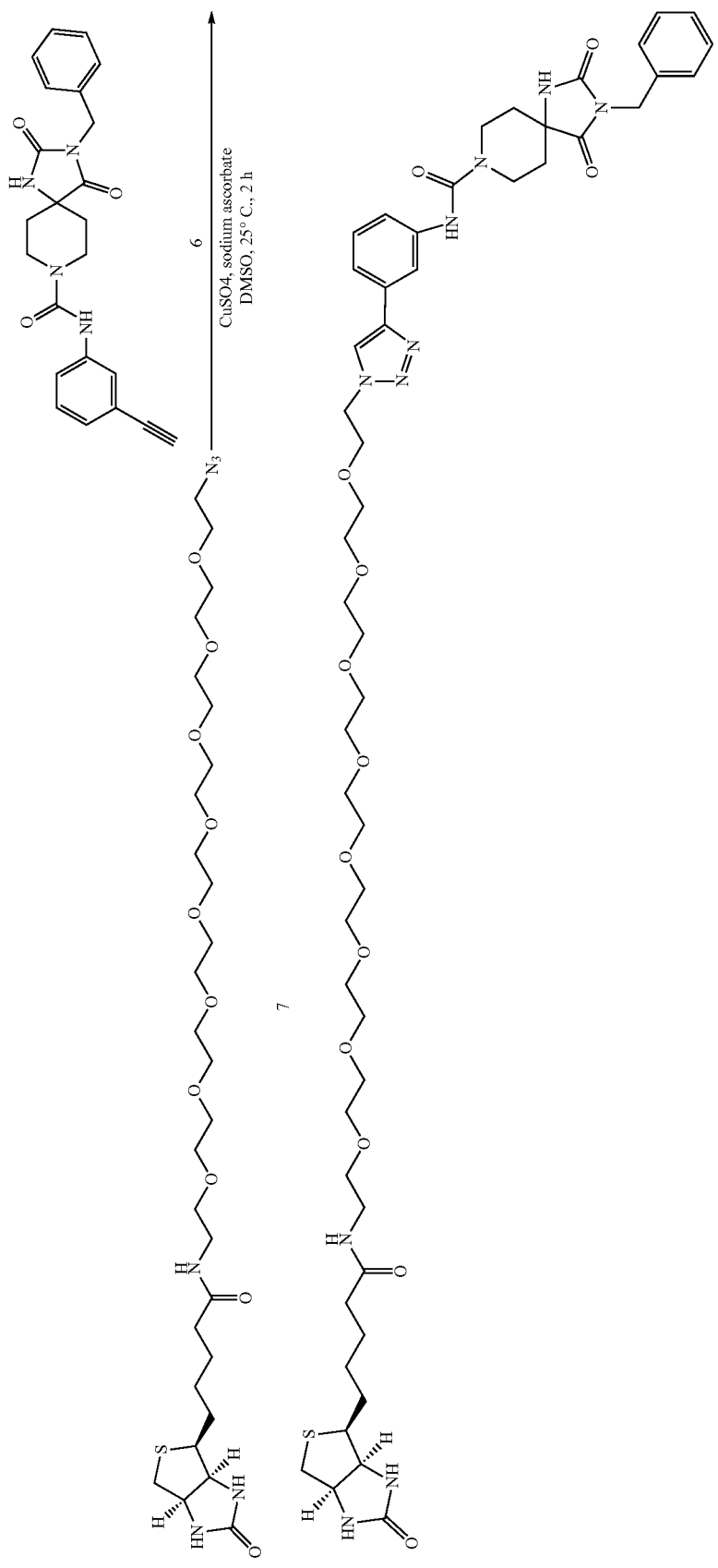

To a solution of compound 7 (223.51 mg, 336.20 μmol, 1.1 eq) and compound 6 (123 mg, 305.63 μmol, 1 eq) in DMSO (1.5 mL) was added CuSO$_4$ (14.63 mg, 91.69 μmol, 14.07 μL, 0.3 eq) and sodium ascorbate (121.10 mg, 611.26 μmol, 2 eq). The mixture was stirred at 25° C. for 2 hr. LCMS indicated the presence of desired product and the reaction mixture was filtered. The residue was purified by prep-HPLC (TFA condition) according to HPLC to yield I-16 (17.33 mg, 15.96 μmol, 5.22% yield, 98.29% purity) as light yellow oil, which was verified checked by QC-LCMS and $^1$H NMR. LCMS: Rt=0.985 min, MS cal.: 1066.52, [1/2M+H]$^+$=534.6. HPLC: Rt=2.375 min. QC-LCMS: Rt=1.963 min, MS cal.: 1066.52, [1/2M+H]$^+$=534.4. $^1$H NMR (400 MHz, CHLOROFORM-d) δ=8.17 (br s, 1H), 8.01 (s, 1H), 7.74 (br s, 1H), 7.61 (br s, 1H), 7.52-7.45 (m, 1H), 7.41 (br d, J=7.6 Hz, 1H), 7.29-7.15 (m, 8H), 6.94-6.84 (m, 1H), 6.25 (br s, 1H), 4.57 (s, 2H), 4.50 (br t, J=4.3 Hz, 2H), 4.43-4.37 (m, 1H), 4.26-4.17 (m, 1H), 3.94 (br d, J=9.9 Hz, 2H), 3.81 (br t, J=4.6 Hz, 2H), 3.60-3.25 (m, 34H), 3.09-2.84 (m, 7H), 2.79 (br dd, J=4.6, 13.0 Hz, 1H), 2.63 (br d, J=12.8 Hz, 1H), 2.11 (br t, J=6.8 Hz, 2H), 2.00-1.86 (m, 2H), 1.68-1.43 (m, 6H), 1.36-1.26 (m, 2H), 1.22-1.15 (m, 1H).

Example 8: Synthesis of N-{4-[1-(26-{5-[(3aS,4S,6aR)-2-oxo-hexahydro-1H-thieno[3,4-d]imidazol-4-yl]pentanamido}-3,6,9,12,15,18,21,24-octaoxahexacosan-1-yl)-1H-1,2,3-triazol-4-yl]phenyl}-3-benzyl-2,4-dioxo-1,3,8-triazaspiro[4.5]decane-8-carboxamide (I-17

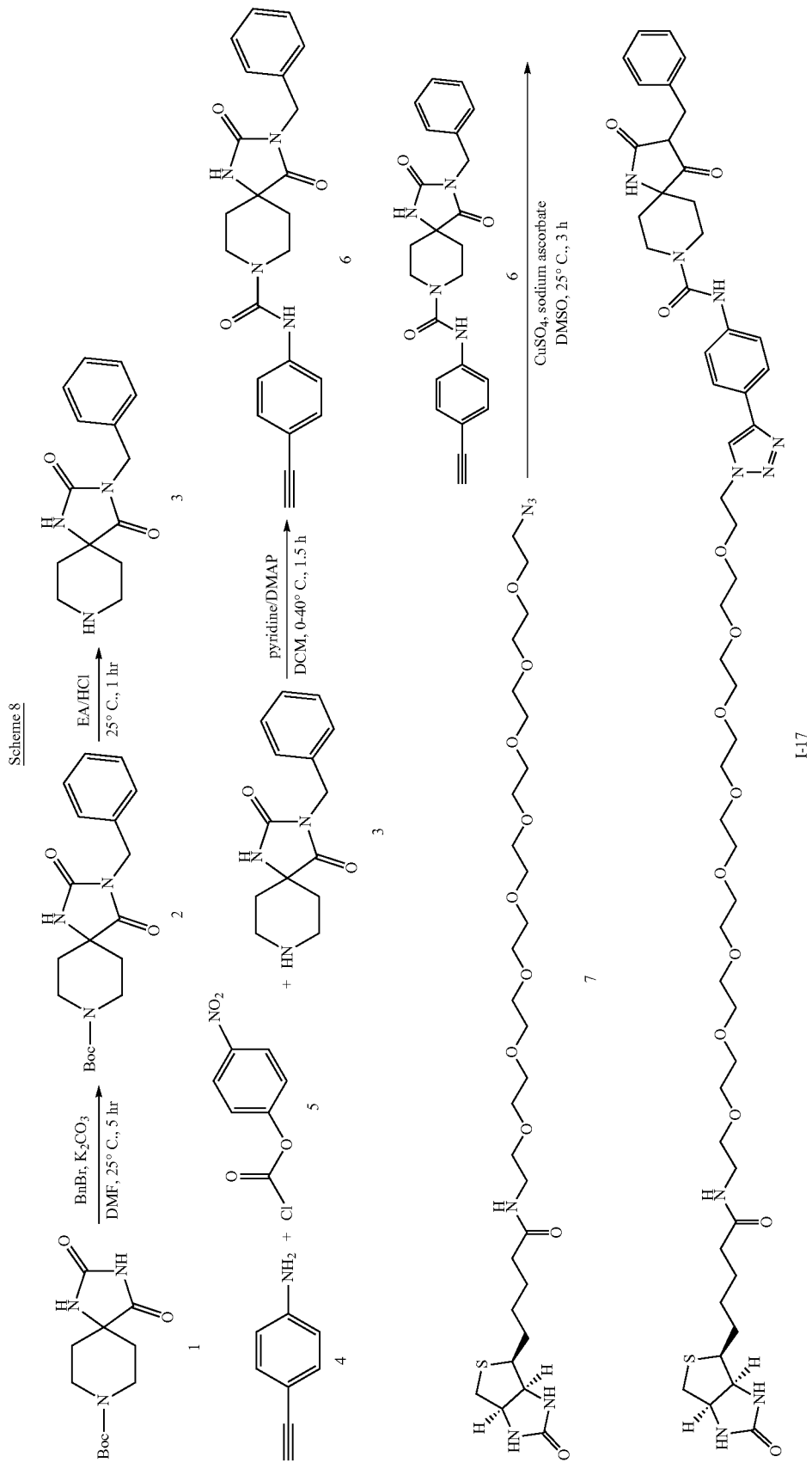
Scheme 8

Step 1: Synthesis of Compound 2

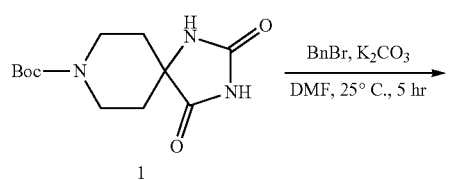

To a solution of compound 1 (3 g, 11.14 mmol, 1 eq) and bromomethylbenzene (2.48 g, 14.48 mmol, 1.72 mL, 1.3 eq) in DMF (25 mL) was added $K_2CO_3$ (4.62 g, 33.42 mmol, 3 eq), then the mixture was stirred at 25° C. for 5 hr. TLC (Petroleum ether:Ethyl acetate=1:1, product Rf=0.51) and indicated that the starting material was consumed completely. The reaction mixture was extracted with ethyl acetate (50 mL×3) and water (50 mL). The combined organic layers were washed with brine, dried over with $Na_2SO_4$, and concentrated under reduced pressure to give a residue which was purified further by silica gel column (Petroleum ether:Ethyl acetate=20:1 to 2:1) to yield compound 2 (2.7 g, 7.51 mmol, 67.43% yield) as a white solid, which was confirmed by $^1H$ NMR. LCMS: Rt=1.224 min, MS cal.: 304.2, [M+H]$^+$=304.2. H NMR (400 MHz, METHANOL-$d_4$) δ ppm 1.49 (s, 9H) 1.62 (dt, J=13.54, 3.81 Hz, 2H) 1.91 (ddd, J=13.82, 9.96, 4.34 Hz, 2H) 3.94 (dt, J=13.94, 4.83 Hz, 2H) 4.51-4.72 (m, 2H) 6.91-7.82 (m, 4H).

Step 2: Synthesis of Compound 3

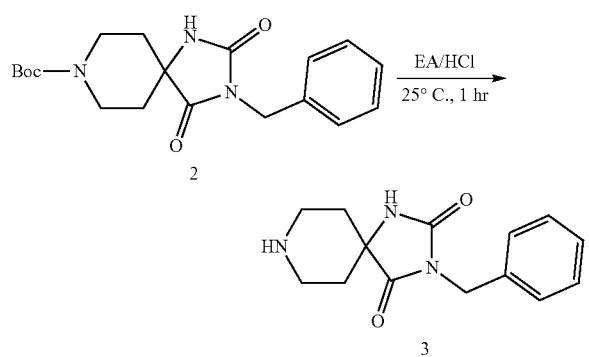

To a solution of compound 2 (2.7 g, 7.51 mmol, 1 eq) in EtOAc (20 mL) was added HCl/EtOAc (4M, 20 mL, 10.65 eq), then the mixture was stirred at 25° C. for 1.5 hr. LCMS indicated that the starting material was consumed completely and the reaction mixture was concentrated under reduced pressure to give a residue that yielded compound 3 (2.15 g, 7.27 mmol, 96.77% yield, HCl) as a white solid, which was used in the next step directly, without further purification. LCMS: Rt=0.912 min, MS cal.: 295.8, [M+H]$^+$=260.2.

Step 3: Synthesis of Compound 6

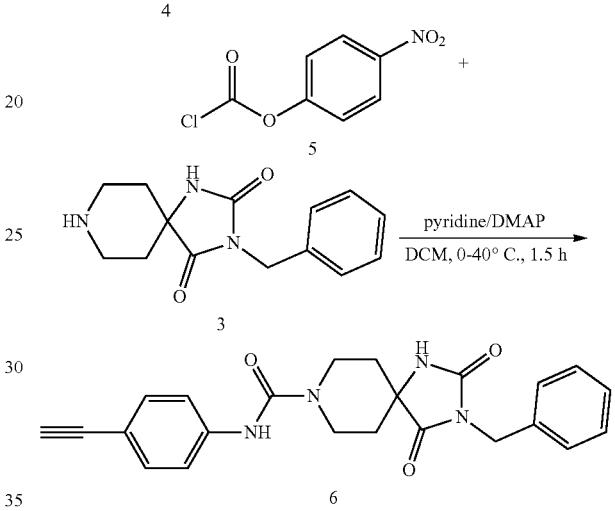

To a mixture of compound 5 (81.78 mg, 405.73 μmol, 1.2 eq) in DCM (2 mL) was added compound 4 (51.49 mg, 439.54 μmol, 1.3 eq) dropwise at 0° C. for 30 min. Then compound 3 (100 mg, 338.11 μmol, 1 eq, HCl), pyridine (80.23 mg, 1.01 mmol, 81.87 μL, 3 eq), and DMAP (123.92 mg, 1.01 mmol, 3 eq) were added and the mixture was stirred at 40° C. for 60 min. LCMS indicated the presence of the desired product and water (5 mL) was added to the reaction mixture, which was then washed with HCl (0.5 M) and water (5 mL×2). The organic layer was dried over $Na_2SO_4$ and concentrated under reduced pressure providing a residue that was purified further by prep-TLC (PE:EA=1:1, Product Rf=0.23) to yield compound 6 (82.6 mg, 205.25 μmol, 60.70% yield) as a white solid which was verified by TLC and $^1H$ NMR. LCMS: Rt=1.165 min, MS cal.: 402.17, [M+H]$^+$=403.1. $^1H$ NMR (400 MHz, DMSO-$d_6$) δ ppm 9.03 (s, 1H), 8.86 (s, 1H), 7.55 (d, J=8.8 Hz, 2H), 7.46-7.24 (m, 7H), 4.61 (s, 2H), 4.07-3.97 (m, 2H), 3.36-3.28 (m, 2H), 1.95-1.82 (m, 2H), 1.68 (br d, J=13.4 Hz, 2H), 0.00 (s, 1H).

Step 4: Synthesis of I-17

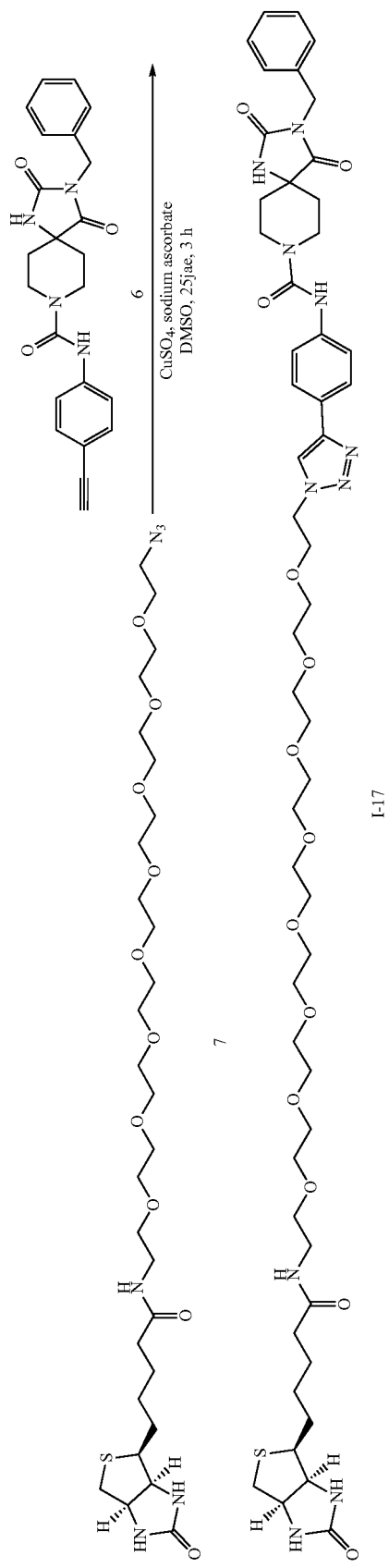

To a mixture of compound 7 (70 mg, 105.29 µmol, 1 eq) and compound 6 (42.37 mg, 105.29 µmol, 1 eq) in DMSO (1 mL) was added $CuSO_4$ (5.04 mg, 31.59 µmol, 4.85 µL, 0.3 eq) and sodium ascorbate (41.72 mg, 210.59 µmol, 2 eq). The mixture was stirred at 25° C. for 2 hr. LCMS indicated the presence of the desired product and the reaction mixture was filter. The residue was purified by prep-HPLC (TFA condition) according to HPLC to yield I-17 (27.43 mg, 24.30 µmol, 23.08% yield, 94.56% purity) as a colorless solid, which was verified by QC-LCMS and $^1$H NMR. QC-LCMS: Rt=0.972 min, MS cal.: 1066.52, $[1/2M+H]^+$=534.6. HPLC: Rt=2.347 min. $^1$H NMR (400 MHz, CHLOROFORM-d) δ ppm 8.47 (br s, 1H), 7.98 (s, 1H), 7.86 (br s, 1H), 7.66 (br d, J=7.9 Hz, 2H), 7.44 (br d, J=7.9 Hz, 2H), 7.30-7.15 (m, 5H), 7.26-7.15 (m, 1H), 6.42 (br s, 1H), 4.61 (br s, 2H), 4.53 (br s, 2H), 4.41 (br s, 1H), 4.21 (br s, 1H), 3.99 (br d, J=10.8 Hz, 2H), 3.85 (br s, 2H), 3.70 (br s, 4H), 3.62-3.41 (m, 31H), 3.43-3.32 (m, 1H), 3.35 (br s, 4H), 3.05 (br s, 1H), 2.80 (br d, J=9.0 Hz, 1H), 2.64 (br d, J=12.1 Hz, 1H), 2.15 (br s, 2H), 1.98 (br d, J=7.9 Hz, 2H), 1.73-1.46 (m, 6H), 1.34 (br d, J=6.6 Hz, 2H).

Example 9: Synthesis of N-{4-[1-(26-{5-[(3aS,4S,6aR)-2-oxo-hexahydro-1H-thieno[3,4-d]imidazol-4-yl]pentanamido}-3,6,9,12,15,18,21,24-octaoxahexacosan-1-yl)-1H-1,2,3-triazol-4-yl]phenyl}-2,4-dioxo-3-phenyl-1,3,8-triazaspiro[4.5]decane-8-carboxamide (I-18

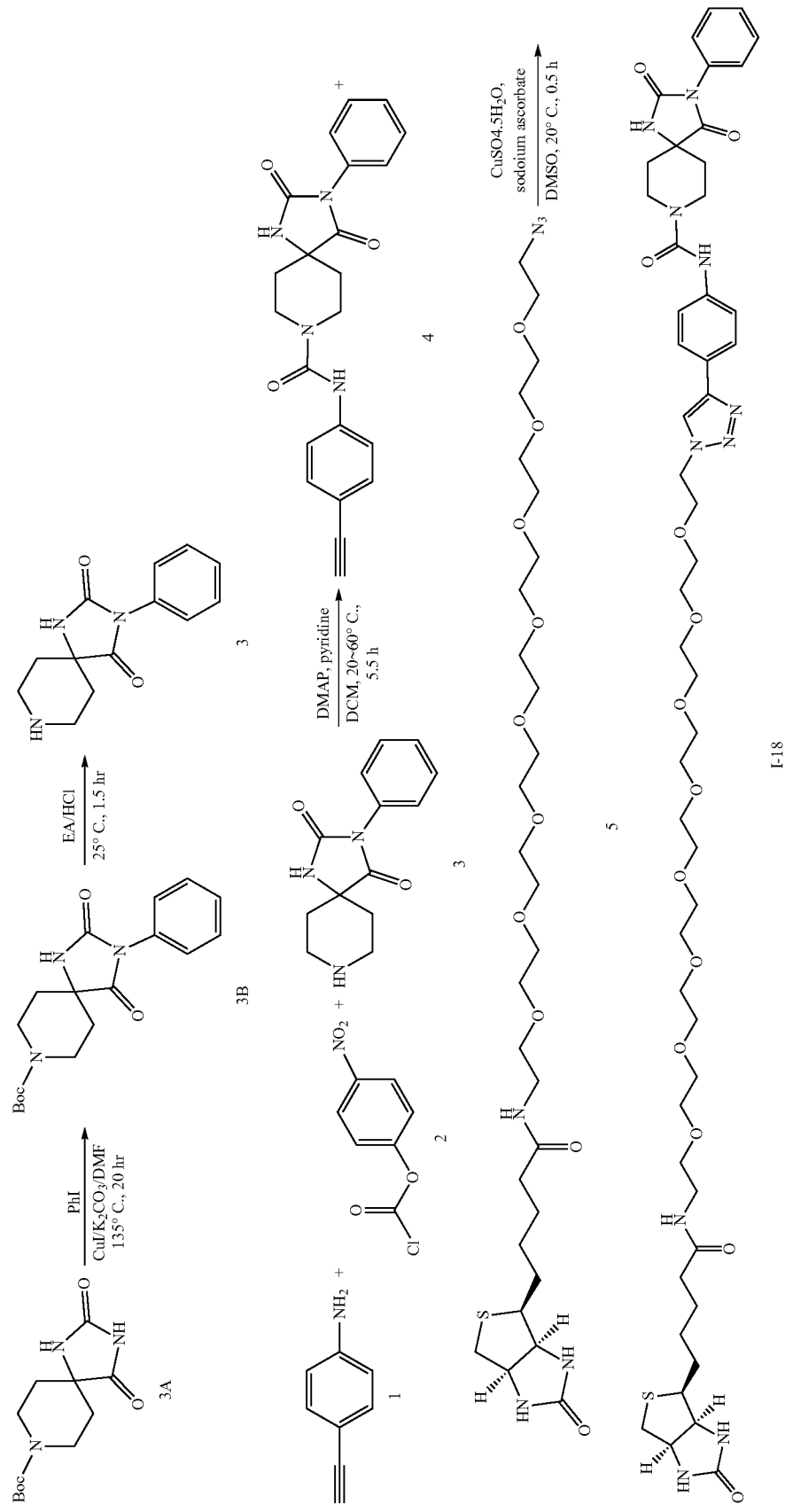

Step 1: Synthesis of Compound 3B

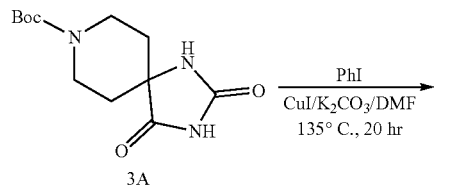

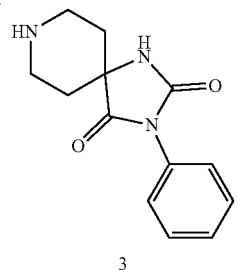

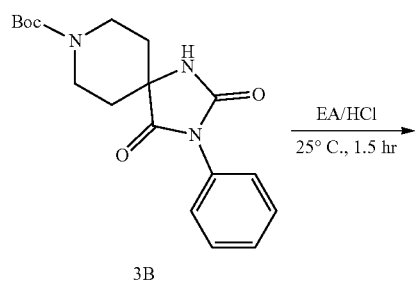

To a solution of compound 3A (3 g, 11.14 mmol, 1 eq) and iodobenzene (3.41 g, 16.71 mmol, 1.86 mL, 1.5 eq) in DMA (30 mL) was added $K_2CO_3$ (4.62 g, 33.42 mmol, 3 eq), CuI (2.12 g, 11.14 mmol, 1 eq), and TMEDA (1.29 g, 11.14 mmol, 1.68 mL, 1 eq), sequentially. After the mixture was degassed with $N_2$ for three times, mixture was heated to 135° C. for 20 hr. LCMS and TLC (Petroleum ether:Ethyl acetate=2:1, Rf=0.49) indicated the starting material was consumed completely. The reaction mixture was extracted with ethyl acetate (50 mL×3) and water (50 mL). The organic layer was washed with brine, dried over $Na_2SO_4$, and concentrated under reduced pressure to give a residue which was purified further by silica gel column (Petroleum ether:Ethyl:acetate=15:1 to 1:1) to yield compound 3B (1.58 g, 4.57 mmol, 41.06% yield) as a yellow solid, which was verified by H NMR. LCMS: Rt=0.912 min, MS cal.: 345.4, $[M-55]^+$=290.2. $^1H$ NMR (400 MHz, METHANOL-d4) δ ppm 1.50 (s, 9H) 1.79 (br d, J=13.45 Hz, 2H) 1.91-2.13 (m, 2H) 3.89-4.22 (m, 2H) 7.22-7.80 (m, 5H).

Step 2: Synthesis of Compound 3

To a solution of compound 3B (1.58 g, 4.57 mmol, 1 eq) in EtOAc (20 mL) was added HCl/EtOAc (4 M, 20 mL, 17.49 eq), then the mixture was stirred at 25° C. for 1.5 hr. LCMS indicated that the starting material was consumed completely. The crude product was concentrated under reduced pressure to give a residue yielding compound 3 (1.23 g, 4.37 mmol, 95.44% yield, HCl) as a yellow solid which was used for next step directly, without further purification. LCMS: Rt=0.819 min, MS cal.: 281.8, $[M-55]^+$=246.1.

Step 3: Synthesis of Compound 4

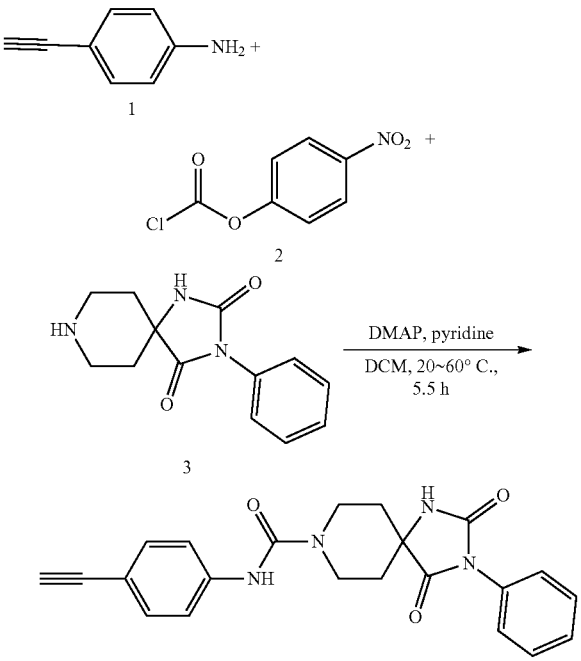

To a solution of compound 2 in DCM (0.5 mL) was added compound 1 (72.26 mg, 358.12 μmol, 1.05 eq) in DCM (2 mL) at 20° C. The mixture was stirred at 20° C. for 0.5 h. TLC (Petroleum ether:Ethyl acetate=3:1, Rf=0.60) indicated one new main spot and the consumption of starting materials. Compound 3 (101.01 mg, 358.52 μmol, 1.05 eq, HCl), pyridine (135.04 mg, 1.71 mmol, 137.80 μL, 5 eq), and DMAP (125.14 mg, 1.02 mmol, 3 eq) were added to the solution at 20° C. Then the reaction was stirred at 60° C. for 5 h. LCMS and TLC (Petroleum ether:Ethyl acetate=1:1, Rf=0.25) indicated the presence of the desired product and that the reaction was complete. The mixture was adjusted to pH=6 with HCl (1 M, 10 mL) and the mixture was extracted with DCM (10 mL×3). The combined DCM layers were washed with brine (15 mL), dried over $Na_2SO_4$, filtered and concentrated to provide a residue that was purified further by prep-TLC (Petroleum ether:Ethyl acetate=1:1) to yield compound 4 (70 mg, 144.17 μmol, 42.22% yield, 80% purity) as a yellow oil which was verified by LCMS and used for next step directly, without further purification. LCMS: Rt=1.097 min, MS cal.: 388.4, $[M+H]^+$=389.2. LCMS: Rt=1.159 min, MS cal.: 388.4, $[M+H]^+$=389.2.

Step 4: Synthesis of I-18

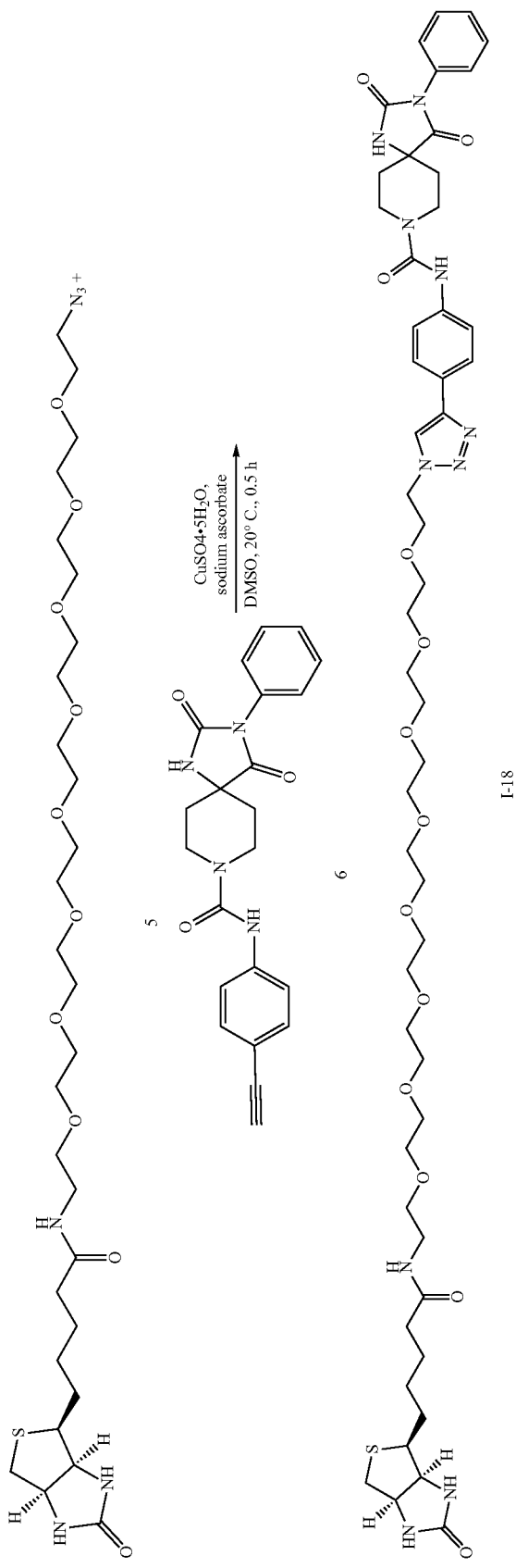

To a solution of compound 6 (42 mg, 108.13 μmol, 1 eq) and compound 5 (71.89 mg, 108.13 μmol, 1 eq) in DMSO (1 mL) was added $CuSO_4 \cdot 5H_2O$ (8.10 mg, 32.44 μmol, 0.3 eq) and sodium ascorbate (42.84 mg, 216.26 μmol, 2 eq) at 20° C. Then the reaction was stirred at 20° C. for 0.5 h. LCMS indicated the presence of the desired product and that the reaction was completed. The mixture was extracted with ethyl acetate (5 mL×3). The combined organic layers were washed with brine (5 mL), dried over $Na_2SO_4$, filtered and concentrated to provide a residue that was purified further by prep-HPLC (TFA condition) according to HPLC to yield I-18 (42.99 mg, 40.63 μmol, 37.57% yield, 99.53% purity) as a yellow solid verified by LCMS and $^1H$ NMR. LCMS: Rt=1.111 min, MS cal.: 1053.2, $[1/2M+H]^+$=527.4. LCMS: Rt=1.806 min, MS cal.: 1053.2, $[M+H]^+$=1053.5. HPLC: Rt=2.221 min. H NMR (400 MHz, CDCl3) δ ppm 1.22-1.37 (m, 3H) 1.38-1.66 (m, 5H) 1.79 (br d, J=13.67 Hz, 2H) 1.87-1.98 (m, 2H) 2.06 (br t, J=7.39 Hz, 2H) 2.53-2.60 (m, 1H) 2.81 (dd, J=12.35, 5.07 Hz, 1H) 3.05-3.12 (m, 1H) 3.17 (q, J=5.73 Hz, 2H) 3.29-3.41 (m, 4H) 3.44-3.52 (m, 21H) 3.53-3.57 (m, 2H) 3.86 (br t, J=5.07 Hz, 1H) 4.03 (br d, J=14.11 Hz, 2H) 4.12 (dd, J=7.61, 4.30 Hz, 1H) 4.30 (br dd, J=7.39, 4.96 Hz, 1H) 4.55 (br t, J=5.07 Hz, 2H) 7.36-7.42 (m, 3H) 7.45-7.51 (m, 2H) 7.55 (d, J=8.60 Hz, 2H) 7.71 (d, J=8.60 Hz, 1H) 7.82 (br t, J=5.51 Hz, 1H) 8.41 (s, 1H) 8.73 (s, 1H) 9.12 (s, 1H).

Example 10: Synthesis of 5-[(3aS,4S,6aR)-2-oxo-hexahydro-1H-thieno[3,4-d]imidazol-4-yl]-N-{26-[4-(4-{2-[4-(2,4-dioxo-3-phenylimidazolidin-1-yl) piperidin-1-yl]-2-oxoethoxy}phenyl)-1H-1,2,3-triazol-1-yl]-3,6,9,12,15,18,21,24-octaoxahexacosan-1-yl}pentanamide, I-19

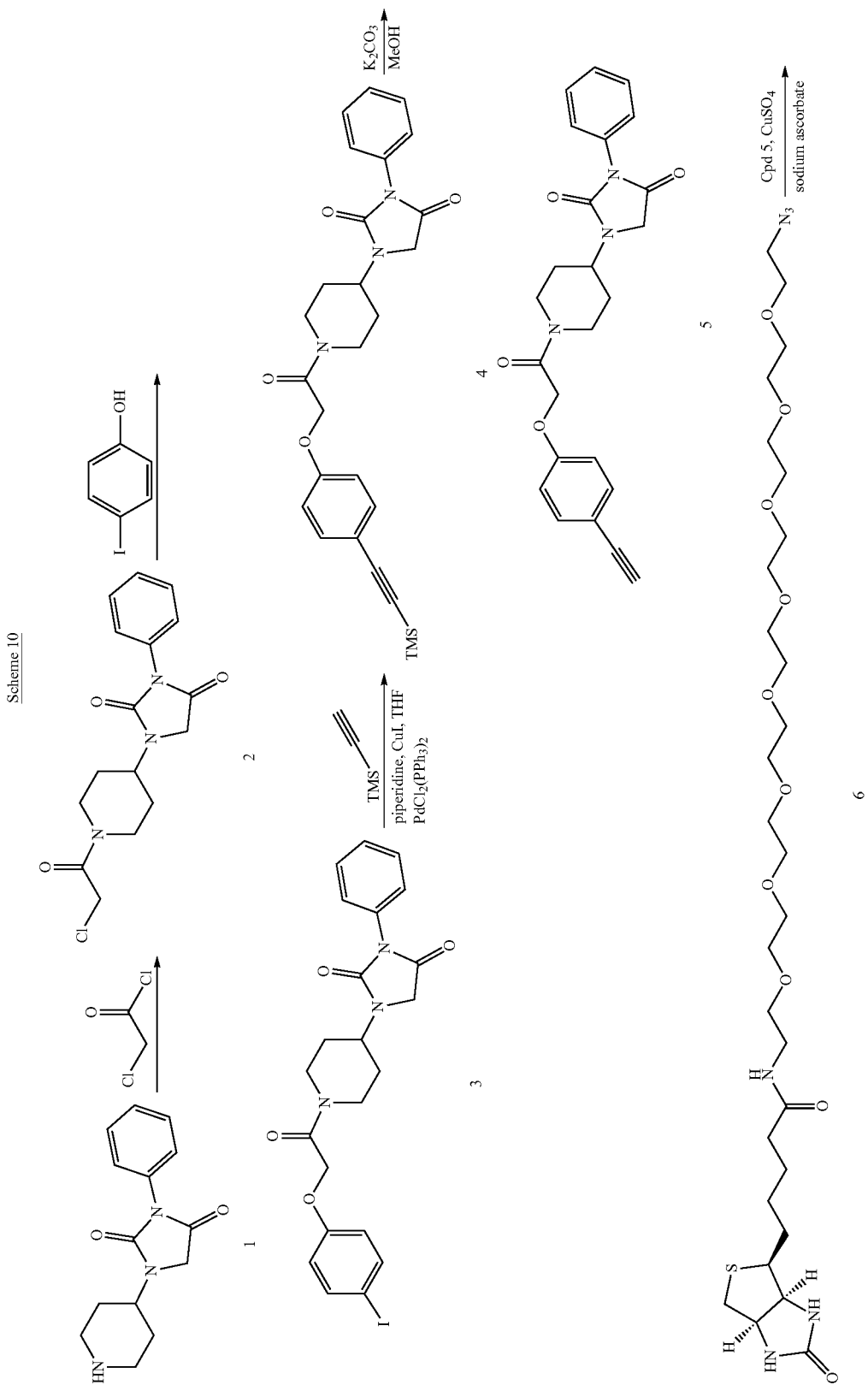

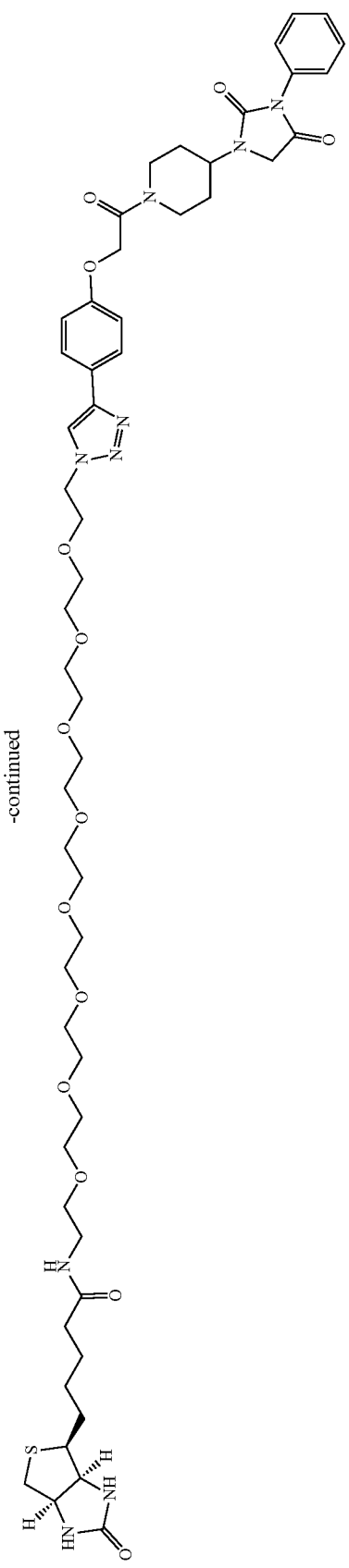
I-19

Step 1: Synthesis of Compound 2

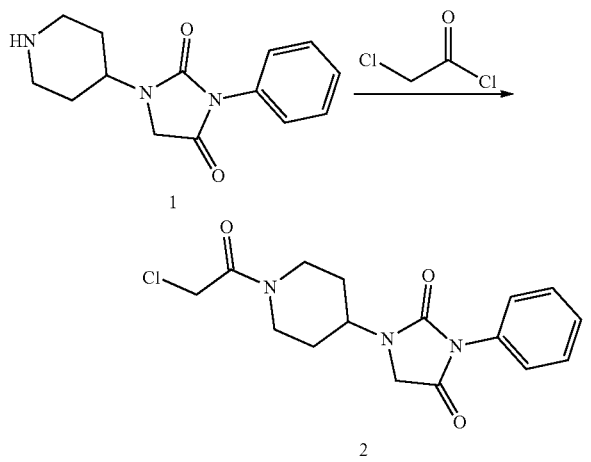

To a solution of compound 1 (200 mg, 676.21 µmol, 1 eq, HCl) in DCM (4 mL) at 0° C. was added TEA (205.28 mg, 2.03 mmol, 282.36 µL, 3 eq) with stirring for 15 min, followed by the addition of 2-chloroacetyl chloride (114.56 mg, 1.01 mmol, 80.68 µL, 1.5 eq) dropwise at 0° C. with stirring for 15 min. The mixture was warmed to 25° C. and stirred for 1 hr. LCMS indicated the presence of the desired product and that the starting material was consumed completely. The reaction mixture was diluted with DCM (15 mL) and acidified to pH=6 with aq. NH$_4$Cl. The organic layer was concentrated under reduced pressure to give a residue which provided compound 2 (128 mg, 381.20 µmol, 56.37% yield) as brown solid, which was used in the next step directly without further purification. LCMS: Rt=1.033 min, MS cal.: 335.1, [1/2M+H]$^+$=336.1.

Step 2: Synthesis of Compound 3

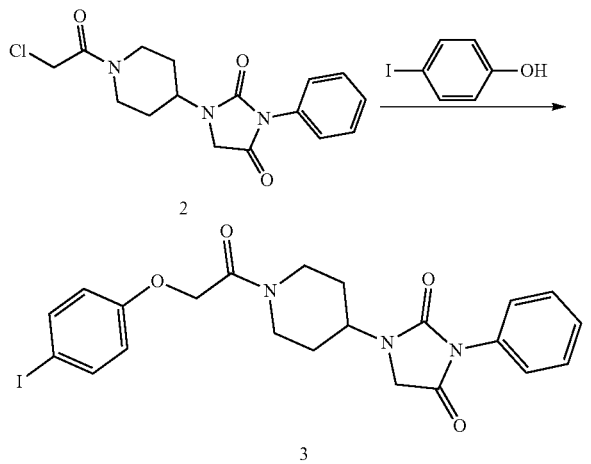

To a solution of compound 2 (120 mg, 357.37 µmol, 1 eq) in DMF (3 mL) was added K$_2$CO$_3$ (148.17 mg, 1.07 mmol, 3 eq) with stirring for 15 min, followed by the addition of 4-iodophenol (157.25 mg, 714.74 µmol, 2 eq) diluted in DMF (2 mL). The mixture was stirred for 15.75 hr at 25° C. LCMS and TLC (Petroleum:EtOAc=0:1, product Rf=0.57) indicated the presence of the desired product and that the starting material was consumed completely. The reaction mixture was diluted with water (20 mL), and extracted by EtOAc (10 mL×2). Then the combined organic layers were washed with brine and dried over anhydrous Na$_2$SO$_4$. The organic phase was concentrated under reduced pressure to give a crude product which was purified by prep-TLC (Petroleum:EtOAc=0:1) to yield compound 3 (130 mg, 237.11 µmol, 66.35% yield, 94.72% purity) as white solid, which was verified by LCMS. LCMS: Rt=1.227 min, MS cal.: 519.1, [M+H]$^+$=520.1.

Step 3: Synthesis of Compound 4

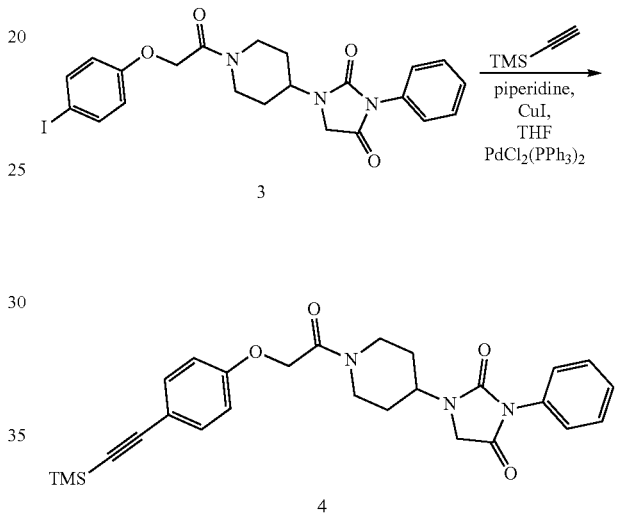

To a solution of compound 3 (300 mg, 577 µmol, 1 eq), ethynyl(trimethyl)silane (85.1 mg, 866 µmol, 120 µL, 1.5 eq) in THF (10 mL) was added CuI (4.40 mg, 23.11 µmol, 0.04 eq) and Pd(PPh$_3$)$_2$Cl$_2$ (8.1 mg, 11.5 µmol, 0.02 eq), and piperidine (1.43 g, 16.7 mmol, 1.65 mL, 29 eq). The mixture was stirred at 20° C. for 2 hr. LCMS showed the reaction was complete, H$_2$O (15 mL) was added, and the mixture was extracted with EtOAc (10 mL). The organic layer was separated, concentrated, and the residue was purified by column chromatography (SiO$_2$, Petroleum ether:Ethyl acetate=5:1 to 0:1) to yield compound 4 (0.28 g, crude) as a brown oil which was used into the next step without further purification.

Step 4: Synthesis of Compound 5

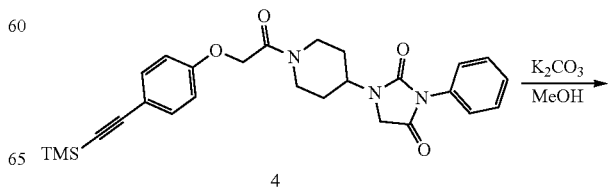

-continued

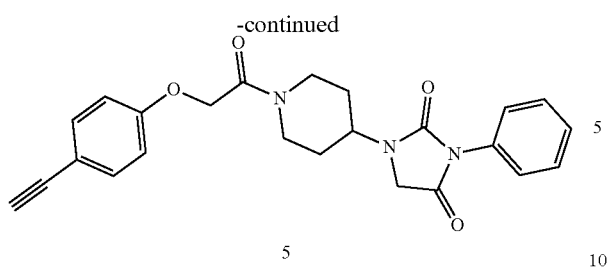

5

To a solution of compound 4 (0.28 g, 571 μmol, 1 eq) in DCM (3 mL) and MeOH (3 mL) was added $K_2CO_3$ (158 mg, 1.14 mmol, 2 eq). The mixture was stirred at 20° C. for 1 hr and LCMS showed the reaction was complete. The mixture was concentrated and the residue was purified by column chromatography ($SiO_2$, Petroleum ether:Ethyl acetate=5:1 to 0:1) to yield compound 5 (0.12 g, 287.46 μmol, 50% yield) as a brown oil which was used into the next step without further purification. LCMS: Rt=1.099 min, MS cal.: 417.2, $[M+H]^+$=418.1.

Step 5: Synthesis of I-19

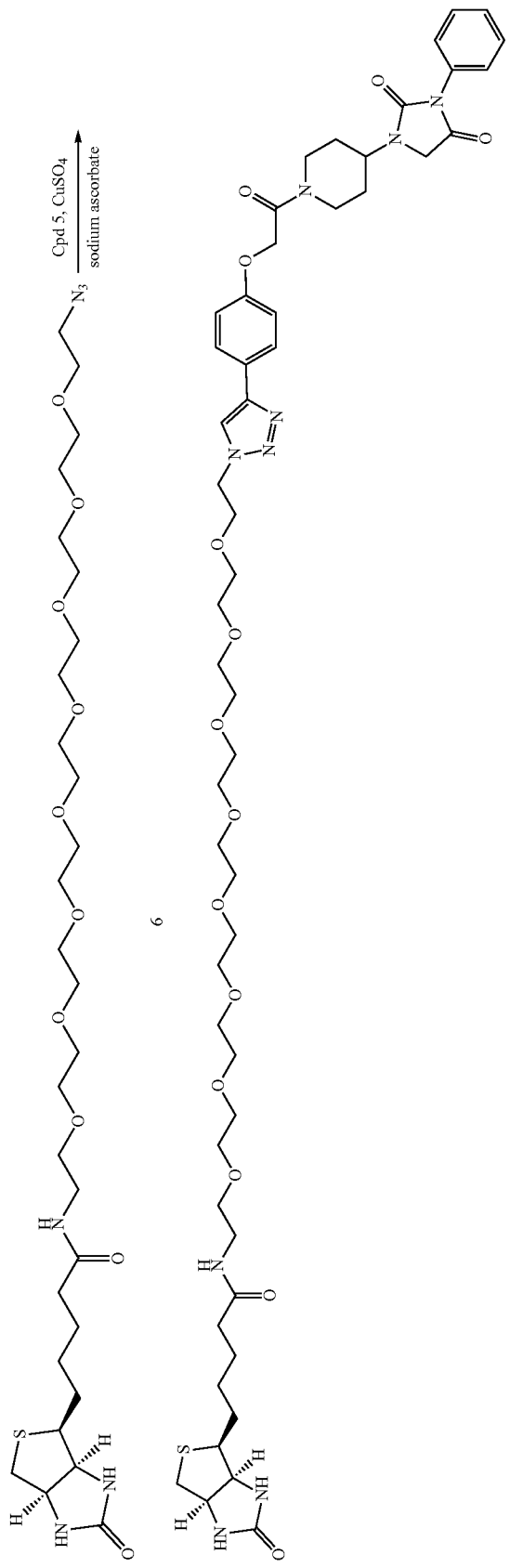

To a solution of compound 5 (60 mg, 143 µmol, 1 eq) and compound 6 (95.55 mg, 143.73 µmol, 1 eq) in DMSO (1 mL) was added sodium ascorbate (57 mg, 287 µmol, 2 eq) and $CuSO_4 \cdot 5H_2O$ (10.7 mg, 43.12 µmol, 0.3 eq). The mixture was stirred at 20° C. for 1 hr. LCMS indicated the reaction was complete. The solution was purified directly by prep-HPLC (column: YMC-Actus Triart C18 100*30 mm*5 um; mobile phase: A: water (10 mM $NH_4HCO_3$), B: MeCN; gradient: 20%-40% in 12 min) to give 1-19 (51.83 mg, 47.89 µmol, 33% yield) as a colorless oil. HPLC: Rt=2.256 min. LCMS: Rt=1.032 min, MS cal.: 1081.5, $[1/2M+H]^+$=542.0. $^1$H NMR (400 MHz, METHANOL-d4) δ ppm 8.10 (s, 1H) 7.58 (br d, J=8.33 Hz, 2H) 7.23-7.32 (m, 2H) 7.14-7.21 (m, 3H) 6.87 (br d, J=8.33 Hz, 2H) 4.40 (br s, 5H) 4.22-4.28 (m, 1H) 3.93-4.10 (m, 2H) 3.86 (s, 3H) 3.72 (brt, J=4.38 Hz, 2H) 3.34-3.46 (m, 30H) 3.07-3.18 (m, 4H) 2.92-3.05 (m, 2H) 2.69 (br dd, J=12.72, 4.82 Hz, 1H) 2.44-2.62 (m, 2H) 1.99 (br t, J=7.02 Hz, 2H) 1.32-1.77 (m, 8H) 1.13-1.27 (m, 2H).

Example 11: Synthesis of I-62

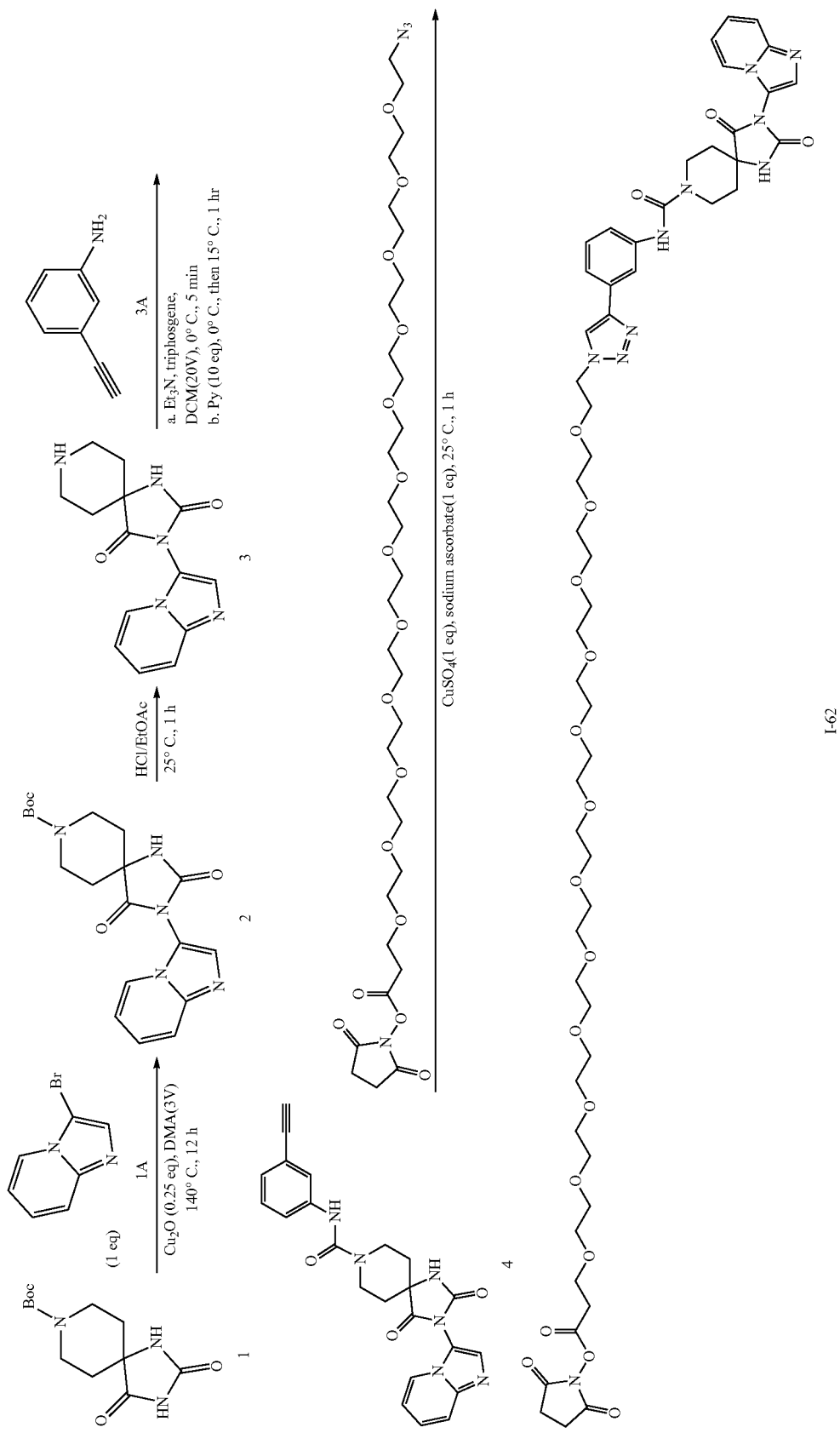

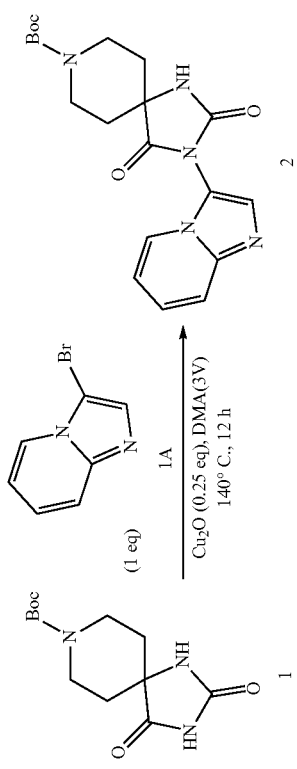

To a solution of compound 1 (0.5 g, 1.86 mmol, 1 eq) in DMA (5 mL) was added compound 1A (365.83 mg, 1.86 mmol, 1 eq) and Cu₂O (132.84 mg, 928.35 umol, 94.88 uL, 0.5 eq). The mixture was stirred at 140° C. for 12 h. LCMS showed the reaction was completed. The mixture was filtered to give crude product. The crude product was purified by prep-HPLC (column: Waters Xbridge Prep OBD C18 150*40 10 u; mobile phase: [water (0.04% NH₃H₂O+10 mM NH4HCO3)-ACN]; B %: 15%-40%, 11 min) to give compound 2 (100 mg, 259.46 umol, 13.97% yield) as a yellow solid. LCMS: RT=1.922 min, MS cal.: 385.4, [M+H]⁺=386.1.

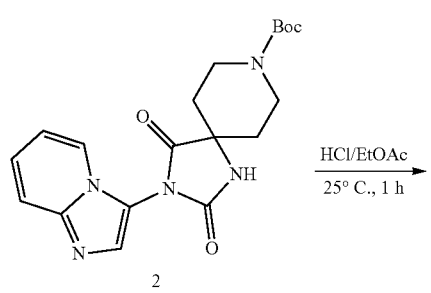

The solution of compound 2 (0.05 g, 129.73 umol, 1 eq) in HCl/EtOAc (2 mL, 4M) was stirred at 25° C. for 0.5 h. LCMS showed the reaction was completed. The mixture was concentrated in vacuum to give compound 3 (30 mg, 105.15 umol, 81.05% yield) as a white solid. LCMS: RT=0.109 min, MS cal.: 285.3, [M+H]⁺=286.1.

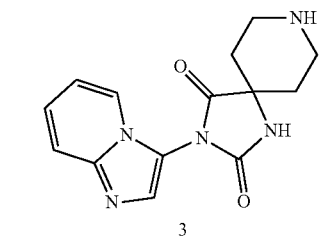

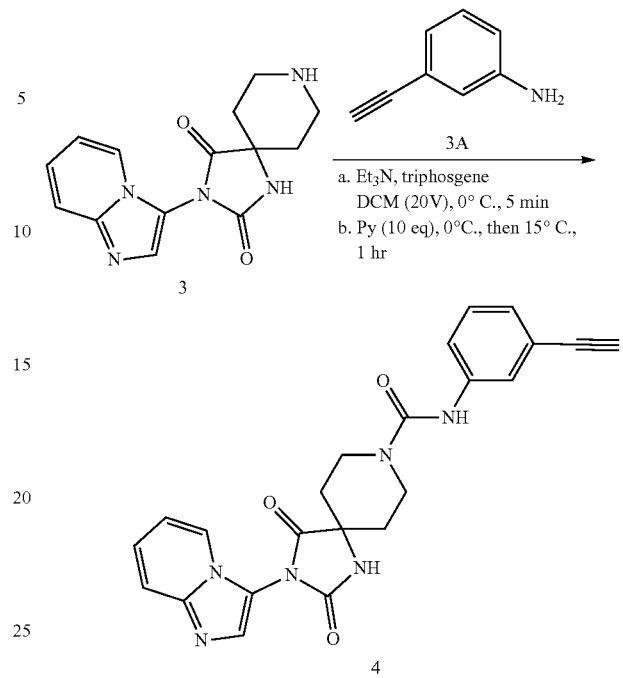

To a solution of TRIPHOSGENE (9.13 mg, 30.77 umol, 0.33 eq) in DCM (2 mL) was added TEA (9.43 mg, 93.24 umol, 12.98 uL, 1 eq) and compound 3A (10.92 mg, 93.24 umol, 1 eq) at 0° C. The mixture was stirred at 0° C. for 0.5 h. Then compound 3 (0.03 g, 93.24 umol, 1 eq, HCl) and Pyridine (44.25 mg, 559.42 umol, 45.15 uL, 6 eq) was added to the solution and stirred at 20° C. for 1 h. LCMS showed the reaction was completed. The mixture was filtered to give crude product. The crude product was purified by prep-HPLC (column: Luna C18 100*30 5 u; mobile phase: [water (0.1% TFA)-ACN]; B %: 7%-47%, 12 min) to give compound 4 (20 mg, 46.68 umol, 50.07% yield) as a white solid. LCMS: RT=0.982 min, MS cal.: 491.2, [M+H]⁺=492.1. ¹H NMR (400 MHz, DMSO-d6) δ ppm 9.43 (s, 1H) 8.74 (s, 1H) 8.56 (d, J=6.8 Hz, 1H) 8.03 (s, 1H) 7.84 (d, J=8.9 Hz, 1H) 7.61-7.72 (m, 3H) 7.50 (d, J=8.2 Hz, 1H) 7.19-7.32 (m, 3H) 7.05 (d, J=7.6 Hz, 1H) 4.13 (s, 1H) 4.00 (d, J=13.8 Hz, 3H) 2.01 (d, J=4.8 Hz, 5H).

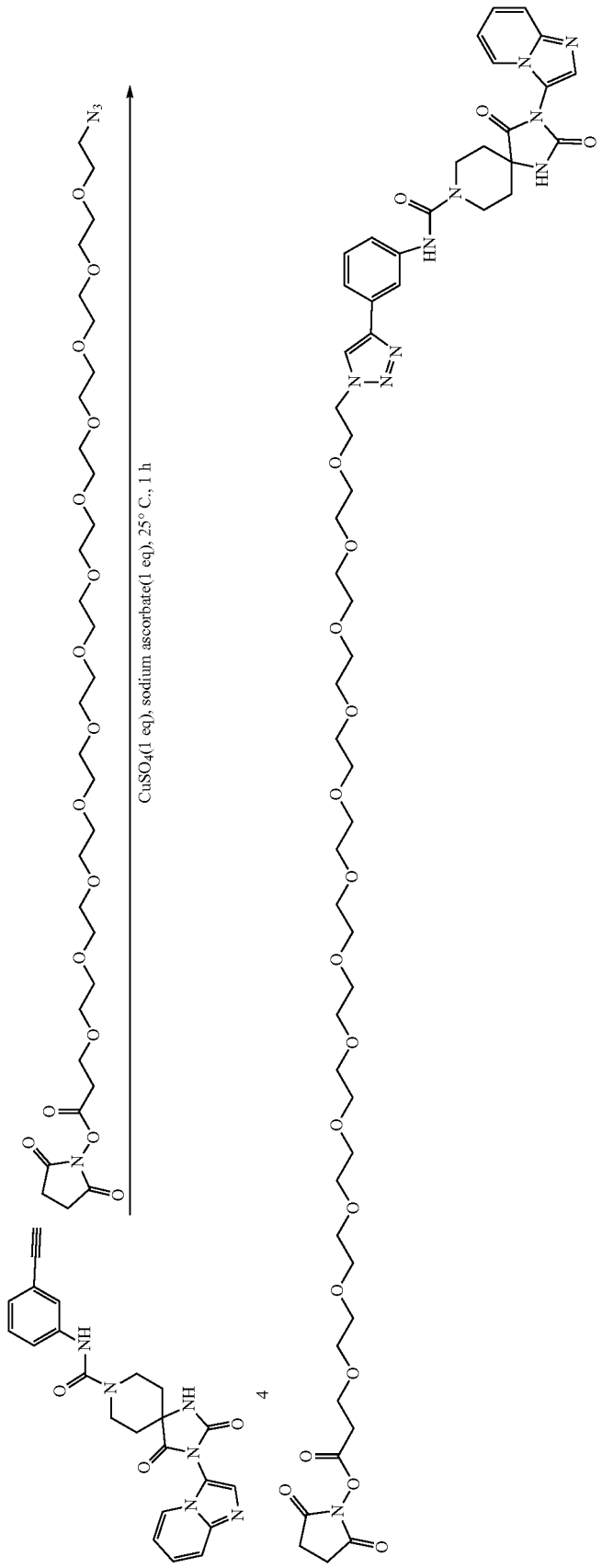

To a solution of compound 4 (0.02 g, 46.68 umol, 1 eq) in DMSO (1 mL) was added compound 5 (34.58 mg, 46.68 umol, 1 eq), $CuSO_4 \cdot 5H_2O$ (11.66 mg, 46.68 umol, 1 eq) and sodium ascorbate (9.25 mg, 46.68 umol, 1 eq). The mixture was stirred at 25° C. for 1 h. LCMS showed the reaction was completed. The mixture was filtered to give crude product. The crude product was prep-HPLC (column: Nano-micro Kromasil C18 100*30 mm 5 um; mobile phase: [water (0.1% TFA)–ACN]; B %: 20%-40%, 10 min) to give I-62 (13.81 mg, 11.81 umol, 25.30% yield) as a yellow oil. LCMS: RT=1.095 min, MS cal.: 1169.2, $[M/2+H]^+$=585.5. $^1H$ NMR (400 MHz, DMSO-d6) δ ppm 9.45 (s, 1H) 8.76 (s, 1H) 8.57 (d, J=6.6 Hz, 1H) 8.45 (s, 1H) 8.00-8.08 (m, 2H) 7.85 (d, J=8.9 Hz, 1H) 7.69 (t, J=7.9 Hz, 1H) 7.48 (d, J=8.2 Hz, 1H) 7.35-7.41 (m, 1H) 7.26-7.34 (m, 2H) 4.57 (t, J=5.1 Hz, 2H) 4.03 (d, J=14.2 Hz, 2H) 3.87 (t, J=5.1 Hz, 2H) 3.71 (t, J=5.9 Hz, 2H) 3.46 (s, 45H) 2.91 (t, J=5.9 Hz, 2H) 2.80 (s, 4H) 2.02 (s, 4H). LCMS: RT=1.501, MS cal.: 1169.2, $[M/2+H]^+$=585.4.

Example 12: Synthesis of 1-63

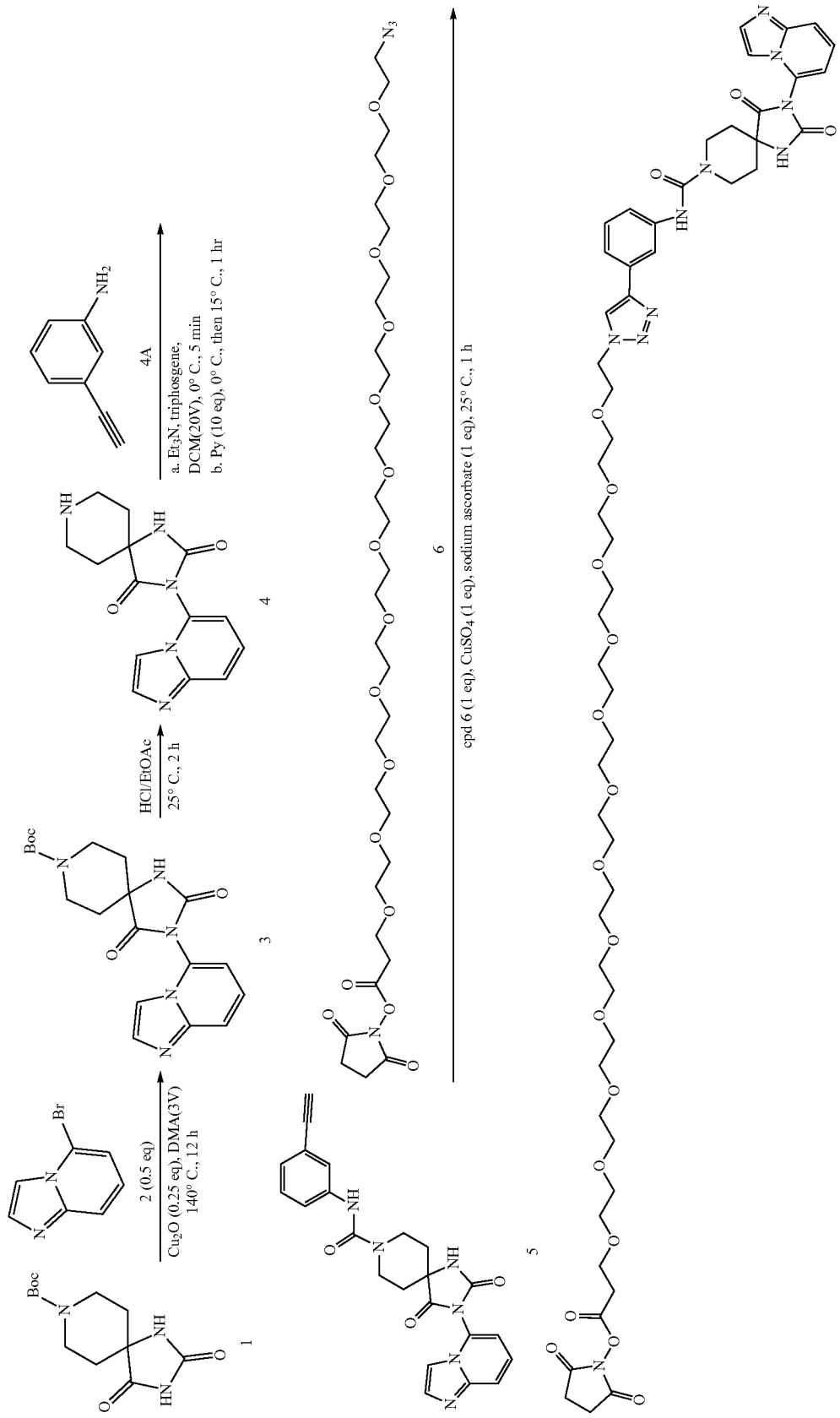

-continued
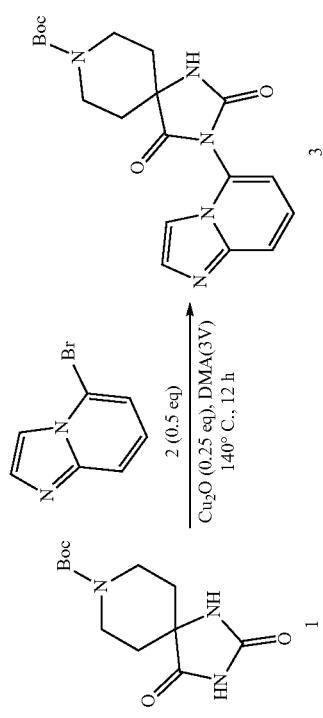

To a solution of compound 1 (0.5 g, 1.86 mmol, 1 eq) in DMA (5 mL) was added compound 2 (365.83 mg, 1.86 mmol, 1 eq) and Cu$_2$O (132.84 mg, 928.35 umol, 94.88 uL, 0.5 eq). The mixture was stirred at 140° C. for 12 h. LCMS and showed the reaction was completed. The mixture was filtered to give crude product. The crude product was purified by prep-HPLC (column: Xtimate C18 10 250 mm*50 mm; mobile phase: [water (0.04% NH$_3$H$_2$O)-ACN]; B %: 15%-45%, 20 min) to give compound 3 (50 mg, 129.73 umol, 6.99% yield) as a white solid. LCMS: RT=0.992 min, MS cal.: 385.4, [M+H]$^+$=386.1.

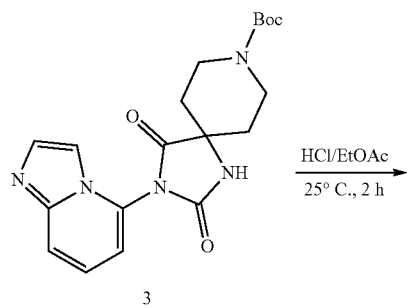

To a solution of compound 3 (43 mg, 111.57 umol, 1 eq) in HCl/EtOAc (3 mL, 4M) was stirred at 15° C. for 40 min. LCMS (RT=0.149 min, m/z 286.1 (M+H)) was detected the desired product MS. The mixture was concentrated to give compound 5 (30 mg, crude) as light yellow solid. LCMS: RT=0.149 min, MS cal.: 285.4, [M+H]$^+$=286.1.

To a solution of triphosgene (5.53 mg, 18.65 umol, 0.3 eq) in DCM (2 mL) was added TEA (6.29 mg, 62.16 umol, 8.65 uL, 1 eq) and compound 4A (7.28 mg, 62.16 umol, 1 eq) at 0° C. The mixture was stirred at 0° C. for 0.5 h. Then compound 4 (0.02 g, 62.16 umol, 1 eq, HCl) and Pyridine (4.92 mg, 62.16 umol, 5.02 uL, 1 eq) was added to the solution and stirred at 20° C. for 1 h. LCMS showed the reaction was completed. The mixture was concentrated in vacuum. The crude product was prep-HPLC (column: Luna C18 100*30 5 u; mobile phase: [water (0.1% TFA)-ACN]; B %: 5%-45%, 10 min) to give compound 5 (10 mg, 23.34 umol, 37.55% yield) was obtained as a white solid. LCMS: RT=0.969 min, MS cal.: 491.2, [M+H]$^+$=492.0. $^1$H NMR (400 MHz, DMSO-d6) δ ppm 9.50 (s, 1H) 8.73 (s, 1H) 8.19 (s, 1H) 8.03 (s, 1H) 7.95 (d, J=9.0 Hz, 1H) 7.74-7.82 (m, 1H) 7.65 (t, J=1.8 Hz, 1H) 7.50 (t, J=6.8 Hz, 1H) 7.26 (t, J=7.9 Hz, 1H) 7.01-7.09 (m, 1H) 4.12 (s, 1H) 4.01 (d, J=14.1 Hz, 2H) 1.98 (s, 4H).

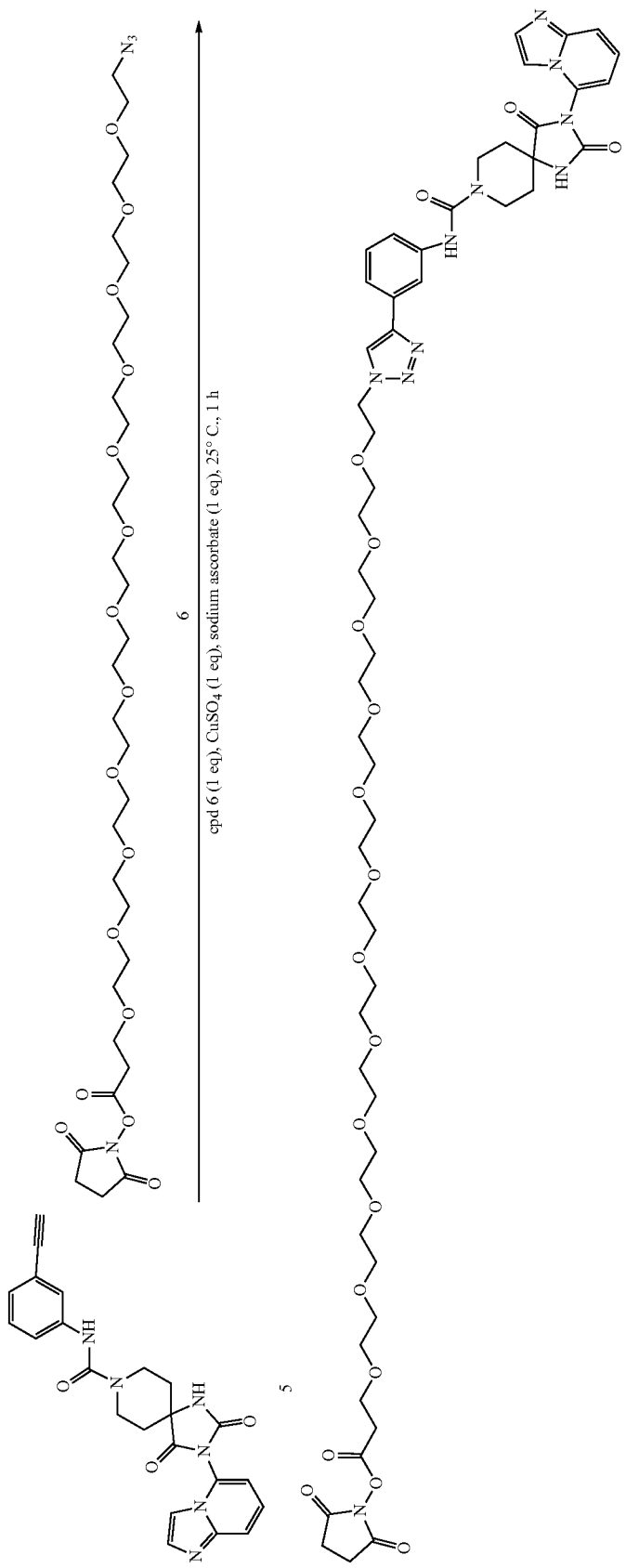

To a solution of compound 5 (10 mg, 23.34 umol, 1 eq) in DMSO (1 mL) was added compound 6 (17.29 mg, 23.34 umol, 1 eq), $CuSO_4 \cdot 5H_2O$ (5.83 mg, 23.34 umol, 1 eq) and sodium ascorbate (4.62 mg, 23.34 umol, 1 eq). The mixture was stirred at 25° C. for 0.5 h. LCMS showed the reaction was completed. The mixture was filtered to give crude product. The crude product was prep-HPLC (column: Luna C18 100*30 5 u; mobile phase: [water (0.1% TFA)–ACN]; B %: 10%-40%, 10 min) to give I-63 (7.33 mg, 6.27 umol, 26.86% yield) as a white solid. LCMS: RT=0.896 min, MS cal.: 1169.2, $[M/2+H]^+$=585.6. $^1H$ NMR (400 MHz, DMSO-d6) δ ppm 9.56 (s, 1H) 8.79 (s, 1H) 8.44 (s, 1H) 7.95-8.05 (m, 2H) 7.85 (t, J=7.8 Hz, 1H) 7.55 (d, J=7.1 Hz, 1H) 7.49 (d, J=8.4 Hz, 1H) 7.34-7.41 (m, 1H) 7.27-7.34 (m, 1H) 4.57 (t, J=4.9 Hz, 2H) 4.04 (d, J=13.7 Hz, 2H) 3.87 (t, J=5.0 Hz, 2H) 3.71 (t, J=6.0 Hz, 2H) 3.61-3.62 (m, 2H) 3.30-3.48 (m, 44H) 2.91 (t, J=6.0 Hz, 2H) 2.80 (s, 5H) 2.16 (d, J=13.4 Hz, 2H) 2.07-2.07 (m, 1H) 1.95-2.06 (m, 1H) 1.94-2.07 (m, 2H). LCMS: RT=2.550n, MS cal.: 1169.2, $[M/2+H]^+$=585.3.

Example 13: Synthesis of 1-64

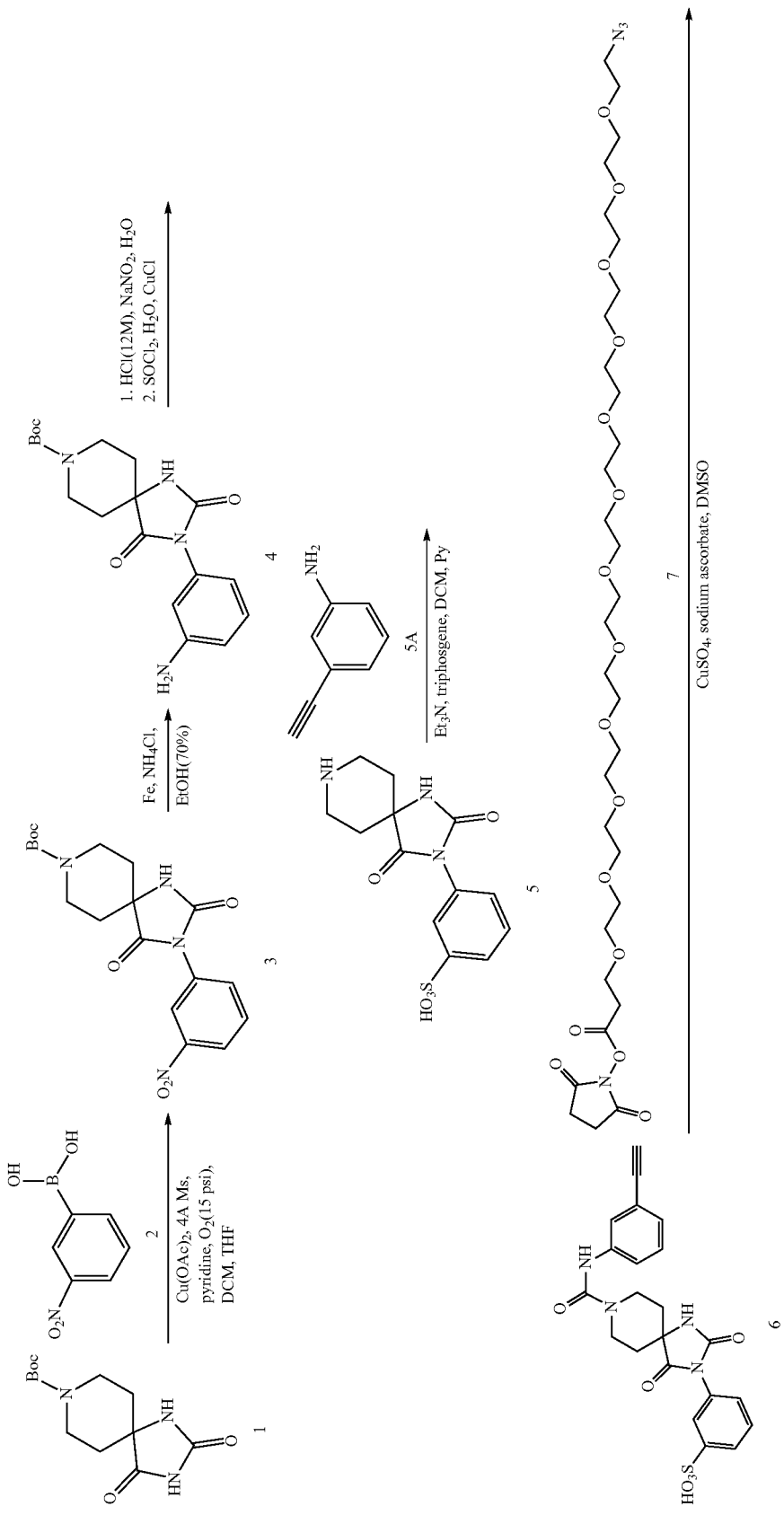

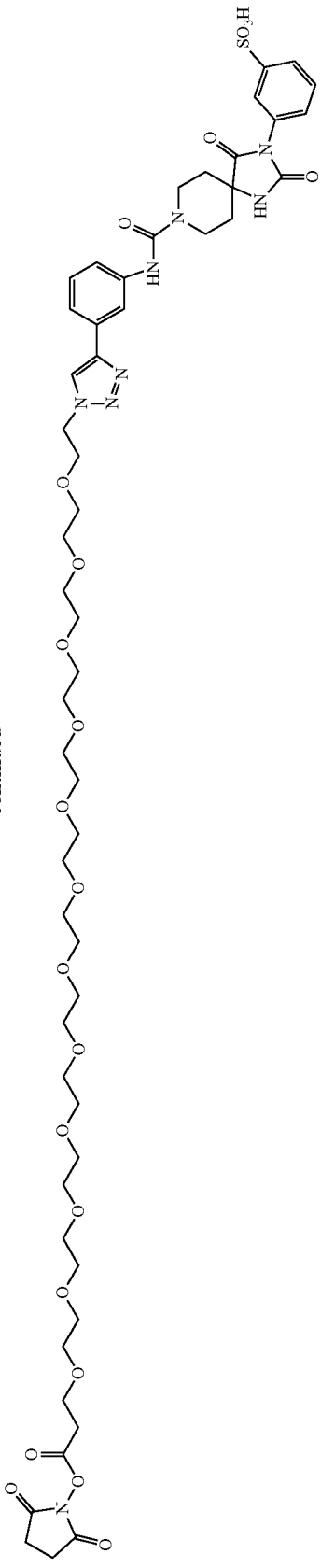
-continued
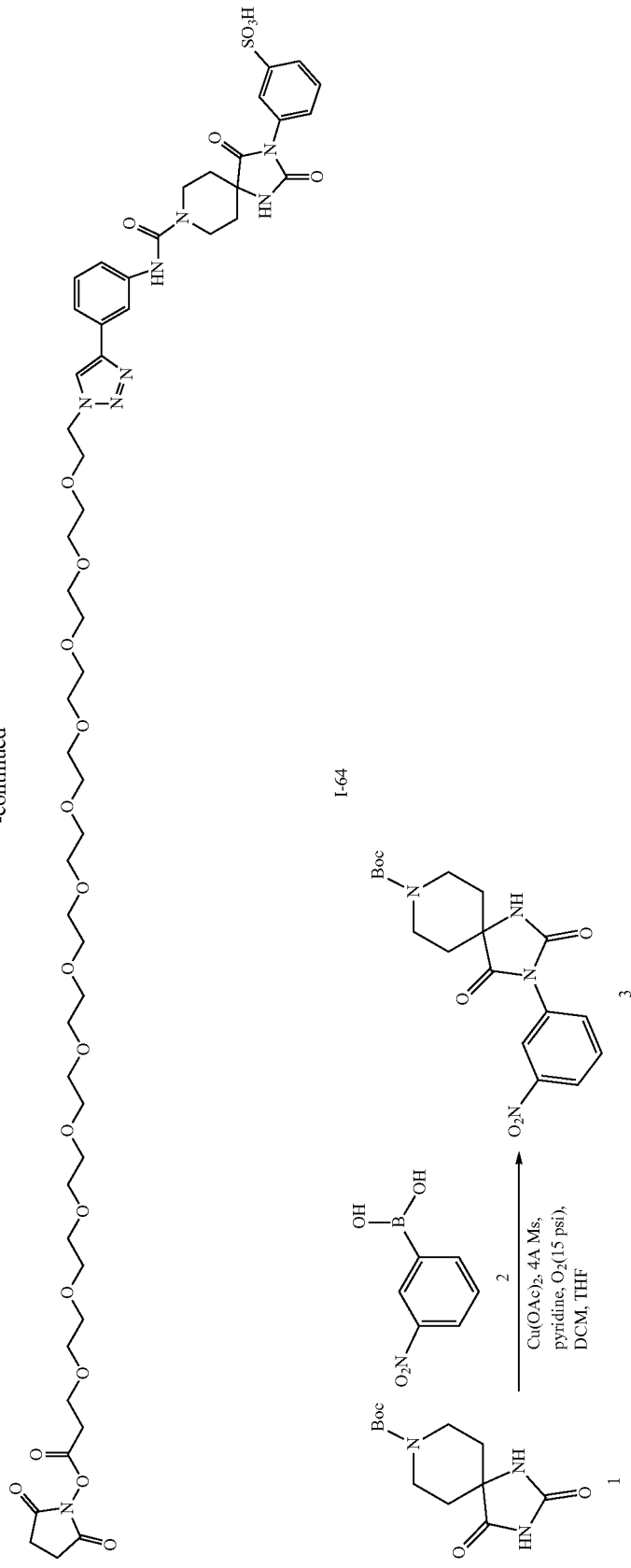
I-64

To a solution of compound 1 (600 mg, 2.23 mmol, 1 eq) and compound 2 (446.30 mg, 2.67 mmol, 1.2 eq) in MeOH (30 mL) and THF (30 mL) was added PYRIDINE (176.24 mg, 2.23 mmol, 179.83 uL, 1 eq), Cu(OAc)$_2$ (404.68 mg, 2.23 mmol, 1 eq) and Molecular sieve 4A (1.2 g, 1.00 eq). The mixture was stirred at 15° C. under O$_2$ (15 psi) for 72 hr. LCMS was detected the desired product MS. The mixture was filtered, added DCM (100 mL), washed with HCl (0.5 M, 20 mL*2), the organic layer was dried with Na$_2$SO$_4$, filtered and concentrated. The residue was purified by column chromatography (SiO$_2$, Petroleum ether/Ethyl acetate=20:1 to 2:1) according to TLC (Plate1, Petroleum ether:Ethyl acetate=1:1, Product R$_f$=0.43). Compound 3 (758 mg, 1.74 mmol, 78.08% yield, 89.6% purity) was obtained as white solid. LCMS: RT=1.353 min, MS cal.: 390.15, [M+Na]$^+$=413.1.

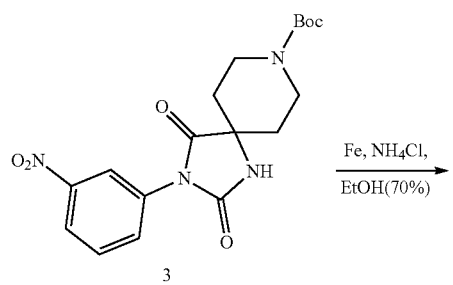

3

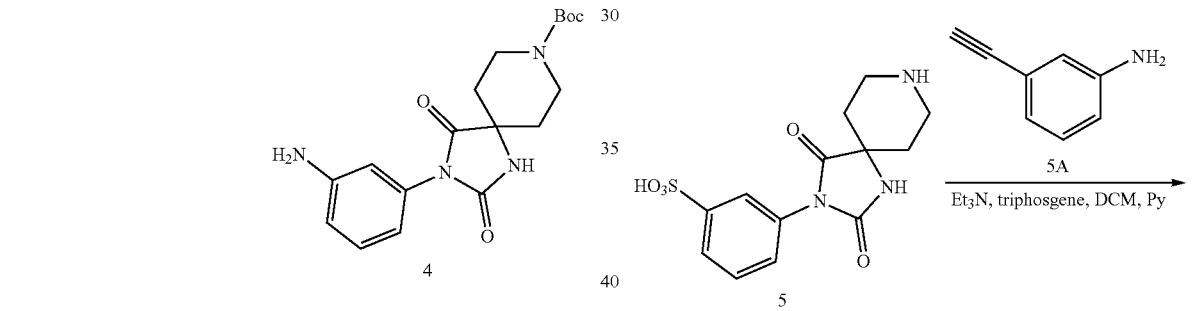

To a solution of compound 3 (200 mg, 512.31 umol, 1 eq) in EtOH (5 mL) was added NH$_4$Cl (82.21 mg, 1.54 mmol, 53.73 uL, 3 eq), HCl (0.5 M, 10.25 uL, 0.01 eq) and Fe (114.44 mg, 2.05 mmol, 4 eq). The mixture was stirred at 80° C. for 2.5 hr. TLC (Petroleum ether:Ethyl acetate=1:1, Product R$_f$=0.26, R$^1$ R$_f$=0.45) showed compound 3 was consumed completely. The mixture was filtered, added water (10 mL), extracted with EtOAc (30 mL*2), the organic layer was dried over Na$_2$SO$_4$, filtered and concentrated. Compound 4 (200 mg, crude) was obtained light yellow solid.

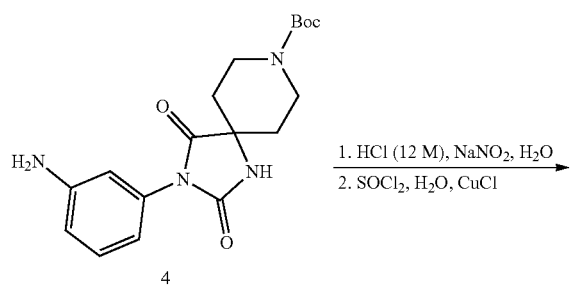

4

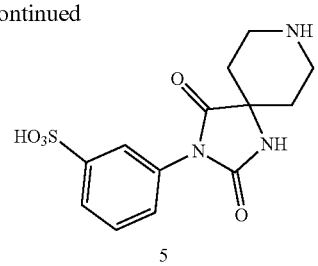

5

To a solution of compound 4 (100 mg, 277.46 umol, 1 eq) was dissolved in HCl (12 M, 508.68 uL, 22 eq) and the resulting solution was cooled to −5° C. A solution of NaNO$_2$ (21.82 mg, 316.31 umol, 1.14 eq) in H$_2$O (0.5 mL) was added slowly with stirring while maintaining the temperature below 0° C. The mixture was stirred for 20 minutes at this temperature. In the second flask, SOCl$_2$ (151.85 mg, 1.28 mmol, 92.59 uL, 4.6 eq) was added drop wise to H$_2$O (1 mL) at −5° C. The resulting solution was allowed to warm to 20° C., and then CuCl (1.37 mg, 13.87 umol, 3.32 e-1 uL, 0.05 eq) was added, and then the reaction mixture was cooled to −5° C. The solution of the first flask was added slowly to the second flask, and the mixture was stirred for 3 hr at −5° C. LCMS was detected the desired product MS. The mixture was filtered. Compound 5 (44 mg, 123.07 umol, 44.36% yield, 91% purity) was obtained as yellow solid. LCMS: RT=0.573 min, MS cal.: 325.07, [M−H]$^+$=324.0.

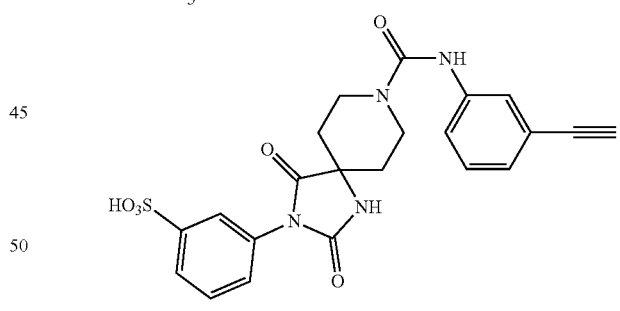

6

To a solution of triphosgene (12.04 mg, 40.57 umol, 0.33 eq) in DCM (2 mL) was added TEA (49.76 mg, 491.79 umol, 68.45 uL, 4 eq) and compound 5A (14.40 mg, 122.95 umol, 1 eq) at −20° C. for 10 min. Then the mixture was added compound 5 (40 mg, 122.95 umol, 1 eq) and PYRIDINE (58.35 mg, 737.69 umol, 59.54 uL, 6 eq), stirred at 25° C. for 30 min. LCMS was detected the desired product MS. The mixture was concentrated. The residue was purified by prep-HPLC (TFA condition). Compound 6 (16 mg, crude) was obtained as white solid. LCMS: RT=1.060 min, MS cal.: 468.11, [M+H]$^+$=468.9.

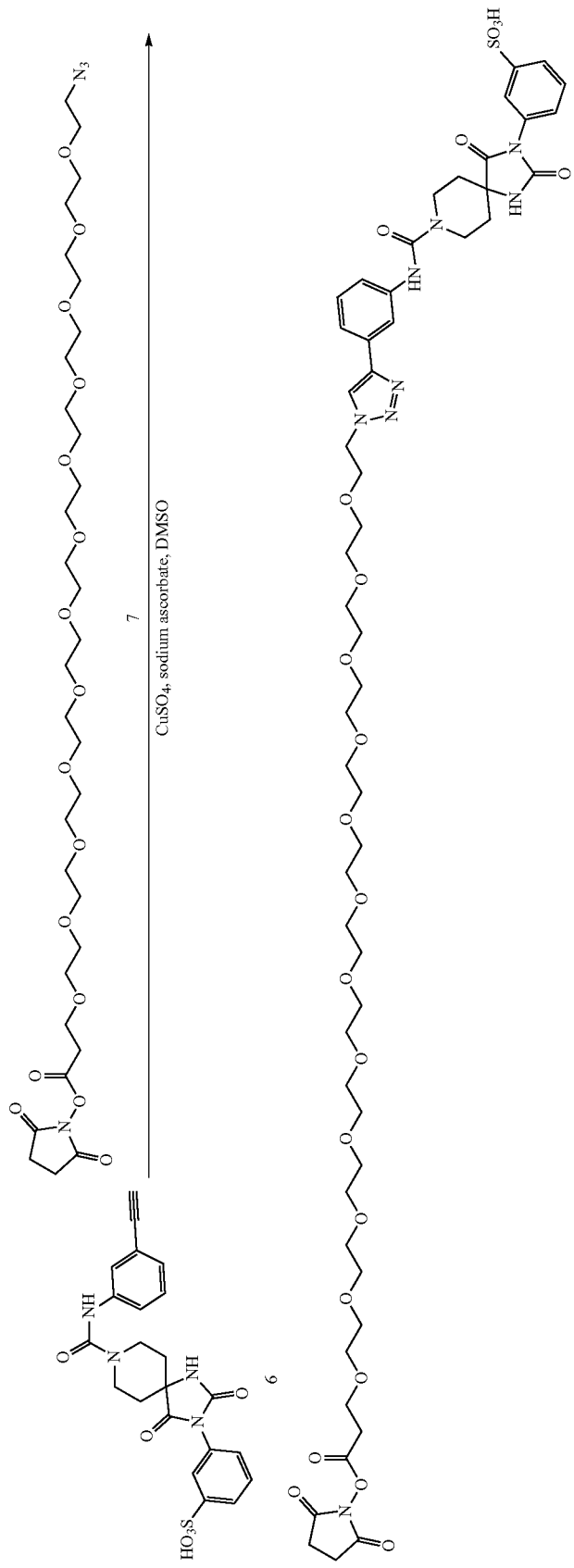

To a solution of compound 6 (14 mg, 29.88 umol, 1 eq) and compound 7 (22.14 mg, 29.88 umol, 1 eq) in DMSO (1 mL) was added CuSO$_4$·5H$_2$O (7.46 mg, 29.88 umol, 1 eq) and sodium; (2R)-2-[(1S)-1,2-dihydroxyethyl]-4-hydroxy-5-oxo-2H-furan-3-olate (11.84 mg, 59.77 umol, 2 eq). The mixture was stirred at 15° C. for 1 hr. LCMS was detected the desired product MS. The mixture was combined. The mixture was filtered. The residue was purified by prep-HPLC (TFA condition) according HPLC. I-64 (24.25 mg, 16.51 umol, 55.23% yield, 82.31% purity) was obtained as colorless oil checked by QCLCMS and HNMR. LCMS: RT=1.078 min, MS cal.: 1208.48, [M/2+H]$^+$=605.6. HPLC: RT=2.152 min. QCLCMS: RT=2.714 min, MS cal.: 1208.48, [M/2+H]$^+$=605.4. $^1$H NMR (400 MHz, DMSO-d$_6$) δ ppm 9.11 (s, 1H), 8.74 (s, 1H), 8.44 (s, 1H), 8.01 (s, 1H), 7.66-7.58 (m, 2H), 7.49-7.41 (m, 2H), 7.40-7.36 (m, 1H), 7.35-7.29 (m, 1H), 7.34-7.28 (m, 1H), 7.28 (s, 1H), 5.75 (s, 1H), 4.56 (br t, J=5.1 Hz, 2H), 4.04 (br d, J=13.8 Hz, 2H), 3.87 (br t, J=5.1 Hz, 2H), 3.70 (br d, J=6.0 Hz, 4H), 3.53-3.45 (m, 47H), 3.34 (br t, J=11.1 Hz, 3H), 2.91 (t, J=5.9 Hz, 2H), 2.80 (s, 4H), 2.59-2.41 (m, 19H), 1.99-1.89 (m, 2H), 1.81 (br d, J=13.3 Hz, 2H).

Example 14: Synthesis of 1-65

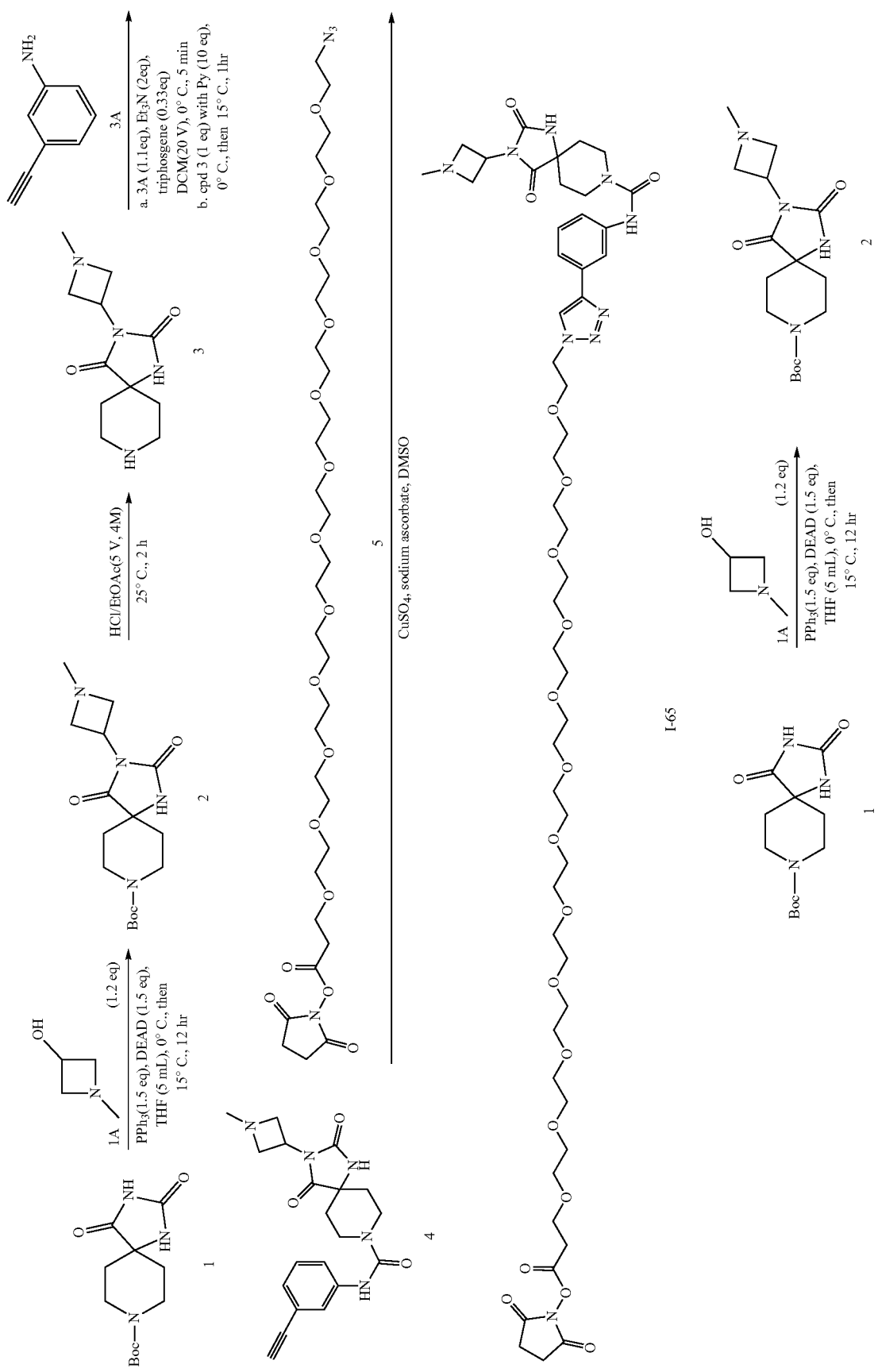

To a solution of compound 1 (0.5 g, 1.86 mmol, 1 eq) and compound 1A (161.75 mg, 1.86 mmol, 1.2 eq) in THF (5 mL) was added PPh$_3$ (633.08 mg, 2.41 mmol, 1.5 eq) and DEAD (420.36 mg, 2.41 mmol, 438.79 uL, 1.5 eq) at 0° C. The mixture was stirred at 15° C. for 12 h. LCMS showed the reaction was completed. The mixture was concentrated in vacuum to give compound 2 (600 mg, crude) as a white solid. LCMS: RT=0.932 min, MS cal.: 338.4, [M+H]$^+$=339.1.

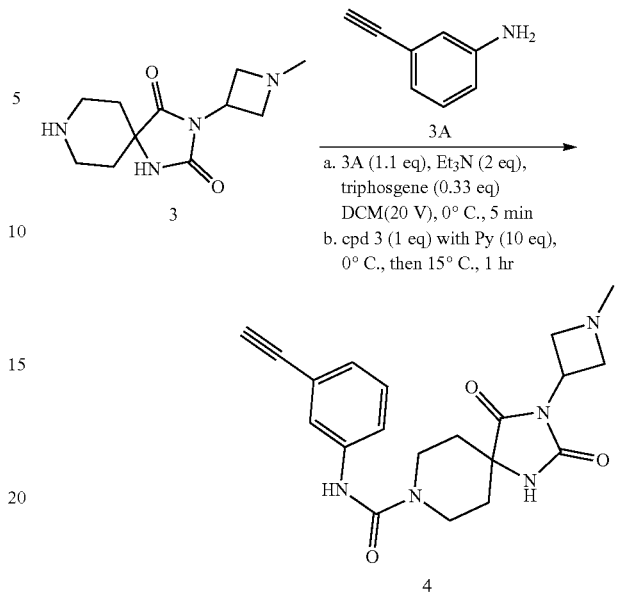

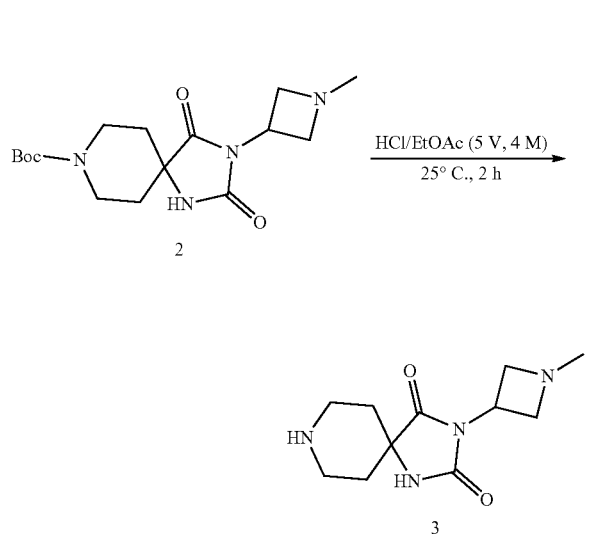 [SMILES: CN1CC(N2C(=O)NC3(CCN(C(=O)OC(C)(C)C)CC3)C2=O)C1 ; CN1CC(N2C(=O)NC3(CCNCC3)C2=O)C1]

The solution of compound 2 (0.2 g, 591.01 umol, 1 eq) in HCl/EtOAc (5 mL, 4 M) was stirred at 25° C. for 2 h. LCMS showed the reaction was completed. The mixture was concentrated in vacuum to give compound 3 (150 mg, 545.96 umol, 92.38% yield, HCl) as a white solid. LCMS: RT=0.107 min, MS cal.: 238.4, [M+H]$^+$=239.1.

To a solution of triphosgene (24.95 mg, 84.08 umol, 0.33 eq) in DCM (5 mL) was added compound 3A (29.85 mg, 254.78 umol, 1 eq) and TEA (103.12 mg, 1.02 mmol, 141.85 uL, 4 eq) at 0° C. The mixture was stirred at 0° C. Then compound 3 (70 mg, 254.78 umol, 1 eq, HCl) and Pyridine (120.92 mg, 1.53 mmol, 123.39 uL, 6 eq) was added to the solution and stirred at 20° C. for 1 h. LCMS the reaction was completed. The mixture was concentrated in vacuum to give crude product. The crude product was purified by prep-HPLC (column: Phenomenex Synergi C18 100*30 mm*4 um; mobile phase: [water (0.1% TFA)–ACN]; B %: 10%-30%, 10 min) to give compound 4 (30 mg, 78.65 umol, 30.87% yield) as a white solid. LCMS: RT=0.938 min, MS cal.: 381.4, [M+H]$^+$=382.1. $^1$H NMR (400 MHz, DMSO-d$_6$) δ ppm 9.08 (s, 1H) 8.70 (s, 1H) 7.63 (s, 1H) 7.41-7.53 (m, 1H) 7.25 (t, J=7.8 Hz, 1H) 7.04 (d, J=7.8 Hz, 1H) 4.65-5.05 (m, 2H) 4.43 (s, 2H) 4.12 (s, 1H) 3.87-4.02 (m, 2H) 3.23-3.31 (m, 2H) 2.91 (s, 3H) 1.77-1.89 (m, 2H) 1.67 (d, J=13.4 Hz, 2H).

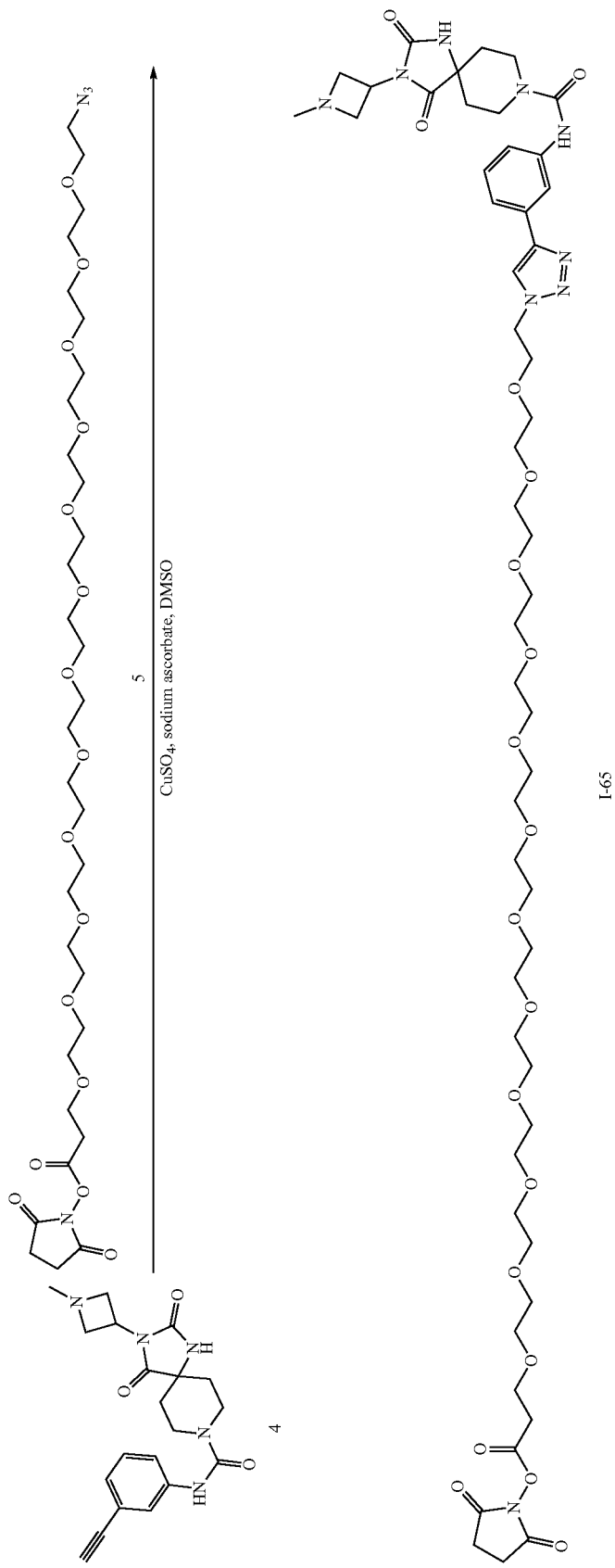

To a solution of compound 4 (0.02 g, 52.43 umol, 1 eq) and compound 5 (38.84 mg, 52.43 umol, 1 eq) in DMSO (1 mL) was added $CuSO_4 \cdot 5H_2O$ (26.18 mg, 104.87 umol, 2 eq) and SODIUM ASCORBATE (20.78 mg, 104.87 umol, 2 eq). The mixture was stirred at 25° C. for 1 h. LCMS showed the reaction was completed. The mixture was filtered to give crude product. The crude product was purified by prep-HPLC (column: Luna C18 100*30 5 u; mobile phase: [water (0.1% TFA)–ACN]; B %: 10%-40%, 10 min) to give I-65 (17.03 mg, 13.51 umol, 25.76% yield, 89% purity) as a white solid. LCMS: RT=1.095 min, MS cal.: 1122.2, $[M/2+H]^+$=562.0. $^1$H NMR (400 MHz, CHLOROFORM-d) δ ppm 8.01-8.15 (m, 2H) 7.87 (s, 1H) 7.68 (s, 1H) 7.56 (d, J=7.9 Hz, 1H) 7.46 (d, J=7.3 Hz, 1H) 7.32 (t, J=7.9 Hz, 1H) 5.12 (s, 1H) 4.41-4.75 (m, 5H) 3.88 (s, 2H) 3.83 (t, J=6.4 Hz, 2H) 3.50-3.69 (m, 48H) 3.04 (s, 2H) 2.90 (t, J=6.4 Hz, 2H) 2.84 (s, 3H) 2.32 (s, 5H) 1.99 (s, 2H) 1.81 (s, 2H). LCMS: RT=1.944 min, MS cal.: 1122.2, $[M/2+H]^+$=561.8.

Example 15: Synthesis of I-66

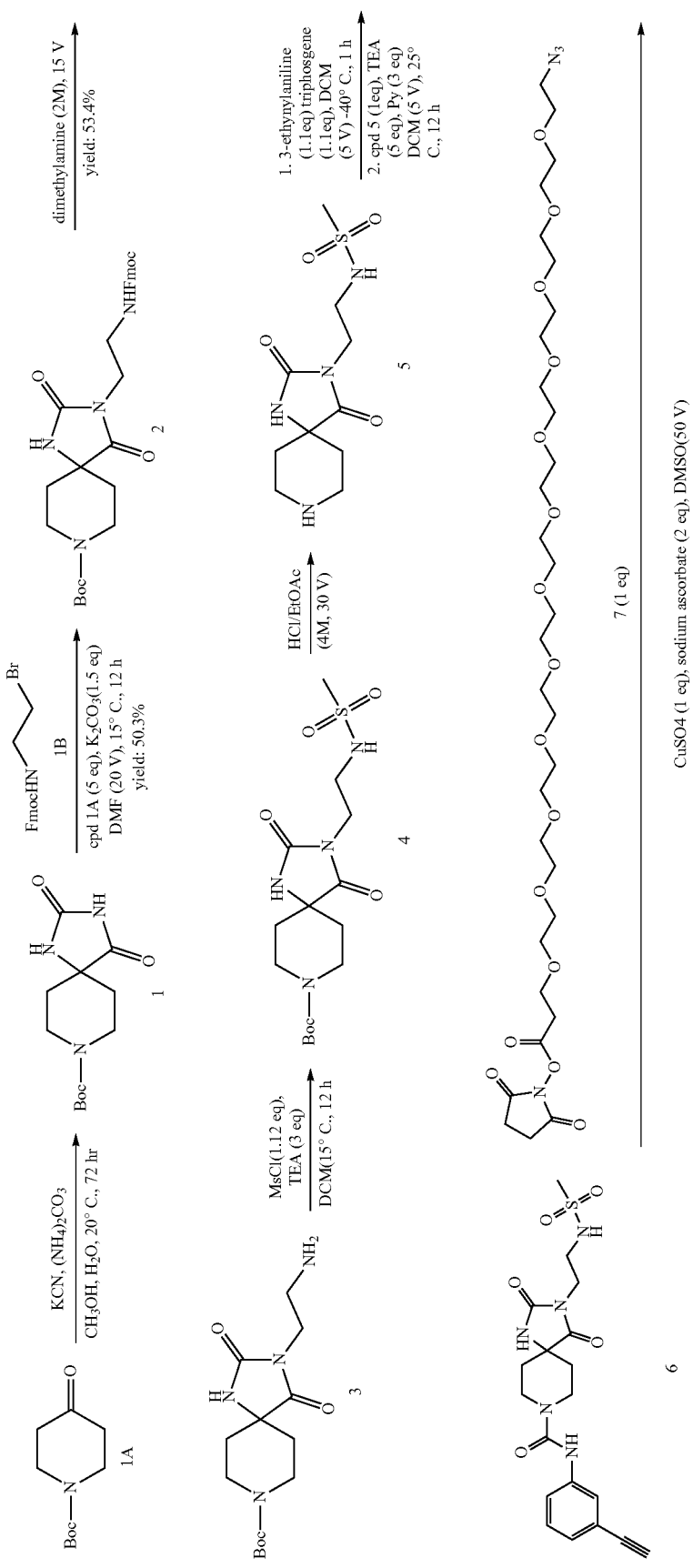

-continued
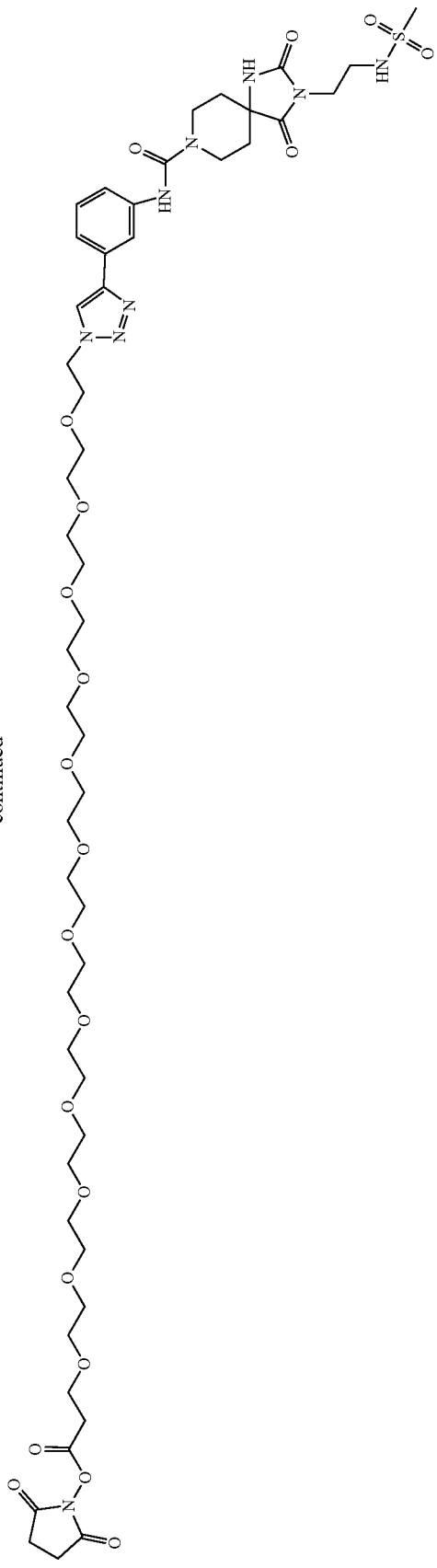

A solution of KCN (23.53 g, 361.36 mmol, 15.48 mL, 2.4 eq) in H₂O (200 mL) was added dropwise to the solution of compound 1A (30 g, 150.57 mmol, 1 eq) and (NH₄)₂CO₃ (31.83 g, 331.25 mmol, 35.36 mL, 2.2 eq) in MeOH (200 mL) and H₂O (200 mL). The mixture was stirred at 20° C. for 72 h. LCMS showed the reaction was completed. The reaction mixture was filtered and concentrated in vacuum to give compound 1 (20 g, 74.27 mmol, 49.33% yield) as a white solid. LCMS: ¹H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

To a solution of compound 2 (240 mg, 448.93 umol, 1 eq) was added N-methylmethanamine (2 M, 10.50 mL, 46.78 eq). The mixture was stirred at 15° C. for 2 hr. LCMS showed the desired compound was detected. The reaction mixture was concentrated under reduced pressure to remove solvent. The residue was washed with Petroleum ether 12 mL (4 mL*3), filtered and the concentrated under reduced pressure to give a residue. The residue was purified by prep-HPLC (basic condition). Compound 3 (62 mg, 198.49 umol, 44.21% yield) was obtained as a white solid. LCMS: RT=1.062 min, MS cal.: 312.1, [M+H]⁺=313.2.

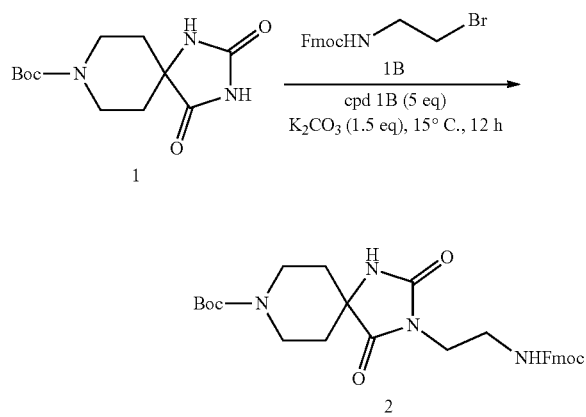

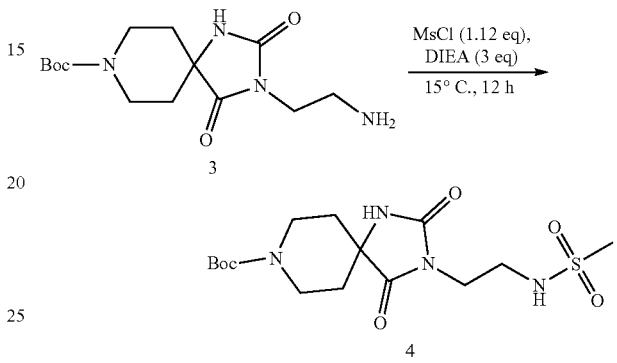

To a solution of compound 1 (300 mg, 1.11 mmol, 1 eq) in DMF (8 mL) was added compound 1B (1.93 g, 5.57 mmol, 5 eq) and K₂CO₃ (230.95 mg, 1.67 mmol, 1.5 eq). The mixture was stirred at 15° C. for 12 h. TLC (Petroleum ether:Ethyl acetate=0:1, R_f=0.4) indicated one major new spot was detected. The reaction mixture was diluted with H₂O 25 mL and extracted with Ethyl acetate 27 mL (9 mL*3). The combined organic layers were washed with brine 20 mL, dried over Na₂SO₄, filtered and concentrated under reduced pressure to give a residue. The residue was purified by column chromatography (Petroleum ether/Ethyl acetate=10:1 to 1:2). Compound 2 (241 mg, 450.80 umol, 40.47% yield) was obtained as a white solid. The structure was confirmed by HNMR. 1H NMR (400 MHz, DMSO-d6) δ ppm 8.73 (s, 1H), 7.87 (d, J=7.5 Hz, 2H), 7.65 (d, J=7.5 Hz, 2H), 7.46-7.37 (m, 3H), 7.34-7.28 (m, 2H), 4.24-4.19 (m, 2H), 4.19-4.13 (m, 1H), 3.76 (br d, J=11.7 Hz, 2H), 3.58 (t, J=6.6 Hz, 1H), 3.41 (br d, J=5.3 Hz, 1H), 3.20-3.12 (m, 2H), 3.09 (br s, 1H), 1.77-1.72 (m, 1H), 1.70-1.61 (m, 2H), 1.54 (br d, J=13.9 Hz, 2H), 1.38 (s, 9H).

To a solution of compound 3 (60 mg, 192.08 umol, 1 eq) in DCM (2 mL) was added MsCl (100 mg, 872.97 umol, 67.57 uL, 4.54 eq), and then DIEA (74.48 mg, 576.25 umol, 100.37 uL, 3 eq) was added dropwise at 0° C. The mixture was stirred at 15° C. for 12 hr. TLC (Dichloromethane:Methanol=10:1, R_f=0.3) indicated Reactant 1 was consumed completely and one new spot formed. The reaction mixture was used for the next step directly without work up. The residue was purified by prep-TLC (Dichloromethane:Methanol=10:1, Rf=0.3). Compound 4 (50 mg, 128.06 umol, 66.67% yield) was obtained as a yellow solid.

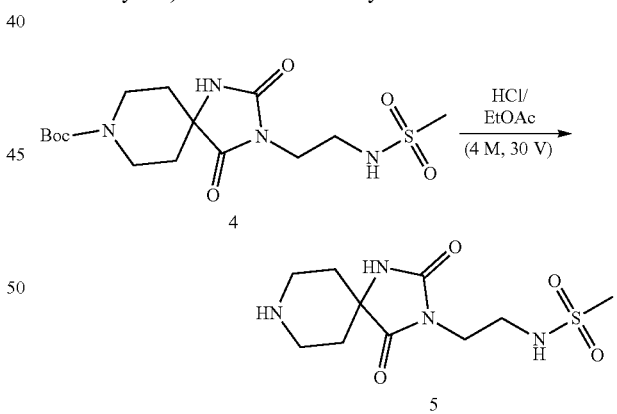

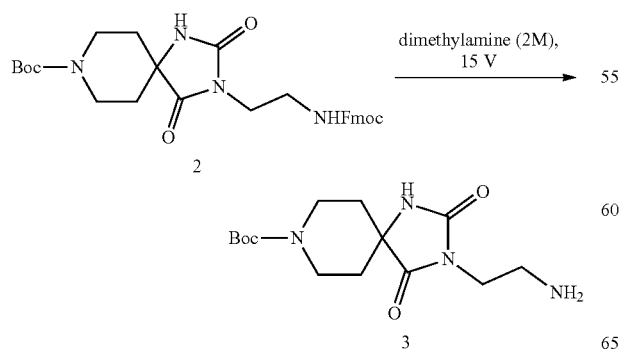

To a solution of compound 4 (45 mg, 115.25 umol, 1 eq) in HCl/EtOAc (4 M, 28.81 uL, 1 eq) was stirred at 15° C. for 2 hrs. LCMS showed the starting material was consumed completely and the desired MS was detected. The reaction mixture was concentrated under reduced pressure to give compound 5 (33 mg, 113.66 umol, 98.62% yield) as a white solid, which was confirmed by H NMR. The residue was used directly next step without purification. LCMS: RT=0.244 min, MS cal.: 290.10, [M+H]⁺=291.1. ¹H NMR (400 MHz, DMSO-d₆) δ=8.89 (s, 2H), 8.58 (br s, 1H), 7.21 (t, J=6.4 Hz, 1H), 3.44 (br t, J=6.1 Hz, 2H), 3.39-3.36 (m, 2H), 3.19-3.05 (m, 4H), 2.87 (s, 3H), 2.06 (br t, J=10.5 Hz, 2H), 1.84 (br d, J=14.7 Hz, 2H).

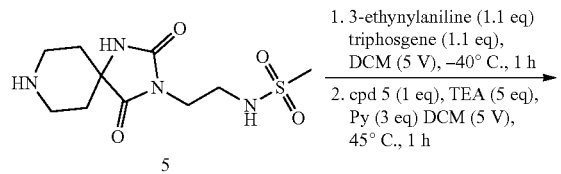

was dried over anhydrous Na$_2$SO$_4$ and concentrated under reduced pressure. The residue was purified by prep-TLC (Dichloromethane:Methanol=10:1) to give compound 6 (44 mg, 101.50 umol, 98.24% yield) as a white solid, which was confirmed by H NMR. LCMS: RT=1.030 min, MS cal.: 433.48, [M+H]$^+$=434.1. $^1$H NMR (400 MHz, CHLOROFORM-d) δ=11.89 (br s, 1H), 7.56 (s, 1H), 7.53 (br s, 1H), 7.44 (br d, J=8.3 Hz, 1H), 7.24-7.18 (m, 1H), 7.18-7.11 (m, 1H), 5.70 (t, J=6.1 Hz, 1H), 4.04-3.93 (m, 1H), 3.68-3.62 (m, 1H), 3.49 (br t, J=10.3 Hz, 1H), 3.42-3.32 (m, 1H), 3.10 (q, J=6.8 Hz, 2H), 3.04 (s, 1H), 2.93 (s, 1H), 2.08 (ddd, J=4.2, 9.8, 13.4 Hz, 1H), 1.81 (br d, J=14.7 Hz, 1H), 1.65 (s, 1H), 1.40 (t, J=7.3 Hz, 2H), 1.47-1.34 (m, 1H).

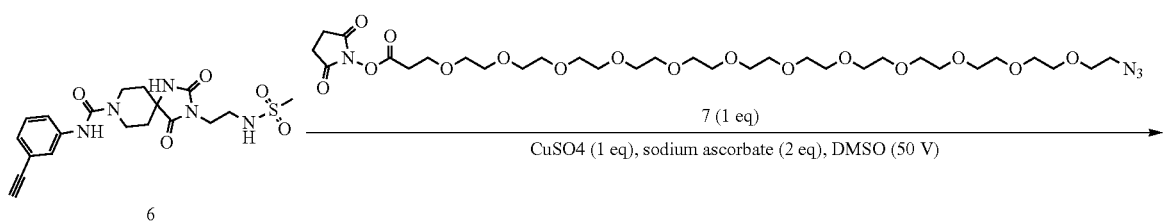

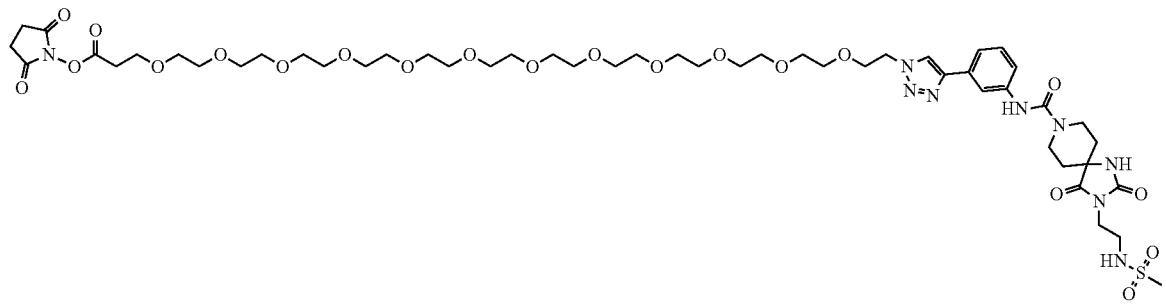

I-66

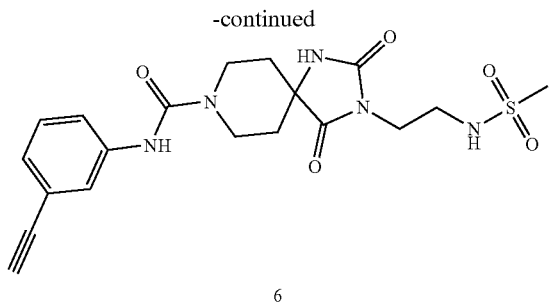

To a solution of 3-ethynylaniline (12.10 mg, 103.33 umol, 1 eq) in DCM (2 mL) was added triphosgene (10.12 mg, 34.10 umol, 0.33 eq) in DCM (2 mL) dropwise at −40° C. stirred for 1 h. Then the reaction mixture was added compound 5 (30 mg, 103.33 umol, 1 eq), Py (49.04 mg, 619.97 umol, 50.04 uL, 6 eq) and TEA (41.82 mg, 413.31 umol, 57.53 uL, 4 eq) in DCM (2 mL) and stirred at 45° C. for 1 h. LCMS showed the starting material was consumed completely and a main peak with desired MS was detected. The reaction mixture was added EtOAc (40 mL), then the mixture was washed with NH4Cl (40 mL). The organic layer A solution of compound 6 (50 mg, 67.50 umol, 1 eq) and compound 7 (29.26 mg, 67.50 umol, 1 eq) in DMSO (1 mL) was added CuSO$_4$·5H$_2$O (16.85 mg, 67.50 umol, 1 eq) and sodium ascorbate (26.74 mg, 134.99 umol, 2 eq) stirred at 25° C. for 1 hr. LCMS showed a peak with desired MS was detected. The reaction mixture was filtered. The filtrate was purified by prep-HPLC (column: Nano-micro Kromasil C18 100*30 mm 5 um; mobile phase: [water (0.1% TFA)−ACN]; B %: 15%-42%, 10 min) to give I-66 (7.84 mg, 6.39 umol, 9.46% yield, 95.67% purity) as a colorless oil, which was confirmed by H NMR and QC LCMS. LCMS: RT=1.982 min, MS cal.: 1174.27, [M/2+H]$^+$=588.1, [M+H]$^+$=1174.6. $^1$H NMR (400 MHz, DMSO-d$_6$) δ=8.83 (s, 1H), 8.71 (s, 1H), 8.44 (s, 1H), 8.01 (s, 1H), 7.46 (br d, J=7.8 Hz, 1H), 7.39-7.35 (m, 1H), 7.34-7.26 (m, 1H), 7.22 (t, J=6.4 Hz, 1H), 4.56 (t, J=5.1 Hz, 2H), 4.00 (br d, J=14.2 Hz, 2H), 3.87 (t, J=5.1 Hz, 2H), 3.71 (t, J=6.1 Hz, 2H), 3.57-3.51 (m, 11H), 3.50-3.48 (m, 24H), 3.48-3.45 (m, 13H), 3.14 (q, J=6.4 Hz, 2H), 2.92 (t, J=5.9 Hz, 2H), 2.88 (s, 3H), 2.80 (s, 4H), 1.82 (br t, J=10.3 Hz, 2H), 1.64 (br d, J=13.7 Hz, 2H). LCMS: RT=2.252 min, MS cal.: 1174.27, [M/2+H]$^+$=587.8, [M+H]$^+$=1174.5.

Example 16: Synthesis of I-67
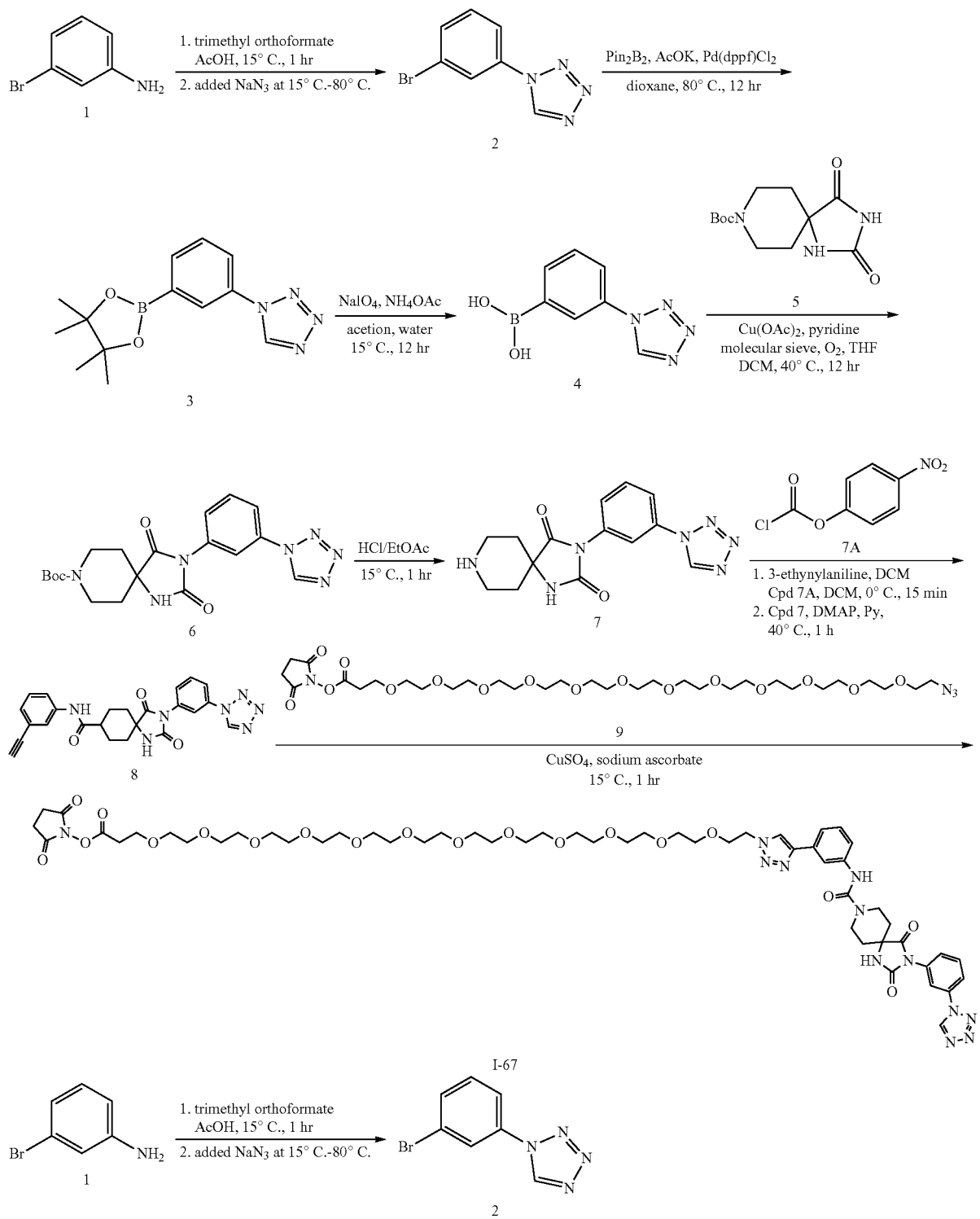
The solution of compound 1 (5 g, 29.07 mmol, 3.16 mL, 1 eq) in AcOH (30 mL) and trimethoxymethane (3.58 g, 33.72 mmol, 3.70 mL, 1.16 eq) was stirred at 15° C. for 1 hour. After then NaN$_3$ (3.14 g, 48.25 mmol, 1.66 eq) was added and the mixture was stirred at 80° C. for 2 hours. LCMS was detected the desired product MS. Added 200 mL H$_2$O to the mixture and filtered. Compound 2 (6 g, crude) was obtained as white solid. LCMS: RT=1.216 min, MS cal.: 223.97, [M+H]-=225.0.

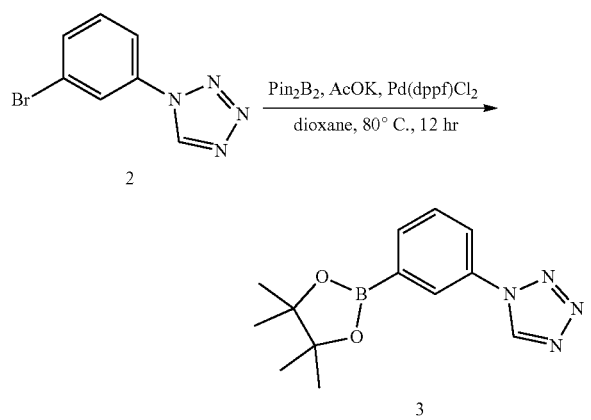

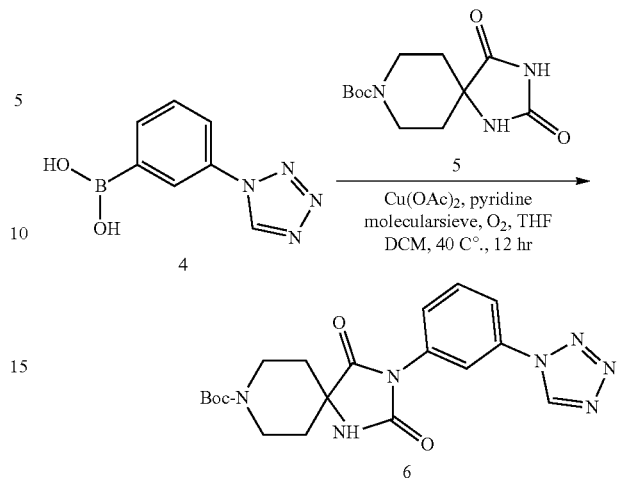

To a solution of compound 2 (2 g, 8.89 mmol, 1 eq) and Pin$_2$B$_2$ (2.71 g, 10.66 mmol, 1.2 eq) in dioxane (20 mL) was added Pd(dppf)Cl$_2$ (650.28 mg, 888.71 umol, 0.1 eq) and potassium; acetate (1.74 g, 17.77 mmol, 2 eq). The mixture was stirred at 80° C. for 12 hr. LCMS was detected the desired product MS. The mixture was added EtOAc (300 mL), filtered and washed with brine (50 mL), the organic layer was dried over Na$_2$SO$_4$, filtered and concentrated. The residue was purified by column chromatography (SiO$_2$, Petroleum ether:Ethyl acetate=10:1 to 7:1) according to TLC (Plate 1, Petroleum ether:Ethyl acetate=1:1, Product R$_f$=0.48). Compound 3 (3.1 g, crude) was obtained as white solid. LCMS: RT=1.204 min, MS cal.: 272.14, [M+H]$^+$=273.1.

To a solution of compound 4 (246.90 mg, 1.30 mmol, 1.00 eq) and compound 5 (350 mg, 1.30 mmol, 1 eq) in DCM (1 mL) and THF (3 mL) was added PYRIDINE (308.41 mg, 3.90 mmol, 314.71 uL, 3 eq), Cu(OAc)$_2$ (236.07 mg, 1.30 mmol, 1 eq), Molecular sieve 4A (700 mg). The mixture was stirred at 40° C. under O$_2$ (15 Psi) for 12 hr. LCMS was detected the desired product MS. The mixture was added DCM (80 mL), filtered and washed with HCl (0.2 M, the organic layer was dried over Na$_2$SO$_4$, filtered and concentrated. Compound 6 (560 mg, crude) was obtained as white solid. LCMS: RT=1.239 min, MS cal.: 413.28, [M+H]$^+$=414.2.

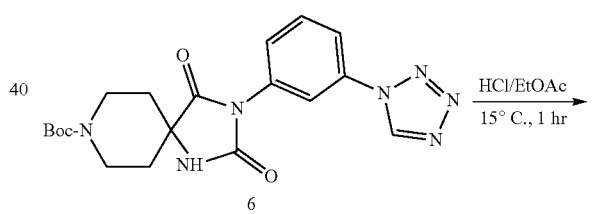

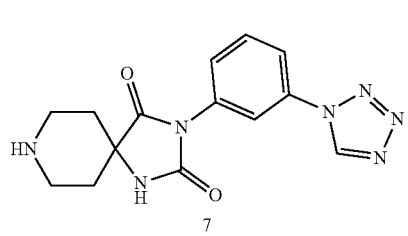

To a solution of compound 3 (500 mg, 1.84 mmol, 1 eq) in acetone (8 mL) and H$_2$O (5 mL) was added NaIO$_4$ (1.18 g, 5.51 mmol, 305.46 uL, 3 eq) and NH$_4$OAc (283.28 mg, 3.67 mmol, 735.00 uL, 2 eq). The mixture was stirred at 15° C. for 12 hr. LCMS was detected the desired product MS. The mixture was filtered, the filter was dissolved with water (5 mL), adjusted pH to 3 (0.2 M HCl), extracted with EtOAC (10 mL), the organic layer was dried with Na$_2$SO$_4$, filtered and concentrated. Compound 4 (258 mg, 1.27 mmol, 69.16% yield, 93.57% purity) was obtained as yellow solid. LCMS: RT=1.239 min, MS cal.: 413.28, [M+H]$^+$=414.2.

To a solution of compound 6 (180 mg, 435.38 umol, 1 eq) in HCl/MeOH (10 mL) was stirred at 15° C. for 1 hr. LCMS was detected the desired product MS. The mixture was added HCl (2M, 15 mL) and EtOAc (10 mL*2), the aqueous layer was concentrated to give compound 7 (120 mg, crude, HCl) as light yellow solid. LCMS: RT=0.765 min, MS cal.: 313.13, [M+H]$^+$=314.2.

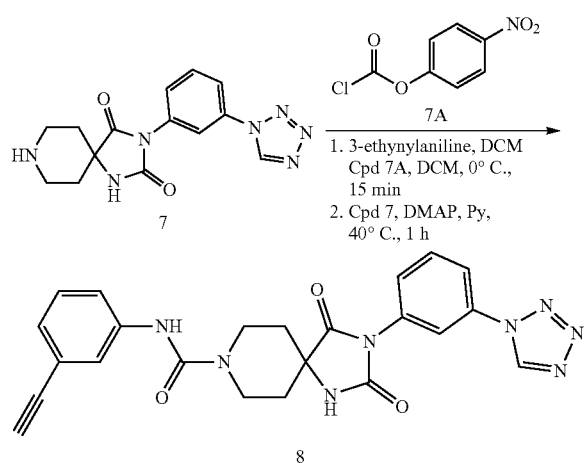

To a solution of compound 7A (34.58 mg, 171.54 umol, 1.2 eq) in DCM (2 mL) was added 3-ethynylaniline (21.77 mg, 185.83 umol, 1.3 eq) at 0° C. for 0.5 hr. The mixture was added PYRIDINE (33.92 mg, 428.85 umol, 34.61 uL, 3 eq) DMAP (34.93 mg, 285.90 umol, 2 eq) and compound 7 (50 mg, 142.95 umol, 1 eq, HCl), stirred at 40° C. for 1 hr. LCMS was detected the desired product MS. The mixture was concentrated. The residue was purified by prep-TLC (Plate 1, Dichloromethane:Methanol=10:1, product R$_f$=0.38). Compound 8 (27 mg, crude) was obtained as yellow oil. LCMS: RT=1.209 min, MS cal.: 456.17, [M+H]$^+$=457.2.

To a solution of compound 9 (24.34 mg, 32.86 umol, 1 eq) and compound 8 (15 mg, 32.86 umol, 1 eq) in DMSO (1 mL) was added CuSO$_4$·5H$_2$O (8.21 mg, 32.86 umol, 1 eq) and sodium; (2R)-2-[(1S)-1,2-dihydroxyethyl]-4-hydroxy-5-oxo-2H-furan-3-olate (13.02 mg, 65.72 umol, 2 eq). The mixture was stirred at 15° C. for 1 hr. LCMS was detected the desired product MS. The mixture was filtered. The filtrate was purified by prep-HPLC (TFA condition) according to HPLC. I-67 (7.77 mg, 6.29 umol, 19.15% yield, 96.97% purity) was obtained as colorless oil checked by QCLCMS and HNMR. LCMS: RT=1.019 min, MS cal.: 1196.53, [M/2+H]$^+$=599.6. HPLC: RT=2.361 min QCLCMS: RT=2.754 min, MS cal.: 1196.53, [M/2+H]$^+$=599.3. $^1$H NMR (400 MHz, DMSO-d$_6$) δ ppm 10.14 (s, 1H), 9.25 (s, 1H), 8.75 (s, 1H), 8.45 (s, 1H), 8.07 (s, 1H), 8.02 (s, 1H), 7.96 (br d, J=8.1 Hz, 1H), 7.78 (t, J=8.1 Hz, 1H), 7.65 (d, J=8.6 Hz, 1H), 7.48 (br d, J=7.8 Hz, 1H), 7.41-7.35 (m, 1H), 7.34-7.26 (m, 1H), 4.57 (t, J=5.1 Hz, 2H), 4.05 (br d, J=13.9 Hz, 2H), 3.87 (t, J=5.1 Hz, 2H), 3.71 (t, J=6.0 Hz, 2H), 3.57-3.45 (m, 50H), 3.48-3.44 (m, 1H), 2.91 (t, J=6.0 Hz, 2H), 2.80 (s, 4H), 2.01-1.92 (m, 2H), 1.89-1.80 (m, 2H).

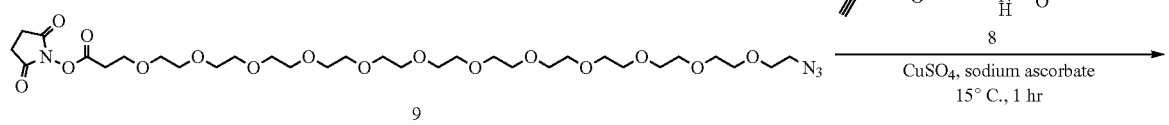

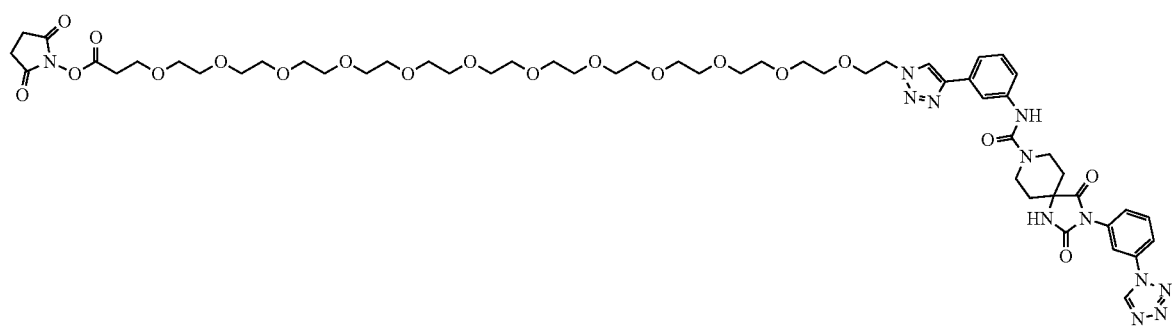

I-67

Example 17: Synthesis of I-68
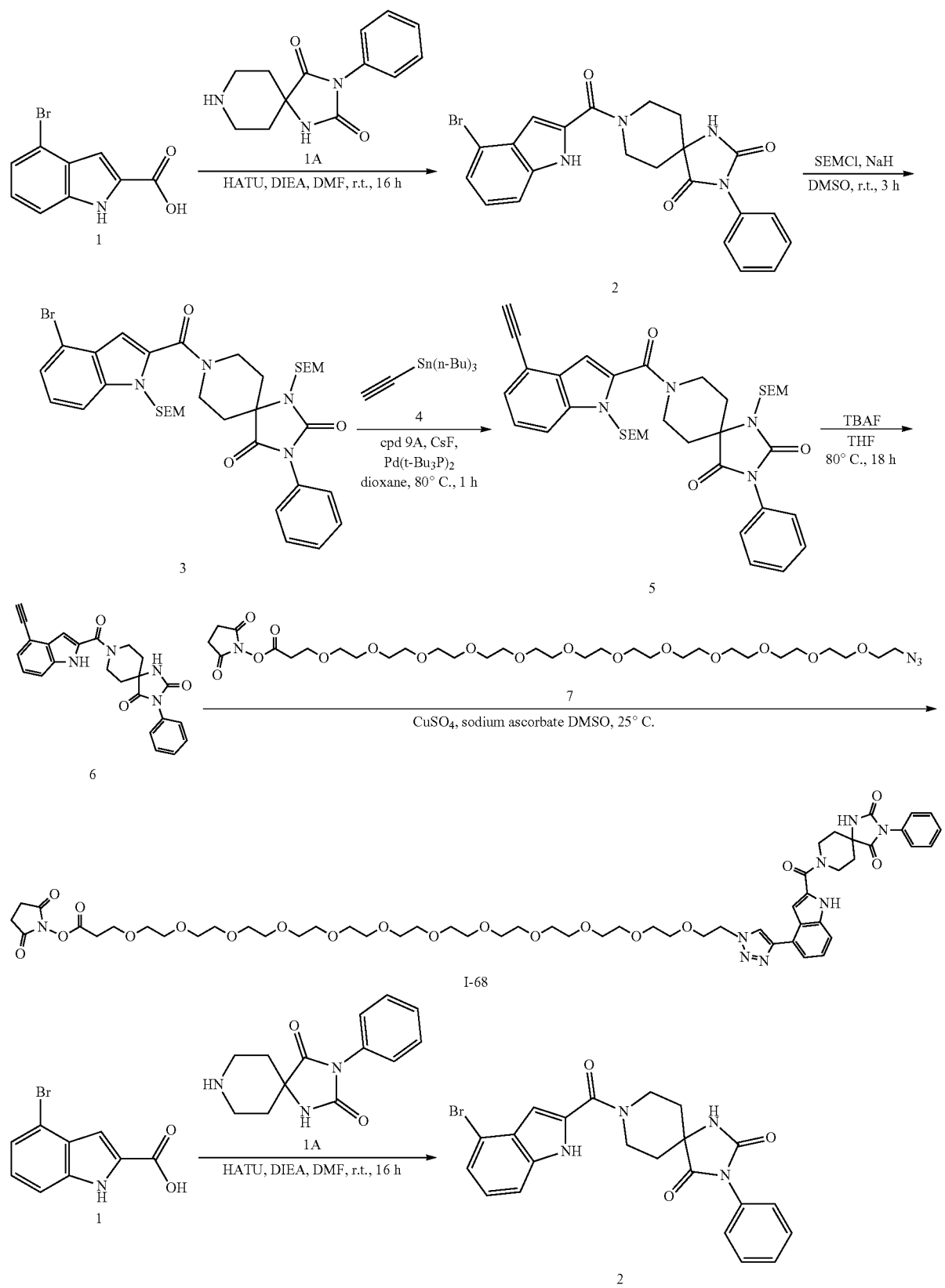

To a solution of compound 1 (0.36 g, 1.49 mmol, 1 eq) and compound 1A (366.33 mg, 1.49 mmol, 1 eq) in DMF (10 mL) was added HATU (851.82 mg, 2.24 mmol, 1.5 eq), DIEA (579.07 mg, 4.48 mmol, 780.41 uL, 3 eq) stirred at 15° C. for 16 hrs. LCMS showed the starting material was consumed and the desired MS was detected. The reaction was triturated with water (20 mL) and filtered. The filter cake was triturated with EtOAc (20 mL) and filtered. The filter cake was concentrated to give compound 2 (0.5 g, 1.07 mmol, 71.64% yield) as a yellow solid, which was confirmed. The residue was used directly next step without purification. LCMS: RT=1.345 min, MS cal.: 467.32, [M+H]$^+$=468.7. $^1$H NMR (400 MHz, DMSO-d$_6$) δ ppm 12.06 (s, 1H), 9.23 (s, 1H), 7.54-7.44 (m, 3H), 7.43-7.36 (m, 3H), 7.30 (d, J=6.8 Hz, 1H), 7.17-7.10 (m, 1H), 6.72 (d, J=2.0 Hz, 1H), 4.38-4.20 (m, 2H), 3.57 (br s, 2H), 2.14-1.96 (m, 2H), 1.89 (br d, J=13.2 Hz, 2H).

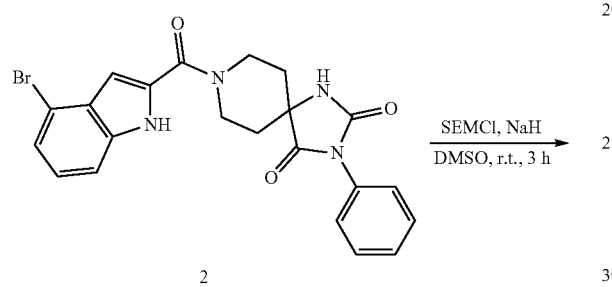

2

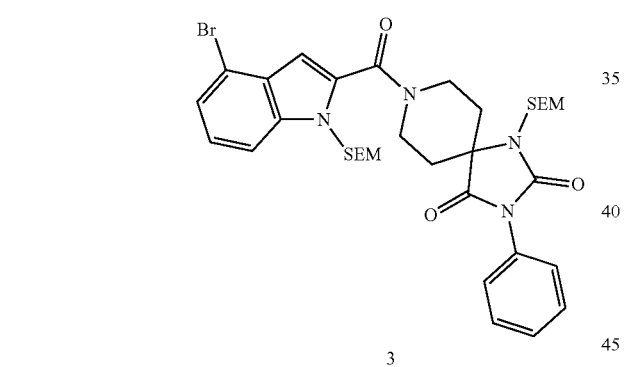

3

To a solution of compound 2 (500.00 mg, 1.07 mmol, 1 eq) in DMSO (10 mL) was added NaH (512.49 mg, 12.81 mmol, 60% purity, 12 eq) stirred at 15° C. for 1 hr. Then added SEM-Cl (2.14 g, 12.81 mmol, 2.27 mL, 12 eq) at 15° C., the mixture was stirred at 15° C. for 2 hrs. LCMS was detected the desired product MS. The reaction was added water (80 mL) and extracted with EtOAc (50*2 mL), then organic phase was dried over Na$_2$SO$_4$ and concentrated. The residue was purified by column (PE:EtOAc=5:1) to give compound 3 (0.6 g, 823.25 umol, 77.11% yield) as a colorless oil, which was confirmed by H NMR. $^1$H NMR (400 MHz, CHLOROFORM-d) δ ppm 7.53-7.46 (m, 3H), 7.44-7.34 (m, 4H), 7.21-7.14 (m, 1H), 6.73-6.73 (m, 1H), 6.73 (s, 1H), 5.68 (s, 2H), 4.98 (s, 2H), 4.80 (br d, J=17.6 Hz, 1H), 4.31 (br d, J=6.2 Hz, 1H), 3.98 (br s, 1H), 3.73-3.60 (m, 3H), 3.58-3.44 (m, 2H), 2.28 (br s, 2H), 1.99 (br s, 2H), 1.00-0.94 (m, 2H), 0.91-0.86 (m, 2H), 0.04 (s, 8H), −0.03-0.06 (m, 9H). LCMS: RT=1.885 min MS cal.: 727.84, [M+Na]-=750.8.

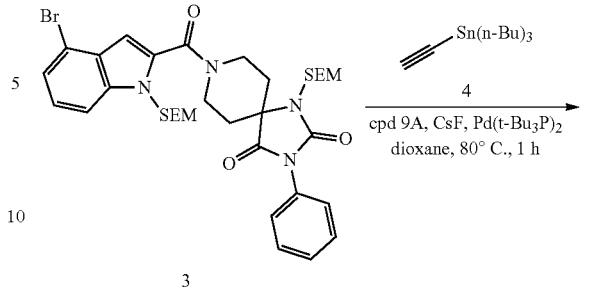

3

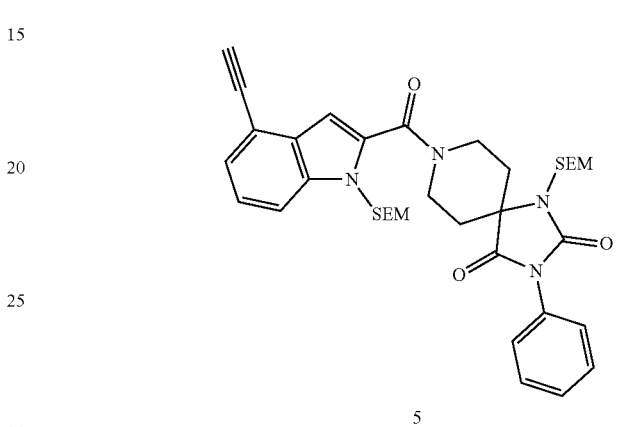

5

To a solution of compound 3 (0.5 g, 686.97 umol, 1 eq) in dioxane (8 mL) was added (70.22 mg, 137.39 umol, 0.2 eq), CsF (313.05 mg, 2.06 mmol, 75.98 uL, 3 eq). Then added tributyl(ethynyl)stannane (432.90 mg, 1.37 mmol, 397.16 uL, 2 eq) at 15° C., the mixture was stirred at 80° C. for 1 hr. TLC (Petroleum ether:Ethyl acetate=2:1, R$_f$=0.35) showed new spot generated. The reaction was added SiO$_2$ (5 g) and concentrated. The residue was purified by column (PE:EtOAc=1:4) to give compound 5 (0.3 g, 445.79 umol, 64.89% yield) as a colorless oil, which was confirmed by H NMR. $^1$H NMR (400 MHz, CHLOROFORM-d) δ ppm 7.57-7.47 (m, 3H), 7.44-7.37 (m, 4H), 7.29 (s, 1H), 7.25 (s, 1H), 6.85 (s, 1H), 5.70 (s, 2H), 4.97 (s, 2H), 4.80 (br d, J=16.6 Hz, 1H), 4.32 (br s, 1H), 4.00 (br s, 1H), 3.80 (br s, 1H), 3.69-3.61 (m, 2H), 3.51 (t, J=8.1 Hz, 2H), 3.33 (s, 1H), 2.28 (br s, 2H), 1.99 (br s, 2H), 1.00-0.93 (m, 2H), 0.90-0.85 (m, 2H), 0.03 (s, 9H), −0.03-0.07 (m, 9H).

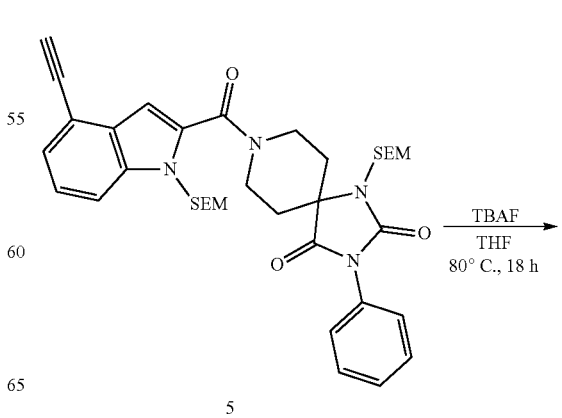

5

-continued

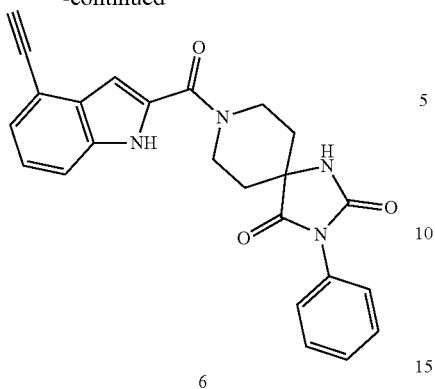

To a solution of compound 5 (300.00 mg, 454.60 umol, 1 eq) in THF (10 mL) was added TBAF (5.94 g, 22.73 mmol, 50 eq) at 15° C., the mixture was stirred at 80° C. for 1 h. TLC (Dichloromethane:Methanol=10:1, $R_f$=0.8) showed new spot generated. The reaction was concentrated. The residue was purified by prep-TLC (Dichloromethane:Methanol=10:1) to give compound 6 (80 mg, 193.50 umol, 42.57% yield) as yellow oil, which was confirmed by H NMR.

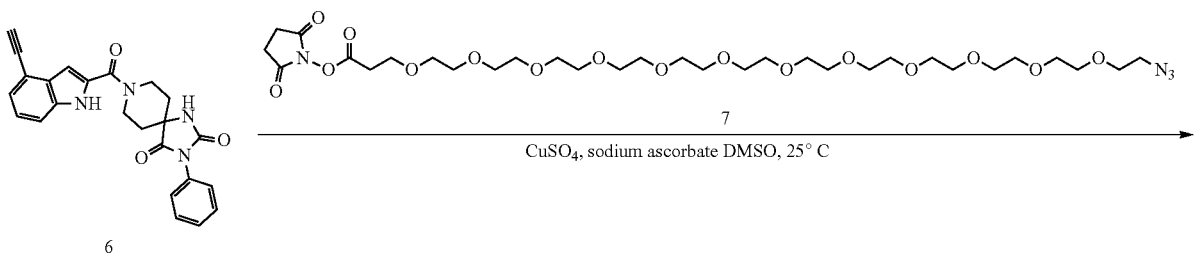

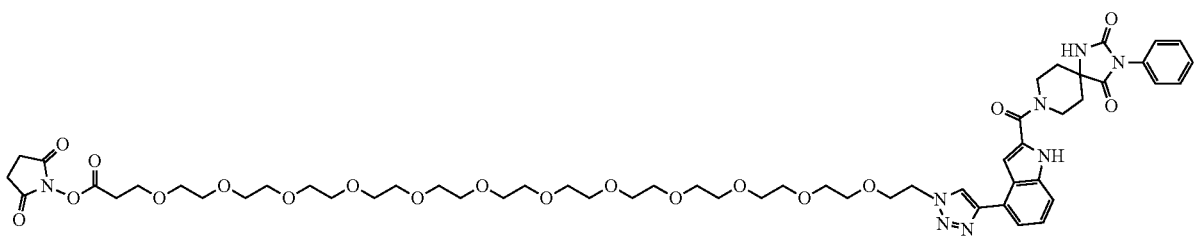

A solution of compound 7 (60 mg, 80.99 umol, 1 eq) and compound 6 (33.41 mg, 80.99 umol, 1 eq) was added CuSO$_4$·5H$_2$O (20.22 mg, 80.99 umol, 1 eq) and sodium ascorbate (32.09 mg, 161.99 umol, 2 eq) in DMSO (2 mL) stirred at 15° C. for 1 hr. LCMS showed a peak with desired MS was detected. The reaction mixture was filtered. The residue was purified by prep-HPLC (column: Nano-micro Kromasil C18 100*30 mm 5 um; mobile phase: [water (0.1% TFA)–ACN]; B %: 33%-43%, 10 min) and lyophilized to give I-68 (7.25 mg, 6.16 umol, 7.61% yield, 97.99% purity) as a colorless oil, which was confirmed by H NMR and QC LCMS. LCMS: RT=1.156 min, MS cal.: 1153.23, [M+H]$^+$=1154.5. LCMS: RT=2.098 min, MS cal.: 1153.52, [M/2+H]$^+$=577.4, [M+H]$^+$=1153.6. $^1$H NMR (400 MHz, CHLOROFORM-d) δ ppm 9.99 (br s, 1H), 8.20 (s, 1H), 7.83 (br s, 1H), 7.52 (br d, J=7.3 Hz, 2H), 7.49-7.41 (m, 5H), 7.39-7.30 (m, 2H), 4.65 (br s, 2H), 4.50 (br s, 2H), 3.94 (br s, 2H), 3.83 (br t, J=6.1 Hz, 2H), 3.65-3.50 (m, 44H), 2.89 (br t, J=6.4 Hz, 2H), 2.82 (br s, 4H), 2.23 (br s, 4H), 1.96 (br s, 2H).

Example 18: Synthesis of I-69
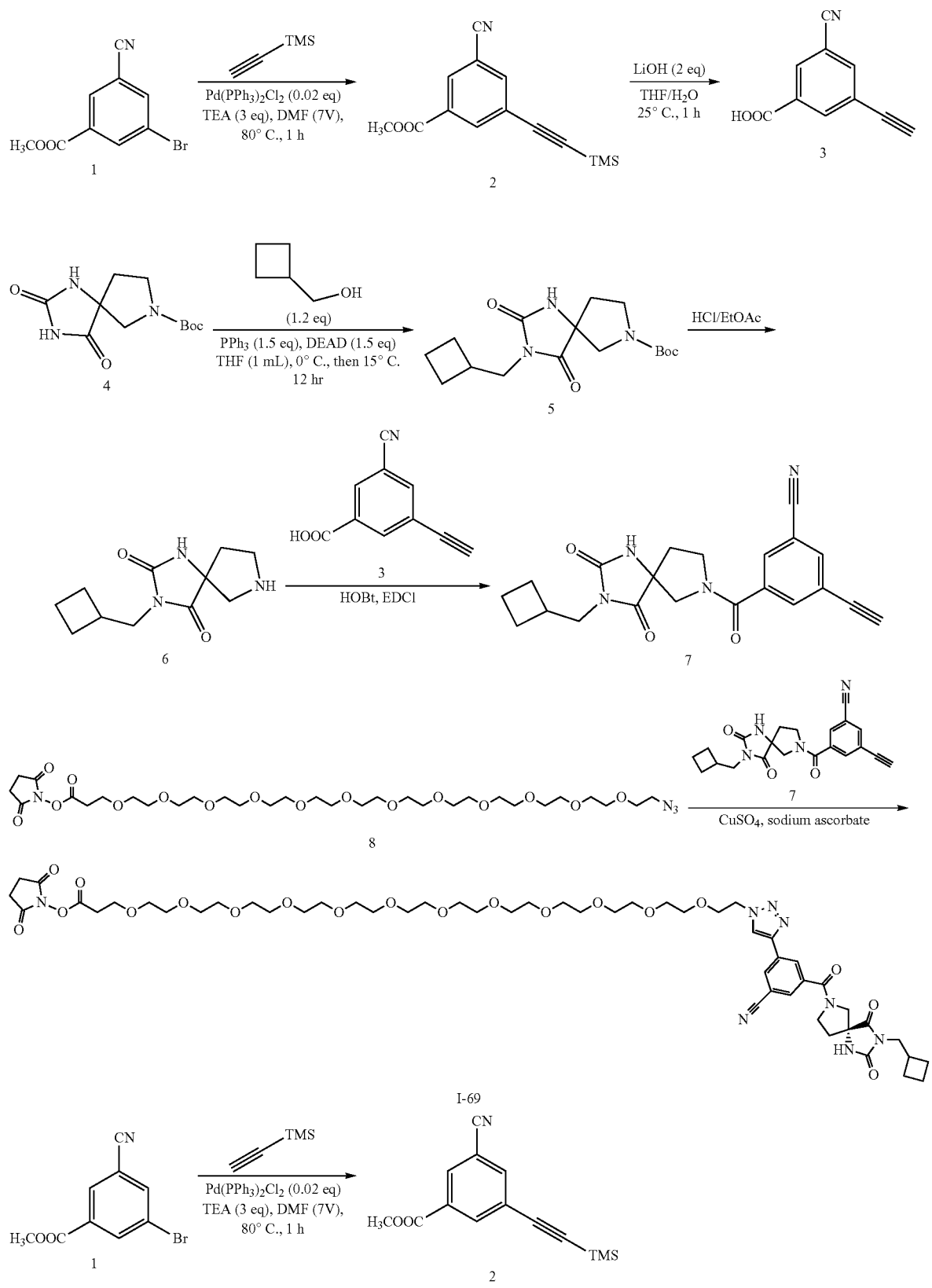

To a solution of compound 1 (0.5 g, 2.08 mmol, 1 eq) in DMF (2 mL) was added ethynyl(trimethyl)silane (409.15 mg, 4.17 mmol, 577.08 uL, 2 eq), TEA (1.05 g, 10.41 mmol, 1.45 mL, 3 eq), CuI (7.93 mg, 41.66 umol, 0.02 eq) and Pd(PPh$_3$)$_2$Cl$_2$ (29.24 mg, 41.66 umol, 0.02 eq) under N$_2$. The mixture was stirred at 80° C. for 1 h. TLC (Petroleum ether/Ethyl acetate=5:1, R$_f$=0.5) showed the reaction was completed. The mixture was filtered to give crude product. The crude product was purified by silica gel chromatography (Petroleum ether/Ethyl acetate=100/1 to 1:1, TLC:Petroleum ether/Ethyl acetate=5:1, R$_f$=0.5) to give compound 2 (0.4 g, 1.55 mmol, 74.62% yield) as a yellow solid.

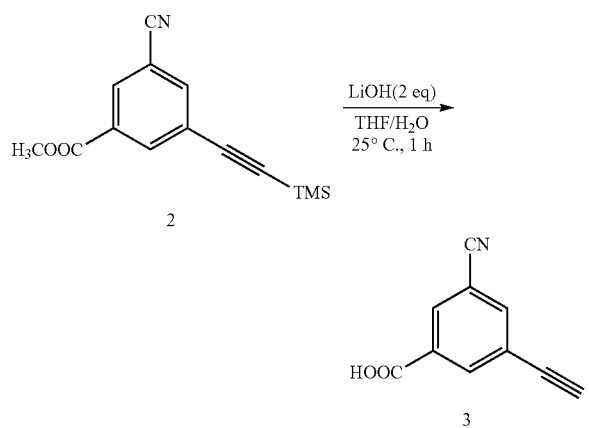

To a solution of compound 2 (0.3 g, 1.17 mmol, 1 eq) in THF (3 mL) was added the solution of LiOH·H$_2$O (97.83 mg, 2.33 mmol, 2 eq) in H$_2$O (3 mL). The mixture was stirred at 25° C. for 1 h. LCMS showed the reaction was completed. The reaction solution was justified by 0.2N HCl to pH=5. The mixture was extracted ethyl acetate (2 mL*2). The combined organic phase was washed with brine (2 mL*2), dried with anhydrous Na$_2$SO$_4$, filtered and concentrated in vacuum to give compound 3 (150 mg, 876.41 umol, 75.18% yield) as a yellow solid. LCMS: RT=2.078 min, MS cal.: 171.1, [M−H]$^+$=170.0.

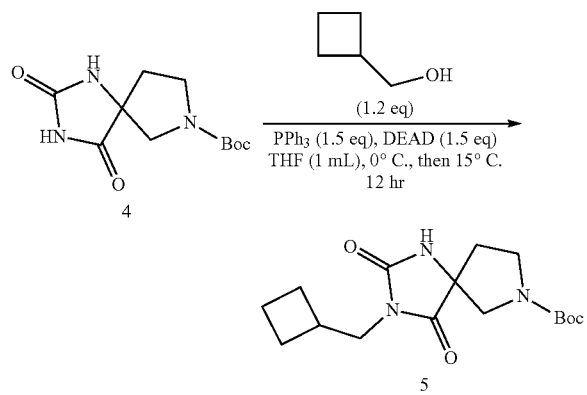

To a solution of compound 4 (0.3 g, 1.18 mmol, 1 eq) and cyclobutylmethanol (101.22 mg, 1.18 mmol, 110.87 uL, 1.2 eq) in THF (3 mL) was added PPh$_3$ (400.72 mg, 1.53 mmol, 1.5 eq) and DEAD (266.07 mg, 1.53 mmol, 277.74 uL, 1.5 eq) at 0° C. The mixture was stirred at 15° C. for 12 h. LCMS showed the reaction was completed. The residue was poured into water (2 mL). The aqueous phase was extracted with ethyl acetate (2 mL*2). The combined organic phase was washed with brine (2 mL*1), dried with anhydrous Na$_2$SO$_4$, filtered and concentrated in vacuum. The crude product was purified by prep-TLC (PE:EA=0:1, R$_f$=0.7) to give compound 5 (700 mg, crude) as a white solid. LCMS: RT=1.185 min, MS cal.: 323.1, [M−56+H]$^+$=268.1.

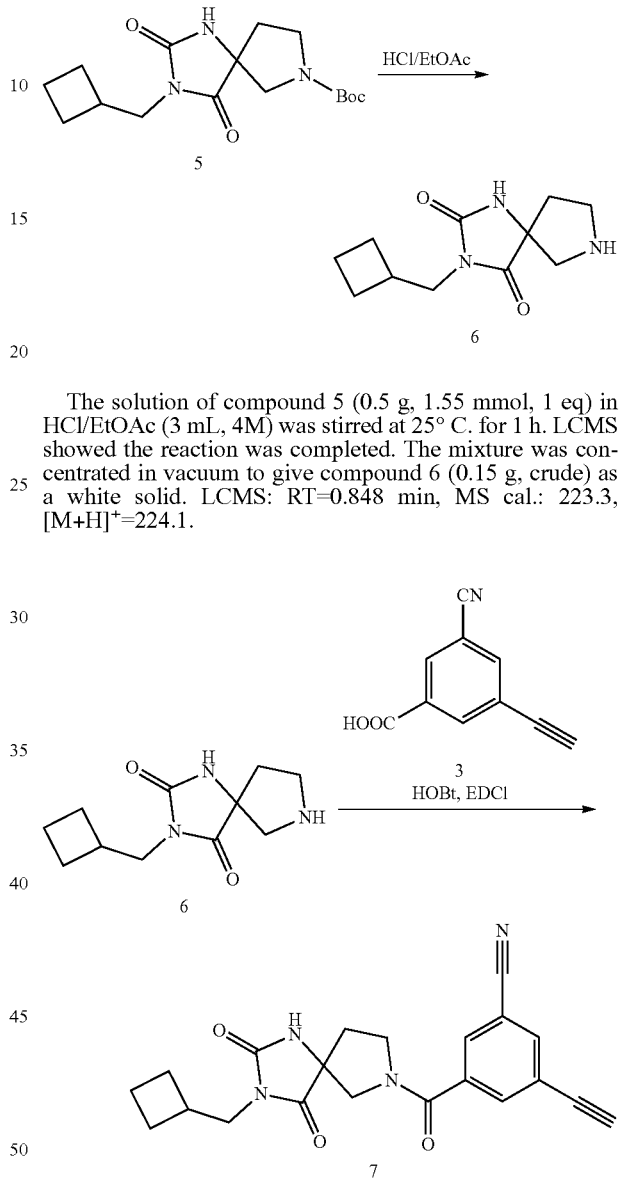

The solution of compound 5 (0.5 g, 1.55 mmol, 1 eq) in HCl/EtOAc (3 mL, 4M) was stirred at 25° C. for 1 h. LCMS showed the reaction was completed. The mixture was concentrated in vacuum to give compound 6 (0.15 g, crude) as a white solid. LCMS: RT=0.848 min, MS cal.: 223.3, [M+H]$^+$=224.1.

To a solution of compound 6 (72.49 mg, 423.51 umol, 1.1 eq) in DCM (5 mL) was added DIEA (248.80 mg, 1.93 mmol, 335.31 uL, 5 eq), HOBt (104.05 mg, 770.02 umol, 2 eq) and EDCI (147.62 mg, 770.02 umol, 2 eq) at 0° C. The mixture was stirred at 0° C. for 1 h. Then compound 3 (0.1 g, 385.01 umol, 1 eq, HCl) was added to the solution. The mixture was stirred at 25° C. for 12 h. LCMS showed the reaction was completed. The residue was poured into water (2 mL). The aqueous phase was extracted with DCM (2 mL*2). The combined organic phase was washed with brine (2 mL*2), dried with anhydrous Na$_2$SO$_4$, filtered and concentrated in vacuum. The crude product was purified by prep-TLC (Petroleum ether:Ethyl acetate=1:1, R$_f$=0.25) to give compound 7 (80 mg, crude) as a yellow solid. LCMS: RT=1.137 min, MS cal.: 376.4, [M+H]$^+$=377.1

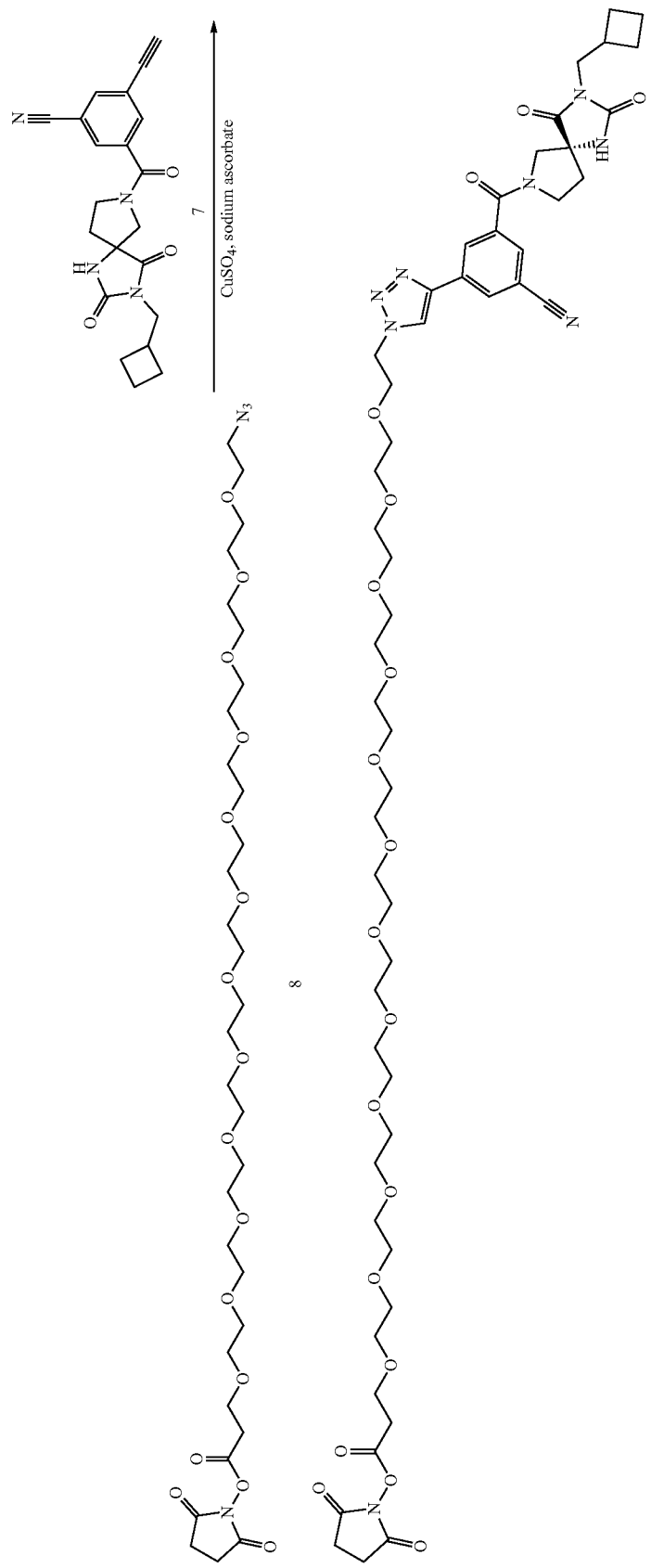

To a solution of compound 7 (30 mg, 79.70 umol, 1 eq) in DMSO (2 mL) was added compound 8 (59.04 mg, 79.70 umol, 1 eq), $CuSO_4 \cdot 5H_2O$ (39.80 mg, 159.40 umol, 2 eq) and sodium ascorbate (31.58 mg, 159.40 umol, 2 eq). The mixture was stirred at 25° C. for 1 h. LCMS showed the reaction was completed. The mixture was filtered to give crude product. The crude product was purified by prep-HPLC (column: Phenomenex Synergi C18 100*30 mm*4 um; mobile phase: [water (0.1% TFA)–ACN]; B %: 25%-45%, 10 min) to give I-69 (5.11 mg, 4.39 umol, 5.51% yield, 96% purity) as a yellow oil. LCMS: RT=1.216 min, MS cal.: 1117.2, $[M/2+H]^+$=553.3. $^1$H NMR (400 MHz, CHLOROFORM-d) δ ppm 8.18-8.39 (m, 4H) 7.70-7.82 (m, 1H) 4.64 (s, 2H) 3.93 (s, 3H) 3.85 (t, J=6.4 Hz, 4H) 3.47-3.71 (m, 43H) 2.91 (t, J=6.4 Hz, 2H) 2.85 (s, 4H) 2.61-2.76 (m, 2H) 2.50 (d, J=9.7 Hz, 1H) 2.16 (s, 1H) 2.01 (s, 2H) 1.64-1.89 (m, 6H). LCMS: RT=2.100 min, MS cal.: 1117.2, $[M/2+H]^+$=559.3.

Example 19: Synthesis of 1-70

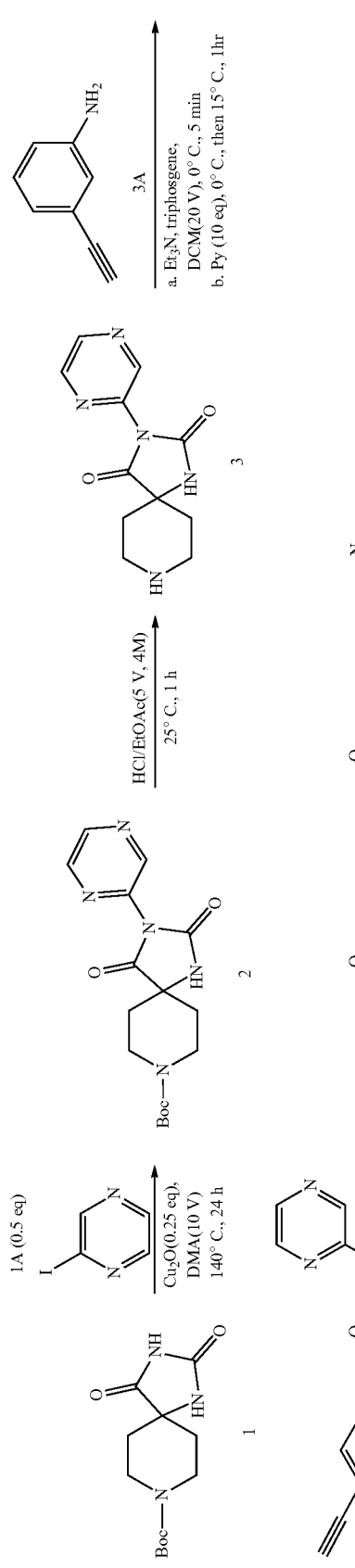
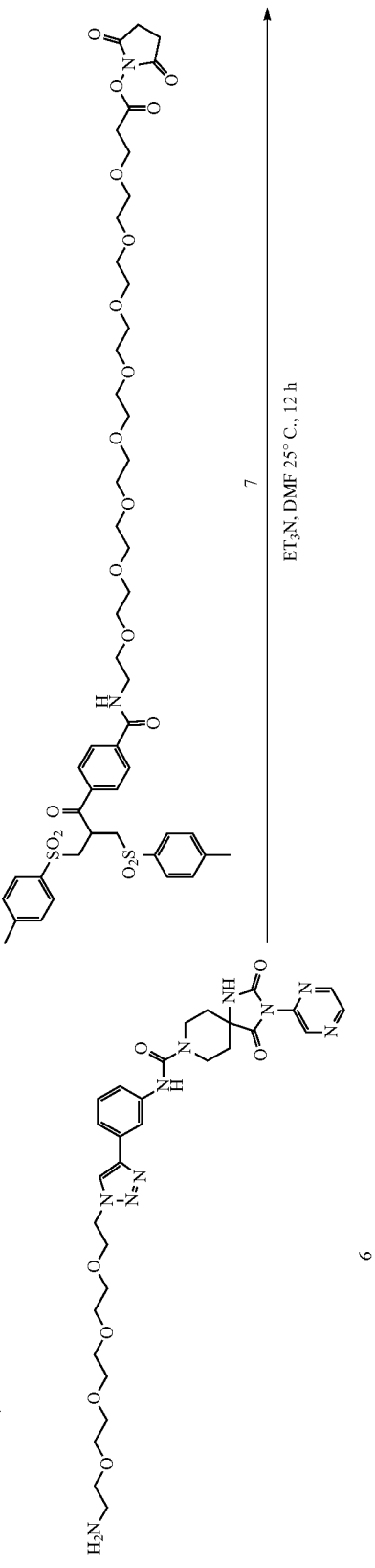

-continued
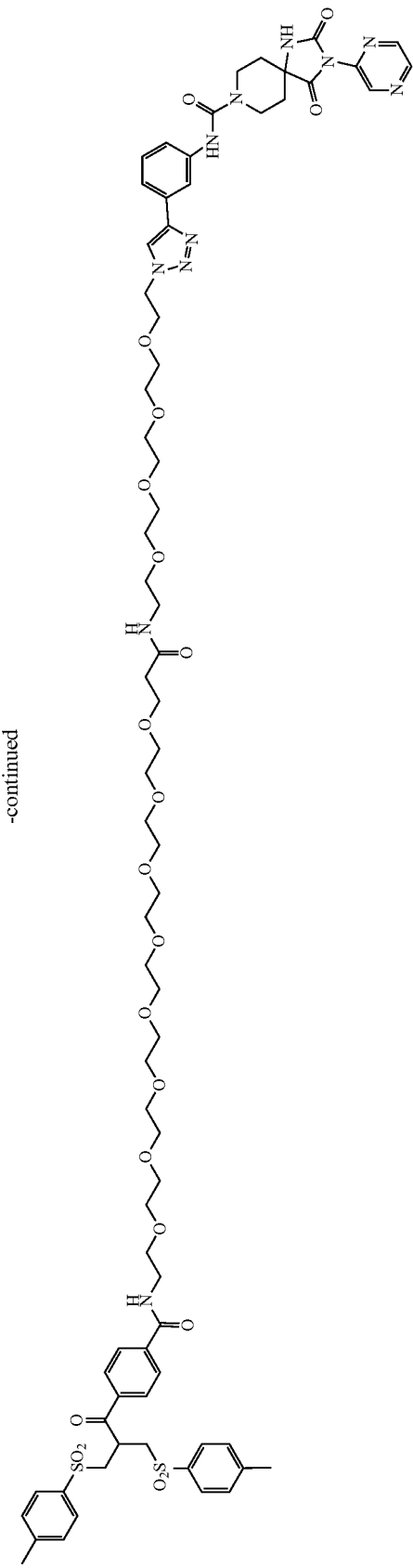
I-70
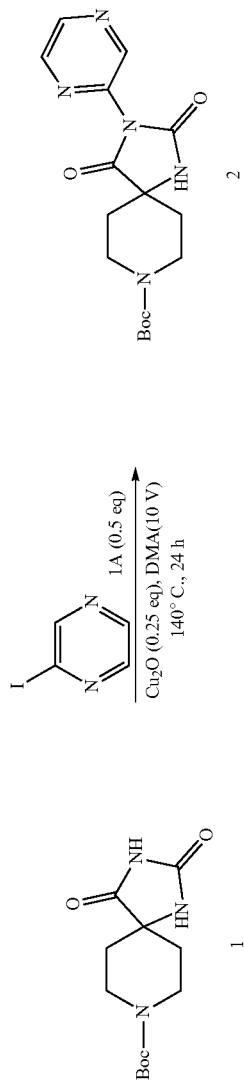
2
1A (0.5 eq)
Cu₂O (0.25 eq), DMA(10 V)
140° C., 24 h
1

To a solution of compound 1 (1 g, 3.71 mmol, 1 eq) in DMA (3 mL) was added compound 1A (382.45 mg, 1.86 mmol, 182.99 uL, 0.5 eq) and Cu₂O (132.84 mg, 928.35 umol, 94.88 uL, 0.25 eq). The mixture was stirred at 140° C. for 24 h. LCMS and show the reaction was completed. The mixture was filtered and the filter liquor was concentrated in vacuum. The crude product was purified by prep-HPLC (column: Agela innoval ods-2 250*80 mm; mobile phase: [water (0.1% TFA)–ACN]; B %: 16%-46%, 30 min) to give compound 2 (0.85 g, 2.45 mmol, 65.90% yield) as a white solid. ¹H NMR (400 MHz, CHLOROFORM-d) δ ppm 8.78 (s, 1H) 8.65 (s, 2H) 6.95 (s, 1H) 4.01 (d, J=13.2 Hz, 2H) 3.26-3.39 (m, 2H) 2.16 (ddd, J=13.6, 9.5, 4.0 Hz, 2H) 1.82 (d, J=13.4 Hz, 2H) 1.49 (s, 9H). LCMS: RT=1.048 min, MS cal.: 347.4, [M-56+H]⁺=292.0.

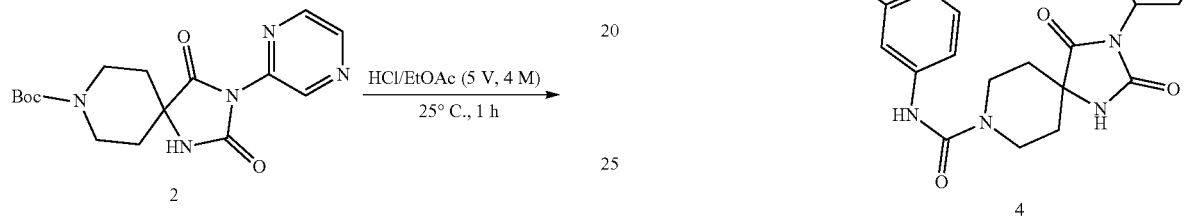

The solution of compound 2 (0.34 g, 978.79 umol, 1 eq) in HCl/EtOAc (10 mL, 4M) was stirred at 25° C. for 1 h. LCMS showed the reaction was completed. The mixture was concentrated in vacuum to give compound 3 (300 mg, crude, HCl) as a white solid. LCMS: RT=0.103 min, MS cal.: 247.1, [M+H]⁺=248.0.

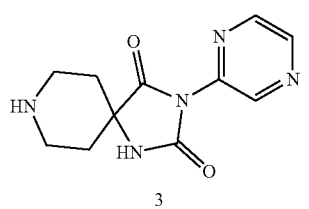

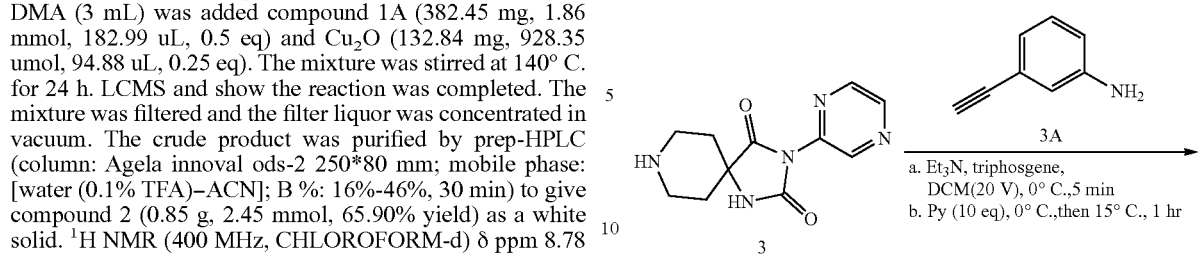

To a solution of triphosgene (17.26 mg, 58.16 umol, 0.33 eq) in DCM (2 mL) was added TEA (71.33 mg, 704.94 umol, 98.12 uL, 4 eq) and compound 3A (20.65 mg, 176.23 umol, 1 eq) at 0° C. The mixture was stirred at 0° C. for 0.5 h. Then compound 3 (50 mg, 176.23 umol, 1 eq, HCl) and Py (83.64 mg, 1.06 mmol, 85.35 uL, 6 eq) was added to the solution and stirred at 50° C. for 2 h. LCMS showed the reaction was completed. The residue was poured into water (5 mL). The aqueous phase was extracted with DCM (2 mL*3). The combined organic phase was washed with brine (2 mL*2), dried with anhydrous Na₂SO₄, filtered and concentrated in vacuum. The residue was purified by prep-TLC (Petroleum ether/Ethyl acetate=0/1, R_f=0.25) to give compound 4 (30 mg, 76.85 umol, 43.60% yield) as a white solid. LCMS: RT=1.036 min, MS cal.: 390.3, [M+H]⁺=391.1.

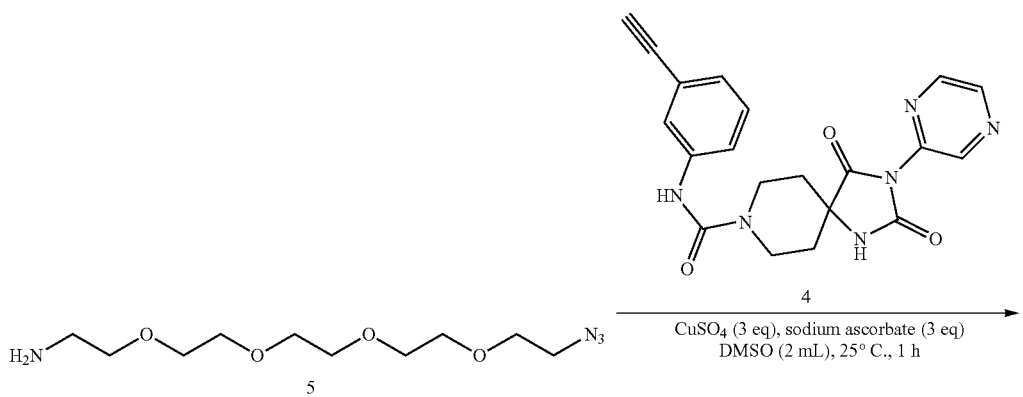

-continued

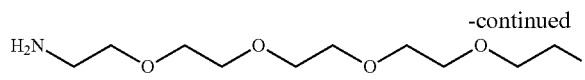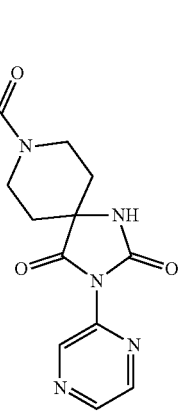

6

To a solution of compound 5 (47.03 mg, 179.31 umol, 1 eq) in DMSO (2 mL) was added compound 4 (0.07 g, 179.31 umol, 1 eq), CuSO$_4$·5H$_2$O (67.15 mg, 268.96 umol, 1.5 eq) and SODIUM ASCORBATE (53.28 mg, 268.96 umol, 1.5 eq). The mixture was stirred at 25° C. for 30 min. LCMS showed the reaction was completed. The mixture was filtered to give crude product. The crude product was purified by prep-HPLC (column: Phenomenex Synergi C18 100*30 mm*4 um; mobile phase: [water (0.1% TFA)–ACN]; B %: 5%-25%, 10 min) to give compound 6 (20 mg, 30.64 umol, 17.09% yield) as a colorless oil. LCMS: RT=0.963 min, MS cal.: 652.3, [M+H]$^+$=653.1.

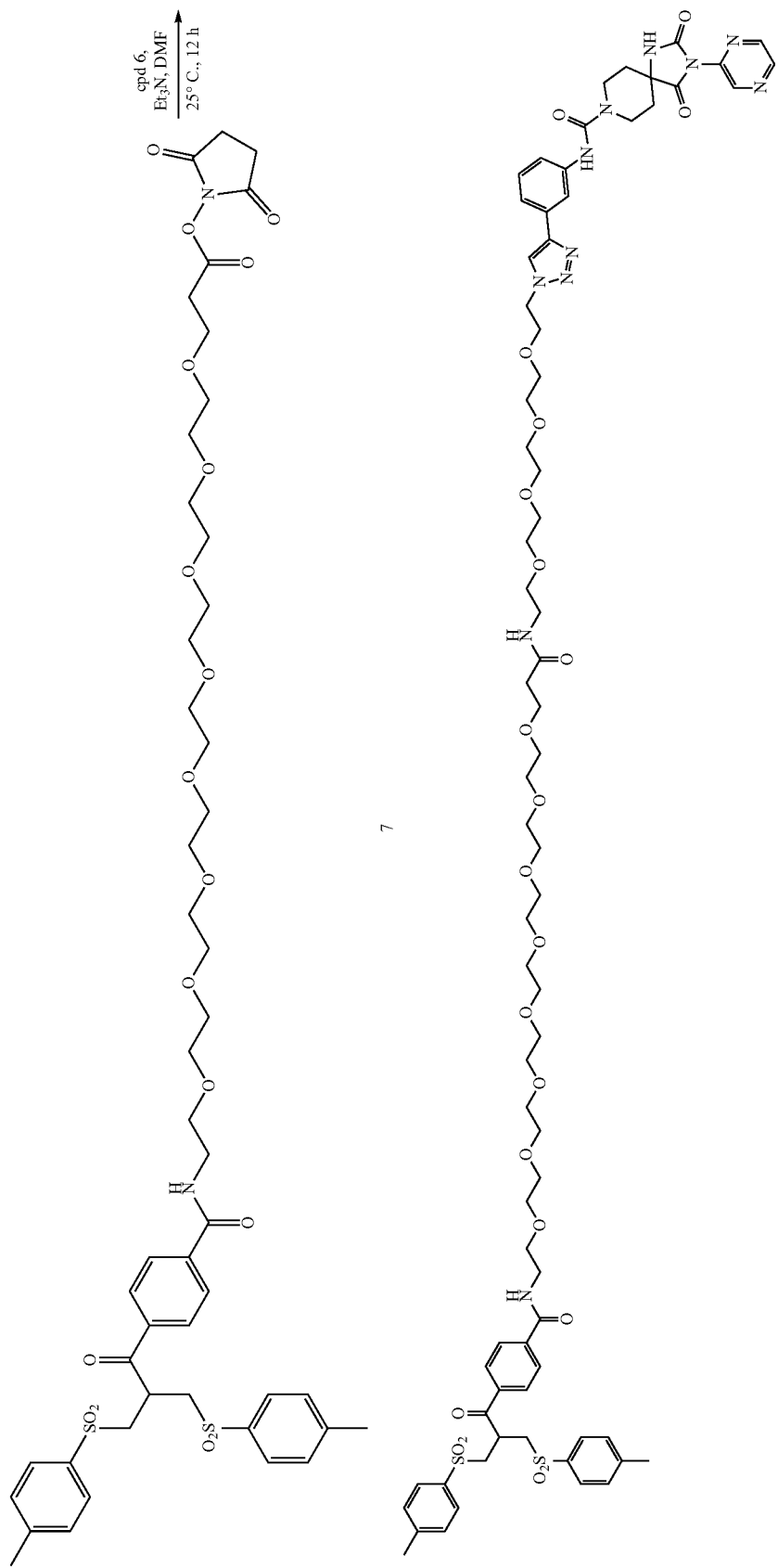

To a solution of compound 7 (20 mg, 26.09 umol, 1 eq, TFA) in DMF (2 mL) was added compound 6 (26.64 mg, 26.09 umol, 1 eq) and TEA (3.96 mg, 39.14 umol, 5.45 uL, 1.5 eq). The mixture was stirred at 20° C. for 0.5 h. LCMS showed the reaction was completed. The mixture was filtered to give crude product. The crude product was purified by prep-HPLC: column: Phenomenex Synergi C18 100*30 mm*4 um; mobile phase: [water (0.1% TFA)–ACN]; B %: 30%-45%, 10 min to give I-70 (9.2 mg, 5.67 umol, 21.72% yield, 96% purity) as a white solid. $^1$H NMR (400 MHz, CHLOROFORM-d) δ ppm 8.79 (s, 1H) 8.62 (d, J=5.5 Hz, 2H) 8.01-8.14 (m, 2H) 7.77-7.90 (m, 3H) 7.51-7.72 (m, 10H) 7.32-7.40 (m, 5H) 6.95 (s, 1H) 4.59 (s, 2H) 4.34-4.40 (m, 1H) 3.99 (s, 2H) 3.91 (s, 1H) 3.45-3.80 (m, 50H) 3.30-3.43 (m, 4H) 2.44-2.51 (m, 7H) 2.18 (s, 3H) 1.99 (s, 1H). LCMS: RT=1.133 min, MS cal.: 1558.7, [M/2+H]$^+$=780.1.

Example 20: Synthesis of I-71

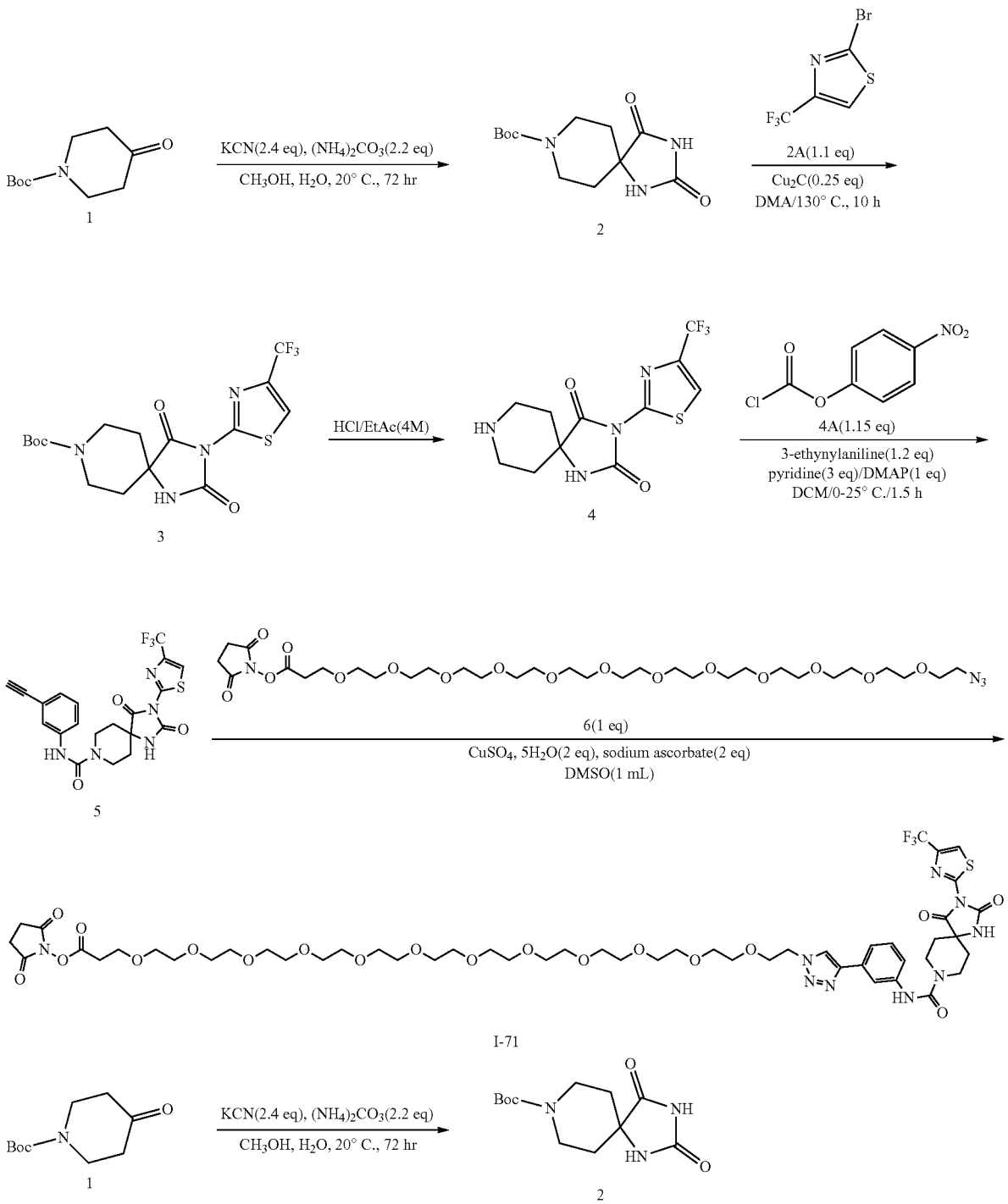

A solution of KCN (23.53 g, 361.36 mmol, 15.48 mL, 2.4 eq) in H$_2$O (400 mL) was added dropwise to the solution of compound 1 (30 g, 150.57 mmol, 1 eq) and (NH$_4$)$_2$CO$_3$ (31.83 g, 331.25 mmol, 35.36 mL, 2.2 eq) in MeOH (200 mL) and H$_2$O (400 mL). The mixture was stirred at 20° C. for 72 h. LCMS showed the reaction was completed. The reaction mixture was filtered and concentrated in vacuum to give product. Compound 2 was used to the next step without any purification. LCMS: RT=0.999 min, MS cal.: 269.1, [M-55]$^+$=214.0.

eq). The mixture was stirred at 25° C. for 5 hr. LCMS showed compound 3 was consumed completely and one main peak with desired mass was detected. The reaction mixture was concentrated under reduced pressure to give a residue. Compound 4 (0.035 g, 109.28 umol, 91.88% yield) was obtained as a white solid which was used to the next step directly. LCMS: RT=0.881 min, MS cal.: 320.06, [M+H]$^+$=321.1.

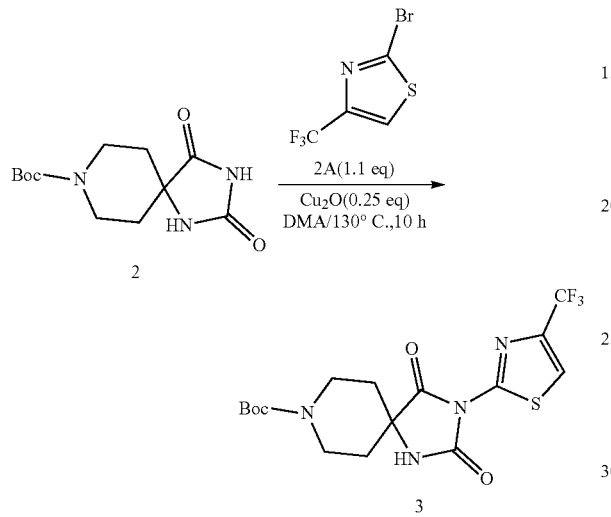

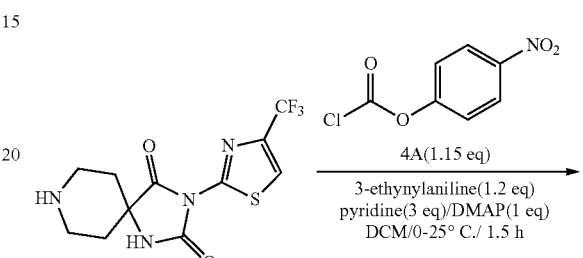

To a solution of compound 2A (189.55 mg, 816.94 umol, 1.1 eq) and compound 2 (0.2 g, 742.68 umol, 1 eq) in DMA (2 mL) was added Cu$_2$O (26.57 mg, 185.67 umol, 18.98 uL, 0.25 eq). The mixture was stirred at 130° C. for 12 hr. TLC (Dichloromethane:Methanol=10:1 R$_f$=0.43) showed it was finished. The residue was diluted with H$_2$O 10 mL and extracted with EtOAc (10 mL*2). The combined organic layers were washed with brine (10 mL*1), dried over Na$_2$SO$_4$, filtered and concentrated under reduced pressure to give a residue. Compound 3 (0.07 g, 94.89 umol, 12.78% yield, 56.99% purity) was obtained as a yellow solid.

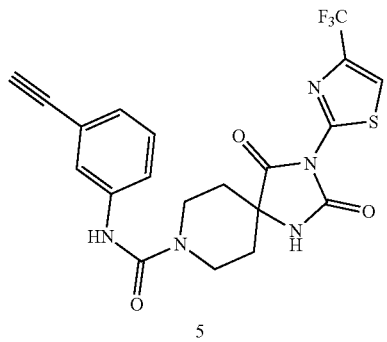

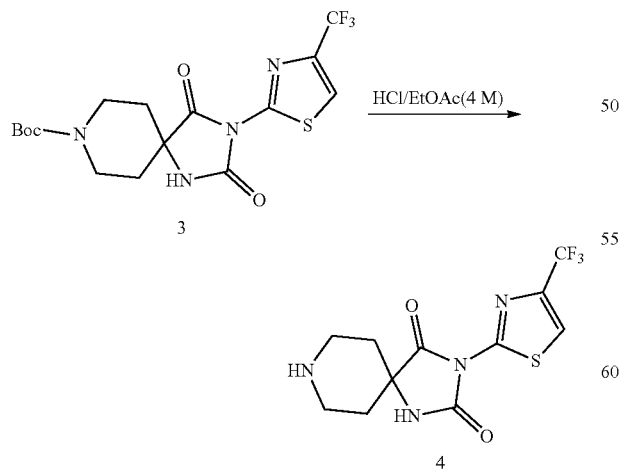

To a solution of compound 3 (0.05 g, 118.93 umol, 1 eq) in EtOAc (1 mL) was added HCl/EtOAc (4 M, 29.73 uL, 1

To a solution of Compound 4A (13.84 mg, 68.69 umol, 1.1 eq) in DCM (2 mL) was added 3-ethynylaniline hydrochloride (10.55 mg, 68.69 umol, 1.1 eq). The mixture was stirred at 0° C. for 0.5 hr. Then pyridine (14.82 mg, 187.33 umol, 15.12 uL, 3 eq) and DMAP (7.63 mg, 62.44 umol, 1 eq) and compound 4 (0.02 g, 62.44 umol, 1 eq) was added to the reaction mixture, it was stirred at 40° C. for 1 hr. LCMS showed compound 4 was consumed completely and one main peak with desired mass was detected. The residue was diluted with H$_2$O 10 mL and extracted with DCM (10 mL*2). The combined organic layers were washed with brine (10 mL*1), dried over Na$_2$SO$_4$, filtered and concentrated under reduced pressure to give a residue. Compound 5 (0.02 g, 43.16 umol, 69.11% yield) was obtained as a white solid. LCMS: RT=1.188 min, MS cal.: 463.09, [M+H]$^+$=464.2.

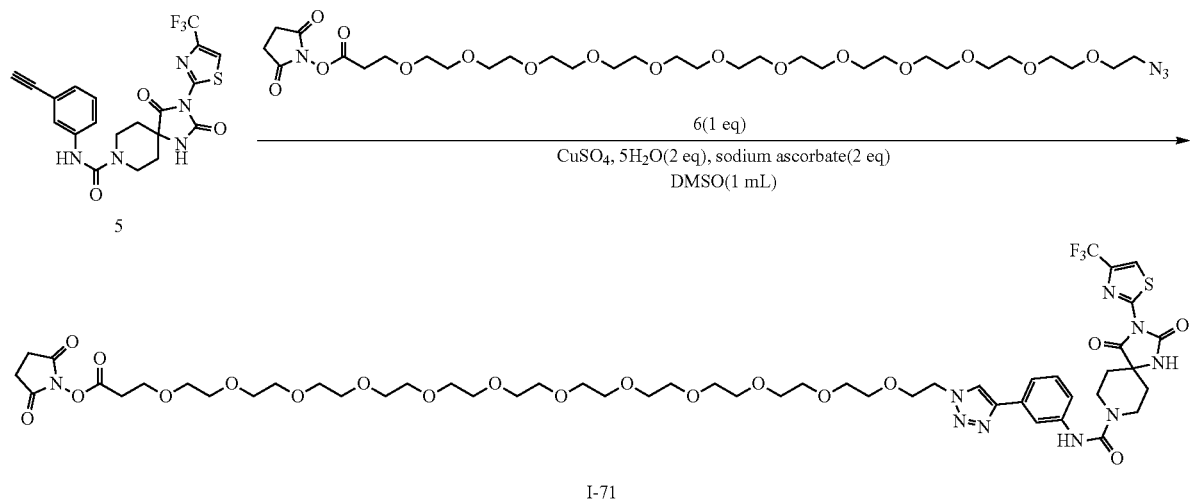

I-71

To a solution of compound 6 (0.015 g, 20.25 umol, 1 eq) and compound 5 (9.38 mg, 20.25 umol, 1 eq) in DMSO (1 mL) was added sodium; ascorbate (8.02 mg, 40.50 umol, 2 eq) and CuSO$_4$·5H$_2$O (10.11 mg, 40.50 umol, 2 eq). The mixture was stirred at 25° C. for 12 hr. LCMS showed compound 6 was consumed completely and one main peak with desired mass was detected. (RT=1.144 min). It was filtered. The residue was purified by prep-HPLC (TFA condition: column: Luna C18 100*30 5 u; mobile phase: [water (0.1% TFA)–ACN]; B %: 20%-50%, 10 min). I-71 (5.97 mg, 4.96 umol, 24.48% yield) was obtained as a yellow oil. LCMS: RT=1.144 min, MS cal.: 1203.46, [M/2+H]$^+$=602.9. QCLCMS: RT=2.228 min, MS cal.: 1203.46, [M/2+H]$^+$=602.7. $^1$H NMR (400 MHz, DMSO-d6) δ ppm 9.59 (s, 1H) 8.75 (s, 1H) 8.45 (s, 1H) 8.38 (s, 1H) 8.02 (s, 1H) 7.27-7.50 (m, 3H) 4.57 (t, J=5.07 Hz, 2H) 4.02 (br d, J=13.94 Hz, 2H) 3.87 (t, J=5.14 Hz, 2H) 3.67-3.75 (m, 2H) 3.53-3.58 (m, 3H) 3.45-3.57 (m, 41H) 2.91 (t, J=5.99 Hz, 2H) 2.80 (s, 4H) 1.80-2.01 (m, 4H).

Example 21: Synthesis of 1-72

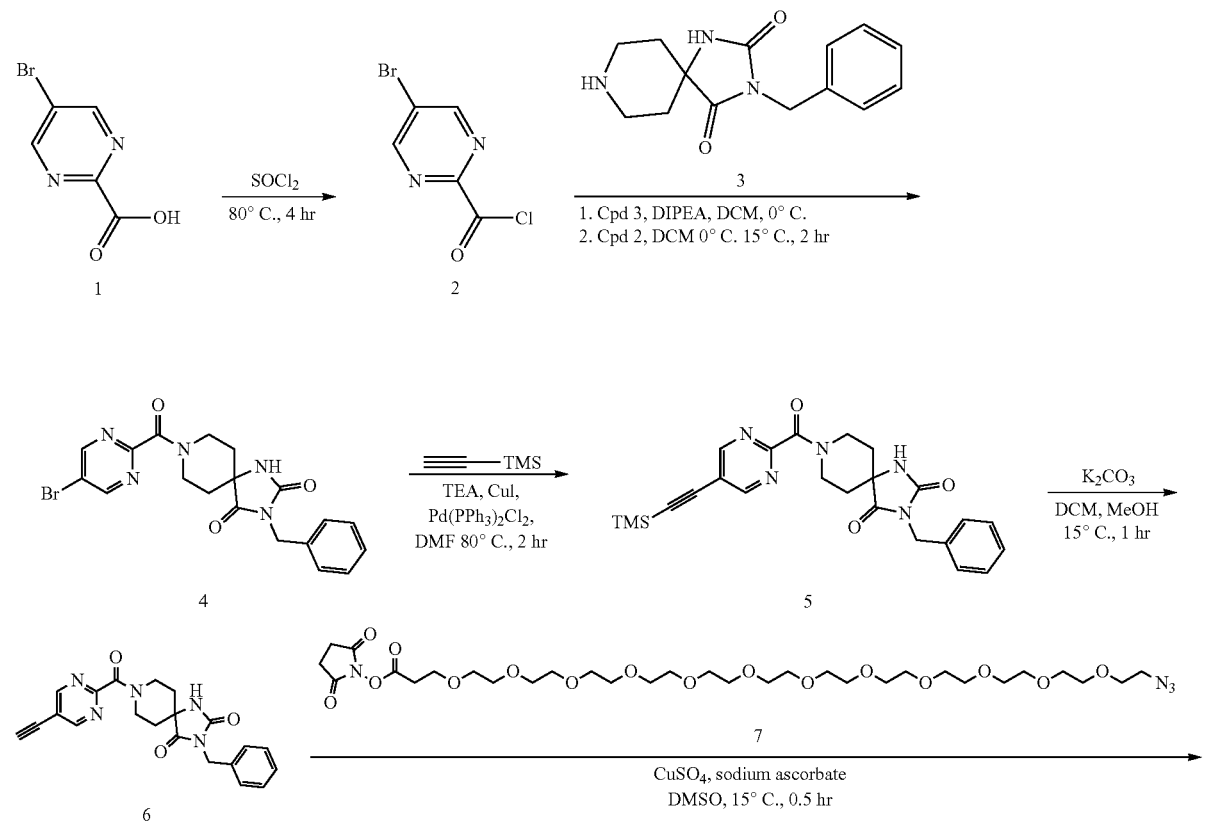

-continued

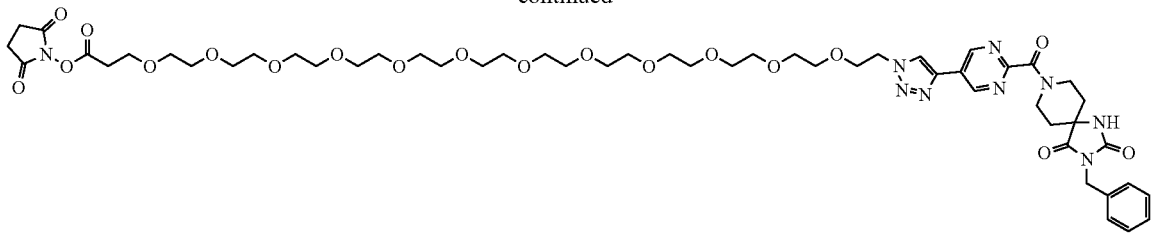

I-72

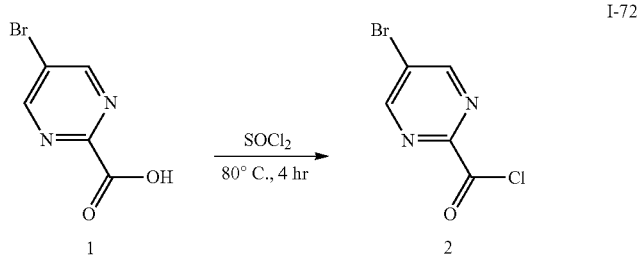

To a solution of SOCl$_2$ (9.38 g, 78.82 mmol, 5.72 mL, 40 eq) was added compound 1 (400 mg, 1.97 mmol, 1 eq). The mixture was stirred at 50° C. for 2 hr, then the mixture was warmed to 80° C. for 4 hr. A sample was quenched with MeOH and LCMS detected the desired methyl ester. The mixture was concentrated under vacuum to give compound 2 (450 mg, crude) as light yellow solid. LCMS: RT=0.653 min, MS cal.: 219.90, [M−Cl+OCH$_3$]$^+$=218.1.

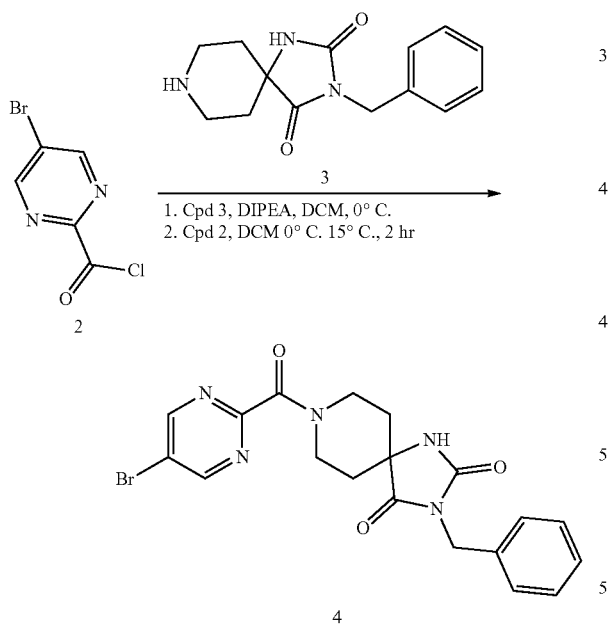

To a solution of compound 3 (50 mg, 169.05 umol, 1 eq, HCl) in DCM (1 mL) was added DIPEA (109.25 mg, 845.27 umol, 147.23 uL, 5 eq) and compound 2 (56.15 mg, 253.58 umol, 1.5 eq) at 0° C. for 0.5 hr. The mixture was stirred at 15° C. for 12 hr. LCMS was detected the desired product MS. The mixture was added DCM (10 mL), washed with HCl (0.2 M), the organic layer was dried over Na$_2$SO$_4$, filtered and concentrated. The residue was purified by prep-TLC according to TLC (Plate 1, Petroleum ether:Ethyl acetate=0:1, Product R$_f$=0.40). Compound 4 (35 mg, 74.84 umol, 44.27% yield, 95% purity) was obtained as white solid. LCMS: RT=1.193 min, MS cal.: 443.06, [M+H]$^+$=444.0.

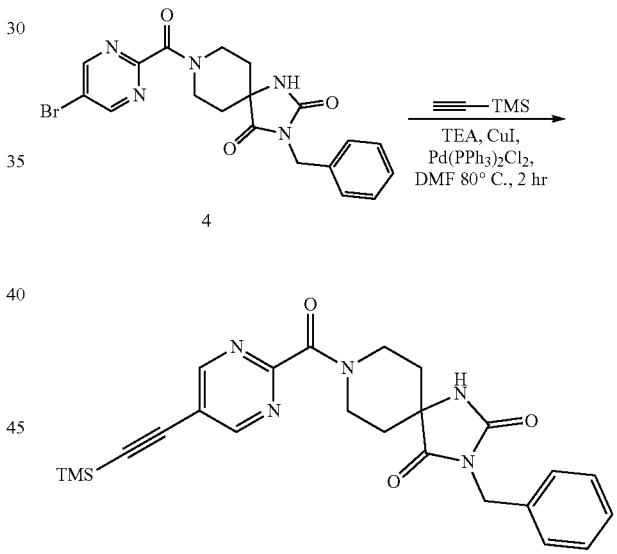

To a solution of compound 4 (20 mg, 45.02 umol, 1 eq) and ethynyl(trimethyl)silane (8.84 mg, 90.03 umol, 12.47 uL, 2 eq) in DMF (0.5 mL) was added TEA (29.15 mg, 288.11 umol, 40.10 uL, 6.4 eq), CuI (85.73 ug, 0.45 umol, 0.01 eq) and Pd(PPh$_3$)$_2$Cl$_2$ (631.94 ug, 0.9 umol, 0.02 eq). The mixture was stirred at 80° C. for 2 hr. LCMS was detected the desired product MS. The mixture was combined. The mixture was added EtOAc (30 mL), filtered, washed with water (10 mL*2), the organic layer was dried over Na$_2$SO$_4$, filtered and concentrated. The residue was purified by prep-TLC according to TLC (Plate 1, Petroleum ether:Ethyl acetate=0:1, Product R$_f$=0.45). Compound 5 (20 mg, crude) was obtained as light yellow solid. LCMS: RT=1.459 min, MS cal.: 461.19, [M+H]$^+$=462.2.

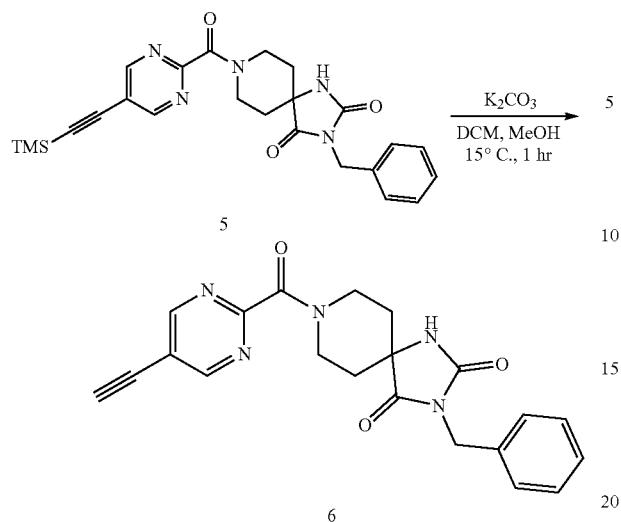

To a solution of compound 5 (10.18 mg, 22.05 umol, 1 eq) in DCM (0.5 mL) and MeOH (0.5 mL) was added $K_2CO_3$ (4.57 mg, 33.08 umol, 1.5 eq). The mixture was stirred at 15° C. for 1 hr. LCMS was detected the desired product MS. The mixture was filtered and concentrated. The residue was purified by prep-TLC according to TLC (Plate 1, Petroleum ether:Ethyl acetate=1:1, Product $R_f$=0). Compound 6 (5 mg, crude) was obtained as yellow solid. LCMS: RT=1.155 min, MS cal.: 389.15, $[M+H]^+$=390.2.

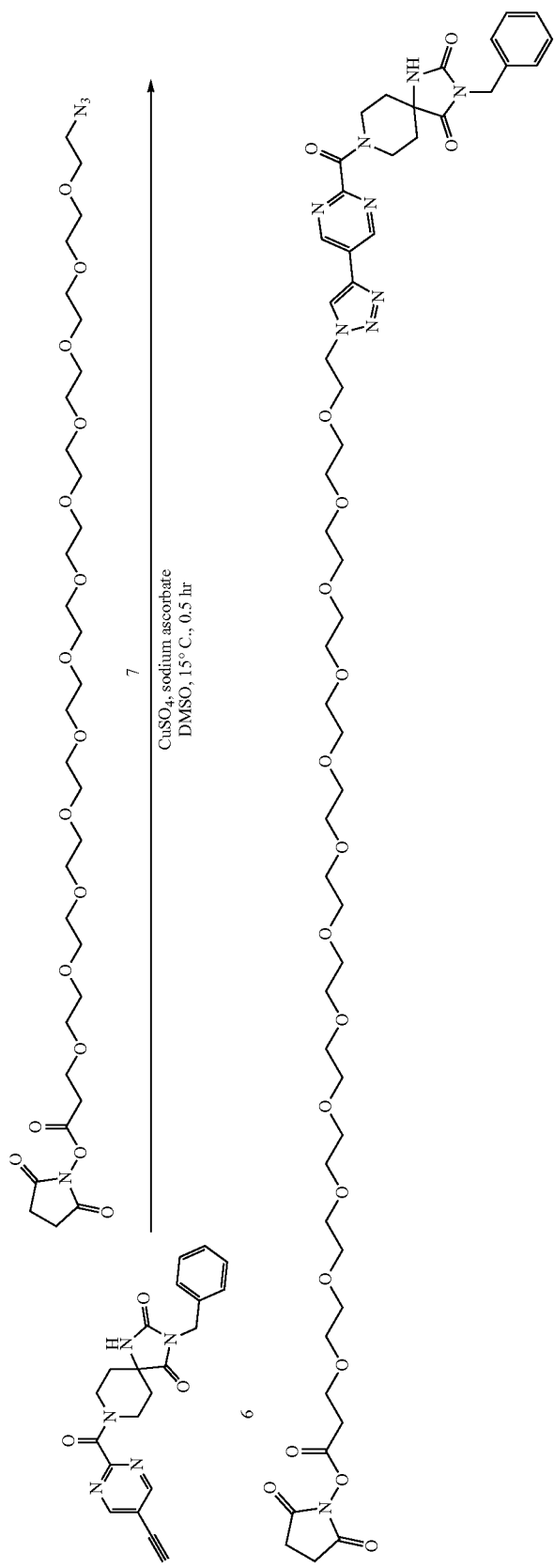

To a solution of compound 7 (9.51 mg, 12.84 umol, 1 eq) and compound 6 (5 mg, 12.84 umol, 1 eq) in DMSO (1 mL) was added $CuSO_4 \cdot 5H_2O$ (3.21 mg, 12.84 umol, 1 eq) and sodium; (2R)-2-[(1S)-1,2-dihydroxyethyl]-4-hydroxy-5-oxo-2H-furan-3-olate (5.09 mg, 25.68 umol, 2 eq). The mixture was stirred at 15° C. for 0.5 hr. LCMS was detected the desired product MS. The mixture was filtered. The residue was purified by prep-HPLC (TFA condition) according to HPLC. I-72 (5.87 mg, 5.13 umol, 39.94% yield, 98.75% purity) was obtained as brown oil checked by QCLCMS and HNMR. LCMS: RT=1.218 min, MS cal.: 1129.52, $[M/2+H]^+$=565.7. HPLC: RT=2.495 min. QCLCMS: RT=2.824 min, MS cal.: 1129.52, $[M/2+H]^+$=565.9. $^1H$ NMR (400 MHz, DMSO-$d_6$) δ ppm 9.33 (s, 2H), 9.07 (s, 1H), 8.82 (s, 1H), 7.37-7.30 (m, 2H), 7.30-7.19 (m, 3H), 4.64 (br t, J=4.8 Hz, 2H), 4.55 (s, 2H), 4.32 (br d, J=13.3 Hz, 1H), 3.87 (br t, J=4.9 Hz, 2H), 3.71 (t, J=5.9 Hz, 2H), 3.54 (br d, J=5.4 Hz, 4H), 3.53-3.44 (m, 47H), 2.92 (t, J=5.9 Hz, 2H), 2.80 (s, 4H), 1.95-1.81 (m, 2H), 1.79-1.70 (m, 1H), 1.59 (br d, J=13.0 Hz, 1H).

Example 22: Synthesis of I-73

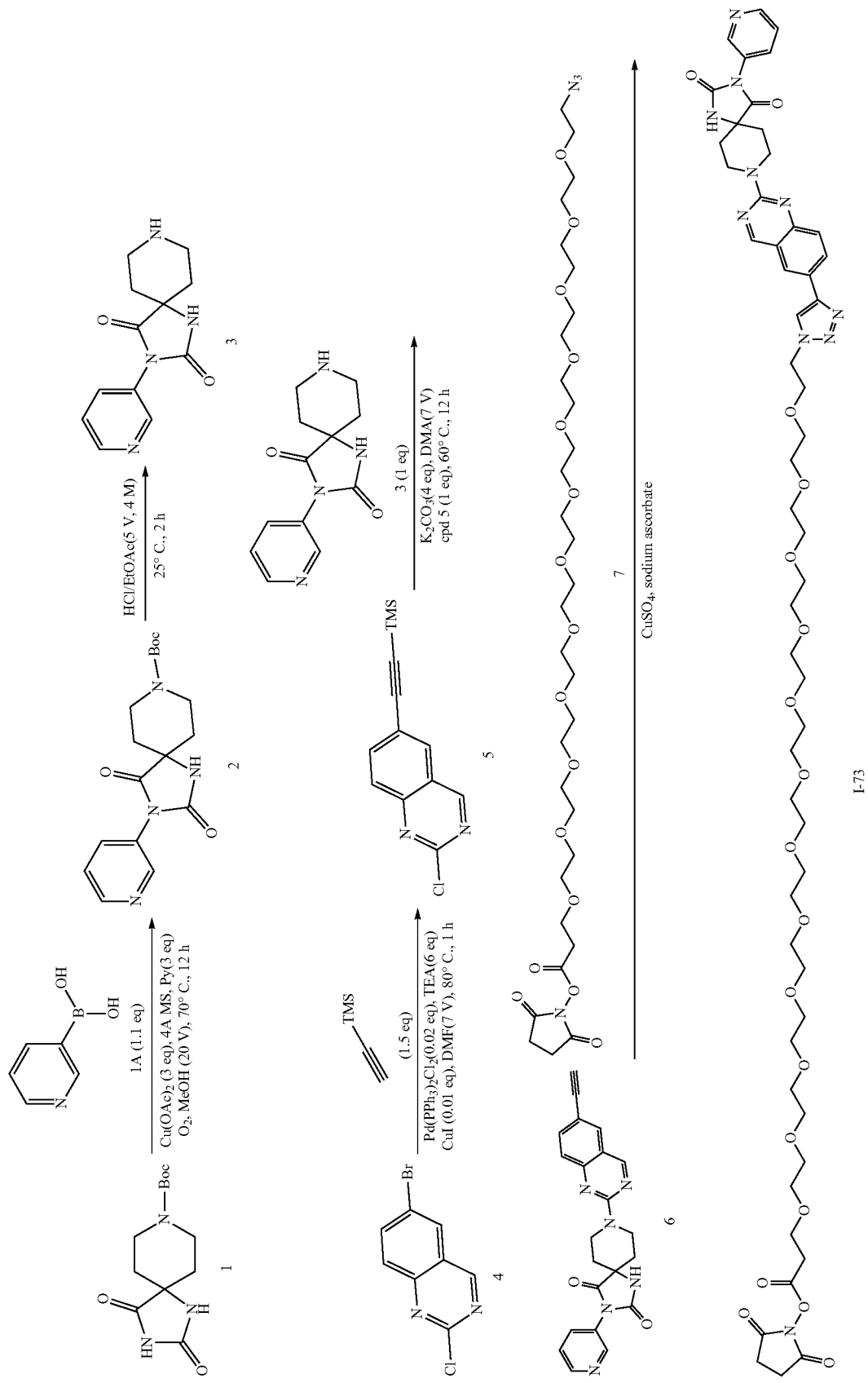

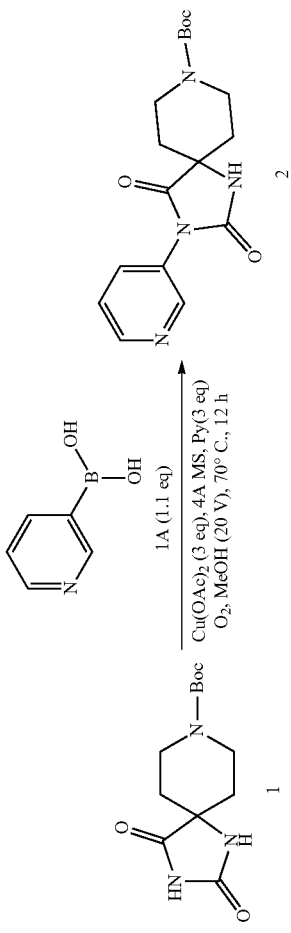

To a solution of compound 1 (1 g, 3.71 mmol, 1 eq) and compound 1A (502.08 mg, 4.08 mmol, 1.1 eq) in MeOH (15 mL) was added Molecular sieve 4A (2 g, 3.71 mmol, 1 eq), Cu(OAc)$_2$ (674.46 mg, 3.71 mmol, 1 eq) and Py (881.19 mg, 11.14 mmol, 899.17 uL, 3 eq). After the mixture was bubbled with oxygen for 10 min, the mixture was stirred under OXYGEN at 70° C. for 12 hr. LCMS and HPLC showed the reaction was completed. The mixture was concentrated in vacuum. The residue was purified by prep-HPLC (column: Phenomenex luna C18 250*50 mm*10 um; mobile phase: [water (0.1% TFA)–ACN]; B %: 5%-35%, 20 min) to give compound 2 (0.2 g, 577.40 umol, 15.55% yield) as a white solid. LCMS: RT=1.005 min, MS cal.: 347.2, [M+H]$^+$=346.3.

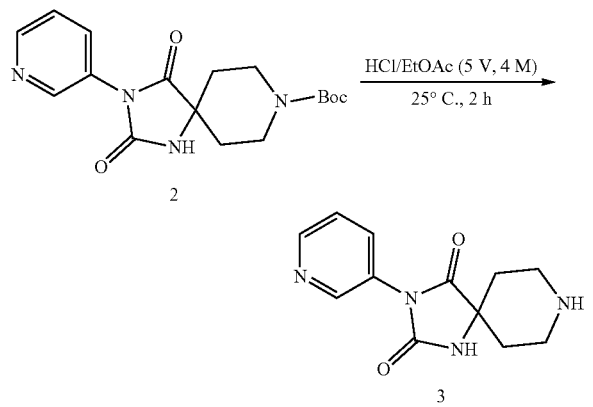

The solution of compound 2 (100 mg, 288.70 umol, 1 eq) in HCl/EtOAc (5 mL) was stirred at 25° C. for 1 h. LCMS showed the reaction was completed. The mixture was concentrated in vacuum to give compound 3 (90 mg, crude, HCl) was obtained as a white solid. LCMS: RT=0.124 min, MS cal.: 247.1, [M+H]$^+$=246.3.

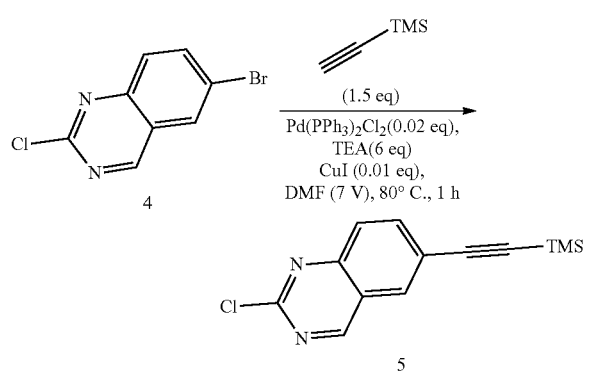

To a solution of compound 4 (0.5 g, 2.05 mmol, 1 eq) in DMF (10 mL) was added ethynyl(trimethyl)silane (302.53 mg, 3.08 mmol, 1.5 eq), Pd(PPh$_3$)$_2$Cl$_2$ (28.83 mg, 41.07 umol, 0.02 eq), CuI (3.91 mg, 20.53 umol, 0.01 eq) and TEA (1.25 g, 12.32 mmol, 1.71 mL, 6 eq) under N$_2$. The mixture was stirred at 80° C. for 1 h. LCMS showed the reaction was completed. The mixture was poured into H$_2$O (2 mL). The aqueous phase was extracted with ethyl acetate (5 mL*2). The combined organic phase was washed with brine (2 mL*2), dried with anhydrous Na$_2$SO$_4$, filtered and concentrated in vacuum. The residue was purified by silica gel chromatography (Petroleum ether/Ethyl acetate=100/1 to 1:1, TLC:Petroleum ether/Ethyl acetate=5:1, R$_f$=0.6) to give compound 5 (200 mg, 766.89 umol, 37.35% yield) as a white solid. LCMS: RT=1.403 min, MS cal.: 261.1, [M+H]$^+$=260.05.

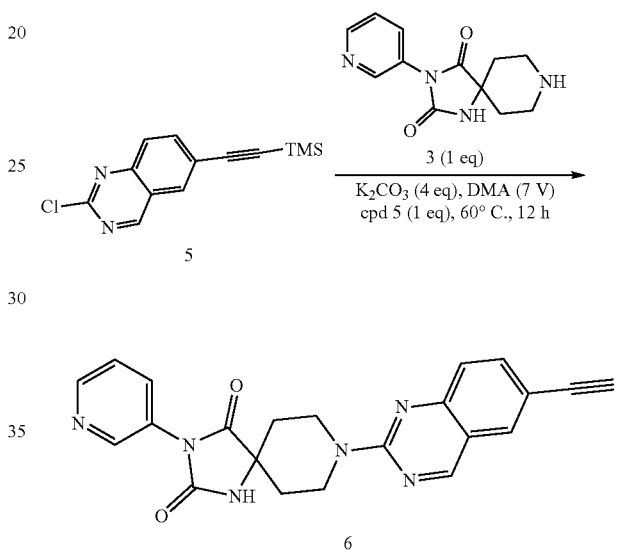

To a solution of compound 5 (90 mg, 345.10 umol, 1 eq) in DMA (3 mL) was added compound 3 (84.99 mg, 345.10 umol, 1 eq) and K$_2$CO$_3$ (190.78 mg, 1.38 mmol, 4 eq). The mixture was stirred at 60° C. for 12 h. TLC (Petroleum ether/Ethyl acetate=0/1, R$_f$=0.7) showed the reaction was completed. The residue was poured into water (2 mL). The aqueous phase was extracted with ethyl acetate (2 mL*2). The combined organic phase was washed with brine (2 mL*3), dried with anhydrous Na$_2$SO$_4$, filtered and concentrated in vacuum. The residue was purified by prep-TLC (Petroleum ether/Ethyl acetate=0/1, R$_f$=0.7) to give compound 6 (50 mg, 125.50 umol, 36.37% yield) as a yellow solid. LCMS: RT=1.059 min, MS cal.: 399.2, [M+H]$^+$=398.1

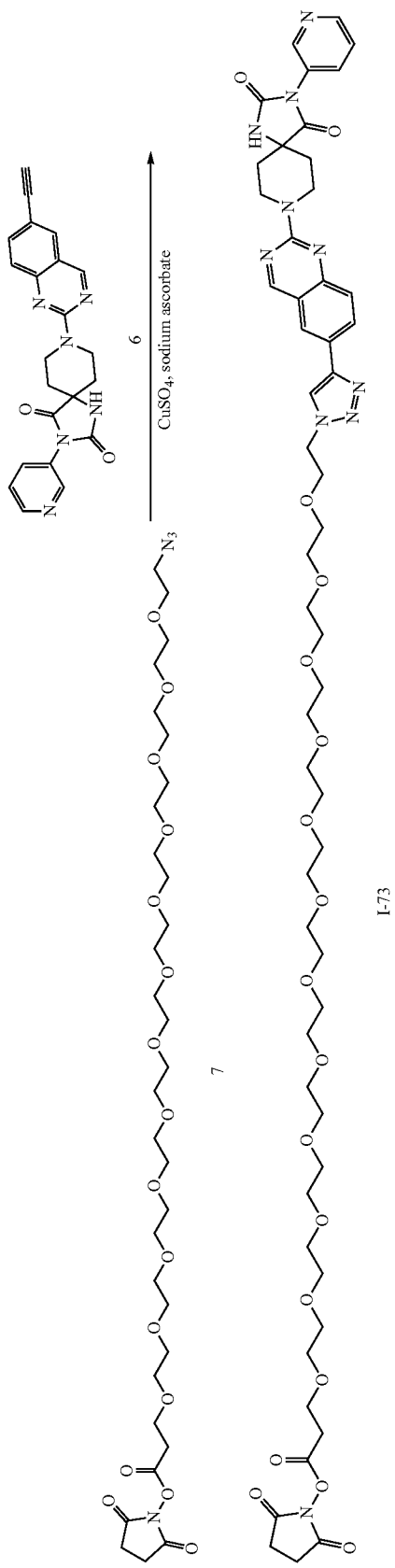

To a solution of compound 6 (30 mg, 75.30 umol, 1 eq) in DMSO (2 mL) was added compound 7 (55.78 mg, 75.30 umol, 1 eq), CuSO$_4$·5H$_2$O (56.40 mg, 225.89 umol, 3 eq) and sodium ascorbate (44.75 mg, 225.89 umol, 3 eq) under N$_2$. The mixture was stirred at 25° C. for 40 min. LCMS showed the reaction was completed. The mixture was filtered to give crude product. The crude product was purified by prep-HPLC (column: Luna C18 100*30 5 u; mobile phase: [water (0.1% TFA)–ACN]; B %: 15%-45%, 10 min) to give I-73 (8.77 mg, 7.08 umol, 9.41% yield, 92% purity) as a white solid. 1H NMR (400 MHz, CHLOROFORM-d) δ 9.23 (s, 1H) 8.39 (s, 1H) 8.25 (s, 2H) 7.92 (s, 1H) 7.46-7.75 (m, 4H) 4.65 (s, 4H) 4.15 (s, 2H) 3.95 (s, 2H) 3.84 (t, J=6.3 Hz, 2H) 3.53-3.75 (m, 44H) 2.90 (t, J=6.3 Hz, 2H) 2.84 (s, 4H) 2.30 (s, 2H) 2.08 (s, 2H). LCMS: RT=1.122 min, MS cal.: 1139.2, [M/2+H]$^+$=570.4. LCMS: RT=2.967 min, MS cal.: 1139.2, [M/2+H]$^+$=570.3.

Example 23: Synthesis of I-74

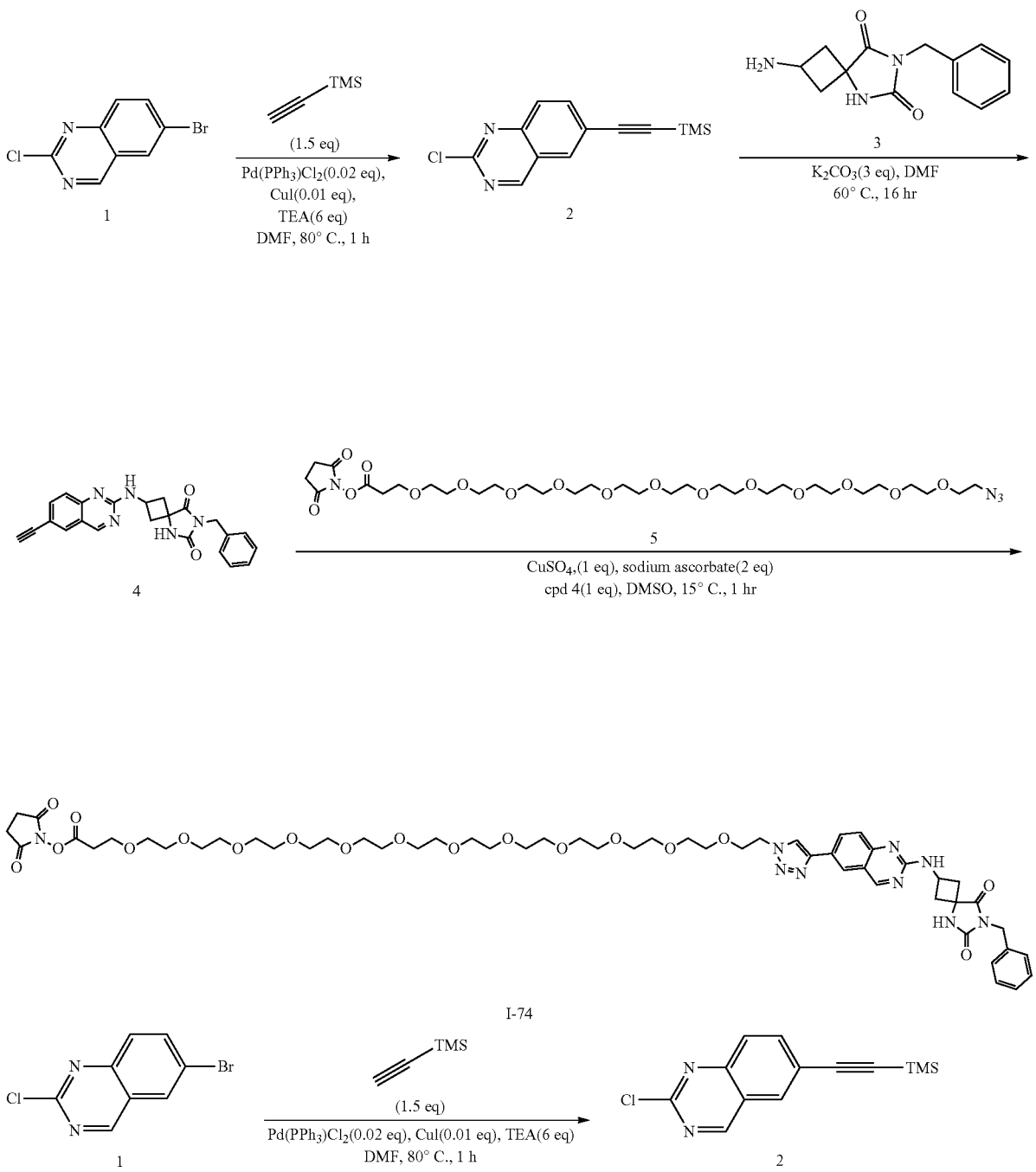

To a solution of compound 1 (0.5 g, 2.05 mmol, 1 eq) in DMF (10 mL) was added ethynyl(trimethyl)silane (302.53 mg, 3.08 mmol, 426.71 uL, 1.5 eq), Pd(PPh$_3$)$_2$Cl$_2$ (28.83 mg, 41.07 umol, 0.02 eq), CuI (3.91 mg, 20.53 umol, 0.01 eq) and TEA (1.25 g, 12.32 mmol, 1.71 mL, 6 eq) under N$_2$. The mixture was stirred at 80° C. for 1 h. LCMS showed the reaction was completed. The mixture was poured into H$_2$O (2 mL). The aqueous phase was extracted with ethyl acetate (5 mL*2). The combined organic phase was washed with brine (2 mL*2), dried with anhydrous Na$_2$SO$_4$, filtered and concentrated in vacuum. The residue was purified by silica gel chromatography (Petroleum ether/Ethyl acetate=100/1 to 1:1, TLC:Petroleum ether/Ethyl acetate=5:1, R$_f$=0.6). Compound 2 (200 mg, 766.89 umol, 37.35% yield) was obtained as a white solid. LCMS: RT=1.403 min, MS cal.: 260.05, [M+H]$^+$=261.1.

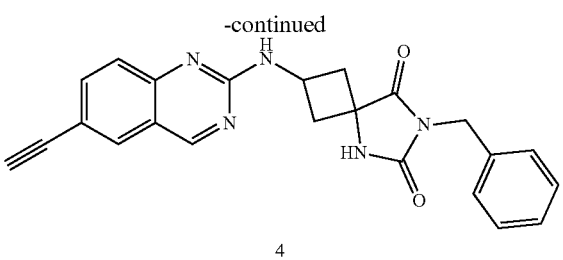

4

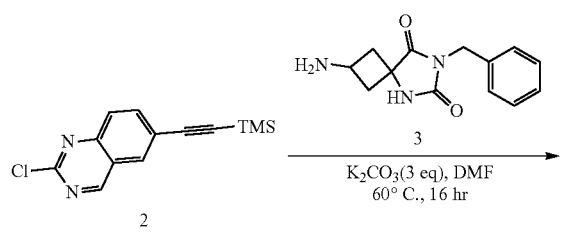

To a solution of compound 3 (65.02 mg, 265.09 umol, 1 eq) and K$_2$CO$_3$ (109.91 mg, 795.28 umol, 3 eq) in DMA (2 mL) was added compound 2 (69.13 mg, 265.09 umol, 1 eq) stirred at 60° C. for 16 hrs. LCMS showed the starting material was consumed completely and the desired MS was detected. The reaction mixture was filtered and filtrate was concentrated. The residue was purified by prep-TLC (Ethyl acetate). To give compound 5 (50 mg, 125.81 umol, 47.46% yield) was obtained as a yellow oil. LCMS: RT=1.247 min, MS cal.: 397.43 [M+H]$^+$=398.0.

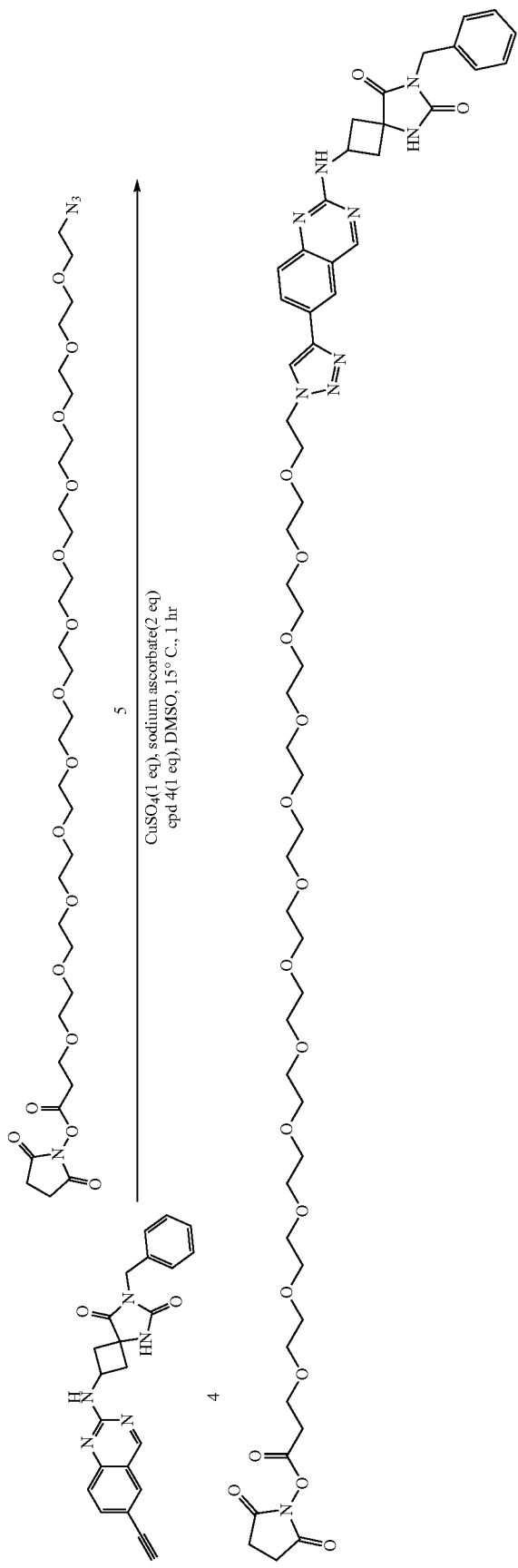

A solution of compound 5 (50 mg, 67.50 umol, 1 eq) and compound 4 (26.82 mg, 67.50 umol, 1 eq) in DMSO (2 mL) was added sodium ascorbate (26.74 mg, 134.99 umol, 2 eq) and CuSO$_4$·5H$_2$O (16.85 mg, 67.50 umol, 1 eq) stirred at 15° C. for 1 h. LCMS showed a peak with desired MS was detected. The reaction mixture was filtered. The residue was purified by prep-HPLC (column: Luna C18 100*30 5 u; mobile phase: [water (0.1% TFA)–ACN]; B %: 15%-40%, 10 min) according to HPLC. I-74 (25.32 mg, 22.18 umol, 32.87% yield, 99.72% purity) was obtained as a colorless oil, which was confirmed by H NMR and QC LCMS. LCMS: RT=1.156 min, MS cal.: 1137.52, [M+H]$^+$=1138.3.

HPLC: RT=2.505 min. QCLCMS: RT=2.756 min, MS cal.: 1137.52, [1/2M+H]$^+$=569.9. $^1$H NMR (400 MHz, CHLOROFORM-d) δ ppm 11.53 (br d, J=4.6 Hz, 1H), 9.32 (br s, 1H), 8.47 (br s, 1H), 8.34 (br d, J=8.6 Hz, 1H), 8.26 (br s, 1H), 7.76 (br d, J=8.6 Hz, 1H), 7.43-7.37 (m, 2H), 7.36-7.24 (m, 6H), 6.57 (s, 1H), 5.07-4.96 (m, 1H), 4.71-4.61 (m, 5H), 3.94 (br s, 2H), 3.83 (br t, J=6.4 Hz, 3H), 3.71-3.53 (m, 62H), 3.09 (br t, J=10.3 Hz, 2H), 2.91-2.87 (m, 1H), 2.92-2.79 (m, 7H), 2.66-2.57 (m, 2H), 2.17 (s, 1H).

Example 24: Synthesis of I-75

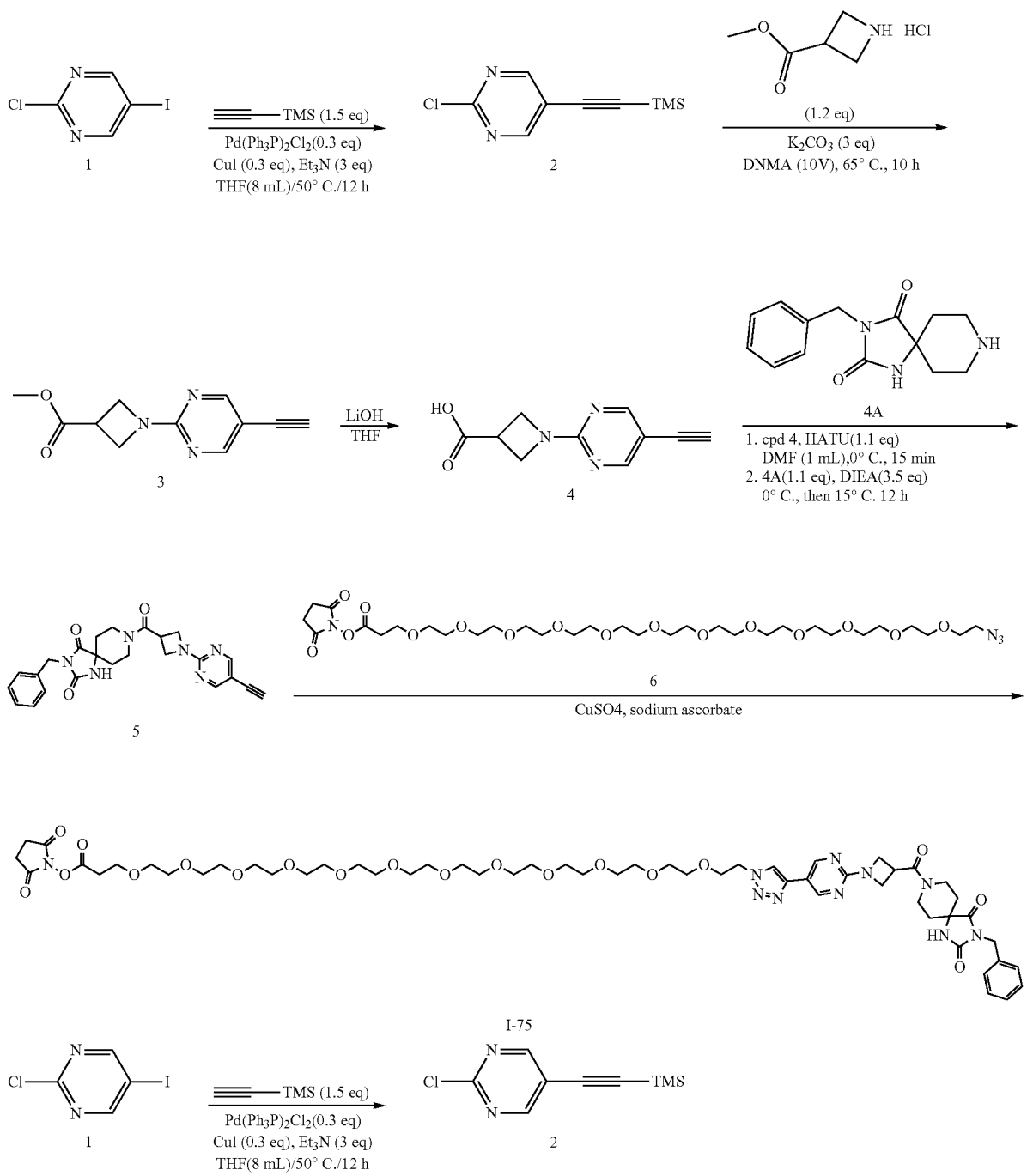

To a mixture of compound 1 (5 g, 20.80 mmol, 1 eq) and ethynyl(trimethyl)silane (4.09 g, 41.59 mmol, 5.76 mL, 2 eq) in THF (50 mL) was added CuI (118.82 mg, 623.88 umol, 0.03 eq), Pd(PPh$_3$)$_2$Cl$_2$ (437.90 mg, 623.88 umol, 0.03 eq) and Et$_3$N (4.21 g, 41.59 mmol, 5.79 mL, 2 eq) under N$_2$. The mixture was purged with N$_2$ for three times and stirred at 50° C. for 12 hrs under N$_2$. TLC showed it was finished (Petroleum ether:Ethyl acetate=5:1 R$_f$=0.24). It was concentrated directly. The residue was purified by column chromatography (SiO$_2$, Petroleum ether/Ethyl acetate=8:1, Petroleum ether:Ethyl acetate=5:1, R$_f$=0.43) to give Compound 2 (2 g, 9.49 mmol, 45.6400 yield) was obtained as a brown solid.

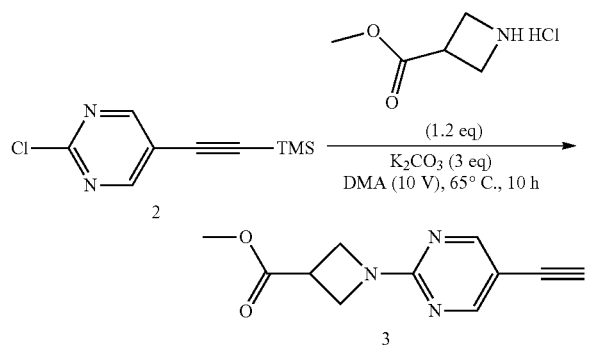

To a solution of compound 2 (0.9 g, 4.27 mmol, 1 eq) in DMA (5 mL) was added K$_2$CO$_3$ (2.95 g, 21.35 mmol, 5 eq) and methyl azetidine-3-carboxylate (776.89 mg, 5.12 mmol, 1.2 eq, HCl). The mixture was stirred at 60° C. for 12 hr. TLC showed it was finished (Petroleum ether:Ethyl acetate=5:1, R$_f$=0.57). It was added with 50 mL H$_2$O, extracted with 50 mL EtOAc, the organic layer was separated and concentrated. The residue was purified by column chromatography (SiO$_2$, Petroleum ether:Ethyl acetate=1:1, R$_f$=0.24) to give compound 3 (0.5 g, 2.30 mmol, 53.90% yield) as a yellow solid.

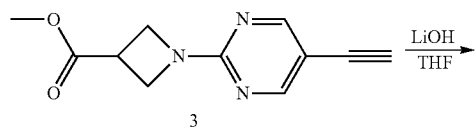

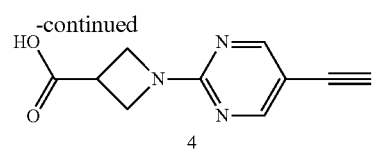

To a solution of compound 3 (0.4 g, 1.84 mmol, 1 eq) in THF (5 mL) was added LiOH·H$_2$O (1 M, 2.21 mL, 1.2 eq). The mixture was stirred at 15° C. for 12 hr. TLC showed it was finished (Petroleum ether:Ethyl acetate=0:1, R$_f$=0.57). It was added with 0.5 M HCl to adjust pH=3, it was extracted with EtOAc 10 mL, the organic layer was separated, dried over Na$_2$SO$_4$, filtered and the filtrate was concentrated to give compound 4 (0.28 g, 1.38 mmol, 74.83% yield obtained as a yellow solid.

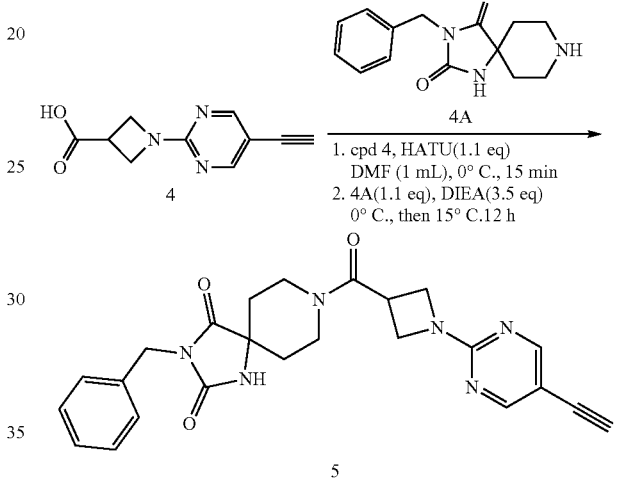

To a solution of compound 4 (41.56 mg, 204.55 umol, 1.1 eq) in DMF (1 mL) was added HATU (84.85 mg, 223.15 umol, 1.2 eq). The mixture was stirred at 15° C. for 10 mins. Then compound 4A (55 mg, 185.96 umol, 1.00 eq, HCl), DIPEA (96.14 mg, 743.84 umol, 129.56 uL, 4 eq) was added, then it was stirred at 15° C. for 12 hr. LCMS showed it was finished. It was added with 10 mLH$_2$O and extracted with 5 mL EtOAc, the organic layer was separated, concentrated to give the crude product compound 5 (50 mg, 112.49 umol, 60.49% yield), which was used into the next step without further purification. LCMS: RT=1.136 min, MS cal.: 444.19 [M+H]$^+$=445.3.

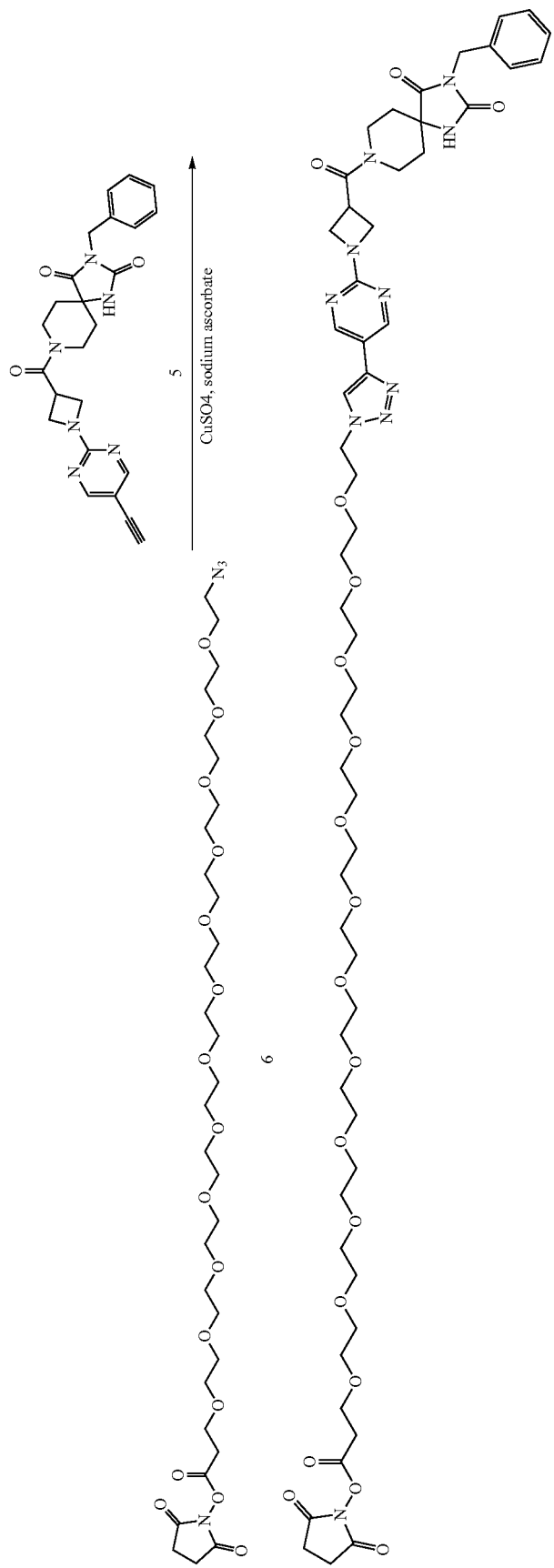

To a solution of compound 6 (50 mg, 67.49 umol, 1 eq) in DMSO (1 mL) was added compound 5 (30 mg, 67.49 umol, 1 eq), $CuSO_4 \cdot 5H_2O$ (5.06 mg, 20.25 umol, 0.3 eq) and sodium ascorbate (26.74 mg, 134.99 umol, 2 eq). The mixture was stirred at 15° C. for 2 hr. LCMS showed it was finished (and HPLC). It was purified by prep-HPLC (column: Nano-micro Kromasil C18 100*30 mm 5 um; mobile phase: [water (0.1% TFA)–ACN]; B %: 27%-47%, 10 min) to give I-75 (40 mg, 32.27 umol, 47.81% yield, 95.62% purity) was obtained as a colorless oil. LCMS: RT=0.900 min, MS cal.: 1184.56, $[Ms/2+H]^+$=593.4. HPLC: RT=2.462 min. $^1$H NMR (400 MHz, DMSO-d6) δ ppm 8.99 (s, 1H) 8.79 (s, 2H) 8.47 (s, 1H) 7.19-7.41 (m, 5H) 4.84 (br s, 2H) 4.51-4.61 (m, 4H) 4.28 (td, J=8.53, 5.44 Hz, 2H) 4.08-4.22 (m, 3H) 3.88-3.96 (m, 1H) 3.81-3.88 (m, 2H) 3.62-3.75 (m, 3H) 3.50-3.56 (m, 12H) 3.44-3.49 (m, 21H) 3.28-3.40 (m, 2H) 3.11-3.24 (m, 1H) 2.92 (t, J=5.99 Hz, 2H) 2.81 (s, 4H) 1.71-1.92 (m, 2H) 1.57-1.68 (m, 2H). LCMS: RT=2.395 min, MS cal.: 1184.56, $[Ms/2+H]^+$=593.3.

Example 25: Synthesis of I-76

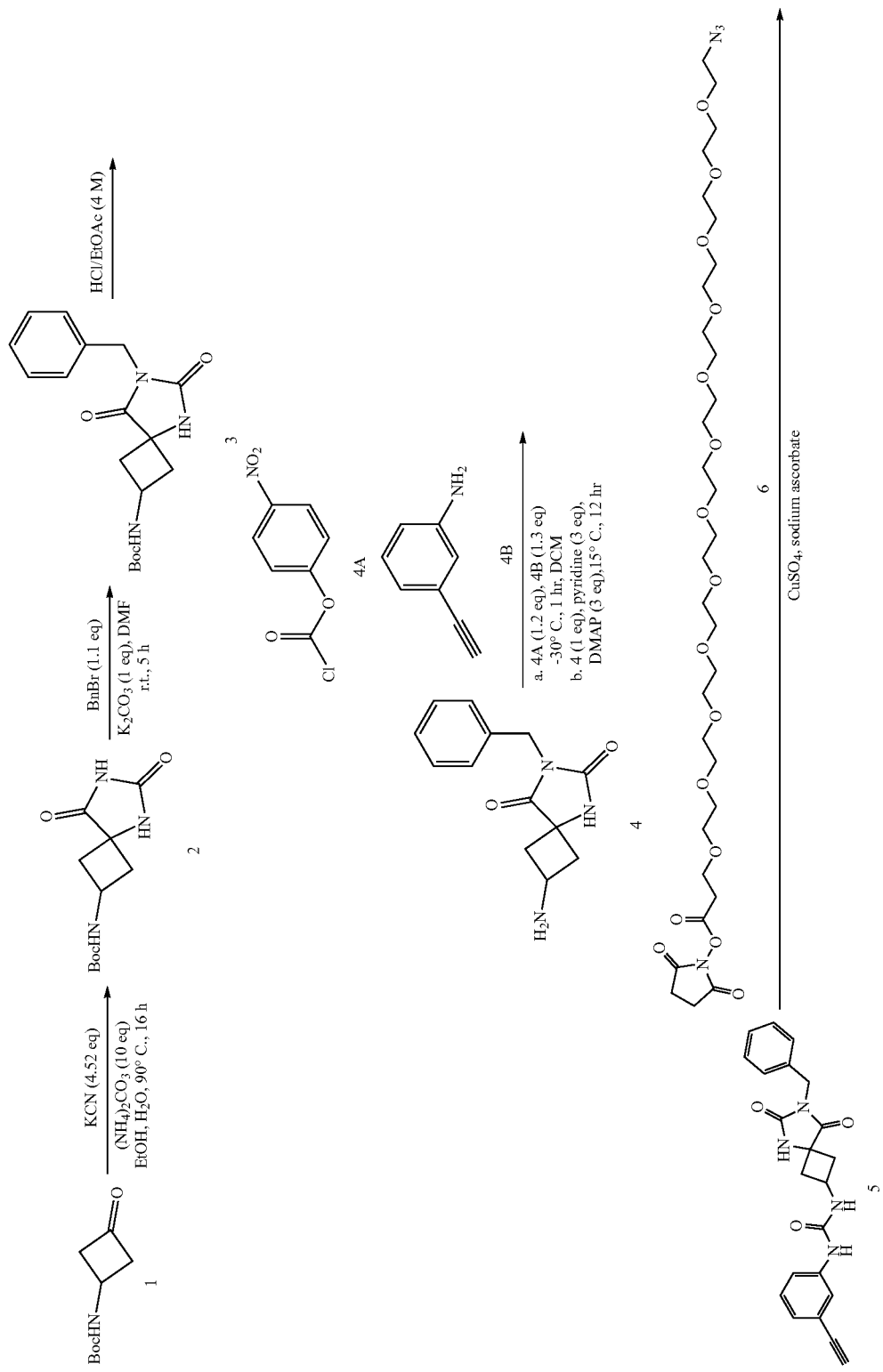

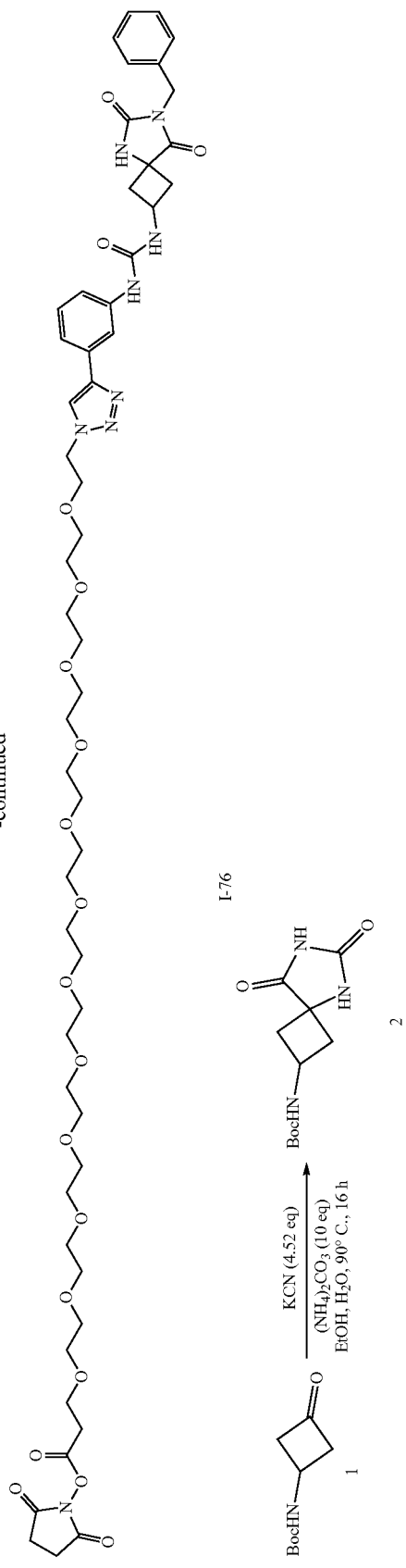
I-76

To a stirring solution of KCN (10.33 g, 158.62 mmol, 6.80 mL, 4.52 eq) and (NH₄)₂CO₃ (33.72 g, 350.93 mmol, 37.47 mL, 10 eq) in Water (45 mL) was added a solution of compound 1 (6.5 g, 35.09 mmol, 1 eq) in EtOH (45 mL) stirred at 90° C. for 16 hrs. TLC (Petroleum ether:Ethyl acetate=0:1, R$_f$=0.43) showed the starting material was consumed completely and a main spot was detected. The reaction was extracted with EtOAc (180 mL*2) and dried over Na₂SO₄. The organic phase was concentrated. The residue was purified by chromatography column (Petroleum ether:Ethyl acetate=1:1 to EA). Compound 2 (15 g, 58.76 mmol, 83.72% yield) as a white solid, which was confirmed by HNMR and LCMS. ¹H NMR (400 MHz, DMSO-d₆) δ 10.60 (s, 1H), 8.26 (s, 1H), 7.27 (br d, J=7.3 Hz, 1H), 4.02-3.89 (m, 1H), 2.55 (br d, J=8.8 Hz, 3H), 2.35-2.25 (m, 1H), 2.23-2.07 (m, 2H), 1.98 (br t, J=9.8 Hz, 1H), 1.37 (d, J=2.2 Hz, 14H), 1.36-1.35 (m, 3H). LCMS: RT=1.094 min, MS cal.: 255.12, [M+H]⁺=256.3.

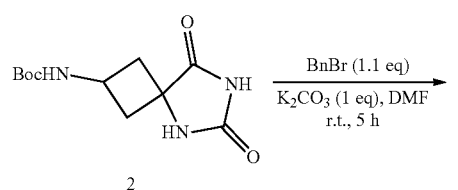

To a solution of compound 2 (0.3 g, 1.18 mmol, 1 eq) in DMF (5 mL) was added K2CO3 (162.42 mg, 1.18 mmol, 1 eq) and BnBr (221.10 mg, 1.29 mmol, 153.54 uL, 1.1 eq) stirred at 25° C. for 5 hrs. LCMS showed the starting material was consumed completely and the desired MS was detected. The reaction mixture was filtered and filtrate was concentrated. The residue was purified by column (Petroleum ether:Ethyl acetate=3:1) to give compound 3 (0.3 g, 868.58 umol, 73.91% yield) as a white solid. LCMS: RT=1.291 min, MS cal.: 345.17, [M+H]⁺=346.2.

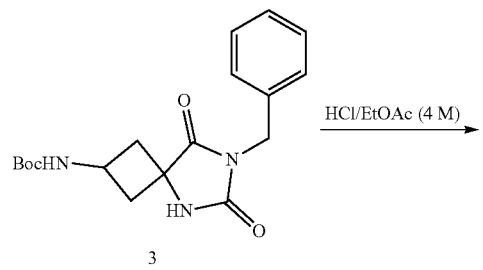

A solution of compound 3 (0.3 g, 868.58 umol, 1 eq) in HCl/EtOAc (4 M, 5 mL, 23.03 eq) was stirred at 25° C. for 2 hrs. TLC (Petroleum ether:Ethyl acetate=3:1, R$_f$=0) showed the starting material was consumed completely and new spot generated. The reaction was concentrated to give compound 4 (0.2 g, 774.64 umol, 89.18% yield, 95% purity) as a white solid, which was confirmed by H NMR. ¹H NMR (400 MHz, DMSO-d₆) δ 8.84 (s, 1H), 8.13 (br s, 3H), 7.42-7.16 (m, 5H), 4.52 (s, 2H), 3.77-3.62 (m, 1H), 2.72-2.65 (m, 3H), 2.52 (br s, 2H).

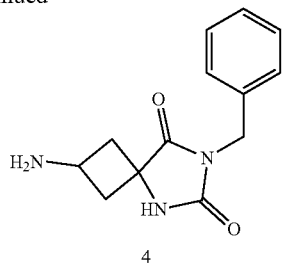

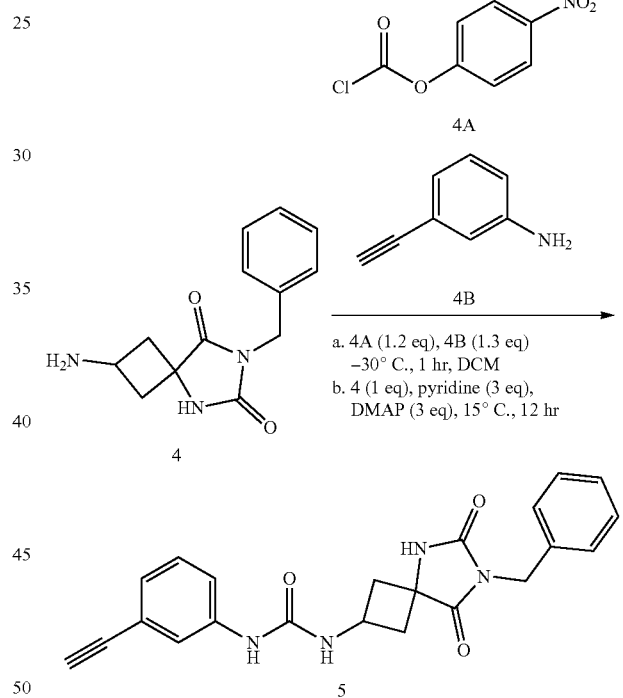

To a solution of compound 4A (59.17 mg, 293.55 umol, 1.2 eq) in DCM (1 mL) was added compound 4B (37.25 mg, 318.01 umol, 1.3 eq) in DCM (1 mL) dropwise at −40° C. stirred for 1 hr. Then the reaction mixture was added compound 4 (60 mg, 244.62 umol, 1 eq), DMAP (89.66 mg, 733.86 umol, 3 eq) and PYRIDINE (58.05 mg, 733.86 umol, 59.23 uL, 3 eq) in MeCN (5 mL) and stirred at 15° C. for 15 hrs. LCMS showed the starting material was consumed completely and a main peak with desired MS was detected. The reaction mixture was added EtOAc (40 mL), then the mixture was washed with brine (40 mL). The organic layer was dried over anhydrous Na₂SO₄ and concentrated under reduced pressure. The residue was purified by chromatography column (SiO₂, EA, Petroleum ether:EtOAc=1:1) to give compound 5 (50 mg, 128.73 umol, 52.62% yield) as a yellow oil, which was confirmed by H NMR. LCMS: RT=1.152 min, MS cal.: 388.15, [M+H]⁺=389.2. ¹H NMR (400 MHz, CHLOROFORM-d) δ 8.09 (d, J=6.8 Hz, 1H), 7.72 (s, 1H), 7.60 (br s, 1H), 7.42-7.35 (m, 2H), 7.33-7.28 (m, 3H), 7.22-7.18 (m, 1H), 7.16-7.07 (m, 2H), 6.56 (d, J=7.1 Hz, 1H), 6.23-6.09 (m, 1H), 4.67 (s, 2H), 4.30-4.19 (m, 1H), 4.33-4.19 (m, 1H), 3.01 (s, 1H), 2.98-2.88 (m, 2H), 2.65-2.53 (m, 2H).

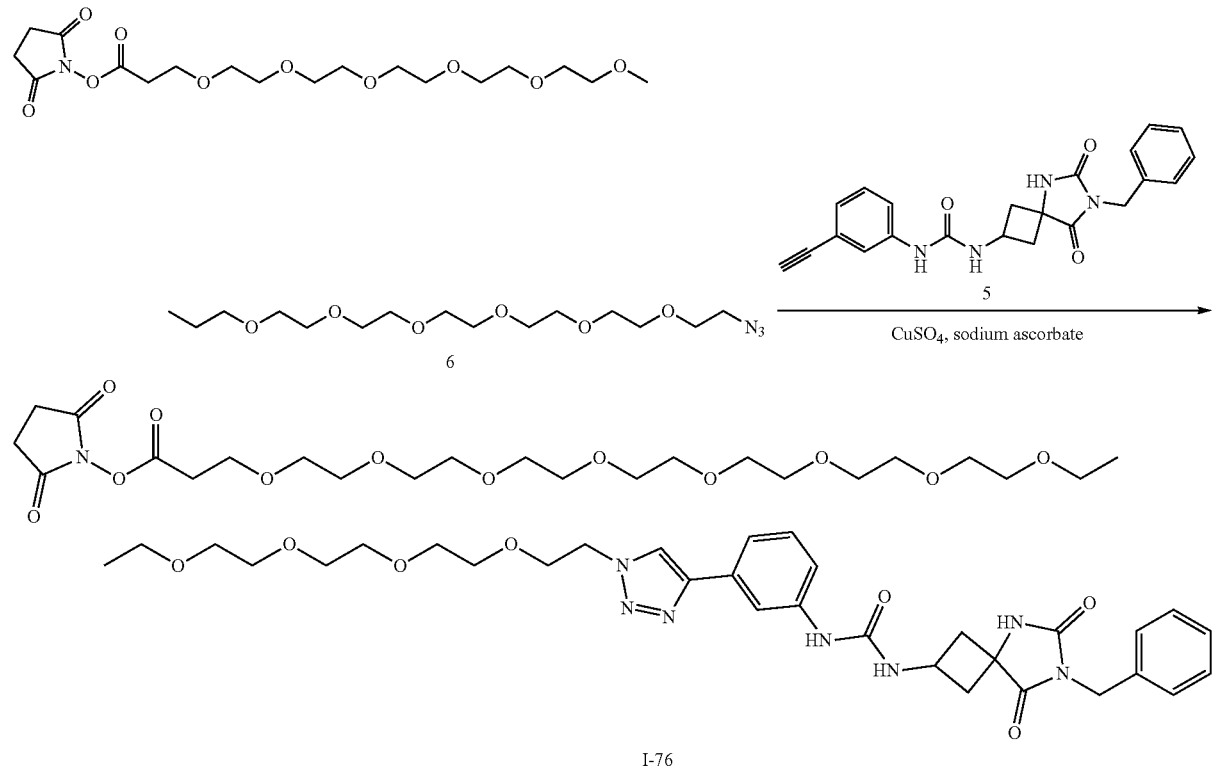

A solution of compound 6 (26.22 mg, 67.50 umol, 1 eq) and compound 5 (50 mg, 67.50 umol, 1 eq) was added CuSO$_4$·5H$_2$O (16.85 mg, 67.50 umol, 1 eq) and sodium ascorbate (26.74 mg, 134.99 umol, 2 eq) in DMSO (2 mL) stirred at 15° C. for 1 hr. LCMS showed a peak with desired MS was detected. The reaction mixture was filtered. The residue was purified by prep-HPLC (column: Nano-micro Kromasil C18 100*30 mm 5 um; mobile phase: [water (0.1% TFA)–ACN]; B %: 31%-49%, 10 min) and lyophilized to give I-76 (30.01 mg, 25.31 umol, 37.49% yield, 95.22% purity) as a colorless oil, which was confirmed by H NMR and QC LCMS. LCMS: RT=1.232 min, MS cal.: 1153.52, [M/2+H]$^+$=1129.5. $^1$H NMR (400 MHz, CHLOROFORM-d) δ 8.01 (br d, J=11.7 Hz, 1H), 7.87 (br d, J=18.1 Hz, 1H), 7.71 (br s, 1H), 7.51-7.41 (m, 2H), 7.40-7.35 (m, 2H), 7.33-7.28 (m, 3H), 7.26 (br s, 1H), 7.20 (br s, 1H), 6.23 (br s, 1H), 4.63 (s, 2H), 4.56 (br d, J=4.4 Hz, 2H), 4.31-4.19 (m, 1H), 3.88 (br s, 2H), 3.83 (br t, J=6.3 Hz, 2H), 3.64-3.58 (m, 38H), 3.54 (s, 7H), 2.95-2.86 (m, 4H), 2.82 (br s, 3H), 2.51 (br d, J=9.0 Hz, 2H). LCMS: T=2.484 min, MS cal.: 1153.52, [M/2+H]$^+$=565.3, [M+H]$^+$=1129.5.

Example 26: Synthesis of I-77

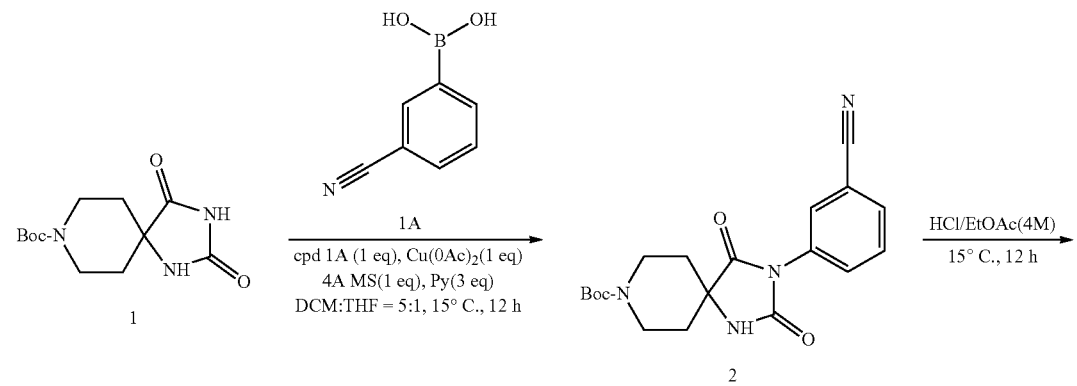

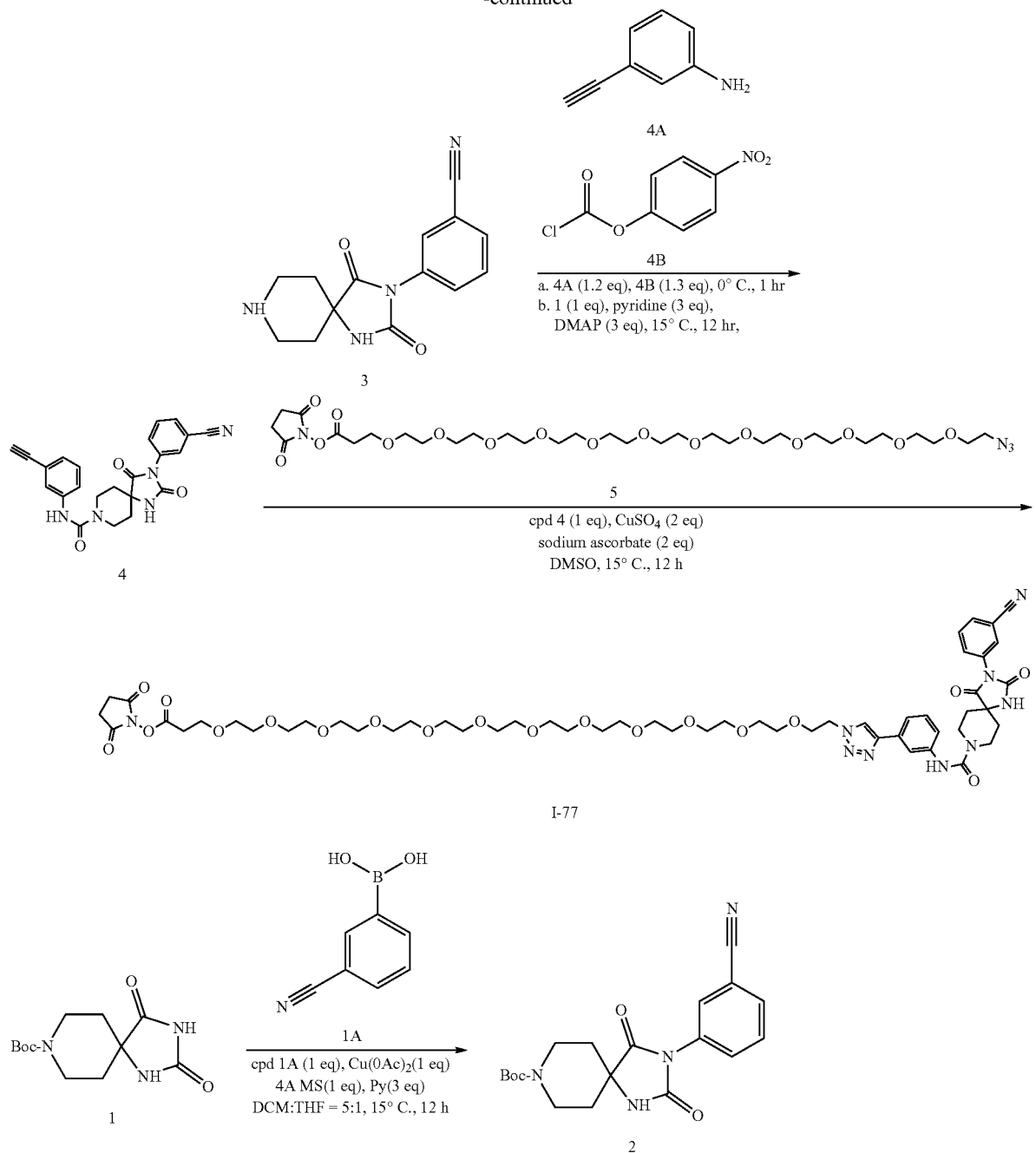

To a solution of compound 1A (54.56 mg, 371.34 umol, 1 eq) and compound 1 (100 mg, 371.34 umol, 1 eq) in DCM (5 mL) and THF (1 mL) was added Cu(OAc)$_2$ (67.45 mg, 371.34 umol, 1 eq), Py (88.12 mg, 1.11 mmol, 89.92 uL, 3 eq) and 4A MS (100 mg, 371.34 umol, 1 eq). The mixture was stirred at 15° C. for 12 hr under oxygen atmosphere. LCMS showed the desired compound was detected. The reaction mixture was filtered. The filtrate was concentrated under reduced pressure to give a residue. The residue was purified by prep-TLC (SiO$_2$, Petroleum ether:Ethyl acetate=1:1). Compound 2 (80 mg, 215.98 umol, 58.16% yield) was obtained as a white solid. LCMS: RT=1.404 min, MS cal.: 370.1, [M−H]$^-$=369.3.

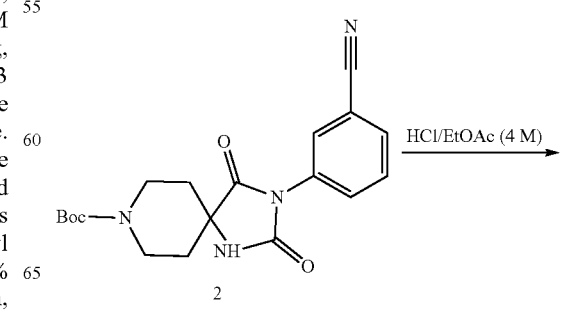

-continued

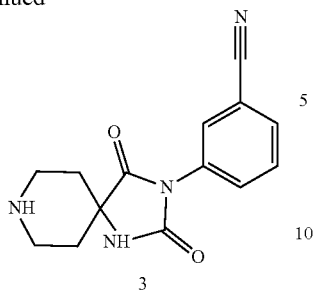

3

-continued

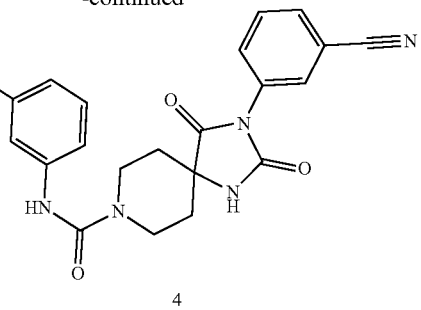

4

The solution of compound 2 (80 mg, 215.98 umol, 1 eq) in HCl/EtOAc (10 mL) was stirred at 15° C. for 3 hr. LCMS showed cpd 2 was consumed completely and desired mass was detected. The reaction mixture was concentrated under reduced pressure to remove solvent. The residue was directly used for the next step without purification. Compound 3 (48 mg, 177.59 umol, 82.22% yield) was obtained as a white solid. LCMS: RT=1.005 min, MS cal.: 270.1, [M−H]$^+$=269.2.

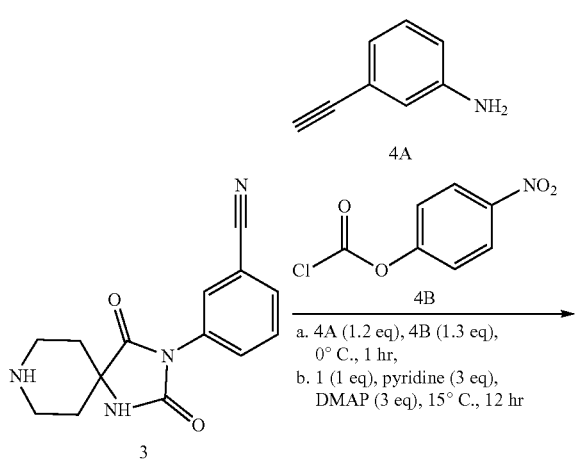

To a solution of compound 3 (42.95 mg, 213.11 umol, 1.2 eq) in DCM (3 mL) was added compound 4A (27.05 mg, 230.87 umol, 1.3 eq) in DCM (1 mL) dropwise at −40° C. Then the reaction mixture was added compound 4B (48 mg, 177.59 umol, 1 eq), Py (42.14 mg, 532.77 umol, 43.00 uL, 3 eq) and DMAP (65.09 mg, 532.77 umol, 3 eq) in DCM (2 mL) and stirred at 25° C. for 16 hrs. LCMS showed the desired compound was detected. The reaction mixture was concentrated under reduced pressure to remove solvent. The residue was purified by prep-TLC (SiO$_2$, DCM:MeOH=10:1, R$_f$=0.2). Compound 4 (43 mg, 104.01 umol, 58.57% yield) was obtained as a white solid. LCMS: RT=1.114 min, MS cal.: 413.15, [M+H]$^+$=414.3.

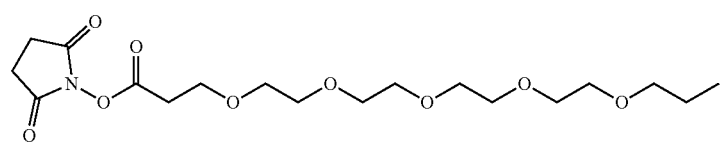

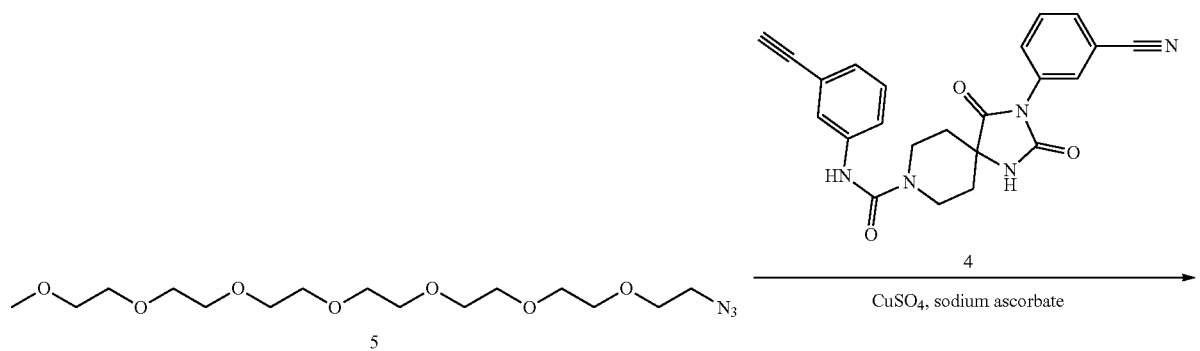

-continued

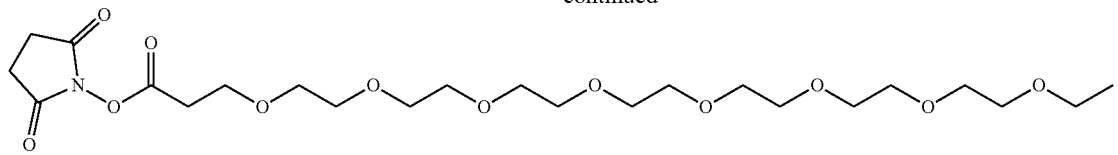

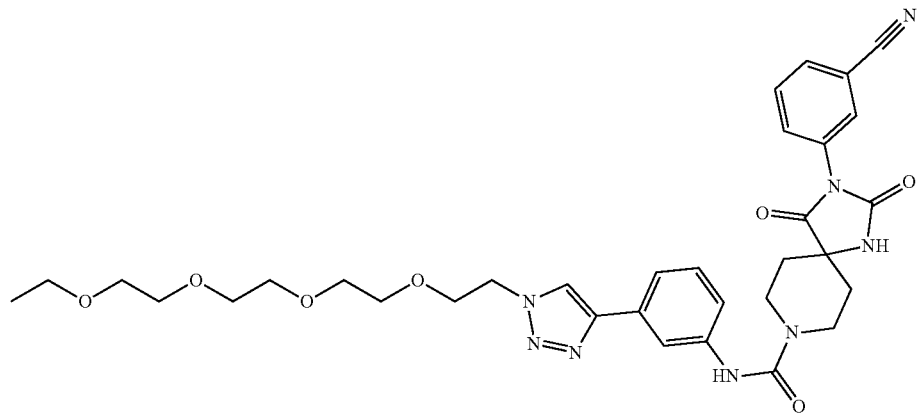

I-77

A mixture of compound 5 (71.67 mg, 96.75 umol, 1 eq), compound 4 (40 mg, 96.75 umol, 1 eq), CuSO$_4$·5H$_2$O (48.32 mg, 193.50 umol, 2 eq), sodium ascorbate (38.33 mg, 193.50 umol, 2 eq) in DMSO (2 mL) was degassed and purged with N$_2$ for 3 times, and then the mixture was stirred at 15° C. for 2 hr under N$_2$ atmosphere. LCMS showed one main peak with desired m/z. The reaction mixture was filtered. The filtrate was used for the next step directly. The residue was purified by prep-HPLC (TFA condition). I-77 (48.98 mg, 42.07 umol, 43.48% yield, 99.13% purity) was obtained as a purple solid. The structure was confirmed by HNMR. The purity was 99.13% according to LCMS (RT=2.505). LCMS: RT=2.059 min, MS cal.: 1153.5, [1/2M+H]$^+$=578.3.

QCLCMS: Rt=2.505 min, MS cal.: 1153.5, [1/2M+H]$^+$=577.8. $^1$H NMR (400 MHz, DMSO-d$_6$) δ ppm 9.25 (s, 1H), 8.75 (s, 1H), 8.45 (s, 1H), 8.02 (s, 1H), 7.95 (t, J=1.5 Hz, 1H), 7.88 (td, J=1.3, 7.6 Hz, 1H), 7.83-7.79 (m, 1H), 7.74-7.69 (m, 1H), 7.48 (br d, J=8.8 Hz, 1H), 7.40-7.36 (m, 1H), 7.33-7.28 (m, 1H), 4.57 (t, J=5.2 Hz, 2H), 4.08-4.00 (m, 2H), 3.87 (t, J=5.2 Hz, 2H), 3.71 (t, J=6.0 Hz, 3H), 3.57-3.53 (m, 3H), 3.53-3.51 (m, 5H), 3.50 (s, 21H), 3.48-3.45 (m, 13H), 3.40-3.31 (m, 3H), 2.92 (t, J=6.0 Hz, 2H), 2.80 (s, 4H), 1.99-1.90 (m, 2H), 1.86-1.79 (m, 2H).

Example 27: Synthesis of I-78

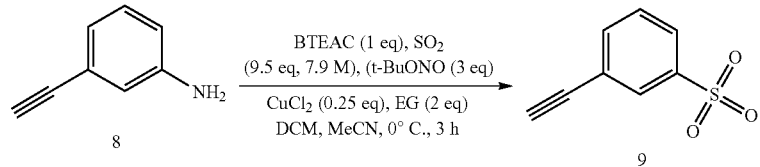

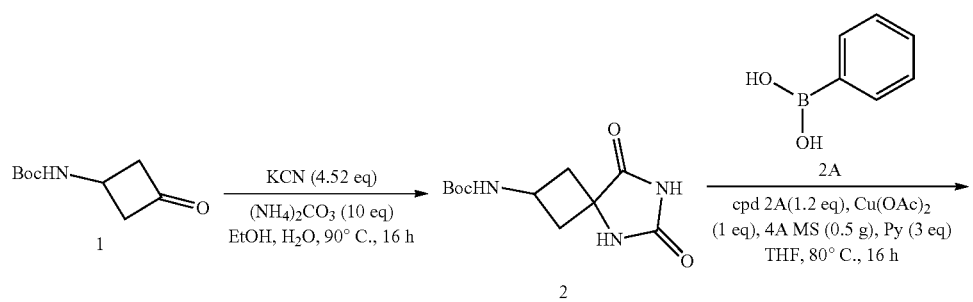

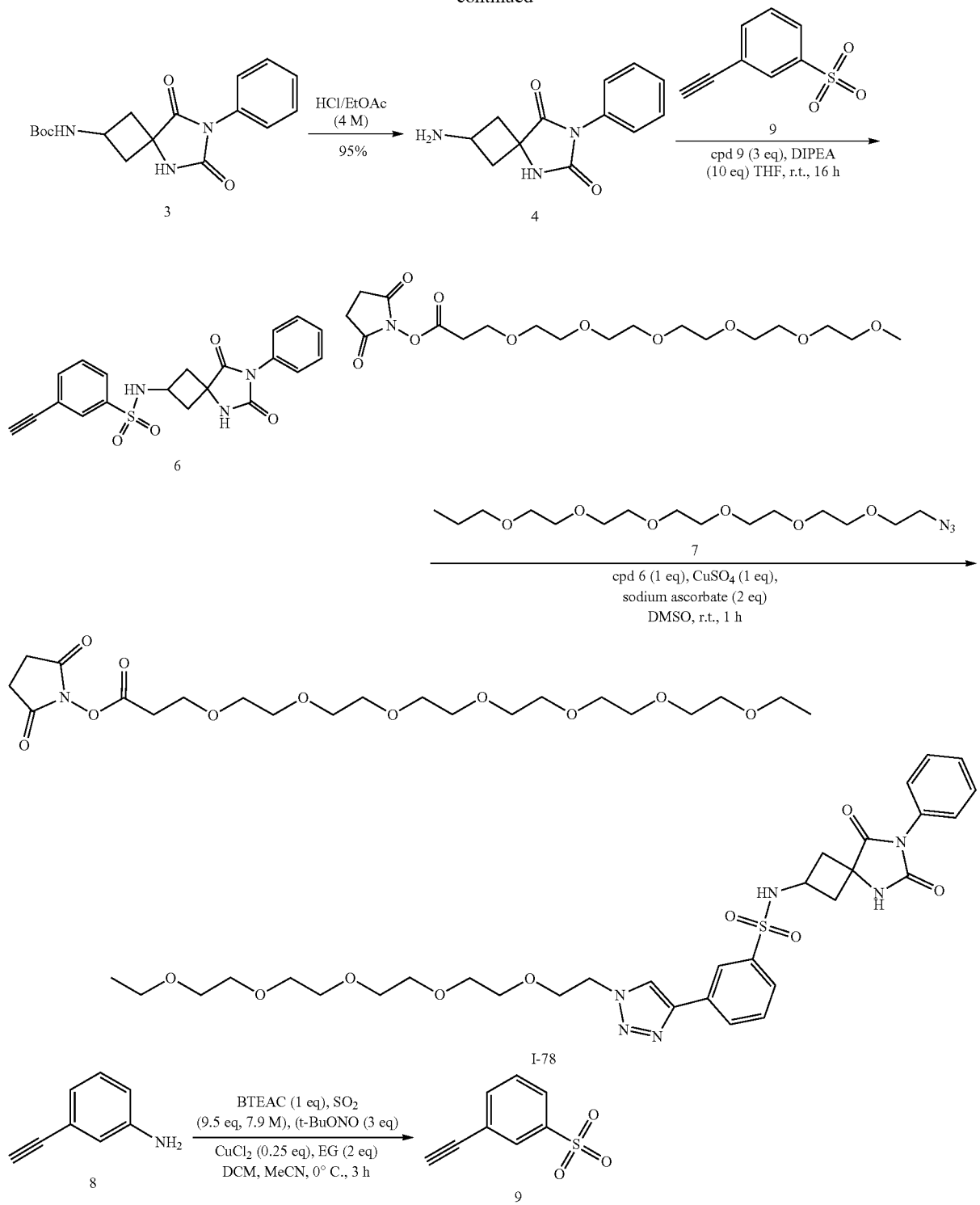

Compound 8 (0.5 g, 4.27 mmol, 1 eq), SO₂ (7.9 M, 5.13 mL, 9.5 eq, in MeCN) and BTEAC (972.16 mg, 4.27 mmol, 1 eq) in DCM-MeCN (3:1, 4.8 mL) was added t-BuONO (1.32 g, 12.80 mmol, 1.52 mL, 3 eq) in 3:1, DCM-MeCN (6.0 mL) stirred at 0° C. for 1 h, the reaction mixture was added CuCl₂ (143.46 mg, 1.07 mmol, 0.25 eq), ETHYLENE GLYCOL (529.83 mg, 8.54 mmol, 477.32 uL, 2 eq) in MeCN (2.0 mL) stirred at 0° C. for 2 h. TLC (Plate 1) showed the starting material was consumed completely. The reaction mixture was concentrated under reduced pressure and the residue partitioned between H₂O (30 mL) and DCM (30 mL) and layers separated. Combined organics were concentrated under reduced pressure. The residue was used directly next step without purification. Compound 9 (0.2 g, 996.80 umol, 23.35% yield) was obtained as a yellow oil.

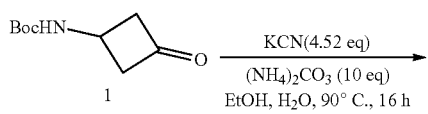

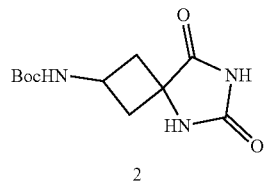

To a stirring solution of KCN (10.33 g, 158.62 mmol, 6.80 mL, 4.52 eq) and $(NH_4)_2CO_3$ (33.72 g, 350.93 mmol, 37.47 mL, 10 eq) in Water (45 mL) was added a solution of compound 1 (6.5 g, 35.09 mmol, 1 eq) in EtOH (45 mL) stirred at 90° C. for 16 hrs. TLC (plate 1, Petroleum ether:Ethyl acetate=0:1, $R_f$=0.43) showed the starting material was consumed completely and a main spot was detected. The reaction was extracted with EtOAc (180 mL*2) and dried over $Na_2SO_4$. The organic phase was concentrated. The residue was purified by chromatography column ($SiO_2$, Petroleum ether:Ethyl acetate=1:1 to 0:1). Compound 2 (15 g, 58.76 mmol, 83.72% yield) as a white solid, which was confirmed by HNMR and LCMS. $^1$H NMR (400 MHz, DMSO-$d_6$) δ 10.60 (s, 1H), 8.26 (s, 1H), 7.27 (br d, J=7.3 Hz, 1H), 4.02-3.89 (m, 1H), 2.55 (br d, J=8.8 Hz, 3H), 2.35-2.25 (m, 1H), 2.23-2.07 (m, 2H), 1.98 (br t, J=9.8 Hz, 1H), 1.37 (d, J=2.2 Hz, 14H), 1.36-1.35 (m, 3H). LCMS: RT=1.094 min, MS cal.: 255.12, [M+H]$^+$=256.3.

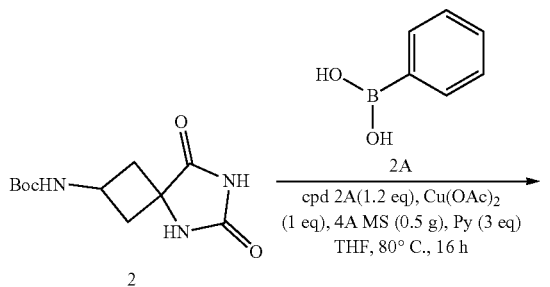

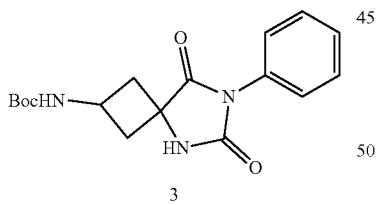

To a solution of compound 2 (0.5 g, 1.57 mmol, 1 eq), compound 2A (229.27 mg, 1.88 mmol, 1.2 eq) and 4A MOLECULAR SIEVE (1.57 mmol, 1 eq) in THF (10 mL) was added $Cu(OAc)_2$ (284.62 mg, 1.57 mmol, 1 eq) and PYRIDINE (371.84 mg, 4.70 mmol, 379.43 uL, 3 eq) stirred at 80° C. for 16 hrs. LCMS showed the starting material was consumed completely and the desired MS was detected. The reaction mixture was filtered and filtrate was concentrated. The residue was purified by chromatography column ($SiO_2$, Petroleum ether:Ethyl acetate=1:1 to DCM:MeOH=10:1) to give compound 3 (0.28 g, 844.99 umol, 53.92% yield) as a yellow oil, which was confirmed by HNMR. LCMS: RT=1.237 min, MS cal.: 331.37 [M−H]$^+$=332.1. $^1$H NMR (400 MHz, DMSO-$d_6$) δ 8.86 (s, 1H), 7.54-7.42 (m, 2H), 7.40-7.31 (m, 4H), 4.35 (t, J=5.1 Hz, 1H), 4.10-3.97 (m, 1H), 3.43 (dd, J=5.1, 7.1 Hz, 1H), 2.78-2.68 (m, 2H), 2.37-2.23 (m, 2H), 1.37 (s, 10H).

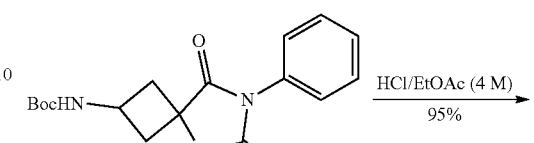

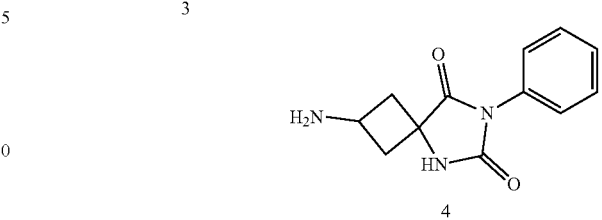

A solution of compound 3 (0.28 g, 844.99 umol, 1 eq) in HCl/EtOAc (4 M, 211.25 uL, 1 eq) was stirred at 25° C. for 2 hrs. LCMS showed the starting material was consumed completely and the desired MS was detected. The reaction mixture was concentrated to give compound 4 (0.2 g, 821.62 umol, 97.23% yield, 95% purity) as a white solid. The residue was used directly next step without purification. LCMS: RT=0.248 min, MS cal.: 231.25, [M+H]$^+$=232.1.

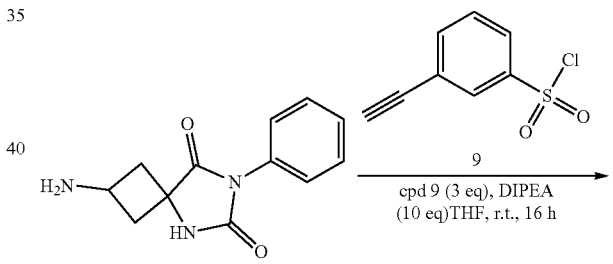

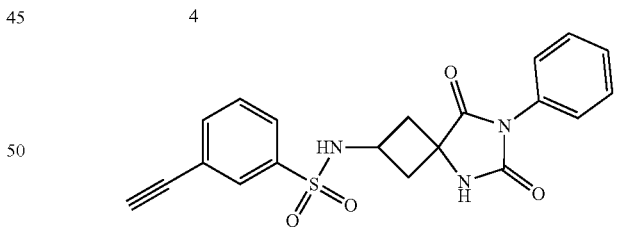

To a solution of compound 4 (0.1 g, 432.43 umol, 1 eq) in DCM (1 mL), compound 9 (200.00 mg, 996.80 umol, 2.31 eq) and DIEA (558.89 mg, 4.32 mmol, 753.22 uL, 10 eq) stirred at 25° C. for 16 hrs. LCMS showed the starting material was consumed completely and the desired MS was detected. The reaction mixture was concentrated. The residue was purified by prep-TLC (DCM:MeOH=10:1) to give compound 6 (60 mg, 151.73 umol, 35.09% yield) as a yellow oil. LCMS: RT=1.231 min, MS cal.: 395.43 [M+H]$^+$=396.0.

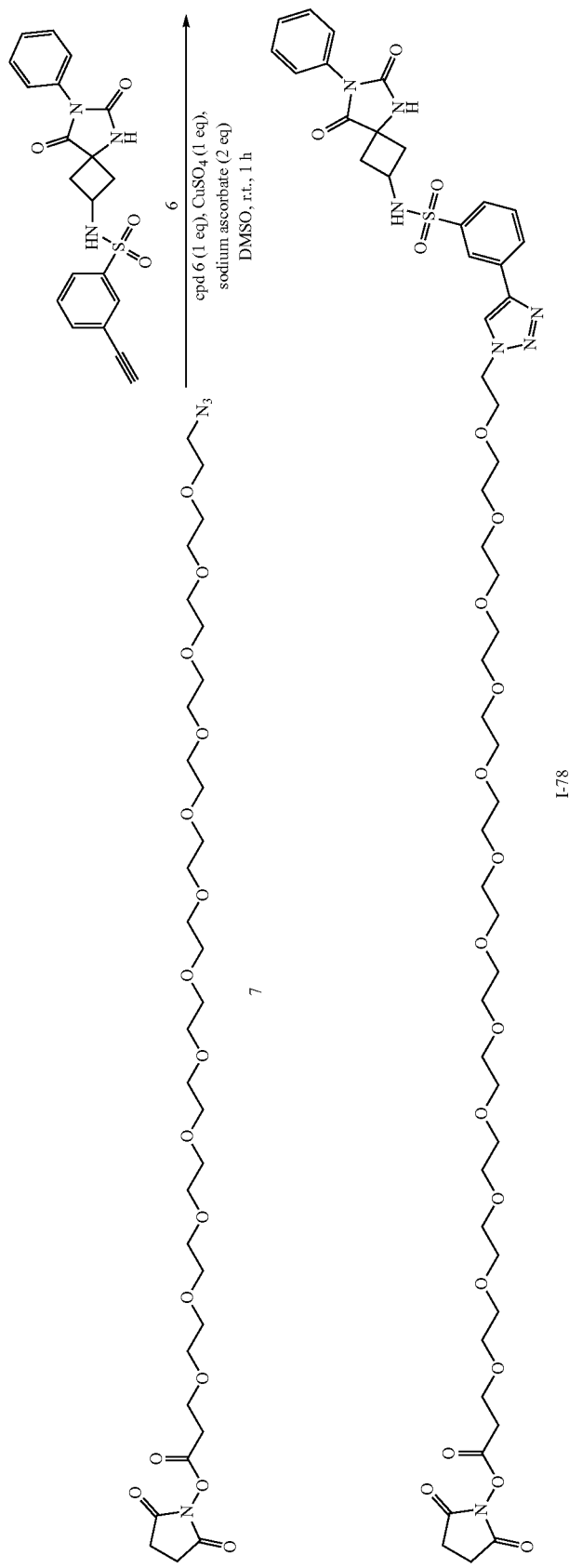

A solution of compound 7 (50 mg, 67.50 umol, 1 eq) and compound 6 (26.69 mg, 67.50 umol, 1 eq) was added CuSO$_4$·5H$_2$O (16.85 mg, 67.50 umol, 1 eq) and sodium; (2R)-2-[(1S)-1,2-dihydroxyethyl]-4-hydroxy-5-oxo-2H-furan-3-olate (26.74 mg, 134.99 umol, 2 eq) in DMSO (1 mL) stirred at 15° C. for 1 hr. LCMS showed a peak with desired MS was detected. The reaction mixture was filtered. The residue was purified by prep-HPLC (column: Nano-micro Kromasil C18 100*30 mm 5 um; mobile phase: [water (0.1% TFA)–ACN]; B %: 27%-47%, 10 min) and lyophilized to give I-78 (26.33 mg, 23.17 umol, 34.33% yield) as a colorless oil, which was confirmed by H NMR and QC LCMS. LCMS: RT=1.217 min, MS cal.: 1136.23, [M+H]$^+$=1136.5. $^1$H NMR (400 MHz, DMSO-d$_6$) δ=8.81 (s, 1H), 8.70 (s, 1H), 8.36-8.30 (m, 2H), 8.08 (br d, J=7.8 Hz, 1H), 7.78-7.66 (m, 2H), 7.46-7.39 (m, 2H), 7.37-7.32 (m, 1H), 7.29 (br d, J=7.3 Hz, 2H), 4.59 (br t, J=4.9 Hz, 2H), 3.88 (t, J=4.9 Hz, 2H), 3.80-3.67 (m, 3H), 3.55-3.44 (m, 44H), 2.92 (t, J=6.1 Hz, 2H), 2.80 (s, 3H), 2.63-2.54 (m, 2H), 2.22 (dt, J=2.4, 9.3 Hz, 2H). LCMS: RT=2.662 min, MS cal.: 1136.23, [M/2+H]$^+$=568.9.

Example 28: Synthesis of I-79

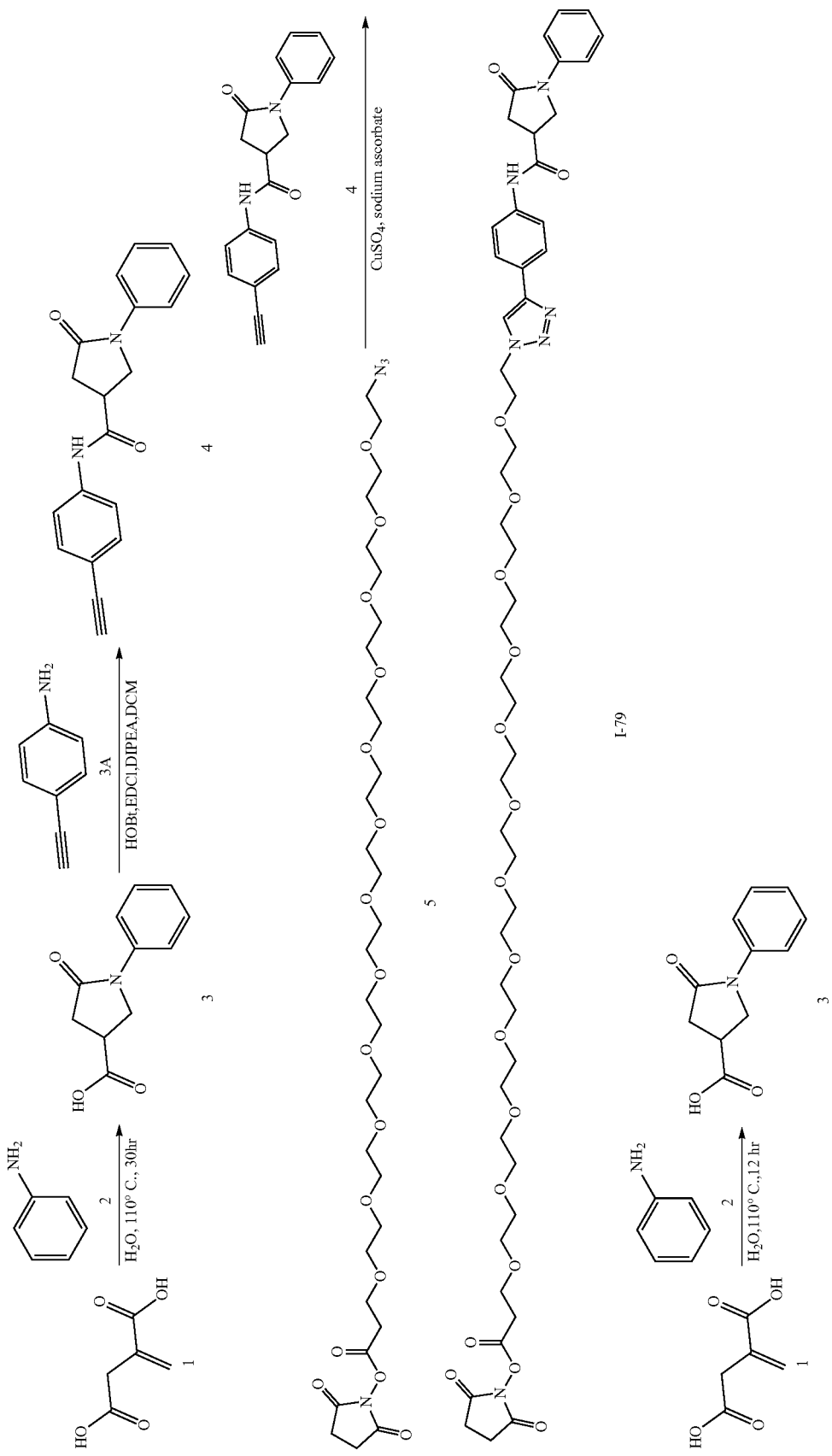

The suspension of compound 1 (2.58 g, 27.67 mmol, 2.53 mL, 1.2 eq) and compound 2 (3 g, 23.06 mmol, 1.91 mL, 1 eq) in H₂O (15 mL) was stirred at 110° C. for 12 hours under autoclave. The reaction was became a black suspension. TLC (Dichloromethane:Methanol=10:1, product R_f=0.19) showed most compound 1 disappeared and detected one new main spot. The mixture was filtered and the filter cake was concentrated in vacuum. The residue was purified by column chromatography (Petrol ether:EtOAc=1:3 to 1:1). Compound 3 (2 g, crude) was obtained as black brown solid.

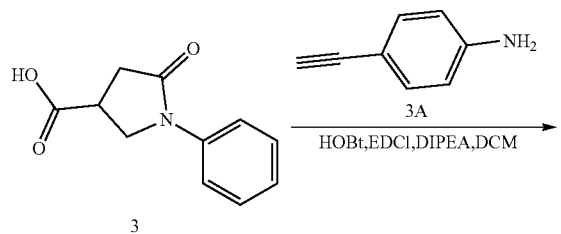

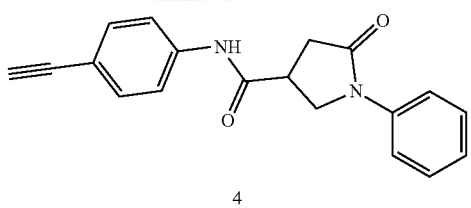

To a solution of compound 3 (105.10 mg, 512.17 umol, 1.2 eq) in DCM (2 mL) was added DIPEA (165.49 mg, 1.28 mmol, 223.03 uL, 3 eq) and HATU (243.43 mg, 640.22 umol, 1.5 eq) compound 3A (50 mg, 426.81 umol, 1 eq). The mixture was stirred at 15° C. for 12 hrs. LCMS showed it was finished. It was washed with 1 mL sat. NH₄Cl, the organic layer was separated and concentrated. Compound 4 (80 mg, 262.86 umol, 61.59% yield) as a yellow solid was used into the next step without further purification. LCMS: RT=1.165 min, MS cal.: 304.3, [M/2+H]⁺=305.2.

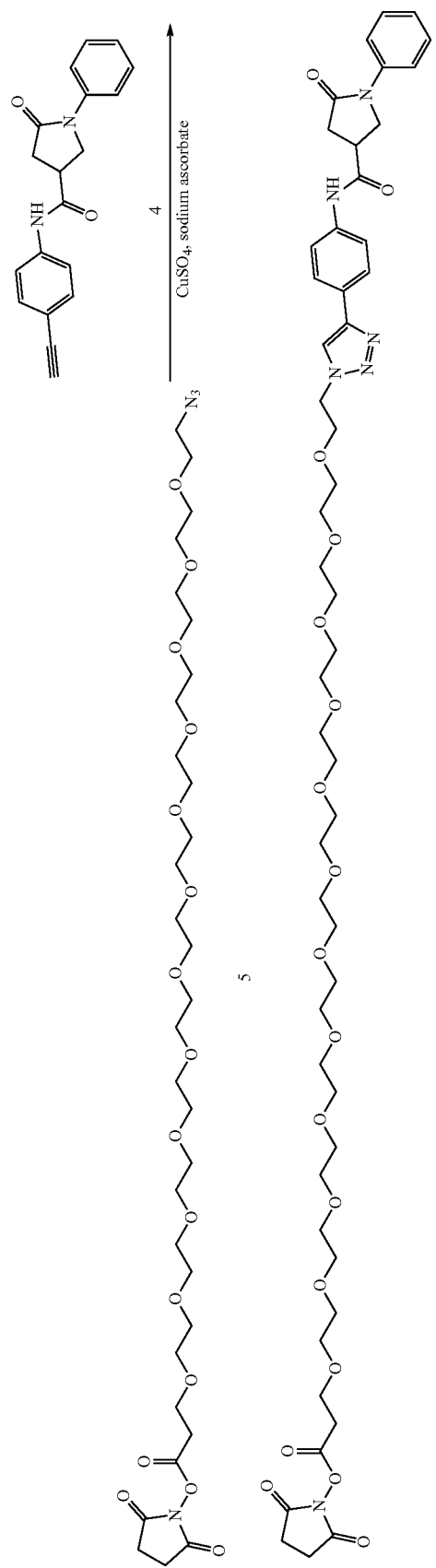

A solution of compound 5 (68 mg, 91.79 umol, 1 eq) and compound 4 in DMSO (2 mL) was added sodium ascorbate (49.89 mg, 251.82 umol, 2.74 eq) and $CuSO_4 \cdot 5H_2O$ (59.86 mg, 239.76 umol, 2.61 eq) stirred at 15° C. for 1 h. LCMS showed a peak with desired MS was detected. The reaction mixture was concentrated by blowing $N_2$ atmosphere. The residue was purified by prep-HPLC (column: Nano-micro Kromasil C18 100*30 mm 5 um; mobile phase: [water (0.1% TFA)–ACN]; B %: 25%-52%, 10 min) to give I-79 (5.52 mg, 5.18 umol, 5.64% yield, 980 purity) as white gum, which was confirmed by H NMR and QC LCMS. LCMS: RT=1.169 min, MS cal.: 1045.1, $[M/2+H]^+$=523.5. $^1$H NMR (400 MHz, CHLOROFORM-d) δ ppm 8.67 (s, 1H) 8.03 (s, 1H) 7.77-7.83 (m, 2H) 7.71 (br d, J=8.31 Hz, 2H) 7.62 (d, J=8.31 Hz, 2H) 7.37 (t, J=8.07 Hz, 2H) 7.13-7.19 (m, 1H) 4.59 (t, J=4.89 Hz, 2H) 4.24 (br t, J=8.56 Hz, 1H) 4.02 (br t, J=9.05 Hz, 1H) 3.90 (t, J 4.89 Hz, 2H) 3.82 (t, J 6.60 Hz, 2 H) 3.51-3.64 (m, 44H) 3.45 (br t, J=8.56 Hz, 1H) 3.06 (dd, J=16.87, 9.05 Hz, 1H) 2.90-2.92 (m, 1H) 2.78-2.91 (m, 6H). QC LCMS: RT=2.076 min, MS cal.: 1045.1, $[M/2+H]^+$=523.3.

Example 29: Synthesis of I-80

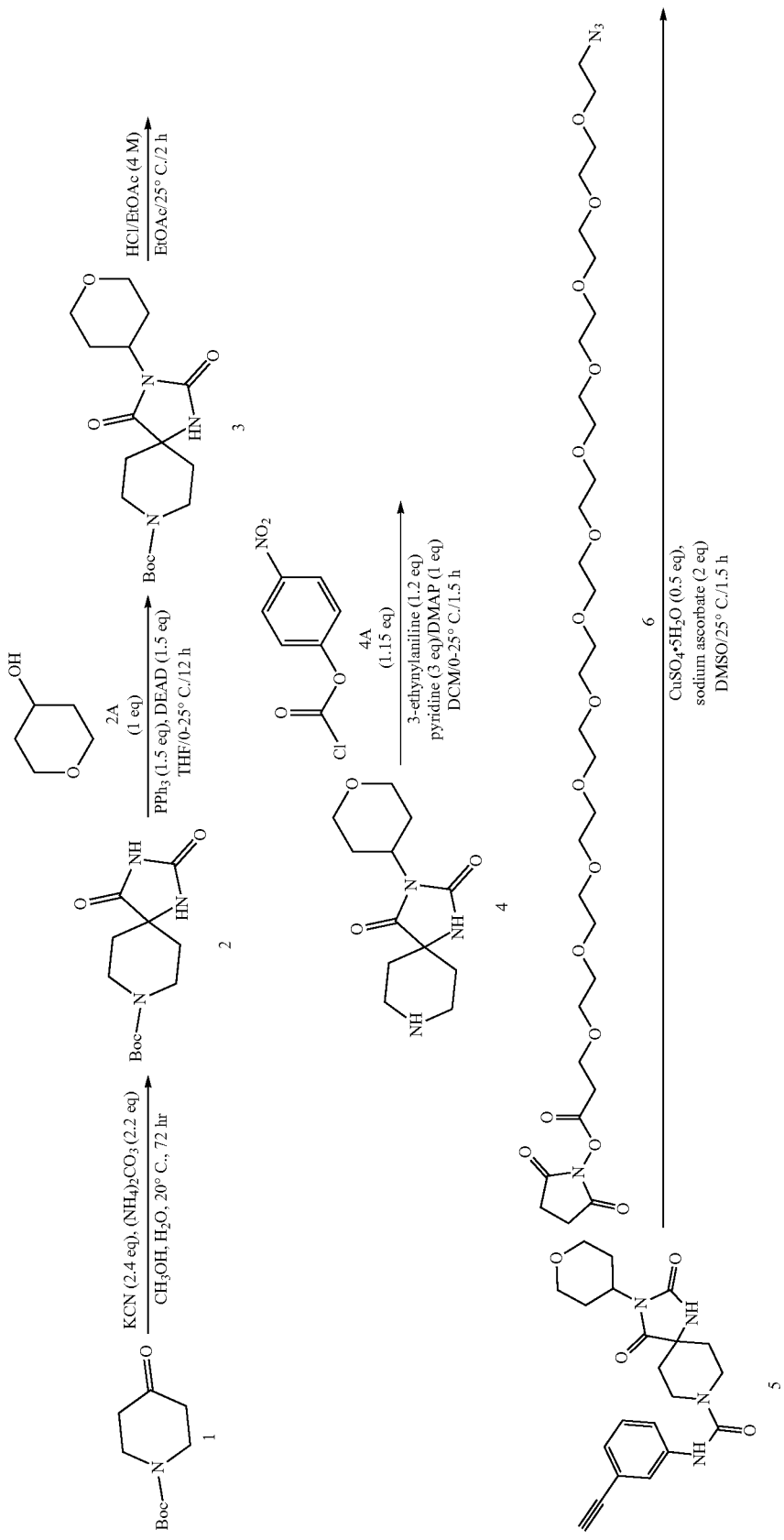

-continued
I-80
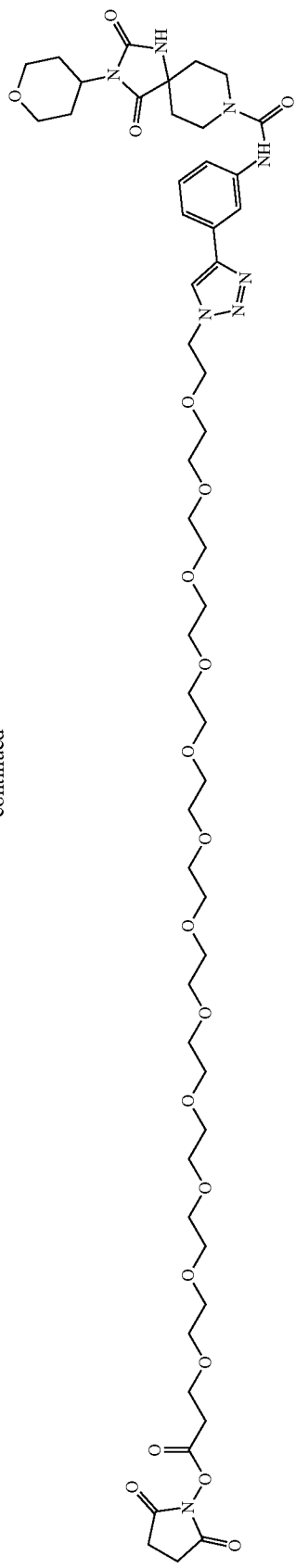
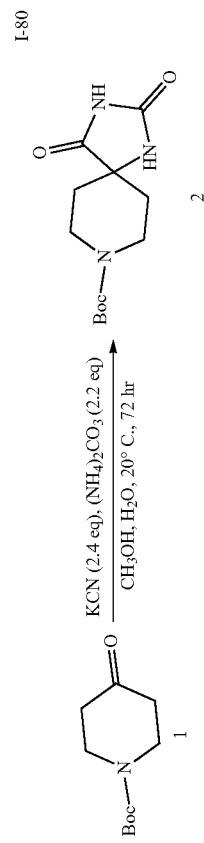
KCN (2.4 eq), (NH₄)₂CO₃ (2.2 eq)
CH₃OH, H₂O, 20° C., 72 hr A solution of KCN (23.53 g, 361.36 mmol, 15.48 mL, 2.4 eq) in H$_2$O (400 mL) was added dropwise to the solution of compound 1 (30 g, 150.57 mmol, 1 eq) and (NH$_4$)$_2$CO$_3$ (31.83 g, 331.25 mmol, 35.36 mL, 2.2 eq) in MeOH (200 mL) and H$_2$O (400 mL). The mixture was stirred at 20° C. for 72 h. LCMS showed the reaction was completed. The reaction mixture was filtered and concentrated in vacuum to give product. Compound 2 was used to the next step without any purification. LCMS: RT=0.999 min, MS cal.: 269.1, [M-55]=214.0.

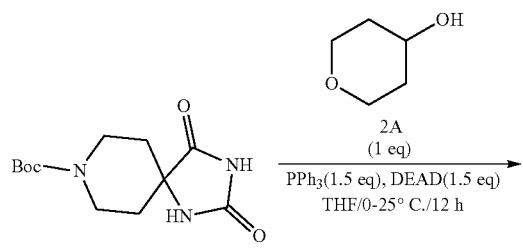

To a solution of compound 2 (0.2 g, 742.68 umol, 1 eq) and compound 2A (113.78 mg, 1.11 mmol, 111.54 uL, 1.5 eq) in THF (3 mL) was added PPh$_3$ (292.19 mg, 1.11 mmol, 1.5 eq) and DEAD (194.01 mg, 1.11 mmol, 202.52 uL, 1.5 eq) at 0° C. The mixture was stirred at 25° C. for 12 hr. LCMS showed compound 2 was consumed completely and one main peak with desired mass was detected. The reaction mixture was concentrated under reduced pressure to remove THF. The residue was diluted with H$_2$O 10 mL and extracted with DCM (20 mL*2). The combined organic layers were washed with brine 10 mL, dried over Na$_2$SO$_4$, filtered and concentrated under reduced pressure to give a residue. Compound 3 (0.15 g, 424.43 umol, 57.15% yield) was obtained as a white solid. LCMS: RT=1.092 min, MS cal.: 353.2, [M-55]$^+$=298.1.

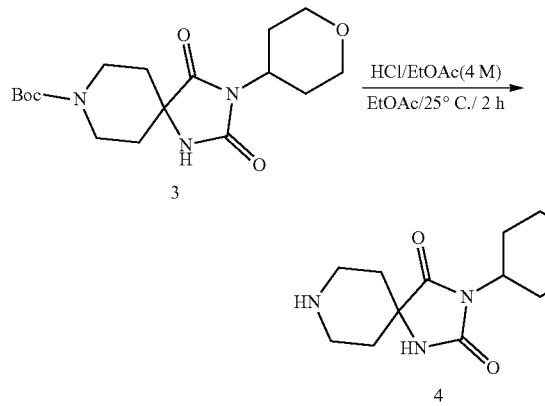

To a solution of compound 3 (0.14 g, 396.14 umol, 1 eq) in EtOAc (3 mL) was added HCl/EtOAc (4 M, 3 mL, 30.29 eq). The mixture was stirred at 25° C. for 12 hr. LCMS showed compound 3 was consumed completely and one main peak with desired mass was detected. It was concentrated under reduced pressure to give a residue. Then added 10 mL H$_2$O and 10 mL EtOAc to it, the reaction mixture was concentrated under reduced pressure to remove EtOAc. The residue was diluted with H$_2$O 10 mL and extracted with EtOAc (10 mL*2). The aqueous phase concentrated under reduced pressure to give a residue. Compound 4 (0.06 g, 207.07 umol, 52.27% yield, HCl) was obtained as a white solid. LCMS: RT=0.276 min, MS cal.: 253.1, [M+H]$^+$=254.2.

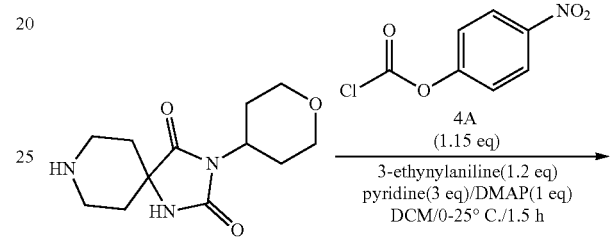

To a mixture of compound 4A (41.74 mg, 207.07 umol, 1.2 eq) in DCM (2 mL) was added dropwise 3-ethynylaniline (34.46 mg, 224.33 umol, 1.3 eq) at 0° C. for 30 min. Then the mixture was added compound 4 (0.05 g, 172.56 umol, 1 eq, HCl), pyridine (40.95 mg, 517.67 umol, 41.78 uL, 3 eq) and DMAP (63.24 mg, 517.67 umol, 3 eq). The mixture was stirred at 40° C. for 1 hr. LCMS showed compound 4 was consumed completely and one main peak with desired mass was detected. Added 10 mL H$_2$O to the reaction mixture, then extracted it with (10 mL*2). The combined organic layers were washed with brine 10 mL, dried over Na$_2$SO$_4$, filtered and concentrated under reduced pressure to give a residue. Compound 5 (0.028 g, 70.63 umol, 40.93% yield) was obtained as a yellow oil. LCMS: RT=1.066 min, MS cal.: 396.2, [M+H]$^+$=397.2.

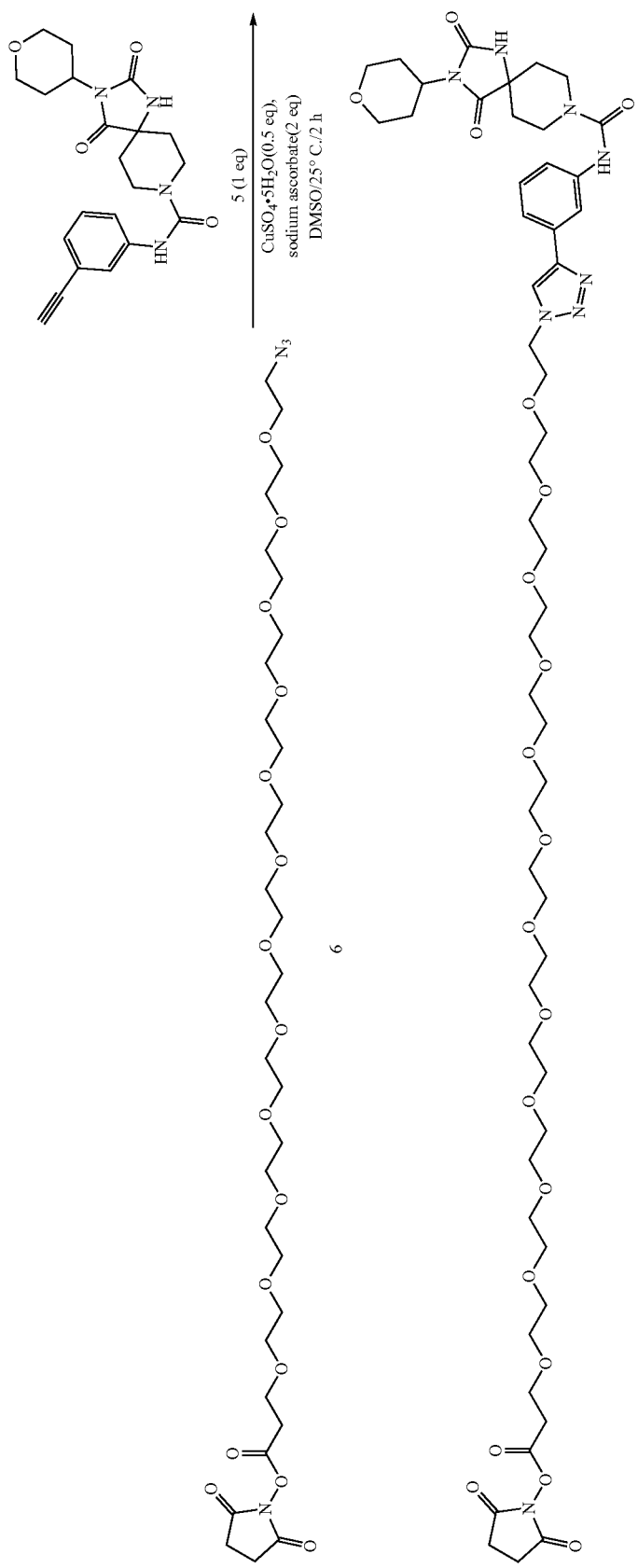

To a solution of compound 6 (0.04 g, 54.00 umol, 1 eq) and compound 5 (21.41 mg, 54.00 umol, 1 eq) in DMSO (1 mL) was added $CuSO_4 \cdot 5H_2O$ (26.96 mg, 107.99 umol, 2 eq) and sodium; ascorbate (21.39 mg, 107.99 umol, 2 eq). The mixture was stirred at 25° C. for 2 hr. LCMS showed compound 6 was consumed completely and one main peak with desired mass was detected. (RT=1.066 min). The reaction mixture was filtered. The residue was purified by prep-HPLC (TFA condition: column: Luna C18 100*30 5 u; mobile phase: [water (0.1% TFA)–ACN]; B %: 15%-43%, 10 min). I-80 (24.18 mg, 21.26 umol, 39.38% yield) was obtained as a yellow oil. 2.02 mg product was used for delivery. LCMS: RT=1.066 min, MS cal.: 1136.5, $[1/2M+H]^+$=569.5. QCLCMS: RT=1.874 min, MS cal.: 1136.5, $[1/2M+H]^+$=569.4 $^1$H NMR (400 MHz, DMSO-d6) δ ppm 8.87 (s, 1H) 8.72 (s, 1H) 8.44 (s, 1H) 8.00 (s, 1H) 7.46 (br d, J=8.19 Hz, 1H) 7.34-7.40 (m, 1H) 7.26-7.34 (m, 1H) 4.56 (t, J=5.07 Hz, 2H) 3.81-4.06 (m, 7H) 3.71 (t, J=5.93 Hz, 2H) 3.45-3.57 (m, 44H) 3.17-3.39 (m, 3H) 2.92 (t, J=5.93 Hz, 2H) 2.80 (s, 4H) 2.26 (qd, J=12.45, 4.58 Hz, 2H) 1.73-1.85 (m, 2H) 1.46-1.63 (in, 4H).

Example 30: Synthesis of I-81

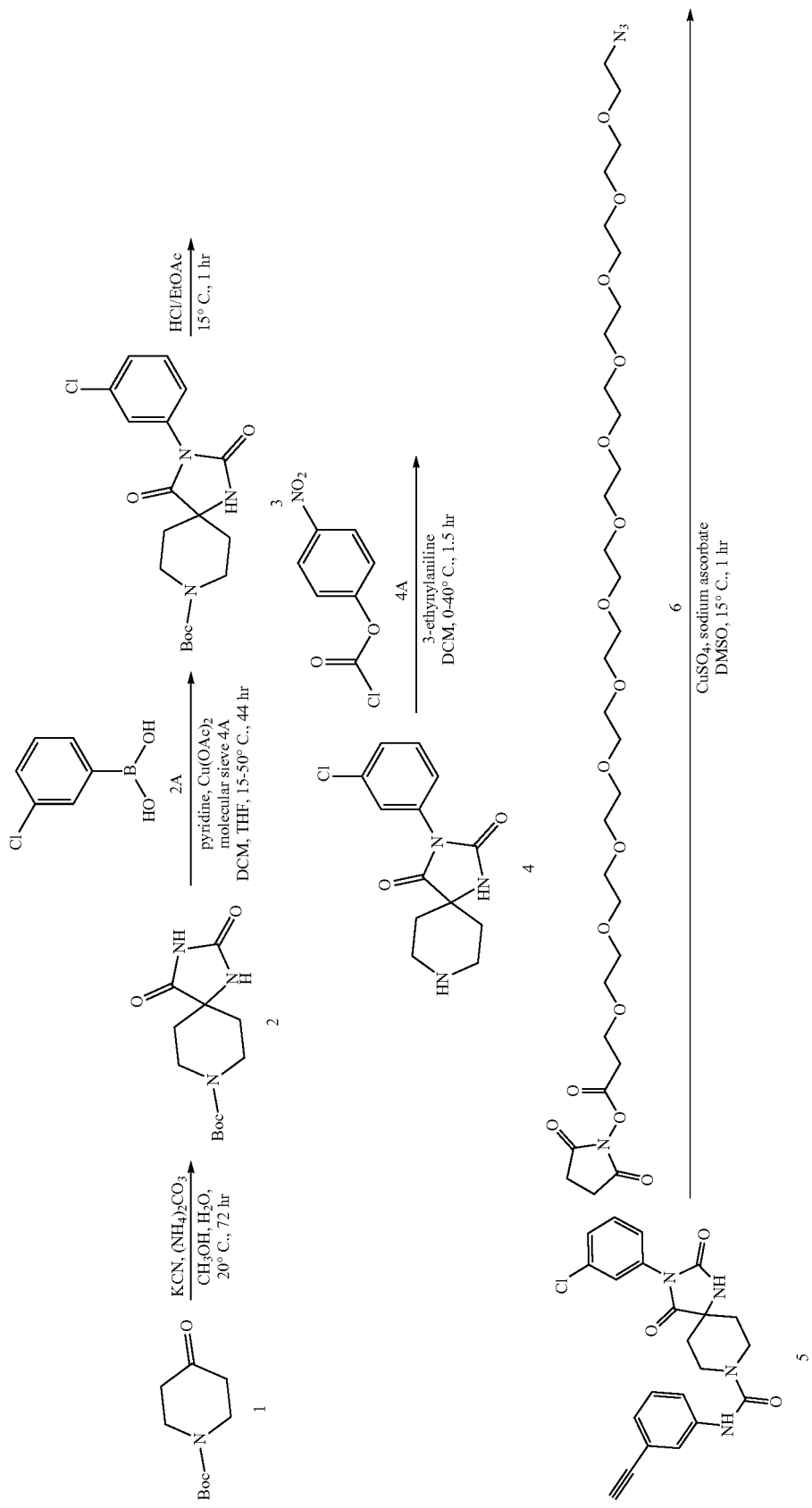

-continued
I-81
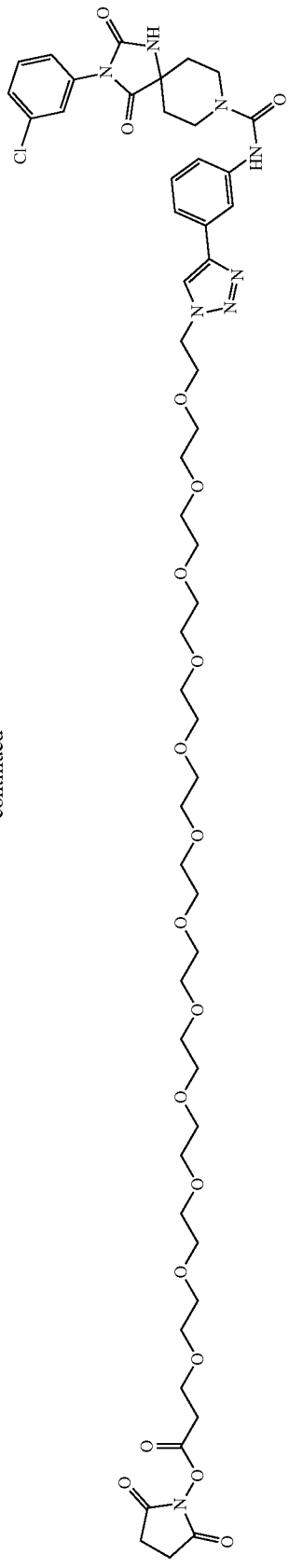
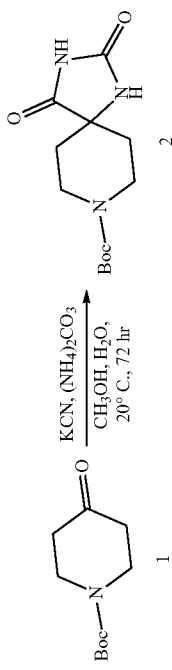

A solution of KCN (23.53 g, 361.36 mmol, 15.48 mL, 2.4 eq) in H₂O (200 mL) was added dropwise to the solution of compound 1 (30 g, 150.57 mmol, 1 eq) and (NH₄)₂CO₃ (31.83 g, 331.25 mmol, 35.36 mL, 2.2 eq) in MeOH (200 mL) and H₂O (200 mL). The mixture was stirred at 20° C. for 72 h. LCMS showed the reaction was completed. The reaction mixture was filtered and concentrated in vacuum to give compound 2 (20 g, 74.27 mmol, 49.33% yield) as a white solid. LCMS: RT=0.999 min, MS cal.: 269.14, [M-55]⁺=214.0. ¹H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

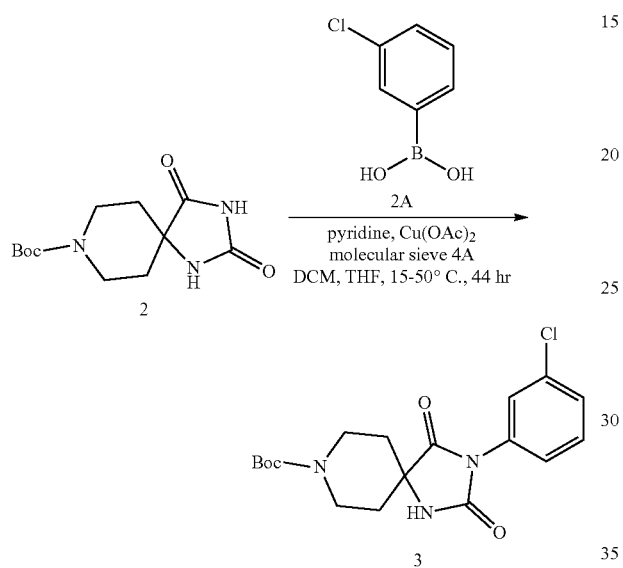

To a solution of compound 2 (400 mg, 1.49 mmol, 1 eq) and compound 2A (278.73 mg, 1.78 mmol, 1.2 eq) in DCM (50 mL) and THF (10 mL) was added pyridine (352.47 mg, 4.46 mmol, 359.67 uL, 3 eq) Molecular sieve 4A (800 mg, 1.49 mmol) oxygen (47.53 mg, 1.49 mmol, 1 eq) Cu(OAc)₂ (269.79 mg, 1.49 mmol, 1 eq). The mixture was stirred at 15° C. for 30 hr, then warmed to 50° C. for 14 hr. LCMS was detected the desired product MS. The mixture was filtered, added CH₂Cl₂ (100 mL), washed with water (50 mL*2), dried with Na₂SO₄, filtered, concentrated. The residue was purified by column chromatography (SiO₂, Petroleum ether: Ethyl acetate=5:1 to 1:1) according to TLC (Plate 1, EtOAC: Petroleum ether=1:1 Product R$_f$=0.30). Compound 3 (488 mg, crude) was obtained as white solid checked by LCMS and HNMR. LCMS: RT=1.416 min, MS cal.: 379.13, [M-55]⁺=324.1. ¹H NMR (400 MHz, DMSO-d₆) δ ppm 9.16 (br s, 1H), 7.69-7.28 (m, 3H), 4.02-3.73 (m, 1H), 3.85 (br s, 1H), 3.41-3.04 (m, 2H), 1.77 (br s, 3H), 1.43 (br s, 9H).

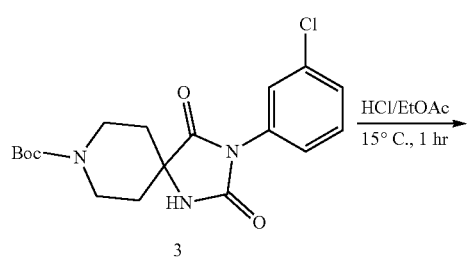

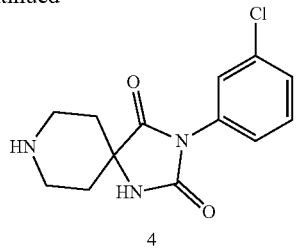

To a solution of compound 3 (100 mg, 263.27 umol, 1 eq) in HCl/EtOAc (8 mL) was stirred at 15° C. for 1 hr. LCMS was detected the desired product MS. The mixture was concentrated. Compound 4 (76 mg, crude, HCl) was obtained as light yellow solid. LCMS: RT=0.727 min, MS cal.: 279.08, [M+H]⁺=280.2.

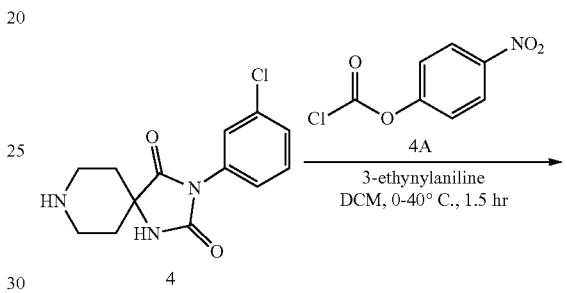

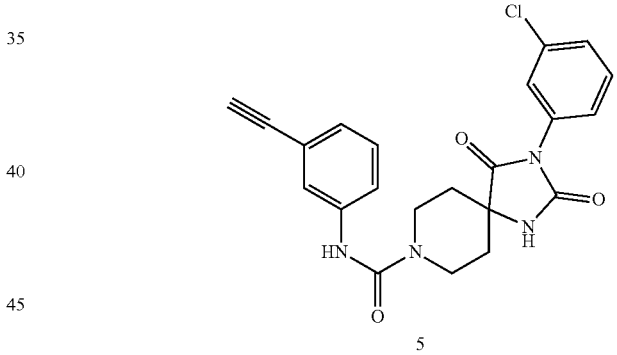

To a solution of compound 4A (65.72 mg, 326.04 umol, 1.2 eq) in DCM (1 mL) was added 3-ethynylaniline (38.19 mg, 326.04 umol, 1.2 eq) at 0° C. for 0.5 hr. The mixture was added DMAP (99.58 mg, 815.10 umol, 3 eq) pyridine (107.46 mg, 1.36 mmol, 109.65 uL, 5 eq) and compound 4 (76 mg, 271.70 umol, 1 eq). The mixture was stirred at 40° C. for 1 hr. LCMS was detected the desired product MS. The mixture was added CH₂Cl₂ (20 mL) to the reaction mixture, then the mixture was washed with water (5 mL*2), the organic layer dried over Na₂SO₄ and concentrated. The residue was purified by prep-TLC according to TLC (Plate 1, Petroleum ether:Ethyl acetate=1:1, product R$_f$=0). The residue was purified by prep-TLC according to TLC (Plate 1, DCM:MeOH=10:1, Product R$_f$=0.40). Compound 5 (40 mg, 91.88 umol, 77.70% yield, 97.13% purity) was obtained as white solid checked by LCMS. LCMS: RT=1.192 min, MS cal.: 422.11, [M+H]⁺=423.1. LCMS: RT=1.341 min, MS cal.: 422.11, [M+H]+=423.1.

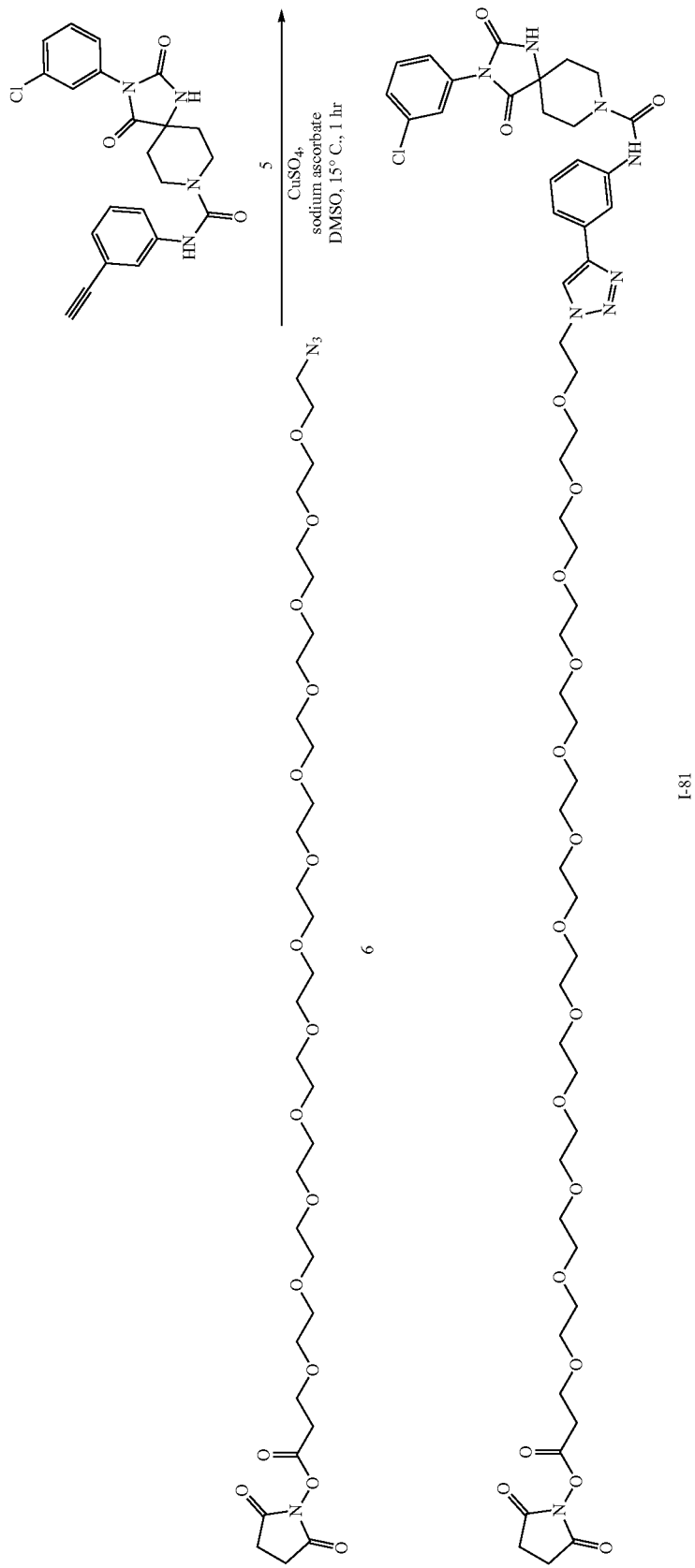

To a solution of compound 6 (53.08 mg, 71.65 umol, 1.01 eq) and compound 5 (30 mg, 70.94 umol, 1 eq) in DMSO (2 mL) was added $CuSO_4 \cdot 5H_2O$ (17.71 mg, 70.94 umol, 1 eq) and sodium; (2R)-2-[(1S)-1,2-dihydroxyethyl]-4-hydroxy-5-oxo-2H-furan-3-olate (28.11 mg, 141.89 umol, 2 eq). The mixture was stirred at 15° C. for 1 hr. LCMS was detected the desired product MS. The mixture was combined. The mixture was filtered. The residue was purified by prep-HPLC (TFA condition) according to HPLC. I-81 (38.58 mg, 32.24 umol, 45.44% yield, 97.23% purity) was obtained as light yellow oil checked by QCLCMS and HNMR. LCMS: RT=1.427 min, MS cal.: 1162.48, $[1/2M+H]^+$=582.4. HPLC: RT=2.903 min. QCLCMS: RT=2.792 min, MS cal.: 1162.48, $[1/2M+H]^+$=582.4. $^1$H NMR (400 MHz, DMSO-d6) δ ppm 9.20 (s, 1H), 8.75 (s, 1H), 8.45 (s, 1H), 8.03 (s, 1H), 7.58-7.46 (m, 4H), 7.44-7.37 (m, 2H), 7.35-7.27 (m, 1H), 4.57 (br t, J=4.8 Hz, 2H), 4.04 (br d, J=13.7 Hz, 2H), 3.87 (br t, J=4.9 Hz, 2H), 3.78-3.64 (m, 14H), 3.55 (br d, J=5.4 Hz, 4H), 3.50 (s, 31H), 3.48-3.45 (m, 1H), 3.48-3.45 (m, 11H), 3.35 (br t, J=11.2 Hz, 3H), 2.92 (t, J=5.9 Hz, 2H), 2.81 (s, 4H), 1.99-1.89 (m, 2H), 1.86-1.77 (m, 2H).

Example 31: Synthesis of I-82

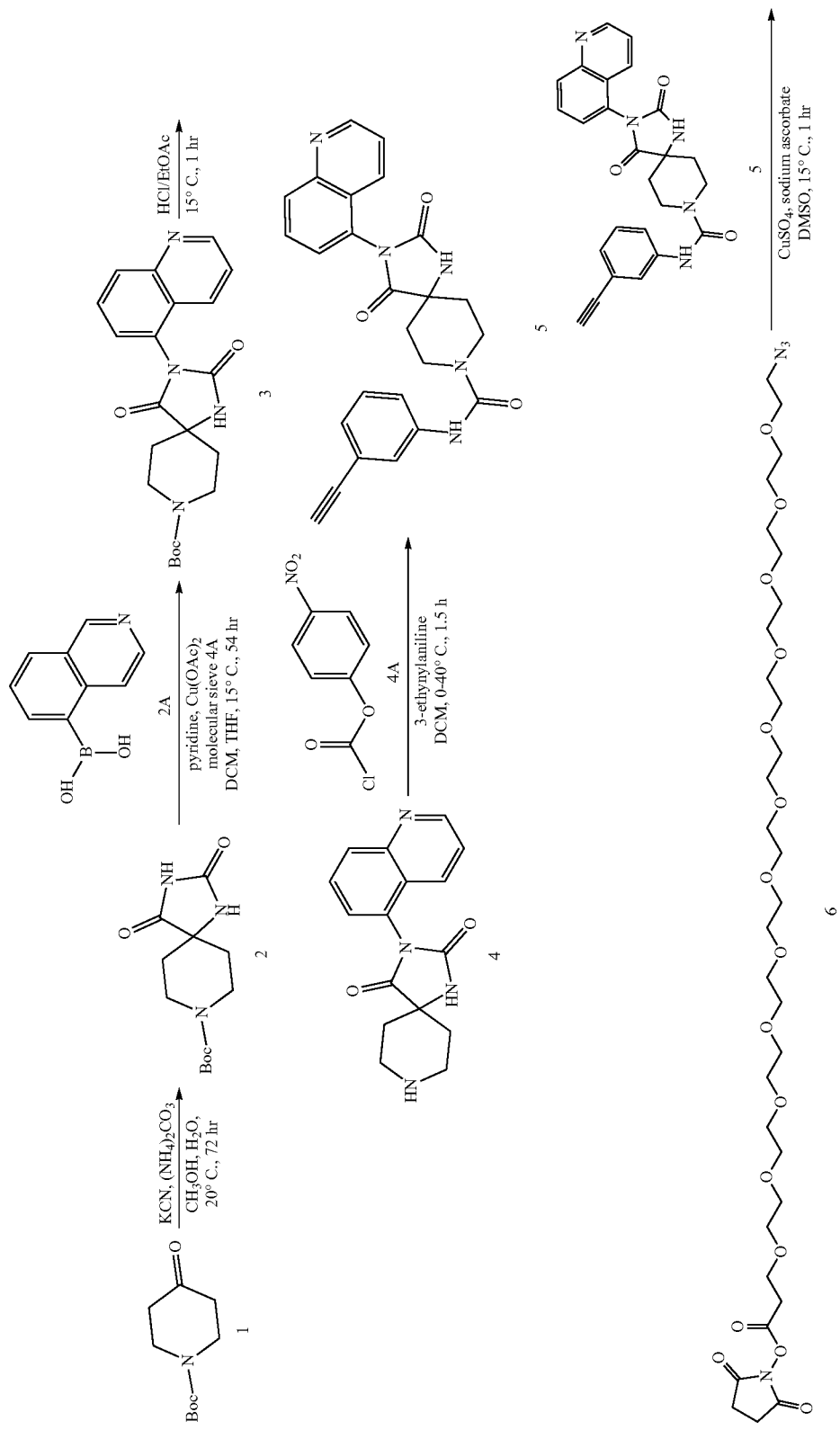

-continued
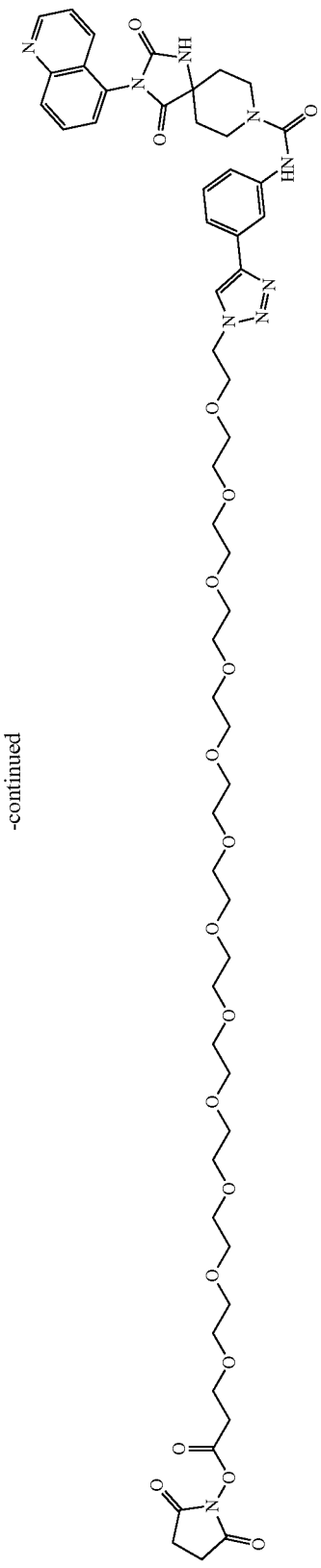
I-82
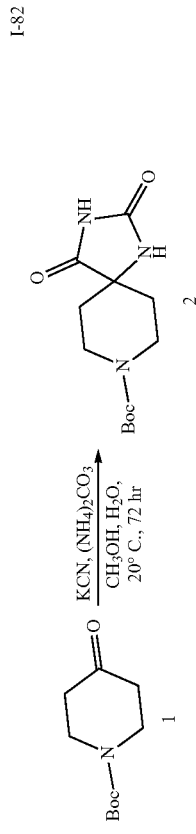

A solution of KCN (23.53 g, 361.36 mmol, 15.48 mL, 2.4 eq) in H$_2$O (200 mL) was added dropwise to the solution of compound 1 (30 g, 150.57 mmol, 1 eq) and (NH$_4$)$_2$CO$_3$ (31.83 g, 331.25 mmol, 35.36 mL, 2.2 eq) in MeOH (200 mL) and H$_2$O (200 mL). The mixture was stirred at 20° C. for 72 h. LCMS showed the reaction was completed. The reaction mixture was filtered and concentrated in vacuum to give compound 2 (20 g, 74.27 mmol, 49.33% yield) as a white solid. LCMS: RT=0.999 min, MS cal.: 269.14, [M-55]$^+$=214.0. $^1$H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

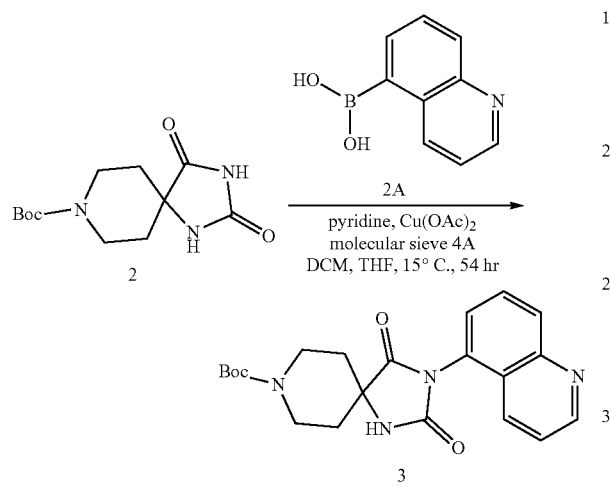

To a solution of compound 2 (400 mg, 1.49 mmol, 1 eq) and compound 2A (308.32 mg, 1.78 mmol, 1.2 eq) in DCM (50 mL) and THF (10 mL) was added pyridine (352.47 mg, 4.46 mmol, 359.67 uL, 3 eq) Molecular sieve 4A (800 mg, 1.86 mmol) Cu(OAc)$_2$ (269.79 mg, 1.49 mmol, 1 eq) and oxygen (47.53 mg, 1.49 mmol, 1 eq). The mixture was stirred at 15° C. under O$_2$ (20 Psi) for 54 hr. LCMS was detected the desired product MS. The mixture was filtered, added CH$_2$Cl$_2$ (100 mL), washed with water (50 mL*2), dried with Na$_2$SO$_4$, filtered, concentrated. The residue was purified by column chromatography (SiO$_2$, Petroleum ether: Ethyl acetate=5:1 to 0:1) according to TLC (Plate 1, EtOAC: Petroleum ether=1:0 Product R$_f$=0.27). Compound 3 (357 mg, crude) was obtained as pink solid checked by LCMS. LCMS: RT=1.095 min, MS cal.: 396.18, [M+H]$^+$=397.2. LCMS: RT=1.087 min, MS cal.: 396.18, [M+H]$^+$=397.2.

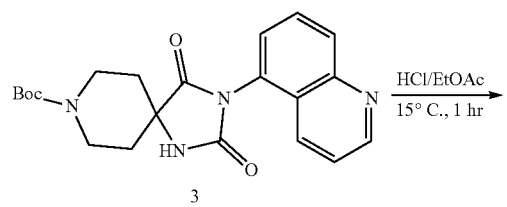

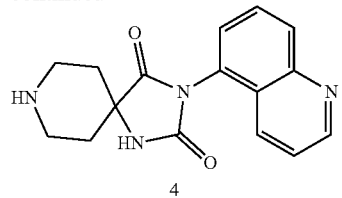

To a solution of compound 3 (100 mg, 252.25 umol, 1 eq) in HCl/EtOAc (8 mL) was stirred at 15° C. for 1 hr. LCMS was detected the desired product MS. The mixture was concentrated. Compound 4 (95 mg, crude, HCl) was obtained as white solid. LCMS: RT=1.063 min, MS cal.: 296.13, [M+H]$^+$=297.3.

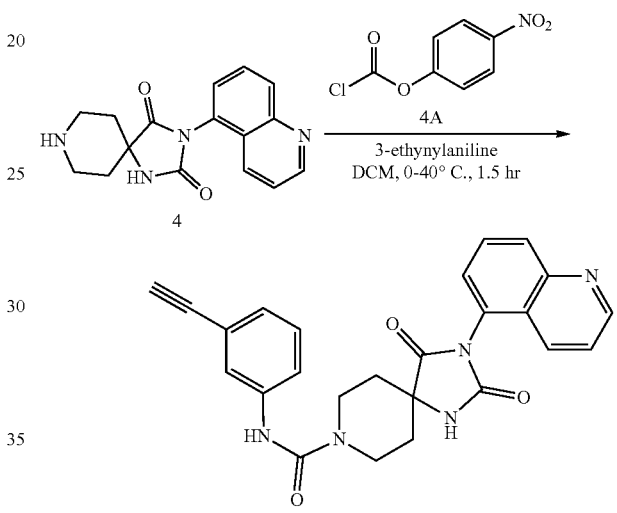

To a solution of compound 4A (77.54 mg, 384.72 umol, 1.2 eq) in DCM (1 mL) was added 3-ethynylaniline (45.07 mg, 384.72 umol, 1.2 eq) and DCM (1 mL) at 0° C. for 0.5 hr. The mixture was added DMAP (117.50 mg, 961.79 umol, 3 eq) pyridine (126.80 mg, 1.60 mmol, 129.38 uL, 5 eq) and compound 4 (95 mg, 320.60 umol, 1 eq). The mixture was stirred at 40° C. for 1 hr. LCMS was detected the desired product MS. The mixture was added CH$_2$Cl$_2$ (20 mL) to the reaction mixture, then the mixture was washed with water (5 mL*2), the organic layer dried with Na$_2$SO$_4$ and concentrated. The residue was purified by prep-TLC according to TLC (Plate 1, Petroleum ether:Ethyl acetate=1:1, product R$_f$=0), LCMS. The residue was purified by prep-TLC according to TLC (Plate 2, Dichloromethane:Methanol=10:1, product R$_f$=0.30). Compound 5 (23 mg, 44.79 umol, 13.97% yield, 85.58% purity) was obtained as white solid checked by LCMS. LCMS: RT=1.026 min, MS cal.: 439.16, [M+H]$^+$=440.2. LCMS: RT=0.908 min, MS cal.: 439.16, [M+H]$^+$=440.3.

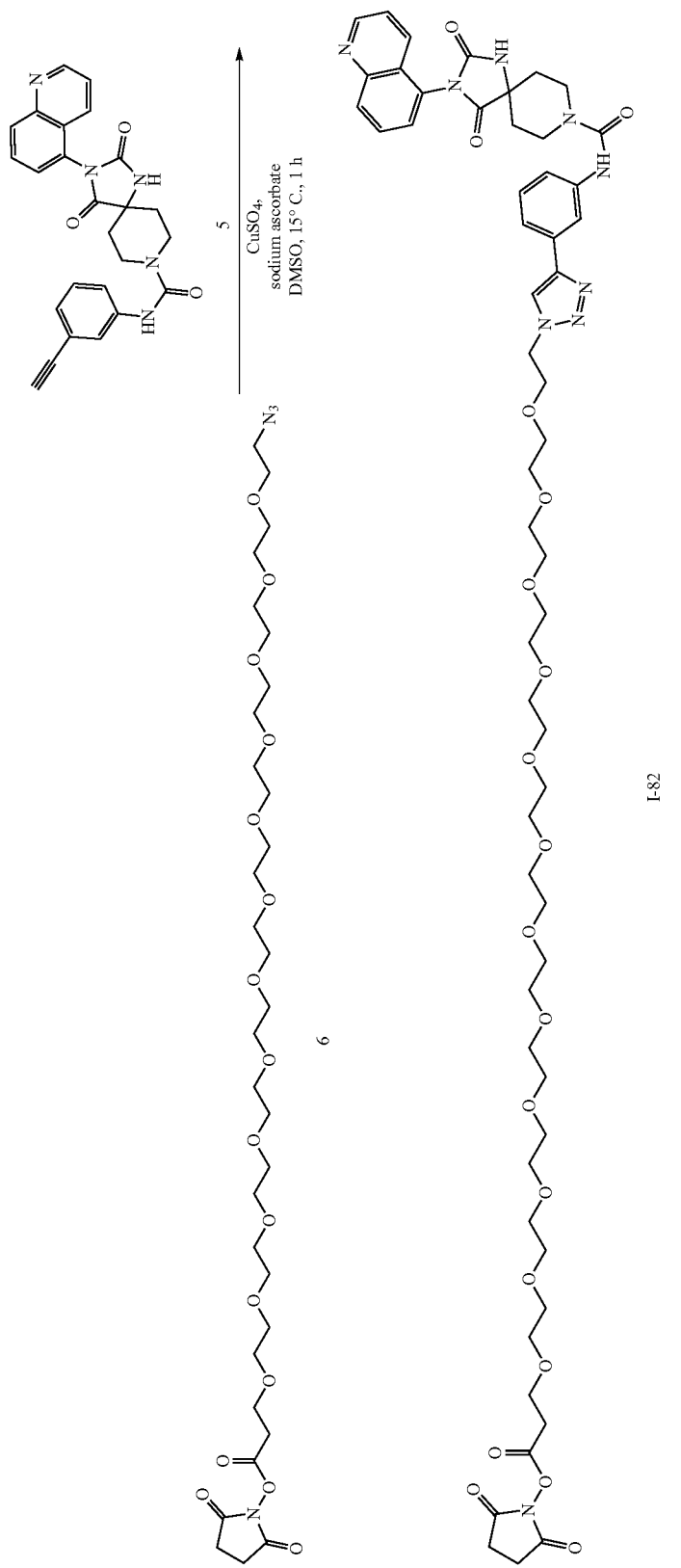

To a solution of compound 6 (33.71 mg, 45.51 umol, 1 eq) and compound 5 (20 mg, 45.51 umol, 1 eq) in DMSO (1.5 mL) was added $CuSO_4 \cdot 5H_2O$ (11.36 mg, 45.51 umol, 1 eq) and sodium; (2R)-2-[(1S)-1,2-dihydroxyethyl]-4-hydroxy-5-oxo-2H-furan-3-olate (18.03 mg, 91.02 umol, 2 eq). The mixture was stirred at 15° C. for 1 hr. LCMS was detected the desired product MS. The mixture was combined. The mixture was filtered. The residue was purified by prep-HPLC (TFA condition) according to HPLC. I-82 (20 79 mg, 15.40 umol, 33.84% yield, 90.88% purity) was obtained as light yellow oil checked by QCLCMS and HNMR. LCMS: RT=1.073 min, MS cal.: 1179.53, $[M/2+H]^+$=591.2. HPLC: RT=2.244 min. QCLCMS: RT=3.273 min, MS cal.: 1179.53, $[M/2+H]^+$=590.8.1H NMR (400 MHz, DMSO-d6) δ ppm 9.32 (s, 1H), 9.05 (br d, J=3.1 Hz, 1H), 8.79 (s, 1H), 8.46 (s, 1H), 8.22 (dd, J=8.4, 18.9 Hz, 2H), 8.04 (s, 1H), 7.94 (t, J=8.0 Hz, 1H), 7.73 (d, J=6.7 Hz, 1H), 7.68 (dd, J=4.3, 8.6 Hz, 1H), 7.50 (br d, J=8.2 Hz, 1H), 7.41-7.37 (m, 1H), 7.35-7.29 (m, 1H), 4.58 (t, J=5.1 Hz, 2H), 4.16-3.93 (m, 17H), 3.88 (br t, J=5.1 Hz, 2H), 3.72 (t, J=5.9 Hz, 2H), 3.58-3.54 (m, 2H), 3.54-3.43 (m, 42H), 3.43-3.37 (m, 1H), 2.92 (t, J=5.9 Hz, 2H), 2.81 (s, 4H), 2.12-1.91 (m, 4H), 1.24 (s, 1H).

Example 32: Synthesis of I-83

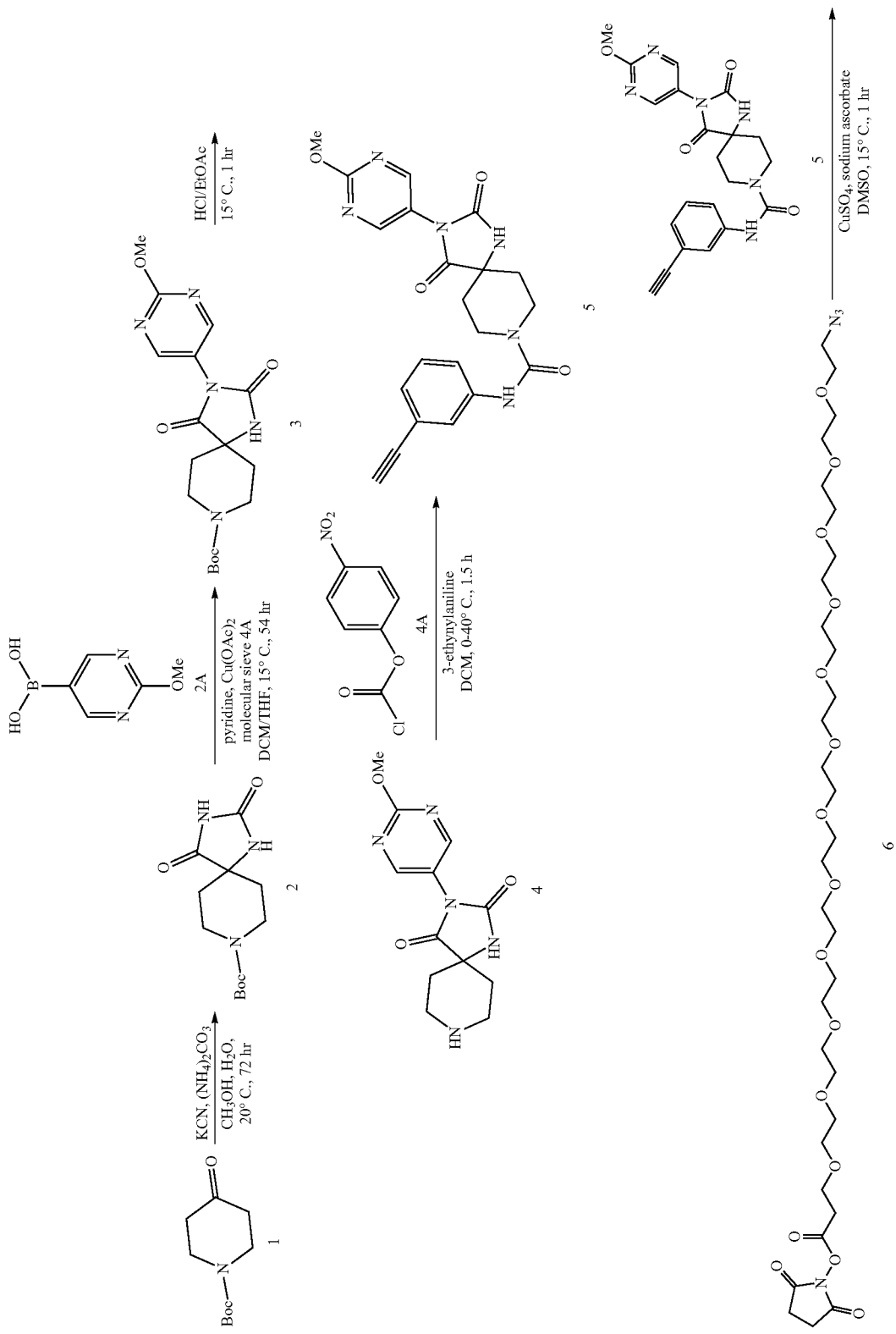

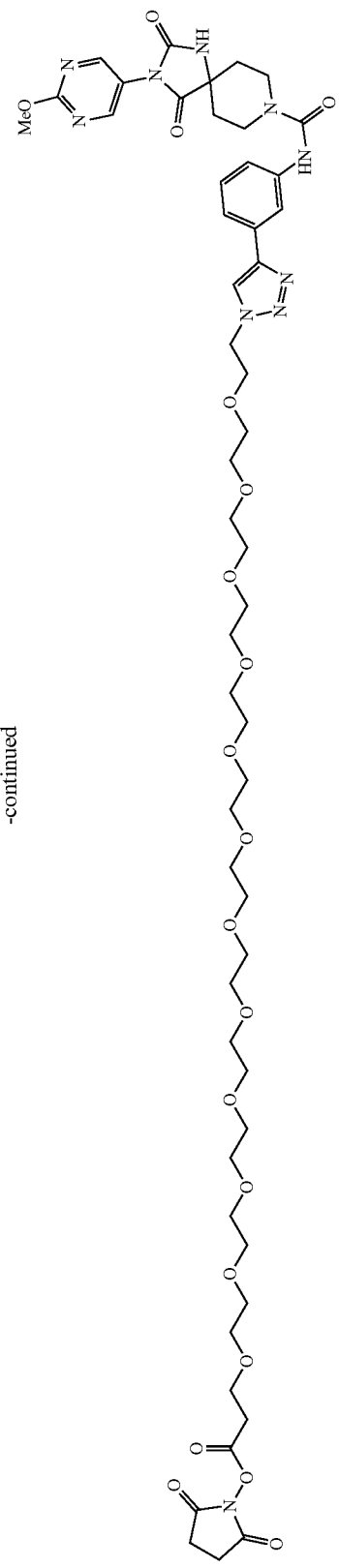
I-83

A solution of KCN (23.53 g, 361.36 mmol, 15.48 mL, 2.4 eq) in H₂O (200 mL) was added dropwise to the solution of compound 1 (30 g, 150.57 mmol, 1 eq) and (NH₄)₂CO₃ (31.83 g, 331.25 mmol, 35.36 mL, 2.2 eq) in MeOH (200 mL) and H₂O (200 mL). The mixture was stirred at 20° C. for 72 h. LCMS showed the reaction was completed. The reaction mixture was filtered and concentrated in vacuum to give compound 2 (20 g, 74.27 mmol, 49.33% yield) as a white solid. LCMS: RT=0.999 min, MS cal.: 269.14, [M-55]⁺=214.0. ¹H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

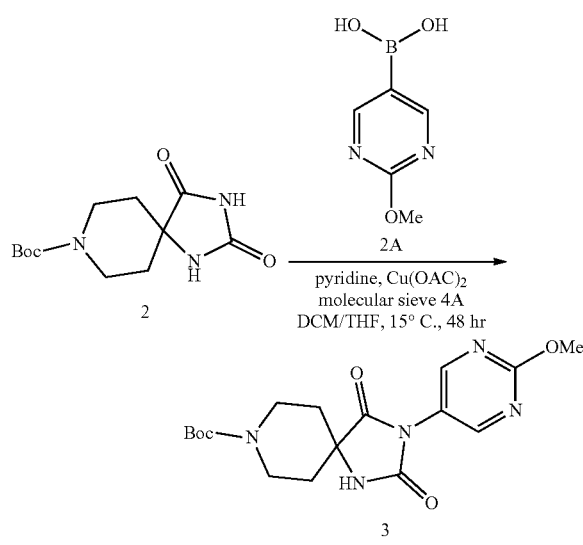

To a solution of compound 2 (400 mg, 1.49 mmol, 1 eq) and compound 2A (274.37 mg, 1.78 mmol, 1.2 eq) in DCM (50 mL) and THF (10 mL) was added pyridine (352.47 mg, 4.46 mmol, 359.67 uL, 3 eq) Molecular sieve 4A (800 mg) Cu(OAc)₂ (269.79 mg, 1.49 mmol, 1 eq) oxygen (47.53 mg, 1.49 mmol, 1 eq). The mixture was stirred at 15° C. under O₂ (20 Psi) for 48 hr. LCMS was detected the desired product MS. The mixture was filtered, added CH₂Cl2 (100 mL), washed with water (50 mL*2), dried with Na₂SO₄, filtered, concentrated. The residue was purified by column chromatography (SiO₂, Petroleum ether/Ethyl acetate=3/1 to 0:1) according to TLC (Plate 1, EtOAC:Petroleum ether=1:0, Product R_f=0.30). Compound 3 (630 mg, crude) was obtained as white solid checked by LCMS. LCMS: RT=1.199 min, MS cal.: 377.17, [M+H]⁺=378.2. LCMS: RT=1.285 min, MS cal.: 377.17, [M+H]⁺=378.5.

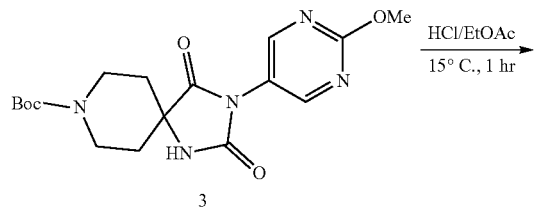

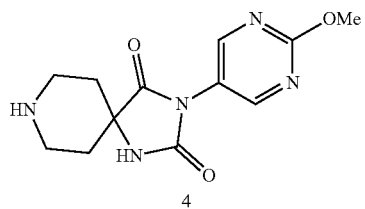

To a solution of compound 3 (100 mg, 264.98 umol, 1 eq) in HCl/EtOAc (8 mL) was stirred at 15° C. for 1 hr. LCMS was detected the desired product MS. The mixture was concentrated. Compound 4 (108 mg, crude, HCl) was obtained as white solid. LCMS: RT=0.377 min, MS cal.: 277.12, [M+H]⁺=278.3.

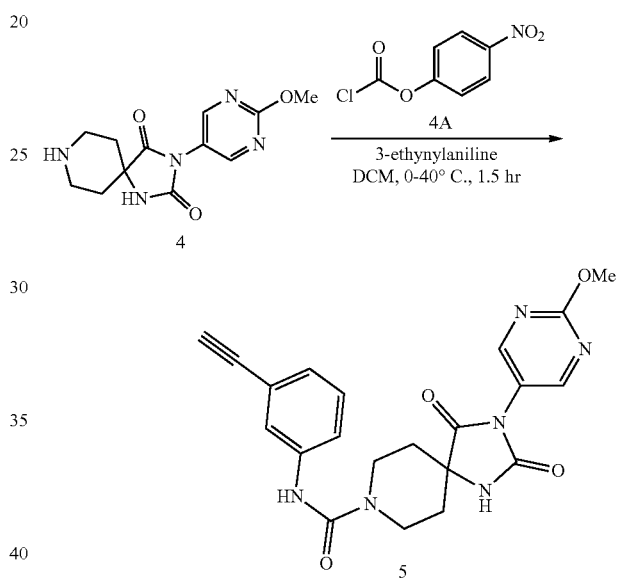

To a solution of compound 4A (83.52 mg, 414.36 umol, 1.3 eq) in DCM (3 mL) was added 3-ethynylaniline (44.81 mg, 382.48 umol, 1.2 eq) at 0° C. for 0.5 hr. Then the mixture was added DMAP (116.82 mg, 956.21 umol, 3 eq), pyridine (126.06 mg, 1.59 mmol, 128.63 uL, 5 eq) and compound 4 (100 mg, 318.74 umol, 1 eq, HCl). The mixture was stirred at 40° C. for 1 hr. LCMS was detected the desired product MS. The mixture was added CH₂Cl₂ (20 mL) to the reaction mixture, then the mixture was washed with water (5 mL*2), the organic layer dried with Na₂SO₄ and concentrated. The residue was purified by prep-TLC according to TLC (Plate 1, Petroleum ether:Ethyl acetate=1:1, product R_f=0), LCMS. The residue was purified by prep-TLC according to TLC (Plate 2, Dichloromethane:Methanol=10:1, product R_f=0.14). Compound 5 (28 mg, 65.71 umol, 20.62% yield, 98.66% purity) was obtained as white solid checked by LCMS. LCMS: RT=1.079 min, MS cal.: 420.15, [M+H]⁺=421.1. LCMS: RT=1.157 min MS cal.: 420.15, [M+H]⁺=421.2.

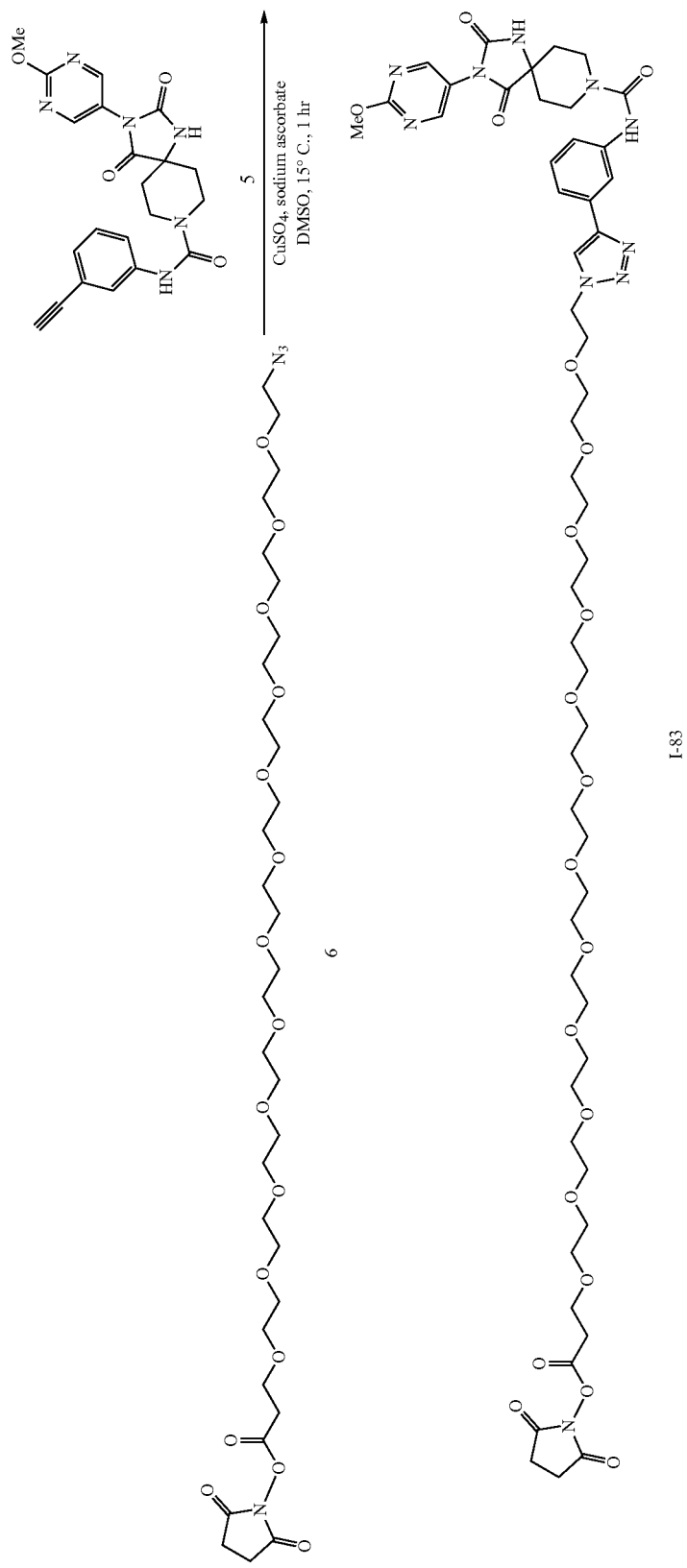

To a solution of compound 6 (44.05 mg, 59.46 umol, 1 eq) and compound 5 (25 mg, 59.46 umol, 1 eq) in DMSO (1 mL) was added $CuSO_4 \cdot 5H_2O$ (14.85 mg, 59.46 umol, 1 eq) and sodium; (2R)-2-[(1S)-1,2-dihydroxyethyl]-4-hydroxy-5-oxo-2H-furan-3-olate (23.56 mg, 118.93 umol, 2 eq). The mixture was stirred at 15° C. for 1 hr. LCMS was detected the desired product MS. The mixture was combined. The mixture was filtered. The residue was purified by prep-HPLC (TFA condition) according to HPLC. I-83 (45.77 mg, 38.38 umol, 64.53% yield, 97.36% purity) was obtained as colourless oil checked by QCLCMS and HNMR. LCMS: RT=1.142 min, MS cal.: 1160.52, $[M/2+H]^+$=581.6. HPLC: RT=2.418 min QCLCMS: RT=3.330 min, MS cal.: 1160.52, $[M/2+H]^+$=581.3. $^1H$ NMR (400 MHz, DMSO-d6) ppm 9.26 (s, 1H), 8.75 (s, 1H), 8.70 (s, 2H), 8.45 (s, 1H), 8.03 (s, 1H), 7.48 (br d, J=7.8 Hz, 1H), 7.41-7.36 (m, 1H), 7.34-7.27 (m, 1H), 4.61-4.54 (m, 2H), 4.03 (br d, J=13.7 Hz, 3H), 3.97 (s, 4H), 3.87 (br t, J=4.5 Hz, 3H), 3.71 (br t, J=5.8 Hz, 3H), 3.50 (s, 32H), 3.48-3.44 (m, 1H), 3.47 (br d, J=5.0 Hz, 12H), 3.41-3.33 (m, 3H), 2.92 (br t, J=5.7 Hz, 3H), 2.81 (s, 4H), 2.07 (s, 1H), 2.01-1.91 (m, 2H), 1.89-1.79 (m, 1H), 1.89-1.79 (m, 1H).

Example 33: Synthesis of I-84

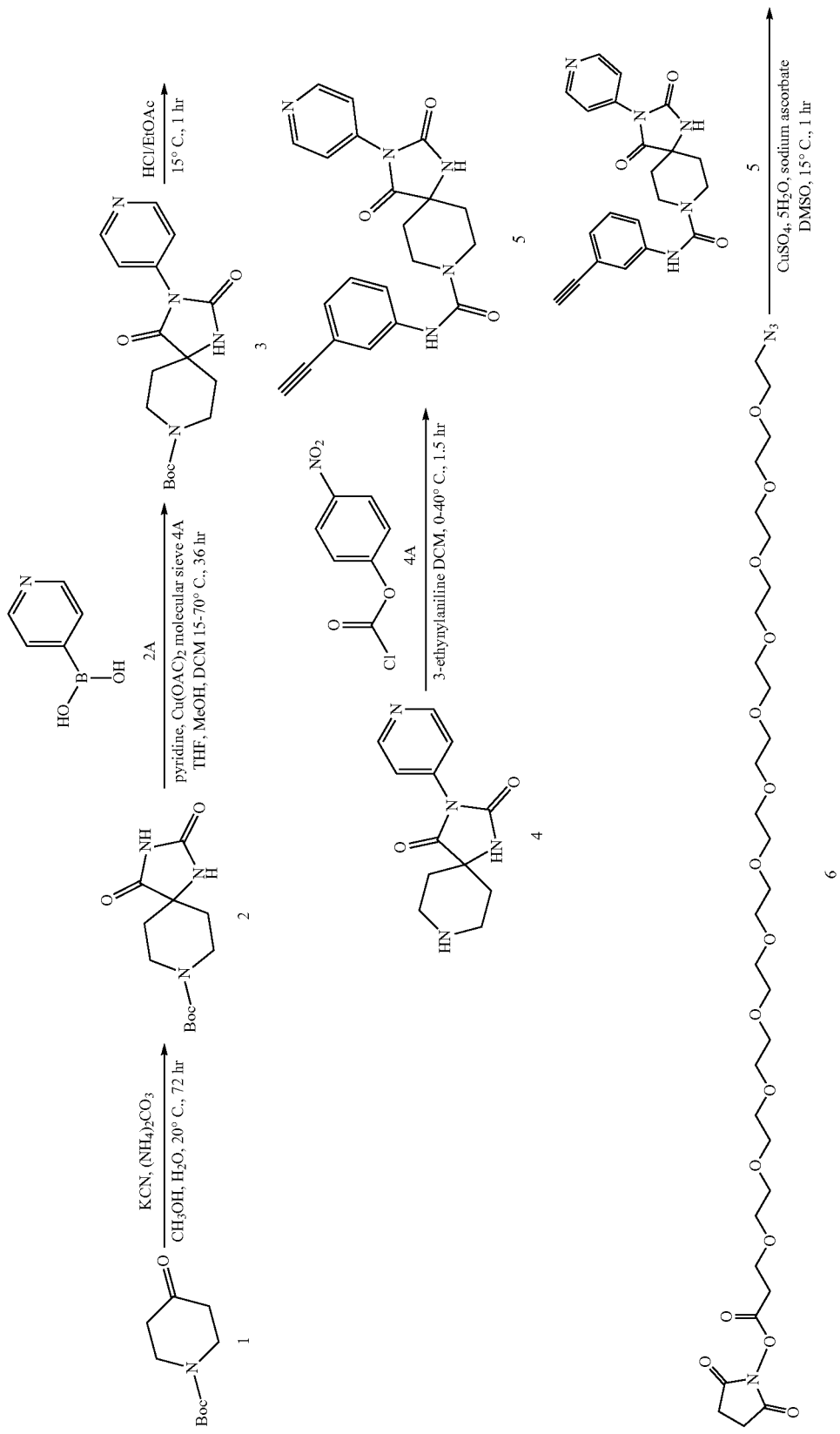

-continued
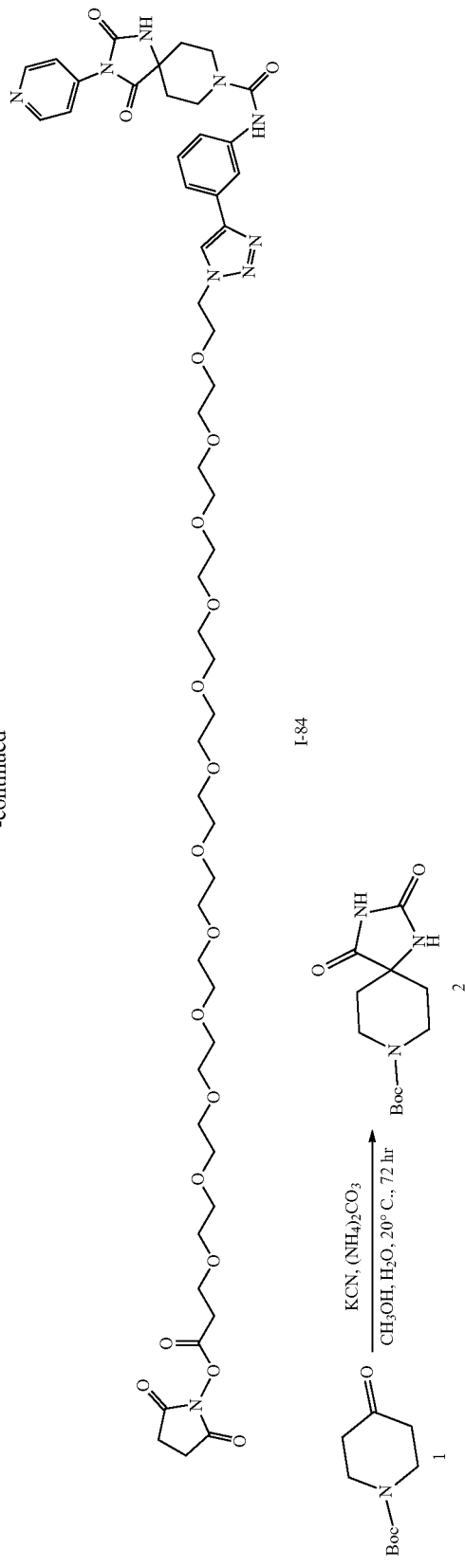
I-84
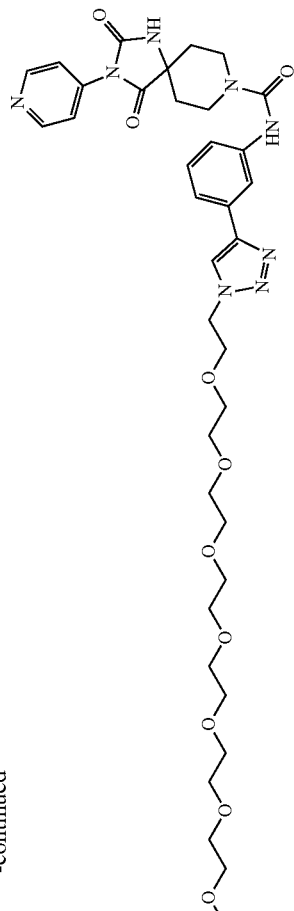
$\xrightarrow{\text{KCN, (NH}_4\text{)}_2\text{CO}_3}{\text{CH}_3\text{OH, H}_2\text{O, 20° C., 72 hr}}$ A solution of KCN (23.53 g, 361.36 mmol, 15.48 mL, 2.4 eq) in H$_2$O (200 mL) was added dropwise to the solution of compound 1 (30 g, 150.57 mmol, 1 eq) and (N$_4$)$_2$CO$_3$ (31.83 g, 331.25 mmol, 35.36 mL, 2.2 eq) in MeOH (200 mL) and H$_2$O (200 mL). The mixture was stirred at 20° C. for 72 h. LCMS showed the reaction was completed. The reaction mixture was filtered and concentrated in vacuum to give compound 2 (20 g, 74.27 mmol, 49.33% yield) as a white solid. LCMS: RT=0.999 min, MS cal.: 269.14, [M-55]$^+$=214.0. $^1$H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

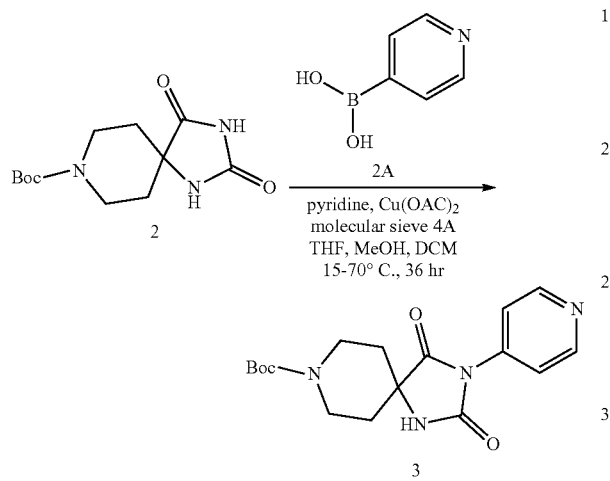

To a solution of compound 2 (400 mg, 1.49 mmol, 1 eq) and compound 2A (219.09 mg, 1.78 mmol, 1.2 eq) in DCM (50 mL) and THF (10 mL) was added pyridine (352.47 mg, 4.46 mmol, 359.67 uL, 3 eq) Molecular sieve 4A (800 mg) Cu(OAc)$_2$ (269.79 mg, 1.49 mmol, 1 eq) oxygen (47.53 mg, 1.49 mmol, 1 eq). The mixture was stirred at 15° C. under O$_2$ (20 Psi) for 12 hr. Then warmed to 50° C. under O$_2$ (20 Psi) for 12 hr. The mixture was concentrated. Then the mixture was added MeOH (50 mL), warmed to 70° C. under O$_2$ (20 Psi) for 12 hr. LCMS was detected the desired product MS. The mixture was filtered and concentrated. The residue was purified by column chromatography (SiO$_2$, Petroleum ether:Ethyl acetate=5:1 to 1:1) according to TLC (Plate1, Petroleum ether:Ethyl acetate=1:1, Product R$_f$=0.27). Compound 3 (380 mg, crude) was obtained as pink solid checked by LCMS. LCMS: RT=1.021 min, MS cal.: 346.16, [M+H]$^+$=346.9. LCMS: RT=1.033 min, MS cal.: 346.16, [M+H]$^+$=347.0.

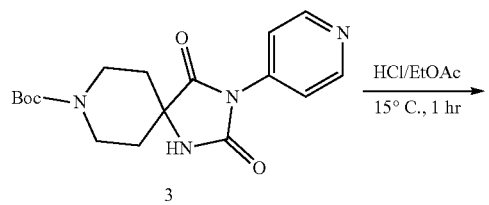

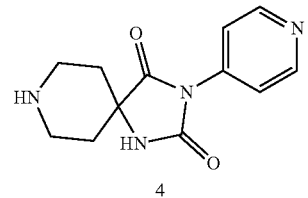

To a solution of compound 3 (250 mg, 721.75 umol, 1 eq) in HCl/EtOAc (30 mL) was stirred at 15° C. for 1 hr. LCMS was detected the desired product MS. The mixture was concentrated. Compound 4 (220 mg, crude, HCl) was obtained as white solid. LCMS: RT=0.156 min, MS cal.: 246.11, [M+H]$^+$=247.1.

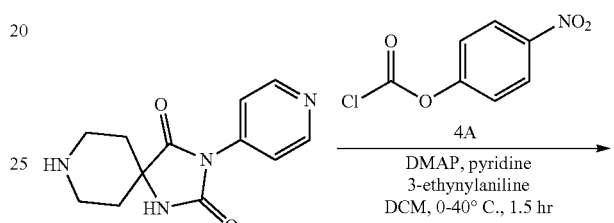

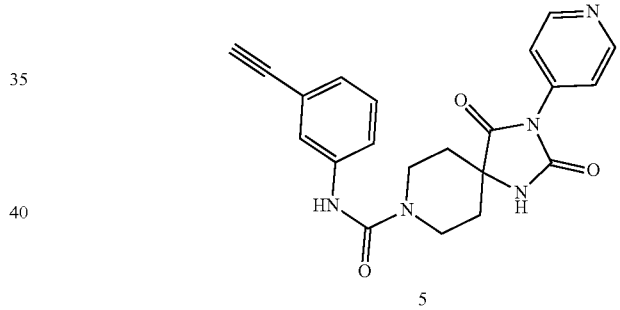

To a solution of compound 4A (188.21 mg, 933.77 umol, 1.2 eq) in DCM (15 mL) was added 3-ethynylaniline (118.50 mg, 1.01 mmol, 1.3 eq) at 0° C. for 0.5 hr, then added DMAP (285.19 mg, 2.33 mmol, 3 eq) pyridine (307.75 mg, 3.89 mmol, 314.03 uL, 5 eq) and compound 4 (220 mg, 778.14 umol, 1 eq, HCl). The mixture was stirred at 40° C. for 1 hr. LCMS was detected the desired product MS. The mixture was added CH$_2$Cl$_2$ (60 mL) to the reaction mixture, then the mixture was washed with water (10 mL*2), the organic layer dried over Na$_2$SO$_4$ and concentrated. The residue was purified by prep-TLC according to TLC (Plate 1, DCM:MeOH=10:1, product R$_f$=0.18). Compound 5 (45 mg, 108.44 umol, 13.94% yield, 93.84% purity) was obtained as white solid checked by LCMS. LCMS: RT=0.995 min, MS cal.: 389.15, [M+H]$^+$=390.1. LCMS: RT=0.996 min, MS cal.: 389.15, [M+H]$^+$=390.2.

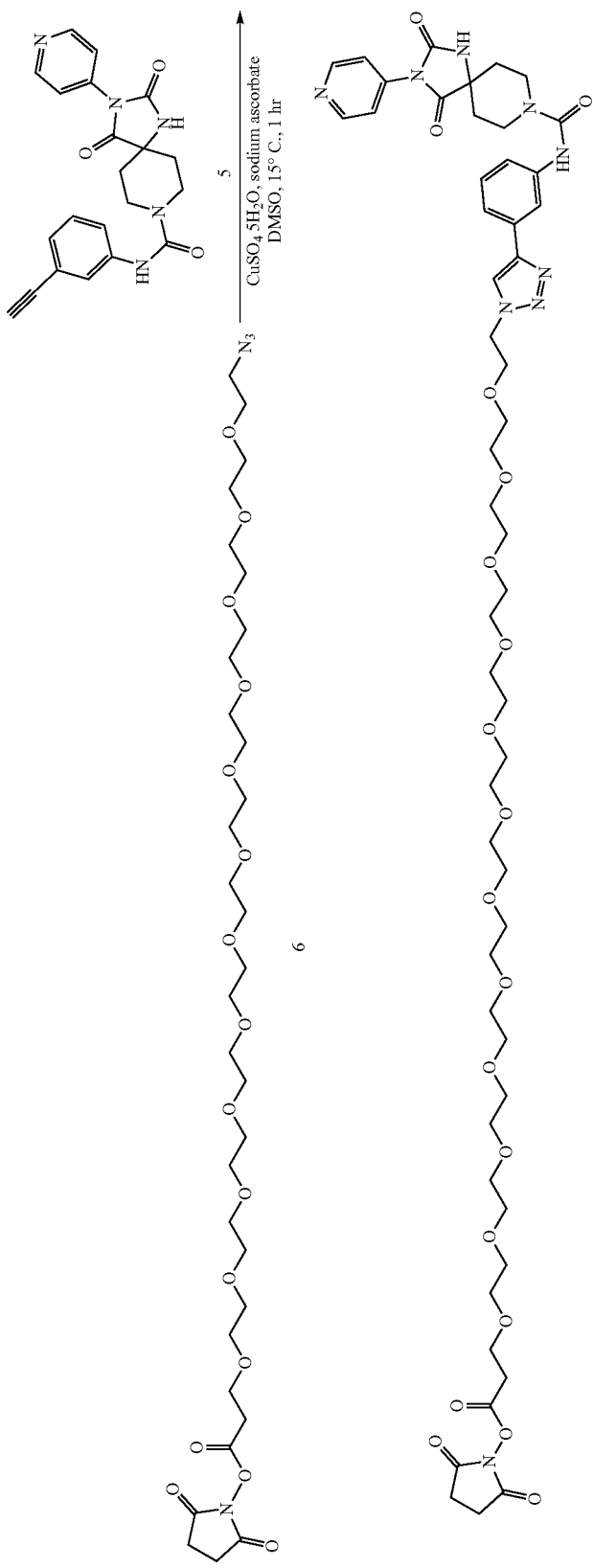

To a solution of compound 6 (57.64 mg, 77.81 umol, 1.01 eq) and compound 5 (30 mg, 77.04 umol, 1 eq) in DMSO (2 mL) was added $CuSO_4 \cdot 5H_2O$ (19.24 mg, 77.04 umol, 1 eq) and sodium; (2R)-2-[(1S)-1,2-dihydroxyethyl]-4-hydroxy-5-oxo-2H-furan-3-olate (30.52 mg, 154.08 umol, 2 eq). The mixture was stirred at 15° C. for 1 hr. LCMS was detected the desired product MS. The mixture was combined. The mixture was filtered. The residue was purified by prep-HPLC (TFA condition) according to HPLC. I-84 (37.86 mg, 30.68 umol, 39.83% yield, 91.59% purity) was obtained as yellow oil checked by QCLCMS and HNMR. LCMS: RT=1.203 min, MS cal.: 1129.52, $[M/2+H]^+$=565.9. HPLC: RT=1.982 min. QCLCMS: RT=2.242 min, MS cal.: 1129.52, $[M/2+H]^+$=565.9. $^1$H NMR (400 MHz, DMSO-d6) δ ppm 9.49 (s, 1H), 8.86-8.81 (m, 1H), 8.83 (br d, J=6.1 Hz, 1H), 8.79-8.76 (m, 1H), 8.78-8.76 (m, 1H), 8.79-8.76 (m, 1H), 8.77 (s, 1H), 8.45 (s, 1H), 8.05-8.02 (m, 1H), 8.06-8.02 (m, 1H), 8.04 (s, 1H), 8.00-8.00 (m, 1H), 7.99-7.94 (m, 1H), 7.96 (d, J=6.5 Hz, 1H), 7.49 (br d, J=8.2 Hz, 1H), 7.41-7.36 (m, 1H), 7.35-7.28 (m, 1H), 4.57 (t, J=5.0 Hz, 2H), 4.10-4.01 (m, 2H), 3.88 (t, J=5.1 Hz, 2H), 3.72 (t, J=6.0 Hz, 2H), 3.68-3.64 (m, 1H), 3.57-3.54 (m, 1H), 3.57-3.54 (m, 1H), 3.48-3.45 (m, 1H), 3.68-3.45 (m, 42H), 3.36 (br t, J=10.9 Hz, 2H), 2.92 (t, J=5.9 Hz, 2H), 2.81 (s, 4H), 2.01-1.92 (m, 2H), 1.89-1.82 (m, 2H).

Example 34: Synthesis of I-85

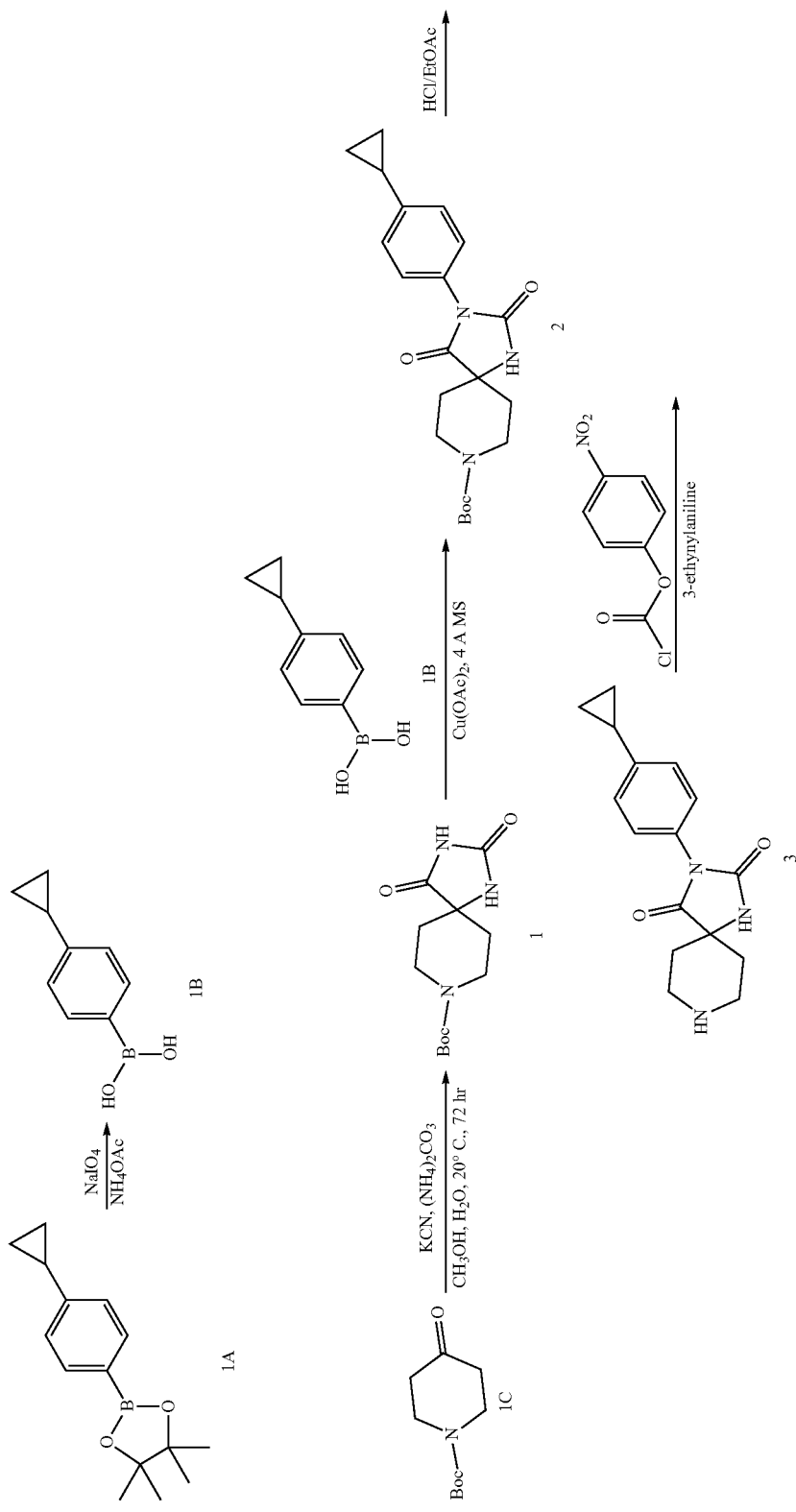

-continued
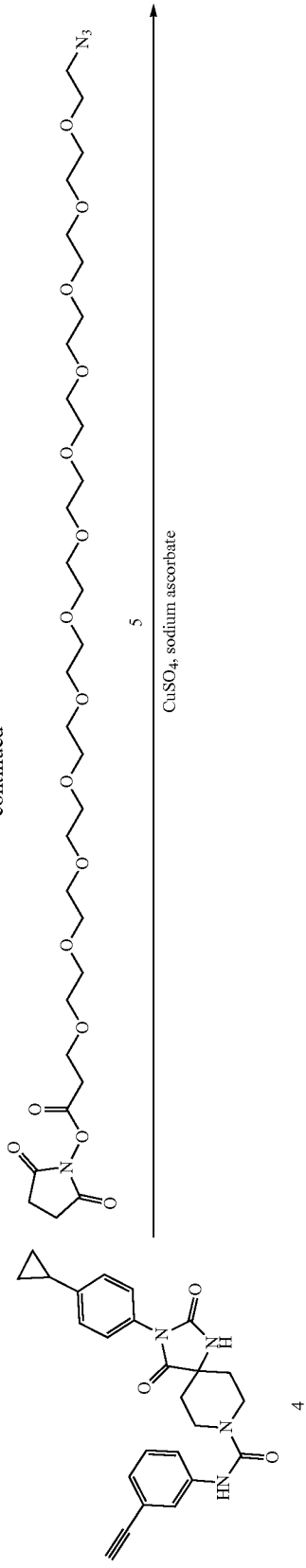
5
CuSO₄, sodium ascorbate
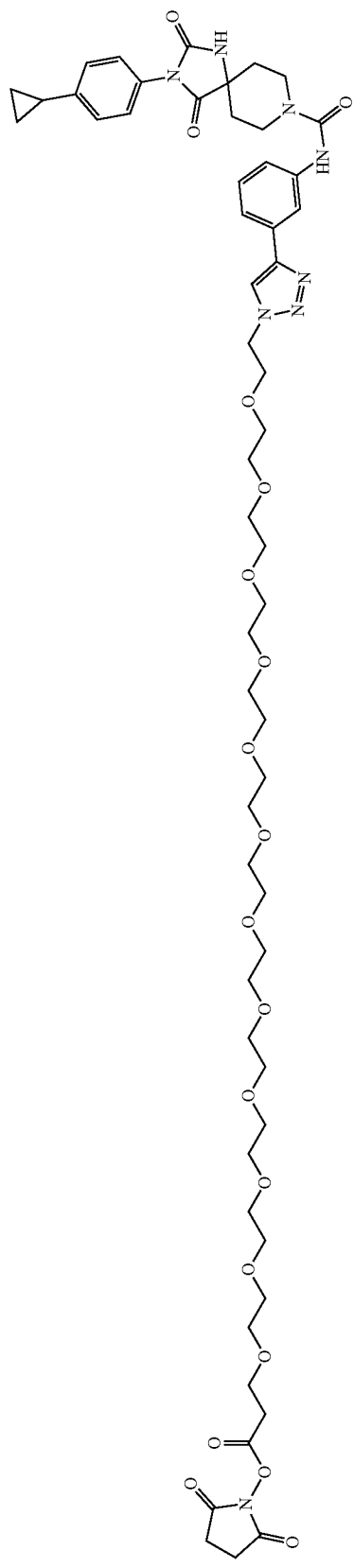
I-85
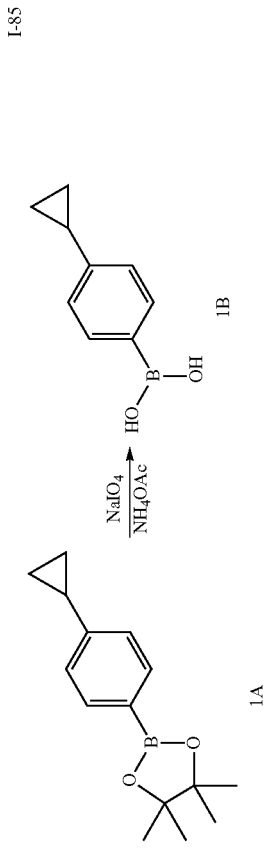

To a solution of compound 1A (0.3 g, 1.23 mmol, 1 eq) in ACETONE (1 mL), Water (0.4 mL) was added NaIO4 (788.50 mg, 3.69 mmol, 204.28 uL, 3 eq), NH4OAc (189.44 mg, 2.46 mmol, 2 eq). The mixture was stirred at 15° C. for 16 hrs. TLC (Dichloromethane Methanol=10:1, Rf=0.43) showed the starting material was consumed completely and a new spot was detected. The reaction mixture was filtered. The residue was triturated with H2O (5 mL) and filtered. The residue was concentrated to give compound 1B (0.3 g, crude) as a yellow solid, which was confirmed by H NMR. 1H NMR (400 MHz, DMSO-d6) δ ppm 7.55 (d, J=7.34 Hz, 2H) 7.08 (br d, J=7.82 Hz, 2H) 1.92 (br d, J=5.38 Hz, 1H) 0.98 (br d, J=8.31 Hz, 2H) 0.69 (br d, J=3.91 Hz, 2H).

To a solution of compound 1 (0.3 g, 1.11 mmol, 1 eq), compound 1B (216.56 mg, 1.34 mmol, 1.2 eq) and Cu(OAc)2 (202.34 mg, 1.11 mmol, 1 eq) in THF (30 mL) was added PYRIDINE (264.36 mg, 3.34 mmol, 269.75 uL, 3 eq) and 4A MOLECULAR SIEVE (1 g) stirred at 80° C. for 16 hrs under O2. LCMS showed the starting material was consumed completely and main peak with desired MS was detected. The reaction mixture was filtered and filtrate was concentrated. The residue was purified by chromatography column (Petroleum ether:Ethyl acetate=5:1) to give compound 2 (120 mg, 311.32 umol, 27.95% yield) as a white solid. LCMS: RT=1.048 min, MS cal.: 385.20, [(M-55)+H]+=330.1.

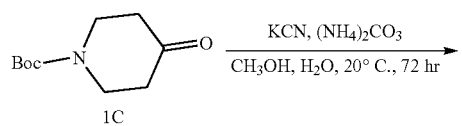

1C

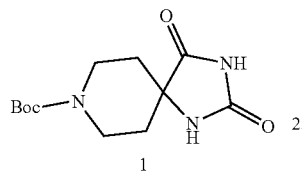

1

A solution of KCN (23.53 g, 361.36 mmol, 15.48 mL, 2.4 eq) in H2O (200 mL) was added dropwise to the solution of compound 1C (30 g, 150.57 mmol, 1 eq) and (NH4)2CO3 (31.83 g, 331.25 mmol, 35.36 mL, 2.2 eq) in MeOH (200 mL) and H2O (200 mL). The mixture was stirred at 20° C. for 72 h. LCMS showed the reaction was completed. The reaction mixture was filtered and concentrated in vacuum to give compound 1 (20 g, 74.27 mmol, 49.33% yield) as a white solid. LCMS: RT=0.999 min, MS cal.: 269.14, [M-55]+=214.0. $^1$H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

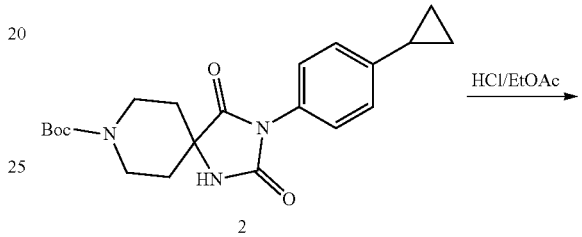

2

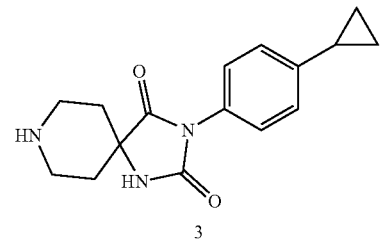

3

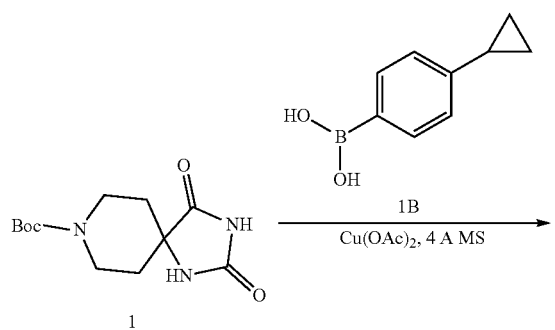

1

To a solution of compound 2 (120 mg, 311.32 umol, 1 eq) in HCl/EtOAc (4 M, 10 mL, 128.49 eq) was stirred at 15° C. for 2 hrs. LCMS showed the starting material was consumed completely and main peak with desired MS was detected. The reaction mixture was concentrated under reduced pressure to give compound 3 (80 mg, 280.37 umol, 90.06% yield, N/A purity) as a white solid. LCMS: RT=0.968 min, MS cal.: 285.15, [M+H]+=286.2.

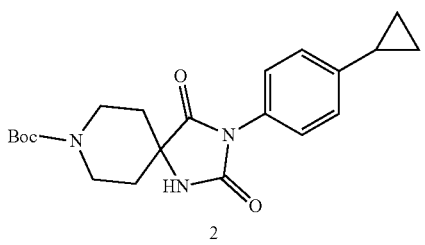

2

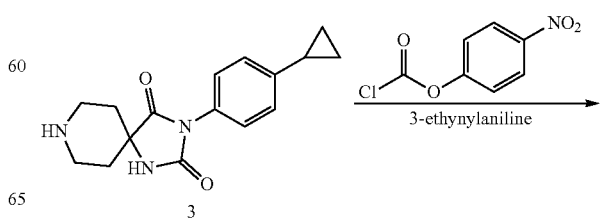

3

-continued

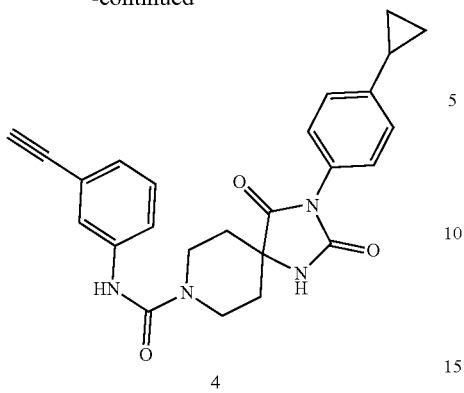

4

To a solution of (4-nitrophenyl) carbonochloridate (67.81 mg, 336.44 umol, 1.2 eq) in DCM (3 mL) was added 3-ethynylaniline (42.70 mg, 364.48 umol, 1.3 eq) in DCM (1 mL) drop wise at −40° C. stirred for 1 h. Then the reaction mixture was added compound 3 (80 mg, 280.37 umol, 1 eq), DMAP (102.76 mg, 841.10 umol, 3 eq) and PYRIDINE (66.53 mg, 841.10 umol, 67.89 uL, 3 eq) in MeCN (5 mL) and stirred at 15° C. for 15 hrs. LCMS showed the starting material was consumed completely and a main peak with desired MS was detected. The reaction mixture was added EtOAc (40 mL), then the mixture was washed with brine (40 mL). The organic layer was dried over anhydrous $Na_2SO_4$ and concentrated under reduced pressure. The residue was purified by chromatography column (Petroleum ether:EtOAc=3:1 to 1:1) to give compound 4 (80 mg, 186.71 umol, 66.59% yield, N/A purity) as a yellow solid. LCMS: RT=1.371 min, MS cal.: 428.18, $[M+H]^+$=429.2.

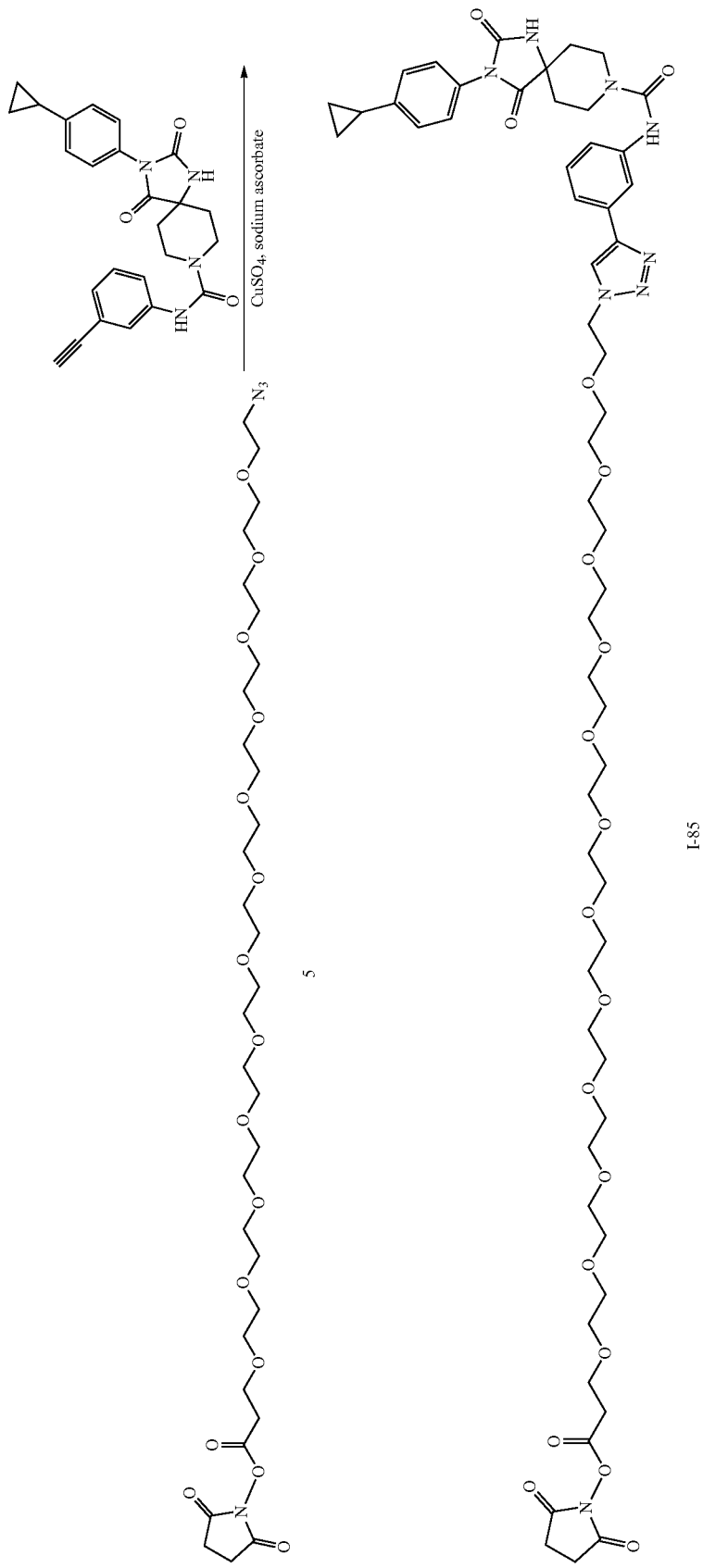

A solution of compound 5 (50 mg, 67.50 umol, 1 eq) and compound 4 (28.92 mg, 67.50 umol, 1 eq) in DMSO (2 mL) was added CuSO$_4$·5H$_2$O (5.06 mg, 20.25 umol, 0.3 eq) and sodium ascorbate (26.74 mg, 134.99 umol, 2 eq) stirred at 15° C. for 1 hr. LCMS showed a peak with desired MS was detected. The reaction mixture was filtered. The filtrate was purified by prep-HPLC (column: Luna C18 100*30 5 u; mobile phase: [water (0.1% TFA)–ACN]; B %: 15%-45%, 10 min) to give I-85 (14.17 mg, 11.65 umol, 17.27% yield, 94.02% purity) as a colorless oil, which was confirmed by H NMR and QC LCMS. $^1$H NMR (400 MHz, CHLOROFORM-d) δ=8.07 (br s, 1H), 7.87 (br s, 1H), 7.64 (br d, J=7.8 Hz, 1H), 7.54-7.45 (m, 2H), 7.34 (br t, J=7.7 Hz, 1H), 7.28-7.28 (m, 1H), 7.26 (br s, 1H), 7.18-7.08 (m, 3H), 4.57 (br s, 2H), 3.98 (br s, 2H), 3.88 (br s, 2H), 3.84 (br t, J=6.4 Hz, 2H), 3.65-3.57 (m, 46H), 2.89 (br t, J=6.3 Hz, 2H), 2.83 (br s, 4H), 2.10 (br s, 2H), 1.95-1.80 (m, 4H), 1.03-0.92 (m, 2H), 0.74-0.67 (m, 2H). LCMS: RT=1.228 min, MS cal.: 1168.55, [M+H]$^+$=1169.9. LCMS: RT=2.295 min, MS cal.: 1168.55, [M/2+H]$^+$=585.4, [M+H]$^+$=1169.6.

Example 35: Synthesis of I-86

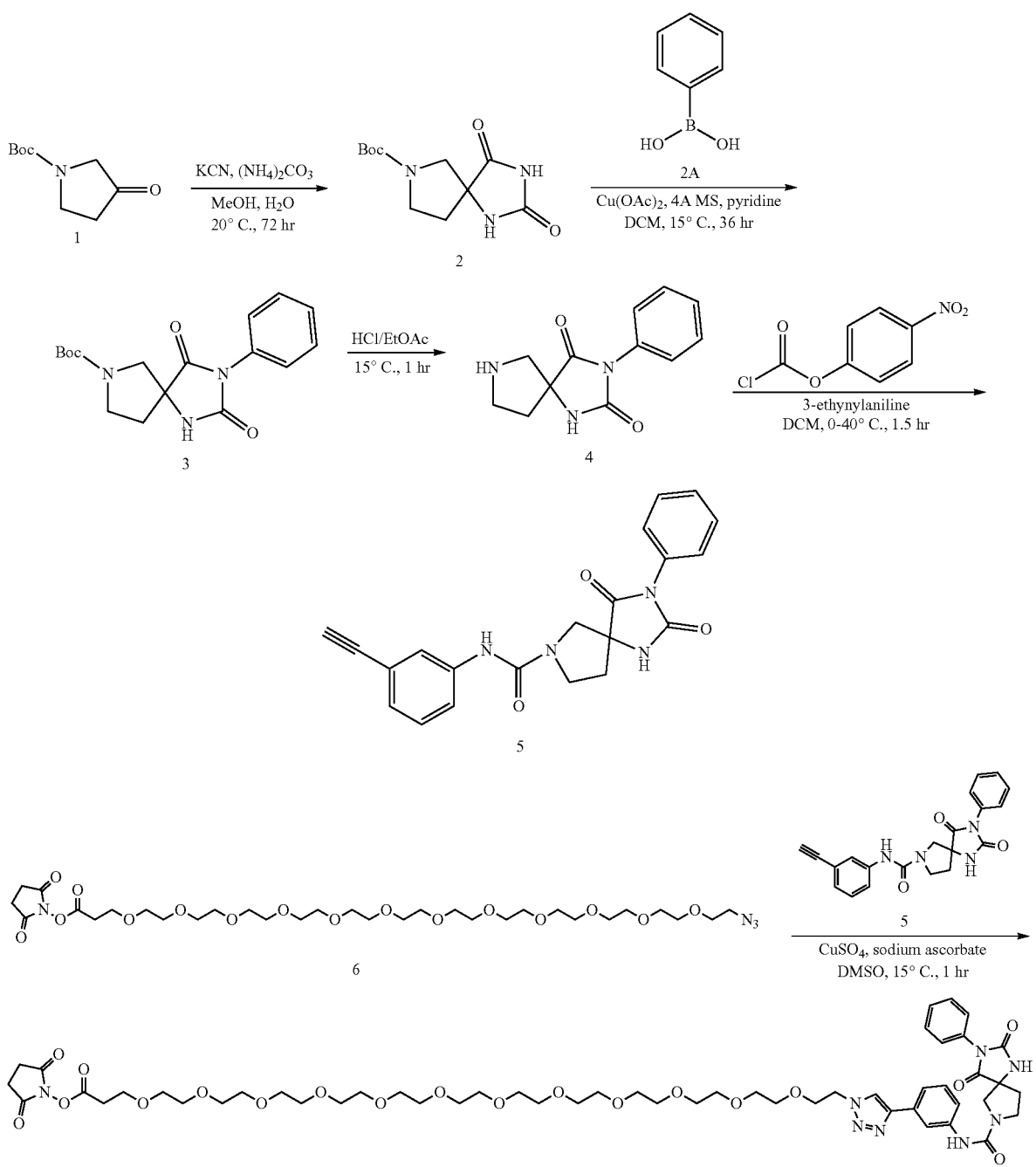

I-86

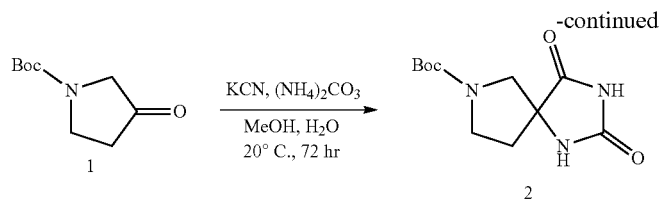

A solution of KCN (4.39 g, 67.49 mmol, 2.89 mL, 2.5 eq) in H₂O (40 mL) was added dropwise to the solution of compound 1 (5 g, 26.99 mmol, 1 eq) and $(NH_4)_2CO_3$ (5.71 g, 59.39 mmol, 6.34 mL, 2.2 eq) in MeOH (40 mL) and H₂O (40 mL). The mixture was stirred at 20° C. for 72 hr. LCMS showed the reaction was completed. The reaction mixture was filtered and concentrated in vacuum to give compound 2 (4 g, 15.67 mmol, 29.02% yield) as a yellow solid. LCMS: RT=0.967 min, MS cal.: 255.12, [M-55]⁺=200.1. ¹H NMR (400 MHz, DMSO-d6) δ ppm 10.76 (br s, 1H) 8.37 (br s, 1H) 3.37-3.52 (m, 3H) 3.28-3.35 (m, 1H) 2.17 (br dd, J=12.2, 8.5 Hz, 1H) 1.89-2.00 (m, 1H) 1.40 (br s, 9H).

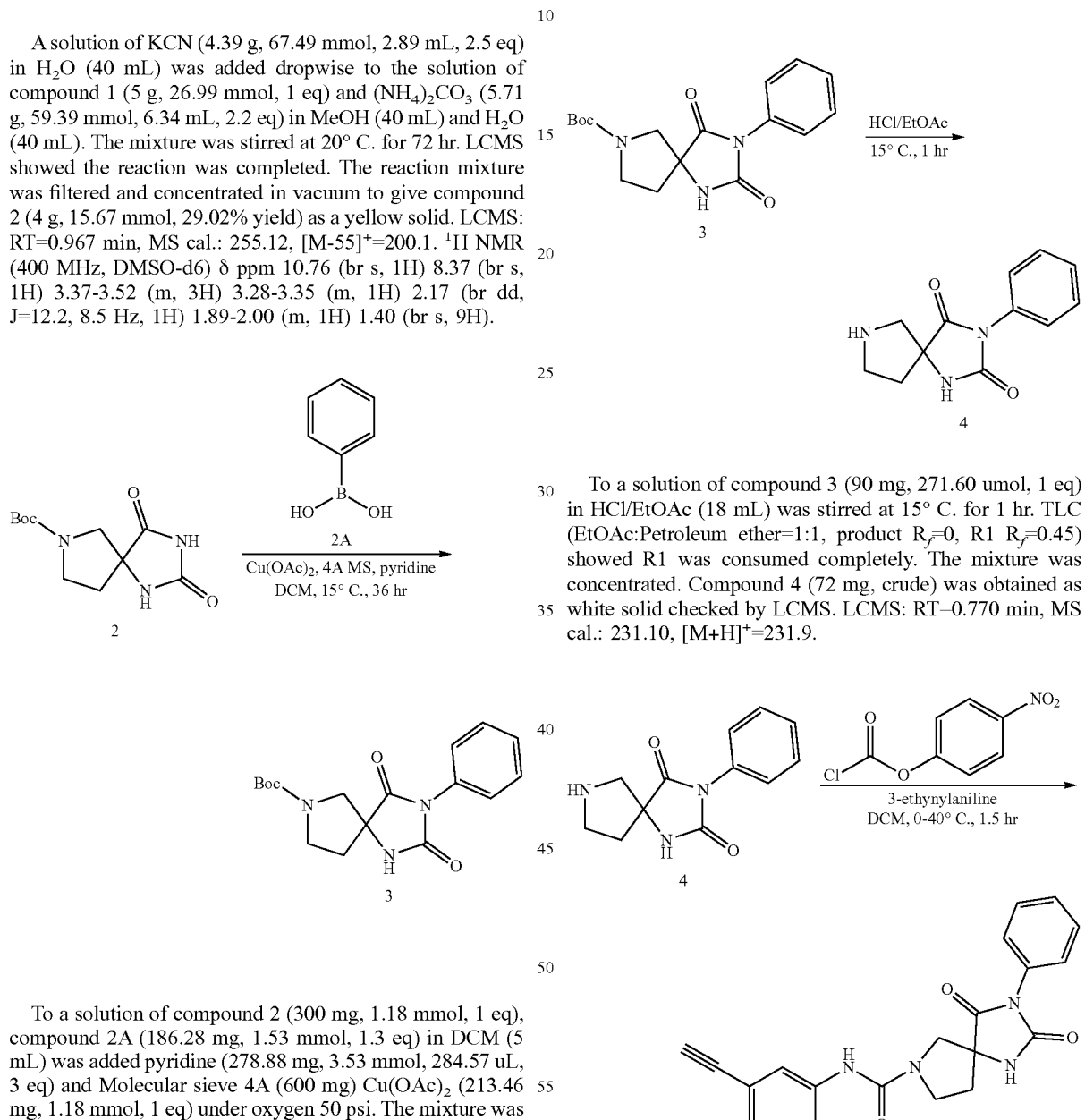

To a solution of compound 2 (300 mg, 1.18 mmol, 1 eq), compound 2A (186.28 mg, 1.53 mmol, 1.3 eq) in DCM (5 mL) was added pyridine (278.88 mg, 3.53 mmol, 284.57 uL, 3 eq) and Molecular sieve 4A (600 mg) Cu(OAc)₂ (213.46 mg, 1.18 mmol, 1 eq) under oxygen 50 psi. The mixture was stirred at 15° C. for 36 hr. TLC showed some reactant 1 was remained (Ethyl acetate:Petroleum ether=1:2, R_f=0.2). LCMS showed the desired Ms was detected. It was added with 30 mL THF and filtered, the filtrate was washed with 0.2 M HCl (20 mL), the organic layer was separated, dried over Na₂SO₄, filtered and the filtrate was concentrated. The residue was purified by column chromatography (SiO₂, Petroleum ether/Ethyl acetate/THF=5/1/0.2 to 1/1/0.2). Compound 3 (100 mg, 301.78 umol, 25.68% yield) was obtained as a yellow solid. LCMS: RT=2.156 min, MS cal.: 331.15, [M-55]⁺=276.0.

To a solution of compound 3 (90 mg, 271.60 umol, 1 eq) in HCl/EtOAc (18 mL) was stirred at 15° C. for 1 hr. TLC (EtOAc:Petroleum ether=1:1, product R_f=0, R1 R_f=0.45) showed R1 was consumed completely. The mixture was concentrated. Compound 4 (72 mg, crude) was obtained as white solid checked by LCMS. LCMS: RT=0.770 min, MS cal.: 231.10, [M+H]⁺=231.9.

To a solution of (4-nitrophenyl) carbonochloridate (31.38 mg, 155.68 umol, 1.2 eq) in DCM (1 mL) was added 3-ethynylaniline (19.76 mg, 168.65 umol, 1.3 eq) and DCM (1 mL) at 0° C. for 0.5 hr, then added pyridine (51.31 mg, 648.65 umol, 52.36 uL, 5 eq), DMAP (47.55 mg, 389.19 umol, 3 eq) and compound 4 (30 mg, 129.73 umol, 1 eq). The mixture was stirred at 40° C. for 1 hr. LCMS was detected the desired product MS. Adding $CH_2Cl_2$ (5 mL) to the reaction mixture, then the mixture was washed with HCl (0.5 M) and water (3 mL×2), the organic layer dried with $Na_2SO_4$ and concentrated. The residue was purified by prep-TLC according to TLC (EtOAC:Petroleum ether=2:1, Product $R_f$=0.14). Compound 5 (30 mg, 77.81 umol, 59.98% yield, 97.11% purity) was obtained as yellow oil checked by LCMS. LCMS: RT=1.198 min, MS cal.: 374.14, $[M+H]^+$=375.0. LCMS: RT=1.177 min, MS cal.: 374.14, $[M+H]^+$=375.0.

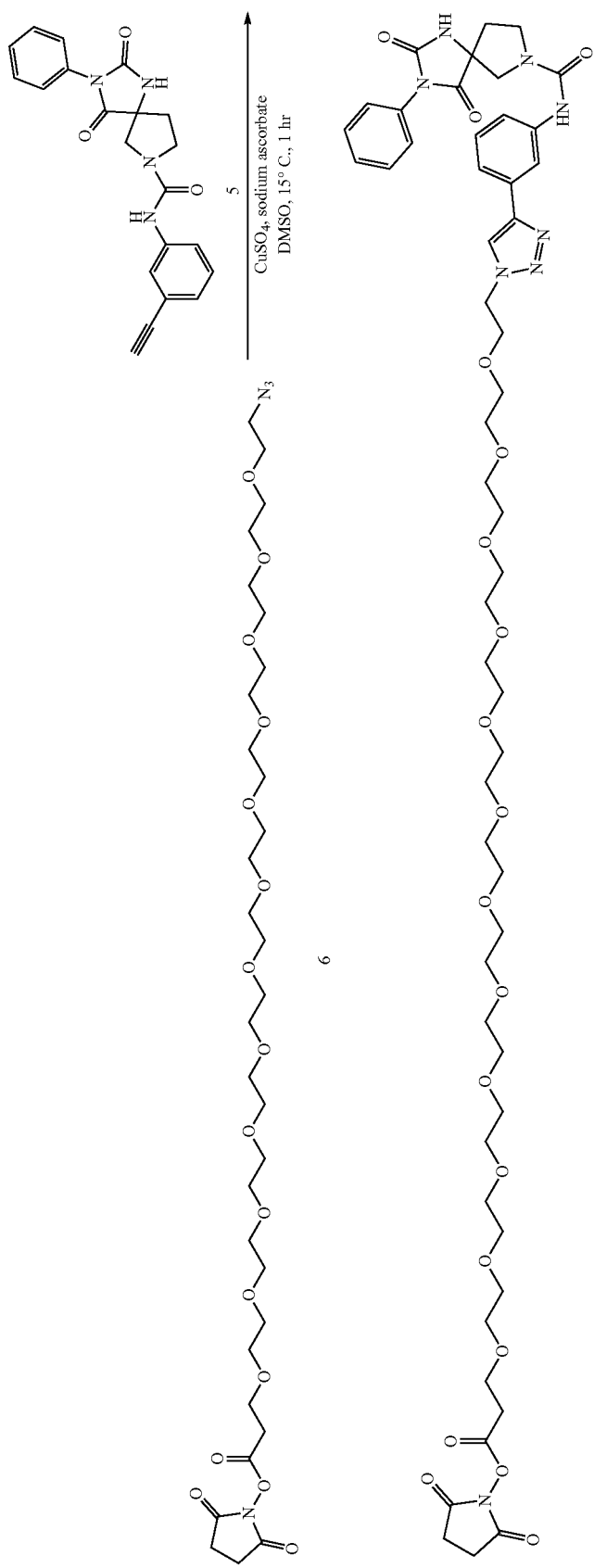

To a solution of compound 6 (51.94 mg, 70.11 umol, 1.05 eq) and compound 5 (25 mg, 66.77 umol, 1 eq) in DMSO (1 mL) was added sodium; (2R)-2-[(1S)-1,2-dihydroxyethyl]-4-hydroxy-5-oxo-2H-furan-3-olate (26.46 mg, 133.55 umol, 2 eq) and $CuSO_4 \cdot 5H_2O$ (5.00 mg, 20.03 umol, 0.3 eq). The mixture was stirred at 15° C. for 1 hr. LCMS was detected the desired product MS. The mixture was combined. The mixture was filtered. The residue was purified by prep-HPLC (TFA condition) according to HPLC. I-86 (40.01 mg, 34.33 umol, 51.41% yield, 95.69% purity) was obtained as yellow oil checked by QCLCMS and HNMR. LCMS: RT=1.149 min, MS cal.: 1114.51, $[M/2+H]^+$=558.5. HPLC: RT=2.544 min. QCLCMS: RT=3.563 min, MS cal.: 1114.51, $[M/2+H]^+$=558.3. $^1$H NMR (400 MHz, DMSO-$d_6$) δ ppm 9.08 (s, 1H), 8.51-8.44 (m, 2H), 8.09 (s, 1H), 7.59-7.46 (m, 3H), 7.46-7.29 (m, 5H), 4.58 (br t, J=4.9 Hz, 2H), 3.91-3.81 (m, 3H), 3.80-3.60 (m, 15H), 3.58-3.43 (m, 45H), 2.93 (t, J=5.9 Hz, 2H), 2.81 (s, 4H), 2.47-2.41 (m, 1H), 2.28-2.20 (m, 1H).

Example 36: Synthesis of I-87

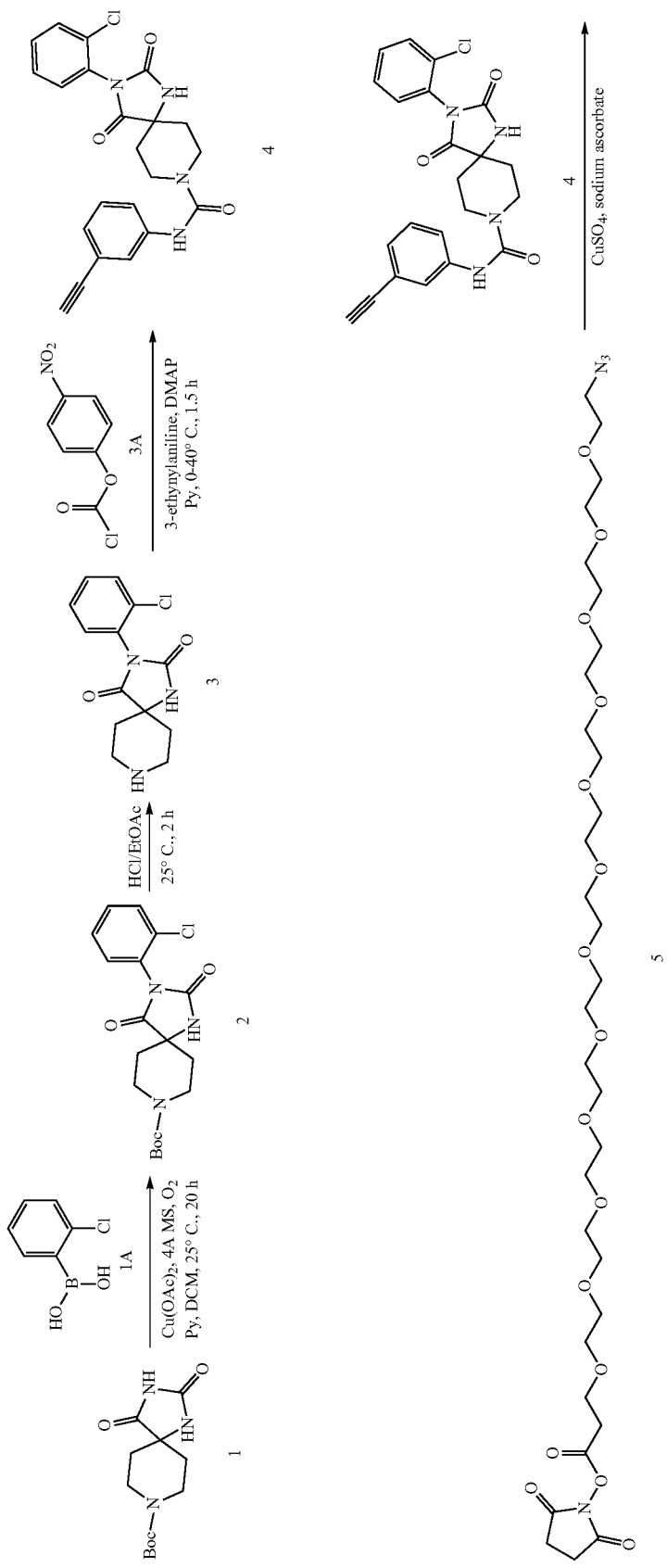

-continued
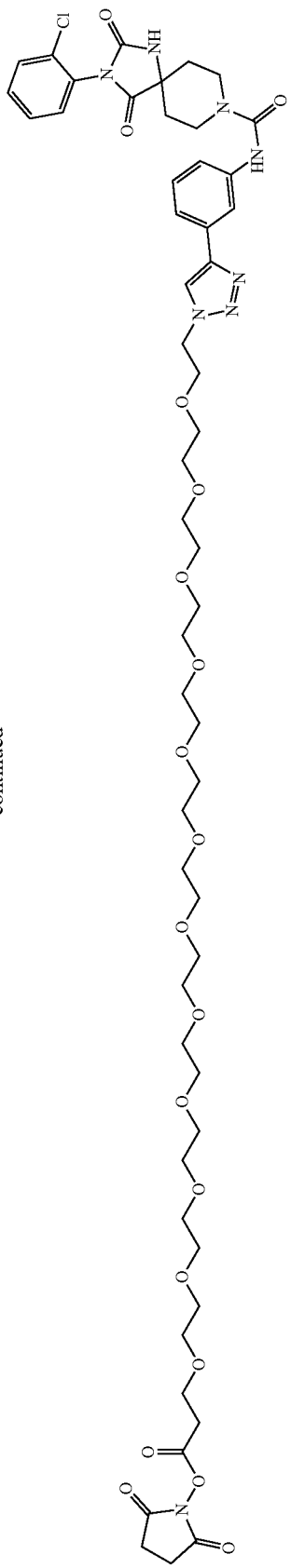
I-87
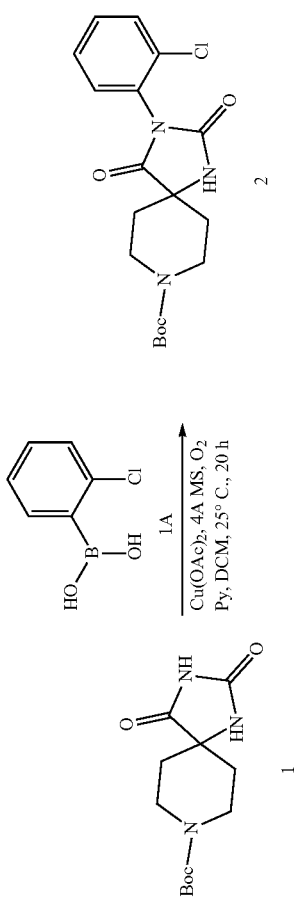

To a solution of compound 1 (0.4 g, 1.49 mmol, 1 eq) and compound 1A (232.27 mg, 1.49 mmol, 1 eq) in DCM (10 mL) was added Molecular sieve 4A (0.2 g, 1.49 mmol, 1 eq), Cu(OAc)₂ (269.78 mg, 1.49 mmol, 1 eq) and Pyridine (352.47 mg, 4.46 mmol, 359.67 uL, 3 eq). After the mixture was bubbled with oxygen for 10 min, the mixture was stirred under OXYGEN (475.31 mg, 14.85 mmol, 10 eq) at 25° C. for 20 h. LCMS showed the reaction was completed. The residue was poured into water (10 mL). The aqueous phase was extracted with DCM (5 mL*2). The combined organic phase was washed with 0.2 M HCl (5 mL*2), dried with anhydrous Na₂SO₄, filtered and concentrated in vacuum. The residue was purified by silica gel chromatography (Petroleum ether/Ethyl acetate=5/1 to 0/1, TLC:Petroleum ether/Ethyl acetate=0:1, R$_f$=0.6) to afford compound 2 (0.22 g, 579.20 umol, 38.99% yield) as a white solid. ¹H NMR (400 MHz, CHLOROFORM-d) δ ppm 7.52-7.59 (m, 1H) 7.38-7.47 (m, 2H) 7.31-7.34 (m, 1H) 6.99 (s, 1H) 3.98 (s, 2H) 3.27 (ddd, J=13.7, 9.9, 3.4 Hz, 2H) 2.09-2.19 (m, 2H) 1.79 (t, J=15.0 Hz, 2H) 1.48 (s, 9H). LCMS: RT=1.198 min, MS cal.: 379.8, [M-56+H]⁺=324.3.

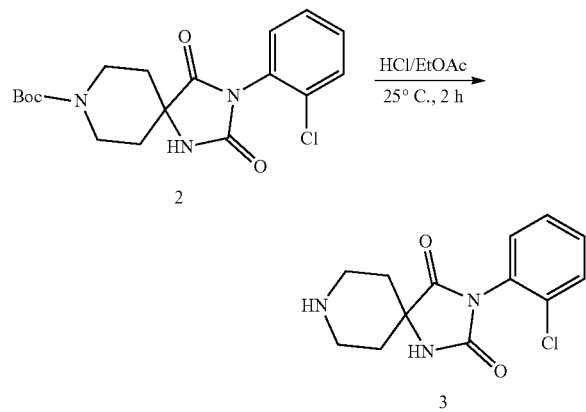

The solution of compound 2 (0.2 g, 526.54 umol, 1 eq) in HCl/EtOAc (5 mL, 4M) was stirred at 25° C. for 2 h. LCMS showed the reaction was completed. The mixture was concentrated in vacuum to give compound 3 (100 mg, 316.27 umol, 60.07% yield, HCl) as a white solid. LCMS: RT=1.037 min, MS cal.: 279.0, [M+H]⁺=280.2.

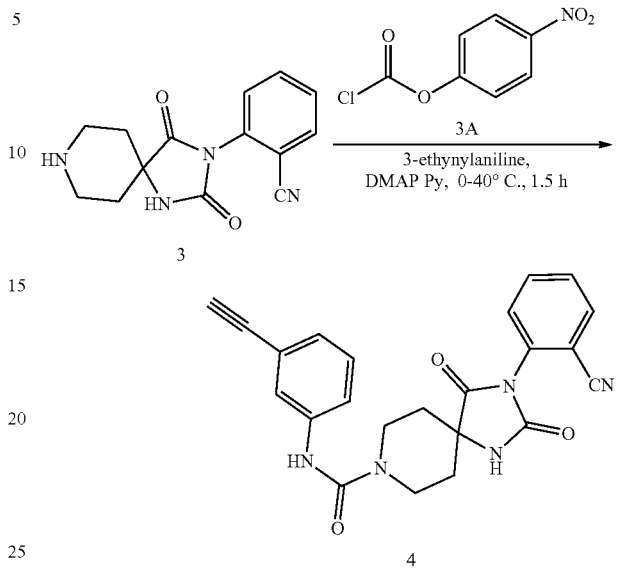

To a mixture of compound 3 in DCM (3 mL) was added drop wise 3-ethynylaniline (22.23 mg, 189.76 umol, 1.2 eq) at 0° C. for 30 min. Then the mixture was added compound 3A (50 mg, 158.14 umol, 1 eq, HCl), Pyridine (37.53 mg, 474.41 umol, 38.29 uL, 3 eq) and DMAP (57.96 mg, 474.41 umol, 3 eq). The mixture was stirred at 40° C. for 60 min. LCMS showed the reaction was completed. The residue was poured into water (2 mL). The aqueous phase was extracted with DCM (2 mL*2). The combined organic phase was washed with brine (2 mL*2), dried with anhydrous Na₂SO₄, filtered and concentrated in vacuum. The residue was purified by silica gel chromatography (Petroleum ether/Ethyl acetate=10/1 to 0/1, TLC:Petroleum ether/Ethyl acetate=1:1, R$_f$=0.2) to afford compound 4 (60 mg, 141.89 umol, 89.73% yield) as a white solid. LCMS: RT=1.172 min, MS cal.: 422.1, [M+H]⁺=423.2.

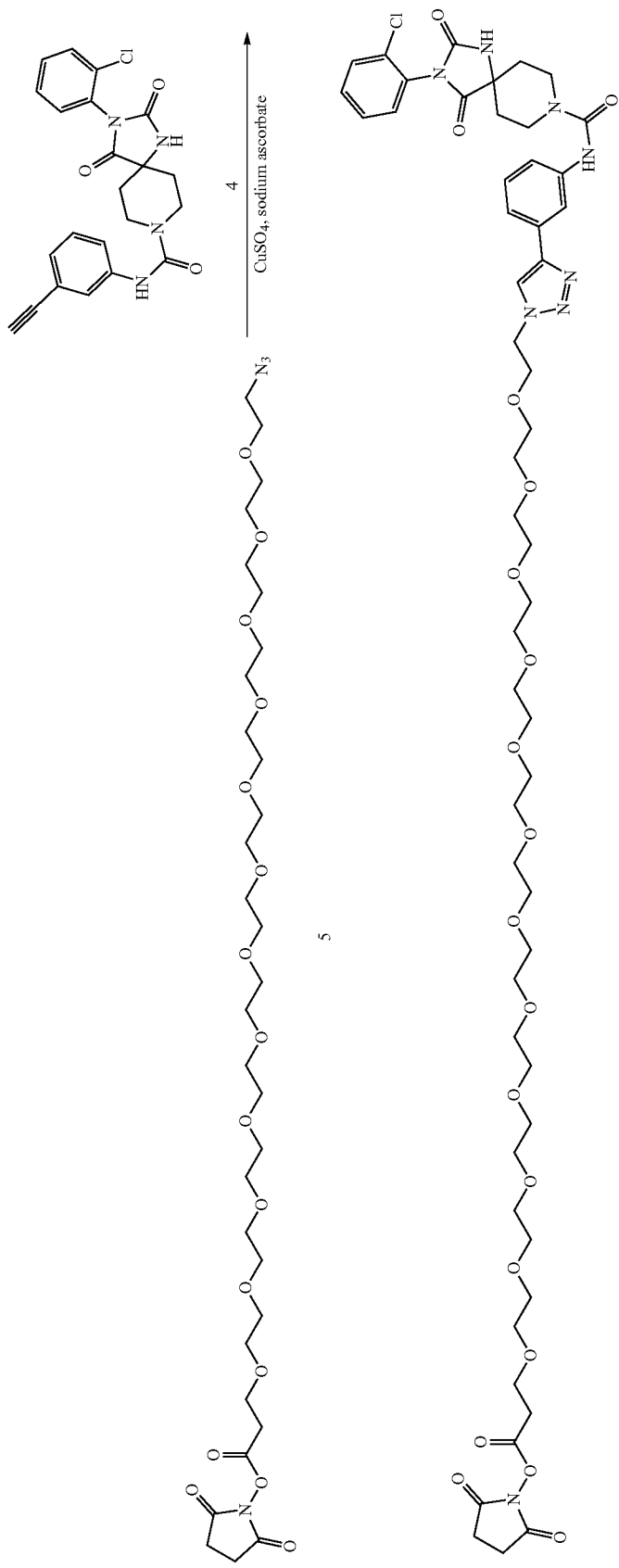

To a solution of compound 5 (0.1 g, 134.99 umol, 1 eq) and compound 4 (57.08 mg, 134.99 umol, 1 eq) in DMSO (2 mL) was added CuSO$_4$·5H$_2$O (101.12 mg, 404.97 umol, 3 eq) and sodium ascorbate (80.23 mg, 404.97 umol, 3 eq) under N$_2$. The mixture was stirred at 25° C. for 2 h. LCMS showed the reaction was completed. The mixture was filtered to give crude product. The crude product was purified by prep-HPLC (column: Luna C18 100*30 5 u; mobile phase: [water (0.1% TFA)–ACN]; B %: 15%-45%, 10 min) to give compound I-87 (20.30 mg, 17.05 umol, 12.63% yield, 97.75% purity) as a colorless oil. $^1$H NMR (400 MHz, CHLOROFORM-d) 6 ppm 8.05 (s, 1H) 7.92 (s, 1H) 7.68 (d, J=8.2 Hz, 1H) 7.51-7.59 (m, 3H) 7.39-7.46 (m, 3H) 7.30-7.36 (m, 2H) 4.55 (t, j=4.3 Hz, 2H) 3.92 (d, J=13.7 Hz, 2H) 3.79-3.88 (m, 4H) 3.56-3.67 (m, 45H) 2.89 (t, J=6.4 Hz, 2H) 2.83 (s, 4H) 2.02-2.14 (m, 2H) 1.89 (d, J=5.7 Hz, 2H). LCMS: RT=2.135 min, MS cal.: 1162.4, [M/2+H]$^+$=582.3. LCMS: RT=1.206 min, MS cal.: 1162.4, [M/2+H]$^+$=582.7.

Example 37: Synthesis of I-88

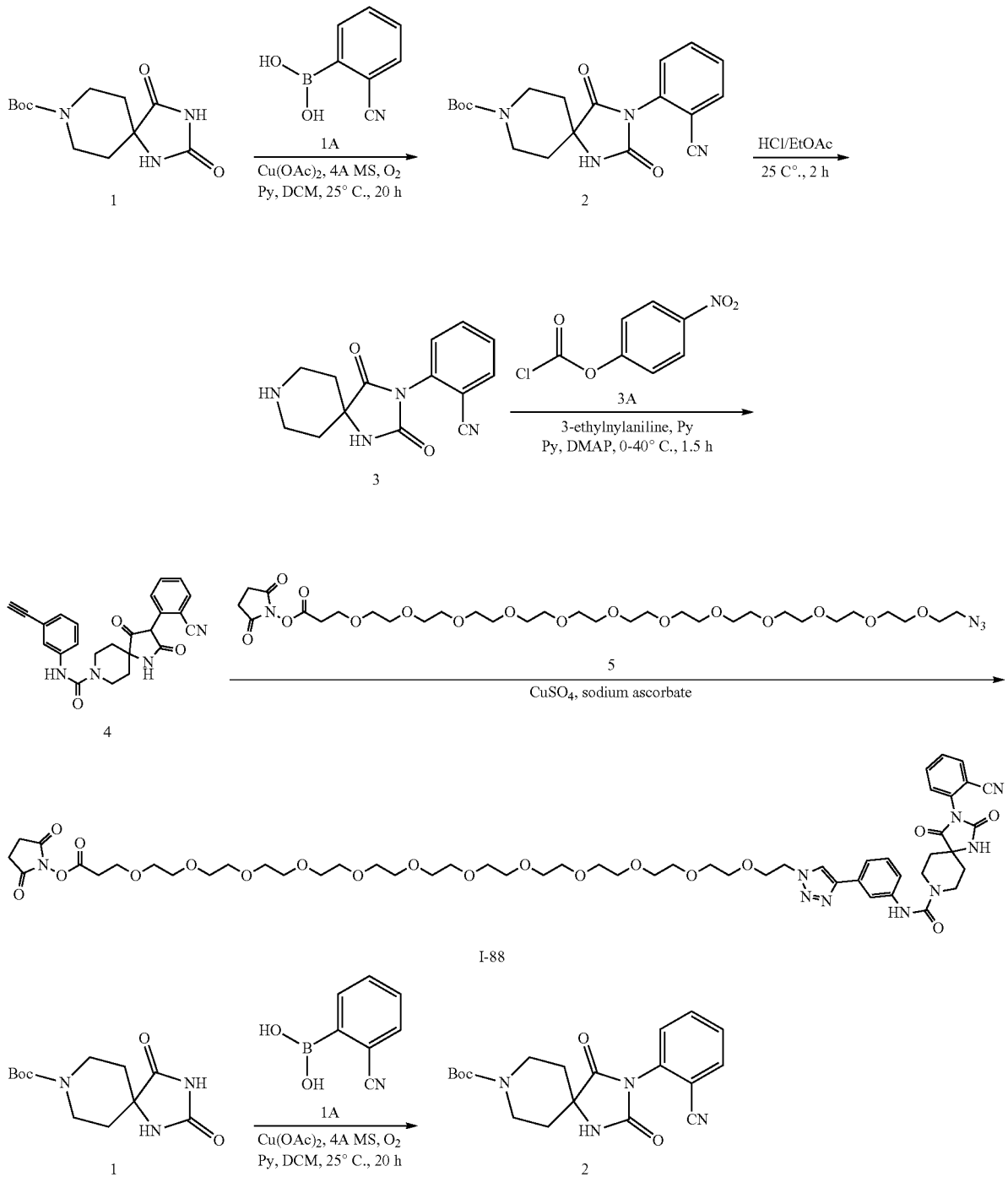

To a solution of compound 1 (0.4 g, 1.49 mmol, 1 eq) and compound 1A (261.91 mg, 1.78 mmol, 1.2 eq) in DCM (10 mL) was added pyridine (352.47 mg, 4.46 mmol, 3 eq), Cu(OAc)$_2$ (269.79 mg, 1.49 mmol, 1 eq) and Molecular sieve 4A (0.2 g, 1.49 mmol, 1 eq. After the mixture was bubbled with oxygen for 10 min, the mixture was stirred under O$_2$ (475.30 mg, 14.85 mmol, 10 eq, 25 psi) at 25° C. for 20 h. The mixture was stirred at 70° C. for another 12 h. LCMS showed the reaction was completed. The residue was poured into water (10 mL). The aqueous phase was extracted with DCM (5 mL*2). The combined organic phase was washed with 0.2N HCl (5 mL*2), dried with anhydrous Na$_2$SO$_4$, filtered and concentrated in vacuum. The residue was purified by silica gel chromatography (Petroleum ether/Ethyl acetate=5:1 to 0/1, TLC:Petroleum ether/Ethyl acetate=0:1, Rf=0.6) to afford compound 2 (0.17 g, 458.96 umol, 30.90% yield) as a white solid. $^1$H NMR (400 MHz, CHLOROFORM-d) δ ppm 7.70-7.85 (m, 2H) 7.52-7.63 (m, 1H) 7.47 (d, J=8.1 Hz, 1H) 7.27 (d, J=3.7 Hz, 1H) 4.01 (d, J=12.6 Hz, 2H) 3.30 (t, J=10.4 Hz, 2H) 2.11-2.22 (m, 2H) 1.76-1.89 (m, 2H) 1.48 (s, 9H). LCMS: RT=1.151 min, MS cal.: 370.40, [M-56+H]$^+$=315.3.

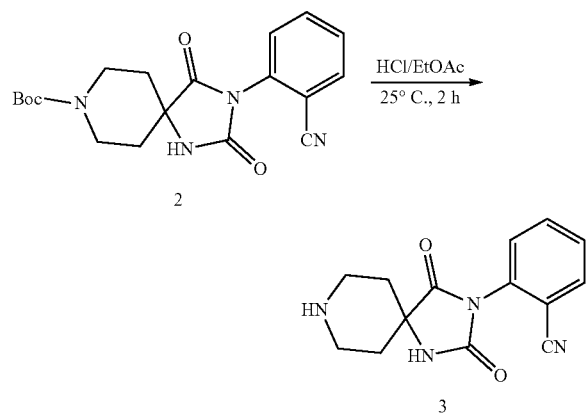

The solution of compound 2 (150 mg, 404.97 umol, 1 eq) in HCl/EtOAc (5 mL) was stirred at 25° C. for 2 h. LCMS showed the reaction was completed. The mixture was concentrated in vacuum to give compound 3 (100 mg, 326.00 umol, 80.50% yield, HCl) as a white solid. LCMS: RT=0.861 min, MS cal.: 270.2, [M+H]$^+$=271.2.

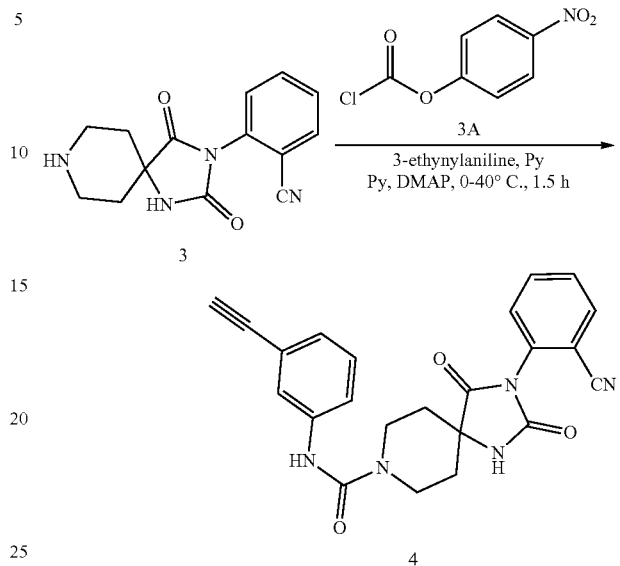

To a mixture of compound 3A (39.43 mg, 195.60 umol, 1.2 eq) in DCM (3 mL) was added drop-wise 3-ethynylaniline (22.91 mg, 195.60 umol, 1.2 eq) at 0° C. for 30 min. Then the mixture was added compound 3 (50 mg, 163.00 umol, 1 eq, HCl), Pyridine (38.68 mg, 489.00 umol, 3 eq) and DMAP (59.74 mg, 489.00 umol, 3 eq). The mixture was stirred at 40° C. for 60 min. LCMS showed the reaction was completed. The residue was poured into water (2 mL). The aqueous phase was extracted with DCM (2 mL*2). The combined organic phase was washed with brine (2 mL*2), dried with anhydrous Na$_2$SO$_4$, filtered and concentrated in vacuum. The residue was purified by silica gel chromatography (Petroleum ether/Ethyl acetate=10/1 to 0/1, TLC: Petroleum ether/Ethyl acetate=1:1, R$_f$=0.2) to afford compound 4 (0.05 g, 120.94 umol, 74.20% yield) as a white solid. LCMS: RT=1.116 min, MS cal.: 413.2, [M+H]$^+$=414.3.

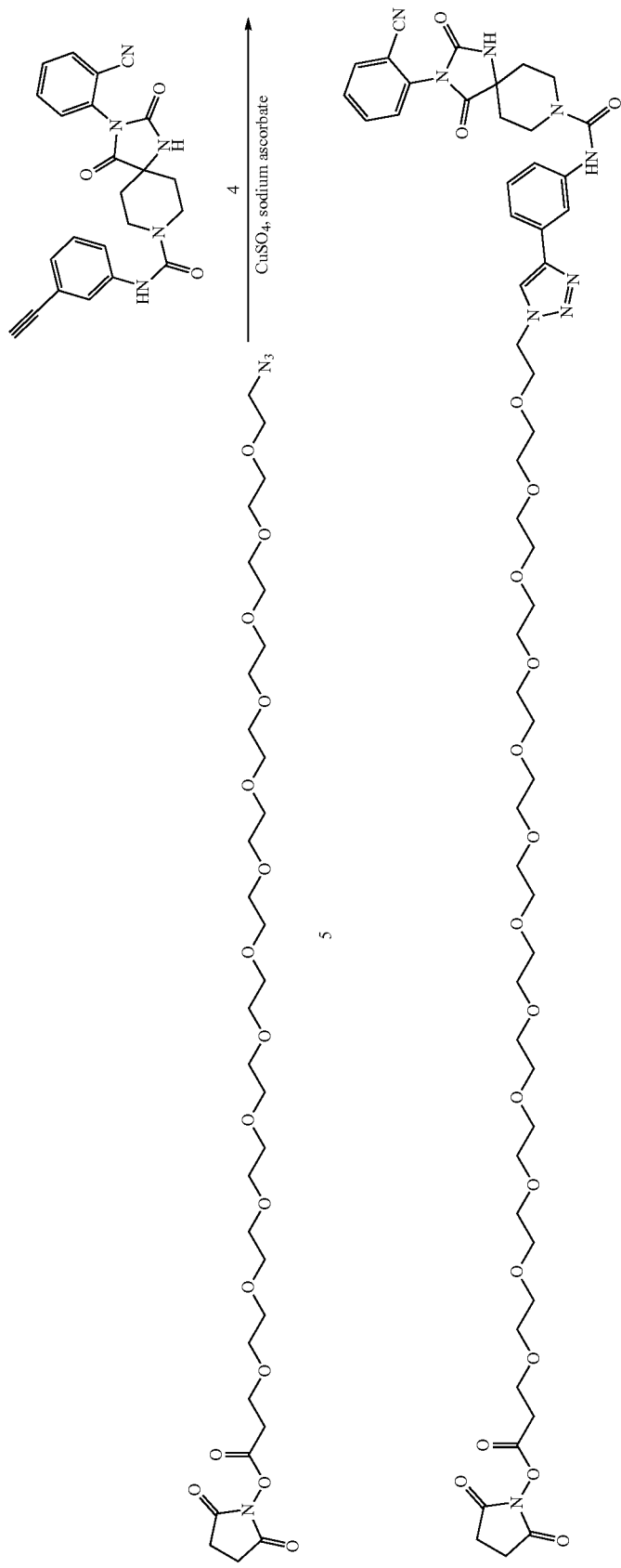

To a solution of compound 4 (0.05 g, 120.94 umol, 1 eq) and compound 5 (89.59 mg, 120.94 umol, 1 eq) in DMSO (2 mL) was added $CuSO_4 \cdot 5H_2O$ (90.59 mg, 362.82 umol, 3 eq) and sodium ascorbate (71.88 mg, 362.82 umol, 3 eq) under $N_2$. The mixture was stirred at 25° C. for 1 h. LCMS showed the reaction was completed. The mixture was filtered to give crude product. The crude product was purified by prep-HPLC (column: Nano-micro Kromasil C18 100*30 mm 5 um; mobile phase: [water (0.1% TFA)–ACN]; B %: 23%-47%, 10 min) to give I-88 (26 mg, 21.83 umol, 18.05% yield, 96.91% purity) as a colorless oil. $^1$H NMR (400 MHz, CHLOROFORM-d) δ ppm 8.06 (s, 1H) 7.88 (s, 1H) 7.72-7.83 (m, 2H) 7.52-7.69 (m, 4H) 7.43-7.52 (m, 2H) 7.34 (d, J=7.1 Hz, 1H) 4.56 (s, 2H) 3.86-4.00 (m, 4H) 3.79-3.85 (m, 2H) 3.50-3.73 (m, 48H) 2.89 (t, J=6.1 Hz, 2H) 2.83 (s, 4H) 2.14 (s, 2H) 1.96 (s, 2H). LCMS: RT=1.102 min, MS cal.: 1153.5, $[M/2+H]^+$=577.9. LCMS: RT=2.028 min, MS cal.: 1153.5, $[M/2+H]^+$=577.8.

Example 38: Synthesis of I-89

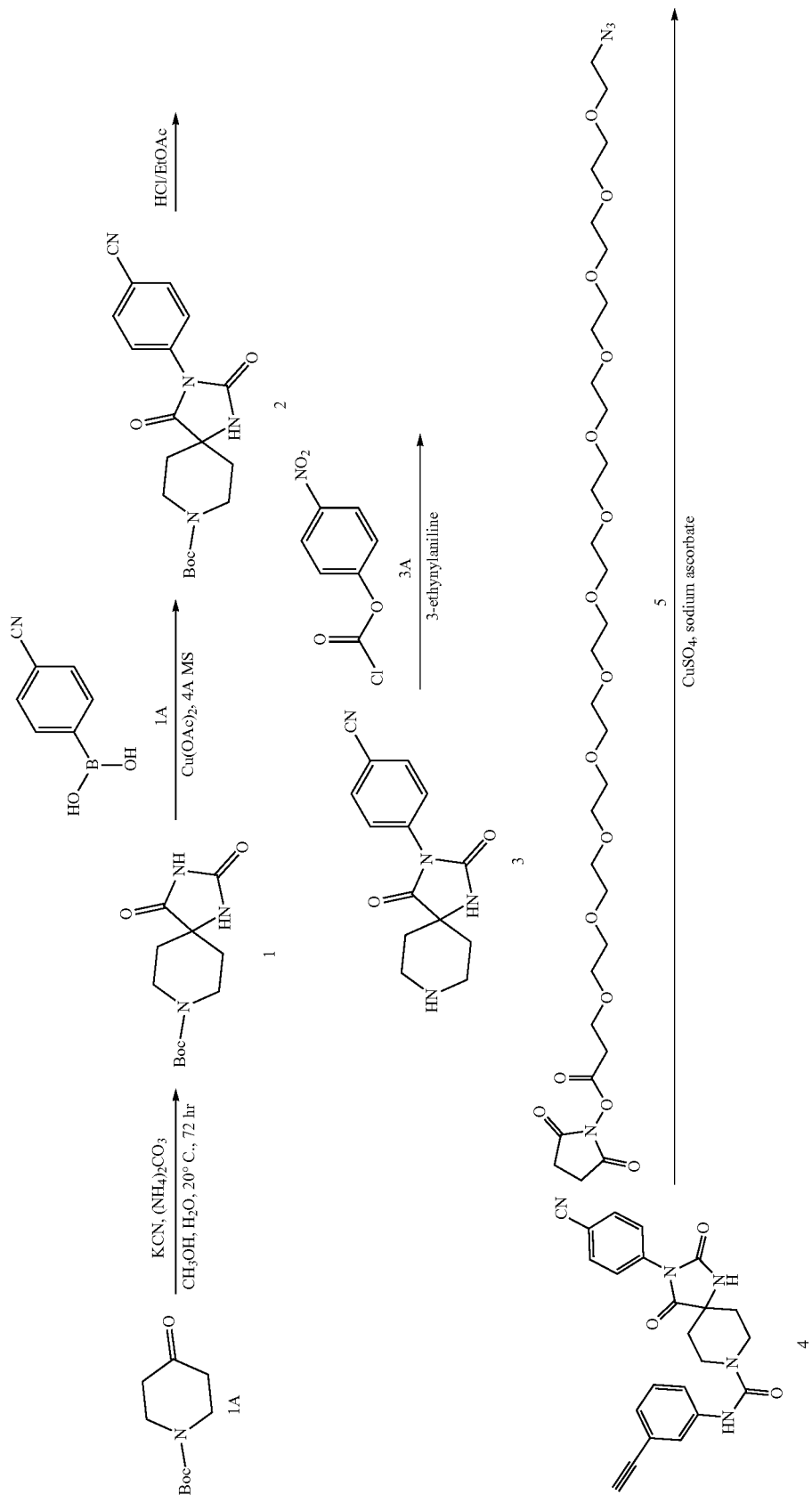

-continued
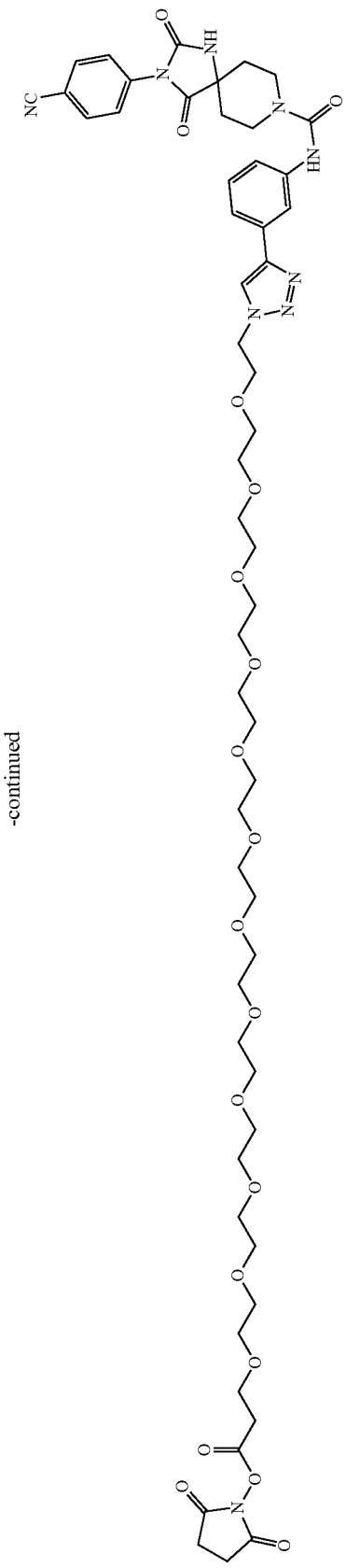
I-89
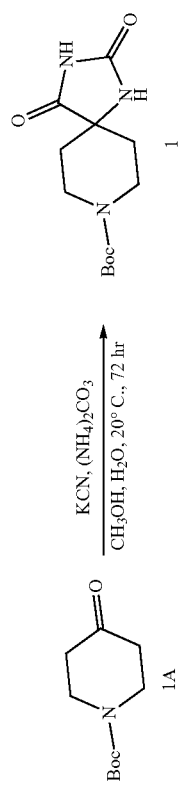
1A → 1
KCN, (NH₄)₂CO₃
CH₃OH, H₂O, 20° C., 72 hr A solution of KCN (23.53 g, 361.36 mmol, 15.48 mL, 2.4 eq) in H₂O (200 mL) was added dropwise to the solution of compound 1A (30 g, 150.57 mmol, 1 eq) and (NH₄)₂CO₃ (31.83 g, 331.25 mmol, 35.36 mL, 2.2 eq) in MeOH (200 mL) and H₂O (200 mL). The mixture was stirred at 20° C. for 72 h. LCMS showed the reaction was completed. The reaction mixture was filtered and concentrated in vacuum to give compound 1 (20 g, 74.27 mmol, 49.33% yield) as a white solid. LCMS: RT=0.999 min, MS cal.: 269.14, [M-55]⁺=214.0. ¹H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

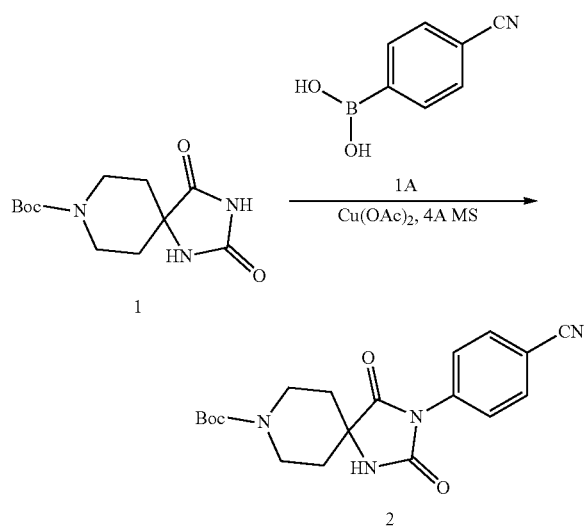

To a solution of compound 1 (0.3 g, 1.11 mmol, 1 eq), compound 1A (196.43 mg, 1.34 mmol, 1.2 eq) and Cu(OAc)₂ (202.34 mg, 1.11 mmol, 1 eq) in toluene (7 mL) was added pyridine (264.35 mg, 3.34 mmol, 269.75 uL, 3 eq) and 4A molecular sieve (1 g) stirred at 15° C. for 40 hrs. LCMS showed the starting material was consumed completely and the desired MS was detected. The reaction mixture was filtered and filtrate was concentrated. The residue was purified by chromatography column (Petroleum ether:Ethyl acetate=1:1 to DCM:MeOH=10:1) to give compound 2 (170 mg, 458.96 umol, 41.20% yield) as a white solid, which was confirmed by H NMR. ¹H NMR (400 MHz, CHLOROFORM-d) δ ppm 7.75-7.82 (m, 2H) 7.66-7.71 (m, 2H) 6.11 (s, 1H) 4.01 (br s, 2H) 3.74 (br d, J=4.89 Hz, 2H) 3.29 (ddd, J=13.82, 9.90, 3.67 Hz, 2H) 2.14 (ddd, J=13.82, 9.66, 3.91 Hz, 2H) 1.49 (s, 9H). LCMS: RT=1.383 min, MS cal.: 429.15 [(M-100)+H]⁺=329.9.

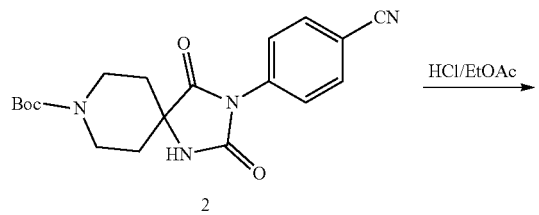

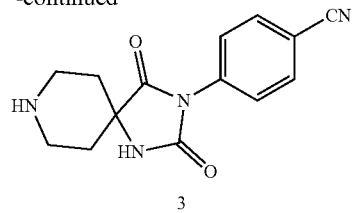

To a solution of compound 2 (165 mg, 445.46 umol, 1 eq) in HCl/EtOAc (4 M, 4 mL, 35.92 eq) was stirred at 15° C. for 2 hrs. LCMS showed the starting material was consumed completely and the desired MS was detected. The reaction mixture was concentrated under reduced pressure to give compound 3 as a white solid, which was confirmed by LCMS. The residue was used directly next step without purification. LCMS: RT=0.852 min, MS cal.: 270.11, [M+H]⁺=269.1.

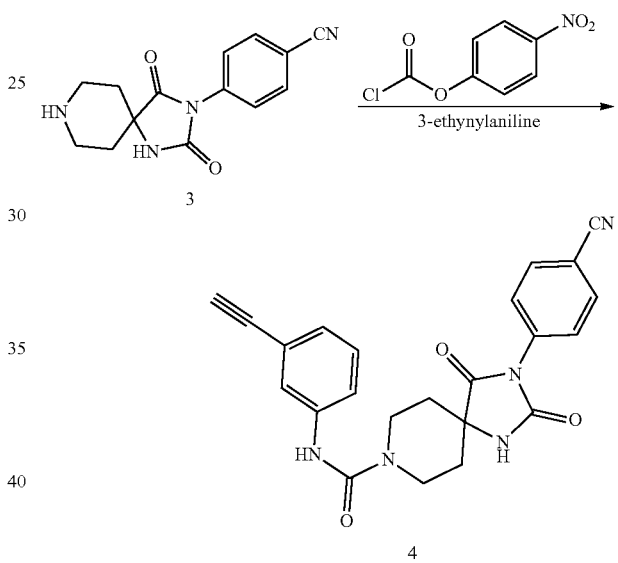

To a solution of (4-nitrophenyl) carbonochloridate (107.39 mg, 532.77 umol, 1.2 eq) in DCM (3 mL) was added 3-ethynylaniline (67.61 mg, 577.17 umol, 1.3 eq) in DCM (1 mL) drop wise at −40° C. stirred for 1 h. Then the reaction mixture was added compound 3 (120 mg, 443.97 umol, 1 eq), DMAP (162.72 mg, 1.33 mmol, 3 eq) and PYRIDINE (105.35 mg, 1.33 mmol, 107.51 uL, 3 eq) in MeCN (5 mL) and stirred at 15° C. for 15 hrs. LCMS showed the starting material was consumed completely and a main peak with desired MS was detected. The reaction mixture was added EtOAc (40 mL), then the mixture was washed with brine (40 mL). The organic layer was dried over anhydrous Na₂SO₄ and concentrated under reduced pressure. The residue was purified by chromatography column (Petroleum ether:EtOAc=3:1 to 1:1) to give compound 4 (120 mg, 290.26 umol, 65.38% yield, N/A purity) as a white solid, which was confirmed by LCMS. LCMS: RT=1.257 min, MS cal.: 413.15, [M+H]⁺=414.1.

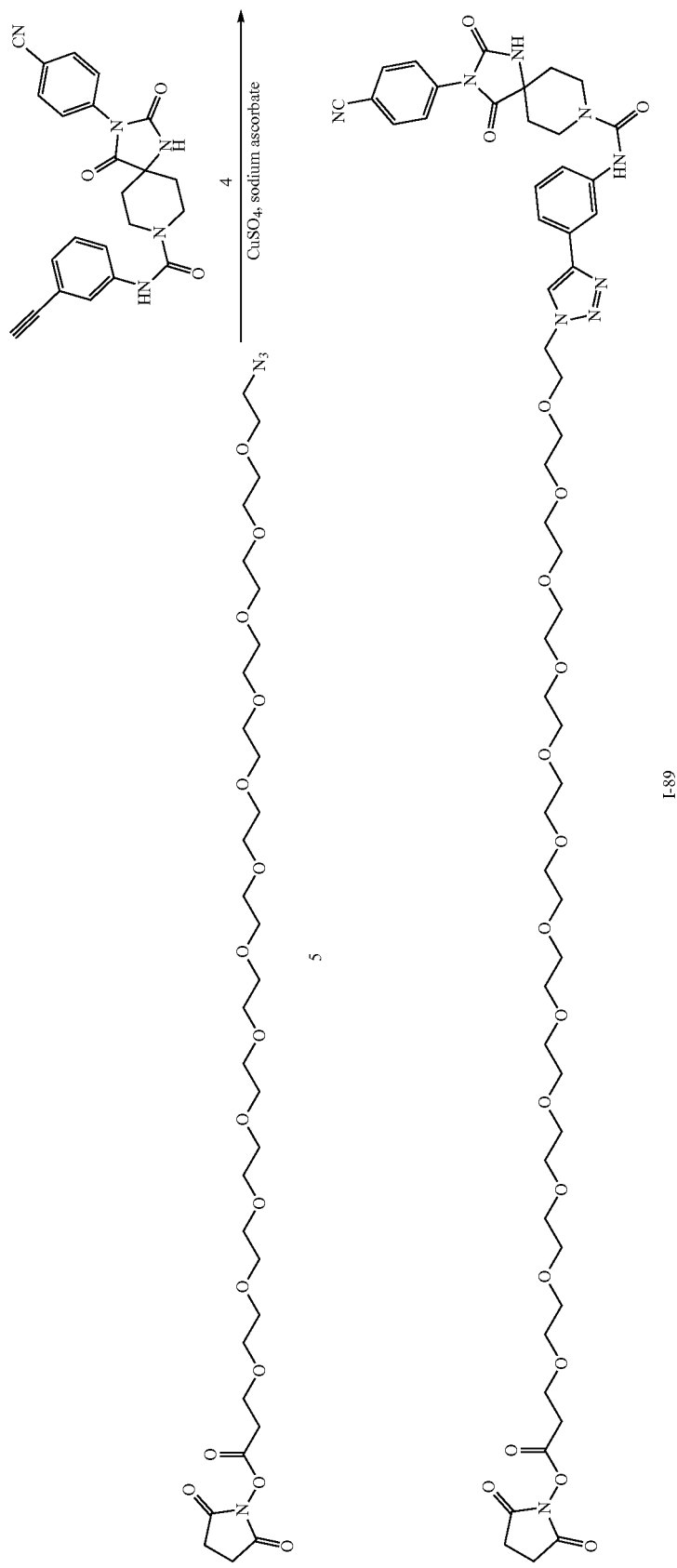
I-89

A solution of compound 5 (50 mg, 67.50 umol, 1 eq) and compound 4 (27.90 mg, 67.50 umol, 1 eq) in DMSO (2 mL) was added $CuSO_4 \cdot 5H_2O$ (5.06 mg, 20.25 umol, 0.3 eq) and sodium ascorbate (26.74 mg, 134.99 umol, 2 eq) stirred at 15° C. for 1 hr. LCMS showed a peak with desired MS was detected. The reaction mixture was filtered. The filtrate was purified by prep-HPLC (column: Luna C18 100*30 5 u; mobile phase: [water (0.1% TFA)–ACN]; B %: 15%-45%, 10 min) to give I-89 (50.84 mg, 43.65 umol, 64.67% yield, 99.10% purity) as a colorless oil, which was confirmed by H NMR and QC LCMS. $^1$H NMR (400 MHz, CHLOROFORM-d) δ ppm 7.96 (s, 1H) 7.77 (d, J=8.31 Hz, 2H) 7.47 (d, J=8.56 Hz, 2H) 7.32-7.37 (m, 2H) 7.27-7.31 (m, 3H) 6.72 (s, 1H) 4.59 (t, J=4.83 Hz, 2H) 4.39 (s, 2H) 4.23 (br d, J=12.47 Hz, 2H) 4.03 (br t, J=11.86 Hz, 1H) 3.91 (t, J=4.83 Hz, 2H) 3.85 (t, J=6.42 Hz, 2H) 3.56-3.70 (m, 44H) 3.16-3.33 (m, 4H) 3.00 (br t, J=12.29 Hz, 2H) 2.90 (t, J=6.42 Hz, 2H) 2.84 (s, 3H) 1.82 (br d, J=12.23 Hz, 2H) 1.60-1.72 (m, 2H). LCMS: RT=1.156 min, MS cal.: 1153.52, [M+H]=1154.5. LCMS: RT=2.071 min, MS cal.: 1153.52, $[M/2+H]^+$=577.8, $[M+H]^+$=1154.4.

Example 39: Synthesis of I-90

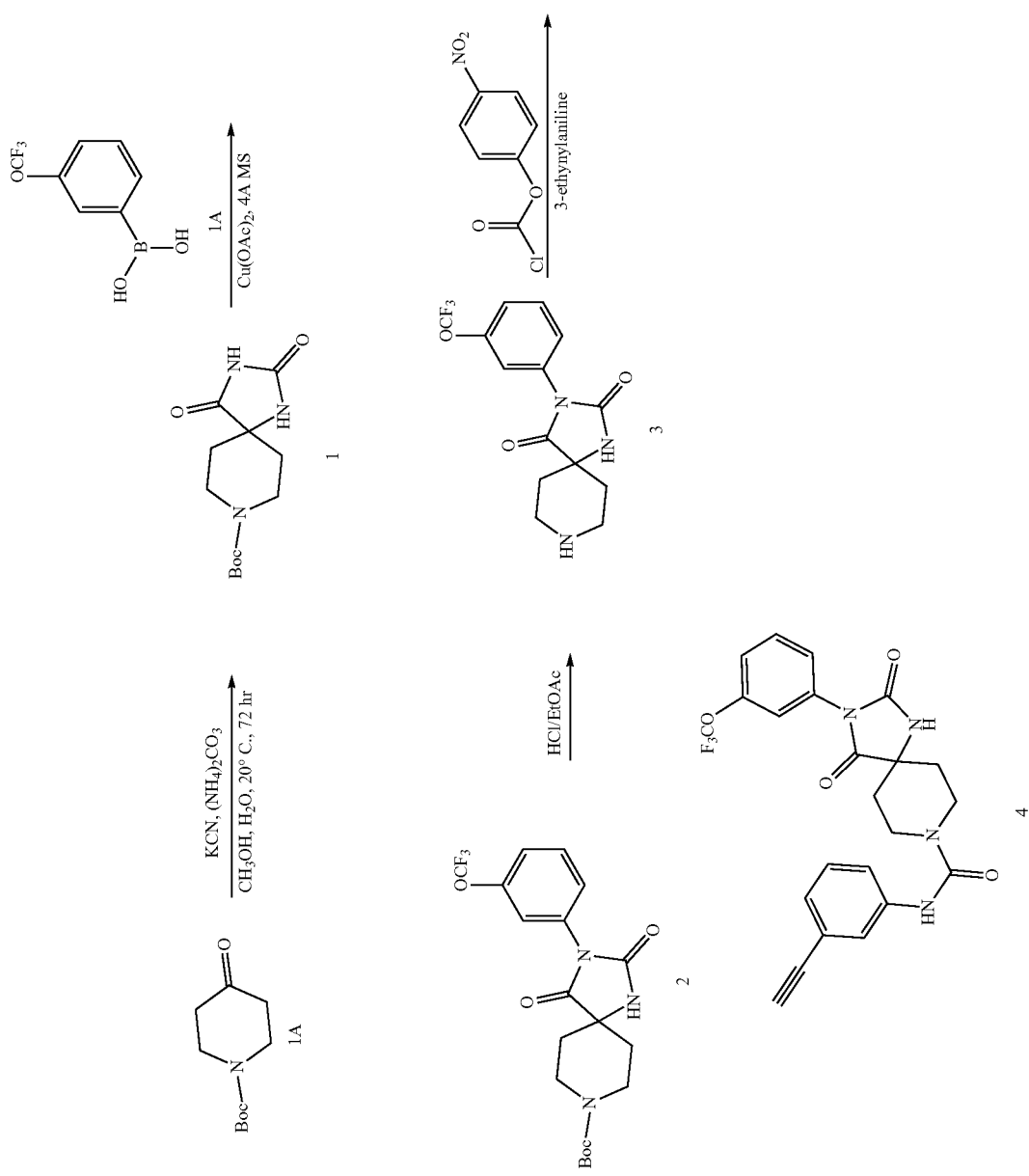

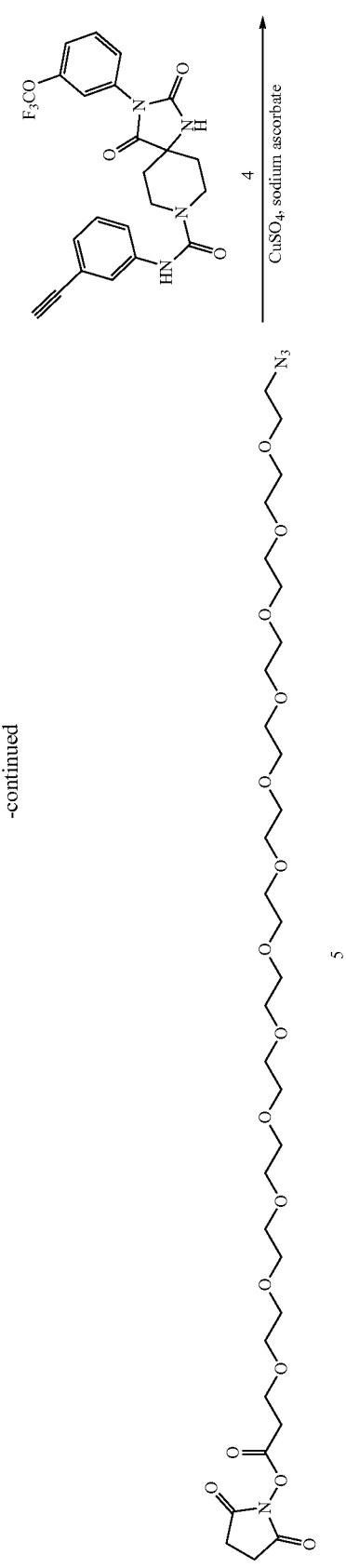
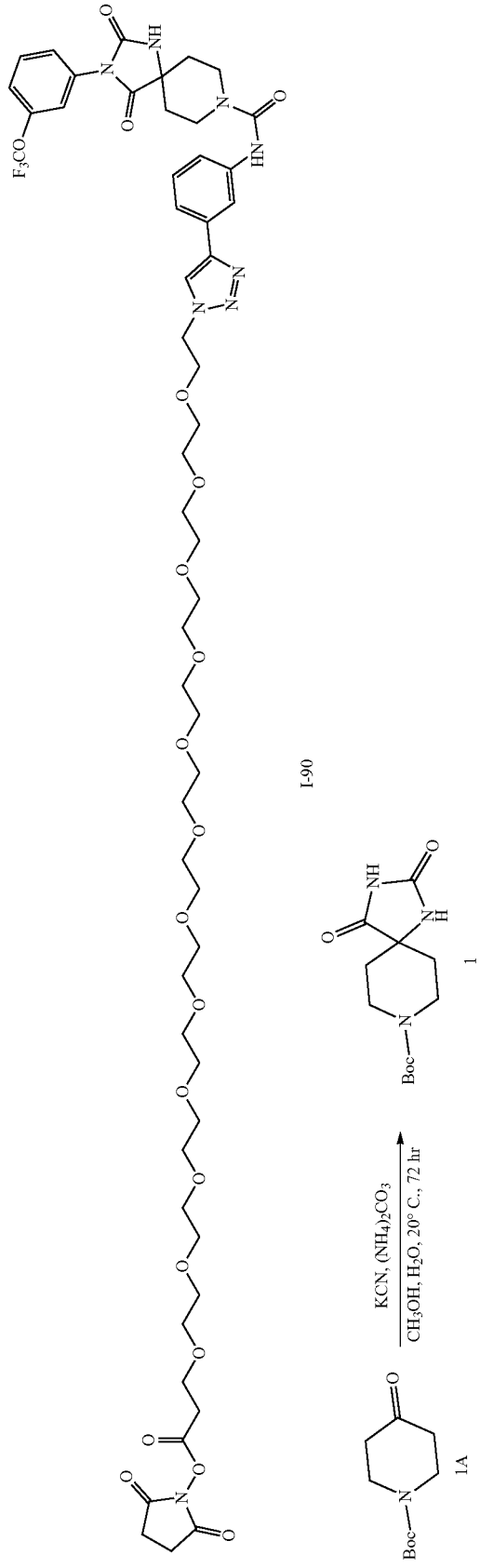
I-90

A solution of KCN (23.53 g, 361.36 mmol, 15.48 mL, 2.4 eq) in H$_2$O (200 mL) was added dropwise to the solution of compound 1A (30 g, 150.57 mmol, 1 eq) and (NH$_4$)$_2$CO$_3$ (31.83 g, 331.25 mmol, 35.36 mL, 2.2 eq) in MeOH (200 mL) and H$_2$O (200 mL). The mixture was stirred at 20° C. for 72 h. LCMS showed the reaction was completed. The reaction mixture was filtered and concentrated in vacuum to give compound 1 (20 g, 74.27 mmol, 49.33% yield) as a white solid. LCMS: RT=0.999 min, MS cal.: 269.14, [M-55]$^+$=214.0. $^1$H NMR (400 MHz, DMSO-d6) δ ppm 10.71 (br s, 1H) 8.51 (s, 1H) 3.80 (br d, J=13.5 Hz, 2H) 3.10 (br s, 2H) 1.60-1.74 (m, 2H) 1.48-1.57 (m, 1H) 1.52 (br d, J=13.2 Hz, 1H) 1.40 (s, 9H).

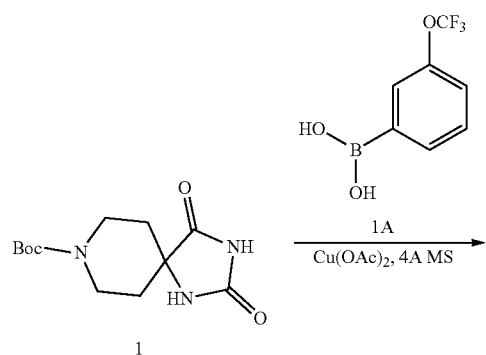

To a solution of compound 1 (0.3 g, 1.11 mmol, 1 eq), compound 1A (275.29 mg, 1.34 mmol, 1.2 eq) and Cu(OAc)$_2$ (202.34 mg, 1.11 mmol, 1 eq) in toluene (5 mL) was added pyridine (264.35 mg, 3.34 mmol, 269.75 uL, 3 eq) and 4A molecular sieve (1 g) stirred at 15° C. for 40 hrs. TLC (Petroleum ether:Ethyl acetate=1:1, R$_f$=0.3) showed the starting material was consumed completely and a new spot was detected. The reaction mixture was filtered and filtrate was concentrated. The residue was purified by chromatography column (Petroleum ether:Ethyl acetate=5:1) to give compound 2 (80 mg, 186.31 umol, 16.72% yield) as a white solid, which was confirmed by LCMS and H NMR. 1H NMR (400 MHz, CHLOROFORM-d) δ ppm 7.38-7.54 (m, 2H) 7.23-7.25 (m, 1H) 6.03 (s, 1H) 4.01 (br s, 1H) 3.29 (brt, J=9.78 Hz, 2H) 2.14 (br t, J=10.03 Hz, 2H) 1.78 (br s, 2H) 1.49 (s, 8H). LCMS: RT=1.383 min, MS cal.: 429.15 [(M-100)+H]$^+$=329.9.

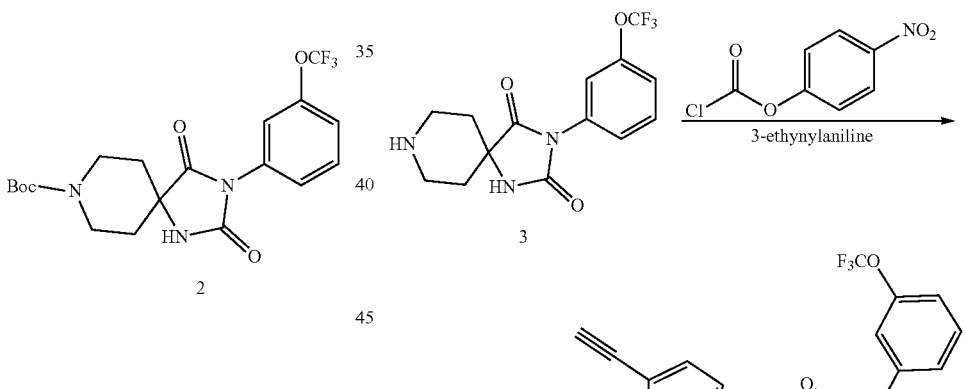

To a solution of compound 2 (75 mg, 174.67 umol, 1 eq) in HCl/EtOAc (4 M, 2.91 uL, 1 eq) was stirred at 15° C. for 2 hrs. LCMS showed the starting material was consumed completely and the desired MS was detected. The reaction mixture was concentrated under reduced pressure to give compound 3 as a white solid, which was confirmed by LCMS. The residue was used directly next step without purification. LCMS: RT=1.043 min, MS cal.: 329.10, [M+H]$^+$=329.9.

To a solution of (4-nitrophenyl) carbonochloridate (43.34 mg, 215.02 umol, 1.2 eq) in DCM (3 mL) was added 3-ethynylaniline (27.29 mg, 232.94 umol, 1.3 eq) in DCM (1 mL) drop wise at −40° C. stirred for 1 h. Then the reaction mixture was added compound 3 (59 mg, 179.18 umol, 1 eq), DMAP (65.67 mg, 537.55 umol, 3 eq) and PYRIDINE (42.52 mg, 537.55 umol, 43.39 uL, 3 eq) in MeCN (5 mL) and stirred at 15° C. for 15 hrs. LCMS showed the starting material was consumed completely and a main peak with desired MS was detected. The reaction mixture was added EtOAc (40 mL), then the mixture was washed with brine (40 mL). The organic layer was dried over anhydrous $Na_2SO_4$ and concentrated under reduced pressure. The residue was purified by chromatography column (EA as fluent phase) to give compound 4 (57 mg, 120.66 umol, 67.34% yield, N/A purity) as a white solid, which was confirmed by LCMS. LCMS: RT=1.349 min, MS cal.: 472.14, $[M+H]^+$=473.2. LCMS: RT=1.201 min, MS cal.: 472.14, $[M+H]^+$=473.1.

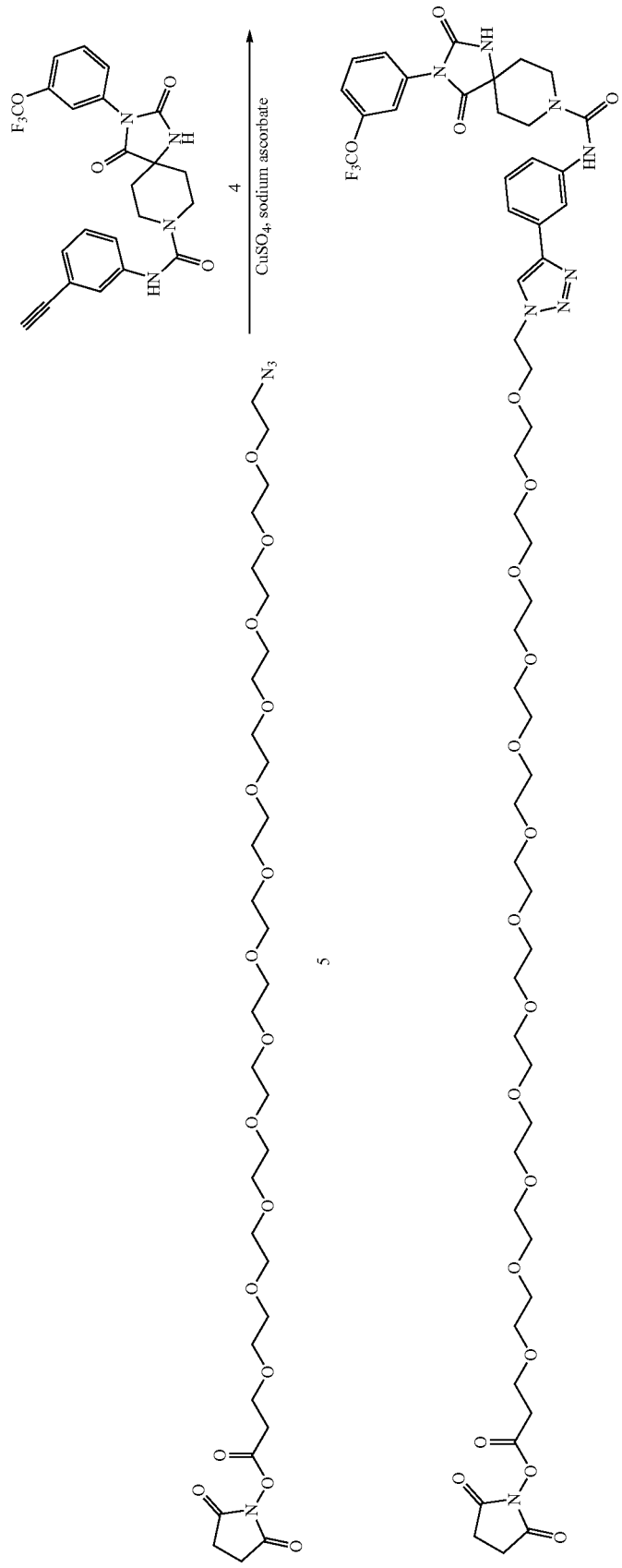

A solution of compound 5 (50 mg, 67.50 umol, 1 eq) and compound 4 (31.89 mg, 67.50 umol, 1 eq) in DMSO (2 mL) was added CuSO$_4$·5H$_2$O (5.06 mg, 20.25 umol, 0.3 eq) and sodium ascorbate (26.74 mg, 134.99 umol, 2 eq) stirred at 15° C. for 1 hr. LCMS showed a peak with desired MS was detected. The reaction mixture was filtered. The filtrate was purified by prep-HPLC (column: Nano-micro Kromasil C18 100*30 mm 5 um; mobile phase: [water (0.1% TFA)–ACN]; B %: 28%-58%, 10 min) to give I-90 (21.81 mg, 18.65 umol, 27.62% yield, 97.76% purity) as a colorless oil, which was confirmed by H NMR and QC LCMS. 1H NMR (400 MHz, CHLOROFORM-d) δ ppm 8.09-8.16 (m, 1H) 7.82-7.89 (m, 1H) 7.55-7.65 (m, 2H) 7.44-7.53 (m, 3H) 7.42 (s, 1H) 7.33-7.39 (m, 1H) 7.22-7.26 (m, 1H) 7.22-7.26 (m, 1H) 6.87-6.93 (m, 1H) 4.57-4.67 (m, 2H) 3.96-4.05 (m, 2H) 3.88-3.93 (m, 2H) 3.84 (t, J=6.36 Hz, 2H) 3.52-3.72 (m, 46H) 2.89 (t, J=6.11 Hz, 2H) 2.84 (br s, 3H) 2.66-2.67 (m, 1H) 2.09-2.22 (m, 2H) 1.87-2.00 (m, 2H). LCMS: RT=1.241 min, MS cal.: 1212.50, [M/2+H]$^+$=607.6, [M+H]$^+$=1213.9. LCMS: RT=2.370 min, MS cal.: 1212.50, [M/2+H]$^+$=607.3.

Example 40: Synthesis of I-91

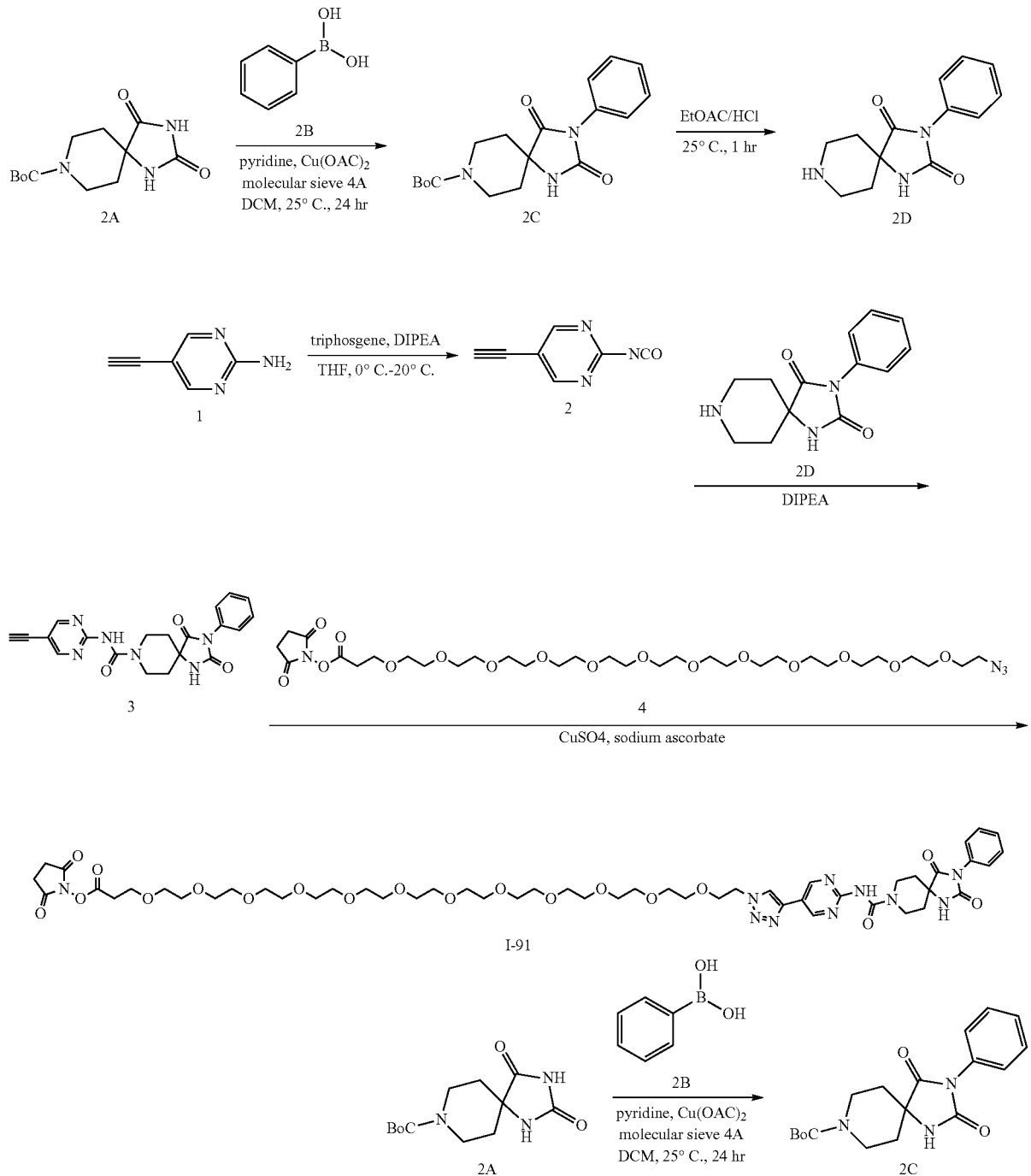

To a solution of compound 2A (13 g, 48.27 mmol, 1 eq) and 2B (7.06 g, 57.93 mmol, 1.2 eq) in DCM (300 mL) was added PYRIDINE (11.46 g, 144.82 mmol, 11.69 mL, 3 eq), molecular sieve 4A (26 g), Cu(OAc)$_2$ (8.77 g, 48.27 mmol, 1 eq) at 20° C. under O$_2$ (20 psi). The mixture was stirred at 20° C. under O$_2$ (20 psi) for 72 hr. TLC (Petroleum ether: EtOAC=1:1, Product R$_f$=0.65) showed the desired product spot was detected. The mixture was combined. The reaction mixture was filtered, the filter liquor washed water (150 mL*2), the organic layer was dried with Na$_2$SO$_4$, filtered, concentrated. The residue was purified by column chromatography twice (SiO$_2$, Petroleum ether:Ethyl acetate=10:1 to 0:1) according to TLC (Plate 2, Petroleum ether:EtOAC=1: 1, Product R$_f$=0.65). To give compound 2C (11.8 g, crude) was obtained as white solid

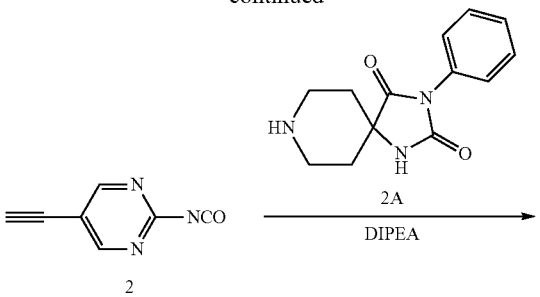

-continued

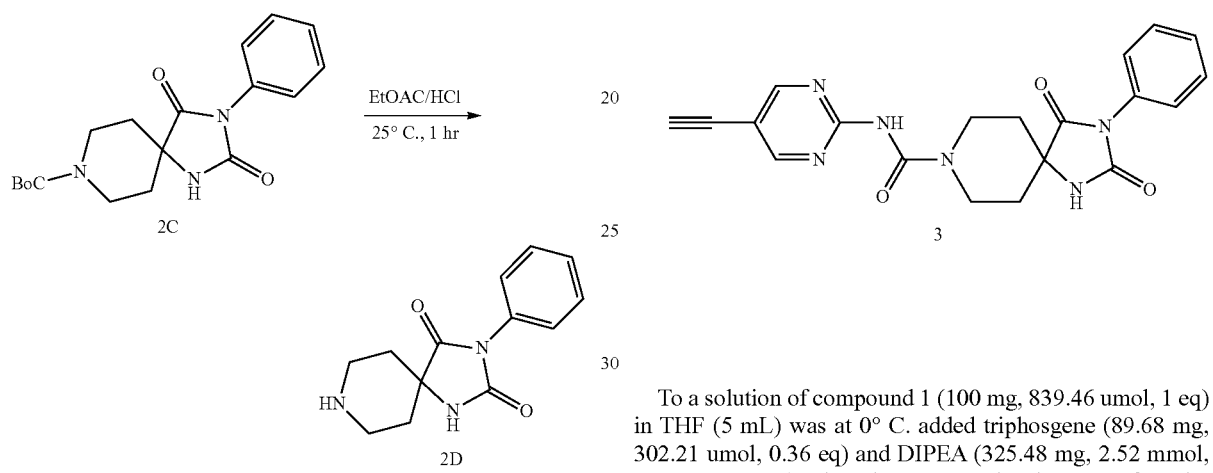

To a solution of compound 2C (3 g, 8.69 mmol, 1 eq) in HCl/EtOAc (60 mL) was stirred at 20° C. for 1 hr. TLC (Plate 1, EtOAc:Petroleum=1:1, product, R$_f$=0.65) showed it was consumed completely. The mixture was concentrated to give compound 2D (2.4 g, crude) as a white solid.

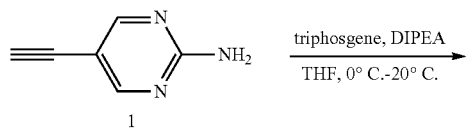

To a solution of compound 1 (100 mg, 839.46 umol, 1 eq) in THF (5 mL) was at 0° C. added triphosgene (89.68 mg, 302.21 umol, 0.36 eq) and DIPEA (325.48 mg, 2.52 mmol, 438.66 uL, 3 eq). The mixture was stirred at 0° C. for 2 hr. LCMS showed the desired product was detected (quenched with MeOH). The yellow solution was used directly and added with compound 2A (352.37 mg, 1.25 mmol, 1.5 eq, HCl), DIPEA (215.52 mg, 1.67 mmol, 290.46 uL, 2 eq) at 0° C., then the mixture was stirred at 50° C. at 12° C. LCMS showed the desired product was detected. It was concentrated directly and purified by prep-HPLC (column: Waters Xbridge 150*25 5 u; mobile phase: [water (10 mM NH$_4$HCO$_3$)–ACN]; B %: 10%-40%, 12 min) to give compound 3 (35 mg, 89.65 umol, 10.75% yield) as a yellow solid. LCMS: RT=1.164 min, MS cal.: 177.05, [M+H]$^+$=178.1. LCMS: RT=1.192 min, MS cal.: 390.14, [M+H]$^+$=391.3.

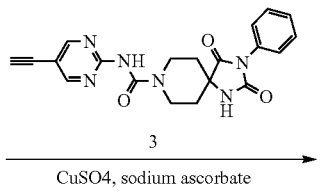

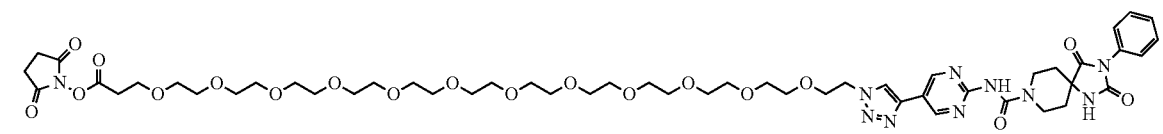

I-91

To a solution of compound 4 (50 mg, 67.50 umol, 1 eq), compound 3 (30 mg, 76.85 umol, 1.14 eq) in DMSO (0.5 mL) was added CuSO$_4$·5H$_2$O (5.06 mg, 20.25 umol, 0.3 eq) and sodium ascorbate (26.74 mg, 134.99 umol, 2 eq). The mixture was stirred at 15° C. for 12 hr. LCMS showed it was good. It was filtered and the filtrate was purified by prep-HPLC column (Luna C18 100*30 5 u; mobile phase: [water (0.1% TFA)–ACN]; B %: 15%-37%, 10 min) to give I-91 (30.3 mg, 23.50 umol, yield: 34.82% yield, 87.73% purity) was obtained as a colorless oil. LCMS: RT=1.105 min, MS cal.: 1130.51, [1/2M+H]$^+$=566.3. $^1$H NMR (400 MHz, DMSO-d6) δ ppm 9.89 (br s, 1H) 9.18 (s, 1H) 8.99 (s, 2H) 8.62 (s, 1H) 7.44-7.52 (m, 2H) 7.35-7.43 (m, 3H) 4.60 (br t, J=4.46 Hz, 2H) 4.01 (br d, J=13.69 Hz, 2H) 3.87 (br t, J=4.59 Hz, 2H) 3.65-3.75 (m, 2H) 3.55 (br s, 13H) 3.50-3.52 (m, 11H) 3.46 (br d, J=3.67 Hz, 21H) 3.33 (br t, J=11.62 Hz, 2H) 2.92 (t, J=5.87 Hz, 2H) 2.80 (br s, 4H) 1.89-2.00 (m, 2H) 1.79 (br d, J=13.08 Hz, 2H). LCMS: RT=1.824 min, MS cal.: 1130.51, [1/2M+H]$^+$=566.3, [M+H]$^+$=1131.5.

Example 41: Synthesis of 1-92

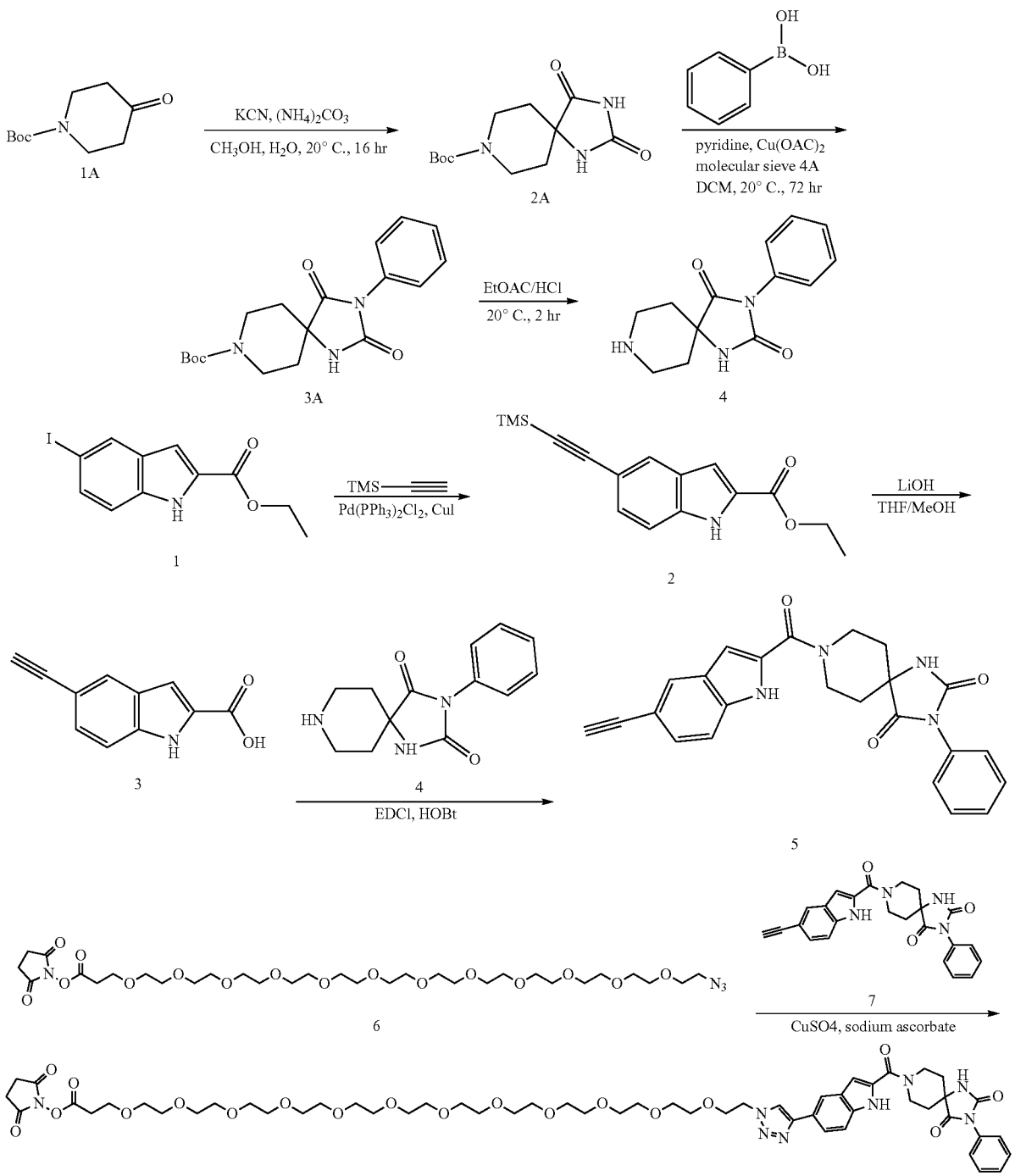

I-92

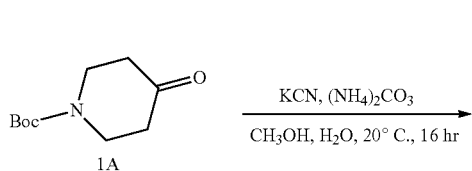
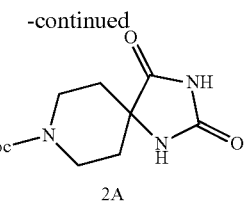

A solution of KCN (27.90 g, 428.47 mmol, 18.36 mL, 2.85 eq) in H₂O (270 mL) was added dropwise to the solution of compound 1A (30 g, 150.57 mmol, 1 eq) and (NH₄)₂CO₃ (31.83 g, 331.25 mmol, 35.36 mL, 2.2 eq) in MeOH (240 mL) and H₂O (270 mL). The mixture was stirred at 20° C. for 16 h. TLC (Plate1, petroleum ether: EtOAC=1:1, product $R_f$=0.16, $R_f$=0.79) showed the starting material was consumed completely. The mixture was added water (200 mL), filtered. The white solid washed with water (300 mL*2) and petroleum ether (300 mL). Compound 2 (26 g, crude) was obtained as white solid checked by HNMR. ¹H NMR (400 MHz, METHANOL-d4) δ ppm 3.95 (td, J=4.7, 13.8 Hz, 2H), 3.27 (br s, 2H), 1.96-1.87 (m, 2H), 1.70-1.63 (m, 2H), 1.49 (s, 8H), 1.55-1.46 (m, 1H).

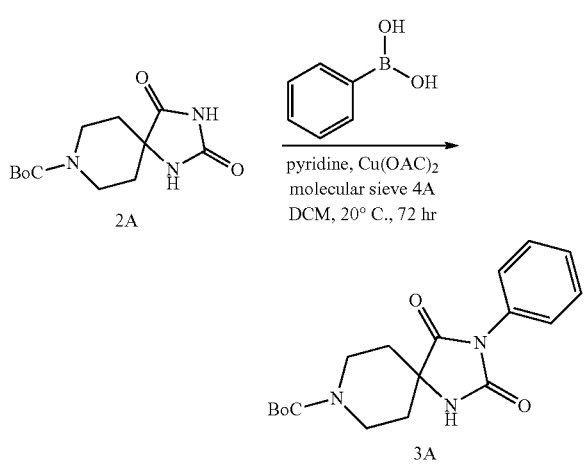

To a solution of compound 2A (13 g, 48.27 mmol, 1 eq) and phenylboronic acid (7.06 g, 57.93 mmol, 1.2 eq) in DCM (300 mL) was added pyridine (11.46 g, 144.82 mmol, 11.69 mL, 3 eq) Molecular sieve 4A (26 g), Cu(OAc)₂ (8.77 g, 48.27 mmol, 1 eq) and oxygen at 20° C. under O₂ (20 psi). The mixture was stirred at 20° C. under O₂ (20 psi) for 72 hr. TLC (Petroleum ether:EtOAC=1:1, Product $R_f$=0.65, $R^1$ $R_f$=0.10) showed the desired product spot. The mixture was combined. The reaction mixture was filtered, the filtrate was washed with water (150 mL*2), the organic layer was dried over Na₂SO₄, filtered, concentrated. The residue was purified by column chromatography (SiO₂, Petroleum ether: Ethyl acetate=10:1 to 0:1) according to TLC (Plate 2, Petroleum ether:EtOAC=1:1, Product $R_f$=0.65). The residue was purified by column chromatography (SiO₂, Petroleum ether:Ethyl acetate=8:1 to 0:1) according to TLC (Plate 3, Petroleum ether:EtOAC=1:1, Product $R_f$=0.65). Compound 3A (11.8 g, crude) was obtained as white solid checked by HNMR. ¹H NMR (400 MHz, METHANOL-d₄) δ ppm 7.50-7.44 (m, 2H), 7.42-7.35 (m, 3H), 3.97 (td, J=4.9, 13.9 Hz, 2H), 2.01 (ddd, J=4.3, 9.9, 13.8 Hz, 2H), 1.81-1.73 (m, 2H), 1.48 (s, 9H).

To a solution of compound 3A (3 g, 8.69 mmol, 1 eq) in HCl/EtOAc (60 mL) was stirred at 20° C. for 1 hr. TLC (Plate 1, EtOAc:Petroleum ether=1:1, product $R_f$=0, $R^1$ $R_f$=0.65) showed the $R^1$ was consumed completely. The mixture was concentrated. Compound 4 (2.4 g, crude) was obtained as white solid checked by HNMR. ¹H NMR (400 MHz, DMSO-d6) δ ppm 9.31 (br s, 1H), 9.25 (s, 1H), 9.01 (br s, 1H), 7.53-7.45 (m, 2H), 7.44-7.35 (m, 3H), 3.21 (br d, J=10.0 Hz, 2H), 2.24-2.15 (m, 2H), 2.01 (br d, J=13.6 Hz, 2H).

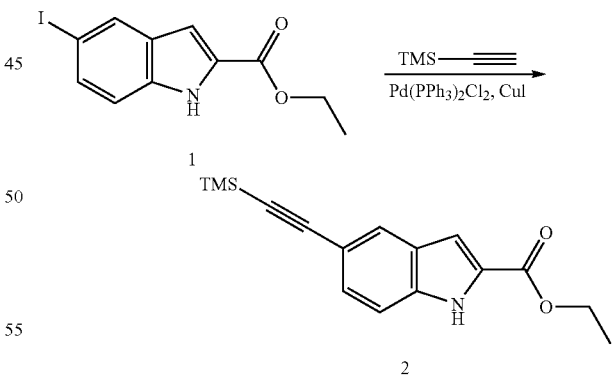

To a solution of compound 1 (0.3 g, 952.06 umol, 1 eq) in DMF (3 mL) was added ethynyl(trimethyl)silane (280.53 mg, 2.86 mmol, 395.67 uL, 3 eq) and CuI (54.40 mg, 285.62 umol, 0.3 eq) and TEA (289.02 mg, 2.86 mmol, 397.55 uL, 3 eq) and Pd(PPh₃)₂Cl₂ (33.41 mg, 47.60 umol, 0.05 eq). The mixture was stirred at 25° C. for 12 hr. TLC (Petroleum ether:Ethyl acetate=5:1, $R_f$=0.43) showed it was finished. Added 10 mL H₂O to the reaction mixture, then extracted it with MTBE (10 mL*3). The combined organic layers were washed with brine 10 mL, dried over Na₂SO₄, filtered and concentrated under reduced pressure to give a residue. The residue was purified by column chromatography (SiO2, Petroleum ether/Ethyl acetate=5/1 to 0/1). Compound 2 (0.23 g, 805.85 umol, 84.64% yield) was obtained as a yellow solid.

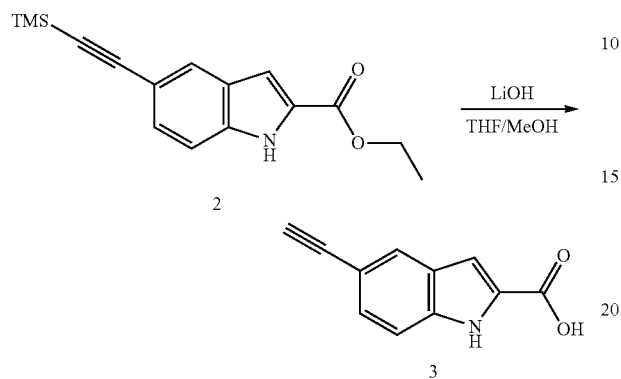

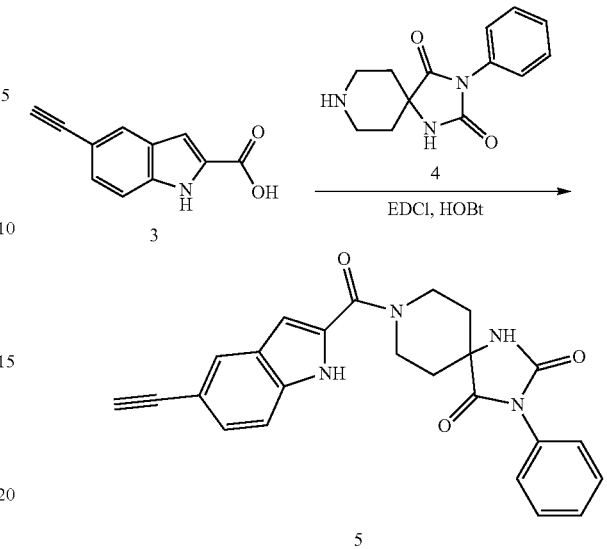

To a solution of compound 2 (0.17 g, 595.63 umol, 1 eq) in THF (2 mL) and dioxane (2 mL) was added LiOH (2 M, 1.49 mL, 5 eq). The mixture was stirred at 25° C. for 12 hr. LCMS showed compound 2 was consumed completely and one main peak with desired mass was detected. The residue was diluted with H₂O 10 mL and extracted with DCM (20 mL*2). The combined organic layers were washed with brine 10 mL, dried over Na₂SO₄, filtered and concentrated under reduced pressure to give a residue. Compound 3 (0.075 g, 405.01 umol, 68.00% yield) was obtained as a white solid. LCMS: Rt=1.081 min, MS cal.: 185.0, [M+H]⁺=186.0.

To a solution of compound 3 (0.075 g, 405.01 umol, 1 eq) and compound 4 (99.34 mg, 405.01 umol, 1 eq) in DMF (3 mL) was added EDCI (155.28 mg, 810.03 umol, 2 eq) and HOBt (109.45 mg, 810.03 umol, 2 eq) and DIEA (157.04 mg, 1.22 mmol, 211.64 uL, 3 eq). The mixture was stirred at 25° C. for 12 hr. LCMS showed compound 3 was consumed completely and one main peak with desired mass was detected. The residue was diluted with H₂O 10 mL and extracted with DCM (20 mL*3). The combined organic layers were washed with brine 10 mL, dried over Na₂SO₄, filtered and concentrated under reduced pressure to give a residue. Compound 5 (0.1 g, 242.46 umol, 59.86% yield) was obtained as a white solid. LCMS: Rt=1.145 min, MS cal.: 412.2, [M+H]⁺=413.3.

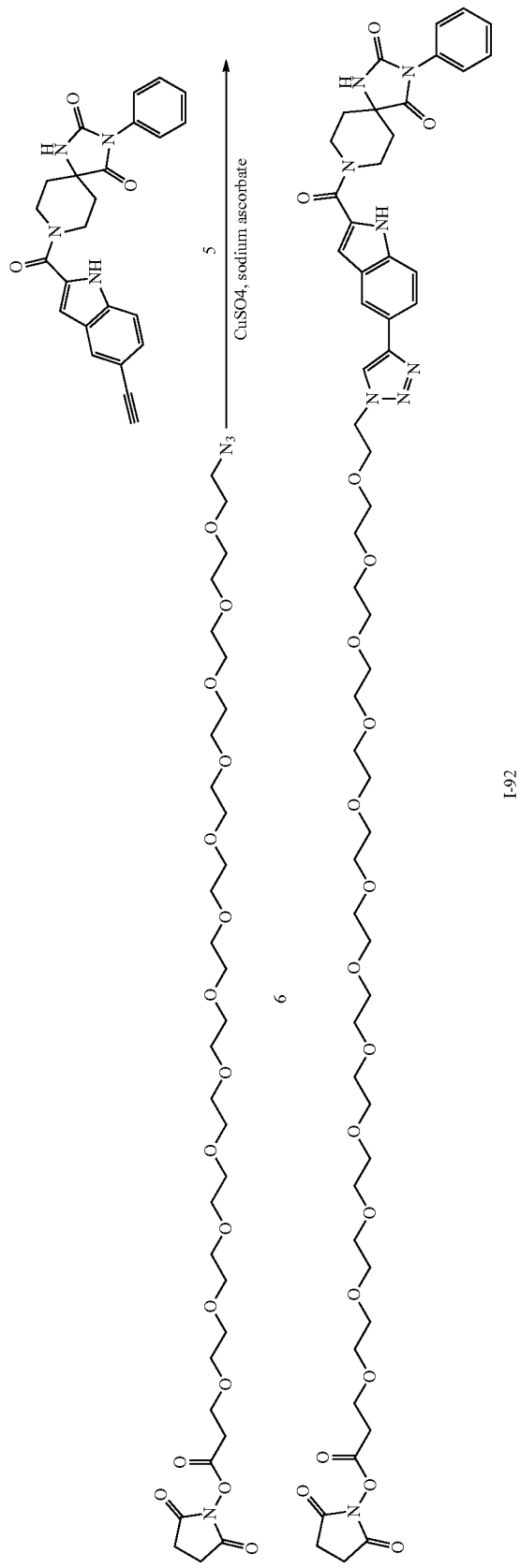

To a solution of compound 6 (0.06 g, 80.99 umol, 1 eq) and compound 5 (40.09 mg, 97.19 umol, 1.2 eq) in DMSO (2 mL) was added CuSO$_4$·5H$_2$O (10.11 mg, 40.50 umol, 0.5 eq) and sodium ascorbate (32.09 mg, 161.99 umol, 2 eq). The mixture was stirred at 25° C. for 12 hr. LCMS showed compound 6 was consumed completely and one main peak with desired mass was detected. Filtered. The residue was purified by prep-HPLC (TFA condition: column: Luna C18 100*30 5 u; mobile phase: [water (0.1% TFA)−ACN]; B %: 20%-50%, 10 min). I-92 (30.77 mg, 26.68 umol, 32.94% yield) was obtained as a yellow oil. LCMS: Rt=1.145 min, MS cal.: 1152.5, [1/2M+H]$^+$=577.4. QCLCMS: Rt=2.115 min, MS cal.: 1152.5, [1/2M+H]$^+$=577.4. $^1$H NMR (400 MHz, DMSO-d6) δ ppm 11.73 (s, 1H) 9.25 (s, 1H) 8.44 (s, 1H) 8.10 (s, 1H) 7.70 (d, J=8.77 Hz, 1H) 7.36-7.52 (m, 6H) 6.91 (s, 1H) 4.56 (br t, J=4.60 Hz, 2H) 4.36 (br d, J=13.59 Hz, 2H) 3.88 (br t, J=4.82 Hz, 2H) 3.71 (br t, J=5.92 Hz, 2H) 3.46-3.58 (m, 48H) 2.92 (t, J=5.92 Hz, 2H) 2.80 (s, 4H) 1.97-2.10 (m, 2H) 1.89 (br d, J=13.15 Hz, 2H).

Example 42: Synthesis of I-93

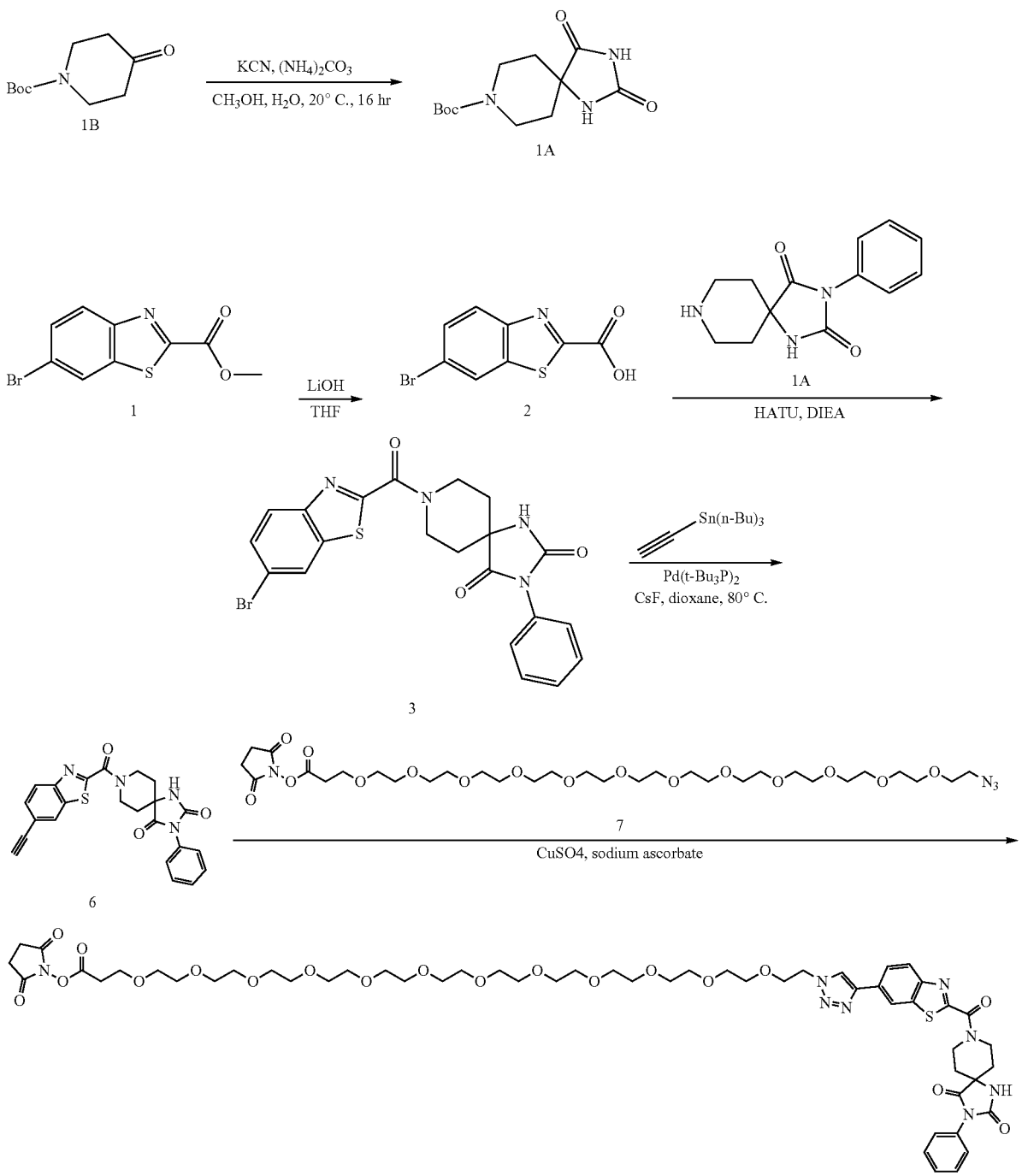

I-93

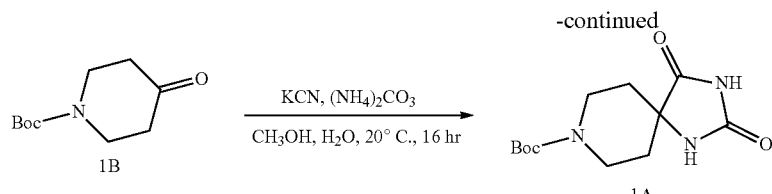

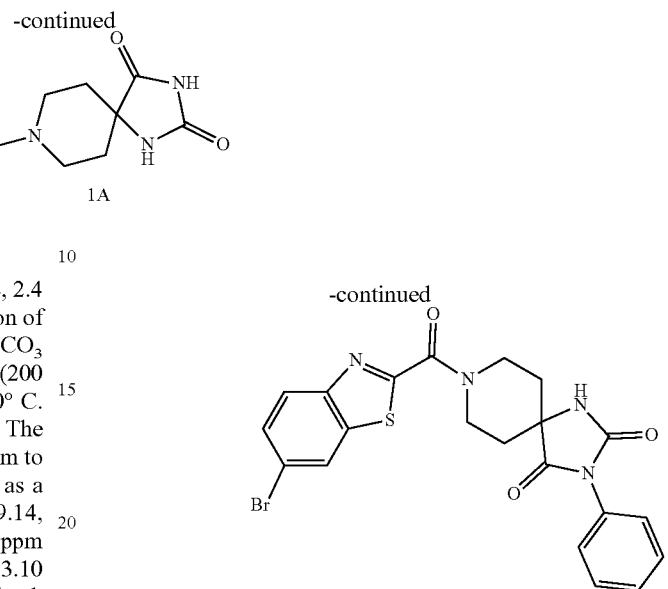

A solution of KCN (23.53 g, 361.36 mmol, 15.48 mL, 2.4 eq) in H$_2$O (200 mL) was added dropwise to the solution of compound 1B (30 g, 150.57 mmol, 1 eq) and (NH$_4$)$_2$CO$_3$ (31.83 g, 331.25 mmol, 35.36 mL, 2.2 eq) in MeOH (200 mL) and H$_2$O (200 mL). The mixture was stirred at 20° C. for 72 h. LCMS showed the reaction was completed. The reaction mixture was filtered and concentrated in vacuum to give compound 1A (20 g, 74.27 mmol, 49.33% yield) as a white solid. LCMS: RT=0.999 min, MS cal.: 269.14, [M-55]$^+$=214.0. $^1$H NMR (400 MHz, DMSO-d6) δ ppm 10.71 (br s, 1H) 8.51 (s, 1H) 3.80 (br d, J=13.5 Hz, 2H) 3.10 (brs, 2H) 1.60-1.74 (m, 2H) 1.48-0.57 (m, 1H) 1.52 (br d, J=13.2 Hz, 1H) 1.40 (s, 9H).

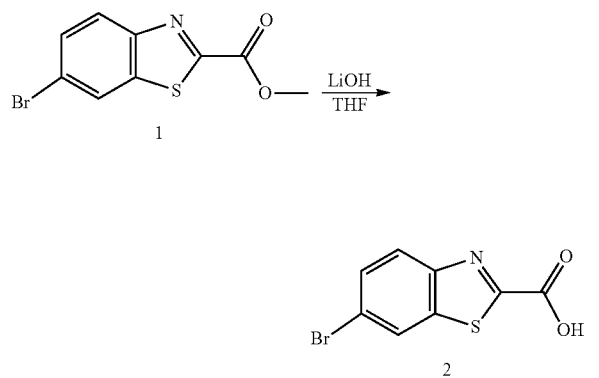

To a solution of compound 1 (0.3 g, 1.10 mmol, 1 eq) in THF (10 mL) was added LiOH·H$_2$O (138.79 mg, 3.31 mmol, 3 eq) stirred at 15° C. for 15 hrs. TLC (Petroleum ether:EtOAc=1:1, R$_f$=0) showed the starting material was consumed and new spot generated. The reaction mixture was concentrated to give compound 2 (410 mg, crude) as a white solid. The residue was used directly next step without purification.

To a solution of compound 2 (242.02 mg, 937.72 umol, 1 eq) and compound 1A (230 mg, 937.72 umol, 1 eq) in DMF (8 mL) was added HATU (534.82 mg, 1.41 mmol, 1.5 eq), DIEA (363.58 mg, 2.81 mmol, 490.00 uL, 3 eq) stirred at 15° C. for 16 hrs. LCMS showed the starting material was still remained and the desired MS was detected. The reaction mixture was added brine (60 mL) and extracted with EtOAc (60 mL*2). The organic phase was dried over Na$_2$SO$_4$ and concentrated. The residue was purified by chromatography column (PE/EA=1/3 to 1/1). Then solid was pulped with DCM (10 mL) to give compound 3 (170 mg, 350.26 umol, 37.35% yield) as a white solid, which was confirmed by H NMR. 1H NMR (400 MHz, DMSO-d6) δ ppm 9.22 (s, 1H) 8.53 (d, J=1.96 Hz, 1H) 8.09 (d, J=8.80 Hz, 1H) 7.77 (dd, J=8.80, 1.96 Hz, 1H) 7.44-7.52 (m, 2H) 7.33-7.43 (m, 3H) 4.93 (br d, J=13.20 Hz, 1H) 4.36 (br d, J=13.20 Hz, 1H) 3.89 (br t, J=11.74 Hz, 1H) 3.43-3.57 (m, 1H) 3.49 (br t, J=10.51 Hz, 1H) 1.84-2.18 (m, 4H). LCMS: RT=1.263 min, MS cal.: 484.02, [M+H]$^+$=485.1, [M+H]$^+$=487.1.

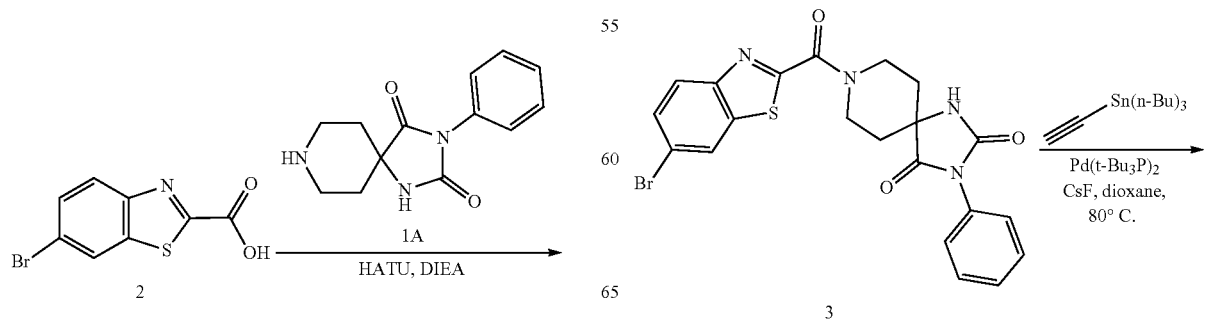

-continued

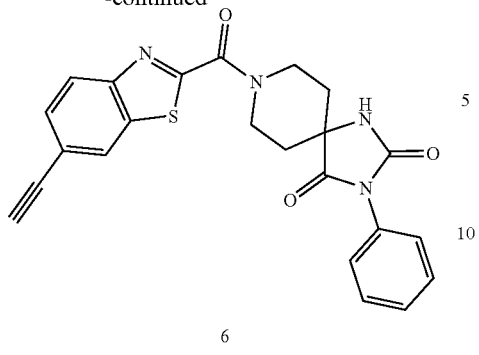

6

To a solution of compound 3 (0.1, 206.04 umol, 1 eq), tributyl(ethynyl)stannane (97.38 mg, 309.05 umol, 89.34 uL, 1.5 eq), palladium; tritert-butylphosphane (9.48 mg, 18.54 umol, 0.09 eq) and CSF (62.59 mg, 412.07 umol, 15.19 uL, 2 eq) in dioxane (1 mL) stirred at 80° C. for 1 hr. LCMS showed the starting material was consumed completely and a main peak with desired MS was detected. The reaction was added DCM (50 mL) and washed with CsF aqueous (50 mL). The residue was purified by chromatography column (Petroleum ether:Ethyl acetate=1:1) to give compound 6 (75 mg, 174.22 umol, 84.56% yield) as a yellow solid, which was confirmed by H NMR. 1H NMR (400 MHz, CHLOROFORM-d) δ ppm 8.12 (d, J=1.10 Hz, 1H) 8.01-8.06 (m, 1H) 7.65 (dd, J=8.60, 1.54 Hz, 1H) 7.40-7.53 (m, 5H) 6.24 (s, 1H) 4.97 (br d, J=7.28 Hz, 1H) 4.30-4.51 (m, 3H) 3.83-3.93 (m, 1H) 3.22 (s, 1H) 2.31-2.37 (m, 2H) 2.01 (br s, 2H). LCMS: RT=1.217 min, MS cal.: 430.11, $[M+H]^+$=431.2.

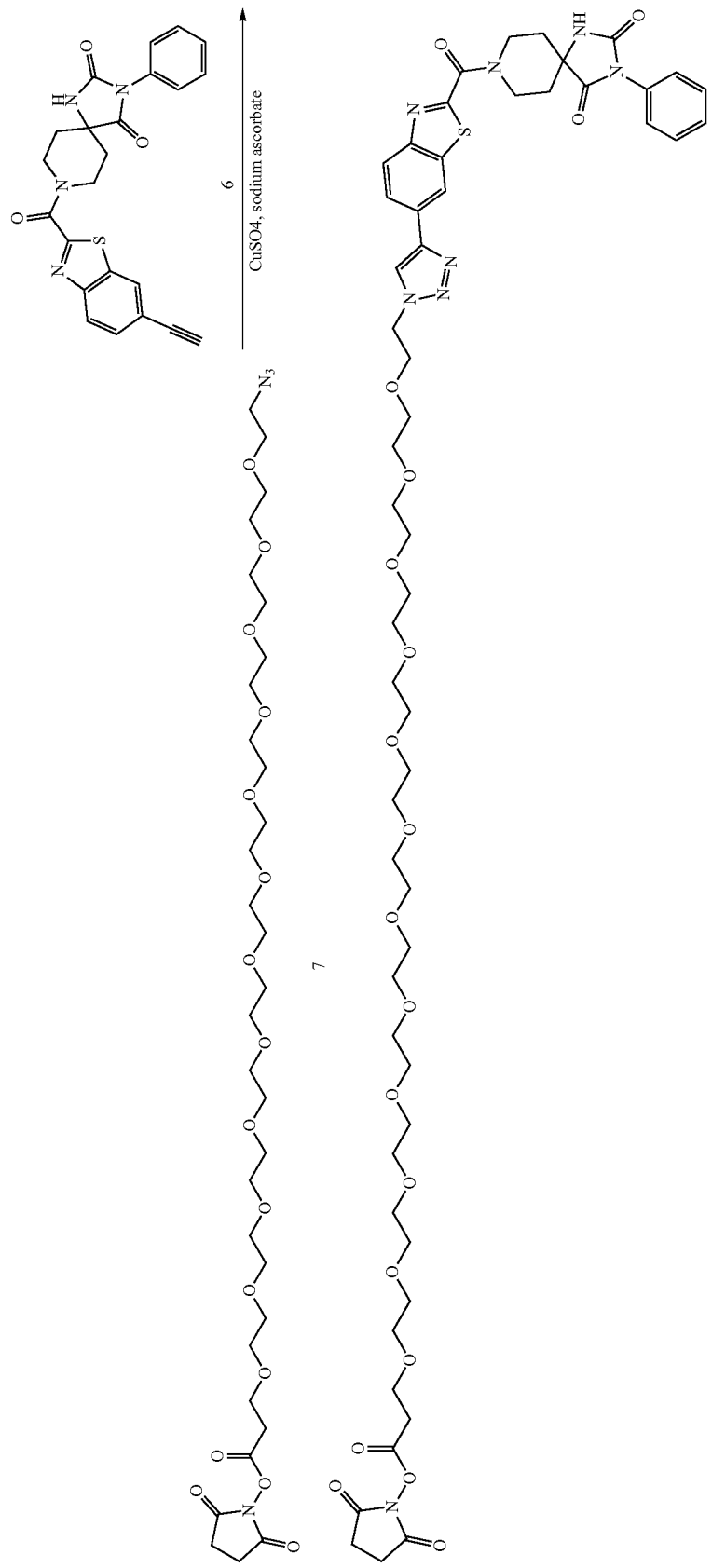

A solution of compound 7 (30 mg, 40.50 umol, 1 eq) and compound 6 (17.43 mg, 40.50 umol, 1 eq) was added CuSO4·5H2O (3.03 mg, 12.15 umol, 0.3 eq) and sodium; (2R)-2-[(1S)-1,2-dihydroxyethyl]-4-hydroxy-5-oxo-2H-furan-3-olate (16.05 mg, 80.99 umol, 2 eq) in DMSO (2 mL) stirred at 15° C. for 1 hr. LCMS showed a peak with desired MS was detected. The reaction mixture was filtered. The residue was purified by prep-HPLC (column: Nano-micro Kromasil C18 100*30 mm 5 um; mobile phase: [water (0.1% TFA)–ACN]; B %0: 32%-52%, 10 min) and lyophilized to give I-93 (5.03 mg, 4.05 umol, 10.0100 yield, 94.38% purity) as a colorless oil, which was confirmed by HNMR and QC LCMS. $^1$H NMR (400 MHz, CHLOROFORM-d) δ ppm 8.51 (s, 1H) 8.21 (s, 1H) 8.01-8.16 (m, 2H) 7.36-7.54 (m, 5H) 6.68 (br dd, 0.1=8.31, 4.89 Hz, 1H) 4.91-5.08 (m, 1H) 4.65 (br s, 2H) 4.42-4.55 (m, 1H) 4.34 (br s, 1H) 3.91-3.97 (m, 2H) 3.85 (br t, J=6.36 Hz, 3H) 3.81-3.82 (m, 1H) 3.74-3.74 (m, 1H) 3.71-3.74 (m, 1H) 3.69-3.69 (m, 1H) 3.69-3.69 (m, 1H) 3.61-3.68 (m, 36H) 3.60 (br s, 6H) 2.91 (br t, J=6.36 Hz, 2H) 2.84 (br s, 3H) 2.24-2.40 (m, 2H) 1.93-2.08 (m, 2H) 1.83 (br s, 3H). LCMS: RT=1.202 min, MS cal.: 1170.48, [M/2+H]$^+$=586.3, [M/2+H]$^+$=1172.7. LCMS: RT=2.282 min, MS cal.: 1170.48, [M/2+H]$^+$=586.3.

Example 43: Synthesis of I-94

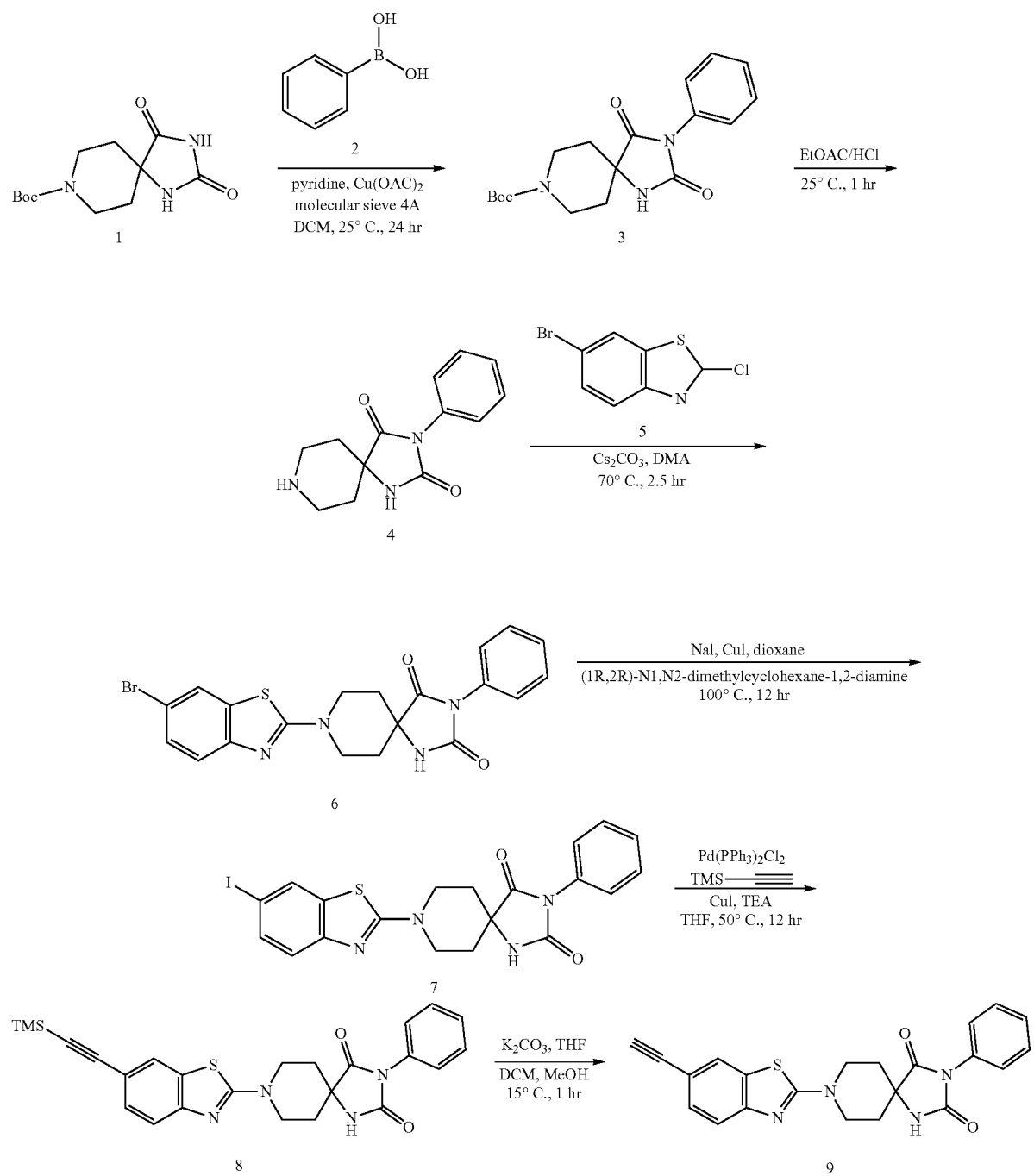

-continued

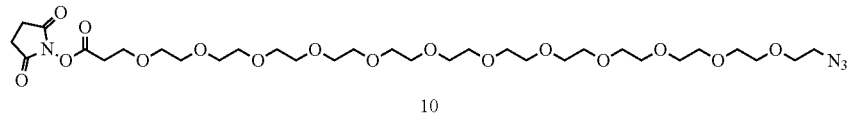
10

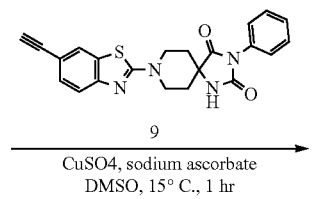
9

CuSO4, sodium ascorbate
DMSO, 15° C., 1 hr

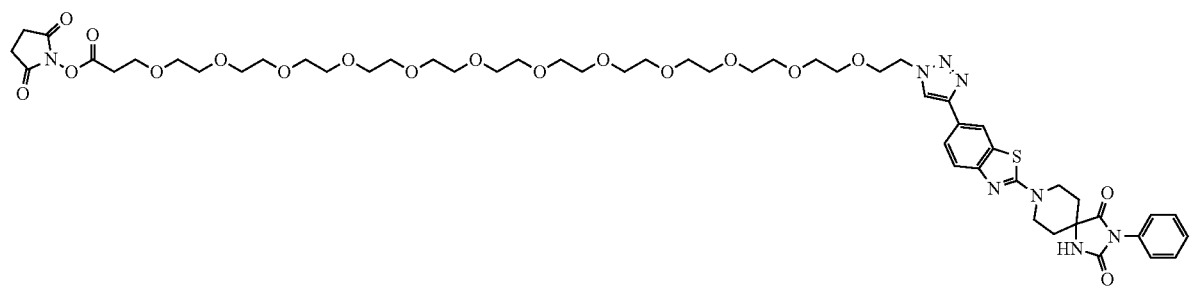
I-94

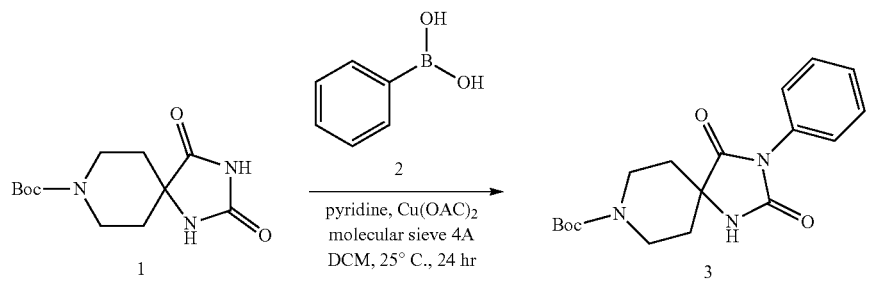 [SMILES: CC(C)(C)OC(=O)N1CCC2(CC1)NC(=O)NC2=O ; OB(O)c1ccccc1 ; CC(C)(C)OC(=O)N1CCC2(CC1)NC(=O)N(c1ccccc1)C2=O]

To a solution of compound 1 (9 g, 33.42 mmol, 1 eq) and compound 2 (4.89 g, 40.10 mmol, 1.2 eq) in DCM (300 mL) was added pyridine (7.93 g, 100.26 mmol, 8.09 mL, 3 eq), molecular sieve 4A (18 g, 33.42 mmol, 1 eq) and Cu(OAc)$_2$ (6.07 g, 33.42 mmol, 1 eq). After the mixture was bubbled with oxygen for 10 min, the mixture was stirred at oxygen atmosphere (20 psi) at 25° C. for 24 hrs. LCMS showed the starting material was still remained and the desired MS was detected. It was also confirmed by TLC (Plate 1, Petroleum ether:EtOAc=2:1, product $R_f$=0.4). The reaction mixture was concentrated under reduced pressure to give a residue. Then the residue was dissolved with THF (400 mL). Then the mixture was filtered. The organic layer was concentrated, and then the operation was repeated for twice to give a crude product. It was purified by silica gel column (Petroleum ether:EtOAc=20:1 to 3:1). It was also confirmed by TLC (Plate 2, Petroleum ether:EtOAc=2:1, product $R_f$=0.4). Compound 3 (7.19 g, 20.82 mmol, 62.29% yield) was obtained as white solid. It was also confirmed by HNMR. LCMS: RT=1.161 min, MS cal.: 345.4, [M-55]$^+$=290.1. $^1$H NMR (400 MHz, METHANOL-d$_4$) δ ppm 7.10-7.90 (m, 5H) 3.98 (dt, J=13.81, 4.71 Hz, 2H) 3.35 (br s, 1H) 2.01 (ddd, J=13.81, 10.09, 4.17 Hz, 2H) 1.78 (br d, J=13.59 Hz, 2H) 1.49 (s, 10H).

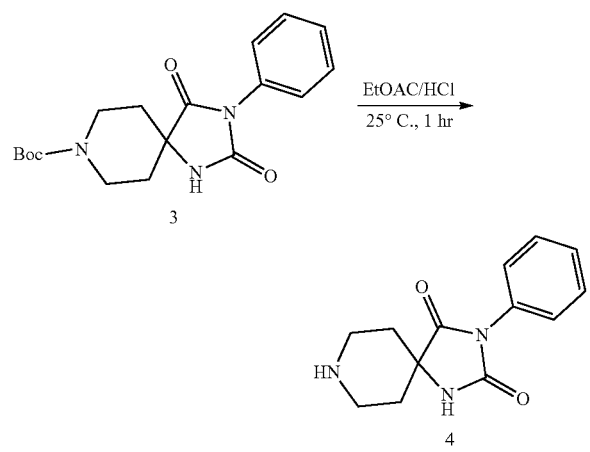

To a mixture of compound 3 (3.9 g, 11.29 mmol, 1 eq) in EtOAc (50 mL) was added HCl/EtOAc (100 mL) (4 M), and then the mixture was stirred at 15° C. for 1 hr. LCMS showed compound 3 was consumed completely and one main peak with desired mass was detected. The reaction mixture was concentrated under reduced pressure to remove half of the solvent, filtered and the filtered cake was concentrated under reduced pressure to give a residue. The crude product was used into the next step without further purification. Compound 4 (3 g, crude) was obtained as a white solid, and checked by HNMR. LCMS: RT=1.052 min, MS cal.: 245.1, [M+H]$^+$=246.0. $^1$H NMR (400 MHz, DMSO-d6) δ ppm 9.41 (br s, 1H), 9.25 (s, 1H), 9.12 (br s, 1H), 7.51-7.43 (m, 2H), 7.41-7.33 (m, 3H), 3.36 (br s, 1H), 3.28-3.15 (m, 2H), 3.08 (br d, J=17.9 Hz, 1H), 2.26-2.11 (m, 2H), 1.99 (br d, J=13.5 Hz, 2H).

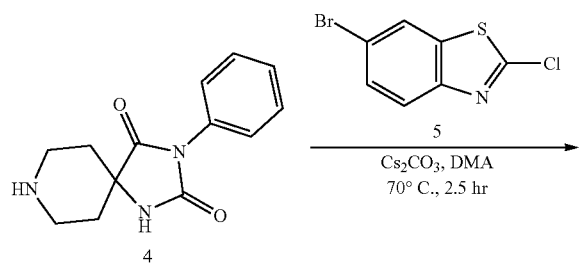

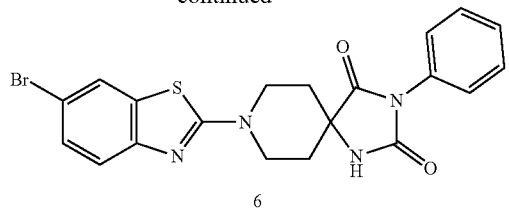

To a solution of compound 5 (200 mg, 804.74 umol, 1 eq) and compound 4 (272.07 mg, 965.69 umol, 1.2 eq, HCl) in DMA (2 mL) was added Cs$_2$CO$_3$ (786.60 mg, 2.41 mmol, 3 eq). The mixture was stirred at 70° C. for 2.5 hr. TLC (Petroleum:EtOAc=1:1, R1 R$_f$=0.98, product R$_f$=0.65) showed the R1 was consumed completely. The mixture was added CH$_2$C2 (15 mL), washed with saturated solution of brine (8 mL*2), the organic layer was dried with Na$_2$SO$_4$, filtered, concentrated. The residue was added MTBE (2.5 mL), filtered. Compound 6 (300 mg, 533.17 umol, 66.25% yield, 81.28% purity) was obtained as white solid checked by LCMS. LCMS: RT=1.267 min, MS cal.: 474.15, [M+H]$^+$=457.1.

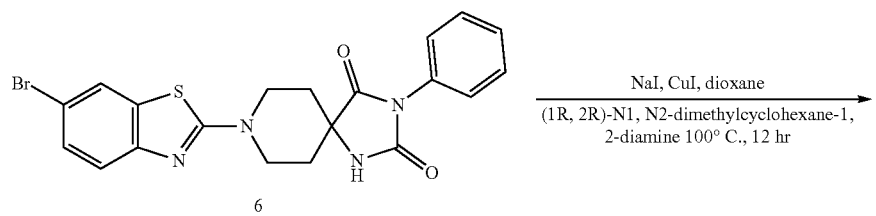

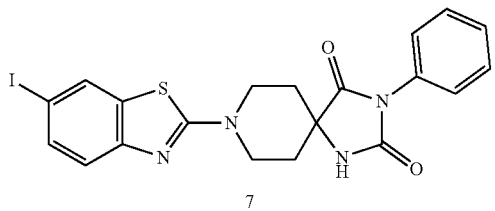

To a solution of compound 6 (150 mg, 327.98 umol, 1 eq) in dioxane (2 mL) was added NaI (147.49 mg, 983.94 umol, 3 eq) and CuI (62.46 mg, 327.98 umol, 1 eq), (1R,2R)—N1,N2-dimethylcyclohexane-1,2-diamine (46.65 mg, 327.98 umol, 1 eq). The mixture was stirred at 100° C. for 12 hr. HPLC was detected the desired product. The mixture was filtered, the filter liquor was added CH$_2$Cl$_2$ (30 mL), washed with brine (10 mL*2), dried with Na$_2$SO$_4$, filtered, concentrated. Compound 7 (88 mg, crude) was obtained as green solid checked by HPLC. HPLC: RT=3.251 min.

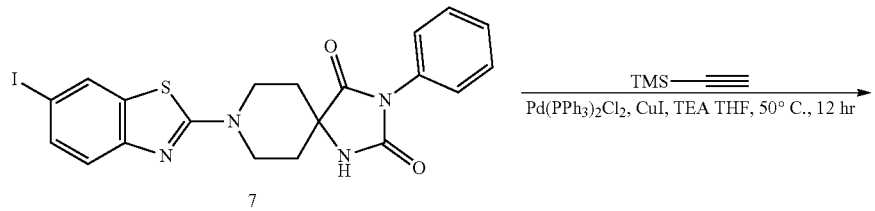

-continued

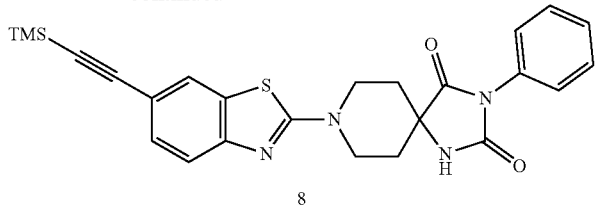
8

To a solution of compound 7 (33 mg, 65.43 umol, 1 eq) and ethynyl(trimethyl)silane (6.43 mg, 65.43 umol, 9.06 uL, 1 eq) in THF (1 mL) was added CuI (1.25 mg, 6.54 umol, 0.1 eq) and TEA (33.11 mg, 327.16 umol, 45.54 uL, 5 eq) Pd(PPh$_3$)$_2$Cl$_2$ (2.30 mg, 3.27 umol, 0.05 eq). The mixture was stirred at 50° C. for 12 hr. LCMS was detected the desired product MS. The mixture was combined. The mixture was added EtOAc (20 mL), washed with water (5 mL*2), the organic layer was dried with Na$_2$SO$_4$, filtered, concentrated. The residue was purified by prep-TLC according to TLC (Plate 1, EtOAc:Petroleum ether=2:1, product R$_f$=0.34). Compound 8 (40 mg, crude) was obtained as black solid checked by LCMS. LCMS: RT=1.539 min, MS cal.: 474.15, [M+H]$^+$=475.1. LCMS: RT=1.534 min, MS cal.: 474.15, [M+H]$^+$=475.1.

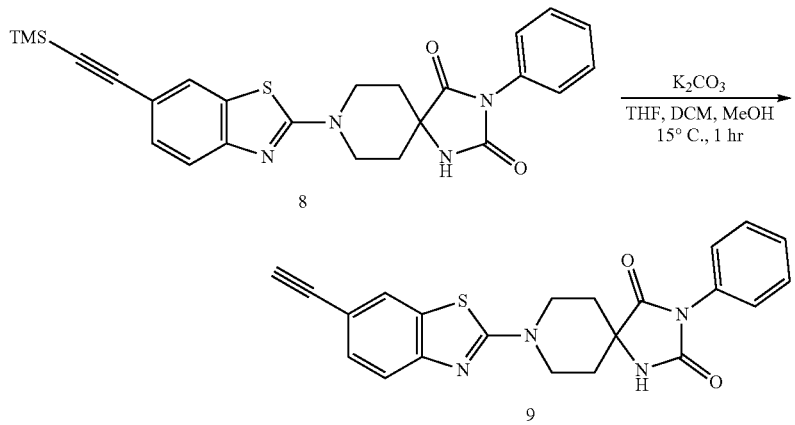

To a solution of compound 8 (35 mg, 73.74 umol, 1 eq) in MeOH (1 mL), THF (0.3 mL) and DCM (1 mL) was added K$_2$CO$_3$ (15.29 mg, 110.61 umol, 1.5 eq). The mixture was stirred at 15° C. for 1 hr. LCMS was detected the desired product MS. TLC (Plate 1, EtOAc:Petroleum ether=1:1, R$^1$ R$_f$=0.44, Product R$_f$=0.36) showed the starting material was consumed completely. The mixture was combined. The mixture was added CH$_2$Cl$_2$ (10 mL), washed with water (3 mL*2), dried with Na$_2$SO$_4$, filtered, concentrated. Compound 9 (31.6 mg, crude) was obtained as yellow solid. LCMS: RT=1.283 min, MS cal.: 402.12, [M+H]$^+$=403.0.

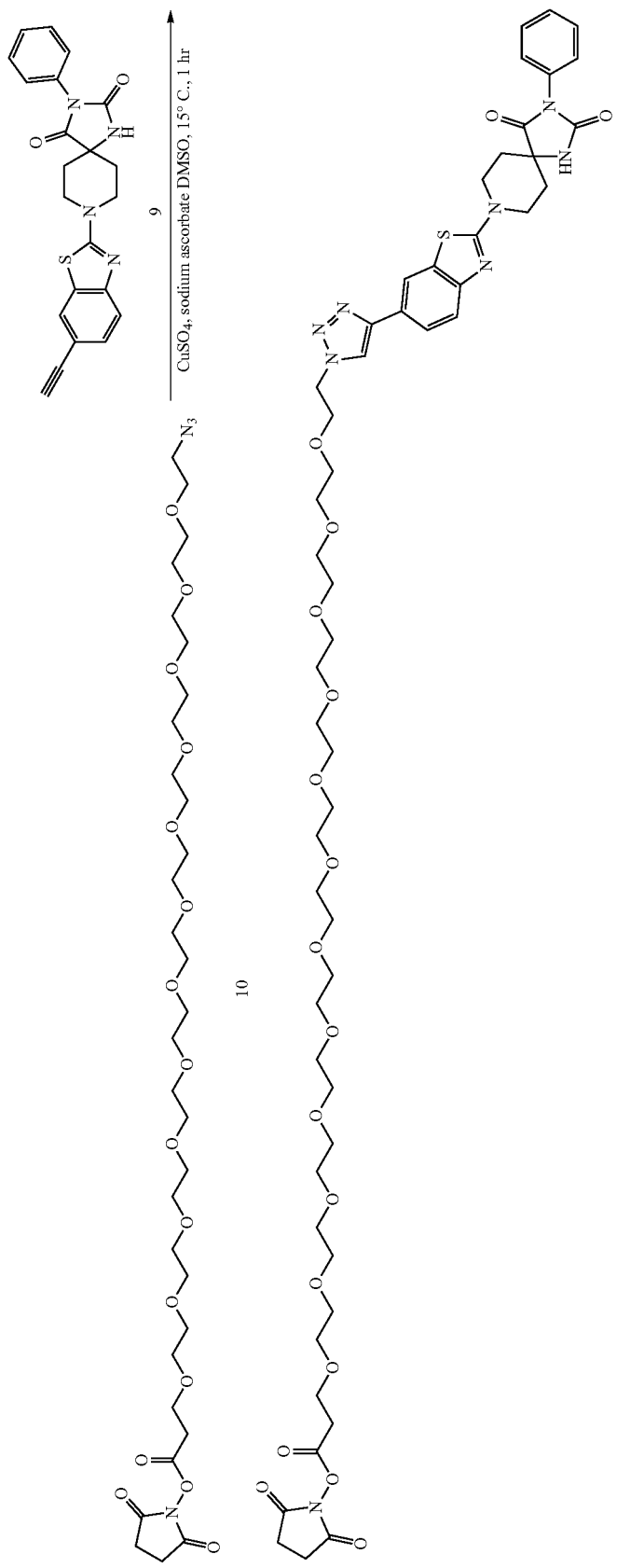

To a solution of compound 10 (46.02 mg, 62.12 umol, 1 eq) and compound 9 (25 mg, 62.12 umol, 1 eq) in DMSO (1 mL) was added CuSO$_4$·5H$_2$O (4.65 mg, 18.64 umol, 0.3 eq) and sodium; (2R)-2-[(1S)-1,2-dihydroxyethyl]-4-hydroxy-5-oxo-2H-furan-3-olate (24.61 mg, 124.23 umol, 2 eq). The mixture was stirred at 15° C. for 1 hr. LCMS was detected the desired product MS. The mixture was filtered. The residue was purified by prep-HPLC (TFA condition) according to HPLC. I-94 (24.54 mg, 20.70 umol, 33.33% yield, 96.45% purity) was obtained as white oil checked by QCLCMS and HNMR. LCMS: RT=1.196 min, MS cal.: 1142.48, [M/2+H]$^+$=572.1. HPLC: RT=2.578 min. QCLCMS: RT=2.894 min, MS cal.: 1142.48, [M/2+H]$^+$=572.4. $^1$H NMR (400 MHz, DMSO-d6) δ ppm 9.23-9.15 (m, 1H), 9.18 (s, 1H), 8.48 (s, 1H), 8.28 (d, J=1.2 Hz, 1H), 7.78 (dd, J=1.6, 8.3 Hz, 1H), 7.59-7.36 (m, 6H), 4.58 (br t, J=4.9 Hz, 2H), 4.07 (br d, J=13.3 Hz, 2H), 3.88 (br t, J=5.0 Hz, 2H), 3.72 (br t, J=6.0 Hz, 3H), 3.64-3.26 (m, 60H), 2.92 (t, J=5.9 Hz, 2H), 2.81 (s, 4H), 2.14-2.03 (m, 2H), 1.98-1.87 (m, 2H).

Example 44: Synthesis of I-95

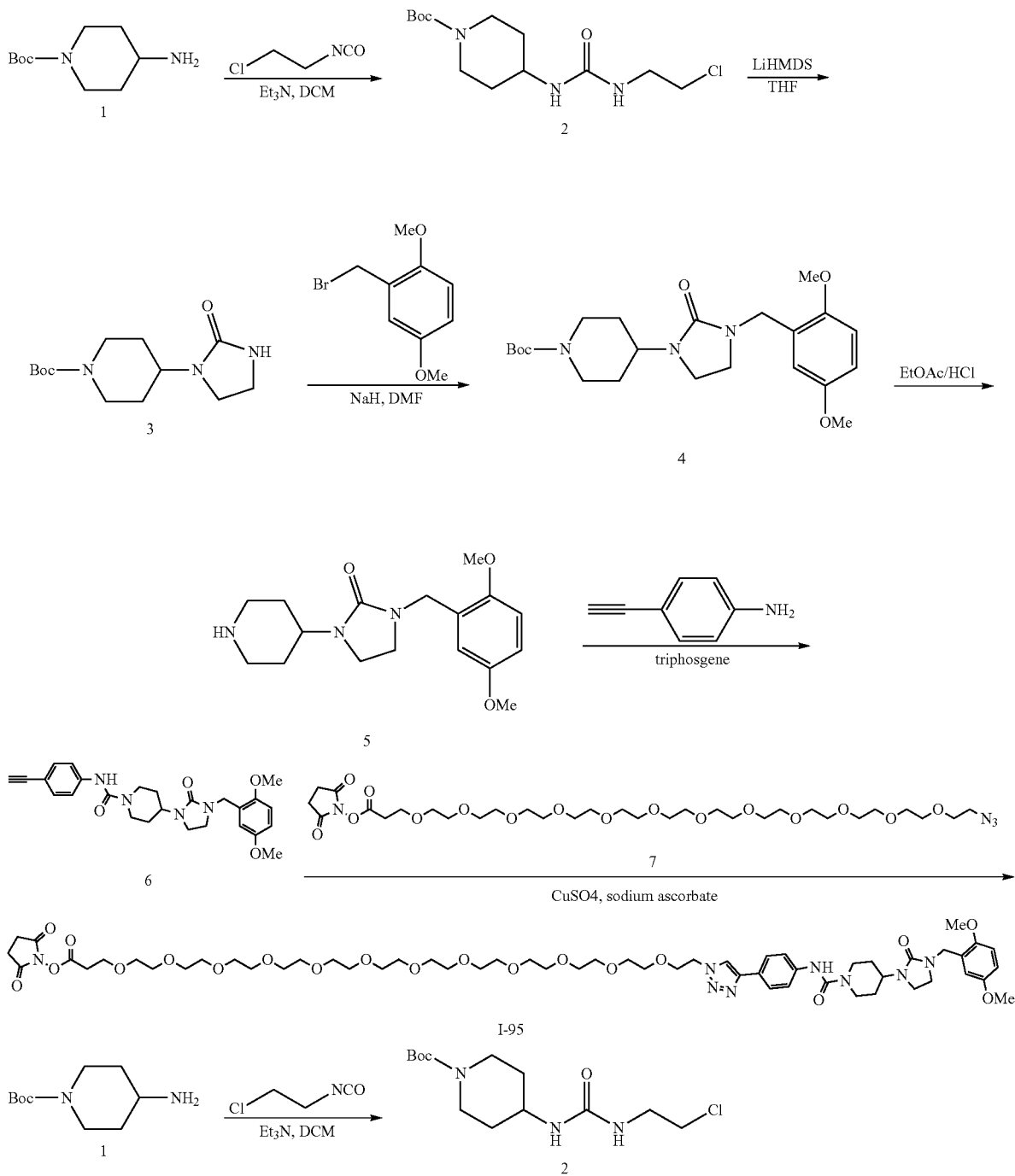

To a solution of compound 1 (2 g, 9.99 mmol, 1 eq) in DCM (20 mL) was added TEA (2.53 g, 24.97 mmol, 3.47 mL, 2.5 eq) and compound 1A (1.16 g, 10.98 mmol, 1.1 eq) at 0° C. with stirring for 15 min. Then the reaction mixture was stirred at 25° C. for 1 hr. TLC (DCM:MeOH=10:1, $R_f$=0.64) showed the starting material was consumed completely and a new spot was detected. The reaction mixture poured into 0.5 N HCl aqueous to pH=5, then the organic layer was washed with brine and dried over with anhydrous $Na_2SO_4$. Finally the organic layer was concentrated under reduced pressure. The residue was purified by silica gel column (Petroleum ether:EtOAc=5:1 to 1:1) to give compound 2 (1.1 g, 3.60 mmol, 36.02% yield) as a white solid.

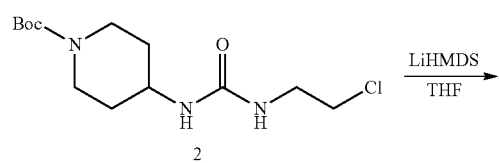

To a solution of compound 2 (1.8 g, 5.89 mmol, 1 eq) in THF (18 mL) was added LiHMDS (1 M, 12.60 mL, 2.14 eq) with stirring drop wise at −40° C. Then the reaction mixture was gradually warmed to 15° C. with stirring for 2 hrs. TLC (DCM/MeOH=20/1, $R_f$=0.5) showed new spots generated and starting materials consumed. It was quenched by saturated $NH_4Cl$ (80 mL) and extracted with EtOAc (80 mL*2). The organic phase was washed with brine (80 mL) and dried over anhydrous $Na_2SO_4$. Finally the organic phase was concentrated under reduced pressure to give compound 3 (1.63 g, crude) as a yellow solid, which was confirmed by TLC. The crude product was used directly next step without purification.

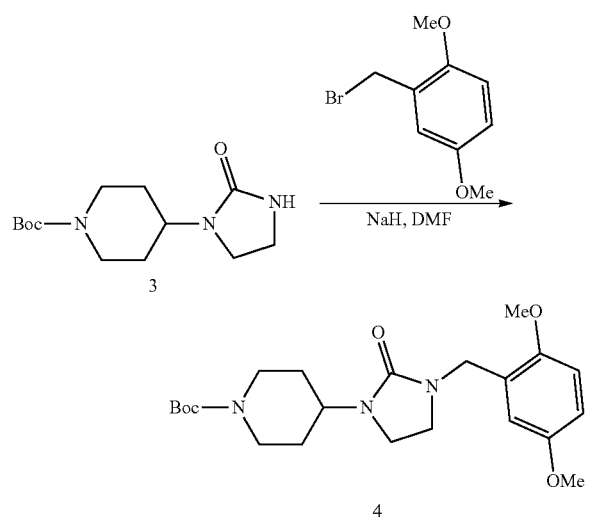

To a solution of compound 3 (0.1 g, 371.28 umol, 1 eq) in DMF (1 mL) was added NaH (22.27 mg, 556.92 umol, 60% purity, 1.5 eq) at 0° C. drop wise with stirring for 30 min. Then the reaction mixture was added 2-(bromomethyl)-1,4-dimethoxy-benzene (128.70 mg, 556.92 umol, 1.5 eq) in DMF (1 mL) drop wise at 0° C. The reaction mixture was stirred at 25° C. for 3 hrs. LCMS showed the starting material was consumed completely and the desired MS was detected. It was quenched by saturated $NH_4Cl$ (40 mL). Then it was extracted EtOAc (30 mL*2). The organic layers were washed with brine and dried over anhydrous $Na_2SO_4$. The organic layer was concentrated under reduced pressure. The residue was purified by chromatography column (Petroleum ether:EtOAc=3:1) to give compound 4 (130 mg, 309.88 umol, 83.46% yield) as a yellow solid, which was confirmed by H NMR. $^1$H NMR (400 MHz, CHLOROFORM-d) δ ppm 6.73-6.88 (m, 3H) 4.39 (s, 2H) 4.12-4.25 (m, 2H) 3.87-3.98 (m, 1H) 3.77 (d, J=10.36 Hz, 6H) 3.23 (s, 4H) 2.70-2.88 (m, 2H) 1.70 (br d, J=10.58 Hz, 2H) 1.55 (br s, 4H) 1.46 (s, 9H). LCMS: RT=1.556 min, MS cal.: 419.24, [M+H]$^+$=442.2, [(M-55)+H]$^+$=364.1.

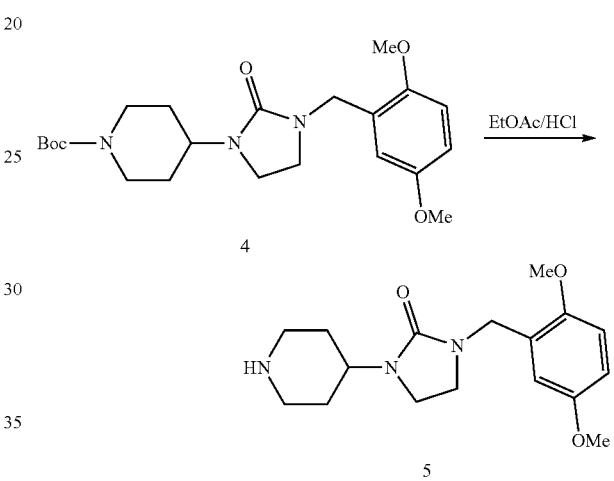

To a solution of compound 4 (130 mg, 309.88 umol, 1 eq) in mixture EtOAc (0.3 mL) and HCl/EtOAc (0.9 mL, 4 M, 674.36 uL, 7.46 eq) was stirred for 2 hrs at 25° C. LCMS showed the starting material was consumed completely and the desired MS was detected. The reaction mixture was concentrated under reduced pressure to give compound 5 (80 mg, 250.47 umol, 80.83% yield, N/A purity) as a yellow oil, which was confirmed by LCMS. LCMS: RT=0.961 min, MS cal.: 319.19, [M+H]$^+$=320.2.

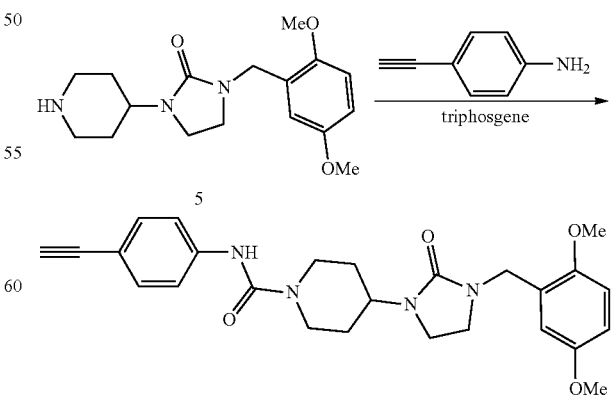

To a solution of (4-nitrophenyl) carbonochloridate (60.58 mg, 300.57 umol, 1.2 eq) in DCM (3 mL) was added 4-ethynylaniline (38.14 mg, 325.61 umol, 1.3 eq) in DCM (1 mL) drop wise at −40° C. Then the reaction mixture was added compound 5 (80 mg, 250.47 umol, 1 eq), pyridine (59.44 mg, 751.41 umol, 60.65 uL, 3 eq) and DMAP (91.80 mg, 751.41 umol, 3 eq) in DCM (2 mL) at −40° C. and stirred at 25° C. for 16 hrs. LCMS showed the starting material was consumed completely and a main peak with desired MS was detected. The reaction mixture was added EtOAc (40 mL), then the mixture was washed with brine (40 mL). The organic layer was dried over anhydrous $Na_2SO_4$ and concentrated under reduced pressure. The residue was purified by chromatography column (EtOAc as fluent phase, as shown TLC, Petroleum ether:EtOAc=1:1, $R_f$=0.24) to give compound 6 (80 mg, 172.96 umol, 69.05% yield) as a yellow solid, which was confirmed by H NMR. 1H NMR (400 MHz, CHLOROFORM-d) δ ppm 7.23-7.38 (m, 5H) 6.68-6.79 (m, 3H) 6.37 (s, 1H) 4.32 (s, 2H) 4.02-4.13 (m, 3H) 3.93 (br t, J=12.02 Hz, 1H) 3.70 (dd, J=10.25, 1.87 Hz, 7H) 3.18 (s, 4H) 2.84-2.97 (m, 3H) 1.94-1.94 (m, 1H) 1.73 (br d, J=12.35 Hz, 2H) 1.46-1.62 (m, 5H). LCMS: RT=1.364 min, MS cal.: 462.23, $[M+H]^+$=463.1.

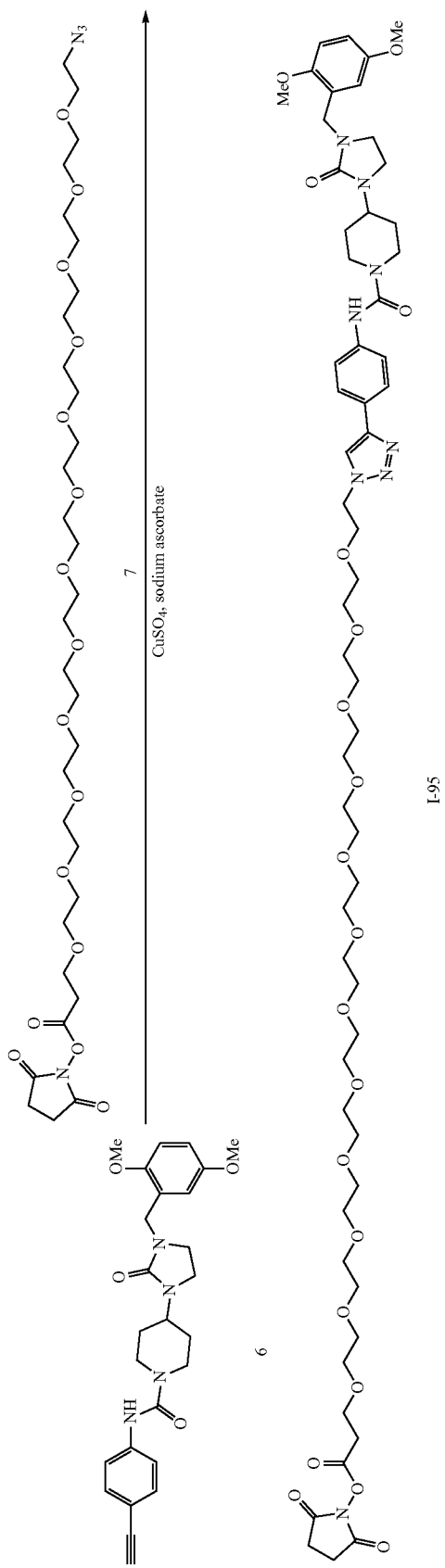

A solution of compound 7 (40 mg, 54.00 umol, 1 eq) and compound 6 (24.98 mg, 54.00 umol, 1 eq) in DMSO (2 mL) was added $CuSO_4 \cdot 5H_2O$ (4.04 mg, 16.20 umol, 0.3 eq) and sodium ascorbate (21.39 mg, 107.99 umol, 2 eq) stirred at 15° C. for 1 hr. LCMS showed a peak with desired MS was detected. The reaction mixture was concentrated by blowing $N_2$ atmosphere. The residue was purified by prep-HPLC (column: Nano-micro Kromasil C18 100*30 mm 5 um; mobile phase: [water (0.1% TFA)–ACN]; B %: 25%-52%, 10 min) to give I-95 (23.87 mg, 19.76 umol, 36.60% yield, 99.63% purity) as a white gum, which was confirmed by H NMR and QC LCMS. 1H NMR (400 MHz, CHLOROFORM-d) δ ppm 7.96 (s, 1H) 7.77 (d, J=8.31 Hz, 2H) 7.47 (d, J=8.56 Hz, 2H) 7.32-7.37 (m, 2H) 7.27-7.31 (m, 3H) 6.72 (s, 1H) 4.59 (t, J=4.83 Hz, 2H) 4.39 (s, 2H) 4.23 (br d, J=12.47 Hz, 2H) 4.03 (br t, J=11.86 Hz, 1H) 3.91 (t, J=4.83 Hz, 2H) 3.85 (t, J=6.42 Hz, 2H) 3.56-3.70 (m, 44H) 3.16-3.33 (m, 4H) 3.00 (br t, J=12.29 Hz, 2H) 2.90 (t, J=6.42 Hz, 2H) 2.84 (s, 3H) 1.82 (br d, J=12.23 Hz, 2H) 1.60-1.72 (m, 2H). LCMS: RT=1.167 min, MS cal.: 1202.60, $[M/2+H]^+$=602.6. LCMS: RT=2.555 min, MS cal.: 1202.60, $[M/2+H]^+$=602.4, $[M+H]^+$=1204.6.

Example 45: Synthesis of I-96

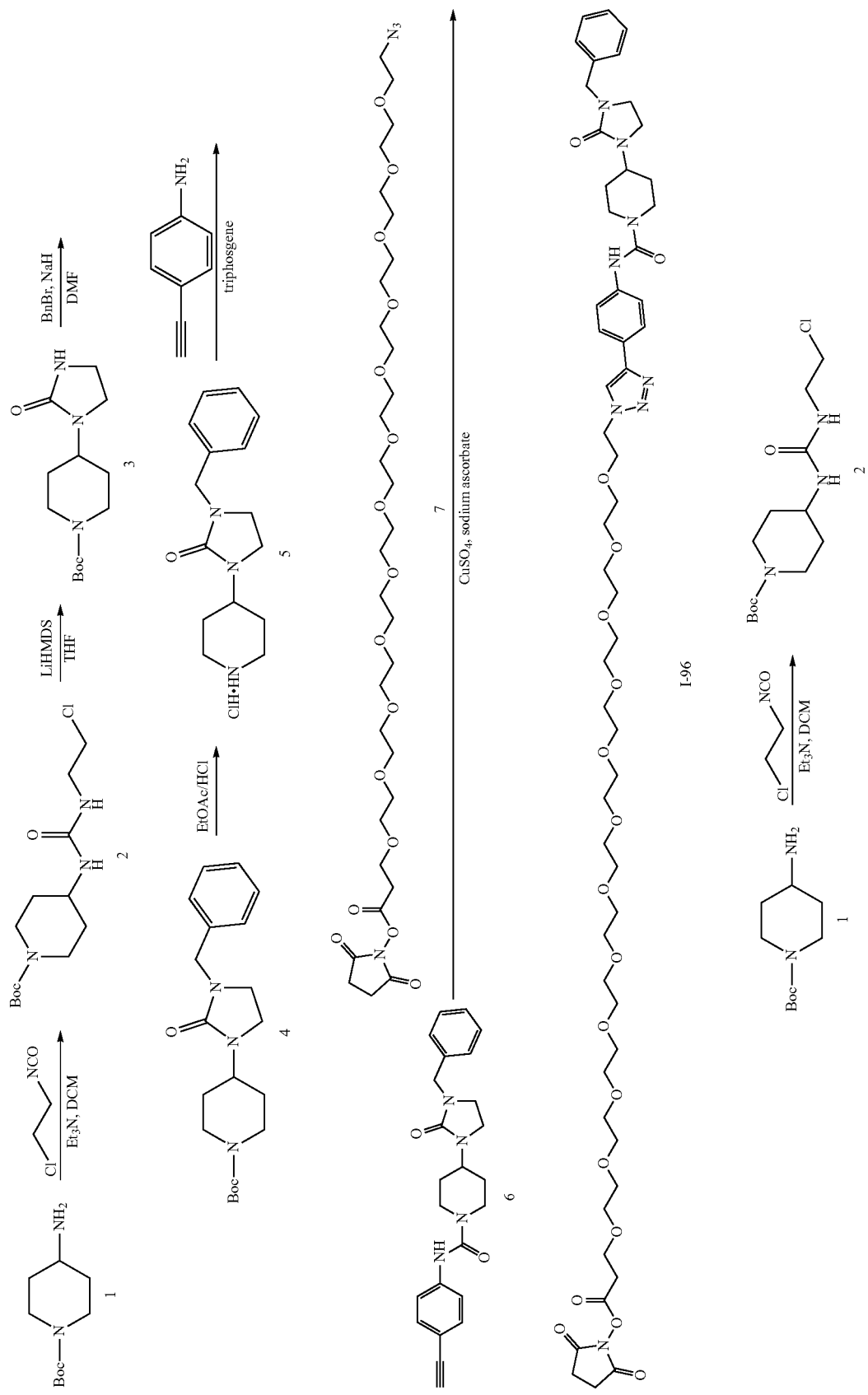

To a solution of compound 1 (2 g, 9.99 mmol, 1 eq) in DCM (20 mL) was added TEA (2.53 g, 24.97 mmol, 3.47 mL, 2.5 eq) and compound 1A (1.16 g, 10.98 mmol, 1.1 eq) at 0° C. with stirring for 15 min. Then the reaction mixture was stirred at 25° C. for 1 hr. TLC (DCM:MeOH=10:1, R$_f$=0.64) showed the starting material was consumed completely and a new spot was detected. The reaction mixture poured into 0.5 N HCl aqueous to pH=5, then the organic layer was washed with brine and dried over with anhydrous Na$_2$SO$_4$. Finally the organic layer was concentrated under reduced pressure. The residue was purified by silica gel column (Petroleum ether:EtOAc=5:1 to 1:1) to give Compound 2 (1.1 g, 3.60 mmol, 36.02% yield) as a white solid.

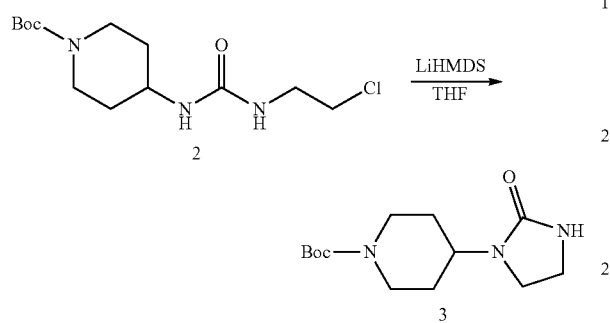

To a solution of compound 2 (0.2 g, 654.02 umol, 1 eq) in THF (2 mL) was added LiHMDS (1 M, 1.4 mL, 2.14 eq) with stirring drop wise at −40° C. Then the reaction mixture was gradually warmed to 15° C. with stirring for 2 hr. LCMS showed a peak with desired MS was detected. It was quenched by saturated NH$_4$Cl (20 mL) and extracted with EtOAc (20 mL*2). The organic phase was washed with brine (20 mL) and dried over anhydrous Na$_2$SO$_4$. Finally the organic phase was concentrated under reduced pressure to give compound 3 (170 mg, 631.17 umol, 96.51% yield) as a yellow solid, which was confirmed by LCMS. The crude product was used directly next step without purification. LCMS: RT=1.142 min, MS cal.: 269.17, [(M-55)+H]$^+$=214.1.

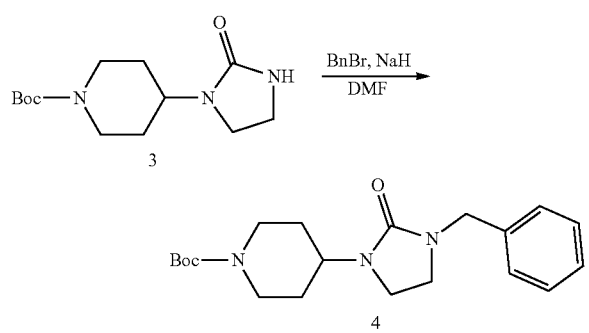

To a solution of compound 3 (0.1 g, 371.28 umol, 1 eq) in DMF (1 mL) was added NaH (22.27 mg, 556.92 umol, 60% purity, 1.5 eq) at 0° C. drop wise with stirring for 30 min. Then the reaction mixture was added BnBr (95.25 mg, 556.92 umol, 66.15 uL, 1.5 eq) in DMF (1 mL) drop wise at 0° C. The reaction mixture was stirred at 25° C. for 3 hrs. LCMS showed the starting material was consumed completely and the desired MS was detected. It was quenched by saturated NH$_4$Cl (40 mL). Then it was extracted EtOAc (30 mL*2). The organic layers were washed with brine and dried over anhydrous Na$_2$SO$_4$. The organic layer was concentrated under reduced pressure. The residue was purified by chromatography column (Petroleum ether:EtOAc=3:1) to give compound 4 (130 mg, 361.65 umol, 97.41% yield) as a yellow solid, which was confirmed by H NMR. $^1$H NMR (400 MHz, METHANOL-d$_4$) δ ppm 7.27-7.38 (m, 5H) 4.38 (s, 2H) 4.10-4.29 (m, 2H) 3.94 (tt, J=12.04, 4.16 Hz, 1H) 3.14-3.30 (m, 4H) 2.80 (brt, J=12.35 Hz, 2H) 1.71 (br d, J=12.13 Hz, 2H) 1.54-1.57 (m, 2H) 1.47 (s, 9H). LCMS: RT=1.332 min, MS cal.: 359.22, [(M-55)+H]$^+$=304.3.

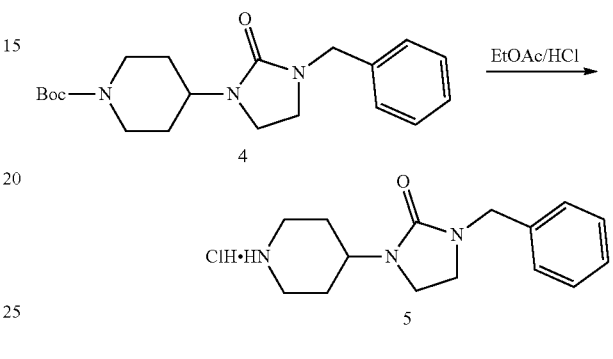

To a solution of compound 4 (130 mg, 361.65 umol, 1 eq) in mixture EtOAc (0.3 mL) and HCl/EtOAc (4 M, 674.36 uL, 7.46 eq) was stirred for 2 hrs at 25° C. LCMS showed the starting material was consumed completely and the desired MS was detected. The reaction mixture was concentrated under reduced pressure to give compound 5 (72 mg, crude) as a yellow solid, which was confirmed by LCMS. LCMS: RT=0.938 min, MS cal.: 259.17, [M+H]$^+$=259.9.

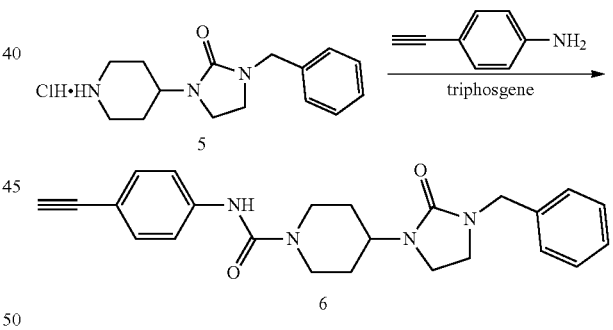

To a solution of (4-nitrophenyl) carbonochloridate (67.15 mg, 333.14 umol, 1.2 eq) in DCM (3 mL) was added 4-ethynylaniline (42.28 mg, 360.91 umol, 1.3 eq) in DCM (1 mL) drop wise at −40° C. Then the reaction mixture was added compound 5 (72 mg, 277.62 umol, 1 eq), pyridine (65.88 mg, 832.86 umol, 67.22 uL, 3 eq) and DMAP (101.75 mg, 832.86 umol, 3 eq) in DCM (2 mL) at −40° C. and stirred at 25° C. for 16 hrs. LCMS showed the starting material was consumed completely and a main peak with desired MS was detected. The reaction mixture was added EtOAc (40 mL), then the mixture was washed with brine (40 mL). The organic layer was dried over anhydrous Na$_2$SO$_4$ and concentrated under reduced pressure. The residue was purified by chromatography column (EtOAc as fluent phase, as shown TLC, Petroleum ether:EtOAc=1:1, R$_f$=0.24) to give compound 6 (50 mg, 124.23 umol, 44.75% yield) as a yellow solid, which was confirmed by H NMR. 1H NMR (400 MHz, CHLOROFORM-d) δ ppm 7.33-7.37 (m, 2H) 7.24-7.29 (m, 3H) 7.20-7.23 (m, 1H) 7.20-7.23 (m, 1H) 6.36 (s, 1H) 4.31 (s, 2H) 4.09 (br d, J=13.89 Hz, 2H) 3.88-4.01 (m, 1H) 3.08-3.23 (m, 4H) 2.87-2.98 (m, 3H) 1.75 (br d, J=11.03 Hz, 2H) 1.49-1.63 (m, 2H). LCMS: RT=1.359 min, MS cal.: 402.21, $[M+H]^+$=403.0, $[M+Na]^+$=425.1.

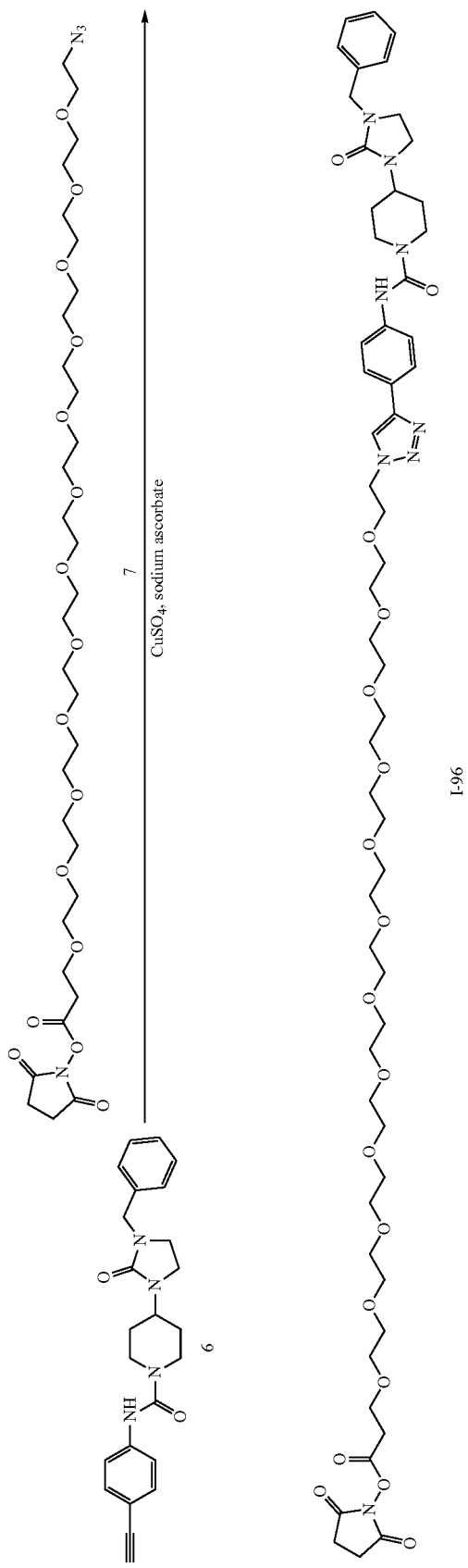

A solution of compound 7 (45 mg, 60.75 umol, 1 eq) and compound 6 (24.45 mg, 60.75 umol, 1 eq) in DMSO (2 mL) was added CuSO₄·5H₂O (4.55 mg, 18.22 umol, 0.3 eq) and sodium ascorbate (24.07 mg, 121.49 umol, 2 eq) stirred at 15° C. for 1 hr. LCMS showed a peak with desired MS was detected. The reaction mixture was concentrated by blowing N₂ atmosphere. The residue was purified by prep-HPLC (column: Luna C18 100*30 5 u; mobile phase: [water (0.1% TFA)–ACN]; B %: 20%-50%, 10 min) to give I-96 (31.46 mg, 26.90 umol, 44.28% yield, 97.74% purity) as a white gum, which was confirmed by H NMR and QC LCMS. 1H NMR (400 MHz, CHLOROFORM-d) δ ppm 7.96 (s, 1H) 7.77 (d, J=8.31 Hz, 2H) 7.47 (d, J=8.56 Hz, 2H) 7.32-7.37 (m, 2H) 7.27-7.31 (m, 3H) 6.72 (s, 1H) 4.59 (t, J=4.83 Hz, 2H) 4.39 (s, 2H) 4.23 (br d, J=12.47 Hz, 2H) 4.03 (brt, J=11.86 Hz, 1H) 3.91 (t, J=4.83 Hz, 2H) 3.85 (t, J=6.42 Hz, 2H) 3.56-3.70 (m, 44H) 3.16-3.33 (m, 4H) 3.00 (br t, J=12.29 Hz, 2H) 2.90 (t, J=6.42 Hz, 2H) 2.84 (s, 3H) 1.82 (br d, J=12.23 Hz, 2H) 1.60-1.72 (m, 2H). LCMS: RT=1.165 min, MS cal.: 1142.57, [M/2+H]⁺=572.6. LCMS: RT=2.216 min, MS cal.: 1142.57, [M/2+H]⁺=572.3, [M+H]⁺=1143.5.

Example 46: Synthesis of I-97

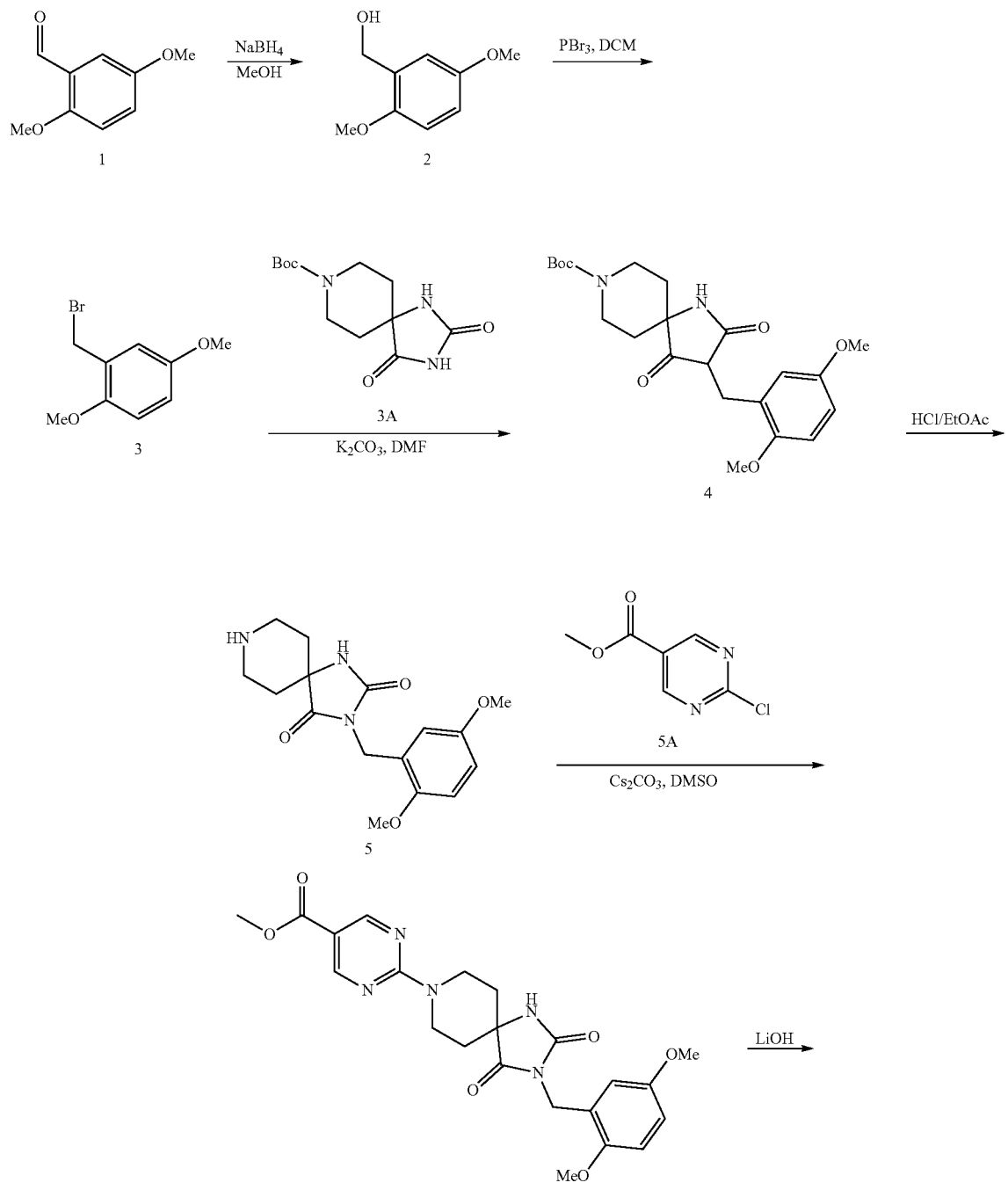

-continued

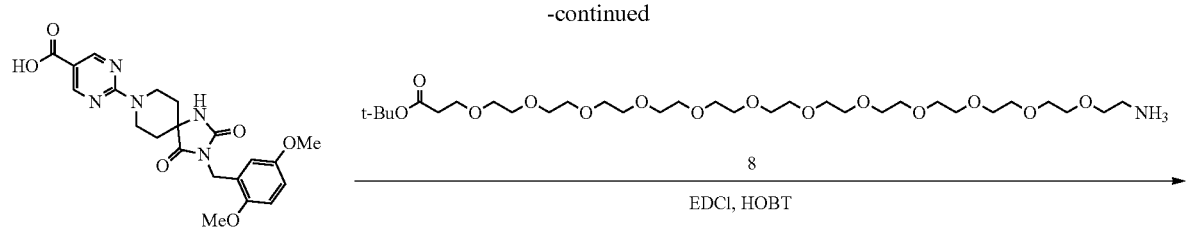

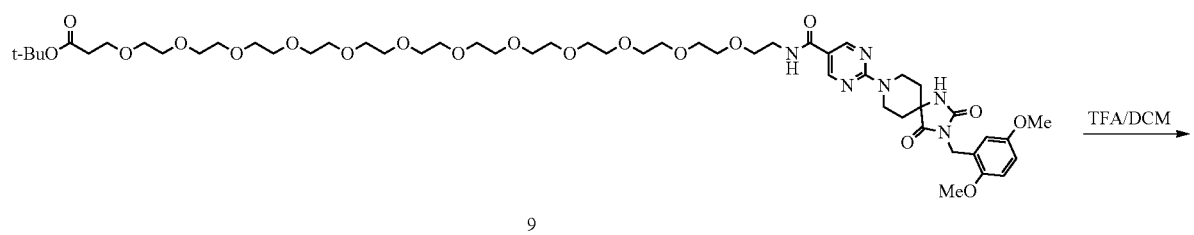

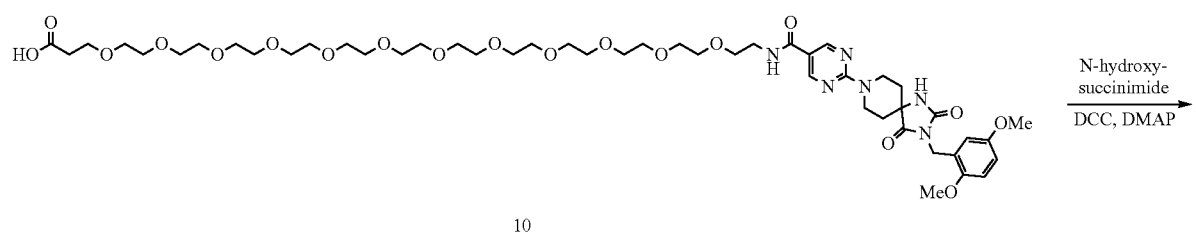

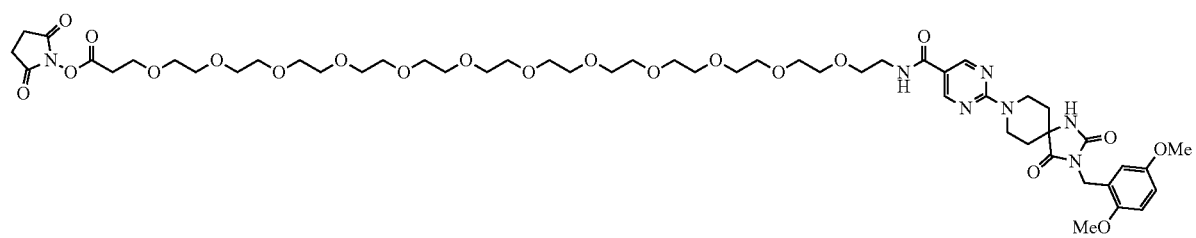

I-97

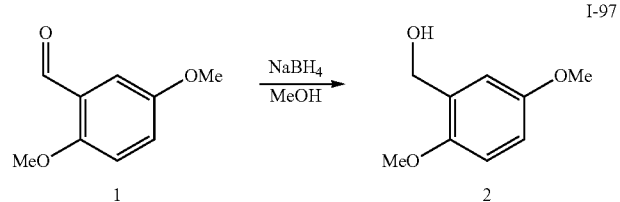

To a solution of compound 1 (4.99 g, 30.03 mmol, 1 eq) in MeOH (70 mL) was added NaBH₄ (1.36 g, 36.03 mmol, 1.2 eq) in portions at −10-0° C. The mixture was stirred at 25° C. for 2 hr. TLC (Plate1, Petroleum ether:Ethyl acetate=3:1, R1 $R_f$=0.4, Product $R_f$=0.3) showed that the starting material was consumed completely. The reaction mixture was quenched with water, and the methanol was removed under vacuum. The residual was then extracted with EtOAc (250 mL), and the organic layer was washed with water and brine and dried over anhydrous Na₂SO₄. The solvent was removed under reduced pressure. Without purification, compound 2 (4.45 g, crude) was obtained as yellow liquid.

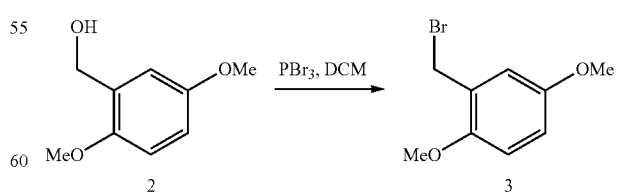

To a mixture of compound 2 (2.23 g, 13.26 mmol, 1.91 mL, 1 eq) in CH₂Cl₂ (50 mL) was added a solution of PBr₃ (6.82 g, 25.19 mmol, 1.9 eq) in CH₂Cl₂ (10 mL) dropwise at −10-0° C. The mixture was stirred at 15° C. for 2 hr. TLC (plate 1, Petroleum ether:Ethyl acetate=5:1, R¹ $R_f$=0.2, P1 $R_f$=0.7) showed the starting material was consumed completely. Deionized water was added. The organic layer was washed with water (50 mL), saturated NaHCO₃ solution (50 mL), and brine (50 mL). The organic layer was dried with anhydrous Na₂SO₄ and concentrated under reduced pressure. Compound 3 (2.41 g, 10.43 mmol, 78.66% yield) was obtained as a yellow solid checked by HNMR. ¹H NMR (400 MHz, CHLOROFORM-d) δ ppm 7.27 (s, 1H), 6.91 (d, J=2.4 Hz, 1H), 6.87-6.79 (m, 2H), 4.55 (s, 2H), 3.87 (s, 3H), 3.78 (s, 3H).

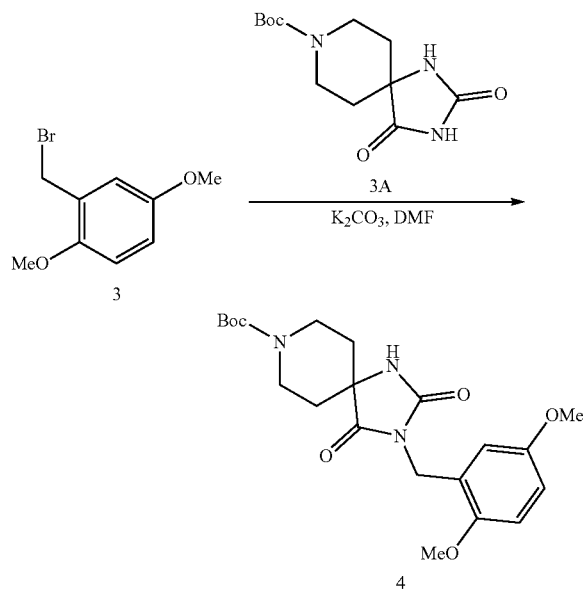

To a solution of compound 3A (300 mg, 1.11 mmol, 1 eq) in DMF (5 mL) was added K₂CO₃ (307.93 mg, 2.23 mmol, 2 eq) and compound 3 (308.92 mg, 1.34 mmol, 1.2 eq). The mixture was stirred at 15° C. for 12 hr. LCMS showed compound 3A was consumed completely and one main peak with desired mass was detected. TLC (Petroleum ether:Ethyl acetate=1:1, $R_f$=0.2) indicated one new spot formed. The reaction mixture was filtered and the filtrate was concentrated under reduced pressure to give a residue. The residue was purified by column chromatography (SiO₂, Petroleum ether:Ethyl acetate=60:1 to 5:1). Compound 4 (410 mg, 669.53 umol, 60.10% yield, 68.5% purity) was obtained as a white solid, and checked by HNMR and LCMS. LCMS: RT=1.196 min, MS cal.: 419.2, [M+H]⁺=420.2. ¹H NMR (400 MHz, CHLOROFORM-d) δ ppm 6.82-6.73 (m, 2H), 6.65 (br s, 1H), 4.68 (s, 2H), 4.12-3.89 (m, 2H), 3.79 (s, 3H), 3.75-3.68 (m, 3H), 3.16 (br t, J=10.8 Hz, 2H), 2.02 (br t, J=10.0 Hz, 2H), 1.68-1.59 (m, 2H), 1.46 (s, 9H).

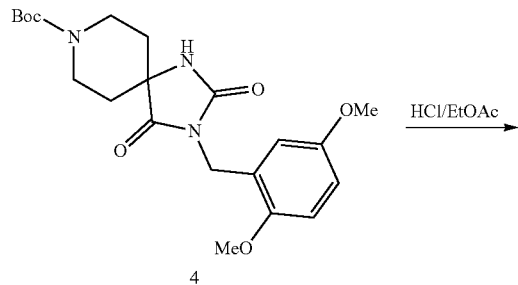

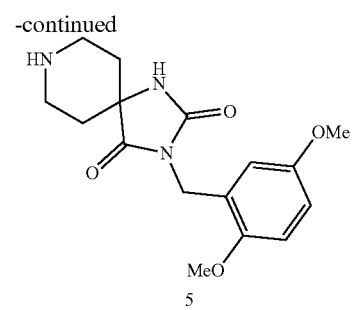

To a mixture of compound 4 (410 mg, 977.42 umol, 1 eq) in EtOAc (5 mL) was added HCl/EtOAc (10 mL) (4 M), and then the mixture was stirred at 15° C. for 12 hr. There was white solid to precipitate. TLC (Petroleum ether:Ethyl acetate=1:1, $R_f$=0) indicated compound 4 was consumed completely and one new spot formed. The reaction mixture was concentrated under reduced pressure to give a residue. The crude product was used into the next step without further purification. Compound 5 (310 mg, crude) was obtained as a white solid, and checked by HNMR. ¹H NMR (400 MHz, DMSO-d6) δ ppm 9.21 (br s, 1H), 9.07 (s, 1H), 8.89 (br s, 1H), 6.92 (d, J=9.0 Hz, 1H), 6.80 (dd, J=3.1, 8.8 Hz, 1H), 6.44 (d, J=3.1 Hz, 1H), 4.46 (s, 2H), 3.73 (s, 3H), 3.67-3.55 (m, 3H), 3.36-3.33 (m, 2H), 3.14 (br d, J=9.9 Hz, 2H), 2.19-2.02 (m, 2H), 1.90-1.72 (m, 2H).

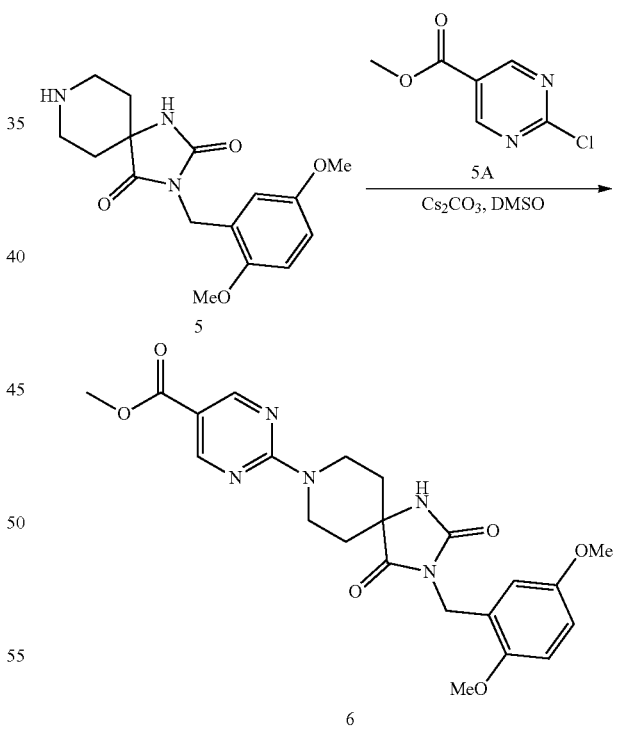

To a mixture of compound 5 (200 mg, 562.09 umol, 1 eq, HCl) in DMSO (5 mL) was added Cs₂CO₃ (549.42 mg, 1.69 mmol, 3 eq) and 5A (97.00 mg, 562.09 umol, 1 eq) at 25° C., the reaction was stirred at 15° C. for 10 hr. LCMS showed compound 5 was consumed completely and one main peak with desired mass was detected. The reaction mixture was added water (15 mL), filtered and the filtered cake was concentrated under reduced pressure to give a residue. The crude product was used into the next step without further purification. Compound 6 (210 mg, 413.53 umol, 73.57% yield, 89.69% purity) was obtained as a white solid, and checked by HNMR and HPLC. LCMS: RT=1.421 min, MS cal.: 455.1, [M+H]+=456.1. ¹H NMR (400 MHz, CHLOROFORM-d) δ ppm 8.85 (s, 2H), 6.79-6.74 (m, 2H), 6.72-6.66 (m, 2H), 4.70 (s, 2H), 4.61 (td, J=4.9, 14.0 Hz, 2H), 3.89 (s, 3H), 3.82-3.76 (m, 3H), 3.73 (s, 3H), 3.69-3.59 (m, 2H), 2.11 (ddd, J=4.1, 9.6, 13.6 Hz, 2H), 1.84-1.66 (m, 2H). HPLC: RT=2.725 min. In some embodiments, LCMS and/or HPLC runs for compounds of the present disclosure may use different conditions and different retention times for the same compound may be observed for different runs.

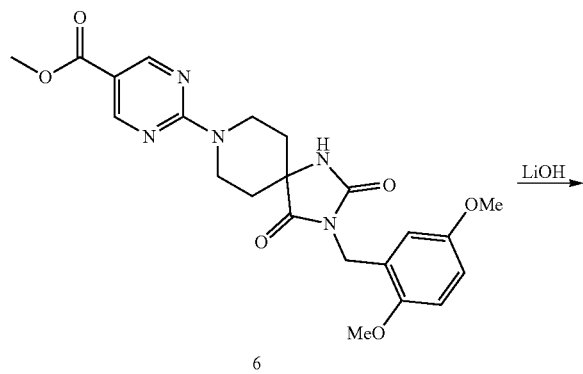

6

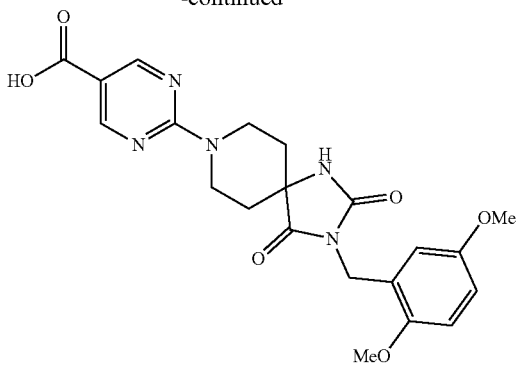

7

To a solution of compound 6 (150 mg, 329.34 umol, 1 eq) in THF (10 mL) MeOH (3 mL) was added LiOH·H₂O (55.28 mg, 1.32 mmol, 4 eq) in H₂O (0.8 mL). The mixture was stirred at 15° C. for 36 hr. LCMS showed part of compound 6 was remained. One new peak with desired compound was detected. The reaction mixture was added water (15 mL), and extracted with Ethyl acetate (20 mL*3). The water layer was added aq.HCl (0.5M) to adjust the pH-4, and extracted with ethyl acetate (20 mL*3). The combined organic layers were dried over Na₂SO₄, filtered and concentrated under reduced pressure to give a residue. The crude product was used into the next step without further purification. Compound 7 (110 mg, 249.19 umol, 75.66% yield) was obtained as a white solid, and checked by HNMR. LCMS: RT=1.139 mins, MS cal.: 441.1, [M+H]+=442.0. ¹H NMR (400 MHz, DMSO-d6) δ ppm 9.04 (s, 1H), 8.80-8.75 (m, 2H), 6.92 (d, J=8.8 Hz, 1H), 6.80 (dd, J=3.0, 8.9 Hz, 1H), 6.44 (d, J=3.1 Hz, 1H), 4.62-4.52 (m, 2H), 4.48 (s, 2H), 3.76-3.70 (m, 3H), 3.65 (s, 3H), 3.57-3.47 (m, 2H), 1.89-1.79 (m, 2H), 1.73-1.65 (m, 2H).

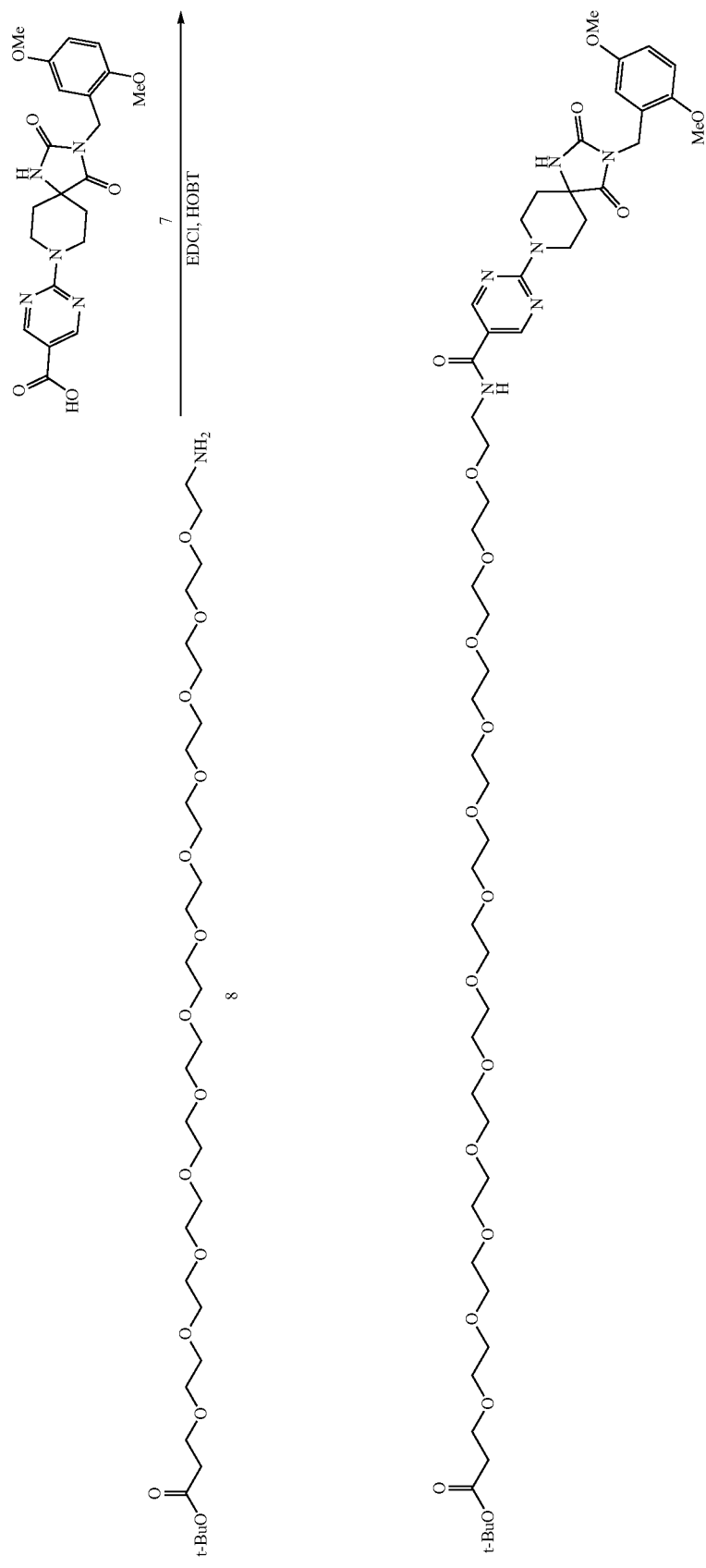

To a solution of compound 8 (137.38 mg, 203.88 umol, 0.9 eq), compound 7 (100 mg, 226.53 umol, 1 eq) in DCM (8 mL), DMF (1 mL) was added EDCI (65.14 mg, 339.80 umol, 1.5 eq) and HOBt (45.91 mg, 339.80 umol, 1.5 eq), DIPEA (117.11 mg, 906.13 umol, 157.83 uL, 4 eq). The mixture was stirred at 15° C. for 12 hr. LCMS showed compound 8 was consumed completely and one main peak with desired mass was detected. The reaction mixture was watched with aq.NH$_4$Cl (10 mL) one time watched with water (10 mL) three times, and extracted with DCM (10 mL*2). The combined organic layers were washed with aq.NaCl (5 mL*1), dried over Na$_2$SO$_4$, filtered and concentrated under reduced pressure to give a residue. The crude product was used into the next step without further purification. Compound 9 (230 mg, crude) was obtained as a yellow oil. LCMS: RT=1.265 mins, MS cal.: 1096.5, [M+H]$^+$=1097.9.

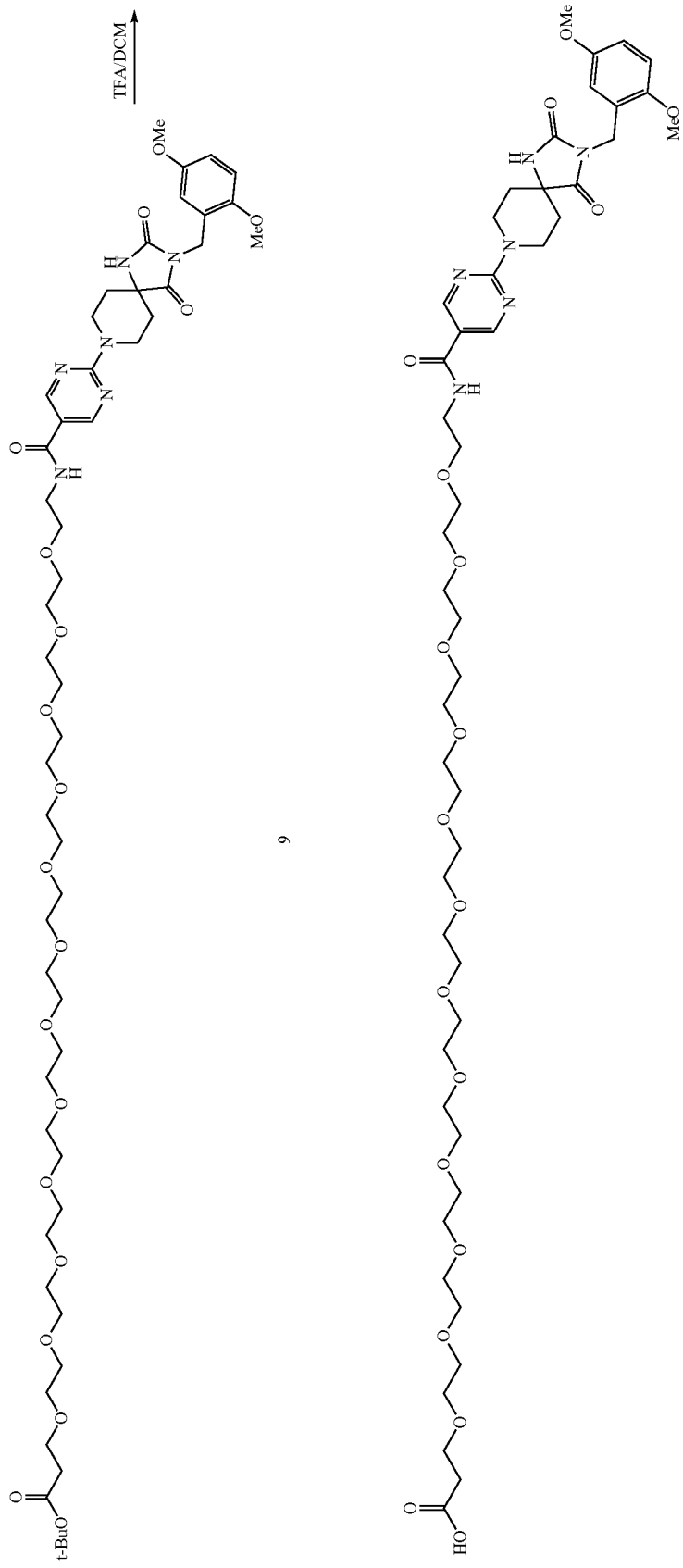

A mixture of compound 9 (100 mg, 91.14 umol, 1 eq) in DCM (6 mL), TFA (3 mL) was stirred at 15° C. for 12 hr. TLC (Dichloromethane:Methanol=8:1, $R_f$=0.05) indicated compound 9 was consumed completely and one new spot formed. The reaction mixture was concentrated under reduced pressure to give a residue. The residue was freeze-dried by the lyophilization. The crude product was used into the next step without further purification. Compound 10 (110 mg, crude) was obtained as a yellow oil.

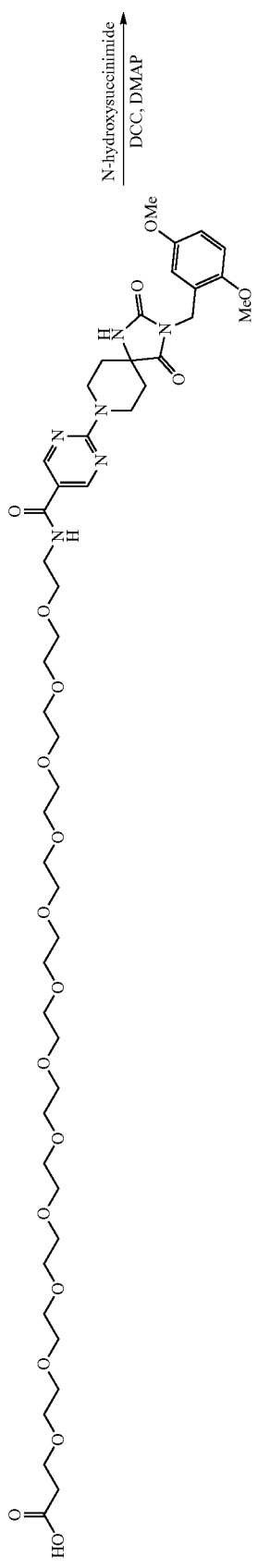
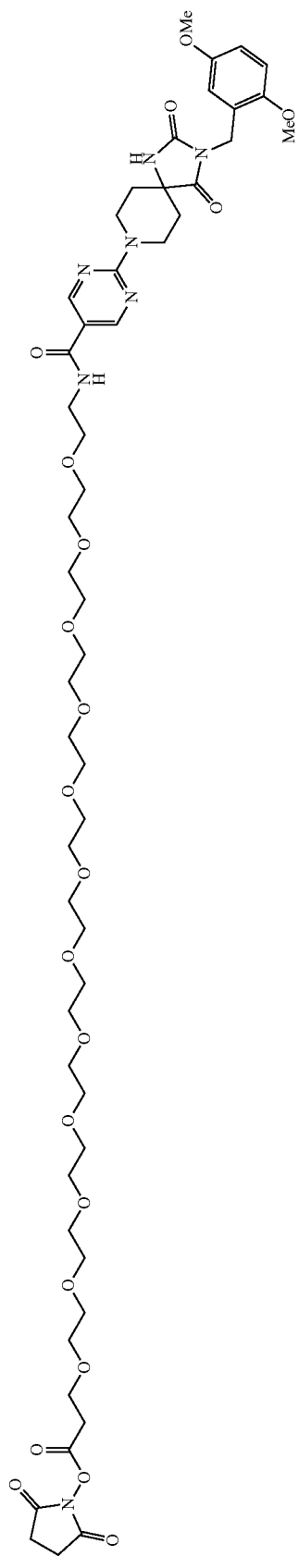
I-97

To a solution of compound 10 (100 mg, 96.05 umol, 1 eq), N-hydroxysuccinimide (33.16 mg, 288.14 umol, 3 eq) in DCM (8 mL), DMSO (1 mL) was added DCC (59.45 mg, 288.14 umol, 58.29 uL, 3 eq) and DMAP (35.20 mg, 288.14 umol, 3 eq). The mixture was stirred at 15° C. for 12 hr. There was solid to precipitate. LCMS and HPLC showed compound 10 was consumed completely and one main peak with desired mass was detected. The reaction mixture was filtered and the filtrate was concentrated under reduced pressure to give a residue. The residue was purified by prep-HPLC (TFA condition). I-97 (40.1 mg, 34.85 umol, 36.29% yield, 98.93% purity) was obtained as a yellow oil, and checked by HNMR and QC LCMS. LCMS: RT=1.037 min, MS cal.: 1137.5, $[M+H]^+$=1138.8. HPLC: RT=2.635 min. QC LCMS: RT=1.156 min, MS cal.: 1137.5, $[1/2M+H]^+$=569.9. $^1$H NMR (400 MHz, CHLOROFORM-d) δ ppm 8.74 (s, 2H), 7.14 (s, 1H), 6.92 (br s, 1H), 6.78-6.70 (m, 2H), 6.65 (d, J=2.4 Hz, 1H), 4.67 (s, 2H), 4.55 (td, J=4.6, 9.1 Hz, 2H), 3.82 (t, J=6.5 Hz, 2H), 3.76 (s, 3H), 3.70 (s, 3H), 3.68-3.53 (m, 50H), 2.88 (t, J=6.4 Hz, 2H), 2.82 (br s, 4H), 2.15-1.97 (m, 2H), 1.72 (br d, J=14.1 Hz, 2H).

Example 47: Biotinylated Ligand ELISA Assay

Coat ELISA plates (Costar 3922) using Neutravidin (Thermo 31000) at 5 μg/ml (100 μl/well) for 1 hour at 37° C. Plates were washed 4 times with PBST (PBS, 0.05% Tween 20-200 μl, 1 minute/wash) then blocked using 200 μl 5% bovine serum albumin (BSA, Heat Shock, Fraction V-American Bio AB01088-00100) in PBST for 2 hours at 25° C. with moderate shaking. BSA was removed and plates were washed. Biotinylated ligands diluted in PBSTB (PBST+0.1% BSA) were then added (100 μl/well) and incubated for 1 hour at 25° C. with gentle shaking. Ligands were removed and plates were washed. Any remaining unoccupied neutravidin binding sites were blocked by adding 100 μM Biotin (Fisher BP232-1) (100 μl/well) and incubated for 1 hour at 25° C. with gentle shaking. Plates were then washed. Biotinylated CD16a protein (158F and 158V) at 10 nM in PBSTB was then added (100 μl/well) and incubated for 1 hour at 25° C. with gentle shaking. Protein was removed and plates were washed. Streptavidin-HRP (Invitrogen 434323) diluted 1:5000 in PBSTB was added (100 μl/well) and incubated for 1 hour at 25° C. with gentle shaking. Wash plates. Substrate (Super Signal ELISA Pico Chemiluminescent Substrate-Thermo 37069) was added (100 μl/well) and plates were incubated for 5 minutes at 25° C. with gentle shaking. Luminescence was then measured on the Biotek Synergy H1 microplate reader.

Table 2 shows the activity (RLU) of selected compounds of this invention. The compound numbers correspond to the compound numbers in Table 1. Compounds having an activity designated as "A" provided a relative luminescence value (RLU) of >100,000; compounds designated as "B" provided a relative luminescence value (RLU) of 10,000-100,000; compounds designated as "C" provided a relative luminescence value (RLU) of 1,000-10,000 and compounds designated as "D" provided a relative luminescence value (RLU) of 1-1,000.

TABLE 2

Biotinylated Ligand ELISA Assay Results

| Compound Number | Biotinylated Ligand ELISA-CD16a158V Binding (RLU) | Biotinylated Ligand ELISA-CD16a158F Binding (RLU) |
|---|---|---|
| I-15 | B | B |
| I-16 | D | D |
| I-17 | D | D |
| I-18 | D | D |
| I-19 | D | D |
| I-21 | A | A |
| I-22 | B | B |
| I-27 | B | B |
| I-28 | B | B |
| I-31 | C | C |
| I-36 | C | C |
| I-39 | C | C |

Example 48: NHS-Ester ELISA Assay

Pretreat ELISA plates (Costar 3922) using 200 μl 500 bovine serum albumin (BSA, Heat Shock, Fraction V-American Bio AB01088-00100) in PBS for 2 hours at 25° C. with moderate shaking. BSA was removed and plates were washed. NHS-Ester ligands were diluted in PBS to 250 μM then added (100 μl/well) and incubated for 1 hour at 37° C. While the plates are incubating, 10 nM biotinylated CD16a protein (158F and 158V) in PBSTB was preincubated with Streptavidin-HRP (Invitrogen 434323) diluted 1:5000 in PBSTB for 1 hour at 25° C. with mixing. Plates are removed from the incubator and washed. CD16a/Streptavidin.HRP mixture was added to the plates (100 μl/well) and incubated for 1 hour at 25° C. with gentle shaking. Wash plates. Substrate (Super Signal ELISA Pico Chemiluminescent Substrate-Thermo 37069) was added (100 μl/well) and plates were incubated for 5 minutes at 25° C. with gentle shaking. Luminescence was then measured on the Biotek Synergy H1 microplate reader.

Table 3 shows the activity (RLU) of selected compounds of this invention. The compound numbers correspond to the compound numbers in Table 1. Compounds having an activity designated as "A" provided a relative luminescence value (RLU) of >100,000; compounds designated as "B" provided a relative luminescence value (RLU) of 10,000-100,000; compounds designated as "C" provided a relative luminescence value (RLU) of 1,000-10,000 and compounds designated as "D" provided a relative luminescence value (RLU) of 1-1,000.

TABLE 3

NHS-Ester ELISA Assay Results

| Compound Number | NHS ester ELISA-CD16a158V Binding (RLU) | NHS ester ELISA-CD16a158F Binding (RLU) |
|---|---|---|
| I-1 | C | B |
| I-2 | C | B |
| I-6 | B | B |
| I-7 | B | C |
| I-8 | B | C |
| I-9 | B | B |
| I-25 | C | C |
| I-26 | C | C |

Example 49: Microscale Thermophoresis

Target proteins (poly-histidine tagged, 600 nM) were fluorescently labeled combination with an equal volume of dye (200 nM, His-Tag labeling kit RED-tris-NTA NanoTemper: MO-L008) PBST. The mixture rotated in the dark for 45 min before being spun down at 12000 rpm for 15 min to remove uncomplexed material. The fluorescence of the removed supernatant was adjusted to for a test concentration of 40-80 nM (2× the final measured). Test ligands were prepared across a 12-point dilution series in a 96-well PCR plate at a volume of 20 uL at 2× the concentration desired for testing (0.2% BSA in PBST). The dilution series was then combined with an equal volume of the labeled target at 2× the concentration desired for testing. Capillaries were added to the wells of the combined target/ligand complex and measured by MST. Measurements were taken using a Nanotemper Monolith NT.115, and the data was analyzed using NanoTemper MO.Control software.

Table 4 shows the equilibrium dissociation constant ($K_d$) of selected compounds of this invention. The compound numbers correspond to the compound numbers in Table 1. Compounds having an activity designated as "A" provided an equilibrium dissociation constant ($K_d$) of 1-100 nM; compounds designated as "B" provided an equilibrium dissociation constant ($K_d$) of 100-500 nM; compounds designated as "C" provided an equilibrium dissociation constant ($K_d$) of 500-1,000 nM and compounds designated as "D" provided an equilibrium dissociation constant ($K_d$) of >1,000 nM. Compounds not tested in the assay are designated as "NA".

TABLE 4

Microscale Thermophoresis Results

| Compound Number | MST-CD16a158V KD (nM) | MST-CD16a158F KD (nM) |
|---|---|---|
| I-27 | NA | B |
| I-28 | NA | B |
| I-29 | B | B |
| I-30 | NA | D |
| I-31 | NA | C |
| I-33 | B | NA |
| I-34 | B | NA |
| I-35 | B | NA |
| I-36 | A | NA |
| I-37 | C | NA |
| I-38 | B | NA |
| I-39 | B | NA |
| I-40 | B | NA |
| I-41 | C | NA |

Example 50: Primary Monocyte or THP Cell ADCP Assay

Bead Preparation

Biotinylated fluorescent beads (Invitrogen, cat #P35372) were thoroughly mixed by vortexing for 1 min. Ten microliters of supplied bead suspension per treatment type were dispensed in Eppendorf tubes, and washed with 1 ml PBS 100 BSA, then re-suspended in 500 uL of 1% BSA in PBS. Test compounds were added to bead suspensions to a final concentration of 50 uM, and biotinylated human IgG whole molecule (Rockland 009-0602) final concentration of 20 ug/mL.

Tubes were incubated at room temperature for 1 hr on a rocking platform.

Following incubation, beads were pelleted in a microcentrifuge at 12,000 g for 5 minutes at room temperature. Supernatants were carefully aspirated and beads were washed 5 times by resuspending in 1 ml of PBS 1% BSA, and centrifuging as described above. Finally, beads were resuspended in 500 ul of PBS 1% BSA and used in ADCP assay.

Primary Monocyte Enrichment by Adhesion

PBMC, freshly isolated from whole blood (Bioreclamation IVT0) using Ficoll-Paque density centrifugation were resuspended in serum-free, supplemented RPMI at $2 \times 10^6$ cells/mL.

Ten milliliters of the resulting cell suspension was seeded into 75-$cm^2$ tissue culture flask (Denville Scientific TC9341) and incubated 2-3 hr at 37° C. 5% $CO_2$ to allow cell adhesion. Following incubation, media was decanted and surface of the flask was carefully washed twice, each time with 10 ml serum-free, supplemented RPMI to remove any residual non-adherent cells. To remove adherent cells, 10 mL of ice-cold 2.5 mM EDTA/PBS solution was added for 10 min on ice. Cells were transferred to a 15-ml conical tube and centrifuge 10 min at 300×g, room temperature, to remove the EDTA/PBS solution. Monocytes were then resuspended in RPMI 10% FCS at $5 \times 10^5$ cells/mL to be used in ADCP assay. Monocyte purity was assessed by staining cells with antibodies to human CD3 FITC (Biolegend 300306), CD19 PeCy7 (Biolegend 302216), CD14 BV421 (BD Biosciences, 565283), and CD16 (Biolegend 302046).

ADCP Assay Using Fresh Primary Monocytes or THP-1 Cells

Monocytes or THP-1 cells (TIB-202 ATCC) were seeded into 96 well round bottom 96 well plates at the density of 105 cells per well in 200 ul, and 10 uL of fluorescent bead suspension prepared as described above was added to each well. Well contents were mixed by pipetting up and down using a multichannel pipet, and plates were incubated at 37C for 18 hrs. After incubation, well contents were transferred into flat bottom black 96 well plates (Costar #3358) and centrifuged for 2 minutes at 300 g to allow for better visualization of the cells. Images were taken using Zoe fluorescent cell imager (Biorad).

Table 5 shows the normalized phagocytosis score of selected compounds of this invention. The compound numbers correspond to the compound numbers in Table 1. Compounds having an activity designated as "A" provided a normalized phagocytosis score of >2.0; compounds designated as "B" provided a normalized phagocytosis score of 1.5-2.0; compounds designated as "C" provided a normalized phagocytosis score of 1.0-1.5 and compounds designated as "D" provided a normalized phagocytosis score of 0.5-1.0. Compounds not tested in the assay are designated as "NA".

TABLE 5

Primary Monocyte and THP cell ADCP assay Results

| Compound Number | ACDP (primary monocytes)-normalized phagocytosis score | ACDP (CD16a negative THP1 cells)-normalized phagocytosis score |
|---|---|---|
| I-16 | B | NA |
| I-17 | C | B |
| I-18 | NA | B |

TABLE 5-continued

Primary Monocyte and THP cell ADCP assay Results

| Compound Number | ACDP (primary monocytes)- normalized phagocytosis score | ACDP (CD16a negative THP1 cells)-normalized phagocytosis score |
|---|---|---|
| I-21 | C | D |
| I-27 | A | B |
| I-36 | B | B |
| I-39 | B | B |

Example 51: NHS-Ester Labeling

Anti-CD20 antibodies Rituximab (Absolute Antibody, Ab-00126-10.3-BT, 1 mg/ml in PBS) and Rituximab FcSilent (Absolute Antibody, Ab-00126-10.0-BT, 1 mg/ml in PBS) were labeled with NHS-Ester MATE analogs by incubating together in 100 mM Na Bicarbonate buffer (Sigma S5761, pH 8.0) for 1 hour at 25° C. Unbound MATE is removed using Amicon centrifugal filters (Millipore UFC503096, 0.5 ml, 30K) by washing twice with 400 ul of Na bicarbonate buffer followed by one wash with PBS (phosphate buffered saline, Gibco 10010).

Example 52: PEG ELISA

MATE conjugated antibodies (2 µg/ml in PBS) were used to coat ELISA plates (Costar 3922) using 100 µl/well for 1 hour at 37° C. Plates were washed 4 times (200 µl PBS, 1 minute/wash) then blocked using 200 µl 5% bovine serum albumin (BSA, Heat Shock, Fraction V-American Bio AB01088-00100) in PBS for 2 hours at 25° C. with moderate shaking. BSA was removed and plates were washed. Unlabeled anti-PEG antibody (Life Diagnostics 9B5-6-25-7) at 0.05 µg/ml in PBSB (PBS, 0.1% BSA) was then added (100 µl/well) and incubated for 1 hour at 25° C. with gentle shaking. Antibody was removed and plates were washed. HRP labeled Goat Anti-mouse IgG$_1$ (Southern Biotech, 1071-05) diluted 1:5000 in PBSB (100 µl/well) was added and incubated for 1 hour at 25° C. with gentle shaking. Wash plates and blot dry. Substrate (Super Signal ELISA Pico Chemiluminescent Substrate-Thermo 37069) was added (100 µl/well) and plates were incubated for 5 minutes at 25° C. with gentle shaking. Luminescence was then measured on the Biotek Synergy H1 microplate reader.

Table 6 shows the anti-PEG antibody binding of selected compounds of this invention. The compound numbers correspond to the compound numbers in Table 1. Compounds having an binding value designated as "A" provided anti-PEG antibody binding of >2.0 relative to Rituximab; compounds designated as "B" provided anti-PEG antibody binding of 1.0-2.0 relative to Rituximab; compounds designated as "C" provided anti-PEG antibody binding of 0.5-1.0 relative to Rituximab.

TABLE 6

PEG ELISA Results[a]

| Compound Number and Description | Anti-PEG Antibody Binding (Normalized* Signal) |
|---|---|
| Rituximab (unlabeled)* | — |
| Rituximab labeled with I-25 (A) | A |
| Fc Silent Ritux. (unlabeled) | C |
| Fc Silent Ritux. Labeled with I-25 (A) | A |

*Note:
Anti-PEG Antibody (1D9-6) at 0.4 ug/mL;
[a]Antibody conjugation condition (A) uses a 1 mM concentration of NHS ester according to the protocol of Example 51.

Example 53: CD16a—MATE ELISA

Coat ELISA plates (Costar 3922) using Neutravidin (Thermo 31000) at 5 µg/ml in PBS (100 µl/well) for 1 hour at 37° C. Plates were washed 4 times with PBST (PBS, 0.05% Tween 20-200 µl, 1 minute/wash) then blocked using 200 µl 5% bovine serum albumin (BSA, Heat Shock, Fraction V-American Bio AB01088-00100) in PBST for 2 hours at 25° C. with moderate shaking. BSA was removed and plates were washed. Biotinylated CD16a protein (158F-Acro Biosystems #CDA-H82E8, 158V-Acro Biosystems #CDA-H82E9) at 5 nM in PBSTB (PBST+0.1% BSA) was then added (100 µl/well) and incubated for 1 hour at 25° C. with gentle shaking. Protein was removed and plates were washed. MATE labeled antibodies diluted to 1 µg/ml in PBSTB (100 µl/well) were added and incubated for 1 hour at 25° C. with gentle shaking. Wash plates. HRP labeled Mouse Anti-Human IgG, F(ab')$_2$ (Jackson Immuno Research 209-035-097) diluted 1:2500 in PBSTB was added (100 µl/well) and incubated for 1 hour at 25° C. with gentle shaking. Wash plates. Substrate (Super Signal ELISA Pico Chemiluminescent Substrate-Thermo 37069) was added (100 µl/well) and plates were incubated for 5 minutes at 25° C. with gentle shaking. Luminescence was then measured on the Biotek Synergy H1 microplate reader.

Table 7 shows the CD16a—MATE ELISA results of selected compounds of this invention. The compound numbers correspond to the compound numbers in Table 1. Compounds designated as "A" provided an ELISA result of >300% relative to Rituximab; compounds designated as "B" provided an ELISA result of 200-300% relative to Rituximab; compounds designated as "C" provided an ELISA result of 100-200% relative to Rituximab; compounds designated as "D" provided an ELISA result of 50-100% relative to Rituximab; and compounds designated as "E" provided an ELISA result of 1-50% relative to Rituximab.

TABLE 7

Lysine Conjugated MATES-CD16a binding ELISA Results

| Compound Number and Description | CD16a158V Normalized* Response (%) | CD16a158F Normalized* Response (%) |
|---|---|---|
| Rituximab (unlabeled)* | C | C |
| Rituximab labeled with I-25 (A)[a] | D | C |
| Rituximab labeled with I-25 (B) | C | B |
| Rituximab labeled with I-9 (D) | C | C |
| Rituximab labeled with I-9 (C) | C | A |
| Rituximab labeled with I-8 (C) | C | C |
| Rituximab labeled with I-6 (C) | C | C |
| Rituximab labeled with I-2 (C) | C | C |
| Rituximab labeled with I-1 (C) | D | D |
| Fc Silent Ritux. (unlabeled) | E | E |

TABLE 7-continued

Lysine Conjugated MATES-CD16a binding ELISA Results

| Compound Number and Description | CD16a158V Normalized* Response (%) | CD16a158F Normalized* Response (%) |
|---|---|---|
| Fc Silent Riuximab labeled with I-25 (A) | E | E |
| Fc Silent Riuximab labeled with I-25 (B) | D | E |
| Fc Silent Riuximab labeled with I-9 (D) | E | E |
| Fc Silent Riuximab labeled with I-9 (C) | E | E |
| Fc Silent Riuximab labeled with I-8 (C) | E | E |
| Fc Silent Riuximab labeled with I-6 (C) | E | E |
| Fc Silent Riuximab labeled with I-2 (C) | E | E |
| Fc Silent Riuximab labeled with I-1 (C) | E | E |

*antibodies tested at 2 ug/mL
[a] Antibody conjugation condition (A) uses a 1 mM concentration of NHS ester, antibody conjugation condition (B) uses a 0.25 mM concentration of NHS ester, antibody conjugation condition (C) uses a 0.1 mM concentration of NHS ester, and antibody conjugation condition (D) uses a 0.02 mM concentration of NHS ester according to the protocol of Example 15X..

Table 8 shows the CD16a—MATE ELISA results of selected compounds of this invention. The compound numbers correspond to the compound numbers in Table 1. Compounds designated as "A" provided an ELISA result of >50% relative to Rituximab; compounds designated as "B" provided an ELISA result of 25-50% relative to Rituximab; compounds designated as "C" provided an ELISA result of 15-25% relative to Rituximab; compounds designated as "D" provided an ELISA result of 5-15% relative to Rituximab; and compounds designated as "E" provided an ELISA result of 1-5% relative to Rituximab.

TABLE 8

Carbohydrate Conjugated MATEs-CD16a binding ELISA results

| Compound Number and Description | CD16a158V Normalized* Response (%) | CD16a158F Normalized* Response (%) |
|---|---|---|
| Rituximab (unlabeled)* | — | — |
| Rituximab (UDP-GalNAz labeled) | C | C |
| Rituximab labeled with I-5 | B | B |
| Rituximab labeled with I-42 | B | B |
| Rituximab labeled with I-4 | B | B |
| Rituximab labeled with I-3 | B | C |
| Fc Silent Ritux. (UDP-GalNAz labeled) | D | D |
| Fc Silent Riuximab labeled with I-5 | D | D |
| Fc Silent Riuximab labeled with I-42 | D | D |
| Fc Silent Riuximab labeled with I-4 | D | D |

*Antibodies tested at 2 ug/mL.

Example 54: Ternary Assay

CD16a fluorescent labeling—Equal volumes of 400 nM CD16a$^{158V}$ or CD16a$^{158F}$ were combined with 600 nM Streptavidin AlexaFluor 488 (Thermo S11223) in PBST (PBS+0.05% Tween 20) and incubated for 30 minutes in the dark at 25° C. with rotation. Dilute 1:40 in buffer (PBS, 1% BSA, 2 mM EDTA, pH 7.4) for a final CD16a concentration of 5 nM.

Cd20/MATE Antibody CD16a Binding—RAJI cells endogenously expressing human CD20 are diluted to 1×10$^6$/ ml in buffer. Cells (50 µl) are combined with MATE labeled Rituximab (50 µl) in V-bottom plates (Falcon 353263) and incubated for 30 minutes at 4° C. Add 150 µl buffer, centrifuge for 5 minutes at 300×g. Remove buffer and resuspend cells in 150 µl CD16a-AF488 conjugate. Incubate for 30 minutes at 4° C. Add 150 µl buffer and centrifuge for 5 minutes at 300×g. Resuspend cells in 200 µl buffer, transfer to 5 ml tubes and analyze by flow cytometry (BD FACSCelesta). Data was collected using BD DIVA software.

Table 9 shows the percent Raji cell-mAb-labeled CD16a Ternary complex formed relative to Rituximab with selected compounds of this invention. The compound numbers correspond to the compound numbers in Table 1. Compounds designated as "A" provided a response >200% relative to Rituximab; compounds designated as "B" provided a response 100-200% relative to Rituximab; compounds designated as "C" provided a response of 10-100% relative to Rituximab; compounds designated as "D" provided a response of 1-10% relative to Rituximab; and compounds designated as "E" provided a response of 0.1-1% relative to Rituximab.

TABLE 9

Ternary Assay Results

| Compound number and description | CD16a158V Normalized* Response (%) | CD16a158F Normalized* Response (% |
|---|---|---|
| Rituximab (unlabeled)* | | |
| Rituximab labeled with I-25 (A)[a] | B | B |
| Rituximab labeled with I-25 (B) | B | A |
| Fc Silent Ritux. (unlabeled) | E | E |
| Fc Silent Riuximab labeled with I-25 (A) | D | D |
| Fc Silent Riuximab labeled with I-25 (B) | D | C |

*Antibodies tested at 2 ug/mL.
[a] Antibody conjugation condition (A) uses a 1 mM concentration of NHS ester and antibody conjugation condition (B) uses a 0.25 mM concentration of NHS ester, according to the protocol of Example 15.

Example 55: Interaction with Various Receptors

Using similar methods as Examples 47 or 53, interactions with a number of receptors were measured. In some embodiments, "stock" is antibody only, and "control" is an antibody that went through the same procedure except using DMSO only as opposed to a compound. When contacted with targeting moieties such as antibodies in the Examples, compounds, e.g., I-95, I-96, etc. can react through their reactive groups

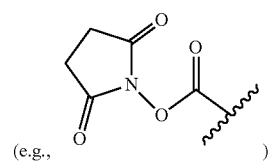 [SMILES: *C(=O)ON1C(=O)CCC1=O]

(e.g., )

with reactive groups of targeting moieties (e.g., —NH$_2$) to form conjugates by forming amide groups (—C(O)NH—). Certain results were presented in Tables below. As demonstrated herein, in some embodiments, compounds of the present disclosure can significantly enhance binding to both low- and high-affinity CD16a. In some embodiments, certain compounds selectively bind to CD16a over one or more other receptors.

TABLE 10

Certain Biotin ELISA Results

| ID | CD16a-158V | | | CD16a-158F | | | CD32a-H167 | | | CD32a-R167 | | |
|---|---|---|---|---|---|---|---|---|---|---|---|---|
| I-36 | −378 | −180 | −282 | 2154 | −1155 | −213 | 1138 | 43 | 249 | 280 | −228 | −1215 |
| I-31 | 2241 | 1940 | 2108 | 1915 | 592 | 1294 | 3965 | 4173 | 4715 | 4134 | 3245 | 4916 |
| I-21 | 5747 | 5338 | 6303 | 6775 | 6468 | 5831 | 15126 | 14461 | 15658 | 12004 | 10942 | 9796 |
| I-19 | −544 | −988 | −964 | −1097 | −1078 | −689 | 276 | 696 | −362 | 2048 | −50 | 349 |
| I-17 | 443 | 2316 | 1591 | 122 | 5830 | 2636 | 1642 | 1978 | 2246 | 11182 | 5954 | 10675 |
| I-16 | 2543 | 5076 | 2414 | 19818 | 20544 | 2349* | 3600 | 3315 | 3632 | 8460 | 31058 | 13897 |
| I-15 | 3136 | 3515 | 1518 | 34842 | 7323* | 23569 | 5263 | 6063 | 4354 | 11818 | 37679* | 11737 |
| I-13 | 4673 | 4920 | 4565 | 10817 | 15276 | 9605 | 15516 | 14898 | 8681 | 8032 | 6483 | 10638 |

| ID | CD64 | | | CD32b | | | CD3ed | | | No Protein | | |
|---|---|---|---|---|---|---|---|---|---|---|---|---|
| I-36 | 54153 | 79621 | 89966 | 98 | 1052 | 486 | 1016 | −29 | −4459 | −764 | −989 | −154 |
| I-31 | 68732 | 70002 | 48114 | 3983 | 3476 | 6119 | 2134 | 3894 | 2741 | 2129 | 3223 | 1542 |
| I-21 | 98211 | 69008 | 131784 | 14249 | 14080 | 11349 | 8285 | 6369 | 7518 | 7902 | 6992 | 7029 |
| I-19 | 40706 | 42386 | 41814 | 2072 | 737 | 1622 | 1852 | 1310 | 797 | 1266 | 122 | 3990 |
| I-17 | 44623 | 46028 | 52372 | 2439 | 955 | 1191 | 1412 | 1083 | 1250 | −236 | −272 | 237 |
| I-16 | 40426 | 53812 | 48052 | 3985 | 5047 | 3438 | 3087 | 4575 | 2480 | 4636 | 2801 | 5055 |
| I-15 | 43288 | 127129* | 49818 | 10786 | 29882* | 8282 | 7926 | 1921 | 46693* | 3931 | 5958 | 23315* |
| I-13 | 45845 | 36876 | 49943 | 7721 | 7105 | 9481 | 4252 | 15476 | 72836* | 6804 | 19233 | 14386 |

*indicates data points that may be excluded during analysis.

TABLE 11

Certain MATE ELISA Results

| Test | CD16a 158V | | | CD16a 158F | | | CD32a H167 | | |
|---|---|---|---|---|---|---|---|---|---|
| Cetuximab Stock | 557543 | 532928 | 529943 | 15855 | 14459 | 14766 | 273263 | 268286 | 272632 |
| Cetuximab + I-96 | 2186681 | 2078514 | 2072135 | 819327 | 765749 | 788792 | 2338090 | 2346689 | 2213024 |
| Cetuximab + I-95 | 2399231 | 2371289 | 2390044 | 987986 | 1000152 | 1012877 | 2433654 | 2486468 | 2397286 |
| Cetuximab Control | 503765 | 480337 | 469282 | 14030 | 14411 | 14081 | 265018 | 264410 | 265400 |
| Daratumumab Stock | 1620411 | 1552077 | 1528816 | 115898 | 112403 | 115267 | 605712 | 610503 | 600562 |
| Daratumumab + I-96 | 2882789 | 2728924 | 2749915 | 1326273 | 1289896 | 1296241 | 2990916 | 2815968 | 2823898 |
| Daratumumab + I-95 | 3047833 | 2968333 | 2914192 | 1642326 | 1575716 | 1583813 | 3122704 | 3113179 | 3018268 |
| Daratumumab Control | 1407940 | 1365053 | 1337882 | 82022 | 81780 | 84907 | 485766 | 481839 | 470053 |
| No Antibody | 117 | 80 | 326 | 311 | 119 | 136 | 244 | 92 | 104 |

| Test | CD32a R157 | | | CD32b | | | CD16b | | |
|---|---|---|---|---|---|---|---|---|---|
| Cetuximab Stock | 66014 | 62721 | 61607 | 4047 | 3689 | 3947 | 856 | 771 | 755 |
| Cetuximab + I-96 | 1838546 | 1788810 | 1784189 | 877143 | 854722 | 838928 | 286225 | 275368 | 317909 |
| Cetuximab + I-95 | 2033693 | 2007077 | 1941991 | 1052716 | 1057385 | 1031705 | 417422 | 409499 | 397621 |
| Cetuximab Control | 62533 | 60692 | 58018 | 4039 | 3862 | 3812 | 812 | 880 | 869 |
| Daratumumab Stock | 191107 | 178941 | 172544 | 26838 | 27508 | 27204 | 9837 | 10111 | 9704 |
| Daratumumab + I-96 | 2426742 | 2380992 | 2382109 | 1235999 | 1213063 | 1258553 | 561396 | 551764 | 577356 |
| Daratumumab + I-95 | 2784744 | 2763329 | 2697889 | 1625771 | 1640163 | 1594964 | 859870 | 850569 | 864323 |
| Daratumumab Control | 125444 | 122409 | 116704 | 9479 | 9358 | 9228 | 3125 | 3086 | 3079 |
| No Antibody | 468 | 151 | 193 | 4205* | 188 | 81 | 150 | 93 | 105 |

| Test | CD3ed | | | CD38 | | |
|---|---|---|---|---|---|---|
| Cetuximab Stock | 299 | 349 | 572 | 827 | 218 | 164 |
| Cetuximab + I-96 | 7931 | 10527 | 8101 | 12215 | 10213 | 11279 |
| Cetuximab + I-95 | 16873 | 16717 | 17170 | 20968 | 20486 | 18548 |
| Cetuximab Control | 264 | 254 | 559 | 1022 | 422 | 368 |
| Daratumumab Stock | 1082 | 156 | 514 | 2774292 | 2759241 | 2729813 |
| Daratumumab + I-96 | 16023 | 15092 | 17080 | 2769603 | 2714239 | 2754398 |
| Daratumumab + I-95 | 39488 | 48916 | 45390 | 2873958 | 2835833 | 2859523 |
| Daratumumab Control | 219 | 257 | 505 | 2893900 | 2774268 | 2739576 |
| No Antibody | 203 | 177 | 153 | 93 | 143 | 109 |

*indicates data points that may be excluded during analysis.

TABLE 12

Certain MATE ELISA Results

| Protein | Control (Cetuximab) | | | Cetuximab + 30-fold I-95 | | | Cetuximab + 10-fold I-95 | | | Cetuximab + 3-fold I-95 | | |
|---|---|---|---|---|---|---|---|---|---|---|---|---|
| CD16a-158V | 610541 | 600643 | 584100 | 2999205 | 2957984 | 3013349 | 2009948 | 2028975 | 2029384 | 709811 | 681963 | 681804 |

TABLE 12-continued

Certain MATE ELISA Results

| Protein | Control (Cetuximab) | | | Cetuximab + 30-fold I-95 | | | Cetuximab + 10-fold I-95 | | | Cetuximab + 3-fold I-95 | | |
|---|---|---|---|---|---|---|---|---|---|---|---|---|
| CD16a-158F | 15073 | 14564 | 15591 | 1432252 | 1383977 | 1412195 | 540636 | 538158 | 530809 | 37828 | 38515 | 40641 |
| CD32a-H167 | 402704 | 376049 | 391827 | 3397342 | 3386450 | 3284697 | 1799444 | 1788024 | 1766351 | 429439 | 434382 | 432308 |
| CD32a-R167 | 87126 | 68955 | 66536 | 2608159 | 2544556 | 2601727 | 1136710 | 1131458 | 1125262 | 156591 | 162013 | 159949 |
| CD32b | 2727 | 2683 | 2816 | 1728897 | 1730620 | 1740102 | 531784 | 523030 | 527285 | 25622 | 26224 | 24985 |
| CD16b | −2116 | −2169 | −1947 | 736655 | 686244 | 748412 | 151672 | 152553 | 153450 | 4411 | 3966 | 3599 |
| CD3ed | 3170 | 2661 | 1580 | −178880 | −193070 | −165296 | −5400 | −6791 | −6806 | 1653 | 953 | 788 |
| CD38 | 1167 | 522 | 342 | −104004 | −122238 | −115736 | −5076 | −5467 | −5581 | 6638 | 389 | 290 |

While we have described a number of embodiments, it is apparent that our basic examples may be altered to provide other embodiments that utilize technologies (e.g., compounds, compositions, methods, etc.) of this disclosure. Therefore, it will be appreciated that scope of any invention of the present disclosure is not to be defined by specific embodiments that have been represented by way of example. For example, it is intended in accordance with the present disclosure that CD16a binding moieties can be bound to therapeutic agents other than mAbs. For instance, in the area of cancer treatment, CD16a binding moieties of the present disclosure, with or without linkers (e.g., those described herein), may be bound to immunology targeting anti-cancer agents such as various types of antibodies (e.g., monoclonal antibodies, polyclonal antibodies, antibody fragments, etc.), peptides, proteins, small molecules, adjuvants, cytokines, oncolytic viruses, vaccines, bi-specific molecules, cellular therapeutic agents, etc.

The invention claimed is:

1. A method of treating a patient having a lymphoma, comprising administering to said patient a compound according to formula I: cells would be therapeutically beneficial in a

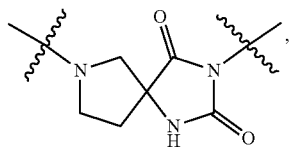

or a pharmaceutically acceptable salt thereof, wherein:
Ring A is phenyl;
Ring B is

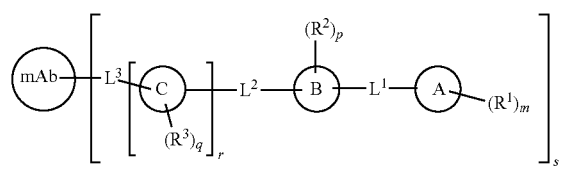

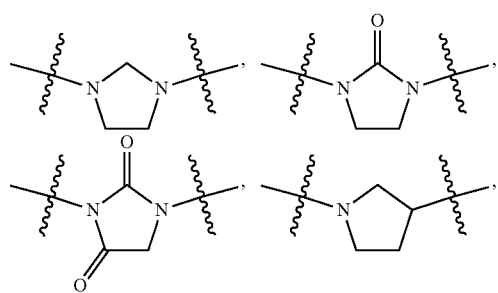

or

Ring C is where Ring

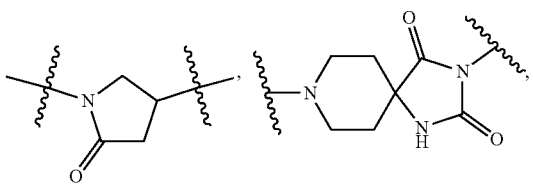

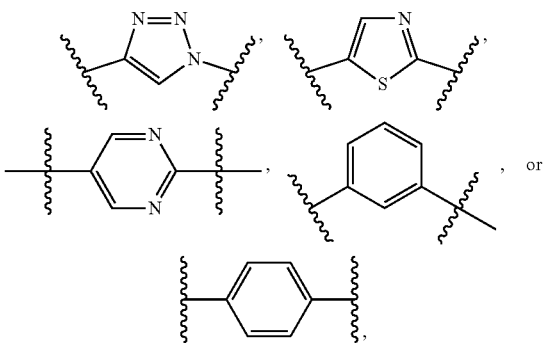

where Ring C can be bonded to another ring C;

$L^1$ is a covalent bond, $CH_2$—, —CH (R)—, or —$C(R)_2$—;

$L^2$ is a covalent bond, —NHC (O)—, —C(O)NH—, —$CH_2$—, —CH (R)—, —$C(R)_2$—, —C(O)—, or —$S(O)_2$—;

$L^3$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC (O)—, —C(O)O—, —C(O)—, —S(O)—, —$S(O)_2$—, —NRS $(O)_2$—, —$S(O)_2$NR—, —NRC(O)—, —C(O) NR—, —OC(O)NR—, —NRC(O)O—,

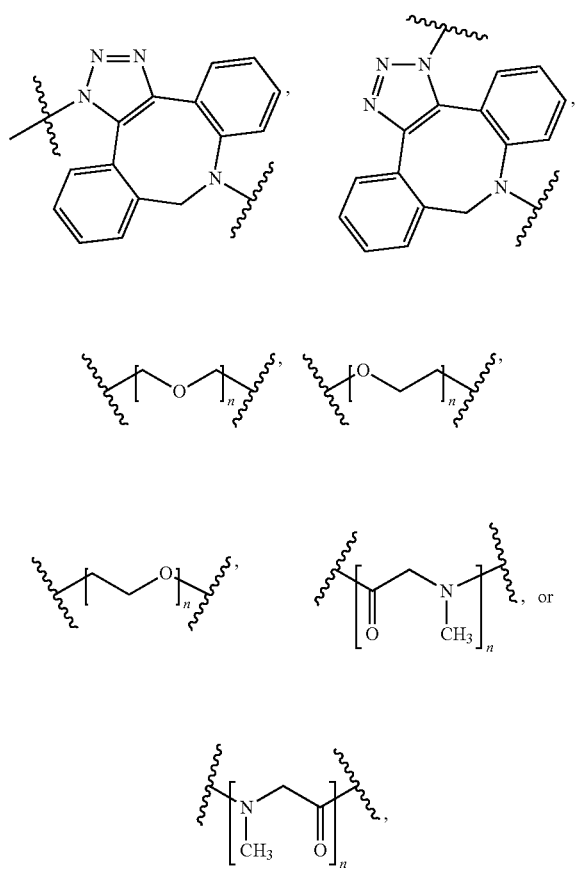

wherein:
each -Cy- is independently is

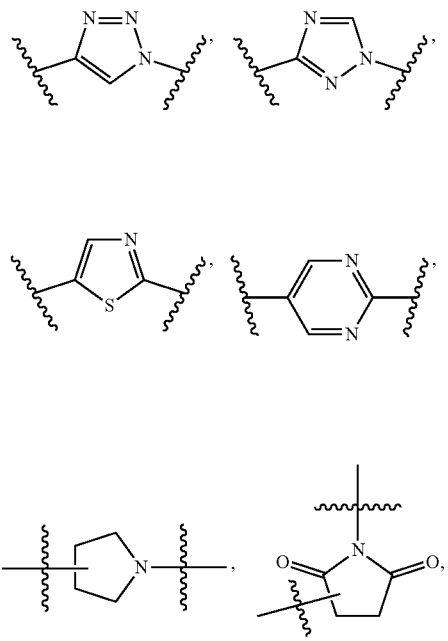

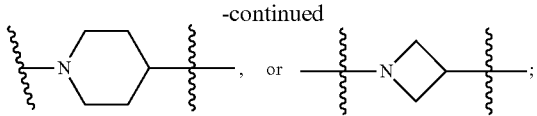

mAb is a monoclonal antibody selected from; adalimumab, cetuximab, daratumumab, rituximab;

each R is independently hydrogen or an optionally substituted group selected from $C_{1-6}$ aliphatic;

each instance of $R^1$, is independently hydrogen, halogen, —CN, —$NO_2$, C(O)R, —C(O) OR, —C(O)N(R)$_2$, —N(R)$_2$, —NRC(O)R, —NRC(O)N(R)$_2$, —NRC(O)OR, —NRS(O)$_2$R, —NRS(O)$_2$N(R)$_2$, —OR, —P(O)(R)$_2$, —SR, —S(O)R, —S(O)$_2$R, —S(O)(NH)R, —S(O)$_2$N(R)$_2$, or R;

each instance of $R^2$ is independently hydrogen, halogen, —CN, —$NO_2$, or $C_{1-3}$ aliphatic;

m is 0, 1, 2, 3, 4 or 5;

each instance of n is independently selected from 1, 2, 3, 4, 5, 6, 7, 8, 9, or 10;

p is 0, 1, or 2;

q is 0, 1, 2, 3, or 4.

2. The method of claim 1, wherein the lymphoma is Hodgkins lymphoma, Non-Hodgkins lymphoma, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, or intravascular large B-cell lymphoma.

3. The method of claim 1, where the compound of formula I is a compound of formula I-a or I-b:

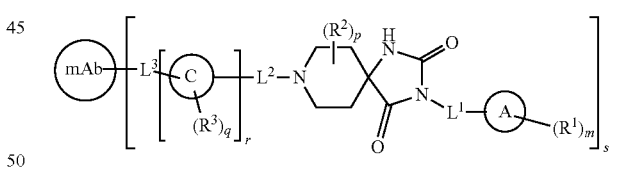

I-a

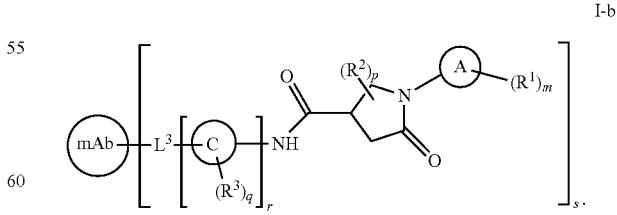

I-b

4. The method of claim 1, wherein Ring A is selected from phenyl or 2,5-dimethyoxy-phenyl.

5. The method of claim 1, wherein Ring B is

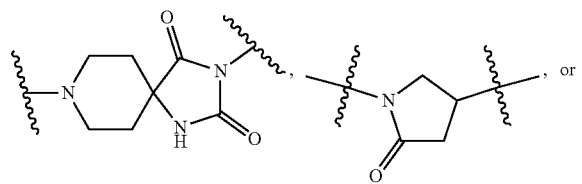

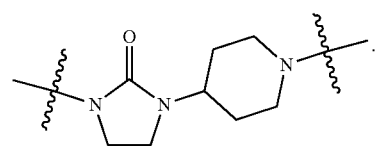

6. The method of claim 1, wherein

L¹ is a covalent bond or —CH₂—;

L² is a covalent bond, —NHC (O)—, —C(O)NH—, —CH₂—, —CH (R)—, —C(O)—, or —S(O)₂—; and L³ is a bivalent, saturated or unsaturated, straight or branched C₁₋₅₀ hydrocarbon chain, wherein 0-6 methylene units of L are independently replaced by -Cy-, —O—, —NR—, —S—, —OC (O)—, —C(O)O—, —C(O)—, —S(O)—, —S(O)₂—, —NRS (O)₂—, —S(O)₂NR—, —NRC (O)—, —C(O)NR—, —OC (O)NR—, —NRC (O)O—

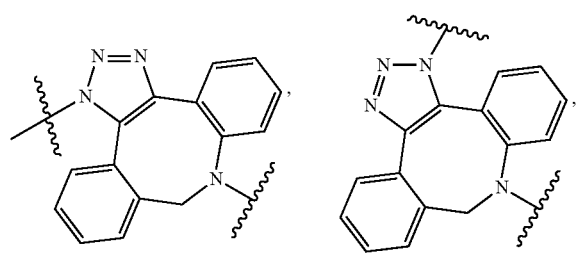

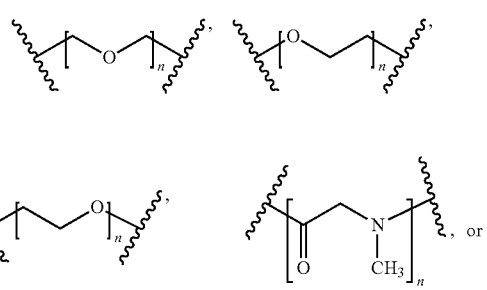

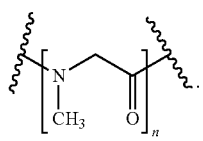

7. The method of claim 1, wherein m is 0, 1, 2, 3, or 4; p is 0 or 1; and q is 0, 1, 2, or 3.

8. The method of claim 3, wherein the compound is of formula I-a:

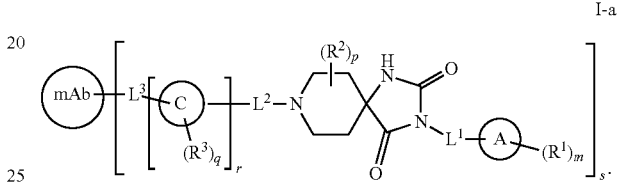

I-a

9. The method of claim 3, wherein

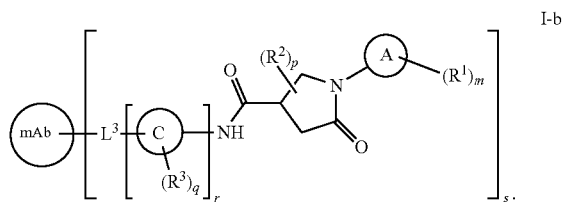

I-b

10. The method of claim 1, wherein Ring C is

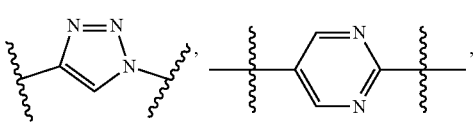

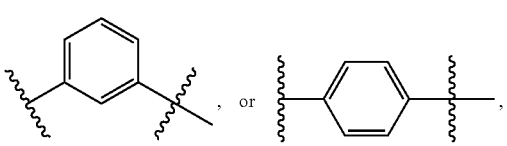

where Ring C is bonded to another Ring.

11. Selected The method of claim 1, wherein the compound is a compound selected from
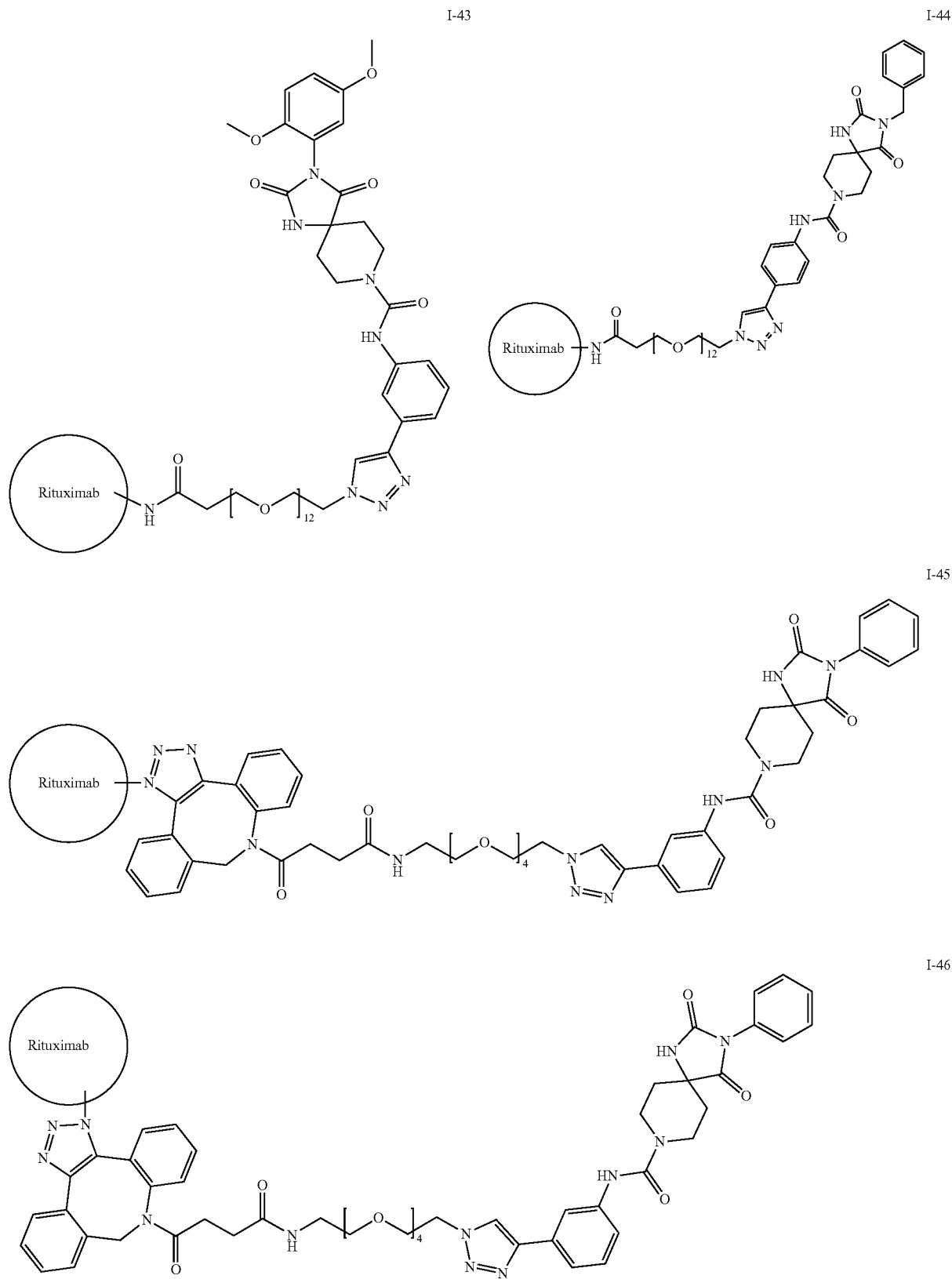

I-47
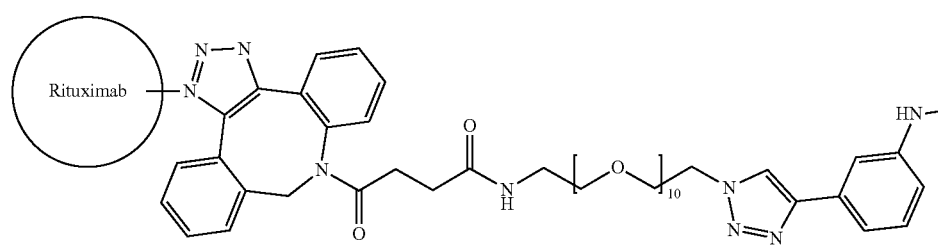
I-48
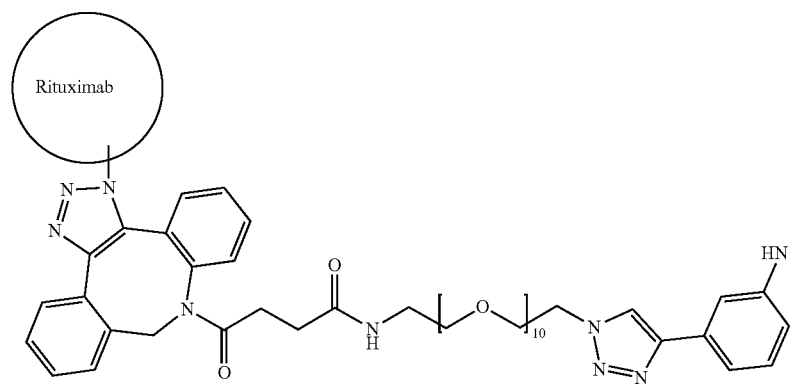
I-49
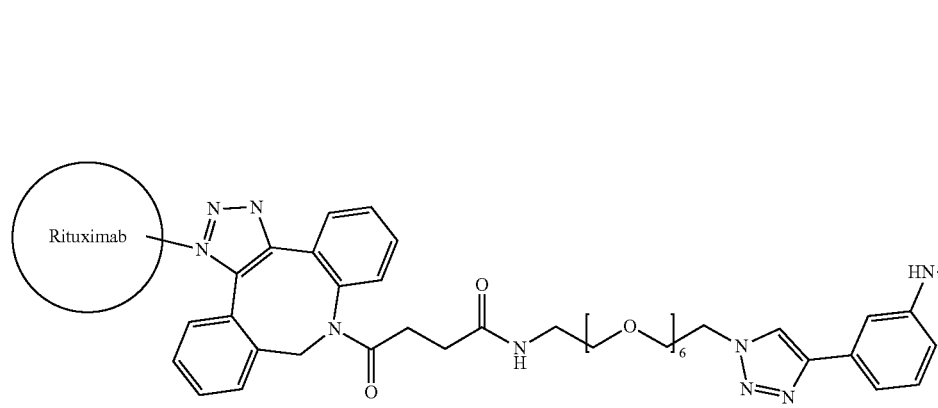
I-50
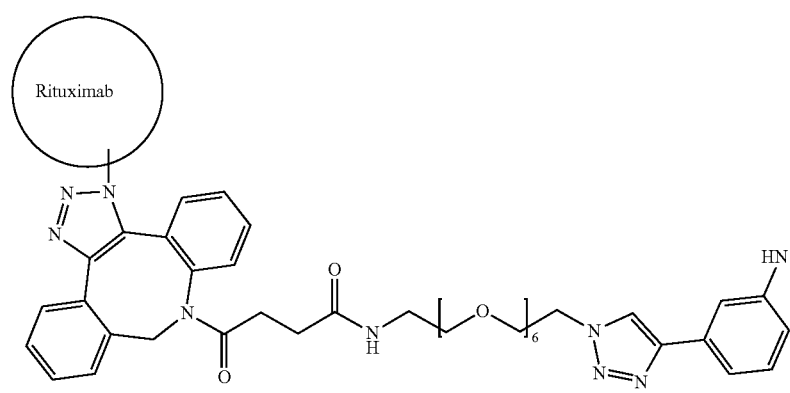

-continued
I-51
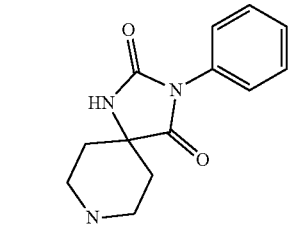
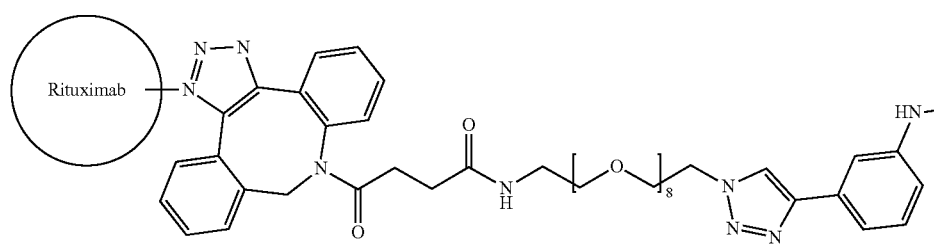
I-52
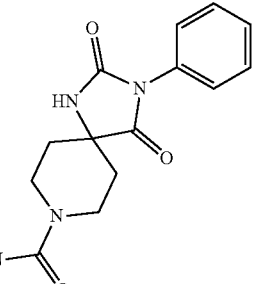
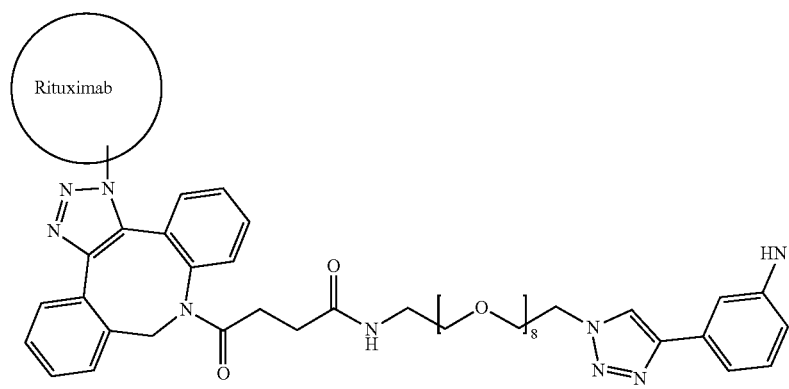
I-53
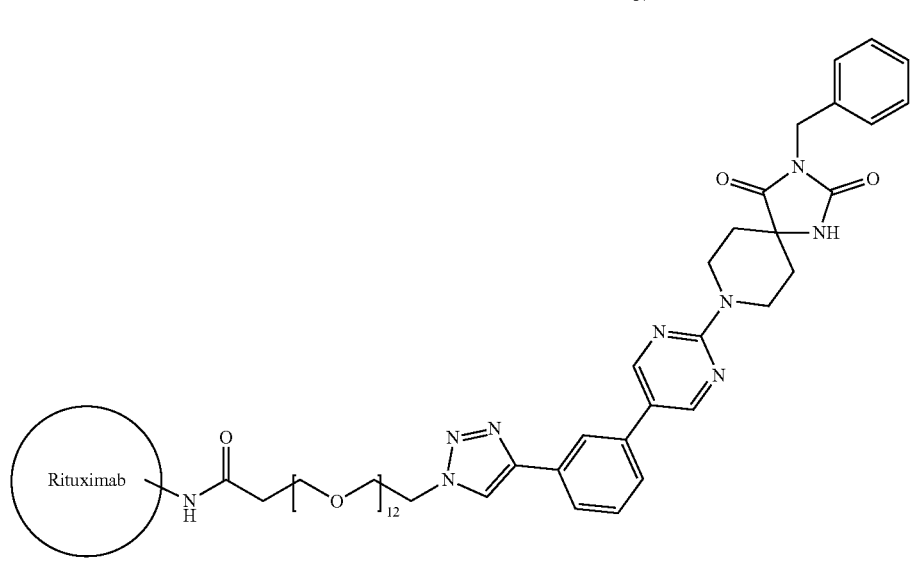
I-54
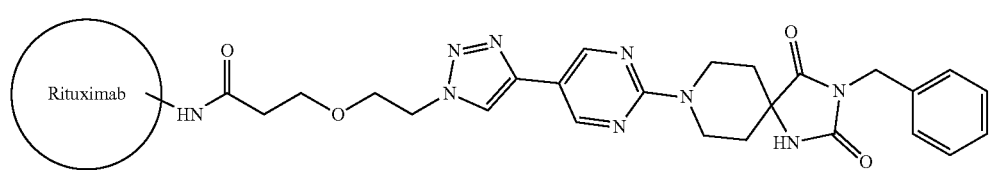

I-55
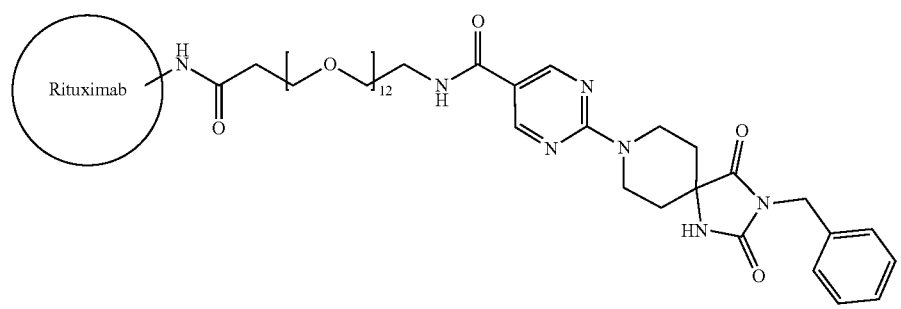
I-56
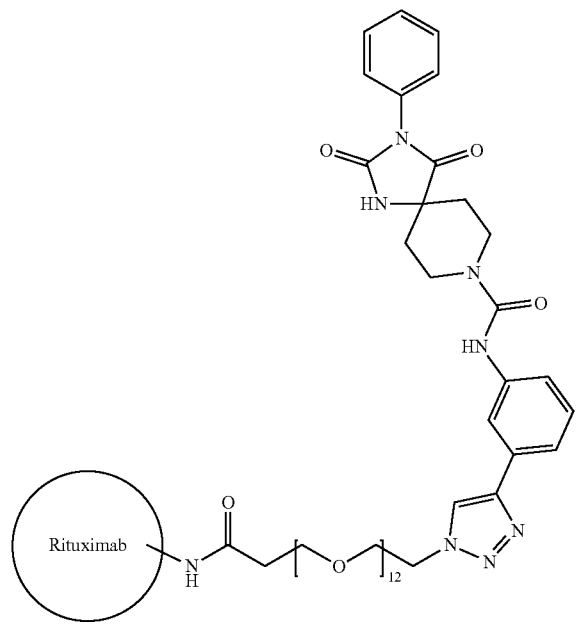
I-57
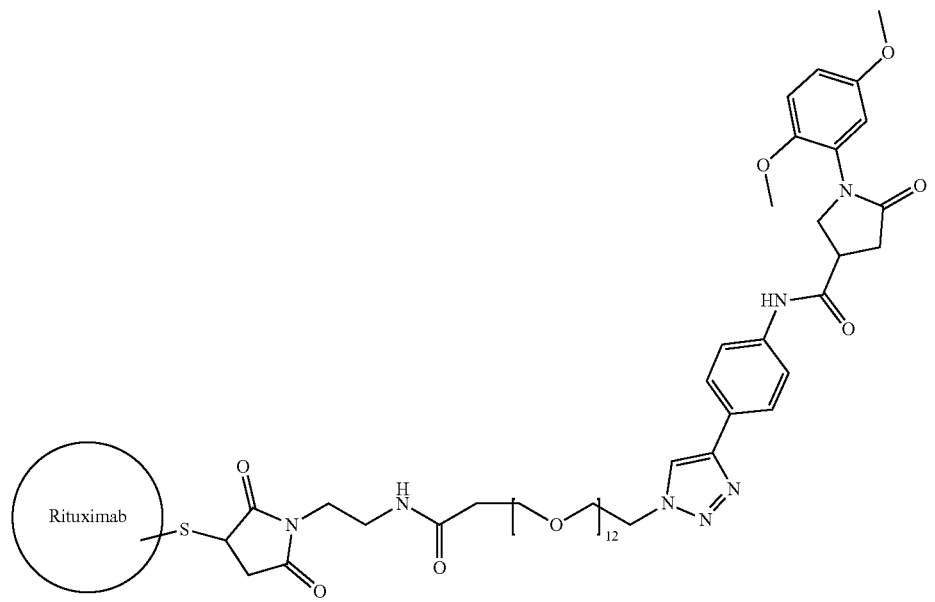

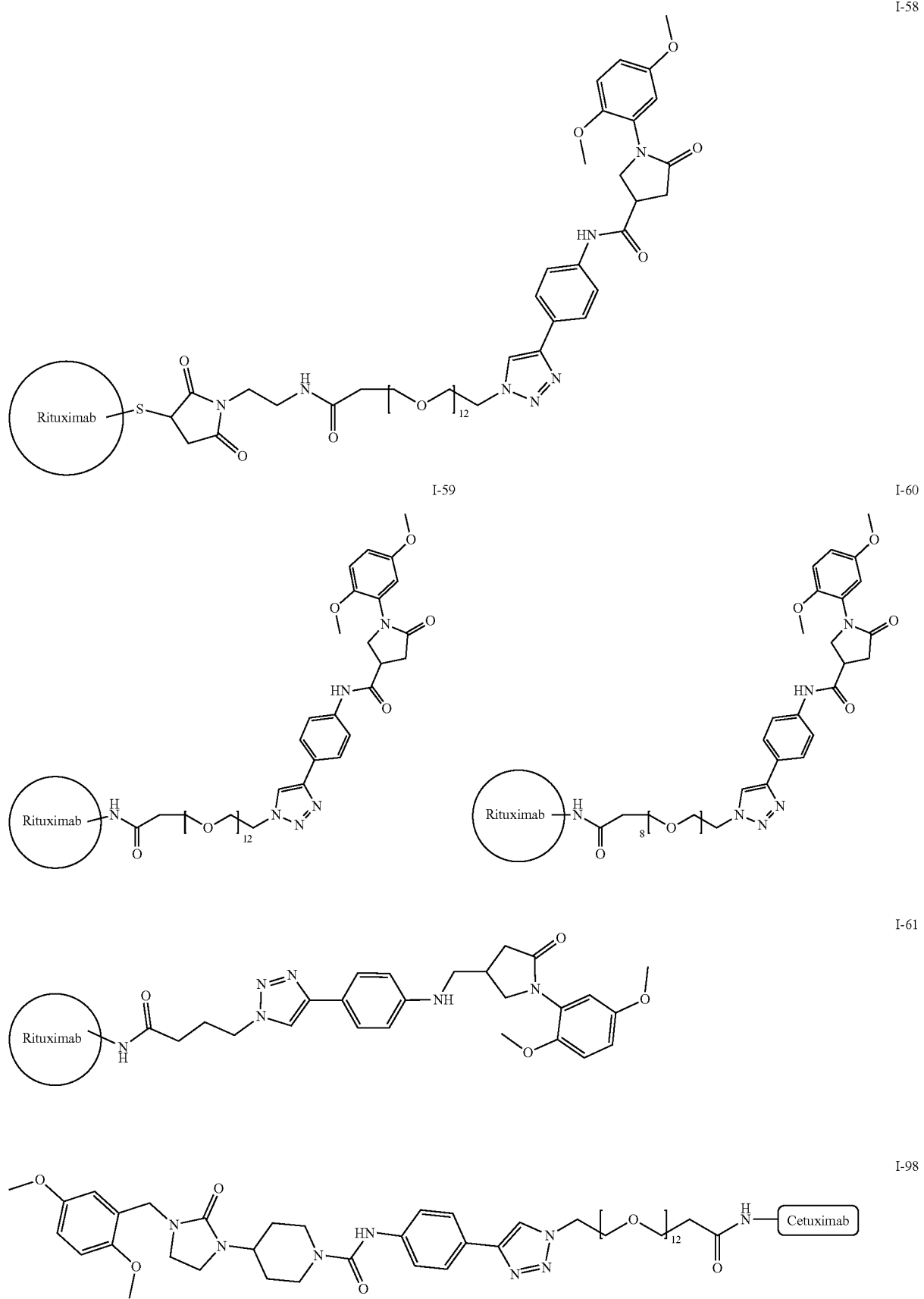

I-99
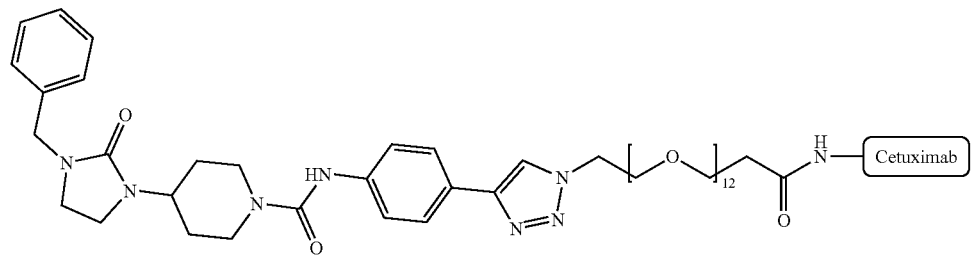
I-100
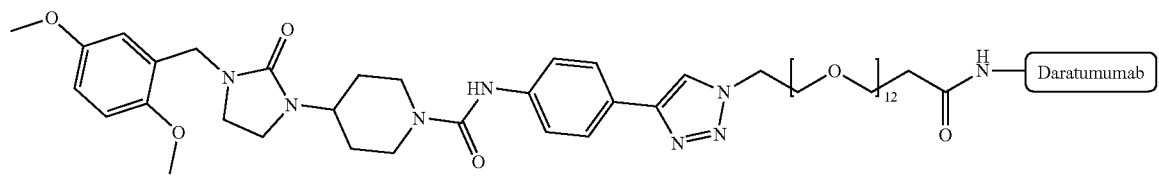
* * * * *